United States Patent
Jacobsen et al.

(10) Patent No.: US 9,499,551 B2
(45) Date of Patent: Nov. 22, 2016

(54) SUBSTITUTED PYRROLO[2,3-B]PYRIDINES FOR TREATING CANCER OR INFLAMMATORY DISEASES

(71) Applicant: Confluence Life Sciences, Inc., St. Louis, MO (US)

(72) Inventors: Eric Jon Jacobsen, Chesterfield, MO (US); James Robert Blinn, O'Fallon, MO (US); John Robert Springer, Wentzville, MO (US); Susan L. Hockerman, Kirkwood, MO (US)

(73) Assignee: Confluence Life Sciences, Inc., Saint Louis, MO (US)

( * ) Notice: Subject to any disclaimer, the term of this patent is extended or adjusted under 35 U.S.C. 154(b) by 0 days.

(21) Appl. No.: 14/604,016

(22) Filed: Jan. 23, 2015

(65) Prior Publication Data

US 2015/0210705 A1    Jul. 30, 2015

Related U.S. Application Data

(60) Provisional application No. 62/007,481, filed on Jun. 4, 2014, provisional application No. 61/931,491, filed on Jan. 24, 2014.

(51) Int. Cl.
| | | |
|---|---|---|
| *C07D 471/04* | (2006.01) | |
| *C07D 221/04* | (2006.01) | |
| *C07D 487/04* | (2006.01) | |

(52) U.S. Cl.
CPC ............ *C07D 487/04* (2013.01); *C07D 471/04* (2013.01)

(58) Field of Classification Search
CPC .......................... C07D 221/04; C07D 471/04
USPC .............. 544/333, 373; 546/113, 199, 276.7; 548/202, 373.1, 518, 950
See application file for complete search history.

(56) References Cited

U.S. PATENT DOCUMENTS

| | | |
|---|---|---|
| 2003/0004350 A1 | 1/2003 | Longo et al. |
| 2006/0110462 A1 | 5/2006 | Papadopoulos et al. |
| 2008/0280917 A1 | 11/2008 | Albrecht et al. |
| 2011/0207732 A1 | 8/2011 | Heinrich et al. |
| 2013/0217951 A1 | 8/2013 | Dorsch et al. |

FOREIGN PATENT DOCUMENTS

| | | |
|---|---|---|
| EP | 2070928 A1 | 6/2009 |
| WO | 9600226 A1 | 1/1996 |
| WO | 0198299 A1 | 12/2001 |
| WO | 2010150211 A2 | 12/2010 |
| WO | WO 2010/150211 A2 | 12/2010 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Morris, et al. e-EROS Encyclopedia of Reagents for Organic Synthesis, 2007, 1-12.*
International Search Report and Written Opinion, PCT Application No. PCT/US2015/12673, dated Apr. 14, 2015, 13 pges.

* cited by examiner

*Primary Examiner* — Douglas M Willis
(74) *Attorney, Agent, or Firm* — Dennis A. Bennett; Brock Levin

(57) ABSTRACT

Disclosed herein are substituted pyrrolopyridine and pyrrolopyrazine compounds and compositions useful in the treatment of TAK mediated diseases, such as cancer, having the structure of Formula (I):

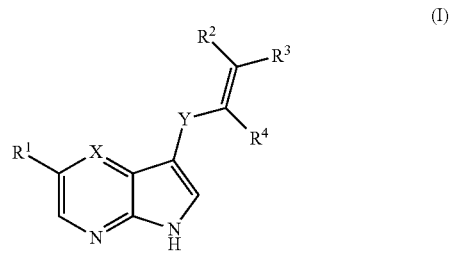

wherein R¹, R², R³, and R⁴ are as defined in the detailed description. Methods of modulation of TAK activity in a human or animal subject are also provided, providing therapeutic benefit to subjects with disease conditions, especially cancer.

10 Claims, No Drawings

SUBSTITUTED PYRROLO[2,3-B]PYRIDINES FOR TREATING CANCER OR INFLAMMATORY DISEASES

CROSS REFERENCE TO RELATED APPLICATIONS

This application claims the benefit of U.S. Provisional Applications No. 61/931,491, filed Jan. 24, 2014, and 62/007,481, filed Jun. 4, 2014, the contents of each are hereby incorporated by reference.

BACKGROUND

Field

The present disclosure relates to new substituted pyrrolopyridine and pyrrolopyrazine compounds and compositions, and their application as pharmaceuticals for the treatment of disease. Methods of modulation of TAK activity in a human or animal subject are also provided for the treatment diseases such as cancer or inflammation.

Description of Related Art

Transforming growth factor β-activated kinase 1 (TAK1, also known as MAP3K7) is an intracellular enzyme that sits at the crossroads of several disease pathways. TAK1 is a member of the mitogen-activated protein kinase (MAPKKK or MAP3K) class of serine/threonine kinases.

TAK1 in Cancer:

Transforming growth factor beta (TGF-β) is a multifunctional secreted polypeptide involved in the regulation of cell proliferation, differentiation and survival (related to apoptosis) and is implicated in multiple aspects of tumor pathogenesis. TGF-β receptors act through several intracellular signaling cascades that include the canonical SMAD pathway as well as the non-canonical Rho GTPase and TAK1 signaling pathways. TGF-β can directly promote tumor invasiveness and metastasis in addition to induction of angiogenesis and suppression of lymphocyte and macrophage proliferation and differentiation, thereby suppressing immune surveillance of the developing tumor. Reduction of TGF-β activity may therefore be a promising target of therapeutic strategies to control tumor growth.

TAK1, a key downstream effector of TGF-β, has been implicated in transformation and metastasis of cancer cells as well as in the development of resistance to chemotherapeutic drugs and ionizing radiation. TAK1 is required for TGF-β initiated R-Ras mediated transformation of mammary epithelial cells, a process that is independent of SMAD signaling but requires TAK1 directed activation of p38 and c-Jun N-terminal kinase (JNK) pathways. It has been shown that TAK1 activation is involved in metastasis and bone destruction by breast carcinoma cells, as well as in the metastasis and lung invasion of colon cancer cells. The TAK1-dependent activation of p38, JNK and nuclear factor κB (NF-κB) pathways was central to promoting these cancer phenotypes. Multiple genotoxic anti-cancer drugs and ionizing radiation have been shown to activate NF-κB and thereby protect cancer cells from DNA damage-induced apoptosis. For example, two anticancer drugs, doxorubicin and etoposide, when tested in multiple cancer cell lines, promoted TAK1-mediated DNA-damage response-pathway that involved the downstream activation of NF-κB, p38 and MK2, conferring chemoresistance and promoting cancer cell survival. The role of TAK1, as a potential mediator of the extreme drug resistance displayed by pancreatic cancer, was studied using an orally, bioavailable small molecule inhibitor of TAK1, LYTAK1. Results demonstrated an increased sensitivity of pancreatic cancer cells to chemotherapeutic drugs gemcitabine and oxaliplatin (Melisi, et al. J. Natl. Cancer Inst. 103, 1190-1204 (2011)).

TAK1 in Inflammation and Autoimmune Disease:

TAK1 is also a key mediator of pro-inflammatory and stress signals. Cellular activation of TAK1 activity is promoted by pro-inflammatory cytokines such as tumor necrosis factor-α (TNF-α) and interleukin-1β (IL-1β) as well as by the engagement of T cell, B cell and toll-like receptors. TAK1 activation induces the downstream nuclear translocation of NF-κB and activation of the JNK and p38 pathways that are central to driving inflammatory and immune responses as well as T cell and B cell development, activation and survival.

Protein-based (biologics) and small molecule drugs that block TNF-α (ENBREL, HUMIRA, REMICADE, SIMPONI) or IL-1β (KINERET) signaling or that limit T cell (ORENCIA, TYSABRI) or B cell (RITUXAN) function have been used to treat a number of autoimmune diseases such as rheumatoid arthritis, psoriatic arthritis, juvenile idiopathic arthritis, ankylosing spondylytis and inflammatory bowel disease (IBD). The essential role of TAK1 in modulating TNF-α and IL-1β signaling and T cell and B cell function make it important in autoimmune diseases.

TAK1 plays a pivotal role in JNK-mediated activation of metalloproteinase (MMP) gene expression and joint destruction in inflammatory arthritis. In animal models of autoimmune arthritis, the targeted knockdown of TAK1 with small interfering RNA (siRNA) provides disease-modifying benefit, both prophylactically and therapeutically. At the molecular and cellular levels, TAK1 knockdown severely impairs JNK and NF-κB signaling, down-regulated expression of pro-inflammatory mediators and constrains the expansion of IL-17A producing T cells that contribute to the pathogenesis of rheumatoid arthritis and other autoimmune diseases. The immunosuppressive impact of TAK1 deletion has also been studied in an animal model of contact hypersensitivity (CHS), a classic T cell-mediated immune response. Both dendritic cells (innate immunity) and T cells (adaptive immunity) play critical roles in the onset of CHS. By specifically deleting TAK1 in dendritic cells in a mouse model, it was shown that TAK1 is essential in dendritic cell-mediated T cell activation and the development of CHS (Zhao, et al. (2011) Cell. Mol. Immunol. 8, 315-324).

Compounds useful as tyrosine kinase inhibitors for treatment of proliferative diseases (e.g., cancer) are reported in WO 96/00226 (Published 4 Jan. 1996). Compounds described therein include azoindolylidene substituted with cyanoalkene, alkoxy and amido substituents.

Compounds useful as modulators of CDK for the treatment of cancer are reported in WO 01/98299 (Published 27 Dec. 2001). Compounds described therein include azaindoles substituted with alkene and amino substituents.

Compounds useful as AKT and CDC7 kinase inhibitors for treatment of cancer are reported in EP 2070928 (Published in 17 Jun. 2008). Compounds described therein include 7-azaindol-3-ylacrylamides substituted with amino substituents.

Compounds useful as JAK and SYK kinase inhibitors for treatment of auto-immune and inflammatory diseases are reported in U.S. Pat. No. 7,902,197 (Published in 8 Mar. 2011). Compounds described therein include pyrrolopyrazines substituted with amino substituents.

BRIEF SUMMARY

The present disclosure provides a compound, or a pharmaceutically acceptable salt, hydrate or solvate thereof, of Formula (I):

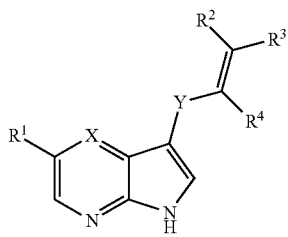

(I)

wherein: $R^1$ is chosen from hydrogen, $C_{1-6}$ alkyl, $OC_{1-6}$ alkyl, $OC_{3-7}$ cycloalkyl, $C_{1-4}$ alkylamino, $N(R^4)_2$, NH$(CH_2)_nC_{3-7}$ cycloalkyl, NHC(O)alkyl, NHC(O)aryl, NHC(O)heteroaryl, cyano, $C(O)N(R^4)_2$, $C(O)C_{1-4}$ alkyl, C(O)aryl, C(O)heteroaryl, $CH_2$aryl, CHFaryl, $CH_2$heteroaryl, CHFheteroaryl, trifluoromethyl, halo, heterocycle, aryl and heteroaryl; wherein each alkyl, cycloalkyl, heterocyclic, aryl or heteroaryl group of $R^1$ may be optionally substituted with one or more $R^5$ substituents; $R^2$ is chosen from hydrogen, F, $C_{1-6}$ alkyl, $C(O)R^4$, CN, $C(O)NH_2$, and C(O)NHMe; $R^3$ is chosen from $C(O)R^4$, CN, $C(O)NH_2$, C(O)NHMe, C(O)alkyl, $C(O)C_{1-6}$ alkylN$(R^4)_2$, and $C(O)C_{1-6}$ alkylOR$^4$; or when $R^2$ is $C(O)R^4$, $C(O)NH_2$, C(O)NHMe, or CN, then $R^3$ is chosen from hydrogen, F and Me; each $R^4$ is independently chosen from hydrogen, $C_{1-6}$ alkyl, and $C_{3-6}$ cycloalkyl; wherein each $R^4$ together with the atoms to which they are attached optionally form an heterocycloalkyl or heteroaryl ring, which may be optionally substituted with one or more $R^5$ substituents; each $R^5$ is independently chosen from $C_{1-6}$ alkyl, $(CH_2)_nC_{3-7}$cycloalkyl, OH, $OC_{1-6}$ alkyl, $OCF_3$, O-aryl, O-heteroaryl, $CH_2$aryl, $CH_2$heteroaryl, CH(OH)aryl, CH(OH)heteroaryl, $O(CH_2)_nC_{3-6}$ cycloalkyl, $C_{1-4}$ alkylamino, $NHC_{3-7}$ cycloalkyl N$(C_{1-4}$ alkyl$)_2$, $N(R^4)_2$, NHC(O)alkyl, NHC(O)aryl, NHC(O)heteroaryl, cyano, $C(O)N(R^4)_2$, $C(O)C_{1-4}$ alkyl, $C(O)OC_{1-6}$ alkyl, C(O)O-aryl, C(O)O-heteroaryl, $C(O)C_{1-6}$ alkyl, $C(O)CF_3$, $C(O)C_{3-7}$ cycloalkyl, C(O)aryl, C(O)heteroaryl, C(O)heterocycle, trifluoromethyl, halo, CN, $S(O)_2$Me, S(O)Me, SMe, aryl, and heteroaryl; wherein each alkyl, cycloalkyl, aryl, heteroaryl or heterocyclic group of $R^5$ may be optionally substituted with one or more $R^6$; each $R^6$ is independently chosen from halo, $C_{1-6}$ alkyl, $C_{3-6}$ cycloalkyl, $CF_3$, OH, OMe, OEt, $OCH_2CH_2F$, $O(CH_2)_nCF_3$, and CN; $R^7$ is chosen from hydrogen, $C_{1-6}$ alkyl, $OC_{1-6}$ alkyl, $OC_{3-7}$ cycloalkyl, $C_{1-4}$ alkylamino, $NHC_{1-6}$ alkyl, $NHC_{3-7}$ alkyl, cyano, trifluoromethyl, halo, aryl and heteroaryl; wherein alkyl, aryl or heteroaryl groups of $R^7$ may be optionally substituted with one or more $R^5$ substituents; X is chosen from $CR^7$ and N; Y is chosen from a bond, $CH_2$, CHF, C(O), and NHC(O); and n is chosen from 0, 1, and 2.

Certain compounds disclosed herein may possess useful TAK modulating activity, and may be used in the treatment or prophylaxis of a disease or condition in which TAK plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for modulating TAK. Other embodiments provide methods for treating a TAK-mediated disorder in a subject in need of such treatment, comprising administering to the subject a therapeutically effective amount of a compound or composition according to the present disclosure. Also provided is the use of certain compounds disclosed herein for use in the manufacture of a medicament for the treatment of a disease or condition ameliorated by the modulation of TAK.

DETAILED DESCRIPTION

Abbreviations and Definitions

To facilitate understanding of the disclosure, a number of terms and abbreviations as used herein are defined below as follows:

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As used herein, two embodiments are "mutually exclusive" when one is defined to be something which is different than the other. For example, an embodiment wherein $R_3$ and $R_4$ combine to form a cycloalkyl is mutually exclusive with an embodiment in which $R_3$ is ethyl and $R_4$ is hydrogen. Similarly, an embodiment wherein Y is $CH_2$ is mutually exclusive with an embodiment wherein Y is NH. However, an embodiment wherein $R_3$ and $R_4$ combine to form a cycloalkyl is mutually exclusive with an embodiment in which Y is $CH_2$."

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

When ranges of values are disclosed, and the notation "from $n_1$ . . . to $n_2$" or "between $n_1$ . . . and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values that it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group.

Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon substituent having one or more double bonds and containing from 2 to 20 carbon atoms. In certain embodiments, the alkenyl will comprise from 2 to 6 carbon atoms. The term "alkenylene" refers to a carbon-carbon double bond system attached at two or more positions such as ethenylene [(—CH=CH—), (—C::C—)]. Examples of suitable alkenyl substituents include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether substituent, wherein the term alkyl is as defined below. Examples of suitable alkyl ether substituents include methoxy, ethoxy, n-propoxy, iso-propoxy, n-butoxy, iso-butoxy, sec-butoxy, tert-butoxy, and the like.

The term "alkyl," as used herein, alone or in combination, refers to a straight-chain or branched-chain alkyl substituent containing from 1 to 20 carbon atoms. In certain embodiments, the alkyl will comprise from 1 to 10 carbon atoms. In further embodiments, the alkyl will comprise from 1 to 6 carbon atoms. Alkyl groups may be optionally substituted as defined herein. Examples of alkyl substituents include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) substituent wherein the term alkyl is as defined above and wherein the sulfur may be singly or doubly oxidized. Examples of suitable alkyl thioether substituents include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon substituent having one or more triple bonds and containing from 2 to 20 carbon atoms. In certain embodiments, the alkynyl comprises from 2 to 6 carbon atoms. In further embodiments, the alkynyl comprises from 2 to 4 carbon atoms. The term "alkynylene" refers to a carbon-carbon triple bond attached at two positions such as ethynylene (—C:::C—, —C≡C—). Examples of alkynyl substituents include ethynyl, propynyl, hydroxypropynyl, butyn-1-yl, Butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl" as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. Polycyclic ring systems may feature rings that are partially saturated. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl substituent derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent substituent C$_6$H$_4$=derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, the cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl substituent having the meaning as defined above wherein one or more hydrogens are replaced with a halogen. Specifically embraced are monohaloalkyl, dihaloalkyl and polyhaloalkyl substituents. A monohaloalkyl substituent, for one example, may have an iodo, bromo, chloro or fluoro atom within the substituent. Dihalo and polyhaloalkyl substituents may have two or more of the same halo atoms or a combination of different halo substituents. Examples of haloalkyl substituents include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon substituent, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom selected from the group consisting of O, S, and N. In certain embodiments, the heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. In addition, the heteroaryl group may contain an oxo group such as the one present in a pyridone group. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl, pyridinone and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each the heteroatom may be independently selected from the group consisting of nitrogen, oxygen, and sulfur In certain embodiments, the hetercycloalkyl will comprise from 1 to 4 heteroatoms as ring members. In further embodiments, the hetercycloalkyl will comprise from 1 to 2 heteroatoms as ring members. In certain embodiments, the hetercycloalkyl will comprise from 3 to 8 ring members in each ring. In further embodiments, the hetercycloalkyl will comprise from 3 to 7 ring members in each ring. In yet further embodiments, the hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms.

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four the members may be heteroatoms selected from the group consisting of O, S, and N, or 2) bicyclic heteroaryl, wherein each of the fused rings comprises five or six ring members, comprising between them one to four heteroatoms selected from the group consisting of O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms selected from the group consisting of O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR, wherein R and R' are independently selected from the group consisting of hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS— group, where R is as defined herein.

The term "nitro," as used herein, alone or in combination, refers to —$NO_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —$SO_3H$ group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —$S(O)_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a $X_3$CS(O)$_2$NR— group with X is a halogen and R as defined herein.

The term "trihalomethanesulfonyl" refers to a $X_3$CS(O)$_2$— group where X is a halogen.

The term "trihalomethoxy" refers to a $X_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that the group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, SCH$_3$, C(O)CH$_3$, CO$_2$CH$_3$, CO$_2$H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R$''$ where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the disclosure encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present disclosure includes all cis, trans, syn, anti, entgegen (E), and zusammen (Z) isomers as well as the appropriate mixtures thereof. Additionally, compounds may exist as tautomers; all tautomeric isomers are provided by this disclosure. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

TAK modulator is used herein to refer to a compound that exhibits an IC50 with respect to TAK activity of no more than about 100 μM and more typically not more than about 50 μM, as measured in the TAK enzyme assay described generally herein below. IC50 is that concentration of modulator that reduces the activity of an enzyme (e.g., TAK) to half-maximal level. Certain compounds disclosed herein have been discovered to exhibit modulation against TAK. In certain embodiments, compounds will exhibit an IC50 with respect to TAK of no more than about 10 μM; in further embodiments, compounds will exhibit an IC50 with respect to TAK of no more than about 5 μM; in yet further embodiments, compounds will exhibit an IC50 with respect to TAK of not more than about 1 μM; in yet further embodiments, compounds will exhibit an IC50 with respect to TAK of not more than about 200 nM, as measured in the TAK binding assay described herein.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present disclosure includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present disclosure contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid.

While it may be possible for the compounds of the subject disclosure to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject disclosure or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations that can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

Gels for topical or transdermal administration may comprise, generally, a mixture of volatile solvents, nonvolatile solvents, and water. In certain embodiments, the volatile solvent component of the buffered solvent system may include lower (C1-C6) alkyl alcohols, lower alkyl glycols and lower glycol polymers. In further embodiments, the volatile solvent is ethanol. The volatile solvent component is thought to act as a penetration enhancer, while also producing a cooling effect on the skin as it evaporates. The nonvolatile solvent portion of the buffered solvent system is selected from lower alkylene glycols and lower glycol polymers. In certain embodiments, propylene glycol is used. The nonvolatile solvent slows the evaporation of the volatile solvent and reduces the vapor pressure of the buffered solvent system. The amount of this nonvolatile solvent component, as with the volatile solvent, is determined by the pharmaceutical compound or drug being used. When too little of the nonvolatile solvent is in the system, the pharmaceutical compound may crystallize due to evaporation of volatile solvent, while an excess may result in a lack of bioavailability due to poor release of drug from solvent mixture. The buffer component of the buffered solvent system may be selected from any buffer commonly used in the art; in certain embodiments, water is used. A common ratio of ingredients is about 20% of the nonvolatile solvent, about 40% of the volatile solvent, and about 40% water. Several optional ingredients can be added to the topical composition. These include, but are not limited to, chelators and gelling agents. Appropriate gelling agents can include, but are not limited to, semisynthetic cellulose derivatives (such as hydroxypropylmethylcellulose) and synthetic polymers, and cosmetic agents.

Lotions include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops may comprise sterile aqueous or oily solutions or suspensions and may be prepared by dissolving the active ingredient in a suitable aqueous solution of a bactericidal and/or fungicidal agent and/or any other suitable preservative, and, in certain embodiments, including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. In addition, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Alternatively, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Alternatively, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

A TAK1 inhibitor can be used in combination with anti-cancer drugs, including but not limited to the following classes: alkylating agents, anti-metabolites, plant alkaloids and terpenoids, topoisomerase inhibitors, cytotoxic antibiotics, angiogenesis inhibitors and tyrosine kinase inhibitors.

For use in cancer and neoplastic diseases a TAK1 inhibitor may be optimally used together with one or more of the following non-limiting examples of anti-cancer agents: (1) alkylating agents, including but not limited to cisplatin (PLATIN), carboplatin (PARAPLATIN), oxaliplatin (ELOXATIN), streptozocin (ZANOSAR), busulfan (MYLERAN) and cyclophosphamide (ENDOXAN); (2) anti-metabolites, including but not limited to mercaptopurine (PURINETHOL), thioguanine, pentostatin (NIPENT), cytosine arabinoside (ARA-C), gemcitabine (GEMZAR), fluorouracil (CARAC), leucovorin (FUSILEV) and methotrexate (RHEUMATREX); (3) plant alkaloids and terpenoids, including but not limited to vincristine (ONCOVIN), vinblastine and paclitaxel (TAXOL); (4) topoisomerase inhibitors, including but not limited to irinotecan (CAMPTOSAR), topotecan (HYCAMTIN) and etoposide (EPOSIN); (5) cytotoxic antibiotics, including but not limited to actinomycin D (COSMEGEN), doxorubicin (ADRIAMYCIN), bleomycin (BLENOXANE) and mitomycin (MITOSOL); (6) angiogenesis inhibitors, including but not limited to sunitinib (SUTENT) and bevacizumab (AVASTIN); and (7) tyrosine kinase inhibitors, including but not limited to imatinib (GLEEVEC), erlotinib (TARCEVA), lapatininb (TYKERB) and axitinib (INLYTA).

Where a subject is suffering from or at risk of suffering from an inflammatory condition, a TAK1 inhibitor compound described herein is optionally used together with one or more agents or methods for treating an inflammatory condition in any combination. Therapeutic agents/treatments for treating an autoimmune and/or inflammatory condition include, but are not limited to any of the following examples: (1) corticosteroids, including but not limited to cortisone, dexamethasone, and methylprednisolone; (2) non-steroidal anti-inflammatory drugs (NSAIDs), including but not limited to ibuprofen, naproxen, acetaminophen, aspirin, fenoprofen (NALFON), flurbiprofen (ANSAID), ketoprofen, oxaprozin (DAYPRO), diclofenac sodium (VOLTAREN), diclofenac potassium (CATAFLAM), etodolac (LODINE), indomethacin (INDOCIN), ketorolac (TORADOL), sulindac (CLINORIL), tolmetin (TOLECTIN), meclofenamate (MECLOMEN), mefenamic acid (PONSTEL), nabumetone (RELAFEN) and piroxicam (FELDENE); (3) immunosuppressants, including but not limited to methotrexate (RHEUMATREX), leflunomide (ARAVA), azathioprine (IMURAN), cyclosporine (NEORAL, SANDIMMUNE), tacrolimus and cyclophosphamide (CYTOXAN); (4) CD20 blockers, including but not limited to rituximab (RITUXAN); (5) Tumor Necrosis Factor (TNF) blockers, including but not limited to etanercept (ENBREL), infliximab (REMICADE) and adalimumab (HUMIRA); (6) interleukin-1 receptor antagonists, including but not limited to anakinra (KINERET); (7) interleukin-6 inhibitors, including but not limited to tocilizumab (ACTEMRA); (8) interleukin-17 inhibitors, including but not limited to AIN457; (9) Janus kinase inhibitors, including but not limited to tasocitinib; and (10) syk inhibitors, including but not limited to fostamatinib.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating TAK-mediated disorders in a human or animal subject in need of such treatment comprising administering to the subject an amount of a compound disclosed herein effective to reduce or prevent the disorder in the subject, in combination with at least one additional agent for the treatment of the disorder that is known in the art. In a related aspect, certain embodiments provide therapeutic compositions comprising at least one compound disclosed herein in combination with one or more additional agents for the treatment of TAK mediated disorders.

Specific diseases to be treated by the compounds, compositions, and methods disclosed herein include, but are not limited to, autoimmune disorders, chronic inflammatory disorders, acute inflammatory disorders, auto-inflammatory disorders, pain, cancer, neoplasia, pancreatic cancer, breast cancer, lung cancer, colorectal cancer, inflammatory disorders, allergic disorders, autoimmune disorders and the like.

In some embodiments, the methods described herein are used to treat a patient in need thereof suffering from pancreatic cancer, non-Hodgkin's lymphoma, chronic lymphocytic leukemia, multiple myeloma, T-cell leukemia and tumors of the head and neck, breast, colon, prostate, lung, skin, liver and ovary.

In some embodiments, methods described herein are used to treat a disease condition comprising administering to a subject in need thereof a therapeutically effective amount of a compound of Formula (I) or pharmaceutically acceptable salt thereof, wherein the condition is cancer which has developed resistance to chemotherapeutic drugs and/or ionizing radiation.

In some embodiments, the methods described herein are used to treat patients with disorders arising from a dysregulated TAK1 molecule or dysregulated activation of TAK1 or related signaling transduction molecules. Examples of TAK1 signaling molecules include TAB1, TAB2, IRAK1, IRAK4, TRAF-6 and IL-6.

In some embodiments, the methods described herein are used to treat patients with disorders arising from activation of p38, JNK or NF-κB signaling pathways.

In some embodiments, the methods described herein are used to treat a patient in need thereof suffering from inflammatory disorders, allergic disorders, autoinflammatory disorders and autoimmune disorders. Examples of disorders include, but are not limited to rheumatoid arthritis, juvenile idiopathic arthritis, psoriatic arthritis, psoriasis, type 2 diabetes, Bechet's disease, chronic gout, cryopyrin associated periodic syndromes, familial Mediterranean fever, neonatal onset multisystem inflammatory disease, ankylosing spondylitis, contact hypersensitivity, chronic obstructive pulmonary disorder, multiple sclerosis and inflammatory bowel disease.

In some embodiments, the methods described herein can be used to treat a patient in need thereof and suffering from neoplasia. Examples of these conditions include but are not limited to the following:

| | | |
|---|---|---|
| acral lentiginous melanoma | fibrolamellar carcinoma | neuroepithelial adenocarcinoma nodular melanoma |
| actinic keratoses | focal nodular hyperplasia | oat cell carcinoma |
| adenocarcinoma | gastrinoma | oligodendroglial |
| adenoid cycstic carcinoma | germ cell tumors | osteosarcoma |
| adenomas | glioblastoma | pancreatic cancer |
| adenosarcoma | glucagonoma | papillary serous adenocarcinoma |
| adenosquamous carcinoma | hemangiblastomas | pineal cell |
| astrocytic tumors | hemangioendothelioma | pituitary tumors |
| bartholin gland carcinoma | hemangiomas | plasmacytoma |
| basal cell carcinoma | hepatic adenoma | pseudosarcoma |
| bronchial gland carcinomas | hepatic adenomatosis | pulmonary blastoma |
| capillary | hepatocellular carcinoma | renal cell carcinoma |
| carcinoids | insulinoma | retinoblastoma |
| carcinoma | intaepithelial neoplasia | rhabdomyosarcoma |
| carcinosarcoma | interepithelial squamous cell neoplasia | sarcoma |
| cavernous | invasive squamous cell carcinoma | serous carcinoma |
| cholangiocarcinoma | large cell carcinoma | small cell carcinoma |
| chondosarcoma | leiomyosarcoma | soft tissue carcinomas |
| choriod plexus papilloma/carcinoma | lentigo maligna melanomas | somatostatin-secreting tumor |
| clear cell carcinoma | malignant melanoma | squamous carcinoma |
| cystadenoma | malignant mesothelial tumors | squamous cell carcinoma |
| endodermal sinus tumor | medulloblastoma | submesothelial |
| endometrial hyperplasia | medulloepithelioma | superficial spreading melanoma |
| endometrial stromal sarcoma | melanoma | undifferentiatied carcinoma |
| endometrioid adenocarcinoma | meningeal | uveal melanoma |
| ependymal | mesothelial | verrucous carcinoma |
| epitheloid | metastatic carcinoma | vipoma |
| Ewing's sarcoma | mucoepidermoid carcinoma | well differentiated carcinoma |
| familial adenomatous polyposis (FAP) | neuroblastoma | Wilm's tumor |

The term patient refers to both humans and nonhuman animals with the abovementioned conditions. Nonhuman animals could be companion animals such as, but not limited to, canine and feline species. Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Compounds

The present disclosure provides a compound, or a pharmaceutically acceptable salt, hydrate or solvate thereof, of Formula (I):

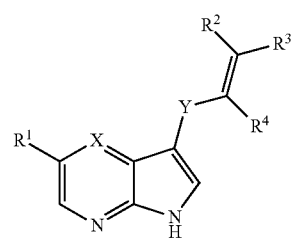

(I)

wherein: $R^1$ is chosen from hydrogen, $C_{1-6}$ alkyl, $OC_{1-6}$ alkyl, $OC_{3-7}$ cycloalkyl, $C_{1-4}$ alkylamino, $N(R^4)_2$, NH$(CH_2)_nC_{3-7}$ cycloalkyl, NHC(O)alkyl, NHC(O)aryl, NHC(O)heteroaryl, cyano, $C(O)N(R^4)_2$, $C(O)C_{1-4}$ alkyl, C(O)aryl, C(O)heteroaryl, CH$_2$aryl, CHFaryl, CH$_2$heteroaryl, CHFheteroaryl, trifluoromethyl, halo, heterocycle, aryl and heteroaryl; wherein each alkyl, cycloalkyl, heterocyclic, aryl or heteroaryl group of $R^1$ may be optionally substituted with one or more $R^5$ substituents; $R^2$ is chosen from hydrogen, F, $C_{1-6}$ alkyl, $C(O)R^4$, CN, $C(O)NH_2$, and C(O)NHMe; $R^3$ is chosen from $C(O)R^4$, CN, $C(O)NH_2$, C(O)NHMe, C(O) alkyl, $C(O)C_{1-6}$ alkylN$(R^4)_2$, and $C(O)C_{1-6}$ alkylOR$^4$; or when $R^2$ is $C(O)R^4$, $C(O)NH_2$, C(O)NHMe, or CN, then $R^3$ is chosen from hydrogen, F and Me; each $R^4$ is independently chosen from hydrogen, $C_{1-6}$ alkyl, and $C_{3-6}$ cycloalkyl; wherein each $R^4$ together with the atoms to which they are attached optionally form an heterocycloalkyl or heteroaryl ring, which may be optionally substituted with one or more $R^5$ substituents; each $R^5$ is independently chosen from $C_{1-6}$ alkyl, $(CH_2)_nC_{3-7}$cycloalkyl, OH, $OC_{1-6}$ alkyl, OCF$_3$, O-aryl, O-heteroaryl, CH$_2$aryl, CH$_2$heteroaryl, CH(OH)aryl, CH(OH)heteroaryl, $O(CH_2)_nC_{3-6}$ cycloalkyl, $C_{1-4}$ alkylamino, NHC$_{3-7}$ cycloalkyl N$(C_{1-4}$ alkyl)$_2$, N$(R^4)_2$, NHC(O)alkyl, NHC(O)aryl, NHC(O)heteroaryl, cyano, $C(O)N(R^4)_2$, $C(O)C_{1-4}$ alkyl, $C(O)OC_{1-6}$ alkyl, C(O)O-aryl, C(O)O-heteroaryl, $C(O)C_{1-6}$ alkyl, C(O)CF$_3$, $C(O)C_{3-7}$ cycloalkyl, C(O)aryl, C(O)heteroaryl, C(O)heterocycle, trifluoromethyl, halo, CN, $S(O)_2$Me, S(O)Me, SMe, aryl, and heteroaryl; wherein each alkyl, cycloalkyl, aryl, heteroaryl or heterocyclic group of $R^5$ may be optionally substituted with one or more $R^6$; each $R^6$ is independently chosen from halo, $C_{1-6}$ alkyl, $C_{3-6}$ cycloalkyl, CF$_3$, OH, OMe, OEt, OCH$_2$CH$_2$CH$_2$F, $O(CH_2)_n$CF$_3$, and CN; $R^7$ is chosen from hydrogen, $C_{1-6}$ alkyl, $OC_{1-6}$ alkyl, $OC_{3-7}$ cycloalkyl, $C_{1-4}$ alkylamino, NHC$_{1-6}$ alkyl, NHC$_{3-7}$ alkyl, cyano, trifluoromethyl, halo, aryl and heteroaryl; wherein alkyl, aryl or heteroaryl groups of R⁷ may be optionally substituted with one or more R⁵ substituents; X is chosen from CR⁷ and N; Y is chosen from a bond, CH₂, CHF, C(O), and NHC(O); and n is chosen from 0, 1, and 2.

In some embodiments, R¹ is chosen from OC$_{1-6}$ alkyl, OC$_{3-7}$ cycloalkyl, C$_{1-4}$ alkylamino, N(R⁴)₂, NH(CH₂)$_n$C$_{3-7}$ cycloalkyl, C(O)N(R⁴)₂, C(O)aryl, C(O)heteroaryl, CH₂aryl, CH₂heteroaryl, heterocycle, aryl and heteroaryl; wherein each alkyl, cycloalkyl, heterocyclic, aryl or heteroaryl group of R¹ may be optionally substituted with one or more R⁵ substituents; R² is chosen from hydrogen, F, C(O)R⁴, CN, C(O)NH₂, and C(O)NHMe; R³ is chosen from C(O)R⁴, CN, C(O)NH₂, C(O)NHMe, C(O)alkyl; or when R² is C(O)R⁴, C(O)NH₂, C(O)NHMe, or CN, then R³ is chosen from hydrogen and Me; each R⁴ is independently chosen from hydrogen, C$_{1-6}$ alkyl, and C$_{3-6}$ cycloalkyl; wherein each R⁴ together with the atoms to which they are attached optionally form an heterocycloalkyl or heteroaryl ring, which may be optionally substituted with one or more R⁵ substituents; each R⁵ is independently chosen from C$_{1-6}$ alkyl, (CH₂)$_n$C$_{3-7}$cycloalkyl, OH, OC$_{1-6}$ alkyl, O-aryl, O(CH₂)$_n$C$_{3-6}$ cycloalkyl, C$_{1-4}$ alkylamino, NHC$_{3-7}$ cycloalkyl, N(R⁴)₂, NHC(O)alkyl, cyano, C(O)N(R⁴)₂, C(O)C$_{1-4}$ alkyl, C(O)OC$_{1-6}$ alkyl, C(O)O-aryl, C(O)O-heteroaryl, C(O)CF₃, C(O)aryl, C(O)heteroaryl, C(O)heterocycle, trifluoromethyl, halo, S(O)₂Me, aryl, and heteroaryl; wherein each alkyl, cycloalkyl, aryl, heteroaryl or heterocyclic group of R⁵ may be optionally substituted with one or more R⁶; each R⁶ is independently chosen from halo, C$_{1-6}$ alkyl, C$_{3-6}$ cycloalkyl, CF₃, OMe, OEt, OCH₂CH₂CH₂F, O(CH₂)$_n$CF₃, and CN; R⁷ is chosen from hydrogen, C$_{1-6}$ alkyl, and cyano; wherein alkyl, aryl or heteroaryl groups of R⁷ may be optionally substituted with one or more R⁵ substituents; X is chosen from CR⁷ and N; Y is chosen from a bond, CH₂, C(O), and NHC(O); and n is chosen from 0, 1, and 2.

In certain embodiments, R¹ is chosen from N(R⁴)₂, C(O)N(R⁴)₂, C(O)aryl, C(O)heteroaryl, heterocycle, aryl and heteroaryl; wherein each alkyl, cycloalkyl, heterocyclic, aryl or heteroaryl group of R¹ may be optionally substituted with one or more R⁵ substituents; R² is chosen from hydrogen, C(O)R⁴, CN, C(O)NH₂, and C(O)NHMe; R³ is chosen from C(O)R⁴, CN, C(O)NH₂, C(O)NHMe, C(O)alkyl; or when R² is C(O)R⁴, C(O)NH₂, C(O)NHMe, or CN, then R³ is chosen from hydrogen and Me; each R⁴ is independently chosen from hydrogen, and C$_{1-6}$ alkyl; wherein each R⁴ together with the atoms to which they are attached optionally form an heterocycloalkyl or heteroaryl ring, which may be optionally substituted with one or more R⁵ substituents; each R⁵ is independently chosen from C$_{1-6}$ alkyl, (CH₂)$_n$C$_{3-7}$ cycloalkyl, OH, OC$_{1-6}$ alkyl, O(CH₂)$_n$C$_{3-6}$ cycloalkyl, C$_{1-4}$ alkylamino, NHC$_{3-7}$ cycloalkyl, N(R⁴)₂, NHC(O)alkyl, cyano, C(O)N(R⁴)₂, C(O)C$_{1-4}$ alkyl, C(O)OC$_{1-6}$ alkyl, C(O)O-aryl, C(O)O-heteroaryl, C(O)CF₃, C(O)aryl, C(O)heteroaryl, trifluoromethyl, halo, S(O)₂Me, aryl, and heteroaryl; wherein each alkyl, cycloalkyl, aryl, heteroaryl or heterocyclic group of R⁵ may be optionally substituted with one or more R⁶; each R⁶ is independently chosen from halo, C$_{1-6}$ alkyl, C$_{3-6}$ cycloalkyl, CF₃, OMe, OEt, O(CH₂)$_n$CF₃, and CN; R⁷ is hydrogen; X is chosen from CR⁷ and N; Y is chosen from a bond, CH₂, and C(O); and n is chosen from 0, 1, and 2.

In some embodiments, the compound is composed of formula (II)

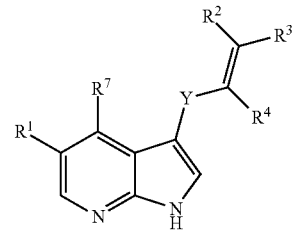

wherein: R¹ is chosen from hydrogen, C$_{1-6}$ alkyl, OC$_{1-6}$ alkyl, OC$_{3-7}$ cycloalkyl, C$_{1-4}$ alkylamino, N(R⁴)₂, NHC(O)alkyl, NHC(O)aryl, NHC(O)heteroaryl, cyano, C(O)N(R⁴)₂, C(O)C$_{1-4}$ alkyl, C(O)aryl, C(O)heteroaryl, CH₂aryl, CHFaryl, CH₂heteroaryl, CHFheteroaryl, trifluoromethyl, halo, aryl and heteroaryl; wherein each alkyl, heterocyclic, aryl or heteroaryl group of R¹ may be optionally substituted with one or more R⁵ substituents; R² is chosen from hydrogen, F, C$_{1-6}$ alkyl, C(O)R⁴, CN, C(O)NH₂, and C(O)NHMe; R³ is chosen from C(O)R⁴, CN, C(O)NH₂, C(O)NHMe, C(O)alkyl, C(O)C$_{1-6}$ alkylN(R⁴)₂, and C(O)C$_{1-6}$ alkylOR⁴; or when R² is C(O)R⁴, C(O)NH₂, C(O)NHMe, or CN, then R³ is chosen from hydrogen, F and Me; each R⁴ is independently chosen from hydrogen, C$_{1-6}$ alkyl, and C$_{3-6}$ cycloalkyl; wherein each R⁴ together with the atoms to which they are attached optionally form an heterocycloalkyl or heteroaryl ring, which may be optionally substituted with one or more R⁵ substituents; each R⁵ is independently chosen from C$_{1-4}$ alkyl, OH, OC$_{1-6}$ alkyl, CH₂aryl, CH₂heteroaryl, O(CH₂)$_n$C$_{3-6}$ cycloalkyl, C$_{1-4}$ alkylamino, NHC$_{3-7}$ cycloalkyl N(C$_{1-4}$ alkyl)₂, N(R⁴)₂, NHC(O)alkyl, NHC(O)aryl, NHC(O)heteroaryl, cyano, C(O)N(R⁴)₂, C(O)C$_{1-4}$ alkyl, C(O)OC$_{1-6}$ alkyl, C(O)C$_{1-6}$ alkyl, C(O)C$_{3-7}$ cycloalkyl, C(O)aryl, C(O)heteroaryl, C(O)heterocycle, trifluoromethyl, halo, CN, S(O)₂Me, S(O)Me, SMe, aryl, and heteroaryl; wherein each alkyl, aryl, heteroaryl or heterocyclic group of R⁵ may be optionally substituted with one or more R⁶; each R⁶ is independently chosen from halo, C$_{1-4}$ alkyl, C$_{3-6}$ cycloalkyl, CF₃, OH, OMe and CN; R⁷ is chosen from hydrogen, C$_{1-6}$ alkyl, OC$_{1-6}$ alkyl, OC$_{3-7}$ cycloalkyl, C$_{1-4}$alkylamino, NHC$_{1-6}$ alkyl, NHC$_{3-7}$ alkyl, cyano, trifluoromethyl, halo, aryl and heteroaryl; wherein alkyl, aryl or heteroaryl groups of R⁷ may be optionally substituted with one or more R⁵ substituents; Y is chosen from a bond, CH₂, CHF, C(O), and NHC(O); and n is chosen from 0, 1, and 2.

In some embodiments, the compound is composed of formula (III):

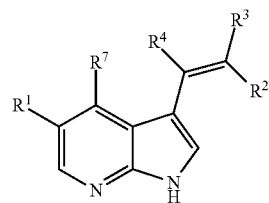

wherein: R¹ is chosen from hydrogen, C$_{1-6}$ alkyl, OC$_{1-6}$ alkyl, OC$_{3-7}$ cycloalkyl, C$_{1-4}$ alkylamino, N(R⁴)₂, NHC(O)alkyl, NHC(O)aryl, NHC(O)heteroaryl, cyano, C(O)N(R⁴)₂, C(O)C$_{1-4}$ alkyl, C(O)aryl, C(O)heteroaryl, CH₂aryl, CHFaryl, CH₂heteroaryl, CHFheteroaryl, trifluoromethyl, halo, aryl and heteroaryl; wherein each alkyl, heterocyclic, aryl or heteroaryl group of $R^1$ may be optionally substituted with one or more $R^5$ substituents; $R^2$ is chosen from hydrogen, F, $C_{1-6}$ alkyl, $C(O)R^4$, CN, $C(O)NH_2$, and $C(O)NHMe$; $R^3$ is chosen from $C(O)R^4$, CN, $C(O)NH_2$, $C(O)NHMe$, $C(O)$alkyl, $C(O)C_{1-6}$ alkylN$(R^4)_2$, and $C(O)C_{1-6}$ alkylOR$^4$; or when $R^2$ is $C(O)R^4$, $C(O)NH_2$, $C(O)NHMe$, or CN, then $R^3$ is chosen from hydrogen, F and Me; each $R^4$ is independently chosen from hydrogen, $C_{1-6}$ alkyl, and $C_{3-6}$ cycloalkyl; wherein each $R^4$ together with the atoms to which they are attached optionally form an heterocycloalkyl or heteroaryl ring, which may be optionally substituted with one or more $R^5$ substituents; each $R^5$ is independently chosen from $C_{1-4}$ alkyl, OH, $OC_{1-6}$ alkyl, $CH_2$aryl, $CH_2$heteroaryl, $O(CH_2)_nC_{3-6}$ cycloalkyl, $C_{1-4}$ alkylamino, $NHC_{3-7}$ cycloalkyl $N(C_{1-4}$ alkyl$)_2$, $N(R^4)_2$, NHC(O)alkyl, NHC(O)aryl, NHC(O)heteroaryl, cyano, $C(O)N(R^4)_2$, $C(O)C_{1-4}$ alkyl, $C(O)OC_{1-6}$ alkyl, $C(O)C_{1-6}$ alkyl, $C(O)C_{3-7}$ cycloalkyl, C(O)aryl, C(O)heteroaryl, C(O)heterocycle, trifluoromethyl, halo, CN, $S(O)_2Me$, S(O)Me, SMe, aryl, and heteroaryl; wherein each alkyl, aryl, heteroaryl or heterocyclic group of $R^5$ may be optionally substituted with one or more $R^6$; each $R^6$ is independently chosen from halo, $C_{1-4}$ alkyl, $C_{3-6}$ cycloalkyl, $CF_3$, OH, OMe and CN; $R^7$ is chosen from hydrogen, $C_{1-6}$ alkyl, $OC_{1-6}$ alkyl, $OC_{3-7}$ cycloalkyl, $C_{1-4}$ alkylamino, $NHC_{1-6}$ alkyl, $NHC_{3-7}$ alkyl, cyano, trifluoromethyl, halo, aryl and heteroaryl; wherein alkyl, aryl or heteroaryl groups of $R^7$ may be optionally substituted with one or more $R^5$ substituents; n is chosen from 0, 1, and 2.

In certain embodiments, $R^1$ is chosen from hydrogen, $C_{1-6}$ alkyl, $OC_{1-6}$ alkyl, $OC_{3-7}$ cycloalkyl, $C_{1-4}$ alkylamino, $NH_2$, $NHC_{1-6}$ alkyl, $N(C_{1-4}$ alkyl$)_2$, cyano, trifluoromethyl, halo, aryl and heteroaryl wherein alkyl, aryl or heteroaryl groups of $R^1$ may be optionally substituted with one or more $R^5$ substituents; $R^2$ is chosen from hydrogen, F, alkyl, $C(O)R^4$, CN, $C(O)NH_2$, and $C(O)NHMe$; $R^3$ is chosen from $C(O)R^4$, CN, $C(O)NH_2$, $C(O)NHMe$, $C(O)$alkyl, $C(O)$alkylN$(R^4)_2$, $C(O)$alkylOR$^4$; or when $R^2$ is $C(O)R^4$, $C(O)NH_2$, $C(O)$NHMe, or CN, $R^3$ is chosen from hydrogen, F and Me; each $R^4$ is independently chosen from hydrogen, $C_{1-6}$ alkyl, and $C_{3-6}$ cycloalkyl; wherein each $R^4$ together with the atoms to which they are attached optionally form an heterocycloalkyl or heteroaryl ring, which may be optionally substituted with one or more $R^5$ substituents; each $R^5$ is independently chosen from $C_{1-4}$ alkyl, OH, $OC_{1-6}$ alkyl, $CH_2$aryl, $CH_2$heteroaryl, $O(CH_2)_nC_{3-6}$ cycloalkyl, $C_{1-4}$ alkylamino, $NHC_{3-7}$ cycloalkyl $N(C_{1-4}$ alkyl$)_2$, $N(R^4)_2$, NHC(O)alkyl, NHC(O)aryl, NHC(O)heteroaryl, cyano, $C(O)N(R^4)_2$, $C(O)C_{1-4}$ alkyl, $C(O)OC_{1-6}$ alkyl, $C(O)C_{1-6}$ alkyl, $C(O)C_{3-7}$ cycloalkyl, C(O)aryl, C(O)heteroaryl, C(O)heterocycle, trifluoromethyl, halo, CN, S(O)2Me, S(O)Me, SMe, aryl, and heteroaryl; wherein each alkyl, aryl, heteroaryl or heterocyclic group of $R^5$ may be optionally substituted with one or more $R^6$; each $R^6$ is independently chosen from halo, $C_{1-4}$ alkyl, $C_{3-6}$ cycloalkyl, $CF_3$, OH, OMe and CN; $R^7$ is chosen from hydrogen, $C_{1-6}$ alkyl, $OC_{1-6}$ alkyl, $OC_{3-7}$ cycloalkyl, $C_{1-4}$ alkylamino, $NHC_{1-6}$ alkyl, $NHC_{3-7}$ alkyl, cyano, trifluoromethyl, halo, aryl and heteroaryl; and n is chosen from 0, 1, and 2.

In certain embodiments, $R^1$ is chosen from hydrogen, $OC_{1-6}$ alkyl, $OC_{3-7}$ cycloalkyl, $NHC_{1-6}$ alkyl, cyano, trifluoromethyl, halo, aryl and heteroaryl wherein alkyl, aryl or heteroaryl groups of $R^1$ may be optionally substituted with one or more $R^5$ substituents; $R^2$ is chosen from hydrogen, F, alkyl, $C(O)R^4$, CN, $C(O)NH_2$, and $C(O)NHMe$; $R^3$ is chosen from $C(O)R^4$, CN, $C(O)NH_2$, $C(O)$alkyl, $C(O)$alkylOR$^4$; or when $R^2$ is $C(O)R^4$, $C(O)NH_2$, $C(O)NHMe$, or CN, $R^3$ is chosen from hydrogen, F and Me; each $R^4$ is independently chosen from hydrogen, $C_{1-6}$ alkyl, and $C_{3-6}$ cycloalkyl; wherein each $R^4$ together with the atoms to which they are attached optionally form an heterocycloalkyl or heteroaryl ring, which may be optionally substituted with one or more $R^5$ substituents; each $R^5$ is independently chosen from $C_{1-4}$ alkyl, OH, $OC_{1-6}$ alkyl, $O(CH_2)_nC_{3-6}$ cycloalkyl, $C_{1-4}$ alkylamino, $NHC_{1-6}$ alkyl, $NHC_{3-7}$ cycloalkyl $N(C_{1-4}$ alkyl$)_2$, NHC(O)alkyl, cyano, trifluoromethyl, halo, aryl, and heteroaryl, wherein alkyl, aryl or heteroaryl groups of $R^5$ may be optionally substituted with $R^6$; each $R^6$ is independently chosen from halo, $CF_3$, OMe and CN; $R^7$ is chosen from hydrogen, $OC_{1-6}$ alkyl, $OC_{3-7}$ cycloalkyl, $NHC_{1-6}$ alkyl, $NHC_{3-7}$ alkyl cyano, trifluoromethyl, halo, aryl and heteroaryl wherein alkyl, aryl or heteroaryl groups of $R^7$ may be optionally substituted with one or more $R^5$ substituents; and n is chosen from 0 and 1.

In some embodiments, the compound is composed of formula (IV):

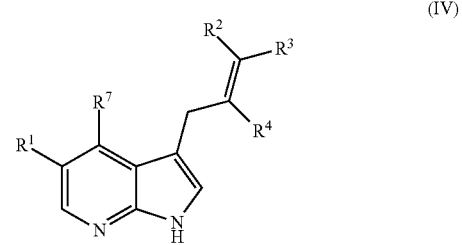

(IV)

wherein: $R^1$ is chosen from hydrogen, $C_{1-6}$ alkyl, $OC_{1-6}$ alkyl, $OC_{3-7}$ cycloalkyl, $C_{1-4}$ alkylamino, $NH_2$, $NHC_{1-6}$ alkyl, $N(C_{1-4}$ alkyl$)_2$, NHC(O)alkyl, NHC(O)aryl, NHC(O) heteroaryl, cyano, $C(O)NH_2$, $C(O)NHR^4$, $C(O)N(R^4)_2$, $C(O)C_{1-4}$ alkyl, trifluoromethyl, halo, aryl and heteroaryl wherein alkyl, aryl or heteroaryl groups of $R^1$ may be optionally substituted with one or more $R^5$ substituents; $R^2$ is chosen from hydrogen, F, alkyl, $C(O)R^4$, CN, $C(O)NH_2$, and $C(O)NHMe$; $R^3$ is chosen from $C(O)R^4$, CN, $C(O)NH_2$, $C(O)NHMe$, $C(O)$alkyl, $C(O)$alkylN$(R^4)_2$, $C(O)$alkylOR$^4$; or when $R^2$ is $C(O)R^4$, $C(O)NH_2$, $C(O)NHMe$, or CN, $R^3$ is chosen from hydrogen, F and Me; each $R^4$ is independently chosen from hydrogen, $C_{1-6}$ alkyl, and $C_{3-6}$ cycloalkyl; wherein each $R^4$ together with the atoms to which they are attached optionally form an heterocycloalkyl or heteroaryl ring, which may be optionally substituted with one or more $R^5$ substituents; each $R^5$ is independently chosen from $C_{1-4}$ alkyl, OH, $OC_{1-6}$ alkyl, $O(CH_2)_nC_{3-6}$ cycloalkyl, $C_{1-4}$ alkylamino, $NH_2$, $NHC_{1-6}$ alkyl, $NHC_{3-7}$ cycloalkyl $N(C_{1-4}$ alkyl$)_2$, NHC(O)alkyl, NHC(O)aryl, NHC(O)heteroaryl, cyano, $C(O)NH_2$, $C(O)NHR^4$, $C(O)N(R^4)_2$, $C(O)C_{1-4}$ alkyl, trifluoromethyl, halo, aryl, and heteroaryl wherein alkyl, aryl or heteroaryl groups of $R^5$ may be optionally substituted with $R^6$; each $R^6$ is independently chosen from halo, $CF_3$, OMe and CN; $R^7$ is chosen from hydrogen, $C_{1-6}$ alkyl, $OC_{1-6}$ alkyl, $OC_{3-7}$ cycloalkyl, $C_{1-4}$ alkylamino, $NHC_{1-6}$ alkyl, $NHC_{3-7}$ alkyl cyano, trifluoromethyl, halo, aryl and heteroaryl wherein alkyl, aryl or heteroaryl groups of $R^7$ may be optionally substituted with one or more $R^5$ substituents; and n is chosen from 0, 1, and 2.

In certain embodiments, $R^1$ is chosen from hydrogen, $C_{1-6}$ alkyl, $OC_{1-6}$ alkyl, $OC_{3-7}$ cycloalkyl, $C_{1-4}$ alkylamino, $NH_2$, $NHC_{1-6}$ alkyl, $N(C_{1-4}$ alkyl$)_2$, cyano, trifluoromethyl, halo, aryl and heteroaryl wherein alkyl, aryl or heteroaryl groups of $R^1$ may be optionally substituted with one or more $R^5$ substituents; $R^2$ is chosen from hydrogen, F, alkyl, $C(O)R^4$, CN, C(O)NH$_2$, and C(O)NHMe; R$^3$ is chosen from C(O)R$^4$, CN, C(O)NH$_2$, C(O)NHMe, C(O)alkyl, C(O)alkylN(R$^4$)$_2$, C(O)alkylOR$^4$; or when R$^2$ is C(O)R$^4$, C(O)NH$_2$, C(O)NHMe, or CN, R$^3$ is chosen from hydrogen, F and Me; each R$^4$ is independently chosen from hydrogen, C$_{1-6}$ alkyl, and C$_{3-6}$ cycloalkyl; wherein each R$^4$ together with the atoms to which they are attached optionally form an heterocycloalkyl or heteroaryl ring, which may be optionally substituted with one or more R$^5$ substituents; each R$^5$ is independently chosen from C$_{1-4}$ alkyl, OH, OC$_{1-6}$ alkyl, O(CH$_2$)$_n$C$_{3-6}$ cycloalkyl, C$_{1-4}$ alkylamino, NH$_2$, NHC$_{1-6}$ alkyl, NHC$_{3-7}$ cycloalkyl N(C$_{1-4}$ alkyl)$_2$, NHC(O)alkyl, NHC(O)aryl, NHC(O)heteroaryl, cyano, C(O)NH$_2$, C(O)NHR$^4$, C(O)N(R$^4$)$_2$, C(O)C$_{1-4}$ alkyl, trifluoromethyl, halo, aryl, and heteroaryl wherein alkyl, aryl or heteroaryl groups of R$^5$ may be optionally substituted with R$^6$; each R$^6$ is independently chosen from halo, CF$_3$, OMe and CN; R$^7$ is chosen from hydrogen, C$_{1-6}$ alkyl, OC$_{1-6}$ alkyl, OC$_{3-7}$ cycloalkyl, C$_{1-4}$ alkylamino, NHC$_{1-6}$ alkyl, NHC$_{3-7}$ alkyl cyano, trifluoromethyl, halo, aryl and heteroaryl wherein alkyl, aryl or heteroaryl groups of R$^7$ may be optionally substituted with one or more R$^5$ substituents; and n is chosen from 0, 1, and 2.

In certain embodiments, R$^1$ is chosen from hydrogen, OC$_{1-6}$ alkyl, OC$_{3-7}$ cycloalkyl, C$_{1-4}$ alkylamino, NHC$_{1-6}$ alkyl, cyano, trifluoromethyl, halo, aryl and heteroaryl wherein alkyl, aryl or heteroaryl groups of R$^1$ may be optionally substituted with one or more R$^5$ substituents; R$^2$ is chosen from hydrogen, F, alkyl, C(O)R$^4$, CN, C(O)NH$_2$, and C(O)NHMe; R$^3$ is chosen from C(O)R$^4$, CN, C(O)NH$_2$, C(O)alkyl, C(O)alkylOR$^4$; or when R$^2$ is C(O)R$^4$, C(O)NH$_2$, C(O)NHMe, or CN, R$^3$ is chosen from hydrogen, F and Me; each R$^4$ is independently chosen from hydrogen, C$_{1-6}$ alkyl, and C$_{3-6}$ cycloalkyl; wherein each R$^4$ together with the atoms to which they are attached optionally form an heterocycloalkyl or heteroaryl ring, which may be optionally substituted with one or more R$^5$ substituents; each R$^5$ is independently chosen from C$_{1-4}$ alkyl, OH, OC$_{1-6}$ alkyl, O(CH$_2$)$_n$C$_{3-6}$ cycloalkyl, C$_{1-4}$ alkylamino, NHC(O)aryl, NHC(O)heteroaryl, cyano, trifluoromethyl, halo, aryl, and heteroaryl wherein alkyl, aryl or heteroaryl groups of R$^5$ may be optionally substituted with R$^6$; each R$^6$ is independently chosen from halo, CF$_3$, OMe and CN; R$^7$ is chosen from hydrogen, C$_{1-6}$ alkyl, OC$_{1-6}$ alkyl, OC$_{3-7}$ cycloalkyl, C$_{1-4}$ alkylamino, NHC$_{1-6}$ alkyl, NHC$_{3-7}$ alkyl cyano, trifluoromethyl, halo, aryl and heteroaryl wherein alkyl, aryl or heteroaryl groups of R$^7$ may be optionally substituted with one or more R$^5$ substituents; and n is chosen from 0 and 1.

In some embodiments, the compound is composed of formula (V):

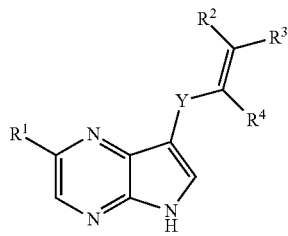

(V)

wherein: R$^1$ is chosen from hydrogen, C$_{1-6}$ alkyl, OC$_{1-6}$ alkyl, OC$_{3-7}$ cycloalkyl, C$_{1-4}$ alkylamino, NH$_2$, NHC$_{1-6}$ alkyl, N(C$_{1-4}$ alkyl)$_2$, NHC(O)alkyl, NHC(O)aryl, NHC(O) heteroaryl, cyano, C(O)NH$_2$, C(O)NHR$^4$, C(O)N(R$^4$)$_2$, C(O)C$_{1-4}$ alkyl, C(O)aryl, C(O)heteroaryl, CH$_2$aryl, CHFaryl, CH$_2$heteroaryl, CHFheteroaryl, trifluoromethyl, halo, aryl and heteroaryl wherein alkyl, heterocyclic, aryl or heteroaryl groups of R$^1$ may be optionally substituted with one or more R$^5$ substituents; R$^2$ is chosen from hydrogen, F, alkyl, C(O)R$^4$, CN, C(O)NH$_2$, and C(O)NHMe; R$^3$ is chosen from C(O)R$^4$, CN, C(O)NH$_2$, C(O)NHMe, C(O)alkyl, C(O)alkylN(R$^4$)$_2$, C(O)alkylOR$^4$; or when R$^2$ is C(O)R$^4$, C(O)NH$_2$, C(O)NHMe, or CN, R$^3$ is chosen from hydrogen, F and Me; each R$^4$ is independently chosen from hydrogen, C$_{1-6}$ alkyl, and C$_{3-6}$ cycloalkyl; wherein each R$^4$ together with the atoms to which they are attached optionally form an heterocycloalkyl or heteroaryl ring, which may be optionally substituted with one or more R$^5$ substituents; each R$^5$ is independently chosen from C$_{1-4}$ alkyl, OH, OC$_{1-6}$ alkyl, CH$_2$aryl, CH$_2$heteroaryl, O(CH$_2$)$_n$C$_{3-6}$ cycloalkyl, C$_{1-4}$ alkylamino, NHC$_{3-7}$ cycloalkyl N(C$_{1-4}$ alkyl)$_2$, N(R$^4$)$_2$, NHC(O)alkyl, NHC(O)aryl, NHC(O)heteroaryl, cyano, C(O)N(R$^4$)$_2$, C(O)C$_{1-4}$ alkyl, C(O)OC$_{1-6}$ alkyl, C(O)C$_{1-6}$ alkyl, C(O)C$_{3-7}$ cycloalkyl, C(O)aryl, C(O)heteroaryl, C(O)heterocycle, trifluoromethyl, halo, CN, S(O)$_2$Me, S(O)Me, SMe, aryl, and heteroaryl; wherein each alkyl, aryl, heteroaryl or heterocyclic group of R$^5$ may be optionally substituted with one or more R$^6$; each R$^6$ is independently chosen from halo, C$_{1-4}$ alkyl, C$_{3-6}$ cycloalkyl, CF$_3$, OH, OMe and CN; Y is chosen from a bond, CH$_2$, CHF, C(O), and NHC(O); and n is chosen from 0, 1, and 2.

In some embodiments, the compound is composed of formula (VI):

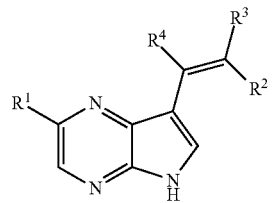

(VI)

wherein: R$^1$ is chosen from hydrogen, C$_{1-6}$ alkyl, OC$_{1-6}$ alkyl, OC$_{3-7}$ cycloalkyl, C$_{1-4}$ alkylamino, NH$_2$, NHC$_{1-6}$ alkyl, N(C$_{1-4}$ alkyl)$_2$, NHC(O)alkyl, NHC(O)aryl, NHC(O) heteroaryl, cyano, C(O)NH$_2$, C(O)NHR$^4$, C(O)N(R$^4$)$_2$, C(O)C$_{1-4}$ alkyl, C(O)aryl, C(O)heteroaryl, CH$_2$aryl, CHFaryl, CH$_2$heteroaryl, CHFheteroaryl, trifluoromethyl, halo, aryl and heteroaryl wherein alkyl, heterocyclic, aryl or heteroaryl groups of R$^1$ may be optionally substituted with one or more R$^5$ substituents; R$^2$ is chosen from hydrogen, F, alkyl, C(O)R$^4$, CN, C(O)NH$_2$, and C(O)NHMe; R$^3$ is chosen from C(O)R$^4$, CN, C(O)NH$_2$, C(O)NHMe, C(O)alkyl, C(O)alkylN(R$^4$)$_2$, C(O)alkylOR$^4$; or when R$^2$ is C(O)R$^4$, C(O)NH$_2$, C(O)NHMe, or CN, R$^3$ is chosen from hydrogen, F and Me; each R$^4$ is independently chosen from hydrogen, C$_{1-6}$ alkyl, and C$_{3-6}$ cycloalkyl; wherein each R$^4$ together with the atoms to which they are attached optionally form an heterocycloalkyl or heteroaryl ring, which may be optionally substituted with one or more R$^5$ substituents; each R$^5$ is independently chosen from C$_{1-4}$ alkyl, OH, OC$_{1-6}$ alkyl, CH$_2$aryl, CH$_2$heteroaryl, O(CH$_2$)$_n$C$_{3-6}$ cycloalkyl, C$_{1-4}$ alkylamino, NHC$_{3-7}$ cycloalkyl N(C$_{1-4}$ alkyl)$_2$, N(R$^4$)$_2$, NHC(O)alkyl, NHC(O)aryl, NHC(O)heteroaryl, cyano, C(O)N(R$^4$)$_2$, C(O)C$_{1-4}$ alkyl, C(O)OC$_{1-6}$ alkyl, C(O)C$_{1-6}$ alkyl, C(O)C$_{3-7}$ cycloalkyl, C(O)aryl, C(O)heteroaryl, C(O)

heterocycle, trifluoromethyl, halo, CN, $S(O)_2Me$, $S(O)Me$, SMe, aryl, and heteroaryl; wherein each alkyl, aryl, heteroaryl or heterocyclic group of $R^5$ may be optionally substituted with one or more $R^6$; each $R^6$ is independently chosen from halo, $C_{1-4}$ alkyl, $C_{3-6}$ cycloalkyl, $CF_3$, OH, OMe and CN; and n is chosen from 0, 1, and 2.

In certain embodiments, $R^1$ is chosen from hydrogen, $C_{1-6}$ alkyl, $OC_{1-6}$ alkyl, $OC_{3-7}$ cycloalkyl, $C_{1-4}$ alkylamino, $NH_2$, $NHC_{1-6}$ alkyl, $N(C_{1-4}$ alkyl$)_2$, NHC(O)alkyl, NHC(O)aryl, NHC(O)heteroaryl, cyano, $C(O)NH_2$, $C(O)NHR^4$, $C(O)N(R^4)_2$, $C(O)C_{1-4}$ alkyl, C(O)aryl, C(O)heteroaryl, $CH_2$aryl, CHFaryl, $CH_2$heteroaryl, CHFheteroaryl, trifluoromethyl, halo, aryl and heteroaryl wherein alkyl, heterocyclic, aryl or heteroaryl groups of $R^1$ may be optionally substituted with one or more $R^5$ substituents; $R^2$ is chosen from hydrogen, F, alkyl, $C(O)R^4$, CN, $C(O)NH_2$, and C(O)NHMe; $R^3$ is chosen from $C(O)R^4$, CN, $C(O)NH_2$, C(O)NHMe, C(O)alkyl, C(O)alkylN($R^4)_2$, C(O)alkylOR$^4$; or when $R^2$ is $C(O)R^4$, C(O)NH$_2$, C(O)NHMe, or CN, $R^3$ is chosen from hydrogen, F and Me; each $R^4$ is independently chosen from hydrogen, $C_{1-6}$ alkyl, and $C_{3-6}$ cycloalkyl; wherein each $R^4$ together with the atoms to which they are attached optionally form an heterocycloalkyl or heteroaryl ring, which may be optionally substituted with one or more $R^5$ substituents; each $R^5$ is independently chosen from $C_{1-4}$ alkyl, OH, $OC_{1-6}$ alkyl, $CH_2$aryl, $CH_2$heteroaryl, $O(CH_2)_nC_{3-6}$ cycloalkyl, $C_{1-4}$ alkylamino, $NHC_{3-7}$ cycloalkyl $N(C_{1-4}$ alkyl$)_2$, $N(R^4)_2$, NHC(O)alkyl, NHC(O)aryl, NHC(O)heteroaryl, cyano, $C(O)N(R^4)_2$, $C(O)C_{1-4}$ alkyl, $C(O)OC_{1-6}$ alkyl, $C(O)C_{1-6}$ alkyl, $C(O)C_{3-7}$ cycloalkyl, C(O)aryl, C(O)heteroaryl, C(O)heterocycle, trifluoromethyl, halo, CN, $S(O)_2Me$, S(O)Me, SMe, aryl, and heteroaryl; wherein each alkyl, aryl, heteroaryl or heterocyclic group of $R^5$ may be optionally substituted with one or more $R^6$; each $R^6$ is independently chosen from halo, $C_{1-4}$ alkyl, $C_{3-6}$ cycloalkyl, $CF_3$, OH, OMe and CN; and n is chosen from 0, 1, and 2.

In certain embodiments, $R^1$ is chosen from hydrogen, $OC_{1-6}$ alkyl, $OC_{3-7}$ cycloalkyl, $NHC_{1-6}$ alkyl, cyano, trifluoromethyl, halo, aryl and heteroaryl wherein alkyl, aryl or heteroaryl groups of $R^1$ may be optionally substituted with one or more $R^5$ substituents; $R^2$ is chosen from hydrogen, F, alkyl, $C(O)R^4$, CN, $C(O)NH_2$, and C(O)NHMe; $R^3$ is chosen from $C(O)R^4$, CN, $C(O)NH_2$, C(O)alkyl, C(O)alkylOR$^4$; or when $R^2$ is $C(O)R^4$, $C(O)NH_2$, C(O)NHMe, or CN, $R^3$ is chosen from hydrogen, F and Me; each $R^4$ is independently chosen from hydrogen, $C_{1-6}$ alkyl, and $C_{3-6}$ cycloalkyl; wherein each $R^4$ together with the atoms to which they are attached optionally form an heterocycloalkyl or heteroaryl ring, which may be optionally substituted with one or more $R^5$ substituents; each $R^5$ is independently chosen from $C_{1-4}$ alkyl, OH, $OC_{1-6}$ alkyl, $CH_2$aryl, $CH_2$heteroaryl, $O(CH_2)_n$ $C_{3-6}$ cycloalkyl, $C_{1-4}$ alkylamino, $NHC_{3-7}$ cycloalkyl $N(C_{1-4}$ alkyl$)_2$, $N(R^4)_2$, NHC(O)alkyl, NHC(O)aryl, NHC(O)heteroaryl, cyano, $C(O)N(R^4)_2$, $C(O)C_{1-4}$ alkyl, $C(O)OC_{1-6}$ alkyl, $C(O)C_{1-6}$ alkyl, $C(O)C_{3-7}$ cycloalkyl, C(O)aryl, C(O)heteroaryl, C(O)heterocycle, trifluoromethyl, halo, CN, $S(O)_2Me$, S(O)Me, SMe, aryl, and heteroaryl; wherein each alkyl, aryl, heteroaryl or heterocyclic group of $R^5$ may be optionally substituted with one or more $R^6$; each $R^6$ is independently chosen from halo, $C_{1-4}$ alkyl, $C_{3-6}$ cycloalkyl, $CF_3$, OH, OMe and CN; and n is chosen from 0 and 1.

In some embodiments, the compound is composed of formula (VII):

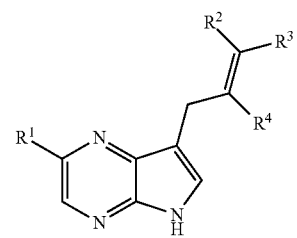

(VII)

wherein: $R^1$ is chosen from hydrogen, $C_{1-6}$ alkyl, $OC_{1-6}$ alkyl, $OC_{3-7}$ cycloalkyl, $C_{1-4}$ alkylamino, $NH_2$, $NHC_{1-6}$ alkyl, $N(C_{1-4}$ alkyl$)_2$, NHC(O)alkyl, NHC(O)aryl, NHC(O)heteroaryl, cyano, $C(O)NH_2$, $C(O)NHR^4$, $C(O)N(R^4)_2$, $C(O)C_{1-4}$ alkyl, trifluoromethyl, halo, aryl and heteroaryl wherein alkyl, aryl or heteroaryl groups of $R^1$ may be optionally substituted with one or more $R^5$ substituents; $R^2$ is chosen from hydrogen, F, alkyl, $C(O)R^4$, CN, $C(O)NH_2$, and C(O)NHMe; $R^3$ is chosen from $C(O)R^4$, CN, $C(O)NH_2$, C(O)NHMe, C(O)alkyl, C(O)alkylN($R^4)_2$, C(O)alkylOR$^4$; or when $R^2$ is $C(O)R^4$, $C(O)NH_2$, C(O)NHMe, or CN, $R^3$ is chosen from hydrogen, F and Me; each $R^4$ is independently chosen from hydrogen, $C_{1-6}$ alkyl, and $C_{3-6}$ cycloalkyl; wherein each $R^4$ together with the atoms to which they are attached optionally form an heterocycloalkyl or heteroaryl ring, which may be optionally substituted with one or more $R^5$ substituents; each $R^5$ is independently chosen from $C_{1-4}$ alkyl, OH, $OC_{1-6}$ alkyl, $O(CH_2)_nC_{3-6}$ cycloalkyl, $C_{1-4}$ alkylamino, $NH_2$, $NHC_{1-6}$ alkyl, $NHC_{3-7}$ cycloalkyl $N(C_{1-4}$ alkyl$)_2$, NHC(O)alkyl, NHC(O)aryl, NHC(O)heteroaryl, cyano, $C(O)NH_2$, $C(O)NHR^4$, $C(O)N(R^4)_2$, $C(O)C_{1-4}$ alkyl, trifluoromethyl, halo, aryl, and heteroaryl wherein alkyl, aryl or heteroaryl groups of $R^5$ may be optionally substituted with $R^6$; each $R^6$ is independently chosen from halo, $CF_3$, OMe and CN; and n is chosen from 0, 1, and 2.

In certain embodiments, $R^1$ is chosen from hydrogen, $C_{1-6}$ alkyl, $OC_{1-6}$ alkyl, $OC_{3-7}$ cycloalkyl, $C_{1-4}$ alkylamino, $NH_2$, $NHC_{1-6}$ alkyl, $N(C_{1-4}$ alkyl$)_2$, cyano, trifluoromethyl, halo, aryl and heteroaryl wherein alkyl, aryl or heteroaryl groups of $R^1$ may be optionally substituted with one or more $R^5$ substituents; $R^2$ is chosen from hydrogen, F, alkyl, $C(O)R^4$, CN, $C(O)NH_2$, and C(O)NHMe; $R^3$ is chosen from $C(O)R^4$, CN, $C(O)NH_2$, C(O)NHMe, C(O)alkyl, C(O)alkylN($R^4)_2$, C(O)alkylOR$^4$; or when $R^2$ is $C(O)R^4$, $C(O)NH_2$, C(O)NHMe, or CN, $R^3$ is chosen from hydrogen, F and Me; each $R^4$ is independently chosen from hydrogen, $C_{1-6}$ alkyl, and $C_{3-6}$ cycloalkyl; wherein each $R^4$ together with the atoms to which they are attached optionally form an heterocycloalkyl or heteroaryl ring, which may be optionally substituted with one or more $R^5$ substituents; each $R^5$ is independently chosen from $C_{1-4}$ alkyl, OH, $OC_{1-6}$ alkyl, $O(CH_2)_nC_{3-6}$ cycloalkyl, $C_{1-4}$ alkylamino, $NH_2$, $NHC_{1-6}$ alkyl, $NHC_{3-7}$ cycloalkyl $N(C_{1-4}$ alkyl$)_2$, NHC(O)alkyl, NHC(O)aryl, NHC(O)heteroaryl, cyano, $C(O)NH_2$, $C(O)NHR^4$, $C(O)N(R^4)_2$, $C(O)C_{1-4}$ alkyl, trifluoromethyl, halo, aryl, and heteroaryl wherein alkyl, aryl or heteroaryl groups of $R^5$ may be optionally substituted with $R^6$; each $R^6$ is independently chosen from halo, $CF_3$, OMe and CN; and n is chosen from 0, 1, and 2.

In certain embodiments, $R^1$ is chosen from hydrogen, $OC_{1-6}$ alkyl, $OC_{3-7}$ cycloalkyl, $C_{1-4}$ alkylamino, $NHC_{1-6}$ alkyl, cyano, trifluoromethyl, halo, aryl and heteroaryl wherein alkyl, aryl or heteroaryl groups of $R^1$ may be optionally substituted with one or more $R^5$ substituents; $R^2$ is chosen from hydrogen, F, alkyl, $C(O)R^4$, CN, $C(O)NH_2$, and C(O)

NHMe; $R^3$ is chosen from $C(O)R^4$, CN, $C(O)NH_2$, $C(O)$ alkyl, $C(O)$alkyl$OR^4$; or when $R^2$ is $C(O)R^4$, $C(O)NH_2$, $C(O)NHMe$, or CN, $R^3$ is chosen from hydrogen, F and Me; each $R^4$ is independently chosen from hydrogen, $C_{1-6}$ alkyl, and $C_{3-6}$ cycloalkyl; wherein each $R^4$ together with the atoms to which they are attached optionally form an heterocycloalkyl or heteroaryl ring, which may be optionally substituted with one or more $R^5$ substituents; each $R^5$ is independently chosen from $C_{1-4}$ alkyl, OH, $OC_{1-6}$ alkyl, $O(CH_2)_nC_{3-6}$ cycloalkyl, $C_{1-4}$ alkylamino, $NHC_{1-6}$ alkyl, $NHC_{3-7}$ cycloalkyl, NHC(O)aryl, NHC(O)heteroaryl, cyano, trifluoromethyl, halo, aryl, and heteroaryl wherein alkyl, aryl or heteroaryl groups of $R^5$ may be optionally substituted with $R^6$; each $R^6$ is independently chosen from halo, $CF_3$, OMe and CN; and n is chosen from 0 and 1. In particular embodiments, the compound is selected from the group consisting of Examples 1-18.

Also provided are embodiments wherein any of embodiment above may be combined with any one or more of these embodiments, provided the combination is not mutually exclusive.

Pharmaceutical Compositions

For treatment of the conditions referred to above, the compounds described herein can be administered as follows:

Oral Administration

The compounds of the present invention may be administered orally, including swallowing, so the compound enters the gastrointestinal tract, or is absorbed into the blood stream directly from the mouth, including sublingual or buccal administration.

Suitable compositions for oral administration include solid formulations such as tablets, pills, cachets, lozenges and hard or soft capsules, which can contain liquids, gels, or powders.

In a tablet dosage form the amount of drug present may be from about 0.05% to about 95% by weight, more typically from about 2% to about 50% by weight of the dosage form.

In addition, tablets may contain a disintegrant, comprising from about 0.5% to about 35% by weight, more typically from about 2% to about 25% of the dosage form. Examples of disintegrants include methyl cellulose, sodium or calcium carboxymethyl cellulose, croscarmellose sodium, polyvinylpyrrolidone, hydroxypropyl cellulose, starch and the like.

Suitable binders, for use in a tablet, include gelatin, polyethylene glycol, sugars, gums, starch, hydroxypropyl cellulose and the like. Suitable diluents, for use in a tablet, include mannitol, xylitol, lactose, dextrose, sucrose, sorbitol and starch.

Suitable surface active agents and glidants, for use in a tablet, may be present in amounts from about 0.1% to about 3% by weight, and include polysorbate 80, sodium dodecyl sulfate, talc and silicon dioxide.

Suitable lubricants, for use in a tablet, may be present in amounts from about 0.1% to about 5% by weight, and include calcium, zinc or magnesium stearate, sodium stearyl fumarate and the like.

Liquid formulations can include emulsions, solutions, syrups, elixirs and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

Compositions for oral administration may be formulated as immediate or modified release, including delayed or sustained release, optionally with enteric coating.

In another embodiment, a pharmaceutical composition comprises a therapeutically effective amount of a compound of Formula (I) or a pharmaceutically acceptable salt thereof, and a pharmaceutically acceptable carrier.

Parenteral Administration

Compounds of the present invention may be administered directly into the blood stream, muscle, or internal organs. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods.

Most parenteral formulations are aqueous solutions containing excipients, including salts, buffering agents and carbohydrates.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions.

Compositions for parenteral administration may be formulated as immediate or modified release, including delayed or sustained release.

Topical Administration

Compounds of the present invention may be administered topically to the skin or transdermally. Formulations for topical administration can include, but are not limited to, lotions, solutions, creams, gels, hydrogels, ointments, foams, implants, patches and the like. Carriers that are pharmaceutically acceptable for topical administration formulations can include water, alcohol, mineral oil, glycerin, polyethylene glycol and the like. Topical administration can also be performed by, for example, electroporation, iontophoresis, phonophoresis and the like.

Compositions for topical administration may be formulated as immediate or modified release, including delayed or sustained release.

Rectal Administration

Suppositories for rectal administration of the compounds of the present invention can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

Other carrier materials and modes of administration known in the pharmaceutical art may also be used. Pharmaceutical compositions of the invention may be prepared by any of the well-known techniques of pharmacy, such as effective formulation and administration procedures. The above considerations concerning effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman, et al., Eds., Pharmaceutical Dosage Forms, Marcel Decker, New York, N.Y., 1980; and Kibbe, et al., Eds., Handbook of Pharmaceutical Excipients ($3^{rd}$ Ed.), American Pharmaceutical Association, Washington, 1999.

Methods of Treatment

The present disclosure provides compounds and pharmaceutical compositions that modulate kinase activity, particularly TAK activity and are thus useful in the treatment or prevention of disorders associated with TAK. Compounds and pharmaceutical compositions of the present disclosure selectively modulate TAK and are thus useful in the treatment or prevention of a range of disorders associated with the activation of TAK include, but are not limited to, autoimmune disorders, chronic inflammatory disorders, acute inflammatory disorders, auto-inflammatory disorders, pain, cancer, neoplasia, pancreatic cancer, breast cancer, lung cancer, colorectal cancer, inflammatory disorders, allergic disorders and other diseases and disorders associated with TAK.

In particular, the compounds of the present disclosure may be used to prevent or treat pancreatic cancer, non-Hodgkin's lymphoma, chronic lymphocytic leukemia, multiple myeloma, T-cell leukemia and tumors of the head and neck, breast, colon, prostate, lung, skin, liver and ovary.

In some embodiments, methods described herein are used to treat a disease condition comprising administering to a subject in need thereof a therapeutically effective amount of a compound of Formula I or II or pharmaceutically acceptable salt thereof, wherein the condition is pancreatic cancer.

In some embodiments the methods described herein are used to treat patients with disorders arising from activation of p38, JNK or NF-κB signaling pathways.

In some embodiments, the methods described herein are used to treat a patient in need thereof suffering from inflammatory disorders, allergic disorders, autoinflammatory disorders and autoimmune disorders. Examples of disorders include, but are not limited to rheumatoid arthritis, juvenile idiopathic arthritis, psoriatic arthritis, psoriasis, type 2 diabetes, Bechet's disease, chronic gout, cryopyrin associated periodic syndromes, familial Mediterranean fever, neonatal onset multisystem inflammatory disease, ankylosing spondylitis, contact hypersensitivity, chronic obstructive pulmonary disorder, multiple sclerosis and inflammatory bowel disease.

In some embodiments, the methods described herein can be used to treat a patient in need thereof and suffering from neoplasia. Examples of these conditions include but are not limited to the following:

| | | |
|---|---|---|
| acral lentiginous melanoma | fibrolamellar carcinoma | neuroepithelial adenocarcinoma nodular melanoma |
| actinic keratoses | focal nodular hyperplasia | oat cell carcinoma |
| adenocarcinoma | gastrinoma | oligodendroglial |
| adenoid cycstic carcinoma | germ cell tumors | osteosarcoma |
| adenomas | glioblastoma | pancreatic cancer |
| adenosarcoma | glucagonoma | papillary serous adenocarcinoma |
| adenosquamous carcinoma | hemangiblastomas | pineal cell |
| astrocytic tumors | hemangioendothelioma | pituitary tumors |
| bartholin gland carcinoma | hemangiomas | plasmacytoma |
| basal cell carcinoma | hepatic adenoma | pseudosarcoma |
| bronchial gland carcinomas | hepatic adenomatosis | pulmonary blastoma |
| capillary | hepatocellular carcinoma | renal cell carcinoma |
| carcinoids | insulinoma | retinoblastoma |
| carcinoma | intaepithelial neoplasia | rhabdomyosarcoma |
| carcinosarcoma | interepithelial squamous cell neoplasia | sarcoma |
| cavernous | invasive squamous cell carcinoma | serous carcinoma |
| cholangiocarcinoma | large cell carcinoma | small cell carcinoma |
| chondosarcoma | leiomyosarcoma | soft tissue carcinomas |
| choriod plexus papilloma/carcinoma | lentigo maligna melanomas | somatostatin-secreting tumor |
| clear cell carcinoma | malignant melanoma | squamous carcinoma |
| cystadenoma | malignant mesothelial tumors | squamous cell carcinoma |
| endodermal sinus tumor | medulloblastoma | submesothelial |
| endometrial hyperplasia | medulloepithelioma | superficial spreading melanoma |
| endometrial stromal sarcoma | melanoma | undifferentiatied carcinoma |
| endometrioid adenocarcinoma | meningeal | uveal melanoma |
| ependymal | mesothelial | verrucous carcinoma |
| epitheloid | metastatic carcinoma | vipoma |
| Ewing's sarcoma | mucoepidermoid carcinoma | well differentiated carcinoma |
| familial adenomatous polyposis (FAP) | neuroblastoma | Wilm's tumor |

In some embodiments, methods described herein are used to treat a disease condition comprising administering to a subject in need thereof a therapeutically effective amount of a compound of Formula I or II or pharmaceutically acceptable salt thereof, wherein the condition is cancer which has developed resistance to chemotherapeutic drugs and/or ionizing radiation.

In some embodiments the methods described herein are used to treat patients with disorders arising from a dysregulated TAK1 molecule or dysregulated activation of TAK1 or related signaling transduction molecules. Examples of TAK1 signaling molecules include TAB1, TAB2, IRAK1, IRAK4, TRAF-6 and IL-6.

Combinations and Combination Therapy

The compounds of the present invention can be used, alone or in combination with other pharmaceutically active compounds, to treat conditions such as those previously described hereinabove. The compound(s) of the present invention and other pharmaceutically active compound(s) can be administered simultaneously (either in the same dosage form or in separate dosage forms) or sequentially. Accordingly, in one embodiment, the present invention comprises methods for treating a condition by administering to the subject a therapeutically-effective amount of one or more compounds of the present invention and one or more additional pharmaceutically active compounds.

In another embodiment, there is provided a pharmaceutical composition comprising one or more compounds of the present invention, one or more additional pharmaceutically active compounds, and a pharmaceutically acceptable carrier.

In another embodiment, the one or more additional pharmaceutically active compounds is selected from the group consisting of anti-cancer drugs, anti-proliferative drugs, and anti-inflammatory drugs.

TAK1 inhibitor compositions described herein are also optionally used in combination with other therapeutic reagents that are selected for their therapeutic value for the condition to be treated. In general, the compounds described herein and, in embodiments where combination therapy is employed, other agents do not have to be administered in the same pharmaceutical composition and, because of different physical and chemical characteristics, are optionally administered by different routes. The initial administration is generally made according to established protocols and then, based upon the observed effects, the dosage, modes of administration and times of administration subsequently modified. In certain instances, it is appropriate to administer a TAK1 inhibitor compound, as described herein, in combination with another therapeutic agent. By way of example only, the therapeutic effectiveness of a TAK1 inhibitor is enhanced by administration of another therapeutic agent (which also includes a therapeutic regimen) that also has therapeutic benefit. Regardless of the disease, disorder or condition being treated, the overall benefit experienced by the patient is either simply additive of the two therapeutic agents or the patient experiences an enhanced benefit.

Therapeutically effective dosages vary when the drugs are used in treatment combinations. Methods for experimentally determining therapeutically effective dosages of drugs and other agents for use in combination treatment regimens are documented methodologies. Combination treatment further includes periodic treatments that start and stop at various times to assist with the clinical management of the patient. In any case, the multiple therapeutic agents (one of which is a TAK1 inhibitor as described herein) are administered in any order, or even simultaneously. If simultaneously, the multiple therapeutic agents are optionally provided in a single, unified form, or in multiple forms (by way of example only, either as a single pill or as two separate pills).

In some embodiments, one of the therapeutic agents is given in multiple doses, or both are given as multiple doses. If not simultaneous, the timing between the multiple doses optionally varies from more than zero weeks to less than twelve weeks.

In addition, the combination methods, compositions and formulations are not to be limited to the use of only two agents, the use of multiple therapeutic combinations are also envisioned. It is understood that the dosage regimen to treat, prevent, or ameliorate the condition(s) for which relief is sought, is optionally modified in accordance with a variety of factors. These factors include the disorder from which the subject suffers, as well as the age, weight, sex, diet, and medical condition of the subject. Thus, the dosage regimen actually employed varies widely, in some embodiments, and therefore deviates from the dosage regimens set forth herein.

The pharmaceutical agents which make up the combination therapy disclosed herein are optionally a combined dosage form or in separate dosage forms intended for substantially simultaneous administration. The pharmaceutical agents that make up the combination therapy are optionally also administered sequentially, with either agent being administered by a regimen calling for two-step administration. The two-step administration regimen optionally calls for sequential administration of the active agents or spaced-apart administration of the separate active agents. The time between the multiple administration steps ranges from a few minutes to several hours, depending upon the properties of each pharmaceutical agent, such as potency, solubility, bioavailability, plasma half-life and kinetic profile of the pharmaceutical agent.

In another embodiment, a TAK1 inhibitor is optionally used in combination with procedures that provide additional benefit to the patient. A TAK1 inhibitor and any additional therapies are optionally administered before, during or after the occurrence of a disease or condition, and the timing of administering the composition containing a TAK1 inhibitor varies in some embodiments. Thus, for example, a TAK1 inhibitor is used as a prophylactic and is administered continuously to subjects with a propensity to develop conditions or diseases in order to prevent the occurrence of the disease or condition. A TAK1 inhibitor and compositions are optionally administered to a subject during or as soon as possible after the onset of the symptoms. While embodiments of the present invention have been shown and described herein, it will be obvious to those skilled in the art that such embodiments are provided by way of example only. Numerous variations, changes, and substitutions will now occur to those skilled in the art without departing from the invention. It should be understood that in some embodiments of the invention various alternatives to the embodiments described herein are employed in practicing the invention.

A TAK1 inhibitor can be used in combination with anti-cancer drugs, including but not limited to the following classes: alkylating agents, anti-metabolites, plant alkaloids and terpenoids, topoisomerase inhibitors, cytotoxic antibiotics, angiogenesis inhibitors and tyrosine kinase inhibitors.

For use in cancer and neoplastic diseases a TAK1 inhibitor may be optimally used together with one or more of the following non-limiting examples of anti-cancer agents: (1) alkylating agents, including but not limited to cisplatin (PLATIN), carboplatin (PARAPLATIN), oxaliplatin (ELOXATIN), streptozocin (ZANOSAR), busulfan (MYLERAN) and cyclophosphamide (ENDOXAN); (2) anti-metabolites, including but not limited to mercaptopurine (PURINETHOL), thioguanine, pentostatin (NIPENT), cytosine arabinoside (ARA-C), gemcitabine (GEMZAR), fluorouracil (CARAC), leucovorin (FUSILEV) and methotrexate (RHEUMATREX); (3) plant alkaloids and terpenoids, including but not limited to vincristine (ONCOVIN), vinblastine and paclitaxel (TAXOL); (4) topoisomerase inhibitors, including but not limited to irinotecan (CAMPTOSAR), topotecan (HYCAMTIN) and etoposide (EPOSIN); (5) cytotoxic antibiotics, including but not limited to actinomycin D (COSMEGEN), doxorubicin (ADRIAMYCIN), bleomycin (BLENOXANE) and mitomycin (MITOSOL); (6) angiogenesis inhibitors, including but not limited to sunitinib (SUTENT) and bevacizumab (AVASTIN); and (7) tyrosine kinase inhibitors, including but not limited to imatinib (GLEEVEC), erlotinib (TARCEVA), lapatininb (TYKERB) and axitinib (INLYTA).

Where a subject is suffering from or at risk of suffering from an inflammatory condition, a TAK1 inhibitor compound described herein is optionally used together with one or more agents or methods for treating an inflammatory condition in any combination. Therapeutic agents/treatments for treating an autoimmune and/or inflammatory condition include, but are not limited to any of the following examples: (1) corticosteroids, including but not limited to cortisone, dexamethasone, and methylprednisolone; (2) non-steroidal anti-inflammatory drugs (NSAIDs), including but not limited to ibuprofen, naproxen, acetaminophen, aspirin, fenoprofen (NALFON), flurbiprofen (ANSAID), ketoprofen, oxaprozin (DAYPRO), diclofenac sodium (VOLTAREN), diclofenac potassium (CATAFLAM), etodolac (LODINE), indomethacin (INDOCIN), ketorolac (TORADOL), sulindac (CLINORIL), tolmetin (TOLECTIN), meclofenamate (MECLOMEN), mefenamic acid (PONSTEL), nabumetone (RELAFEN) and piroxicam (FELDENE); (3) immunosuppressants, including but not limited to methotrexate (RHEUMATREX), leflunomide (ARAVA), azathioprine (IMURAN), cyclosporine (NEORAL, SANDIMMUNE), tacrolimus and cyclophosphamide (CYTOXAN); (4) CD20 blockers, including but not limited to rituximab (RITUXAN); (5) Tumor Necrosis Factor (TNF) blockers, including but not limited to etanercept (ENBREL), infliximab (REMICADE) and adalimumab (HUMIRA); (6) interleukin-1 receptor antagonists, including but not limited to anakinra (KINERET); (7) interleukin-6 inhibitors, including but not limited to tocilizumab (ACTEMRA); (8) interleukin-17 inhibitors, including but not limited to AIN457; (9) Janus kinase inhibitors, including but not limited to tasocitinib; and (10) syk inhibitors, including but not limited to fostamatinib.

General Synthetic Methods for Preparing Compounds

Compounds of the present invention can be prepared using methods illustrated in general synthetic schemes and experimental procedures detailed below. General synthetic schemes and experimental procedures are presented for purposes of illustration and are not intended to be limiting. Starting materials used to prepare compounds of the present invention are commercially available or can be prepared using routine methods known in the art. Representative procedures for the preparation of compounds of the invention are outlined in Schemes 1-7 below. Solvents and reagents, whose synthetic preparations are not described below, can be purchased at Sigma-Aldrich or Fisher Scientific.

Scheme 1 highlights the synthesis of the 5-substituted pyrrolopyridines or 5-substituted pyrrolopyrazines with a vinyl substituent directly attached to the heterocycle at the 3-position. Reaction halo 1a with an amine or alcohol $R^1$ substituent in the presence of a base such as KOH in DMSO provides 1b. Alternatively, the formation of 1b can occur by the reaction of commercially available 1c (Z=OH or $NH_2$) with the desired sulfonate or halide of $R^{100}$ in the presence of a base such as potassium carbonate in acetonitrile or DMF. Intermediate 1b may be also prepared using a tosyl protecting group to facilitate the nucleophilic addition. Protection of commercially available 1a as the desired tosylate occurs by treating 1a with sodium hydride followed by toluene sulfony chloride in THF to give 1d. Reaction of 1d with the desired alcohol or amine under palladium-catalyzed coupline conditions using $Pd_2(dba)_3$ or other similar catalysts and BINAP or other chelating ligands in dioxane provides 1e. Deprotection using lithium hydroxide or cesium carbonate in a solvent such as THF or ethanol provides 1b. Aryl analogs of 1b ($R^{100}$=Aryl) may be prepared by the reaction of 1a with an aryl or heteroaryl boronic acid using a palladium catalyst under Suzuki conditions. Iodination of 1b with a halogenating agent such as NIS furnishes 1f. Protection of the indole nitrogen on 1f using tosyl chloride and sodium hydride in a solvent such as THF or DMF provides 1g. Heck coupling of 1g with the desired acrylate in the presence of a palladium catalyst in DMF gives 1h. The desired final compounds may then be obtained by deprotecting 1h using a base such as lithium hydroxide in water to give 1i. In certain cases $R^8$ may be manipulated to a different substituent following methods common to those skilled in the art. This could be the hydrolysis of an ester to a carboxylic acid and subsequent formation of an amide before the final deprotection.

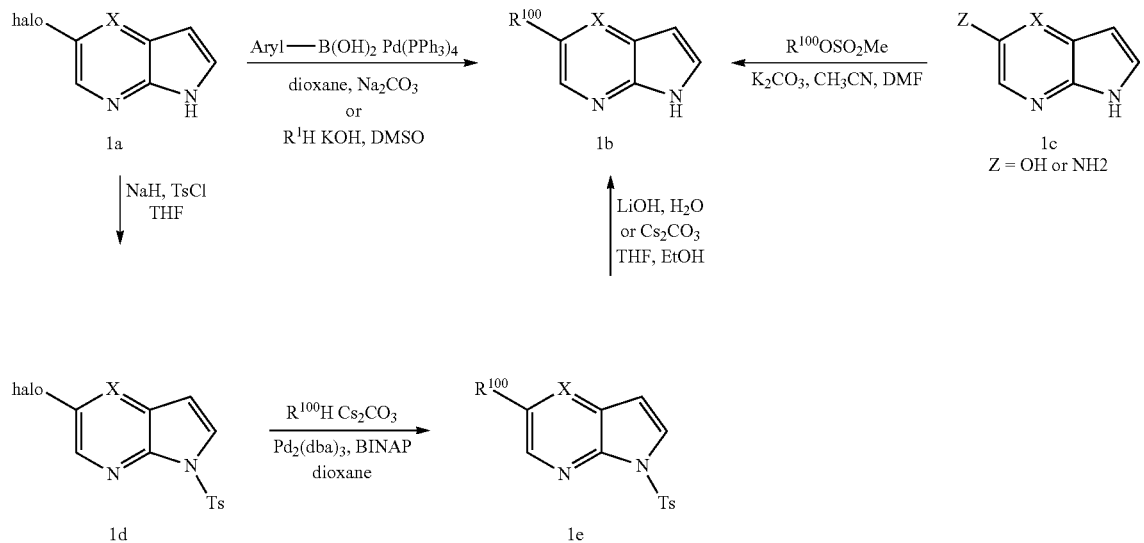

Scheme 1. Preparation of Alkenyl Substituted Pyrrolopyridines and Pyrrolopyrazines -continued

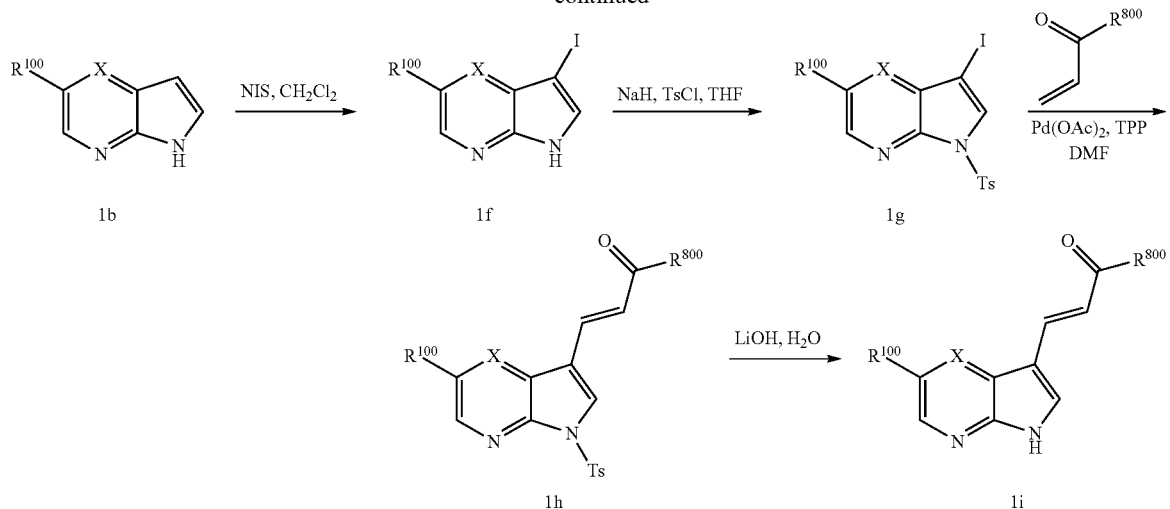

Scheme 2 highlights the synthesis of the 5-substituted pyrrolopyridines or pyrrolopyrazines with an allyl substituent directly attached to the heterocycle at the 3-position. Reaction of 1g under Heck conditions with allyltributyl tin in the presence of a palladium catalyst such as tetrakis (triphenylphospine)palladium(0) in toluene provides 2a. Allyl 2a is reacted with the desired alkene in the presence of a Grubbs catalyst in dichloromethane, which furnishes 2b. The desired final compounds may then be obtained by deprotecting 2b using a base such as lithium hydroxide in water to give 2c.

Scheme 2. Preparation of Allyl Substituted Pyrrolopyridines and Pyrrolopyrazines

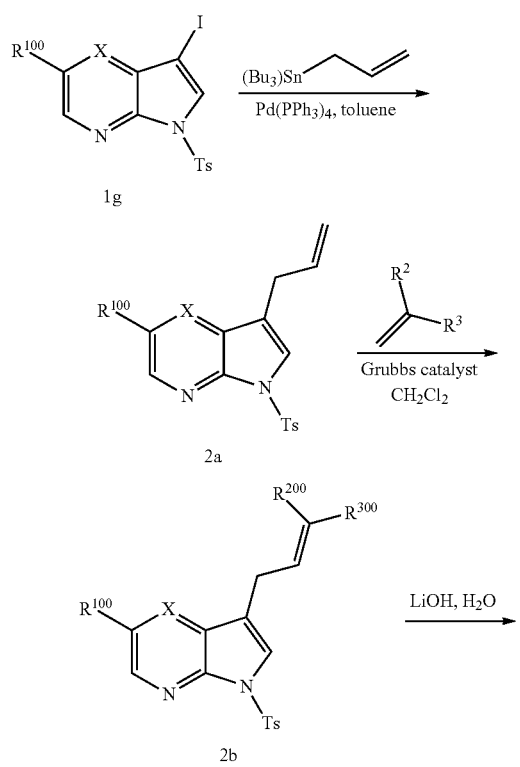

-continued

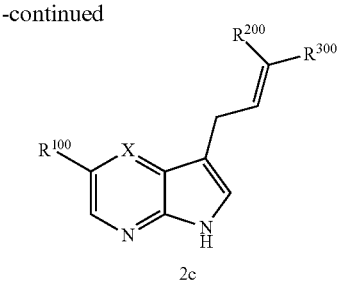

Scheme 3 highlights the synthesis of the 4-substituted pyrrolopyridines with a vinyl substituent directly attached to the heterocycle at the 3-position. Reaction halo 3a with an amine or alcohol $R^7$ substituent in the presence of a base such as KOH in DMSO provides 3b. Alternatively, the formation of 3b can occur by the reaction of commercially available 3c (Z=OH or $NH_2$) with the desired sulfonate or halide of $R^{100}$ in the presence of a base such as potassium carbonate in acetonitrile or DMF. Aryl analogs of 3b ($R^{700}$=Aryl) may be prepared by the reaction of 3a with an aryl or heteroaryl boronic acid using a palladium catalyst under Suzuki conditions. Iodination of 3b with a halogenating agent such as NIS furnishes 3d. Protection of the indole nitrogen on 3d using tosyl chloride and sodium hydride in a solvent such as THF or DMF provides 3e. Heck coupling of 3e with the desired acrylate in the presence of a palladium catalyst in DMF gives 3f. The desired final compounds may then be obtained by deprotecting 3f using a base such as lithium hydroxide in water to give 3g. The tosyl group of 3f may also be removed under acidic conditions or with tetrabutyl ammonium fluoride in THF to give 3g. In certain cases $R^8$ may be manipulated to a different substituent following methods common to those skilled in the art. This could be the hydrolysis of an ester to a carboxylic acid and subsequent formation of an amide before the final deprotection.

Scheme 3. Preparation of Alkenyl Substituted Pyrrolopyridines

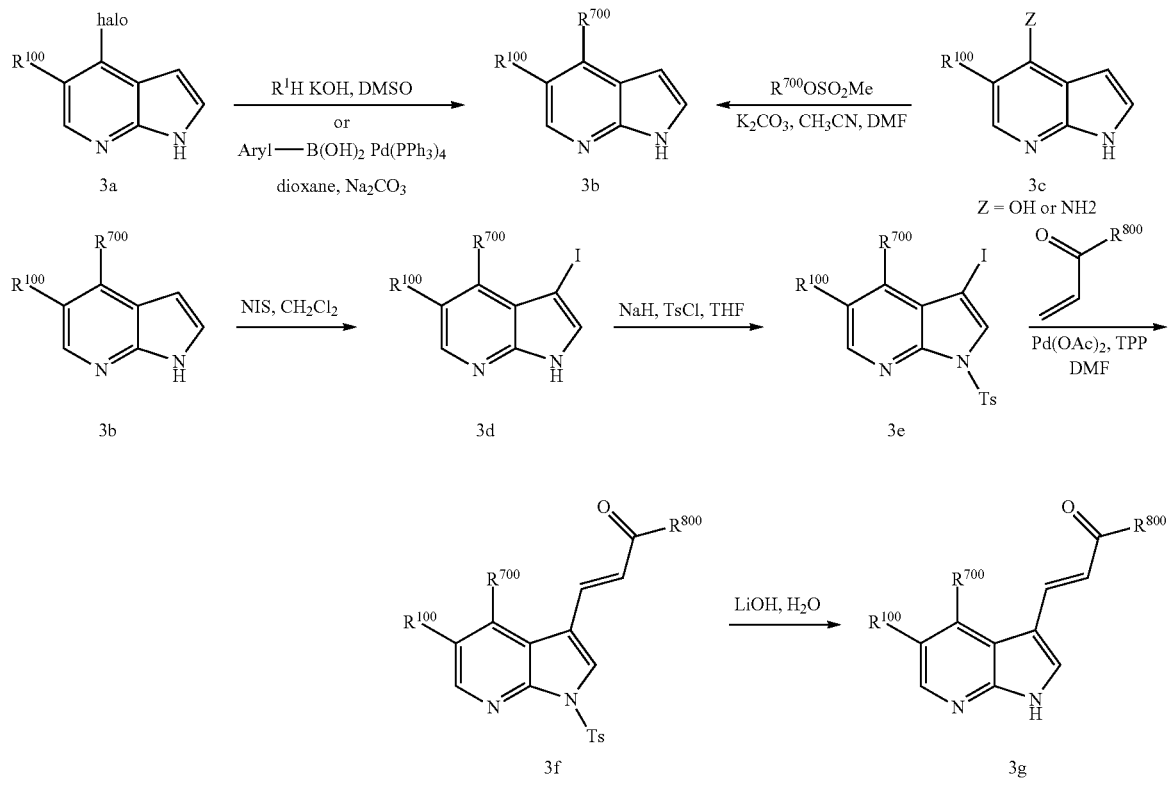

Scheme 4 highlights the synthesis of the 4-substituted pyrrolopyridines with an allyl substituent directly attached to the heterocycle at the 3-position. Reaction of 3e under Heck conditions with allyltributyl tin in the presence of a palladium catalyst in toluene provides 4a. Allyl 4a is reacted with the desired alkene in the presence of a Grubbs catalyst in dichloromethane, which furnishes 4b. The desired final compounds may then be obtained by deprotecting 4b using a base such as lithium hydroxide in water to give 4c.

Scheme 4. Preparation of Allyl Substituted Pyrrolopyridines

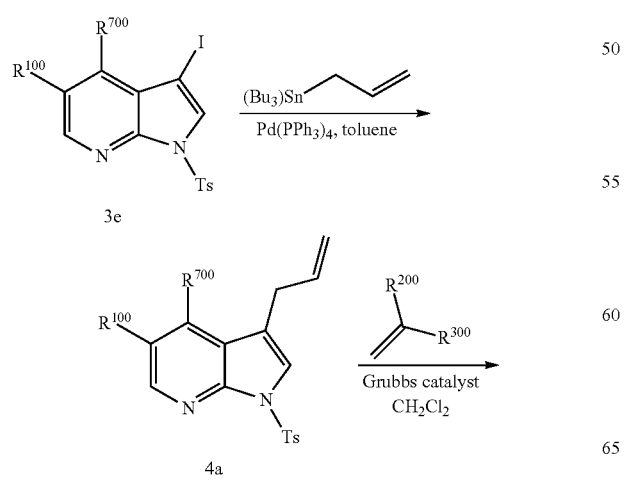

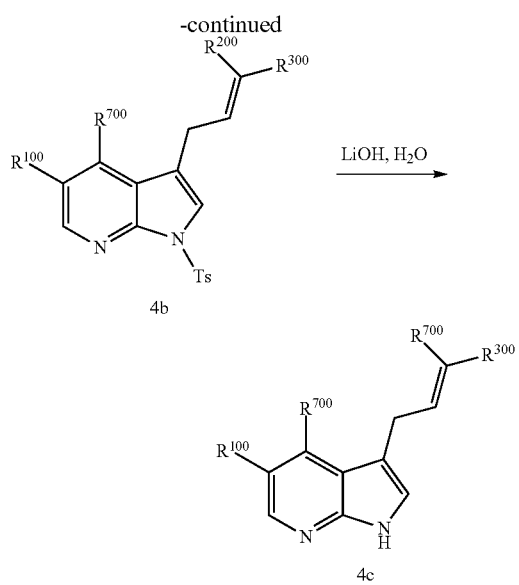

Scheme 5 highlights the synthesis of substituted pyrrolopyridines or pyrrolopyrazines with an unsaturated carbonyl substituent directly attached to the heterocycle at the 3-position. Reaction of 1a with the desired carboxylic acid halide in the presence of a Lewis acid catalyst such as aluminum chloride in dichloromethane provides 5a after workup.

Scheme 5. Preparation of Carbonyl Substituted Pyrrolopyridines and Pyrrolopyrazines

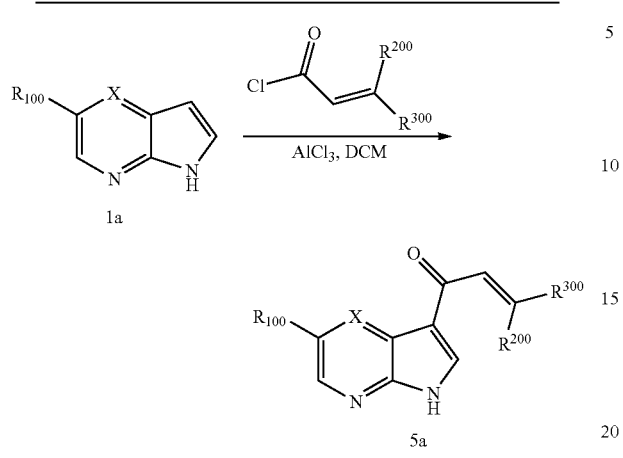

Scheme 6 highlights the synthesis of substituted pyrrolopyridines or pyrrolopyrazines with an amide substituent directly attached to the heterocycle at the 3-position. Reaction of commercially available 6a with the desired acid halide in a solvent such as methylene chloride in the presence of a base such as diisopropylethylamine provides 6b. Alternatively, the appropriate carboxcylic acid may be reacted with 6a under standard amide coupling conditions such as HATU in DMF to give 6b.

Scheme 6. Preparation of 3-Amido Substituted Pyrrolopyridines and Pyrrolopyrazines

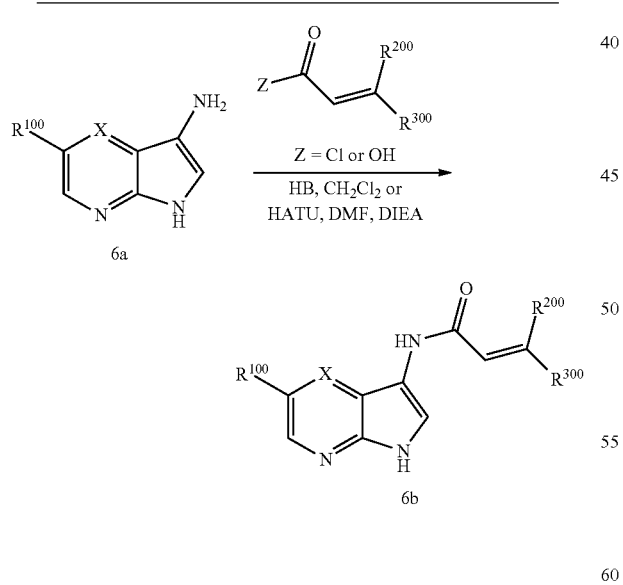

Scheme 7 highlights the synthesis of substituted pyrrolopyridines or pyrrolopyrazines with an unsaturated nitrile substituent attached to the heterocycle at the 3-position. Reaction of commercially available 7a with the desired malonylnitrile reagent in THF in the presence of a base such as piperidine provides 7b.

Scheme 7. Preparation of 3-Vinylnitrile Substituted Pyrrolopyridines and Pyrrolopyrazines

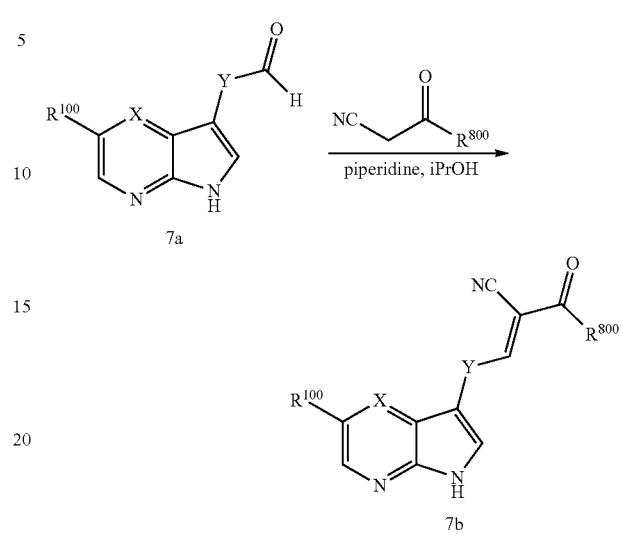

EXAMPLES

The invention is further illustrated by the following examples.

Example 1

3-(5-Phenyl-1H-pyrrolo[2,3-b]pyridin-3-yl)-acrylamide

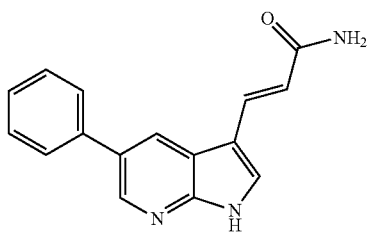 [SMILES: NC(=O)/C=C/c1c[nH]c2ncc(-c3ccccc3)cc12]

Step 1: 5-Phenyl-1H-pyrrolo[2,3-b]pyridine

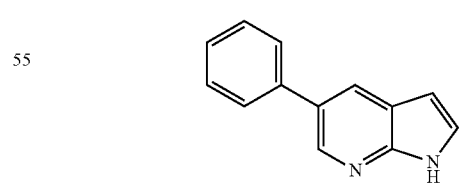

To a solution of 5-bromo-1H-pyrrolo[2,3-b]pyridine (196 mg, 1.0 mmol) in dioxane (7 mL) and water (3 mL) was added phenylboronic acid (146 mg, 1.2 mmol), potassium carbonate (414 mg, 3.0 mmol) and [1,1'-Bis(diphenylphosphino)ferrocene]dichloropalladium(II) (36 mg, 0.05 mmol). The mixture was treated to microwave radiation at 120° C.

for 30 minutes. The resulting solution was partitioned between ethyl acetate and water and filtered through celite. The filtrate layers were separated and the organic layer was washed with water and brine and dried over magnesium sulfate. The solution was filtered and concentrated in vacuo. The crude material was purified using normal phase chromatography (ethyl acetate/heptane) to provide the desired material as a white solid (125 mg, 64% yield): MS (ES) m/z 195 (M+H).

Step 2: 3-Iodo-5-phenyl-1H-pyrrolo[2,3-b]pyridine

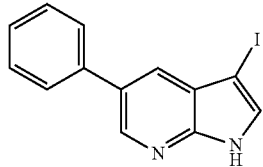 [SMILES: Ic1c[nH]c2ncc(-c3ccccc3)cc12]

To a solution of the compound of 5-phenyl-1H-pyrrolo[2,3-b]pyridine (step 1, 125 mg, 0.64 mmol) in dichloromethane (3 mL) was added N-iodosuccinimide (145 mg, 0.64 mmol) and the solution was stirred for two hours at ambient temperature. The reaction was quenched with water and the layers were separated. The organic layer was washed with water and brine and dried over magnesium sulfate. The solution was concentrated in vacuo to provide the iodo compound as a red semi-solid and used without further purification: MS (ES) m/z 321 (M+H).

Step 3: 3-Iodo-5-phenyl-1-(toluene-4-sulfonyl)-1H-pyrrolo[2,3-b]pyridine

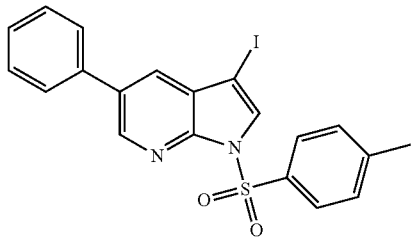 [SMILES: Cc1ccc(S(=O)(=O)n2cc(I)c3cc(-c4ccccc4)cnc32)cc1]

To a cooled solution of 3-iodo-5-phenyl-1H-pyrrolo[2,3-b]pyridine (step 2, 0.64 mmol) in tetrahydrofuran (3 mL) was added sodium hydride, 60% (23 mg, 0.96 mmol) followed by p-toluenesulfonyl chloride (122 mg, 0.64 mmol). The solution was stirred for 18 hours at ambient temperature. The reaction was quenched with water and extracted with ethyl acetate. The organic layer was washed with water and brine and dried over magnesium sulfate. The solution was filtered and concentrated in vacuo. The crude material was purified using normal phase chromatography (ethyl acetate/heptane) to provide the tosylated compound as a tan solid (191 mg, 63% yield): MS (ES) m/z 475 (M+H).

Step 4: 3-[5-Pyridin-2-yl-1-(toluene-4-sulfonyl)-1H-pyrrolo[2,3-b]pyridin-3-yl]-acrylamide

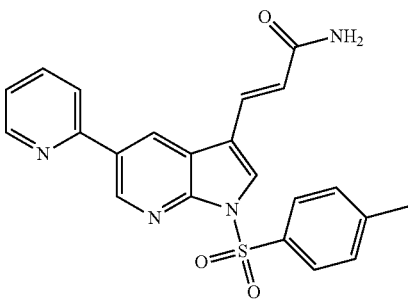 [SMILES: Cc1ccc(S(=O)(=O)n2cc(/C=C/C(N)=O)c3cc(-c4ccccn4)cnc32)cc1]

A solution of 3-iodo-5-phenyl-1-(toluene-4-sulfonyl)-1H-pyrrolo[2,3-b]pyridine (step 3, 191 mg, 0.40 mmol), acrylamide (142 mg, 2.0 mmol), tri(o-tolyl)phosphine (49 mg, 0.16 mmol), palladium(II) acetate (9 mg, 0.04 mmol) and triethylamine (0.17 mL, 1.2 mmol) in N,N-dimethylformamide (2 mL) was treated with microwave radiation at 150° C. for 30 minutes. The reaction was partitioned between ethyl acetate and water. The organic layer was washed with water and brine and dried over magnesium sulfate. The solution was filtered and concentrated in vacuo. The crude material was purified using normal phase chromatography (ethyl acetate/heptane) to provide the acrylamide as a colorless oil (96 mg, 57%): MS (ES) m/z 418 (M+H).

Step 5: 3-(5-Phenyl-1H-pyrrolo[2,3-b]pyridin-3-yl)-acrylamide

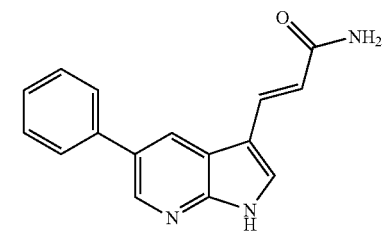 [SMILES: NC(=O)/C=C/c1c[nH]c2ncc(-c3ccccc3)cc12]

To a solution of 3-[5-pyridin-2-yl-1-(toluene-4-sulfonyl)-1H-pyrrolo[2,3-b]pyridin-3-yl]-acrylamide (step 4, 96 mg, 0.23 mmol) in dioxane (1 mL) was added 1.5M LiOH (1 mL) and the slurry was stirred at ambient temperature for 18 hours. The solution was partitioned between ethyl acetate and water. The organic layer was washed with water and brine and dried over magnesium sulfate. The solution was filtered and concentrated in vacuo. The crude material was purified using normal phase chromatography (ethyl acetate/heptane) to provide the title compound as a white solid (18 mg, 30% yield): $^1$H NMR (400 MHz, DMSO-$d_6$) δ 12.17 (s, 1H), 8.59 (s, 1H), 8.45 (s, 1H), 7.94 (s, 1H), 7.78 (s, 1H), 7.76 (s, 1H), 7.51-7.54 (m, 2H), 7.60 (d, J=15.65 Hz, 1H), 7.38-7.43 (m, 2H), 6.90 (br s, 1H), 6.70 (d, J=16.04 Hz, 1H); MS (ES) m/z 264 (M+H).

Example 2

(E)-3-(5-(2,4-Difluorophenyl)-1H-pyrrolo[2,3-b]pyridin-3-yl)acrylamide

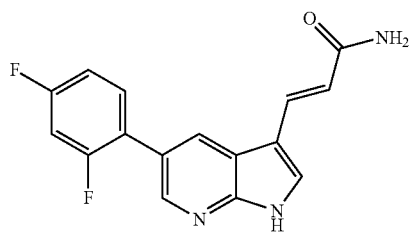 [SMILES: NC(=O)/C=C/c1c[nH]c2ncc(-c3ccc(F)cc3F)cc12]

Following Example 1, but substituting 2,4-difluorophenylboronic acid for phenylboronic acid in step 1 provided the title compound after purification: ¹H NMR (400 MHz, DMSO-$d_6$) δ 12.25 (s, 1H), 8.41 (s, 1H), 8.35 (s, 1H), 7.98 (s, 1H), 7.67-7.73 (m, 1H), 7.59 (d, J=16.04 Hz, 1H), 7.42-7.48 (m, 1H), 7.34 (br s, 1H), 7.24-7.29 (m, 1H), 6.89 (br s, 1H), 6.43 (d, J=16.04 Hz, 1H); MS (ES) m/z 300 (M+H).

Example 3

(E)-3-(5-(1-Phenyl-1H-pyrazol-3-yl)-1H-pyrrolo[2,3-b]pyridin-3-yl)acrylamide

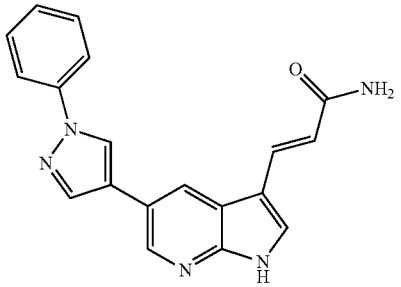 [SMILES: NC(=O)/C=C/c1c[nH]c2ncc(-c3cnn(-c4ccccc4)c3)cc12]

Following Example 1, but substituting 1-phenyl-1H-pyrazole-3-boronic acid for phenylboronic acid in step 1 provided the title compound after purification: ¹H NMR (400 MHz, DMSO-$d_6$) δ 12.12 (s, 1H), 9.08 (s, 1H), 8.71 (s, 1H), 8.52 (s, 1H), 8.34 (s, 1H), 7.91-7.93 (m, 3H), 7.60 (d, J=16.04 Hz, 1H), 7.53-7.57 (m, 2H), 7.33-7.38 (m, 1H), 7.29 (br s, 1H), 6.95 (br s, 1H), 6.69 (d, J=16.04 Hz, 1H); MS (ES) m/z 330 (M+H).

Example 4

(E)-3-(2-Phenyl-5H-pyrrolo[2,3-b]pyrazin-7-yl)acrylamide

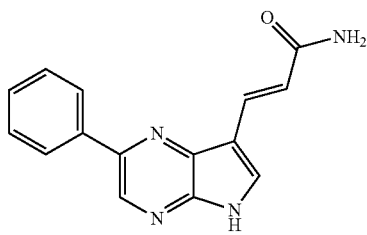 [SMILES: NC(=O)/C=C/c1c[nH]c2ncc(-c3ccccc3)nc12]

Following Example 1, but substituting 5-bromo-1H-pyrrolo[2,3-b]pyrazine for 5-bromo-1H-pyrrolo[2,3-b]pyridine in step 1 provided the title compound after purification: ¹H NMR (400 MHz, DMSO-$d_6$) δ 12.44 (s, 1H), 8.95 (s, 1H), 8.29 (s, 1H), 8.27 (s, 1H), 8.22 (s, 1H), 8.22 (s, 1H), 7.66 (br s, 1H), 7.55-7.62 (m, 3H), 7.47-7.53 (m, 1H), 7.28 (d, J=15.26 Hz, 1H), 6.93 (br s, 1H); MS (ES) m/z 265 (M+H).

Example 5

(E)-3-(5-(1-Methyl-1H-pyrazol-4-yl)-1H-pyrrolo[2,3-b]pyridin-3-yl)acrylamide

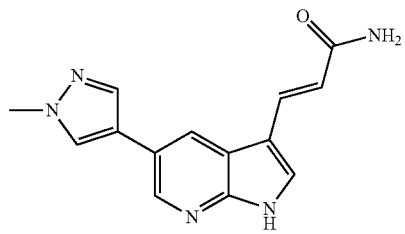 [SMILES: Cn1cc(-c2cnc3[nH]cc(/C=C/C(N)=O)c3c2)cn1]

Following Example 1, but substituting 1-methyl-1H-pyrazole-4-boronic acid for phenylboronic acid in step 1 provided the title compound after purification: ¹H NMR (400 MHz, DMSO-$d_6$) δ 12.03 (br s, 1H), 8.5 (s, 1H), 8.3 (s, 1H), 8.2 (s, 1H), 7.9 (s, 1H), 7.86 (m 1H), 7.5 (m, 1H), 7.2 (br s, 1H), 6.9 (br s, 1H), 6.67 (m, 1H), 3.9 (s, 3H); MS (ES) m/z 268 (M+H).

Example 6

(E)-3-(2-(1-Methyl-1H-pyrazol-4-yl)-5H-pyrrolo[2,3-b]pyrazin-7-yl)acrylamide

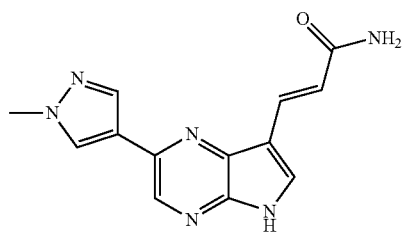 [SMILES: Cn1cc(-c2cnc3[nH]cc(/C=C/C(N)=O)c3n2)cn1]

Following Example 1, but substituting 1-methyl-1H-pyrazole-4-boronic acid for phenylboronic acid and 5-bromo-1H-pyrrolo[2,3-b]pyrazine for 5-bromo-1H-pyrrolo[2,3-b]pyridine in step 1 provided the title compound after purification: ¹H NMR (400 MHz, DMSO-$d_6$) δ 8.66 (s, 1H), 8.45 (s, 1H), 8.26 (s, 1H), 8.10 (s, 1H), 7.58-7.52 (m, 2H), 7.30 (d, J=15.6 Hz, 1H) 6.89 (br s, 1H), 3.93 (s, 3H); MS (ES) m/z 269 (M+H).

Example 7

(E)-3-(4-Isopropoxy-1H-pyrrolo[2,3-b]pyridin-3-yl)acrylamide

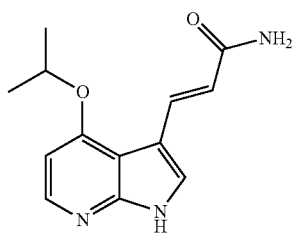 [SMILES: CC(C)Oc1ccnc2[nH]cc(/C=C/C(N)=O)c12]

Step 1: 4-Isopropoxy-1H-pyrrolo[2,3-b]pyridine

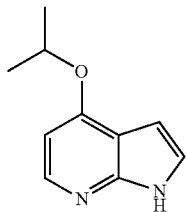

A mixture of 1H-pyrrolo[2,3-b]pyridin-4-ol (5.0 g, 37 mmol), isopropyl methanesulfonate (6.1 g, 45 mmol) and K$_2$CO$_3$ (10.3 g, 74.6 mmol) in a mixture of acetonitrile dimethylformamide (2:1, 150 mL) was stirred at 90° C. for 16 h. After cooling to RT the reaction mixture was diluted with water and extracted with ethyl acetate (3×150 mL). The organic layer was washed with ice water, dried over sodium sulfate and concentrated under reduced pressure to give the title compound as a white solid (3.5 g, 53%) which was used without purification: $^1$H NMR (400 MHz, DMSO-d$_6$) δ 11.4 (br s, 1H), 8.04 (m, 1H), 7.23 (m, 1H) 6.62 (m, 1H), 6.36 (m 1H), 4.85 (m, 1H), 1.36 (s, 6H); MS (ES) m/z 177 (M+H).

Step 2: 3-Iodo-4-isopropoxy-1H-pyrrolo[2,3-b]pyridine

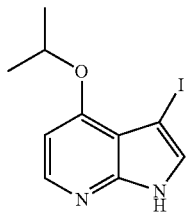

To a solution of 4-isopropoxy-1H-pyrrolo[2,3-b]pyridine (Step 1, 3.5 g, 20 mmol) in DCM (100 mL), was added NIS (4.93 g, 21.9 mmol) and the mixture stirred at RT for 3 h. The reaction mixture was diluted with ether and washed with water and saturated sodium bicarbonate solution. The organic layer was dried over anhydrous sodium sulfate and concentrated under reduced pressure to give the crude title compound which was used without purification (5.15 g, 85%): $^1$H NMR (400 MHz, DMSO-d$_6$) δ 11.84 (br s, 1H), 8.10 (m, 1H), 7.43 (s, 1H), 6.67 (m, 1H), 4.91 (m, 1H), 1.35 (s, 6H); MS (ES) m/z 303 (M+H).

Step 3: 3-Iodo-4-isopropoxy-1-(toluene-4-sulfonyl)-1H-pyrrolo[2,3-b]pyridine

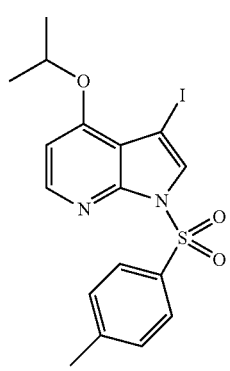 [SMILES: Cc1ccc(S(=O)(=O)n2cc(I)c3c(OC(C)C)ccnc32)cc1]

To a solution of 3-iodo-4-isopropoxy-1H-pyrrolo[2,3-b]pyridine (Step 2, 5.0 g, 17 mmol) in THF (100 mL), was added NaH (0.79 g, 20 mmol) at 0° C. and stirred at same temperature for 0.5 h. Tosyl chloride (3.46 g, 18.2 mmol) was added and the mixture stirred at rt for 2.5 h. The reaction mixture was diluted with ice water, extracted with ethyl acetate (3×150 mL), and the organic layer concentrated to give crude product. The crude product was purified by silica gel (100-200 mesh) column chromatography (10% to 20% ethyl acetate/pet ether) to provide 5 g of the title compound (66%): $^1$H NMR (400 MHz, DMSO-d$_6$) δ 8.22 (m, 1H), 7.99 (m, 2H) 7.85 (s, 1H), 7.42 (m, 2H), 6.92 (m, 1H), 4.84 (m, 1H), 2.50 (s, 3H), 1.35 (s, 6H); MS (ES) m/z 457 (M+H).

Step 4: 3-[4-Isopropoxy-1-(toluene-4-sulfonyl)-1H-pyrrolo[2,3-b]pyridin-3-yl]-acrylamide

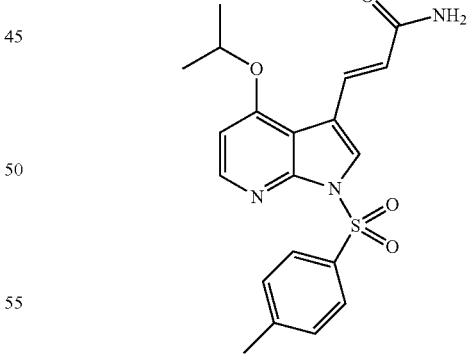

To a solution of 3-iodo-4-isopropoxy-1-(toluene-4-sulfonyl)-1H-pyrrolo[2,3-b]pyridine (Step 3, 1.0 g, 2.2 mmol) in DMF (15 mL) were added acrylamide (230 mg, 3.20 mmol) and triethylamine (0.78 mL, 5.5 mmol) and the mixture degassed for 10 min. At this time Pd(OAc)$_2$ (42 mg, 0.19 mmol) and tri(o-tolyl)phosphine (33 mg, 0.19 mmol) were added and the mixture stirred at 80° C. for 3 h. After cooling to RT, the reaction mixture was diluted with ice water and extracted with ethyl acetate (3×25 ml). The crude title compound was purified by column chromatography (100-200, 70-80% ethyl acetate/pet ether) to afford the title compound (410 mg, 46%): $^1$H NMR (400 MHz, DMSO-$d_6$) δ 8.22 (d, 1H), 8.06 (s, 1H), 8.03 (m, 2H), 7.71-7.67 (m, 1H), 7.43-7.41 (m, 2H), 7.36 (br s 1H), 7.03 (br s 1H), 6.96-6.94 (d, 1H), 6.70-6.67 (m, 1H), 4.87 (m, 1H), 2.33 (s, 3H), 1.33 (s, 6H); MS (ES) m/z 400 (M+H).

Step 5: 3-(4-Isopropoxy-1H-pyrrolo[2,3-b]pyridin-3-yl)-acrylamide

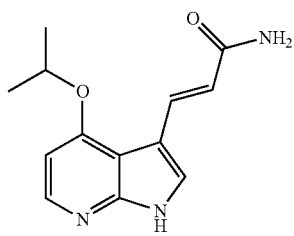 [SMILES: CC(C)Oc1ccnc2[nH]cc(/C=C/C(N)=O)c12]

To a solution of 3-[4-isopropoxy-1-(toluene-4-sulfonyl)-1H-pyrrolo[2,3-b]pyridin-3-yl]-acrylamide (Step 4, 300 mg, 0.75 mmol) in THF (15 mL) was added TBAF (1M in THF, 3.75 mL) and the solution stirred at RT for 12 h. The reaction mixture was concentrated under reduced pressure, diluted with ice water, and extracted with ethyl acetate (3×25 mL). The crude material was purified by reverse phase prep HPLC to provide 20 mg of the title compound (11%): $^1$H NMR (400 MHz, DMSO-$d_6$) δ 11.95 (br s, 1H), 8.08 (m, 1H), 7.80-7.76 (m, 1H), 7.68 (br s, 1H), 7.19 (br s 1H), 6.77 (br s, 1H), 6.71-6.70 (m, 1H), 6.51-6.47 (m, 1H), 4.87 (m, 1H), 1.33 (s, 6H); MS (ES) m/z 246. (M+H).

Example 8

3-(5-Isopropoxy-1H-pyrrolo[2,3-b]pyridin-3-yl)-acrylamide

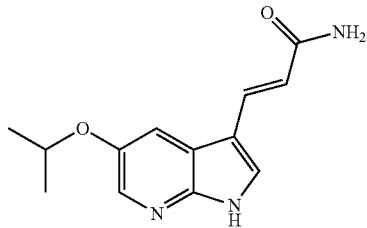 [SMILES: CC(C)Oc1cnc2[nH]cc(/C=C/C(N)=O)c2c1]

Following Example 7, but substituting 1H-pyrrolo[2,3-b]pyridin-5-ol for 1H-pyrrolo[2,3-b]pyridin-4-ol in step 1 provided the title compound after purification: $^1$H NMR (400 MHz, DMSO-$d_6$) δ 11.95 (br s, 1H), 8.08 (d, 1H), 7.80-7.76 (m, 1H), 7.68 (br s, 1H), 7.19 (br s, 1H), 6.77 (br s, 1H), 6.71-6.70 (m, 1H), 6.51-6.47 (m, 1H), 4.87 (m, 1H), 1.33 (s, 6H); MS (ES) m/z 246 (M+H).

Example 9

3-(5-Isopropylamino-1H-pyrrolo[2,3-b]pyridin-3-yl)-acrylamide

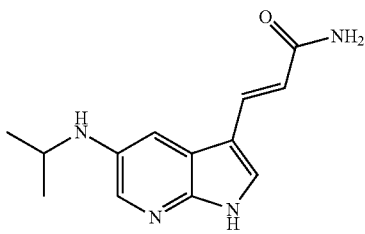

Step 1: Isopropyl-(1H-pyrrolo[2,3-b]pyridin-5-yl)-amine

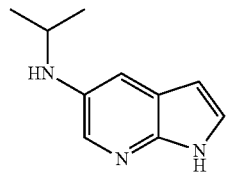

To a de-gassed solution of 5-bromo-7-azaindazole (20.0 g, 102 mmol), isopropylamine (30.27 g, 512.2 mmol) and LiHMDS (256 mL, 256 mmol) in THF (100 mL), were added Pd$_2$(dba)$_3$ (4.96 g, 5.12 mmol) and X-Phos (2.40 g, 5.12 mmol). The mixture was stirred at 100° C. for 12 h. After cooling to RT, the reaction mixture was diluted with ice water and extracted with (3×25 mL) ethyl acetate. The organic layers were dried over sodium sulfate and concentrated. The crude product was purified by silica gel column chromatography (70-80% ethyl acetate/pet ether) to afford 3.05 g of the title compound (16%): $^1$H NMR (400 MHz, DMSO-$d_6$) δ 11.14 (br s, 1H), 7.73 (s, 1H), 7.24 (m, 1H), 7.04 (s, 1H), 6.18 (m, 1H), 4.86 (m, 1H), 3.53 (m, 1H), 1.10 (s, 6H); MS (ES) m/z 176 (M+H).

Step 2: (3-Iodo-1H-pyrrolo[2,3-b]pyridin-5-yl)-isopropyl-amine

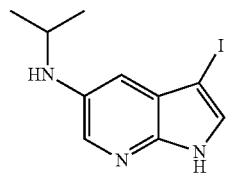

To a solution of isopropyl-(1H-pyrrolo[2,3-b]pyridin-5-yl)-amine (Step 1, 2.00 g, 11.4 mmol) in DCM (50 mL) was added NIS (2.82 g, 12.6 mmol) and the mixture stirred at rt for 3 h. The reaction mixture was diluted with ether, washed with water and saturated sodium bicarbonate solution. The organic layer was dried over sodium sulphate and concentrated under reduced pressure to provide 2.42 g of the title compound (70%). $^1$H NMR (400 MHz, DMSO-$d_6$) δ 11.44

(br s, 1H), 7.77 (m, 1H), 7.47 (s, 1H), 6.70 (s, 1H), 5.20 (s, 1H), 3.57 (m, 1H), 1.15 (s, 6H); MS (ES) m/z 456 (M+H).

Step 3: [3-Iodo-1-(toluene-4-sulfonyl)-1H-pyrrolo[2,3-b]pyridin-5-yl]-isopropyl-amine

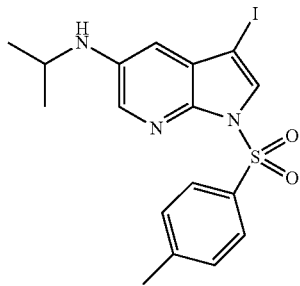 [SMILES: Cc1ccc(S(=O)(=O)n2cc(I)c3cc(NC(C)C)cnc32)cc1]

To a cooled solution of (3-iodo-1H-pyrrolo[2,3-b]pyridin-5-yl)-isopropyl-amine (Step 2, 2.0 g, 6.6 mmol) in THF (50 mL) was added NaH (0.318 g, 7.97 mmol). The mixture was stirred at 0° C. for 0.5 h and then tosyl chloride (1.39 g, 7.03 mmol) was added. The mixture was stirred at RT for 2 h and then diluted with ice water and extracted with ethyl acetate (3×150 mL). The combined organic layers were dried over anhydrous $Na_2SO_4$ and concentrated to give the crude desired product. The crude product was purified by silica gel column chromatography (20-30% ethyl acetate/pet ether) to afford 2.05 g of the title compound (68%): $^1$H NMR (400 MHz, DMSO-$d_6$) δ 7.94-7.92 (m, 2H), 7.88 (s, 1H) 7.81 (m, 2H), 7.42-7.31 (m, 2H), 6.60 (s, 1H), 5.75-5.73 (d, 1H), 3.58 (m, 1H), 2.37 (s, 3H), 1.13 (s, 6H); MS (ES) m/z 456 (M+H).

Step 4: 3-[5-Isopropylamino-1-(toluene-4-sulfonyl)-1H-pyrrolo[2,3-b]pyridin-3-yl]-acrylamide

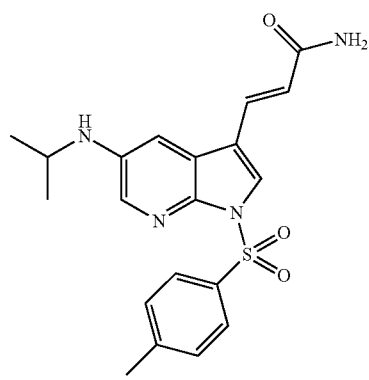 [SMILES: Cc1ccc(S(=O)(=O)n2cc(/C=C/C(N)=O)c3cc(NC(C)C)cnc32)cc1]

To a de-gassed solution of [3-iodo-1-(toluene-4-sulfonyl)-1H-pyrrolo[2,3-b]pyridin-5-yl]-isopropyl-amine (800 mg, 1.75 mmol), acrylamide (195 mg, 2.63 mmol) and triethylamine (0.61 mL, 4.37 mmol) in DMF (15 mL) were added $Pd(OAc)_2$ (19 mg, 0.08 mmol) and tri(o-tolyl)phosphine (26 mg, 0.08 mmol). The mixture was stirred at 80° C. for 3 h and then allowed to cool to RT. The reaction mixture was diluted with ice water and extracted with ethyl acetate (3×25 mL). The organic layers were dried over anhydrous $Na_2SO_4$ and concentrated. The crude material was purified by column chromatography on 100-200 mesh silica gel (70-80% ethyl acetate/pet ether) to afford the title compound (404 mg, 57%): $^1$H NMR (400 MHz, DMSO-$d_6$) δ 8.08 (s, 1H), 7.94-7.92 (m, 2H), 7.84 (s, 1H), 7.50-7.49 (m, 2H), 7.41-7.39 (m, 2H), 7.23 (s, 1H), 7.05 (s, 1H), 6.62-6.58 (m, 1H), 5.68-5.66, 1H), 3.55 (m, 1H), 2.33 (s, 3H), 1.51 (s, 6H); MS (ES) m/z 399 (M+H).

Step 5: 3-[5-Isopropylamino-1-(toluene-4-sulfonyl)-1H-pyrrolo[2,3-b]pyridin-3-yl]-acrylamide

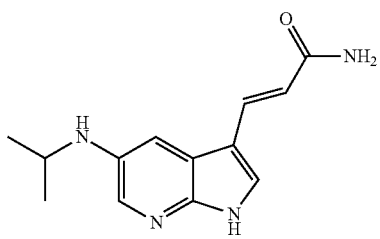 [SMILES: CC(C)Nc1cnc2[nH]cc(/C=C/C(N)=O)c2c1]

To a solution of 3-[5-isopropylamino-1-(toluene-4-sulfonyl)-1H-pyrrolo[2,3-b]pyridin-3-yl]-acrylamide (400 mg, 1.00 mmol) in a mixture of THF, MeOH and $H_2O$ (3:1:1, 25 mL) was added $LiOH.H_2O$ (63 mg, 1.5 mmol)) and the mixture stirred at 60° C. for 1 h. After cooling to RT the reaction mixture was concentrated under reduced pressure. The crude was diluted with ice water and extracted with ethyl acetate (3×25 mL). The organic layers were dried over anhydrous $Na_2SO_4$ and concentrated. The crude material was purified by rev-prep HPLC to give 60 mg of the title compound (25%): $^1$H NMR (400 MHz, DMSO-$d_6$) δ 11.60 (br s, 1H), 7.80 (s, 1H), 7.65 (s, 1H), 7.58-7.53 (d, 1H), 7.32-7.29 (m, 2H), 6.78 (s, 1H), 6.43 (d, 1H), 5.14 (d, 1H), 3.67 (m, 1H), 1.26 (s, 6H); MS (ES) m/z 245 (M+H).

Example 10

3-(2-Isopropylamino-5H-pyrrolo[2,3-b]pyrazin-7-yl)-acrylamide

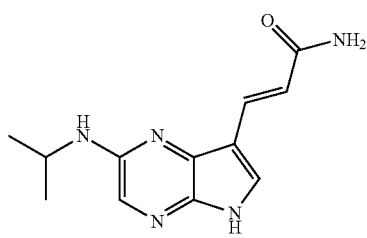 [SMILES: CC(C)Nc1cnc2[nH]cc(/C=C/C(N)=O)c2n1]

Step 1: 5-Bromo-3-trimethylsilanylethynyl-pyrazin-2-ylamine

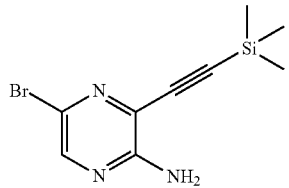

To a stirred solution of 3,5-dibromo-pyrazin-2-ylamine (50.0 g, 198 mmol) in DMF (500 mL) and DIPEA (76.6 g, 595 mmol) was added bis(triphenylphosphine)palladium(II) chloride (6.81 g, 0.0490 mmol), CuI (3.76 g, 19.7 mmol) and TMS acetylene (23.33 g, 238.0 mmol). The reaction mixture was stirred at 90° C. for 3 h. After cooling to RT, the reaction mixture was poured into ice cold water (200 mL) and extracted with ethyl acetate (2×250 mL). The organic layer was separated, washed with water (200 mL) and brine (200 mL), dried over anhydrous sodium sulfate and concentrated to afford crude product. The crude material was purified by column chromatography on 100-200 mesh silica gel (5-10% ethyl acetate in pet ether) to afford the title compound (25.0 g, 46.4%): $^1$H NMR (400 MHz, CDCl$_3$) δ 8.04 (s, 1H), 5.06 (br s, 2H), 0.29 (s, 9H); MS (ES) m/z 271 (M+H).

Step 2: 2-Bromo-5H-pyrrolo[2,3-b]pyrazine

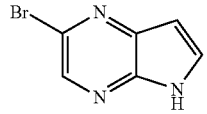

A solution of 5-bromo-3-trimethylsilanylethynyl-pyrazin-2-ylamine (Step 1, 8.0 g, 30 mmol) in N-methyl-2-pyrrolidone (NMP, 20 mL) was added dropwise to a stirred suspension of potassium tert-butoxide (6.6 g, 59 mmol) in NMP (30 mL) at 80° C. The mixture was stirred at the same temperature for 3 h. The mixture was allowed to cool to RT and ice cold water (50 mL) was added. The reaction mixture extracted with ethyl acetate (2×100 mL), the organic layer separated, washed with water, dried over anhydrous sodium sulphate and concentrated under reduced pressure. The crude material was purified by trituration with diethyl ether to afford pure title compound (3.2 g, 55%): $^1$H NMR (400 MHz, DMSO-d$_6$) δ 12.35 (br s, 1H), 8.35 (s, 1H), 7.96 (d, J=3.6 Hz, 1H), 6.63 (d, J=3.6 Hz, 1H); MS (ES) m/z 199 (M+H).

Step 3: 2-Bromo-5-(toluene-4-sulfonyl)-5H-pyrrolo[2,3-b]pyrazine

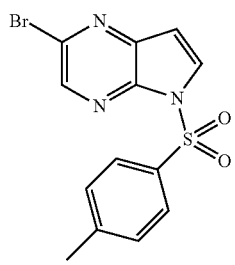 [SMILES: Cc1ccc(S(=O)(=O)n2ccc3nc(Br)cnc32)cc1]

Sodium hydride (0.909 g, 28.7 mmol) was added portionwise to a solution of 2-bromo-5H-pyrrolo[2,3-b]pyrazine (Step 2, 3.0 g, 15 mmol) in THF (100 mL) at 0° C. Tosyl chloride (5.46 g, 28.7 mmol) was added to the mixture at 0° C. which was allowed to warm to RT and stir for 1 h. The reaction mixture was quenched with ice cold water and extracted with ethyl acetate (2×50 mL). The organic layer was separated, dried over anhydrous sodium sulfate, filtered and concentrated. The crude material was purified by column chromatography on 100-200 mesh silica gel (15-10% ethyl acetate/pet ether) to afford the title compound (3.5 g, 65%): $^1$H NMR (400 MHz, DMSO-d$_6$) δ 8.59 (s, 1H), 8.38 (d, J=4.4 Hz, 1H), 8.0 (d, J=8.0 Hz, 2H), 7.45 (d, J=8.0 Hz, 2H), 7.03 (d, J=4.4 Hz, 1H), 2.36 (s, 3H); MS (ES) m/z 353 (M+H).

Step 4: Isopropyl-[5-(toluene-4-sulfonyl)-5H-pyrrolo[2,3-b]pyrazin-2-yl]-amine

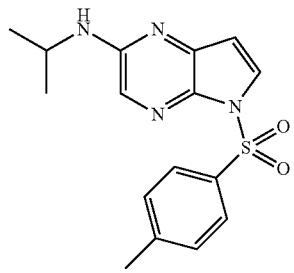 [SMILES: Cc1ccc(S(=O)(=O)n2ccc3nc(NC(C)C)cnc32)cc1]

To a solution of 2-bromo-5-(toluene-4-sulfonyl)-5H-pyrrolo[2,3-b]pyrazine (Step 3, 2.0 g, 6.6 mmol) in dioxane (20 mL) was added isopropylamine (3.88 g, 65.8 mmol) and cesium carbonate (3.17 g, 9.70 mmol) at RT. The reaction mixture was deoxygenated by purging with argon gas and then Pd$_2$(dba)$_3$ (0.595 g, 0.650 mmol), and BINAP (0.040 g, 0.65 mmol) were added. The reaction mixture was heated to 90° C. in a sealed tube and maintained for 16 h. After cooling to room temperature the reaction mixture was filtered through celite and the filtrate concentrated under reduced pressure. The crude material was purified by column chromatography on 100-200 mesh silica gel (20-25% ethyl acetate/pet ether) to afford the title compound (0.700 g, 32%): $^1$H NMR (400 MHz, DMSO-d$_6$) δ 7.88 (d, J=8.0 Hz, 2H), 7.83 (d, J=4.0 Hz, 1H), 7.65 (s, 1H), 7.40 (d, J=8.4 Hz, 2H), 6.90 (d, J=7.6 Hz, 1H), 6.63 (d, J=3.6 Hz, 1H), 3.97-3.92 (m, 1H), 2.34 (s, 3H), 1.13 (d, J=6.4 Hz, 6H); MS (ES) m/z 331 (M+H).

Step 5: Isopropyl-(5H-pyrrolo[2,3-b]pyrazin-2-yl)-amine

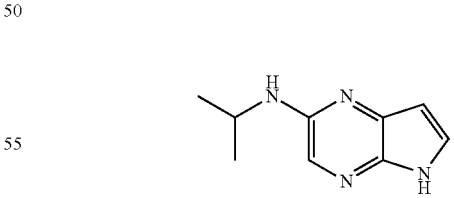

To a solution of Isopropyl-[5-(toluene-4-sulfonyl)-5H-pyrrolo[2,3-b]pyrazin-2-yl]-amine (Step 4, 0.700 g, 2.11 mmol) in ethanol (3.0 mL) and THF (2.0 mL) was added cesium carbonate (3.44 g, 10.5 mmol) and the mixture stirred at 60° C. for 4 h. After cooling to room temperature the reaction mixture was concentrated under reduced pressure. The crude residue was diluted with water (20 mL) and extracted with ethyl acetate (2×50 mL). The organic layer was separated, dried over anhydrous sodium sulfate and concentrated. The residue was purified by column chromatography on 100-200 mesh silica gel (40-50% ethyl acetate/pet ether) to afford the title compound (0.330 g, 88%): ¹H NMR (400 MHz, DMSO-d₆) δ 11.30 (br s, 1H), 7.56 (s, 1H), 7.39-7.37 (m, 1H), 6.23-6.20 (m, 2H), 4.02-3.97 (m, 1H), 1.16 (d, J=6.4 Hz, 6H); MS (ES) m/z 177 (M+H).

Step 6: (7-Iodo-5H-pyrrolo[2,3-b]pyrazin-2-yl)-isopropyl-amine

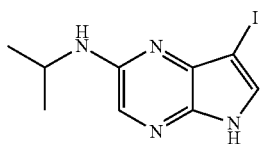

To a solution of isopropyl-(5H-pyrrolo[2,3-b]pyrazin-2-yl)-amine (Step 5, 0.330 g, 1.87 mmol) in DMF (4 mL) was added N-iodo succinimide (379 mg, 1.69 mmol) at 0° C. The reaction mixture was allowed to warm to RT and was stirred for 30 min. The reaction mixture was quenched with ice cold water (20 mL) and extracted with ethyl acetate (2×25 mL). The organic layer was separated, dried over anhydrous sodium sulfate and concentrated under reduced pressure to afford 430 mg (75%) of the title compound: ¹H NMR (400 MHz, DMSO-d₆) δ 11.80 (br s, 1H), 7.58-7.57 (m, 2H), 6.50 (d, J=7.6 Hz, 1H), 4.08-4.03 (m, 1H), 1.16 (d, J=6.4 Hz, 6H); MS (ES) m/z 303 (M+H).

Step 7: [7-Iodo-5-(toluene-4-sulfonyl)-5H-pyrrolo[2,3-b]pyrazin-2-yl]-isopropyl-amine

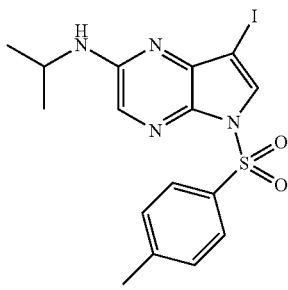 [SMILES: Cc1ccc(S(=O)(=O)n2cc(I)c3nc(NC(C)C)cnc32)cc1]

Sodium hydride (84.6 mg, 2.12 mmol) was added portionwise to a solution of (7-iodo-5H-pyrrolo[2,3-b]pyrazin-2-yl)-isopropyl-amine (Step 6, 430 mg, 1.41 mmol) in THF (15 mL) at 0° C. Tosyl chloride (403 mg, 2.12 mmol) was added and the mixture allowed to warm to RT and stir for 1 h. The reaction mixture was quenched with ice cold water and extracted with ethyl acetate (2×50 mL). The organic layer was separated, dried over anhydrous sodium sulfate and concentrated to afford the title compound (0.430 g, 66%): ¹H NMR (400 MHz, DMSO-d₆) δ 8.04 (s, 1H), 7.91 (d, J=8.0 Hz, 2H), 7.66 (s, 1H), 7.41 (d, J=8.0 Hz, 2H), 7.10 (d, J=7.6 Hz, 1H), 4.02-3.97 (m, 1H), 2.34 (s, 3H), 1.15 (d, J=6.4 Hz, 6H); MS (ES) m/z 457 (M+H).

Step 8: 3-[2-Isopropylamino-5-(toluene-4-sulfonyl)-5H-pyrrolo[2,3-b]pyrazin-7-yl]-acrylamide

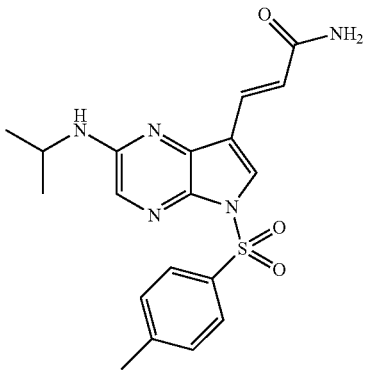 [SMILES: Cc1ccc(S(=O)(=O)n2cc(/C=C/C(N)=O)c3nc(NC(C)C)cnc32)cc1]

To a solution of [7-iodo-5-(toluene-4-sulfonyl)-5H-pyrrolo[2,3-b]pyrazin-2-yl]-isopropyl-amine (Step 7, 200 mg, 0.439 mmol) in DMF (10 mL) and TEA (110 mg, 1.10 mmol) at RT, was added acrylamide (46.1 mg, 0.659 mmol). The reaction mixture was deoxygenated by purging with argon gas and then tri-o-tolyl phosphine (6.6 mg, 0.021 mmol) and palladium acetate (4.7 mg, 0.021 mmol) were added. The reaction mixture was heated to 120° C. in a microwave and maintained for 30 min. After cooling to RT the reaction mixture was filtered through celite and the filtrate concentrated under reduced pressure. The crude residue was purified by column chromatography on 100-200 mesh silica gel (5% MeOH/DCM) to afford purified title compound (0.120 g, 68%): ¹H NMR (400 MHz, DMSO-d₆) δ 8.16 (s, 1H), 7.90 (d, J=8.8 Hz, 2H), 7.69 (s, 1H), 7.55 (br s, 1H), 7.44-7.40 (m, 3H), 7.15 (d, J=15.6 Hz, 1H), 7.04-7.00 (m, 2H), 4.16-4.11 (m, 1H), 2.34 (s, 3H), 1.17 (d, J=6.4 Hz, 6H); MS (ES) m/z 400 (M+H).

Step 9: 3-(2-Isopropylamino-5H-pyrrolo[2,3-b]pyrazin-7-yl)-acrylamide

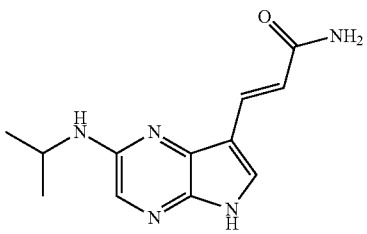 [SMILES: CC(C)Nc1cnc2[nH]cc(/C=C/C(N)=O)c2n1]

To a solution of 3-[2-isopropylamino-5-(toluene-4-sulfonyl)-5H-pyrrolo[2,3-b]pyrazin-7-yl]-acrylamide (120 mg, 0.300 mmol) in methanol (1.0 mL) and THF (5.0 mL) was added lithium hydroxide (14.4 mg, 0.601 mmol) and the mixture stirred at RT for 6 h. The reaction mixture was concentrated under reduced pressure and the crude residue diluted with water (20 mL) and extracted with ethyl acetate (2×50 mL). The organic layer was separated, dried over anhydrous sodium sulfate and concentrated. The crude material was purified by Prep. HPLC to afford 44 mg of the title compound: ¹H NMR (400 MHz, DMSO-d₆) δ 11.68 (br s, 1H), 7.70 (d, J=2.8 Hz, 1H), 7.16 (s, 1H), 7.46 (d, J=15.6

Hz, 1H) 7.35 (br s, 1H), 6.94 (d, J=16 Hz, 1H), 6.74 (br s, 1H), 6.51 (s, 1H), 6.40 (d, J=8.0 Hz, 1H), 4.21-4.16 (m, 1H), 1.20 (d, J=6.4 Hz, 6H); MS (ES) m/z 246 (M+H).

Example 11

(E)-3-(5-(3-Methoxyphenyl)-1H-pyrrolo[2,3-b]pyridin-3-yl)acrylamide

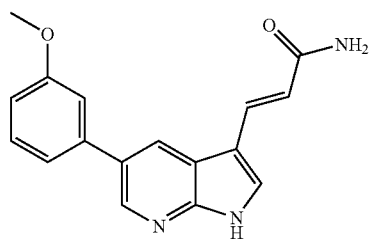 [SMILES: COc1cccc(-c2cnc3[nH]cc(/C=C/C(N)=O)c3c2)c1]

Following Example 1, but substituting 3-methoxyphenylboronic acid for phenylboronic acid in step 1 provided the title compound after purification: $^1$H NMR (400 MHz, DMSO-d$_6$) δ DATA; MS (ES) m/z DATA (M+H).

Example 12

(E)-3-(5-(4-Methoxyphenyl)-1H-pyrrolo[2,3-b]pyridin-3-yl)acrylamide

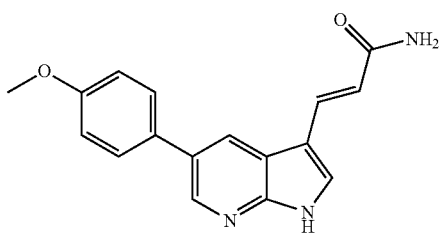 [SMILES: COc1ccc(-c2cnc3[nH]cc(/C=C/C(N)=O)c3c2)cc1]

Following Example 1, but substituting 4-methoxyphenylboronic acid for phenylboronic acid in step 1 provided the title compound after purification: $^1$H NMR (400 MHz, DMSO-d$_6$) δ DATA; MS (ES) m/z DATA (M+H).

Example 13

3-(5-Pyridin-3-yl-1H-pyrrolo[2,3-b]pyridin-3-yl)-acrylamide

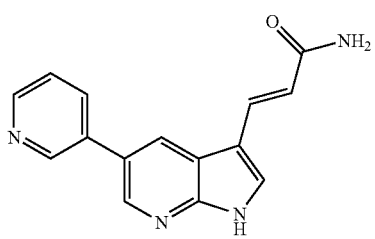 [SMILES: NC(=O)/C=C/c1c[nH]c2ncc(-c3cccnc3)cc12]

Following Example 1, but substituting 3-pyridylboronic acid for phenylboronic acid in step 1, provided the title compound after purification: $^1$H NMR (400 MHz, DMSO-d$_6$) δ 12.31 (s, 1H), 9.15 (s, 1H), 8.73 (d, J=5.08 Hz, 1H), 8.70 (s, 1H), 8.61 (s, 1H), 8.45 (d, J=7.05 Hz, 1H), 7.62 (d, J=16.04, 1H), 7.75-7.79 (m, 1H), 7.99 (s, 1H), 7.32 (br s, 1H), 6.94 (br s, 1H), 6.73 (d, J=15.65 Hz, 1H); MS (ES) m/z 265 (M+H).

Example 14

1-(5-Phenyl-1H-pyrrolo[2,3-b]pyridin-3-yl)-but-2-en-1-one

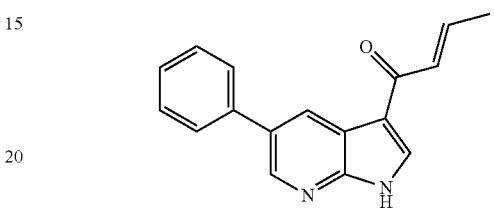

To a solution of 5-phenyl-1H-pyrrolo[2,3-b]pyridine (Example 1, Step 1, 50.0 mg, 0.256 mmol) in DCM (2 mL), was added aluminum chloride (170 mg, 1.28 mmol). The resulting mixture stirred for 15 min and was cooled to 5° C. But-2-enoyl chloride (56 mg, 0.64 mmol) was added dropwise and the resulting solution allowed to warm to RT and stir for 1 h. Upon consumption of the starting material the reaction mixture was cooled to 5° C. and MeOH was added dropwise until gas evolution ceased. The resulting solution was concentrated under reduced pressure and the residue diluted with ice water and extracted with ethyl acetate (3×25 mL). The organic layer was dried over anhydrous Na$_2$SO$_4$ and concentrated. The crude material was purified by silica gel (100-200 mesh) column chromatography (0 to 5% MeOH/methylene chloride) to afford the title compound (10 mg, 15%). $^1$H NMR (400 MHz, CHCl$_3$-d$_6$) δ 8.95 (s, 1H), 8.64 (s, 1H), 8.06 (d, J=2 Hz, 1H), 7.68 (d, J=7.8 Hz, 2H), 7.50 (t, J=8.6 Hz, 2H), 7.40 (t, J=6.6 Hz, 1H), 3.36 (d, J=2 Hz, 3H), 4.03 (q, J=5.8 Hz, 1H), 3.23 (m, 1H), 2.82 (m, 1H); MS (ES) m/z 263 (M+H).

Example 15

2-Methyl-1-(5-phenyl-1H-pyrrolo[2,3-b]pyridin-3-yl)-but-2-en-1-one

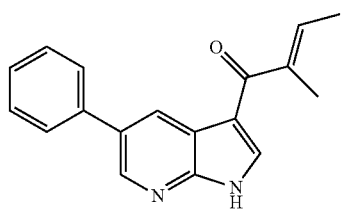 [SMILES: C/C=C(\C)C(=O)c1c[nH]c2ncc(-c3ccccc3)cc12]

Following Example 14, but substituting but-2-enoyl chloride for 2-methyl-but-2-enoyl chloride provided the title compound as a white solid after purification (29 mg, 40%): $^1$H NMR (400 MHz, DMSO-d$_6$) δ 12.55 (br s, 1H), 8.62 (s, 2H), 8.12 (s, 1H), 7.71 (d, J=7 Hz, 2H), 7.51 (t, J=7.4 Hz, 2H), 7.40 (t, J=7.4 Hz, 1H), 6.47 (t, J=5.4 Hz, 1H), 1.88 (t, J=5 Hz, 6H); MS (ES) m/z 277 (M+H).

Example 16

3-Methyl-1-(5-phenyl-1H-pyrrolo[2,3-b]pyridin-3-yl)-but-2-en-1-one

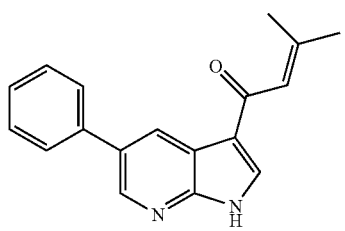 [SMILES: CC(C)=CC(=O)c1c[nH]c2ncc(-c3ccccc3)cc12]

Following Example 14, but substituting 3-methyl-but-2-enoyl chloride for 2-methyl-but-2-enoyl chloride provided the title compound after purification as an off white solid (39 mg, 55%): $^1$H NMR (400 MHz, DMSO-d$_6$) δ 12.52 (br s, 1H), 8.77 (d, J=2.3 Hz, 1H), 8.61 (d, J=2.3 Hz, 1H), 8.55 (d, J=3.1 Hz, 1H), 7.71 (d, J=7 Hz, 2H), 7.51 (t, J=7.4 Hz, 2H), 7.40 (t, J=7.4 Hz, 1H), 6.90 (s, 1H), 2.20 (s, 3H), 1.98 (s, 3H); MS (ES) m/z 277 (M+H).

Example 17

3-[5-(4-Cyano-phenyl)-1H-pyrrolo[2,3-b]pyridin-3-yl]-acrylamide

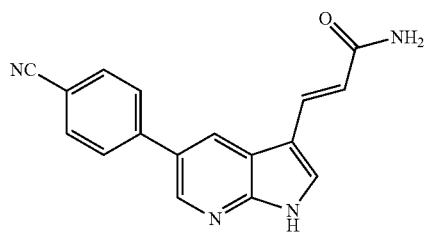 [SMILES: N#Cc1ccc(-c2cnc3[nH]cc(/C=C/C(N)=O)c3c2)cc1]

Following Example 1, but substituting 4-cyanophenylboronic acid for phenylboronic acid in step 1 provided the title compound after purification: $^1$H NMR (400 MHz, DMSO-d$_6$) δ 12.28 (s, 1H), 8.68 (s, 1H), 8.56 (s, 1H), 7.98-8.03 (m, 5H), 7.60 (d, J=16.04 Hz, 1H), 7.35 (br s, 1H), 6.92 (br s, 1H), 6.72 (d, J=16.04 Hz, 1H); MS (ES) m/z 289 (M+H).

Example 18

3-[5-(3-Cyano-phenyl)-1H-pyrrolo[2,3-b]pyridin-3-yl]-acrylamide

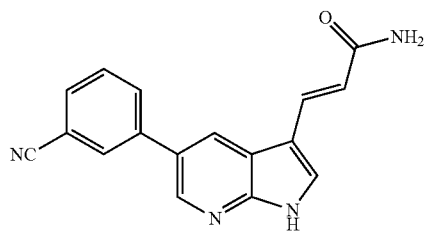 [SMILES: N#Cc1cccc(-c2cnc3[nH]cc(/C=C/C(N)=O)c3c2)c1]

Following Example 1, but substituting 3-cyanophenylboronic acid for phenylboronic acid in step 1 provided the title compound after purification: $^1$H NMR (400 MHz, DMSO-d$_6$) δ 12.25 (s, 1H), 8.66 (s, 1H), 8.54 (s, 1H), 8.29 (s, 1H), 8.14 (d, J=7.83 Hz, 1H), 7.97 (s, 1H), 7.87 (d, J=7.82 Hz, 1H), 7.73 (t, 1H), 7.61 (d, J=16.05 Hz, 1H), 7.33 (br s, 1H), 6.93 (br s, 1H), 6.72 (d, J=16.04 Hz, 1H); MS (ES) m/z 289 (M+H).

Example 226

(E)-2-Cyano-3-(5-phenyl-1H-pyrrolo[2,3-b]pyridin-3-yl)acrylamide

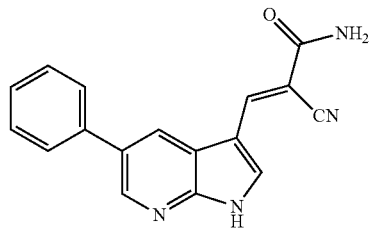 [SMILES: N#C/C(=C\c1c[nH]c2ncc(-c3ccccc3)cc12)C(N)=O]

Step 1:
5-Phenyl-1H-pyrrolo[2,3-b]pyridine-3-yl)acrylamide

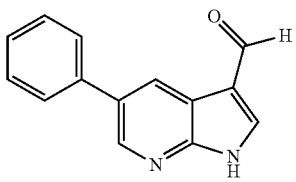 [SMILES: O=Cc1c[nH]c2ncc(-c3ccccc3)cc12]

Following Example 1, Step 1, but substituting 3-pyridylboronic acid for phenylboronic acid and 5-bromo-1H-pyrrolo[2,3-b]pyridine-3-carbaldehyde for 5-bromo-1H-pyrrolo[2,3-b]pyridine provided 5-phenyl-1H-pyrrolo[2,3-b]pyridine-3-yl)acrylamide after purification as a white solid: MS (ES) m/z 223 (M+H).

Step 2: (E)-2-Cyano-3-(5-phenyl-1H-pyrrolo[2,3-b]pyridin-3-yl)acrylamide

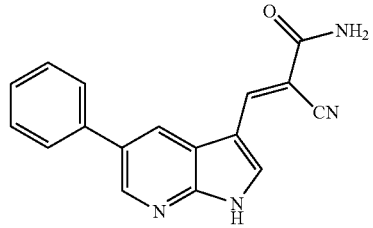 [SMILES: N#C/C(=C\c1c[nH]c2ncc(-c3ccccc3)cc12)C(N)=O]

To a solution of 5-phenyl-1H-pyrrolo[2,3-b]pyridine-3-yl)acrylamide (50 mg, 0.253 mmol) in THF (2 mL) was added 2-cyanoacetamide (25.5 mg, 0.304 mmol) and piperdine (27 μl 0.27 mmol). The resulting solution was allowed to stir at room temperature for 12 hours. The resulting precipitate was filtered and washed with 2×5 mL cold THF and dried on the filter paper under vacuum to produce 32 mg (43.7% yield) of (E)-2-cyano-3-(5-phenyl-1H-pyrrolo[2,3-b]pyridin-3-yl)acrylamide as a pale yellow solid: $^1$H NMR (400 MHz, DMSO-d$_6$) δ ppm, 12.63 (s, 1H), 8.69 (s, 1H), 8.52 (d, J=5.42 Hz, 1H), 7.76-7.58 (m, 5H), 7.34 (s, 1H), 5.08 (s, 1H); MS (ES) m/z 289 (M+H).

The following compounds can generally be made using the methods described above. It is expected that these compounds when made will have activity similar to those that have been made in the examples above.

The following compounds can generally be made using the methods described above. It is expected that these compounds when made will have activity similar to those that have been prepared. The following compounds are represented herein using the Simplified Molecular Input Line Entry System, or SMILES. SMILES is a modern chemical notation system, developed by David Weininger and Daylight Chemical Information Systems, Inc., that is built into all major commercial chemical structure drawing software packages. Software is not needed to interpret SMILES text strings, and an explanation of how to translate SMILES into structures can be found in Weininger, D., J. Chem. Inf. Comput. Sci. 1988, 28, 31-36. All SMILES strings used herein, as well as many IUPAC names, were generated using CambridgeSoft's ChemDraw 10.0.

TABLE 1

Compound Examples — Spectral Data

| Example | Structure | Name | Spectral Data |
|---|---|---|---|
| 20 | 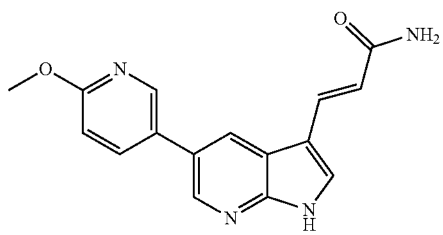 [SMILES: COc1ccc(-c2cnc3[nH]cc(/C=C/C(N)=O)c3c2)cn1] | (E)-3-(5-(6-methoxypyridin-3-yl)-1H-pyrrolo[2,3-b]pyridin-3-yl)acrylamide | $^1$H NMR (400 MHz, DMSO-d$_6$) δ ppm, 12.20 (s, 1H), 8.59 (s, 1H), 8.58 (s, 1H), 8.46 (s, 1H), 8.13 (d, J = 8.61 Hz, 1H), 7.59 (d, J = 16.04, 1H), 7.34 (br. s, 1H), 6.97 (d, J = 8.61 Hz, 1H), 6.94 (br. s, 1H), 6.70 (d, J = 16.04 Hz, 1H), 3.92 (s, 3H). MS (ES) m/z 295 (M + H). |
| 23 | 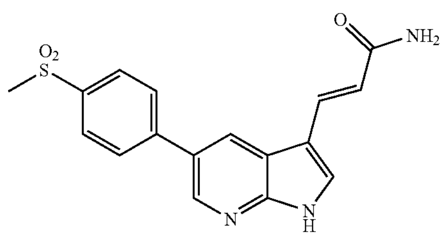 [SMILES: CS(=O)(=O)c1ccc(-c2cnc3[nH]cc(/C=C/C(N)=O)c3c2)cc1] | (E)-3-(5-(4-(methylsulfonyl)phenyl)-1H-pyrrolo[2,3-b]pyridin-3-yl)acrylamide | MS (ES) m/z 342 (M + H). |
| 32 | 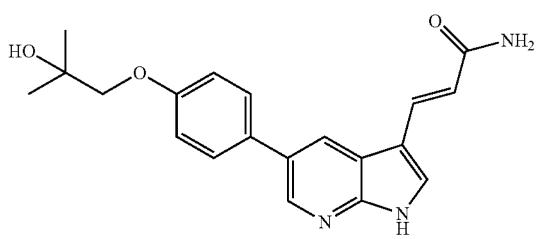 [SMILES: CC(C)(O)COc1ccc(-c2cnc3[nH]cc(/C=C/C(N)=O)c3c2)cc1] | (E)-3-(5-(4-(2-hydroxy-2-methylpropoxy)phenyl)-1H-pyrrolo[2,3-b]pyridin-3-yl)acrylamide | $^1$H NMR (400 MHz, DMSO-d$_6$) δ ppm, 12.12 (s, 1H), 8.54 (d, J = 1.95 Hz, 1H), 8.40 (d, J = 1.95 Hz, 1H), 7.92 (s, 1H), 7.68 (d, J = 8.60 Hz, 2H), 7.59 (d, J = 16.04 Hz, 1H), 7.38 (s, 1H), 7.08 (d, J = 8.60 Hz, 2H), 6.90 (s, 1H), 6.68 (d, J = 16.04 Hz, 1H), 4.67 (s, 1H), 3.78 (s, 2H), 1.23 (s, 6H). MS (ES) m/z 352 (M + H). |
| 226 | 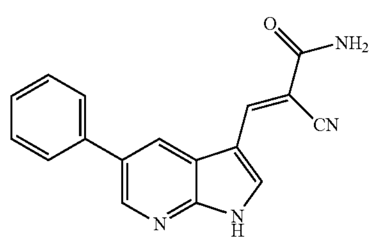 [SMILES: N#C/C(=C\c1c[nH]c2ncc(-c3ccccc3)cc12)C(N)=O] | (E)-2-cyano-3-(5-phenyl-1H-pyrrolo[2,3-b]pyridin-3-yl)acrylamide | $^1$H NMR (400 MHz, DMSO-d$_6$) δ ppm, 12.63 (s, 1H), 8.69(s, 1H), 8.52 (d, J = 5.42 Hz, 1H), 7.76 - 7.58 (m, 5H), 7.34 (s, 1H), 5.08 (s, 1H); MS (ES) m/z 289 (M + H). MS (ES) m/z 289 (M + H). |
| 232 | 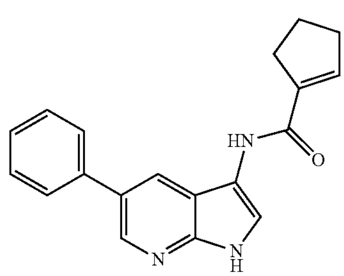 [SMILES: O=C(Nc1c[nH]c2ncc(-c3ccccc3)cc12)C1=CCCC1] | N-(5-phenyl-1H-pyrrolo[2,3-b]pyridin-3-yl)cyclopent-1-enecarboxamide | $^1$H NMR(400 MHz, DMSO-d$_6$) δ ppm, 11.40 (s, 1H), 9.73 (s, 1H), 8.54 (d, J = 7.44 Hz, 2H), 7.76 (m, 3H), 7.44 (m, 3H), 6.72 (s, 1H), 2.73-2.63 (m, 4H), 1.93 (t, J = 7.83 Hz, 2H), MS (ES) m/z 304 (M + H). |

TABLE 1-continued

Compound Examples — Spectral Data

| Example | Structure | Name | Spectral Data |
|---|---|---|---|
| 233 | 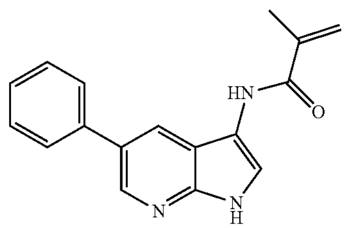 [SMILES: C=C(C)C(=O)Nc1c[nH]c2ncc(-c3ccccc3)cc12] | N-(5-phenyl-1H-pyrrolo[2,3-b]pyridin-3-yl)methacrylamide | ¹H NMR (400 MHz, DMSO-d₆) δ ppm, 11.50 (s, 1H), 9.92 (s, 1H), 8.54 (dd, J = 1.96 Hz, 16.82 Hz, 2H), 7.84 (s, 1H), 7.72 (d, J = 7.04 Hz, 2H), 7.50 (t, J = 7.82 Hz, 2H), 7.37 (t, J = 7.43 Hz, 1H), 5.85 (s, 1H), 5.52 (s, 1H), 2.00 (s, 3H). MS (ES) m/z 278 (M + H). |
| 234 | 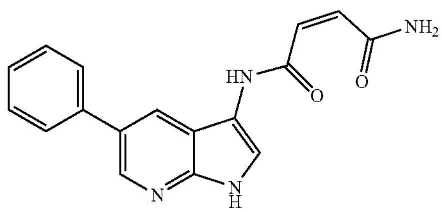 [SMILES: NC(=O)/C=C\C(=O)Nc1c[nH]c2ncc(-c3ccccc3)cc12] | N¹-(5-phenyl-1H-pyrrolo[2,3-b]pyridin-3-yl)maleamide | ¹H NMR(400 MHz, DMSO-d₆) δ ppm, 11.70 (s, 1H), 10.81 (s, 1H), 8.57 (d, J = 1.95 Hz, 1H), 8.48 (d, J = 1.95 Hz, 1H), 8.04 (d, J = 2.35 Hz, 1H), 7.71 (d, J = 7.83 Hz, 2H), 7.51 (t, J = 7.44 Hz, 1H), 7.38 (d, J = 7.44 Hz, 1H), 7.07 (d, J = 11.34 Hz, 1H), 6.33 (d, J = 10.95 Hz, 1H), 3.43 (s, 2H). MS (ES) m/z 307 (M + H). |
| 235 | 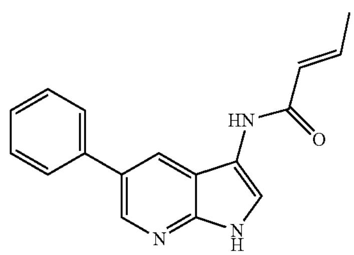 [SMILES: C/C=C/C(=O)Nc1c[nH]c2ncc(-c3ccccc3)cc12] | (E)-N-(5-phenyl-1H-pyrrolo[2,3-b]pyridin-3-yl)but-2-enamide | ¹H NMR (400 MHz, DMSO-d₆) δ ppm, 11.46 (s, 1H), 10.10 (s, 1H), 8.54-8.48 (m, 2H), 7.95-7.90 (m, 1H), 7.72-7.69 (m, 2H), 7.52-7.48 (m, 2H), 7.39-7.35 (m, 1H), 6.83-6.74 (m, 1H), 6.24 (dd, J = 1.57 Hz, 13.69 Hz, 1H), 1.39 (d, J = 7.04 Hz, 3H). MS (ES) m/z 278 (M + H). |
| 236 | 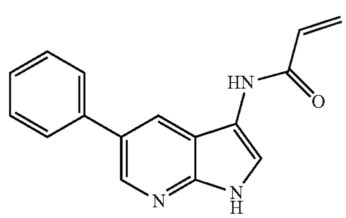 [SMILES: C=CC(=O)Nc1c[nH]c2ncc(-c3ccccc3)cc12] | N-(5-phenyl-1H-pyrrolo[2,3-b]pyridin-3-yl)acrylamide | ¹H NMR (400 MHz, DMSO-d₆) δ ppm, 11.53 (s, 1H), 10.31 (s, 1H), 8.53 (dd, J = 1.95 Hz, 2H), 7.71 (d, J = 7.05 Hz, 2H), 7.51 (t, J = 7.43 Hz, 1H), 6.58-6.51 (m, 1H), 6.26 (dd, J = 1.95 Hz, 14.87 Hz, 1H), 5.75 (dd, J = 1.96 Hz, 8.22 Hz, 1H). MS (ES) m/z 264 (M + H). |
| 237 | 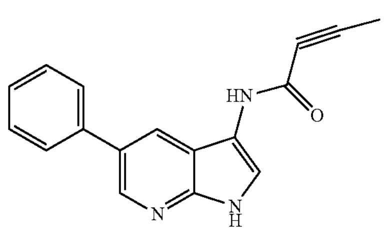 [SMILES: CC#CC(=O)Nc1c[nH]c2ncc(-c3ccccc3)cc12] | N-(5-phenyl-1H-pyrrolo[2,3-b]pyridin-3-yl)but-2-ynamide | ¹H NMR (400 MHz, DMSO-d₆) δ ppm, 11.50 (s, 1H), 10.86 (s, 1H), 8.55 (dd, J = 1.95 Hz, 27.39 Hz, 2H), 7.91 (s, 3H), 7.77 (d, J = 2.73 Hz, 1H), 7.67 (d, J = 7.43 Hz, 2H), 7.47 (t, J = 7.44 Hz, 1H), 7.33 (t, J = 7.44 Hz, 1H). MS (ES) m/z 276 (M + H). |
| 238 | 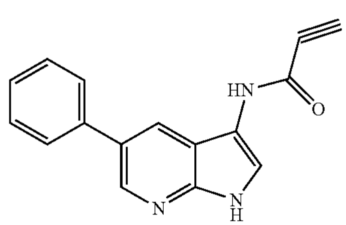 [SMILES: C#CC(=O)Nc1c[nH]c2ncc(-c3ccccc3)cc12] | N-(5-phenyl-1H-pyrrolo[2,3-b]pyridin-3-yl)propiolamide | ¹H NMR (400 MHz, DMSO-d₆) δ ppm, 11.60 (s, 1H), 10.92 (s, 1H), 8.62-8.55 (m, 2H), 7.57-7.37 (m, 2H), 2.89 (s, 1H). MS (ES) m/z 262 (M+30H). |

TABLE 1-continued

Compound Examples — Spectral Data

| Example | Structure | Name | Spectral Data |
| --- | --- | --- | --- |
| 239 | 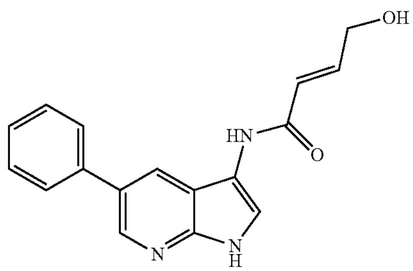 [SMILES: O=C(/C=C/CO)Nc1c[nH]c2ncc(-c3ccccc3)cc12] | (E)-4-hydroxy-N-(5-phenyl-1H-pyrrolo[2,3-b]pyridin-3-yl)but-2-enamide | $^1$H NMR (400 MHz, DMSO-d$_6$) δ ppm, 11.42 (s, 1H), 10.19 (s, 1H), 8.51 (m, 1H), 7.89 (d, J = 2.34 Hz, 2H), 7.67 (d, J = 2.34 Hz, 2H), 7.67 (d, J = 7.04 Hz, 2H), 7.49-7.45 (m, 2H), 6.86-6.80 (m, 1H), 6.43 (d, J = 15.25 Hz, 1H), 5.12 (t, J = 5 Hz, 1H), 4.17 (s, 2H). MS (ES) m/z 294 (M + H). |
| 240 | 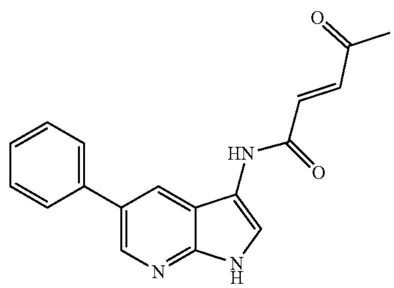 [SMILES: CC(=O)/C=C/C(=O)Nc1c[nH]c2ncc(-c3ccccc3)cc12] | (E)-4-oxo-N-(5-phenyl-1H-pyrrolo[2,3-b]pyridin-3-yl)pent-2-enamide | $^1$H NMR (400 MHz, DMSO-d$_6$) δ ppm, 11.61 (s, 1H), 10.75 (s, 1H), 8.54 (d, J = 1.95 Hz, 1H), 8.48 (d, J = 1.95 Hz, 1H), 7.97 (d, J = 2.74 Hz, 1H), 7.70-7.67 (m, 2H), 7.50-7.46 (m, 2H), 7.37-7.33 (m, 1H), 7.13 (d, J = 15.65 Hz, 1H), 6.91-6.87 (d, J = 15.65 Hz, 1H), 2.24 (s, 1H). MS (ES) m/z 306 (M + H). |
| 241 | 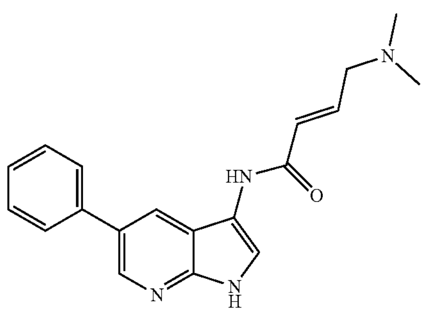 [SMILES: CN(C)C/C=C/C(=O)Nc1c[nH]c2ncc(-c3ccccc3)cc12] | (E)-4-(dimethylamino)-N-(5-phenyl-1H-pyrrolo[2,3-b]pyridin-3-yl)but-2-enamide | $^1$H NMR (400 MHz, DMSO-d$_6$) δ ppm, 11.47 (s, 1H), 10.26 (s, 1H), 8.53-8.49 (m, 2H), 8.31 (dd, J = 1.17 Hz, 7.04 Hz, 1H), 7.89 (d, J = 2.34 Hz, 1H), 7.68-7.66 (m, 1H), 7.47 (t, J = 7.47 Hz, 2H), 7.36-7.30 (m, 1H), 6.55 (d, J = 15.26 Hz, 1H), 6.39 (d, J = 15.26 Hz, 1H), 2.83 (d, J = 9 Hz, 2H), 2.25 (d, J = 6.65 Hz, 6H). MS (ES) m/z 321 (M + H). |
| 242 | 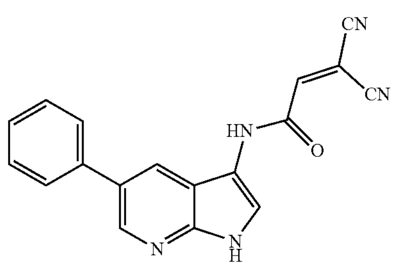 [SMILES: N#CC(C#N)=CC(=O)Nc1c[nH]c2ncc(-c3ccccc3)cc12] | 2-((5-phenyl-1H-pyrrolo[2,3-b]pyridin-3-yl)methylene)malononitrile | $^1$H NMR(400 MHz, DMSO-d$_6$) δ ppm, 12.96 (s, 1H), 8.72-8.52 (m, 4H), 7.79-7.41 (m, 5H). MS (ES) m/z 271 (M + H). |
| 244 | 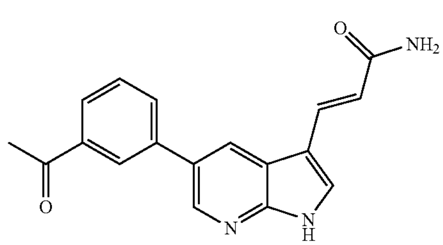 [SMILES: CC(=O)c1cccc(-c2cnc3[nH]cc(/C=C/C(N)=O)c3c2)c1] | (E)-3-(5-(3-acetylphenyl)-1H-pyrrolo[2,3-b]pyridin-3-yl)acrylamide | $^1$H NMR(400 MHz, DMSO-d6) δ ppm, 12.26 (s, 1H), 8.65 (s, 1H), 8.53 (s, 1H), 8.36-8.31 (m, 1H), 8.10-8.03 (m, 1H), 8.28 (s, 1H), 7.72-7.68 (m, 2H), 7.61 (d, J = 16.04 Hz, 1H), 7.41 (br. s, 1H), 6.93 (br. s, 1H), 6.73 (d, J = 16.05 Hz, 1H), 3.33 (s, 3H). MS (ES) m/z 306 (M + H). |

TABLE 1-continued

Compound Examples — Spectral Data

| Example | Structure | Name | Spectral Data |
|---|---|---|---|
| 245 | 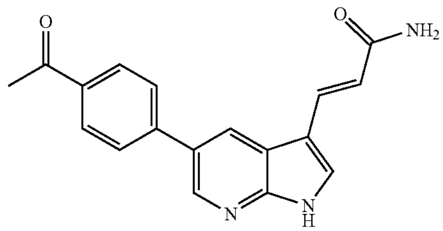 [SMILES: CC(=O)c1ccc(-c2cnc3[nH]cc(/C=C/C(N)=O)c3c2)cc1] | (E)-3-(5-(4-acetylphenyl)-1H-pyrrolo[2,3-b]pyridin-3-yl)acrylamide | $^1$H NMR (400 MHz, DMSO-d$_6$) δ ppm, 12.23 (s, 1H), 8.68 (s, 1H), 8.09 (d, J= 8.22 Hz, 2H), 7.98 (s, 1H), 7.96 (d, J = 8.66 Hz, 2H), 7.61 (d, J = 16.04 Hz, 1H), 7.38 (br. s, 1H), 6.95 (br. s, 1H), 6.72 (d, J = 16.04 Hz, 1H), 3.35 (s, 3H). MS (ES) m/z 306 (M + H). |
| 246 | 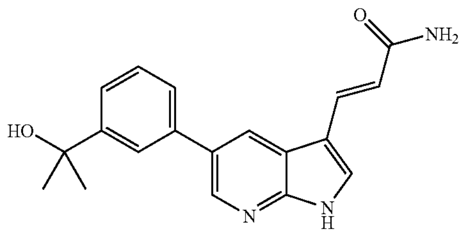 [SMILES: CC(C)(O)c1cccc(-c2cnc3[nH]cc(/C=C/C(N)=O)c3c2)c1] | (E)-3-(5-(3-(2-hydroxypropan-2-yl)phenyl)-1H-pyrrolo[2,3-b]pyridin-3-yl)acrylamide | $^1$H NMR(400 MHz, DMSO-d$_6$) δ ppm, 12.18 (s, 1H), 8.55 (s, 1H), 8.42 (s, 1H), 7.95 (s, 1H), 7.80 (s, 1H), 7.61 (d, J = 17.61 Hz, 1H), 7.54-7.44 (m, 3H), 7.38 (br. s, 1H), 6.91 (br. s, 1H), 6.67 (d, J = 15.25 Hz, 1H), 1.51 (s, 6H). MS (ES) m/z 322 (M + H). |
| 247 | 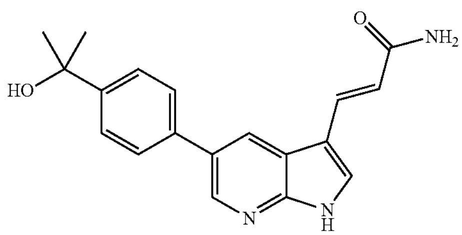 [SMILES: CC(C)(O)c1ccc(-c2cnc3[nH]cc(/C=C/C(N)=O)c3c2)cc1] | (E)-3-(5-(4-(2-hydroxypropan-2-yl)phenyl)-1H-pyrrolo[2,3-b]pyridin-3-yl)acrylamide | $^1$H NMR(400 MHz, DMSO-d$_6$) δ ppm, 12.18 (s, 1H), 8.56 (s, 1H), 8.43 (s, 1H), 7.94 (s, 1H), 7.68 (d, J = 8.22 Hz, 2H), 7.61-7.57 (m, 3H), 7.38 (br. s, 1H), 6.92 (br. s), 6.70 (d, J = 16.04 Hz, 1H), 1.48 (s, 6H). MS (ES) m/z 322 (M + H). |
| 248 | 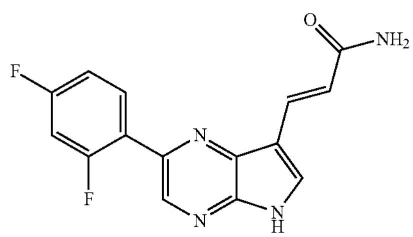 [SMILES: NC(=O)/C=C/c1c[nH]c2ncc(-c3ccc(F)cc3F)nc12] | (E)-3-(2-(2,4-difluorophenyl)-5H-pyrrolo[2,3-b]pyrazin-7-yl)acrylamide | $^1$H NMR (400 MHz, DMSO-d$_6$) δ ppm, 12.57 (s, 1H), 8.70 (d, J = 2.35 Hz, 1H), 8.29 (d, J = 2.74 Hz, 1H), 8.20-8.14 (m, 1H), 7.62 (br. s, 1H), 7.60 (d, J = 15.65 Hz, 1H), 7.51-7.45 (m, 1H), 7.32-7.27 (m, 1H), 7.18 (d, J = 15.65 Hz, 1H), 6.94 (br. s, 1H). MS (ES) m/z 301 (M + H). |
| 249 | 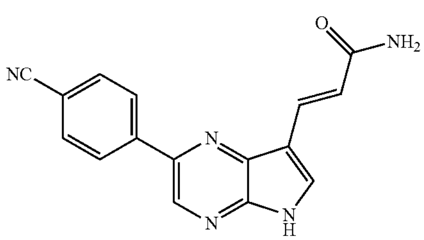 [SMILES: N#Cc1ccc(-c2cnc3[nH]cc(/C=C/C(N)=O)c3n2)cc1] | (E)-3-(2-(4-cyanophenyl)-5H-pyrrolo[2,3-b]pyrazin-7-yl)acrylamide | $^1$H NMR (400 MHz, DMSO-d$_6$) δ ppm, 12.60 (s, 1H), 9.10 (s, 1H), 8.52 (d, J = 8.21 Hz, 2H), 8.30 (s, 1H), 8.00 (d, J = 8.22 Hz, 2H), 7.70 (br. s, 1H), 7.60 (d, J = 15.65 Hz, 1H), 7.30 (d, J = 15.26 Hz, 1H), 6.98 (br. s, 1H). MS (ES) m/z 290 (M + H). |
| 250 | 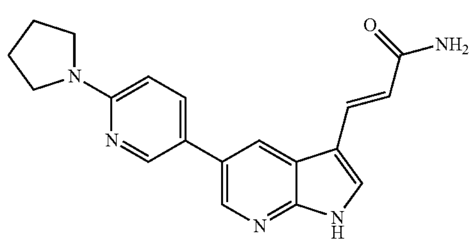 [SMILES: NC(=O)/C=C/c1c[nH]c2ncc(-c3ccc(N4CCCC4)nc3)cc12] | (E)-3-(5-(6-(pyrrolidin-1-yl)pyridin-3-yl)-1H-pyrrolo[2,3-b]pyridin-3-yl)acrylamide | $^1$H NMR (400 MHz, DMSO-d$_6$) δ ppm, 12.16 (s, 1H), 8.53 (d, J = 1.96 Hz, 1H), 8.51 (d, J = 2.35 Hz, 1H), 8.39 (d, J = 2.34 Hz, 1H), 7.93 (d, J = 2.34 Hz, 1H), 7.92-7.91 (m, 1H), 7.58 (d, J = 15.65 Hz, 1H), 7.37 (br. s, 1H), 6.92 (br. s, 1H), 6.69 (d, J = 16.04 Hz, 1H), 6.57 (d, J = 9.00 Hz, 1H), 3.46-3.43 (m, 4H), 1.99-1.96 (m, 4H). MS (ES) m/z 334 (M + H). |

US 9,499,551 B2

TABLE 1-continued

Compound Examples — Spectral Data

| Example | Structure | Name | Spectral Data |
|---|---|---|---|
| 251 | 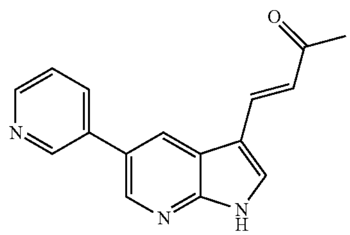 [SMILES: CC(=O)/C=C/c1c[nH]c2ncc(-c3cccnc3)cc12] | (E)-4-(5-(pyridin-3-yl)-1H-pyrrolo[2,3-b]pyridin-3-yl)but-3-en-2-one | $^1$H NMR (400 MHz, DMSO-d$_6$) δ ppm, 12.51 (s, 1H), 9.14 (s, 1H), 8.75 (s, 1H), 8.70-8.68 (m, 2H), 8.43 (br. s, 1H), 8.20 (s, 1H), 7.86 (d, J = 16.43 Hz, 1H), 7.68 (br. s, 1H), 6.92 (d, J = 16.43 Hz, 1H), 2.33 (s, 3H). MS (ES) m/z 264 (M + H). MS (ES) m/z 264 (M + H). |
| 252 | 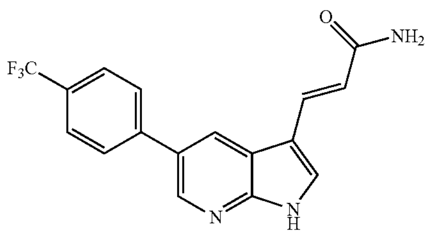 [SMILES: NC(=O)/C=C/c1c[nH]c2ncc(-c3ccc(C(F)(F)F)cc3)cc12] | (E)-3-(5-(4-(trifluoromethyl)phenyl)-1H-pyrrolo[2,3-b]pyridin-3-yl)acrylamide | $^1$H NMR (400 MHz, DMSO-d$_6$) δ ppm, 12.32 (s, 1H), 8.73 (s, 1H), 8.63 (s, 1H), 8.46 (s, 2H), 7.97 (s, 1H), 7.87 (d, J = 8.22 Hz, 2H), 7.61 (d, J = 16.04 Hz, 1H), 7.34 (br. S, 1H), 6.92 (br. S, 1H), 6.71 (d, J = 15.65 Hz, 1H). MS (ES) m/z 332 (M + H). |
| 253 | 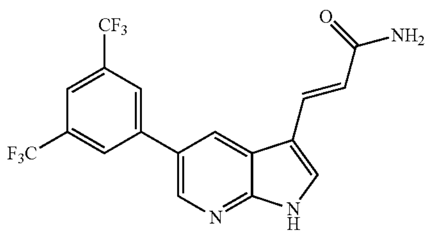 | (E)-3-(5-(3,5-bis(trifluoromethyl)phenyl)-1H-pyrrolo[2,3-b]pyridin-3-yl)acrylamide | $^1$H NMR (400 MHz, DMSO-d$_6$) δ ppm, 12.31 (s, 1H), 8.66 (s, 1H), 8.54 (s, 1H), 8.02 (d, J = 8.61 Hz, 2H), 8.12 (s, 1H), 8.00 (s, 1H), 7.65 (d, J = 16.04 Hz, 1H), 7.45 (br. S, 1H), 6.92 (br. S, 1H), 6.68 (d, J = 16.04 Hz, 1H). MS (ES) m/z 400 (M + H). |
| 254 | 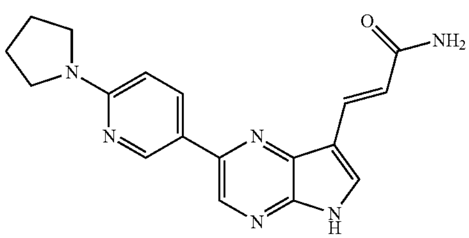 [SMILES: NC(=O)/C=C/c1c[nH]c2ncc(-c3ccc(N4CCCC4)nc3)nc12] | (E)-3-(2-(6-(pyrrolidin-1-yl)pyridin-3-yl)-5H-pyrrolo[2,3-b]pyrazin-7-yl)acrylamide | $^1$H NMR (400 MHz, DMSO-d$_6$) δ ppm, 12.16 (s, 1H), 8.82 (d, J = 2.35 Hz, 1H), 8.39 (d, J = 2.34 Hz, 1H), 7.93 (d, J = 2.34 Hz, 1H), 7.92-7.91 (m, 1H , 7.58 (d, J = 15.65 Hz, 1H), 7.37 (br. s, 1H), 6.92 (br. s, 1H), 6.69 (d, J = 16.04 Hz, 1H), 6.57 (d, J = 9.00 Hz, 1H), 3.46-3.43 (m, 4H), 1.99-1.96 (m, 4H). MS (ES) m/z 335 (M + H). |
| 255 | 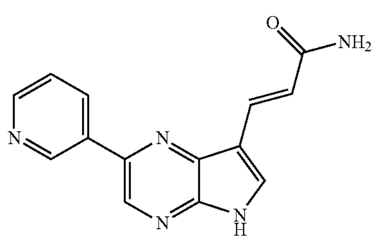 [SMILES: NC(=O)/C=C/c1c[nH]c2ncc(-c3cccnc3)nc12] | (E)-3-(2-(pyridin-3-yl)-5H-pyrrolo[2,3-b]pyrazin-7-yl)acrylamide | MS (ES) m/z 266 (M + H). |
| 256 | 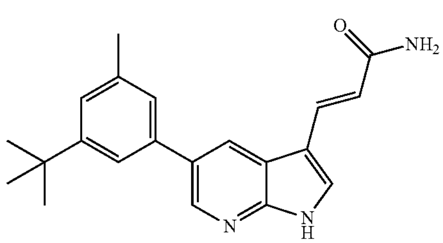 [SMILES: Cc1cc(-c2cnc3[nH]cc(/C=C/C(N)=O)c3c2)cc(C(C)(C)C)c1] | (E)-3-(5-(3-(tert-butyl)-5-methylphenyl)-1H-pyrrolo[2,3-b]pyridin-3-yl)acrylamide | $^1$H NMR(400 MHz, DMSO-d$_6$) δ ppm, 12.16 (s, 1H), 8.53 (s, 1H), 8.38 (s, 1H), 7.94 (s, 1H), 7.61 (d, J = 15.65 Hz, 1H), 7.46 (s, 1H), 7.33 (br. s, 1H), 7.25 (s, 1H), 6.90 (br. s, 1H), 6.66 (d, J = 15.65 Hz, 1H), 2.41 (s, 3H), 1.36 (s, 9H). MS (ES) m/z 334 (M + H). |

TABLE 1-continued

Compound Examples — Spectral Data

| Example | Structure | Name | Spectral Data |
| --- | --- | --- | --- |
| 257 | 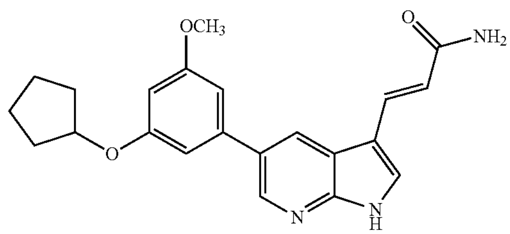 [SMILES: COc1cc(OC2CCCC2)cc(-c2cnc3[nH]cc(/C=C/C(N)=O)c3c2)c1] | (E)-3-(5-(3-(cyclopentyloxy)-5-methoxyphenyl)-1H-pyrrolo[2,3-b]pyridin-3-yl)acrylamide | $^1$H NMR (400 MHz, DMSO-$d_6$) δ ppm, 12.17 (s, 1H), 8.50 (d, J = 1.96 Hz, 1H), 8.36 (d, J = 1.96 Hz, 1H), 7.94 (d, J = 2.35 Hz, 1H), 7.62 (d, J = 16.04 Hz, 1H), 7.44 (s, 3H), 7.34 (s, 1H), 6.90 (s, 1H), 6.64 (d, J = 16.04 Hz, 1H), 1.37 (s, 18H). MS (ES) m/z 376 (M + H). |
| 258 | 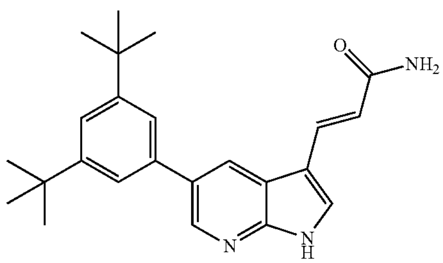 [SMILES: CC(C)(C)c1cc(-c2cnc3[nH]cc(/C=C/C(N)=O)c3c2)cc(C(C)(C)C)c1] | (E)-3-(5-(3,5-di-tert-butylphenyl)-1H-pyrrolo[2,3-b]pyridin-3-yl)acrylamide | $^1$H NMR(400 MHz, DMSO-$d_6$) δ ppm, 12.17 (s, 1H), 8.50 (d, J = 1.96 Hz, 1H), 8.36 (d, J = 1.96 Hz, 1H), 7.94 (d, J = 2.35 Hz, 1H), 7.62 (d, J = 16.04 Hz, 1H), 7.44 (s, 3H), 7.34 (s, 1H), 6.90 (s, 1H), 6.64 (d, J = 16.04 Hz, 1H), 1.37 (s, 18H). MS (ES) m/z 376 (M + H). |
| 259 | 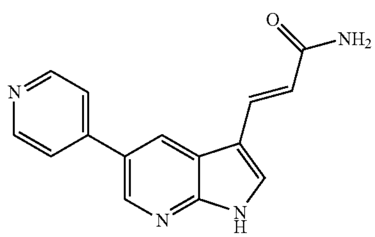 [SMILES: NC(=O)/C=C/c1c[nH]c2ncc(-c3ccncc3)cc12] | (E)-3-(5-(pyridin-4-yl)-1H-pyrrolo[2,3-b]pyridin-3-yl)acrylamide | $^1$H NMR(400 MHz, DMSO-$d_6$) δ ppm, 8.63-8.60 (m, 3H), 8.46 (d, J = 1.95 Hz, 1H), 7.89 (s, 1H), 7.82-7.80 (m, 2H), 7.60 (d, J = 15.65 Hz, 1H), 7.20 (br. s, 1H), 6.68 (br. s, 1H), 6.50 (d, J = 15.65 Hz, 1H). MS (ES) m/z 265 (M + H). |
| 260 | 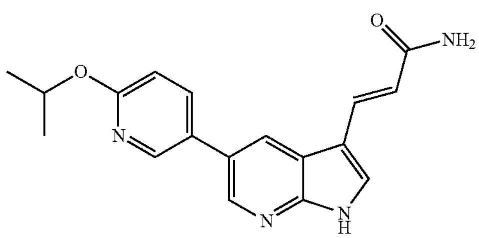 [SMILES: CC(C)Oc1ccc(-c2cnc3[nH]cc(/C=C/C(N)=O)c3c2)cn1] | (E)-3-(5-(6-isopropoxypyridin-3-yl)-1H-pyrrolo[2,3-b]pyridin-3-yl)acrylamide | $^1$H NMR (400 MHz, DMSO-$d_6$) δ ppm, 12.20 (s, 1H), 8.58 (d, J = 1.57 Hz, 1H), 8.56 (d, J = 2.35 Hz, 1H), 8.46 (d, J = 1.96 Hz, 1H), 8.10 (dd, J = 8.60, 2.74 Hz, 1H), 7.94 (d, J = 2.74 Hz, 1H), 7.59 (d, J = 15.65 Hz, 1H), 7.34 (br. s, 1H), 6.92 (br. s, 1H), 6.89 (d, J = 8.61 Hz, 1H), 6.72 (d, J = 16.04 Hz, 1H), 5.33-5.30 (m, 1H), 1.34 (d, J = 6.26 Hz, 6H). MS (ES) m/z 323 (M + H). |
| 261 | 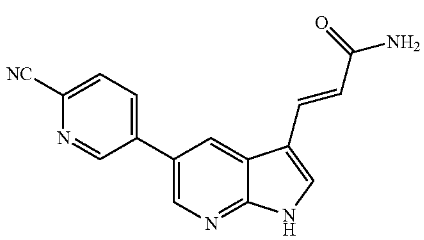 [SMILES: N#Cc1ccc(-c2cnc3[nH]cc(/C=C/C(N)=O)c3c2)cn1] | (E)-3-(5-(6-cyanopyridin-3-yl)-1H-pyrrolo[2,3-b]pyridin-3-yl)acrylamide | MS (ES) m/z 290 (M + H). |
| 262 | 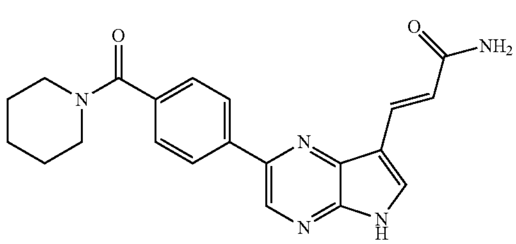 [SMILES: NC(=O)/C=C/c1c[nH]c2ncc(-c3ccc(C(=O)N4CCCCC4)cc3)nc12] | (E)-3-(5-(4-(piperidine-1-carbonyl)phenyl)-1H-pyrrolo[2,3-b]pyridin-3-yl)acrylamide | MS (ES) m/z 375 (M + H). |

TABLE 1-continued

Compound Examples — Spectral Data

| Example | Structure | Name | Spectral Data |
|---|---|---|---|
| 263 | 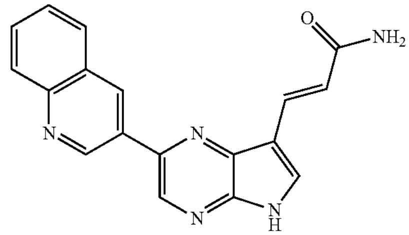 [SMILES: NC(=O)/C=C/c1c[nH]c2ncc(-c3cnc4ccccc4c3)nc12] | (E)-3-(2-(quinolin-3-yl)-5H-pyrrolo[2,3-b]pyrazin-7-yl)acrylamide | $^1$H NMR (400 MHz, DMSO-d$_6$) δ ppm, 12.55 (br s, 1H), 9.88 (d, J= 2.0 Hz, 1H), 9.20 (s, 2H), 8.29 (s, 1H), 8.16 (d, J = 7.2 Hz, 1H), 8.11 (d, J = 8.4 Hz, 1H), 7.83 (t, J = 7.2 Hz, 1H), 7.74 (s, 1H), 7.70 (t, J = 8.0 Hz, 1H), 7.64 (d, J = 15.6 Hz, 1H), 7.37 (d, J = 15.6 Hz, 1H), 6.97 (s, 1H) ppm.MS (ES) m/z 316 (M + H). |
| 264 | 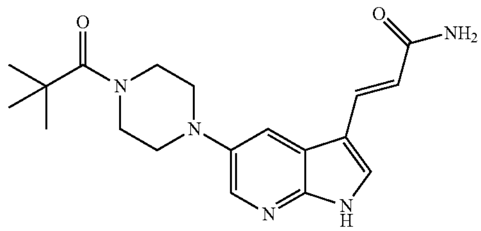 [SMILES: CC(C)(C)C(=O)N1CCN(c2cnc3[nH]cc(/C=C/C(N)=O)c3c2)CC1] | (E)-3-(5-(4-pivaloylpiperazin-1-yl)-1H-pyrrolo[2,3-b]pyridin-3-yl)acrylamide | $^1$H NMR(400 MHz, MeOD-d$_6$) δ ppm, 8.15 (d, J = 2.4 Hz, 1H), 7.90 (d, J = 2.8 Hz, 1H), 7.71 (d, J = 16 Hz, 1H), 7.70 (s, 1H), 6.62 (d, J = 16 Hz, 1H), 3.90 (m, 4H), 3.22 (m, 4H), 1.33 (s, 9H). MS (ES) m/z 356 (M + H). |
| 265 | 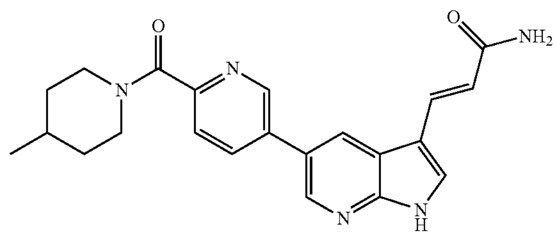 [SMILES: CC1CCN(C(=O)c2ccc(-c3cnc4[nH]cc(/C=C/C(N)=O)c4c3)cn2)CC1] | (E)-3-(5-(6-(4-methylpiperidine-1-carbonyl)pyridin-3-yl)-1H-pyrrolo[2,3-b]pyridin-3-yl)acrylamide | $^1$H NMR(400 MHz, DMSO-d$_6$) δ ppm, 8.96 (d,J = 2.0 Hz, 1H), 8.63-8.61 (m, 2H), 8.30 (dd, J$_1$ = 2.0 Hz, J$_2$ = 8.0 Hz, 1H), 7.83 (s, 1H), 7.76 (d, J =16.0 Hz, 1H), 7.69 (J$_1$ = 0.4 Hz, J$_2$ = 8.0 Hz, 1H), 6.78 (d, J = 16.0 Hz, 1H), 4.67-4.63 (m, 1H), 3.81-3.77 (m, 1H), 3.19-3.11 (m, 1H), 2.95-2.87 (m, 1H), 1.85-1.63 (m, 3H), 1.32-1.19 (m, 2H), 1.00 (d, J = 6.8 Hz, 3H). MS (ES) m/z 389 (M + H). |
| 266 | 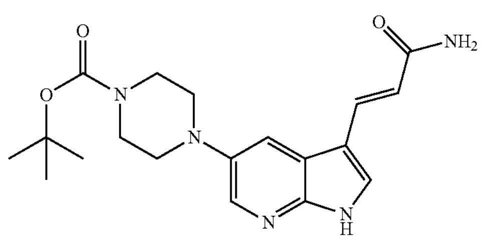 [SMILES: CC(C)(C)OC(=O)N1CCN(c2cnc3[nH]cc(/C=C/C(N)=O)c3c2)CC1] | (E)-tert-butyl 4-(3-(3-amino-3-oxoprop-1-en-1-yl)-1H-pyrrolo[2,3-b]pyridin-5-yl)piperazine-1-carboxylate | $^1$H NMR (400 MHz, DMSO-d$_6$) δ ppm, 11.89 (s, 1H), 8.16 (d, J = 2.35 Hz, 1H), 7.81 (d, J = 2.74 Hz, 1H), 7.75 (d, J = 2.34 Hz, 1H), 7.54 (d, J = 16.04 Hz, 1H), 7.33 (br. s, 1H), 6.87 (br. s, 1H), 6.53 (d, J = 16.04 Hz, 1H), 3.55-3.53 (m, 4H), 3.12-3.09 (m, 4H), 1.43 (s, 9H). MS (ES) m/z 372 (M + H). |
| 267 | 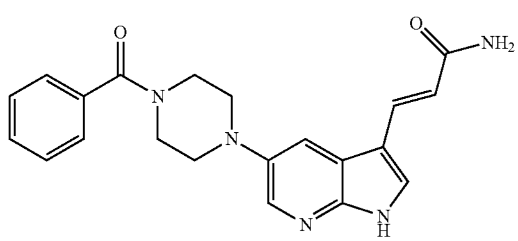 [SMILES: NC(=O)/C=C/c1c[nH]c2ncc(N3CCN(C(=O)c4ccccc4)CC3)cc12] | (E)-3-(5-(4-benzoylpiperazin-1-yl)-1H-pyrrolo[2,3-b]pyridin-3-yl)acrylamide | $^1$H NMR (400 MHz, MeOD-d$_6$) δ ppm, 8.06 (d,J = 2.4 Hz, 1H), 7.77 (d, J = 2.8 Hz, 1H), 7.68 (s, 1H), 7.54 (d, J = 16.8 Hz, 1H), 7.41-7.38 (m, 5H), 5.90 (d, J = 16.8 Hz, 1H), 3.88 (m, 2H), 3.57 (m, 2H), 3.20-2.95 (m, 4H). MS (ES) m/z 358 (M + H). |
| 268 | 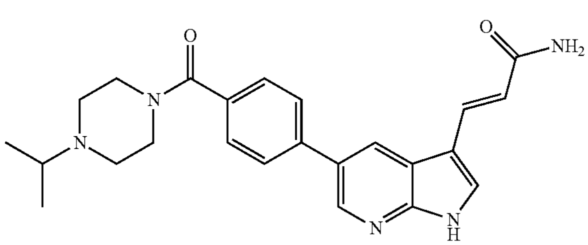 [SMILES: CC(C)N1CCN(C(=O)c2ccc(-c3cnc4[nH]cc(/C=C/C(N)=O)c4c3)cc2)CC1] | (E)-3-(5-(4-(4-isopropyl-piperazine-1-carbonyl)phenyl)-1H-pyrrolo[2,3-b]pyridin-3-yl)acrylamide | $^1$H NMR (400 MHz, DMSO-d$_6$) δ ppm, 12.21 (s, 1H), 8.63 (d, J = 1.95 Hz, 1H), 8.63 (d, J = 1.95 Hz, 1H), 8.50 (d, J = 1.96 Hz, 1H), 7.96 (d, J = 2.35 Hz, 1H), 7.84 (d, J = 8.22 Hz, 2H), 7.63 (d, J = 16.04 Hz, 1H), 7.52 (d, J = 8.21 Hz, 2H), 7.36 (br. s, 1H), 6.92 (br. s, 1H), 6.71 (d, J = 15.65 Hz, 1H), 3.63-3.57 (m, 2H) 3.38-3.33 (m, 2H), 2.72-2.68 (m, 1H), 2.50-2.39 (m, 2H), 1.27-1.24 (m, 2H), 0.98 (d, 6H). MS (ES) m/z 418 (M + H). |

TABLE 1-continued

Compound Examples — Spectral Data

| Example | Name | Spectral Data |
|---|---|---|
| 269 | (E)-tert-butyl(1-(3-(3-amino-3-oxoprop-1-en-1-yl)-1H-pyrrolo[2,3-b]pyridin-5-yl)azetidin-3-yl)carbamate | $^1$H NMR (400 MHz, DMSO-d$_6$) δ ppm, 11.79 (s, 1H), 7.76 (s, 1H), 7.65 (d, J = 2.3 Hz, 1H), 7.57 (d, J = 6.6 Hz, 1H), 7.52 (d, J = 15.6 Hz, 1H), 7.31 (s, 1H), 7.20 (d, J = 2.3 Hz, 1H), 6.80 (s, 1H), 6.45 (d, J = 15.6 Hz, 1H), 4.44 (m, 1H), 4.16 (t, J = 7.4 Hz, 2H), 3.62 t, J = 6.2 Hz, 2H), 1.40 (s, 9H). MS (ES) m/z 358 (M + H). |
| 270 | (E)-4-(3-(3-amino-3-oxoprop-1-en-1-yl)-1H-pyrrolo[2,3-b]pyridin-5-yl)-N-cyclopropyl-benzamide | $^1$H NMR (400 MHz, DMSO-d$_6$) δ ppm, 12.23 (s, 1H), 8.65 (d, J = 1.96 Hz, 1H), 8.52 (s, 1H), 7.97-7.96 (m, 3H), 7.87 (d, J = 8.22 Hz, 2H), 7.61 (d, J = 16.04 Hz, 1H), 7.36 (br. s, 1H), 6.92 (br. s, 1H), 6.71 (d, J = 16.04 Hz, 1H), 2.91-2.88 (m, 1H), 0.74-0.71 (m, 2H), 0.61-0.60 (m, 2H). MS (ES) m/z 347 (M + H). |
| 271 | (E)-3-(5-(4-(2-ethoxyethyl)piperazin-1-yl)-1H-pyrrolo[2,3-b]pyridin-3-yl)acrylamide | $^1$H NMR (400 MHz, DMSO-d$_6$) δ ppm, 11.96 (s, 1H), 8.20 (d, J = 2.35 Hz, 1H), 7.84 (d, J = 2.74 Hz, 1H), 7.77 (d, J = 2.35 Hz, 1H), 7.56 (d, J = 15.65 Hz, 1H), 7.34 (br. s, 1H), 6.90 (br. s, 1H), 6.51(d, J = 16.045 Hz, 1H), 3.83-3.75 (m, 4H), 3.65-3.62 (m, 2H), 3.53 (q, 2H), 3.46-3.38 (m, 2H), 3.33-3.30 (m, 2H), 3.17-3.14 (m, 2H), 1.17 (t, 3H). MS (ES) m/z 344 (M + H). |
| 272 | (E)-3-(5-(2-isopropoxy-6-(trifluoromethyl)pyridin-4-yl)-1H-pyrrolo[2,3-b]pyridin-3-yl)acrylamide | $^1$H NMR (400 MHz, DMSO-d$_6$) δ ppm, 12.33 (s, 1H), 8.79 (s, 1H), 8.66 (s, 1H), 8.00 (s, 1H), 7.90 (s, 1H), 7.62 (d, J = 15.65 Hz, 1H), 7.49 (s, 1H), 7.34 (br. s, 1H), 6.95 (br. s, 1H), 6.72 (d, J = 16.04 Hz, 1H), 5.32 (m, 1H), 1.37 (s, 6H). MS (ES) m/z 391 (M + H). |
| 273 | (E)-3-(5-(2-(4-methylpiperazin-1-yl)pyridin-4-yl)-1H-pyrrolo[2,3-b]pyridin-3-yl)acrylamide | MS (ES) m/z 363 (M + H). |
| 274 | (E)-3-(5-(4-fluorobenzyl)-1H-pyrrolo[2,3-b]pyridin-3-yl)acrylamide | $^1$H NMR(400 MHz, DMSO-d$_6$) δ ppm, 11.85 (s, 1H), 8.13 (s, 1H), 7.79 (s, 1H), 7.72 (s, 1H), 7.54 (d, J = 16.04 Hz, 1H), 7.40-7.37 (m, 2H), 7.33 (br. s, 1H), 7.20-7.15 (m, 2H), 6.86 (br. s, 1H), 6.52 (d, J = 16.04 Hz, 1H), 3.56 (s, 2H), 3.18-3.16 (m, 4H), 2.60-2.57 (m, 4H). MS (ES) m/z 380 (M + H). |

TABLE 1-continued

Compound Examples — Spectral Data

| Example | Structure | Name | Spectral Data |
|---|---|---|---|
| 275 | 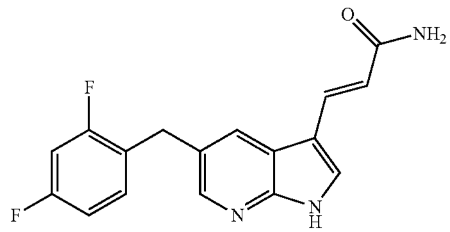 [SMILES: NC(=O)/C=C/c1c[nH]c2ncc(Cc3ccc(F)cc3F)cc12] | (E)-3-(5-(2,4-difluorobenzyl)-1H-pyrrolo[2,3-b]pyridin-3-yl)acrylamide | $^1$H NMR (400 MHz, DMSO-d$_6$) δ ppm, 11.85 (s, 1H), 8.12 (s, 1H), 7.78 (s, 1H), 7.72 (s, 1H), 7.52 (d, J = 15.65 Hz, 1H), 7.53-7.47 (m, 1H), 7.32 (br. s, 1H), 7.26-7.21 (m, 1H), 7.12-7.08 (m, 1H), 6.85 (br. s, 1H), 6.51 (d, J = 16.04 Hz, 1H), 3.60 (s, 2H), 3.31 (br. s, 4H), 2.61 (br. s, 4H). MS (ES) m/z 398 (M + H). 1H NMR(400 MHz, MeOD-d6) δ ppm 8.16 (d,J =2.8 Hz, 1H), 7.92 (d, J =2.4 Hz, 1H), 7.73 |
| 276 | 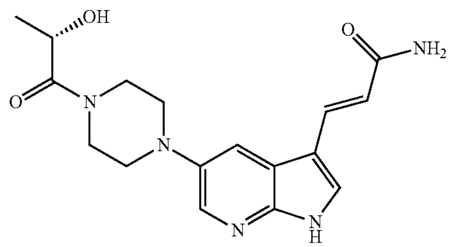 [SMILES: C[C@H](O)C(=O)N1CCN(c2cnc3[nH]cc(/C=C/C(N)=O)c3c2)CC1] | (S,E)-3-(5-(4-(2-hydroxypropanoyl)piperazin-1-yl)-1H-pyrrolo[2,3-b]pyridin-3-yl)acrylamide | $^1$H NMR (400 MHz, MeOD-d$_6$) δ ppm, 8.16 (d, J = 2.8 Hz, 1H) 7.92 (d, J = 2.4 Hz, 1H), 7.73 (d, J = 16 Hz, 1H), 7.72 (s, 1H), 6.63 (d, J = 16 Hz, 1H), 4.66 (q, J = 6.8 Hz, 1H), 3.95-3.75 (m, 4H), 3.25 (m, 4H), 1.38 (d, J = 6.8 Hz, 3H). MS (ES) m/z 344 (M + H). |
| 277 | 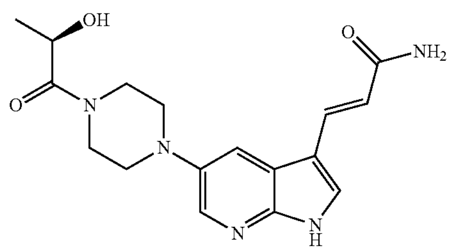 [SMILES: C[C@@H](O)C(=O)N1CCN(c2cnc3[nH]cc(/C=C/C(N)=O)c3c2)CC1] | (R,E)-3-(5-(4-(2-hydroxypropanoyl)piperazin-1-yl)-1H-pyrrolo[2,3-b]pyridine-3-yl)acrylamide | $^1$H NMR(400 MHz, MeOD-d$_6$) δ ppm, 8.15 (d, J = 2.4 Hz, 1H), 7.92 (d, J = 2.8 Hz, 1H), 7.71 (d, J = 16 Hz, 1H), 7.70 (s, 1H), 6.62 (d, J = 16 Hz, 1H), 4.66 (q, J = 6.4 Hz, 1H), 4.00-3.75 (m, 4H), 3.23 (m, 4H), 1.38 (d, J = 6.4 Hz, 3H). MS (ES) m/z 344 (M + H). |
| 278 | 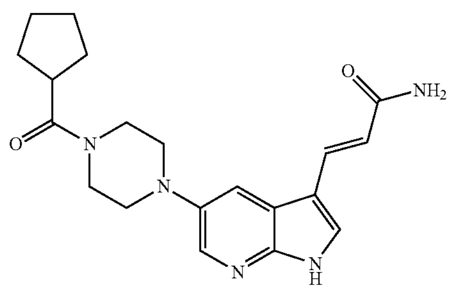 [SMILES: NC(=O)/C=C/c1c[nH]c2ncc(N3CCN(C(=O)C4CCCC4)CC3)cc12] | (E)-3-(5-(4-(cyclopentane-carbonyl)piperazin-1-yl)-1H-pyrrolo[2,3-b]pyridin-3-yl)acrylamide | $^1$H NMR (400 MHz, MeOD-d$_6$) δ ppm, 8.16 (d, J = 2.4 Hz, 1H), 7.92 (d, J = 2.4 Hz, 1H), 7.73 (d, J = 16 Hz, 1H), 7.71 (s, 1H), 6.38 (d, J = 16 Hz, 1H), 3.84 (m, 4H), 3.25 (m, 2H), 3.19 (m, 2H), 3.13 (m, 1H), 2.00-1.61 (m, 8H). MS (ES) m/z 368 (M + H). |
| 279 | 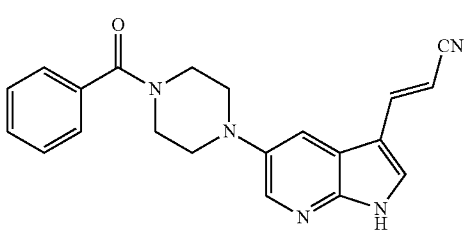 [SMILES: N#C/C=C/c1c[nH]c2ncc(N3CCN(C(=O)c4ccccc4)CC3)cc12] | (E)-3-(5-(4-benzoylpiperazin-1-yl)-1H-pyrrolo[2,3-b]pyridin-3-yl)acrylonitrile | $^1$H NMR (400 MHz, MeOD-d$_6$) δ ppm, 8.06 (d,J = 2.4 Hz, 1H), 7.77 (d, J = 2.8 Hz, 1H), 7.68 (s, 1H), 7.54 (d, J= 16.8 Hz, 1H), 7.41-7.38 (m, 5H), 5.90 (d, J = 16.8 Hz, 1H), 3.88 (m, 2H), 3.57 (m, 2H), 3.20-2.95 (m, 4H). MS (ES) m/z 358 (M + H). |
| 280 | 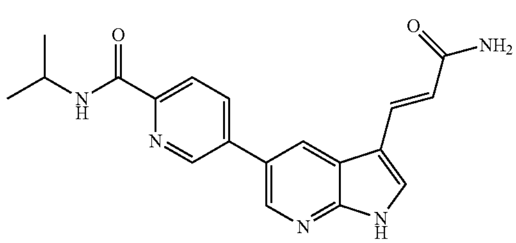 | (E)-5-(3-(3-amino-3-oxoprop-1-en-1-yl)-1H-pyrrolo[2,3-b]pyridin-5-yl)-N-isopropyl-picolinamide | $^1$H NMR (400 MHz, MeOD-d$_6$) δ ppm, 9.05 (d,J = 1.2 Hz, 1H), 8.72 (s, 1H), 8.60 (s, 1H), 8.49 (d, J = 8.4 Hz, 1H), 8.39 (dd, J$_1$ = 2.0 Hz, J$_2$ = 8.0 Hz, 1H), 8.14 (d, J = 8.4 Hz, 1H), 7.99 (s, 1H), 7.62 (d, J = 15.6 Hz, 1H), 7.32 (s, 1H), 6.94 (s, 1H), 6.73 (d, J = 16.0 Hz, 1H), 4.19-4.13 (m, 1H), 1.23 (d, J = 6.4 Hz, 6H). MS (ES) m/z 362 (M + H). |

TABLE 1-continued

Compound Examples — Spectral Data

| Example | Structure | Name | Spectral Data |
| --- | --- | --- | --- |
| 281 | 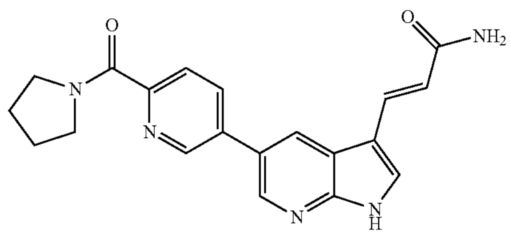 [SMILES: NC(=O)/C=C/c1c[nH]c2ncc(-c3ccc(C(=O)N4CCCC4)nc3)cc12] | (E)-3-(5-(6-(pyrrolidine-1-carbonyl)pyridin-3-yl)-1H-pyrrolo[2,3-b]pyridin-3-yl)acrylamide | $^1$H NMR (400 MHz, DMSO-d$_6$) δ ppm, 12.27 (br s, 1H), 9.04 (d, J = 1.6 Hz, 1H), 8.70 (d, J = 1.6 Hz, 1H), 8.59 (d, J = 2.0 Hz, 1H), 8.34 (dd, J$_1$ = 2.4 Hz, J$_2$ = 8.8 Hz, 1H), 7.98 (s, 1H), 7.87 (d, J = 8.0 Hz, 1H), 7.61 (d, J = 15.6 Hz, 1H), 7.33 (s, 1H), 6.93 (s, 1H), 6.73 (d, J = 16.0 Hz, 1H), 3.71 (t, J = 6.4 Hz, 2H), 3.54 (t, J = 6.4 Hz, 2H), 1.88 (s, 4H). MS (ES) m/z 362 (M + H). |
| 282 | 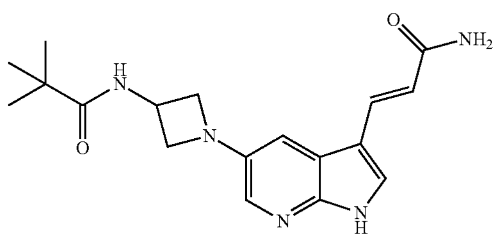 [SMILES: CC(C)(C)C(=O)NC1CN(c2cnc3[nH]cc(/C=C/C(N)=O)c3c2)C1] | (E)-3-(5-(3-pivalamidoazetidin-1-yl)-1H-pyrrolo[2,3-b]pyridin-3-yl)acrylamide | $^1$H NMR (400 MHz, DMSO-d$_6$) δ ppm, 11.78 (br s, 1H), 7.99 (d, J = 7.2 Hz, 1H), 7.77-7.68 (m, 2H), 7.53 (d, J = 16.4 Hz, 1H), 7.32 (s, 1H), 7.23 (m, 1H), 6.83 (s, 1H), 6.47 (d, J = 16.0 Hz, 1H), 4.70-4.67 (m, 1H), 4.22-4.18 (m, 2H), 3.75-3.71 (m, 2H), 1.10 (s, 9H). MS (ES) m/z 342 (M + H). |
| 283 | 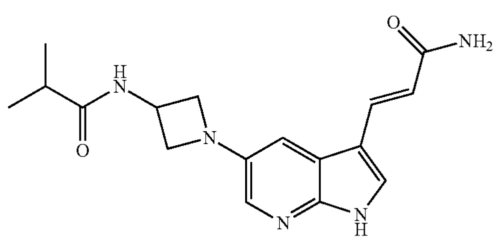 [SMILES: CC(C)C(=O)NC1CN(c2cnc3[nH]cc(/C=C/C(N)=O)c3c2)C1] | (E)-3-(5-(3-isobutyramidoazetidin-1-yl)-1H-pyrrolo[2,3-b]pyridin-3-yl)acrylamide | $^1$H NMR (400 MHz, MeOD-d$_6$) δ ppm, 7.91 (d, J = 2.4 Hz, 1H), 7.80 (d, J = 2.4 Hz, 1H), 7.67 (d, J = 15.6 Hz, 1H), 7.56 (s, 1H), 7.02 (d, J = 15.6 Hz, 1H), 4.32-4.28 (m, 1H), 3.79-3.70 (m, 2H), 3.33-3.24 (m, 1H), 2.59-2.51 (m, 1H), 1.18-1.14 (m, 6H). MS (ES) m/z 328 (M + H). |
| 284 | 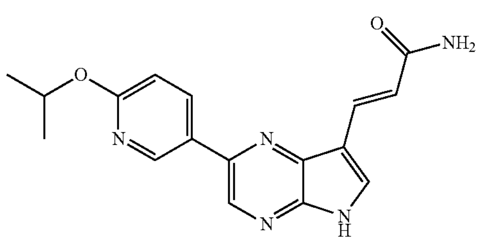 [SMILES: CC(C)Oc1ccc(-c2cnc3[nH]cc(/C=C/C(N)=O)c3n2)cn1] | (E)-3-(2-(6-isopropoxypyridin-3-yl)-5H-pyrrolo[2,3-b]pyrazin-7-yl)acrylamide | $^1$H NMR (400 MHz, DMSO-d$_6$) δ ppm, 12.17 (br s, 1H), 9.08 (d, J = 2.0 Hz, 1H), 8.93 (s, 1H), 8.56 (dd, J = 8.4 Hz and 2.4 Hz, 1H), 8.19 (s, 1H), 7.70 (s, 1H), 7.57 (d, J = 15.6 Hz, 1H), 7.28 (d, J = 15.6 Hz, 1H), 6.89 (s, 1H), 6.87 (d, J = 8.4 Hz, 1H), 5.34 (m, 1H), 1.34 (d, J = 6.0 Hz, 6H). MS (ES) m/z 324 (M + H). |
| 285 | 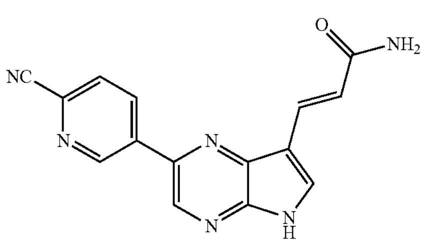 [SMILES: N#Cc1ccc(-c2cnc3[nH]cc(/C=C/C(N)=O)c3n2)cn1] | (E)-3-(2-(6-cyanopyridin-3-yl)-5H-pyrrolo[2,3-b]pyrazin-7-yl)acrylamide | $^1$H NMR(400 MHz, MeOD-d$_6$) δ ppm, 9.70 (d, J = 2.0 Hz, 1H), 9.17 (s, 1H), 8.90 (dd, J = 8.4 Hz and 2.0 Hz, 1H), 8.50 (br s, 2H), 8.31 (s, 1H), 8.19 (d, J = 8.4 Hz, 1H), 7.72 (s, 1H), 7.58 (d, J = 15.6 Hz, 1H), 7.32 (d, J = 15.6 Hz, 1H), 6.96 (s, 1H). MS (ES) m/z 391 (M + H). |
| 286 | 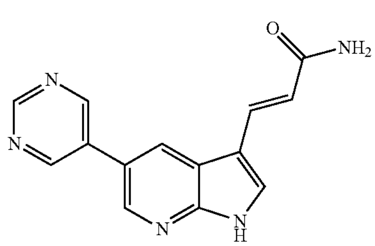 [SMILES: NC(=O)/C=C/c1c[nH]c2ncc(-c3cncnc3)cc12] | (E)-3-(5-(pyrimidin-5-yl)-1H-pyrrolo[2,3-b]pyridin-3-yl)acrylamide | $^1$H NMR(400 MHz, DMSO-d$_6$) δ ppm, 12.28 (s, 1H), 9.27 (s, 1H), 9.23 (s, 1H), 8.73 (d, J = 1.9 Hz, 1H), 8.62 (d, J = 1.95 Hz, 1H), 7.99 (s, 1H0, 7.60 (d, J = 16 Hz, 1H), 7.28 (s, 1H), 6.95 (s, 1H), 6.74 (d, J = 16 Hz, 1H). MS (ES) m/z 266 (M + H). |

TABLE 1-continued

Compound Examples — Spectral Data

| Example | Structure | Name | Spectral Data |
| --- | --- | --- | --- |
| 287 | 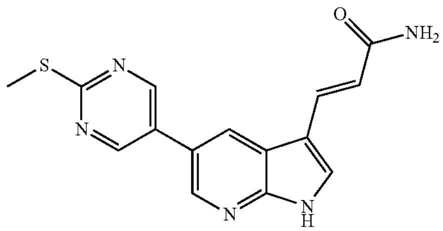 [SMILES: CSc1ncc(-c2cnc3[nH]cc(/C=C/C(N)=O)c3c2)cn1] | (E)-3-(5-(2-(methylthio)pyrimidin-5-yl)-1H-pyrrolo[2,3-b]pyridin-3-yl)acrylamide | $^1$H NMR (400 MHz, DMSO-d$_6$) δ ppm, 12.28 (s, 1H), 9.10 (s, 1H), 9.06 (s, 1H), 8.69 (d, J = 1.9 HZ, 1H), 8.57 (s, 1H), 8.01 (s, 1H), 7.59 (d, J = 16 Hz, 1H), 7.26 (s, 1H), 6.95 (s, 1H), 6.73 (d, J = 16 Hz, 1H), 2.59 (s, 3H). MS (ES) m/z 312 (M + H). |
| 288 | 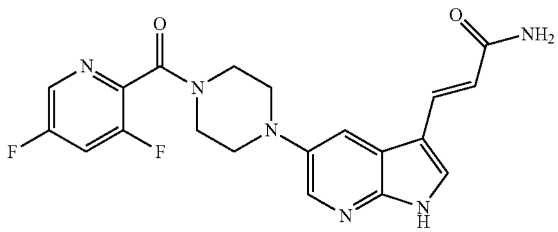 [SMILES: NC(=O)/C=C/c1c[nH]c2ncc(N3CCN(C(=O)c4ncc(F)cc4F)CC3)cc12] | (E)-3-(5-(4-(3,5-difluoropicolinoyl)piperazin-1-yl)-1H-pyrrolo[2,3-b]pyridin-3-yl)acrylamide | $^1$H NMR (400 MHz, DMSO-d$_6$) δ ppm, 11.92 (s, 1H), 8.62 (s, 1H), 8.17-6.16 (m, 2H), 7.82 (d, J = 1.96 Hz, 1H), 7.78 (s, 1H), 7.54 (d, 16.04 Hz, 1H), 7.34 (br. s, 1H), 6.87 (br. s, 1H), 6.53 (d, J = 16.04 Hz, 1H), 3.93-3.88 (m, 2H), 3.49-3.44 (m, 2H), 3.29-3.24 (m, 2H), 3.15-3.10 (m, 2H). MS (ES) m/z 413 (M + H). |
| 289 | 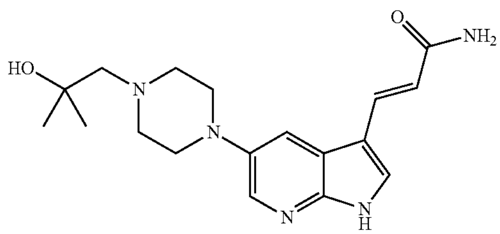 [SMILES: CC(C)(O)CN1CCN(c2cnc3[nH]cc(/C=C/C(N)=O)c3c2)CC1] | (E)-3-(5-(4-(2-hydroxy-2-methylpropyl)piperazin-1-yl)-1H-pyrrolo[2,3-b]pyridin-3-yl)acrylamide | $^1$H NMR (400 MHz, DMSO-d$_6$) δ ppm, 11.96 (s, 1H), 8.19 (d, J = 2.35 Hz, 1H), 7.84 (d, J = 2.34 Hz, 1H), 7.77 (d, J = 2.74 Hz, 1H), 7.56 (d, J = 16.04 Hz, 1H), 7.33 (br. s, 1H), 6.89 (br. s, 1H), 6.53 (d, J = 16.04 Hz, 1H), 3.71-3.69 (m, 4H), 3.39-3.35 (m, 4H), 3.24 (s, 2H), 1.29 (s, 6H). MS (ES) m/z 344 (M + H). |
| 290 | 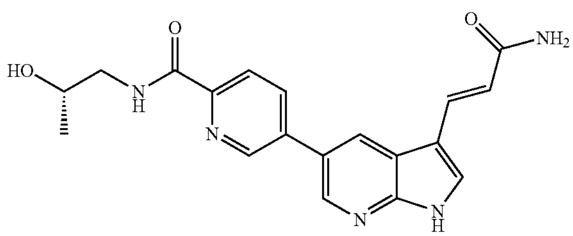 [SMILES: C[C@H](O)CNC(=O)c1ccc(-c2cnc3[nH]cc(/C=C/C(N)=O)c3c2)cn1] | (S,E)-5-(3-(3-amino-3-oxoprop-1-en-1-yl)-1H-pyrrolo[2,3-b]pyridin-5-yl)-N-(2-hydroxypropyl)picolinamide | $^1$H NMR (400 MHz, DMSO-d$_6$) δ ppm, 12.23 (s, 1H), 8.66 (s, 1H), 8.53 (s, 2H), 8.01 (d, J = 8.21 Hz, 2H), 7.96 (s, 1H), 7.88 (d, J = 8.61 Hz, 2H), 7.61 (d, J = 16.04 Hz, 1H), 7.37 (br. s, 1H), 6.93 (br. s, 1H), 6.71 (d, J = 16.04 Hz, 1H), 4.78 (s, 1H) 3.81 (s, 1H), 3.66 (s, 2H), 1.08 (d, J = 6.26 Hz, 3H). MS (ES) m/z 365 (M + H). |
| 291 | 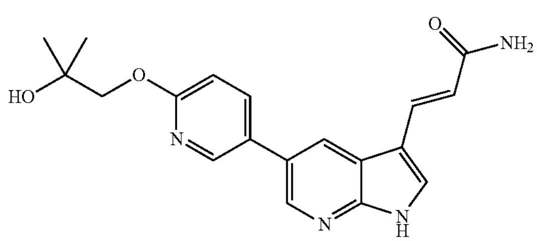 [SMILES: CC(C)(O)COc1ccc(-c2cnc3[nH]cc(/C=C/C(N)=O)c3c2)cn1] | (E)-3-(5-(6-(2-hydroxy-2-methylpropoxy)pyridin-3-yl)-1H-pyrrolo[2,3-b]pyridin-3-yl)acrylamide | $^1$H NMR (400 MHz, DMSO-d$_6$) δ ppm, 12.19 (s, 1H), 8.58 (d, J = 1.95 Hz, 1H), 8.55 (d, J = 2.74 Hz, 1H), 8.46 (d, J = 2.35 Hz, 1H), 8.12 (dd, J = 8.61, 2.74 Hz, 1H), 7.94 (s, 1H), 7.60 (d, J = 16.04 Hz, 1H), 7.33 (br. s, 1H), 6.97 (d, J = 28.61 Hz, 1H), 6.92 (br. s, 1H), 6.71 (d, J = 16.04 Hz, 1H), 4.67 (s, 1H) 4.12 (s, 2H), 1.22 (s, 6H). MS (ES) m/z 353 (M + H). |
| 292 | 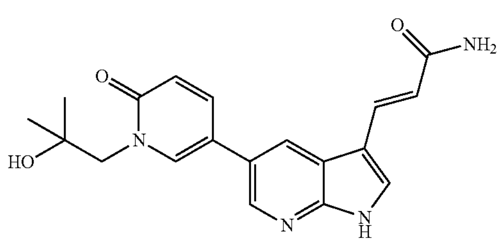 [SMILES: CC(C)(O)Cn1cc(-c2cnc3[nH]cc(/C=C/C(N)=O)c3c2)ccc1=O] | (E)-3-(5-(1-(2-hydroxy-2-methylpropyl)-6-oxo-1,6-dihydropyridin-3-yl)-1H-pyrrolo[2,3-b]pyridin-3-yl)acrylamide | MS (ES) m/z 353 (M + H). |

TABLE 1-continued

Compound Examples — Spectral Data

| Example | Structure | Name | Spectral Data |
|---|---|---|---|
| 293 | 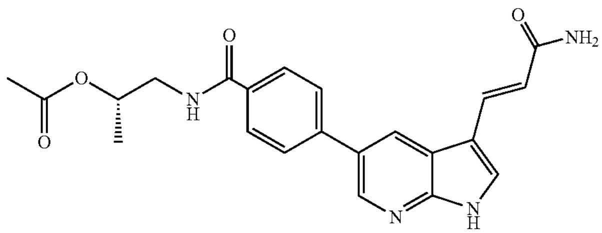 [SMILES: CC(=O)O[C@@H](C)CNC(=O)c1ccc(-c2cnc3[nH]cc(/C=C/C(N)=O)c3c2)cc1] | (S,E)-1-(4-(3-(3-amino-3-oxoprop-1-en-1-yl)-1H-pyrrolo[2,3-b]pyridin-5-yl)benzamido)propan-2-yl acetate | $^1$H NMR (400 MHz, DMSO-d$_6$) δ ppm, 12.20 (s, 1H), 8.62 (s, 1H), 8.49 (s, 1H), 7.95-7.93 (m, 3H), 7.84 (d, J = 8.61 Hz, 2H), 7.57 (d, J = 16.04 Hz, 1H), 7.34 (br. s, 1H), 6.89 (br. s, 1H), 6.68 (d, J = 16.05 Hz, 1H), 5.01-4.93 (m, 1H), 3.20-3.08 (m, 2H), 1.96 (s, 3H, 1.19-1.12 (m, 3H). MS (ES) m/z 407 (M + H). |
| 294 | 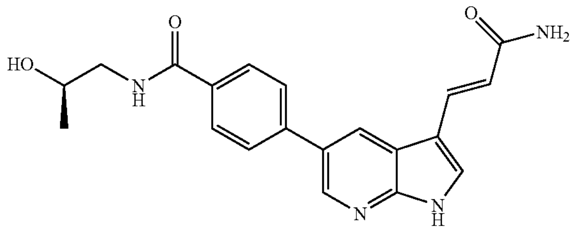 [SMILES: C[C@@H](O)CNC(=O)c1ccc(-c2cnc3[nH]cc(/C=C/C(N)=O)c3c2)cc1] | (R,E)-4-(3-(3-amino-3-oxoprop-1-en-1-yl)-1H-pyrrolo[2,3-b]pyridin-5-yl)-N-(2-hydroxypropyl)benzamide | $^1$H NMR (400 MHz, DMSO-d$_6$) δ ppm, 12.26 (s, 1H), 8.65 (s, 1H), 8.52 (s, 2H), 8.01 (d, J = 8.22 Hz, 2H), 7.96 (s, 1H), 7.88 (d, J = 8.21 Hz, 2H), 7.61 (d, J = 15.65 Hz, 1H), 7.37 (br. s, 1H), 6.91 (br. s, 1H), 6.71 (d, J = 15.65 Hz, 1H), 4.82 (s, 1H), 3.82 (s, 1H), 3.24 (s, 2H), 1.08 (d, 3H). MS (ES) m/z 365 (M + H). |
| 295 | 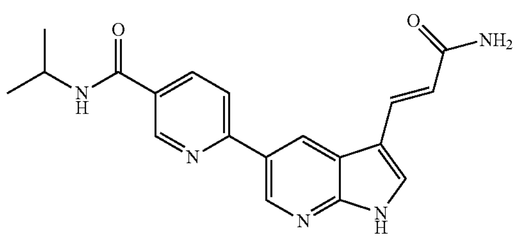 [SMILES: CC(C)NC(=O)c1ccc(-c2cnc3[nH]cc(/C=C/C(N)=O)c3c2)nc1] | (E)-6-(3-(3-amino-3-oxoprop-1-en-1-yl)-1H-pyrrolo[2,3-b]pyridin-5-yl)-N-isopropyl-nicotinamide | $^1$H NMR (400 MHz, DMSO-d$_6$) δ ppm, 12.31 (br s, 1H), 9.11 (dd, J$_1$ =1.6 Hz, J$_2$ = 11.6 Hz, 1H), 8.93 (d, J = 2.0 Hz, 1H), 8.50 (d, J = 7.6 Hz, 1H), 8.32 (dd, J$_1$ = 2.0 Hz, J$_2$ = 8.0 Hz, 1H), 8.22 (d, J = 8.4 Hz, 1H), 7.99 (s, 1H), 7.64 (d, J = 15.6 Hz, 1H), 7.50 (s, 1H), 6.96 (s, 1H), 6.71 (d, J = 16.0 Hz, 1H), 4.17-4.12 (m, 1H), 1.21 (d, J = 6.8 Hz, 6H). MS (ES) m/z 350 (M + H). |
| 296 | 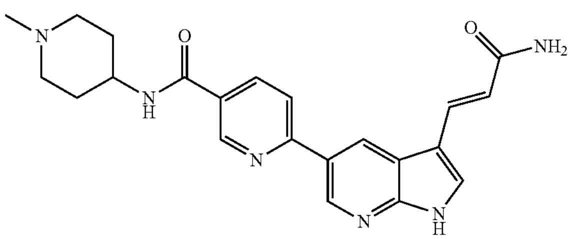 [SMILES: CN1CCC(NC(=O)c2ccc(-c3cnc4[nH]cc(/C=C/C(N)=O)c4c3)nc2)CC1] | (E)-6-(3-(3-amino-3-oxoprop-1-en-1-yl)-1H-pyrrolo[2,3-b]pyridin-5-yl)-N-(1-methylpiperidin-4-yl)nicotinamide | $^1$H NMR (400 MHz, DMSO-d$_6$) δ ppm, 12.31 (s, 1H), 9.10 (dd, J$_1$ = 1.6 Hz, J$_2$ = 13.2 Hz, 1H), 8.92 (d, J = 2.0 Hz, 1H), 8.58 (d, J = 7.2 Hz, 1H), 8.31 (dd, J$_1$ = 2.0 Hz, J$_2$ = 8.4 Hz, 1H), 8.22 (d, J = 8.4 Hz, 1H), 7.98 (s, 1H), 7.63 (d, J = 16.4 Hz, 1H), 7.48 (s, 1H), 6.96 (s, 1H), 6.69 (d, J = 15.6 Hz, 1H), 3.87 (m, 1H), 3.10-3.07 (m, 2H), 2.49 (s, 3H), 1.93-1.89 (m, 2H), 1.72-1.68 (m, 2H). MS (ES) m/z 405 (M + H). |
| 297 | 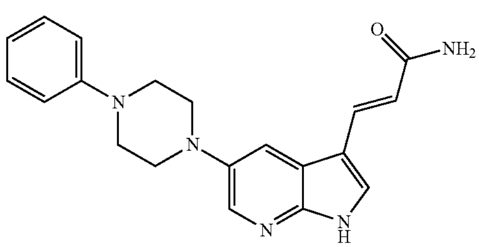 [SMILES: NC(=O)/C=C/c1c[nH]c2ncc(N3CCN(c4ccccc4)CC3)cc12] | (E)-3-(5-(4-phenylpiperazin-1-yl)-1H-pyrrolo[2,3-b]pyridin-3-yl)acrylamide | $^1$H NMR (400 MHz, MeOD-d$_6$) δ ppm, 8.19 (d,J = 2.4 Hz, 1H), 7.92 (d, J = 2.4 Hz, 1H), 7.73 (d, J = 16 Hz, 1H), 7.71 (s, 1H), 7.28 (t, J = 8.0 Hz, 2H), 7.06 (d, J = 8.0 Hz, 2H), 6.88 (t, J=8.0 Hz, 1H), 6.64 (d, J = 16 Hz, 1H), 3.39 (m, 8H). MS (ES) m/z 348 (M + H). |
| 298 | 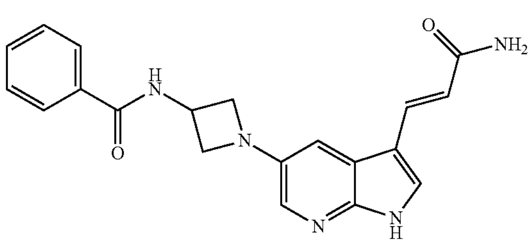 [SMILES: NC(=O)/C=C/c1c[nH]c2ncc(N3CC(NC(=O)c4ccccc4)C3)cc12] | (E)-N-(1-(3-(3-amino-3-oxoprop-1-en-1-yl)-1H-pyrrolo[2,3-b]pyridin-5-yl)azetidin-3-yl)benzamide | $^1$H NMR (400 MHz, DMSO-d$_6$) δ ppm, 11.80 (br s, 1H), 9.03 (d, J = 6.8 Hz, 1H), 7.89 (d, J = 7.2 Hz, 2H), 7.78-7.71 (m, 2H), 7.56-7.45 (m, 4H), 7.33 (s, 1H), 7.27 (d, J = 2.0 Hz, 1H), 6.84 (s, 1H), 6.48 (d, J = 16 Hz, 1H), 4.94-4.88 (m, 1H), 4.33-4.28 (m, 2H), 3.89-3.84 (m, 2H). MS (ES) m/z 362 (M + H). |

TABLE 1-continued

Compound Examples — Spectral Data

| Example | Structure | Name | Spectral Data |
| --- | --- | --- | --- |
| 299 | 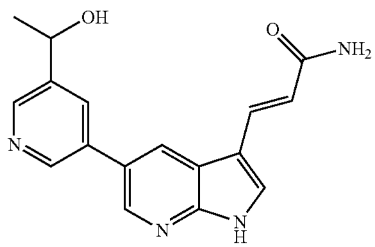 [SMILES: CC(O)c1cncc(-c2cnc3[nH]cc(/C=C/C(N)=O)c3c2)c1] | (E)-3-(5-(5-(1-hydroxyethyl)pyridin-3-yl)-1H-pyrrolo[2,3-b]pyridin-3-yl)acrylamide | $^1$H NMR (400 MHz, DMSO-$d_6$) δ ppm, 12.52 (s, 1H), 9.35 (s, 1H), 9.01 (s, 1H), 8.66 (d, J = 1.6 Hz, 1H), 8.48 (s, 1H), 8.27 (s, 1H), 7.66 (s, 1H), 7.61 (d, J = 15.6 Hz, 1H), 7.26 (d, J = 15.6 Hz, 1H), 6.94 (s, 1H), 5.44 (d, J = 4.8 Hz, 1H), 4.94 (m, 1H), 1.48 (d, J = 7.2 Hz, 3H). MS (ES) m/z 310 (M + H). |
| 300 | 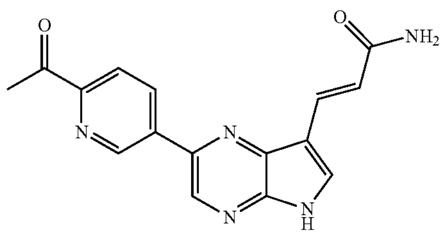 [SMILES: CC(=O)c1ccc(-c2cnc3[nH]cc(/C=C/C(N)=O)c3n2)cn1] | (E)-3-(2-(6-acetylpyridin-3-yl)-5H-pyrrolo[2,3-b]pyrazin-7-yl)acrylamide | $^1$H NMR (400 MHz, DMSO-$d_6$) δ ppm, 12.58 (br s, 1H), 9.66 (d, J = 2.0 Hz, 1H), 9.15 (s, 1H), 8.86 (dd, J = 8.0 Hz and 2.0 Hz, 1H), 8.29 (s, 2H), 8.08 (d, J = 8.4 Hz, 1H), 7.74 (s, 1H), 7.59 (d, J = 15.6 Hz, 1H), 7.34 (d, J = 15.6 Hz, 1H), 6.96 (s, 1H), 2.70 (s, 3H). MS (ES) m/z 308 (M + H). |
| 301 | 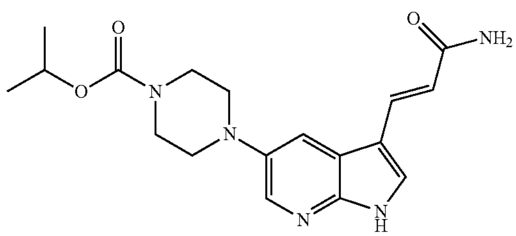 [SMILES: CC(C)OC(=O)N1CCN(c2cnc3[nH]cc(/C=C/C(N)=O)c3c2)CC1] | (E)-isopropyl 4-(3-(3-amino-3-oxoprop-1-en-1-yl)-1H-pyrrolo[2,3-b]pyridin-5-yl)piperazine-1-carboxylate | $^1$H NMR (400 MHz, DMSO-$d_6$) δ ppm, 11.90 (s, 1H), 8.16 (s, 1H), 7.81 (s, 1H), 7.75 (s, 1H), 7.54 (d, J = 15.65 Hz, 1H, 7.33 (br. s, 1H), 6.87 (br. s, 1H), 6.53 (d, J = 16.04 Hz, 1H), 4.84-4.78 (m, 1H), 3.58-3.56 (m, 4H), 3.15-3.09 (m, 4H), 1.21 (d, 6H). MS (ES) m/z 358 (M + H). |
| 302 | 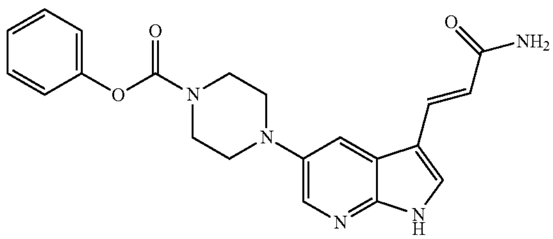 [SMILES: NC(=O)/C=C/c1c[nH]c2ncc(N3CCN(C(=O)Oc4ccccc4)CC3)cc12] | (E)-phenyl 4-(3-(3-amino-3-oxoprop-1-en-1-yl)-1H-pyrrolo[2,3-b]pyridin-5-yl)piperazine-1-carboxylate | MS (ES) m/z 392 (M + H). |
| 303 | 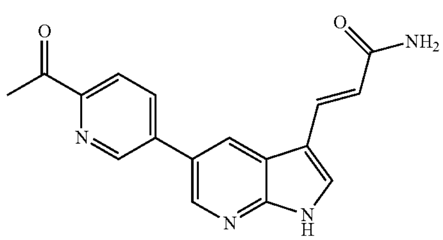 [SMILES: CC(=O)c1ccc(-c2cnc3[nH]cc(/C=C/C(N)=O)c3c2)cn1] | (E)-3-(5-(6-acetylpyridin-3-yl)-1H-pyrrolo[2,3-b]pyridin-3-yl)acrylamide | $^1$H NMR (400 MHz, DMSO-$d_6$) δ ppm, 12.32 (s, 1H), 9.20 (s, 1H), 8.76 (s, 1H), 8.65 (s, 1H), 8.46-8.42 (m, 1H), 8.08 (d, 1H), 8.00 (s, 1H), 7.61 (d, J = 15.65 Hz, 1H), 7.33 (br. s, 1H), 6.95 (br. s, 1H), 6.75 (d, J = 15.65 Hz, 1H), 2.69 (s, 3H). MS (ES) m/z 307 (M + H). |
| 304 | 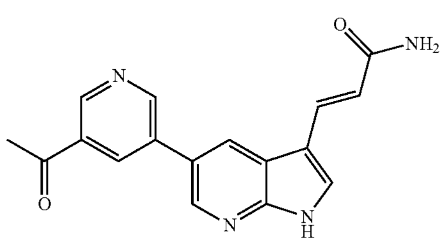 [SMILES: CC(=O)c1cncc(-c2cnc3[nH]cc(/C=C/C(N)=O)c3c2)c1] | (E)-3-(5-(5-acetylpyridin-3-yl)-1H-pyrrolo[2,3-b]pyridin-3-yl)acrylamide | $^1$H NMR (400 MHz, DMSO-$d_6$) δ ppm, 12.33 (s, 1H), 9.22 (s, 1H), 9.13 (s, 1H), 8.72 (s, 1H), 8.62-8.61 (m, 2H), 7.99 (s, 1H), 7.62 (d, J = 15.65 Hz, 1H), 7.32 (br. s, 1H), 6.93 (br. s, 1H), 6.72 (d, J = 16.04 Hz, 1H), 2.75 (s, 3H). MS (ES) m/z 307 (M + H). |

TABLE 1-continued

Compound Examples — Spectral Data

| Example | Structure | Name | Spectral Data |
|---|---|---|---|
| 305 | 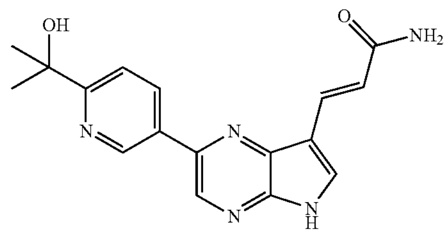 [SMILES: CC(C)(O)c1ccc(-c2cnc3[nH]cc(/C=C/C(N)=O)c3n2)cn1] | (E)-3-(2-(6-(2-hydroxypropan-2-yl)pyridin-3-yl)-5H-pyrrolo[2,3-b]pyrazin-7-yl)acrylamide | $^1$H NMR (400 MHz, MeOD-d$_6$) δ ppm, 9.21 (d, J = 2.0 Hz, 1H), 8.79 (s, 1H), 8.53 (dd, J = 8.4 Hz and 2.0 Hz, 1H), 7.96 (s, 2H), 7.76 (d, J = 8.4 Hz, 1H), 7.65 (d, J = 15.6 Hz, 1H), 7.40 (d, J = 15.6 Hz, 1H), 1.53 (s, 6H). MS (ES) m/z 324 (M + H). |
| 306 | 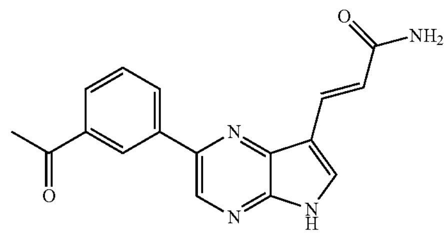 [SMILES: CC(=O)c1cccc(-c2cnc3[nH]cc(/C=C/C(N)=O)c3n2)c1] | (E)-3-(2-(3-acetylphenyl)-5H-pyrrolo[2,3-b]pyrazin-7-yl)acrylamide | $^1$H NMR (400 MHz, DMSO-d$_6$) δ ppm, 12.51 (s, 1H), 9.06 (s, 1H), 8.72 (s, 1H), 8.56 (d, J = 7.83 Hz, 1H), 8.26 (s, 1H), 8.03 (d, J = 7.43 Hz, 1H), 7.72 (d, J = 7.83 Hz, 1H), 7.70 (d, J = 7.82 Hz, 1H), 7.63 (br. s, 1H), 7.61 (d, J = 15.65 Hz, 1H), 7.28 (d, J = 15.65 Hz, 1H), 6.94 (br. s, 1H), 2.73 (s, 3H). MS (ES) m/z 307 (M + H). |
| 307 | 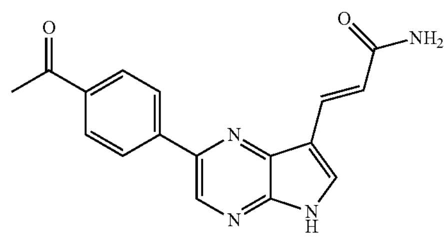 | (E)-3-(2-(4-acetylphenyl)-5H-pyrrolo[2,3-b]pyrazin-7-yl)acrylamide | $^1$H NMR (400 MHz, DMSO-d$_6$) δ ppm, 12.53 (s, 1H), 9.08 (s, 1H), 8.46 (d, J = 8.22 Hz, 2H), 8.23 (s, 1H), 8.11 (d, J = 8.61 Hz, 2H), 7.67 (br. s, 1H), 7.60 (d, J = 15.65 Hz, 1H), 7.31 (d, J = 15.65 Hz, 1H), 6.96 (br. s, 1H), 2.65 (s, 3H). MS (ES) m/z 307 (M + H). |
| 308 | 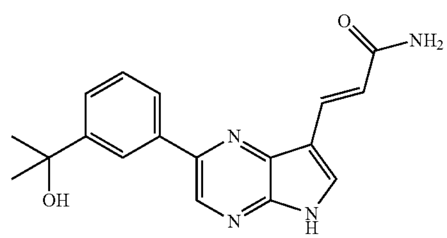 [SMILES: CC(C)(O)c1cccc(-c2cnc3[nH]cc(/C=C/C(N)=O)c3n2)c1] | (E)-3-(2-(3-(2-hydroxypropan-2-yl)phenyl)-5H-pyrrolo[2,3-b]pyrazin-7-yl)acrylamide | $^1$H NMR (400 MHz, DMSO-d$_6$) δ ppm, 12.43 (s, 1H), 8.91 (s, 1H), 8.23 (d, J = 9.39 Hz, 2H), 8.11 (d, J = 7.04 Hz, 1H), 7.61 (d, J = 15.65 Hz, 1H), 7.57-7.55 (m, 2H), 7.49-7.46 (m, 1H), 7.24 (d, J = 15.65 Hz, 1H), 5.12 (s, 1H), 1.52 (s, 3H). MS (ES) m/z 323 (M + H). |
| 309 | 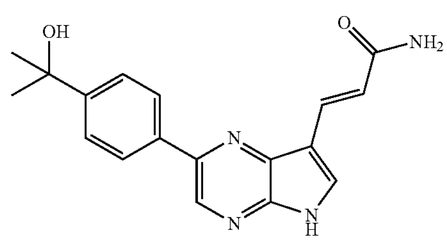 | (E)-3-(2-(4-(2-hydroxypropan-2-yl)phenyl)-5H-pyrrolo[2,3-b]pyrazin-7-yl)acrylamide | $^1$H NMR (400 MHz, DMSO-d$_6$) δ ppm, 12.41 (s, 1H), 8.91 (s, 1H), 8.20-8.17 (m, 3H), 7.63-7.58 (m, 4H), 7.28 (d, J = 15.65 Hz, 1H), 6.92 (br. s, 1H), 5.11 (s, 1H), 1.48 (s, 3H). MS (ES) m/z 323 (M + H). |
| 310 | 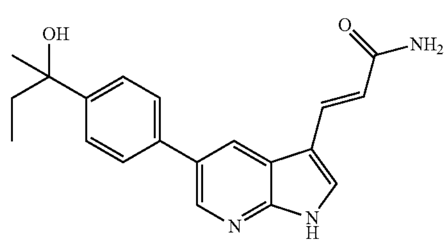 [SMILES: CCC(C)(O)c1ccc(-c2cnc3[nH]cc(/C=C/C(N)=O)c3c2)cc1] | (E)-3-(5-(4-(2-hydroxybutan-2-yl)phenyl)-1H-pyrrolo[2,3-b]pyridin-3-yl)acrylamide | $^1$H NMR (400 MHz, DMSO-d$_6$) δ ppm, 12.15 (s, 1H), 8.57 (s, 1H), 8.44 (s, 1H), 7.93 (s, 1H), 7.68 (d, J = 8.22 Hz, 2H), 7.60 (d, J = 15.65 Hz, 1H), 7.55 (d, J = 8.22 Hz, 2H), 7.37 (br. s, 1H), 6.90 (br. s, 1H), 6.70 (d, J = 15.65 Hz, 1H), 4.88 (s, 1H), 1.76-1.73 (m, 2H), 1.45 (s, 3H), 0.73 (t, J = 7.43 Hz, 3H). MS (ES) m/z 336 (M + H). |

TABLE 1-continued

Compound Examples — Spectral Data

| Example | Structure | Name | Spectral Data |
|---|---|---|---|
| 311 | 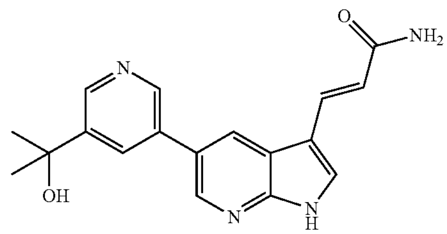 [SMILES: CC(C)(O)c1cncc(-c2cnc3[nH]cc(/C=C/C(N)=O)c3c2)c1] | (E)-3-(5-(5-(2-hydroxypropan-2-yl)pyridin-3-yl)-1H-pyrrolo[2,3-b]pyridin-3-yl)acrylamide | $^1$H NMR (400 MHz, DMSO-d$_6$) δ ppm, 12.25 (s, 1H), 8.82 (s, 1H), 8.73 (s, 1H), 8.62 (s, 1H), 8.52 (s, 1H), 8.17 (s, 1H), 7.98 (s, 1H), 7.62 (d, J = 15.65 Hz, 1H), 7.34 (br. s, 1H), 6.93 (br. s, 1H), 6.71 (d, J = 15.65 Hz, 1H), 5.32 (s, 1H), 1.55 (s, 6H). MS (ES) m/z 323 (M + H). |
| 312 | 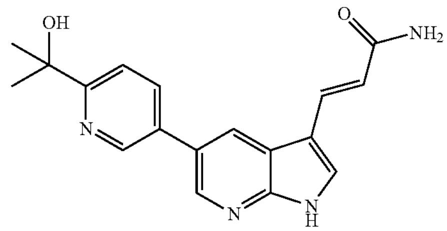 [SMILES: CC(C)(O)c1ccc(-c2cnc3[nH]cc(/C=C/C(N)=O)c3c2)cn1] | (E)-3-(5-(6-(2-hydroxypropan-2-yl)pyridin-3-yl)-1H-pyrrolo[2,3-b]pyridin-3-yl)acrylamide | $^1$H NMR(400 MHz, DMSO-d$_6$) δ ppm, 12.23 (s, 1H), 8.89 (d, J = 2.35 Hz, 1H), 8.63 (d, J = 1.95 Hz, 1H), 8.52 (s, 1H), 8.18-8.16 (m, 1H), 7.96 (d, J = 2.74 Hz, 1H), 7.79 (d, J = 8.22 Hz, 1H), 7.60 (d, J = 16.05 Hz, 1H), 7.34 (br. s, 1H), 6.94 (br. s, 1H), 6.73 (d, J = 16.04 Hz, 1H), 1.50 (s, 6H). MS (ES) m/z 323 (M + H). |
| 313 | 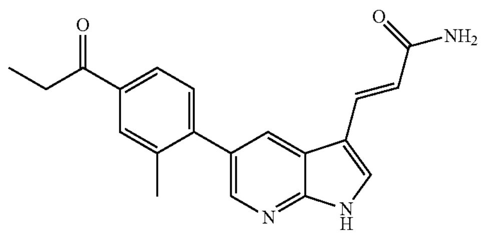 [SMILES: CCC(=O)c1ccc(-c2cnc3[nH]cc(/C=C/C(N)=O)c3c2)c(C)c1] | (E)-3-(5-(2-methyl-4-propionylphenyl)-1H-pyrrolo[2,3-b]pyridin-3-yl)acrylamide | $^1$H NMR(400 MHz, DMSO-d$_6$) δ ppm, 12.23 (s, 1H), 8.27-8.22 (m, 2H), 7.95 (s, 2H), 7.89 (d, J = 7.81 Hz, 1H), 7.57 (d, J = 16 Hz, 1H), 7.46 (d, J = 7.8 Hz, 1H), 7.26 (s, 1H), 7.82 (s, 1H), 6.60 (d, J = 16 Hz, 1H), 3.09 (m, 3H), 2.36 (s, 3H), 1.12 (t, J = 7.21 Hz, 2H). MS (ES) m/z 334 (M + H). |
| 314 | 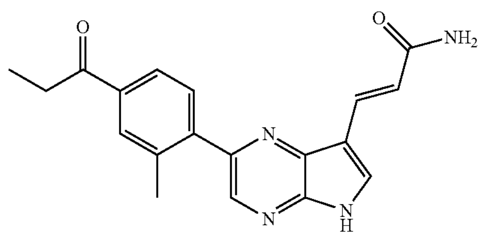 [SMILES: CCC(=O)c1ccc(-c2cnc3[nH]cc(/C=C/C(N)=O)c3n2)c(C)c1] | (E)-3-(2-(2-methyl-4-propionylphenyl)-5H-pyrrolo[2,3-b]pyrazin-7-yl)acrylamide | $^1$H NMR (400 MHz, DMSO-d$_6$) δ ppm, 12.01 (s, 1H), 8.37 (s, 1H), 8.19 (s, 1H0, 7.96-7.88 (m, 2H), 7.64 (d, J = 7.83 Hz, 1H), 7.58 (d, J = 15.26 Hz, 1H), 7.45 (s, 1H), 6.98 (d, J = 15.26 Hz, 1H), 6.68 (s, 1H), 2.69-2.65 (m, 2H), 2.30-2.27 (m, 3H), 1.21-1.16 (m, 3H). MS (ES) m/z 335 (M + H). |
| 315 | 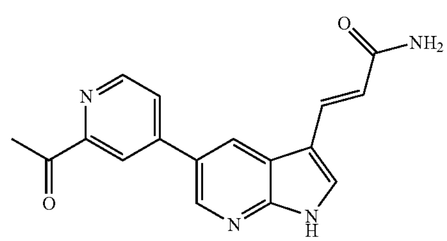 [SMILES: CC(=O)c1cc(-c2cnc3[nH]cc(/C=C/C(N)=O)c3c2)ccn1] | (E)-3-(5-(2-acetylpyridin-4-yl)-1H-pyrrolo[2,3-b]pyridin-3-yl)acrylamide | $^1$H NMR (400 MHz, DMSO-d$_6$) δ ppm, 12.34 (s, 1H), 8.83 (d J = 5.09 Hz, 1H), 8.75 (s, 1H), 8.65 (s, 1H), 8.32 (s, 1H), 8.12 (dd, J = 5.09, 1.96 Hz, 1H), 8.01 (s, 1H), 7.63 (d, J = 16.04, 1H), 7.37 (br. s, 1H), 6.94 (br. s, 1H), 6.72 (d, J = 16.04, 1H), 2.71 (s, 3H). MS (ES) m/z 307 (M + H). |
| 316 | 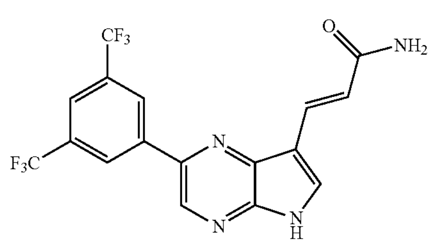 [SMILES: NC(=O)/C=C/c1c[nH]c2ncc(-c3cc(C(F)(F)F)cc(C(F)(F)F)c3)nc12] | (E)-3-(2-(3,5-bis(trifluoromethyl)phenyl)-5H-pyrrolo[2,3-b]pyrazin-7-yl)acrylamide | $^1$H NMR (400 MHz, DMSO-d$_6$) δ ppm, 12.63 (s, 1H), 9.21 (s, 1H), 8.84 (s, 2H), 8.33 (s, 1H), 8.21 (s, 1H), 7.63 (d, J = 15.65 Hz, 1H), 7.95 (br. s, 1H), 7.15 (d, J = 16.4 Hz, 1H), 6.95 (br. s, 1H). MS (ES) m/z 401 (M + H). |

TABLE 1-continued

Compound Examples — Spectral Data

| Example | Structure | Name | Spectral Data |
|---|---|---|---|
| 317 | 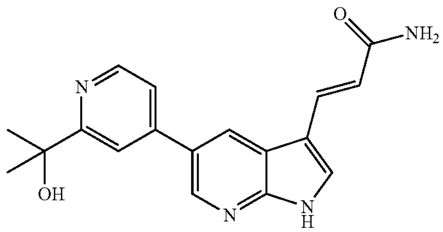 [SMILES: CC(C)(O)c1cc(-c2cnc3[nH]cc(/C=C/C(N)=O)c3c2)ccn1] | (E)-3-(5-(2-(2-hydroxypropan-2-yl)pyridin-4-yl)-1H-pyrrolo[2,3-b]pyridin-3-yl)acrylamide | ¹H NMR (400 MHz, DMSO-d₆) δ ppm, 12.32 (s, 1H), 8.69 (s, 1H), 8.60 - 8.57 (m, 2H), 8.04 (s, 1H), 8.00 (d, J = 2.74 Hz, 1H), 7.68 (s, 1H), 7.63 (d, J = 16.04 Hz, 1H), 7.39 (br. s, 1H), 6.94 (br. s, 1H), 6.69 (d, J = 15.65 Hz, 1H), 1.52-1.47 (m, 6H). MS (ES) m/z 323 (M + H). |
| 318 | 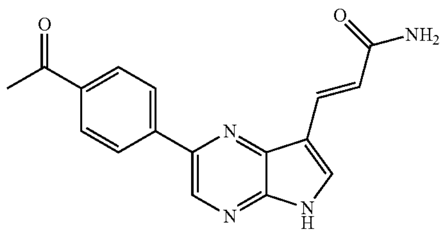 | (E)-3-(2-(4-acetylphenyl)-5H-pyrrolo[2,3-b]pyrazin-7-yl)acrylamide | MS (ES) m/z 361 (M + H). |
| 319 | 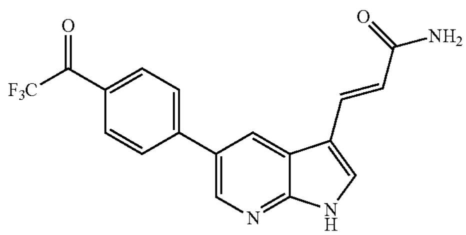 [SMILES: NC(=O)/C=C/c1c[nH]c2ncc(-c3ccc(C(=O)C(F)(F)F)cc3)cc12] | (E)-3-(5-(4-(2,2,2-trifluoroacetyl)phenyl)-1H-pyrrolo[2,3-b]pyridin-3-yl)acrylamide | MS (ES) m/z 360 (M + H). |
| 320 | 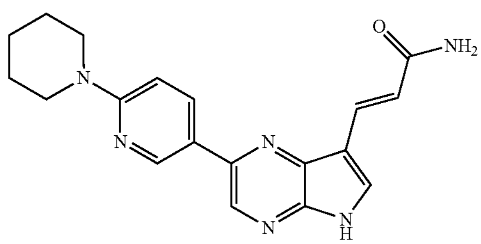 | (E)-3-(2-(6-(piperidin-1-yl)pyridin-3-yl)-5H-pyrrolo[2,3-b]pyrazin-7-yl)acrylamide | ¹H NMR (400 MHz, DMSO-d₆) δ ppm, 12.33 (s, 1H), 9.02 (d, J = 2.4 Hz, 1H), 8.85 (s, 1H), 8.37 (dd, J = 8.8 Hz and 2.8 Hz, 1H), 8.14 (d, J = 2.8 Hz, 1H), 7.68 (s, 1H), 7.56 (d, J= 15.2 Hz, 1H), 7.26 (d, J = 15.2 Hz, 1H), 6.94-6.87 (m, 2H), 3.62 (m, 4H), 1.70-1.50 (m, 6H). MS (ES) m/z 349 (M + H). |
| 321 | 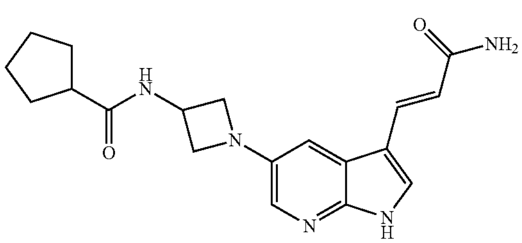 [SMILES: NC(=O)/C=C/c1c[nH]c2ncc(N3CC(NC(=O)C4CCCC4)C3)cc12] | (E)-N-(1-(3-(3-amino-3-oxoprop-1-en-1-yl)-1H-pyrrolo[2,3-b]pyridin-5-yl)azetidin-3-yl)cyclopentanecarboxamide | ¹H NMR (400 MHz, DMSO-d₆) δ ppm, 11.79 (s, 1H), 7.45 (d, J = 7.2 Hz, 1H), 7.76 (d, J = 2.0 Hz, 1H), 7.66 (d, J = 2.4 Hz, 1H), 7.52 (d, J = 15.6 Hz, 1H), 7.32 (s, 1H), 7.22 (d, J = 2.4 Hz, 1H), 6.84 (s, 1H), 6.45 (d, J = 15.6 Hz, 1H), 4.64-4.62 (m, 1H), 4.21-4.16 (m, 2H), 3.66-3.62 (m, 2H), 2.55-2.48 (m, 1H), 1.75-1.70(m, 2H), 1.63-1.58 (m, 4H), 1.51-1.48 (m, 2H). MS (ES) m/z 353 (M + H). |
| 322 | 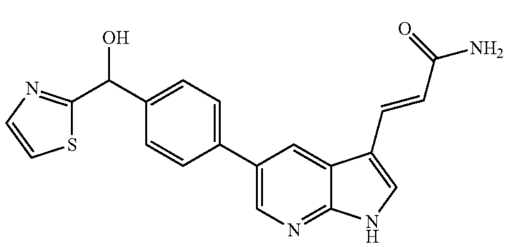 [SMILES: NC(=O)/C=C/c1c[nH]c2ncc(-c3ccc(C(O)c4nccs4)cc3)cc12] | (E)-3-(5-(4-(hydroxy(thiazol-2-yl)methyl)phenyl)-1H-pyrrolo[2,3-b]pyridin-3-yl)acrylamide | MS (ES) m/z 377 (M + H). |

TABLE 1-continued

Compound Examples — Spectral Data

| Example | Structure | Name | Spectral Data |
|---|---|---|---|
| 323 | 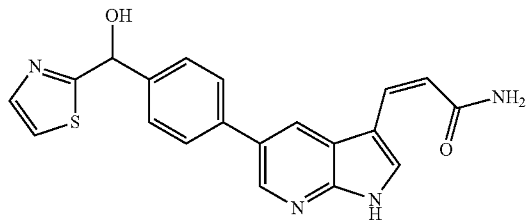 [SMILES: NC(=O)/C=C\c1c[nH]c2ncc(-c3ccc(C(O)c4nccs4)cc3)cc12] | (Z)-3-(5-(4-(hydroxy(thiazol-2-yl)methyl)phenyl)-1H-pyrrolo[2,3-b]pyridin-3-yl)acrylamide | $^1$H NMR (400 MHz, DMSO-d$_6$) δ ppm, 12.21 (s, 1H), 8.60-8.50 (m, 2H), 8.45-8.40 (m, 2H), 7.95-7.90 (m, 4H), 7.35 (s, 1H), 6.90 (s, 1H), 6.69-6.65 (m, 1H), 6.03 (s, 1H), 5.75 (s, 1H). MS (ES) m/z 377 (M + H). |
| 324 | 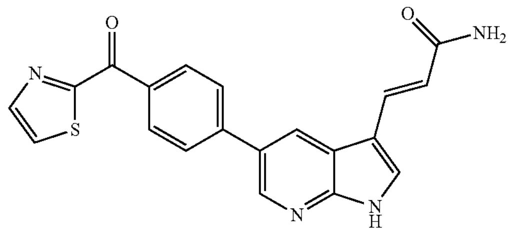 [SMILES: NC(=O)/C=C/c1c[nH]c2ncc(-c3ccc(C(=O)c4nccs4)cc3)cc12] | (E)-3-(5-(4-(thiazole-2-carbonyl)phenyl)-1H-pyrrolo[2,3-b]pyridin-3-yl)acrylamide | $^1$H NMR (400 MHz, DMSO-d$_6$) δ ppm, 12.29 (s, 1H), 8.73 (d, J = 1.5 Hz, 1H), 8.60 (d, J = 1.5 Hz, 1H), 8.56 (d, J = 5.6 Hz, 1H), 8.30 (dd, J = 2.7 Hz, 13.6 Hz, 2H), 8.04 (d, J = 8.2 Hz, 1H), 7.97 (d, J = 2.3 Hz, 2H), 7.62 (d, J = 16 Hz, 1H), 7.39 (s, 1H), 7.21 (s, 1H), 6.92 (s, 1H), 6.74 (d, J = 16 Hz, 1H) MS (ES) m/z 375 (M + H). |
| 325 | 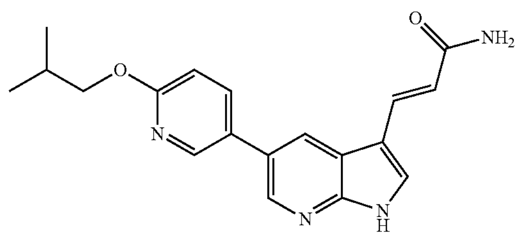 [SMILES: CC(C)COc1ccc(-c2cnc3[nH]cc(/C=C/C(N)=O)c3c2)cn1] | (E)-3-(5-(6-isobutoxypyridin-3-yl)-1H-pyrrolo[2,3-b]pyridin-3-yl)acrylamide | $^1$H NMR (400 MHz, DMSO-d$_6$) δ ppm, 12.26 (s, 1H), 8.57 (d, J = 1.96 Hz, 1H), 8.55 (d, J = 2.74 Hz, 1H), 8.44 (d, J = 1.96 Hz, 1H), 8.13-8.10 (m, 1H), 7.93 (s, 1H), 7.59 (d, J = 16.04 Hz, 1H), 7.33 (br. s, 1H), 6.96 (d, J = 8.61 Hz, 1H), 6.90 (br. s, 1H), 6.70 (d, J = 16.04 Hz, 1H) 4.10 (d, J = 6.65 Hz, 2H), 2.11-2.03 (m, 1H), 0.99 (d, J = 6.65 Hz, 6H). MS (ES) m/z 337 (M + H). |
| 326 | 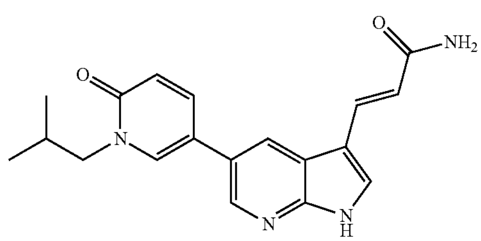 [SMILES: CC(C)Cn1cc(-c2cnc3[nH]cc(/C=C/C(N)=O)c3c2)ccc1=O] | (E)-3-(5-(1-isobutyl-6-oxo-1,6-dihydropyridin-3-yl)-1H-pyrrolo[2,3-b]pyridin-3-yl)acrylamide | $^1$H NMR (400 MHz, DMSO-d$_6$) δ ppm, 12.15 (s, 1H), 8.50 (d, J = 1.96 Hz, 1H), 8.34 (d, J = 1.96 Hz, 1H), 8.12 (d, J = 2.73 Hz, 1H), 7.93 - 7.89 (m, 2H), 7.59 (d, J = 16.04 Hz, 1H), 7.32 (br. s, 1H), 6.91 (br. s, 1H), 6.66 (d, J = 16.04 Hz, 1H), 6.55 (d, J = 9.39 Hz, 1H), 3.82 (d, J = 7.43 Hz, 2H), 2.20 - 2.13 (m, 1H), 0.90 (d, J = 6.65 Hz, 6H). MS (ES) m/z 337 (M + H). |
| 327 | 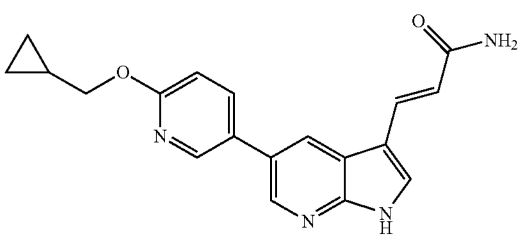 [SMILES: NC(=O)/C=C/c1c[nH]c2ncc(-c3ccc(OCC4CC4)nc3)cc12] | (E)-3-(5-(6-(cyclopropylmethoxy)pyridin-3-yl)-1H-pyrrolo[2,3-b]pyridin-3-yl)acrylamide | $^1$H NMR (400 MHz, DMSO-d$_6$) δ ppm, 12.19 (s, 1H), 8.58 (s, 1H), 8.55 (s, 1H), 8.45 (s, 1H), 8.12 (d, J = 8.60 Hz, 1H), 7.94, (s, 1H), 7.59 (d, J = 15.65 Hz, 1H), 7.33 (br. s, 1H), 6.97 (d, J = 8.61 Hz, 1H), 6.92 (br. s, 1H), 6.71 (d, J = 16.04 Hz, 1H), 4.16 (d, J = 7.05 Hz, 2H), 1.32-1.23 (m, 1H), 0.59-0.57 (m, 2 H), 0.36-0.34 (m, 2H). MS (ES) m/z 335 (M + H). |
| 328 | 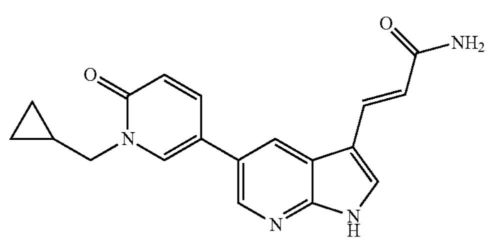 [SMILES: NC(=O)/C=C/c1c[nH]c2ncc(-c3ccc(=O)n(CC4CC4)c3)cc12] | (E)-3-(5-(1-(cyclopropylmethyl)-6-oxo-1,6-dihydropyridin-3-yl)-1H-pyrrolo[2,3-b]pyridin-3-yl)acrylamide | $^1$H NMR (400 MHz, DMSO-d$_6$) δ ppm, 12.16 (s, 1H), 8.51 (d, J = 2.35 Hz, 1H), 8.35 (d, J = 1.95 Hz, 1H), 8.19 (d, J = 2.35 Hz, 1H), 7.93-7.89 (m, 2H), 7.59 (d, J = 15.65 Hz, 1H), 7.31 (br. s, 1H), 6.92 (br. s, 1H), 6.66 (d, J = 15.65 Hz, 1H), 6.55 (d, J = 9.39 Hz, 1H), 3.85 (d, J = 7.43 Hz, 2H), 1.35-1.30 (m, 1H), 0.52-0.43 (m, 4H). MS (ES) m/z 335 (M + H). |

TABLE 1-continued

Compound Examples — Spectral Data

| Example | Structure | Name | Spectral Data |
|---|---|---|---|
| 329 | 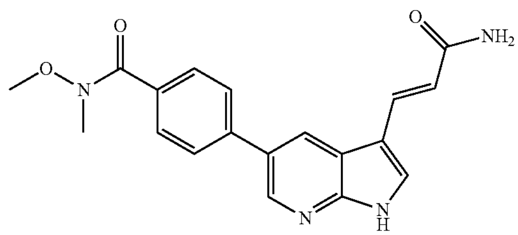 [SMILES: CON(C)C(=O)c1ccc(-c2cnc3[nH]cc(/C=C/C(N)=O)c3c2)cc1] | (E)-4-(3-(3-amino-3-oxoprop-1-en-1-yl)-1H-pyrrolo[2,3-b]pyridin-5-yl)-N-methoxy-N-methyl-benzamide | $^1$H NMR (400 MHz, DMSO-d$_6$) δ ppm, 12.22 (s, 1H), 8.65 (d, J = 1.9 Hz, 1H), 8.52 (d, J = 1.9 Hz, 1H), 7.96 (s, 1H), 7.86 (d, J = 8.2 Hz, 2H), 7.74 (d, J = 8.2 Hz, 2H), 7.60 (d, J = 16 Hz, 1H), 7.37 (s, 1H), 6.91 (s, 1H), 6.72 (d, J = 16 Hz, 1H), 3.58 (s, 3H), 3.27 (s, 3H). MS (ES) m/z 351 (M + H). |
| 330 | 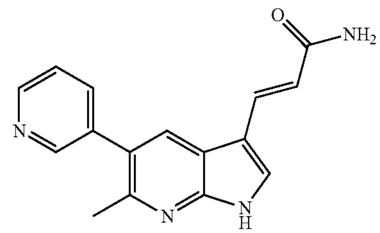 [SMILES: Cc1nc2[nH]cc(/C=C/C(N)=O)c2cc1-c1cccnc1] | (E)-3-(6-methyl-5-(pyridin-3-yl)-1H-pyrrolo[2,3-b]pyridin-3-yl)acrylamide | $^1$H NMR (400 MHz, DMSO-d$_6$) δ ppm, 12.05 (s, 1H), 8.66 (d, J = 2.3 Hz, 1H), 8.62 (m, 1H) 8.09 (s, 1H), 7.91 (m, 1H), 7.86 (m, 1H), 7.55 (s, 1H), 7.52 (m, 1H), 7.27 (s, 1H), 6.83 (s, 1H), 6.59 (d, J = 16 Hz, 1H), 2.41 (s, 3H). MS (ES) m/z 279 (M + H). |
| 331 | 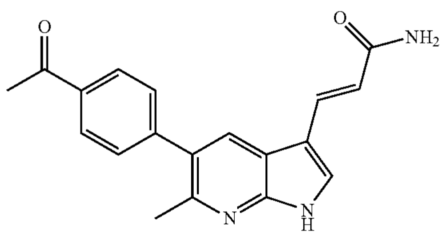 | (E)-3-(5-(4-acetylphenyl)-6-methyl-1H-pyrrolo[2,3-b]pyridin-3-yl)acrylamide | $^1$H NMR (400 MHz, DMSO-d$_6$) δ ppm,12.04 (s, 1H), 8.07-8.00 (m, 2H), 7.86 (s, 1H), 7.62 (d, J = 7.82 Hz, 2H), 7.54 (d, J = 16.04 Hz, 1H), 7.29 (s, 1H), 6.82 (s, 1H), 6.57 (d, J = 16.04 Hz, 1H), 2.67 (s, 3H), 2.08 (s, 3H). MS (ES) m/z 329 (M + H). |
| 332 | 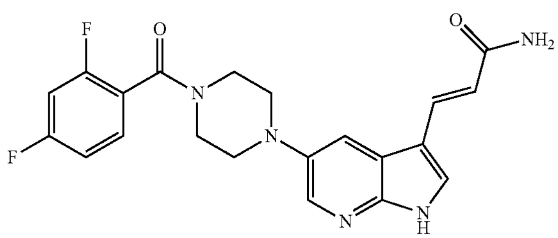 [SMILES: NC(=O)/C=C/c1c[nH]c2ncc(N3CCN(C(=O)c4ccc(F)cc4F)CC3)cc12] | (E)-3-(5-(4-(2,4-difluorobenzoyl)piperazin-1-yl)-1H-pyrrolo[2,3-b]pyridin-3-yl)acrylamide | $^1$H NMR (400 MHz, DMSO-d$_6$) δ ppm, 11.91 (s, 1H), 8.57 (d, J = 18.39 Hz, 1H), 8.17 (d, J = 2.35 Hz, 1H), 8.06 (d, J = 13.3 Hz, 1H), 7.78 (d, J = 2.74 Hz, 1H), 7.63 (d, J = 16.04 Hz, 1H), 7.58-7.55 (m, 2H), 6.98 (s, 1H), 6.86 (s, 1H), 6.69 (d, J = 16.04 Hz, 1H), 3.44-3.33 (m, 8H). MS (ES) m/z 412 (M + H). |
| 333 | 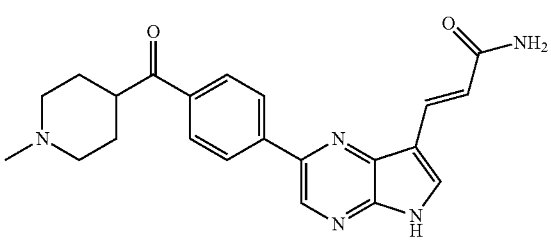 [SMILES: CN1CCC(C(=O)c2ccc(-c3cnc4[nH]cc(/C=C/C(N)=O)c4n3)cc2)CC1] | (E)-3-(2-(4-(1-methylpiperidine-4-carbonyl)phenyl)-5H-pyrrolo[2,3-b]pyrazin-7-yl)acrylamide | $^1$H NMR (400 MHz, DMSO-d$_6$) δ ppm, 12.55 (s, 1H), 9.09 (s, 1H), 8.48 (d, J = 8.2 Hz, 2H), 8.27 (s, 1H), 8.14 (d, J = 7.8 Hz, 2H), 7.65 (s, 1H), 7.61 (d, J = 15.7 Hz, 1H), 7.30 (d, J = 15.7 Hz, 1H), 6.98 (s, 1H), 3.52 (s, 3H), 3.21-3.20 (m, 1H), 2.20-2.17 (m, 4H), 1.65-1.60 (m, 4H). MS (ES) m/z 390 (M + H). |
| 334 | 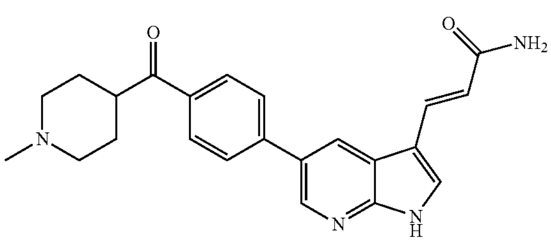 [SMILES: CN1CCC(C(=O)c2ccc(-c3cnc4[nH]cc(/C=C/C(N)=O)c4c3)cc2)CC1] | (E)-3-(5-(4-(1-methylpiperidine-4-carbonyl)phenyl)-1H-pyrrolo[2,3-b]pyridin-3-yl)acrylamide | $^1$H NMR (400 MHz, DMSO-d$_6$) δ ppm, 12.55 (s, 1H), 8.48 (d, J = 8.2 Hz, 2H), 8.27 (s, 1H), 8.14 (d, J = 7.8 Hz, 2H), 7.65 (s, 1H), 7.61 (d, J = 16 Hz, 1H), 7.30 (d, J = 16 Hz, 1H), 6.98 (s, 1H), 3.52 (s, 3H), 3.21-3.20 (m, 1H), 2.20-2.17 (m, 4H), 1.65-1.60 (m, 4H). MS (ES) m/z 389 (M + H). |

TABLE 1-continued

Compound Examples — Spectral Data

| Example | Name | Spectral Data |
|---|---|---|
| 335 | (E)-3-(4-(4-isopropylbenzoyl)piperazin-1-yl)-1H-pyrrolo[2,3-b]pyridin-3-yl)acrylamide | $^1$H NMR (400 MHz, DMSO-d$_6$) δ ppm, 11.89 (s, 1H), 8.17 (d, J = 2.35 Hz, 1H), 7.81 (d, J = 2.7 Hz, 1H), 7.75 (d, J = 2.35 Hz, 1H), 7.54 (d, J = 16.04 Hz, 1H), 7.40-7.33 (m, 5H), 6.86 (s, 1H), 6.52 (d, J = 16 Hz, 1H), 3.78-3.57 (m, 8H), 2.94 (m, 1H), 1.19 (d, J = 7.02Hz, 6H). MS (ES) m/z 418 (M + H). |
| 336 | (E)-3-(5-(6-(2-ethoxyethoxy)pyridin-3-yl)-1H-pyrrolo[2,3-b]pyridin-3-yl)acrylamide | $^1$H NMR (400 MHz, DMSO-d$_6$) δ ppm, 12.19 (s, 1H), 8.59 (d, J = 1.96 Hz, 1H), 8.57 (d, J = 2.73 Hz, 1H), 8.46 (d, J = 1.96 Hz, 1H), 8.13 (dd, J = 8.60, 2.74 Hz, 1H), 7.94 (s, 1H), 7.59 (d, J = 15.65 Hz, 1H), 7.33 (br. s, 1H), 6.99 (d, J = 8.61 Hz, 1H), 6.92 (br. s, 1H), 6.71 (d, J = 15.65 Hz, 1H), 4.43 (t, J = 4.69 Hz, 2H), 3.75-3.72 (m, 2H), 3.53 (q, J = 7.04 Hz, 2H), 1.14 (t, J = 7.04 Hz, 3H). MS (ES) m/z 353 (M + H). |
| 337 | (E)-3-(5-(1-(2-ethoxyethyl)-6-oxo-1,6-dihydropyridin-3-yl)-1H-pyrrolo[2,3-b]pyridin-3-yl)acrylamide | $^1$H NMR (400 MHz, DMSO-d$_6$) δ ppm, 12.15 (s, 1H), 8.48 (d, J = 1.96 Hz, 1H), 8.34 (d, J = 1.96 Hz, 1H), 8.08 (d, J = 2.35 Hz, 1H), 7.93 (d, J = 2.74 Hz, 1H), 7.90 (d, J = 2.35 Hz, 1H), 7.59 (d, J = 15.65 Hz, 1H), 7.30 (br. s, 1H), 6.92 (br. s, 1H), 6.66 (d, J = 16.04 Hz, 1H), 6.55 (d, J = 9.39 Hz, 1H), 4.17-4.14 (m, 2H), 3.69 - 3.66 (m, 2H), 3.46 (q, J = 7.04 Hz, 2H), 1.07 (t, J = 7.04 H, 3H). MS (ES) m/a 353 (M + H). |
| 338 | (E)-3-(5-benzoyl-1H-pyrrolo[2,3-b]pyridin-3-yl)acrylamide | $^1$H NMR (400 MHz, DMSO-d$_6$) δ ppm, 12.55 (s, 1H), 8.63 (d, J = 2.35 Hz, 1H), 8.59 (d, J = 1.95 Hz, 1H), 8.10 (s, 1H), 7.82 (d, J = 7.04 Hz, 2H), 7.75-7.64 (m, 1H), 7.63-7.58 (m, 3H), 7.42 (s, 1H), 6.93 (s, 1H), 6.62 (d, J = 16.04 Hz, 1H). MS (ES) m/z 292 (M + H). |
| 339 | (E)-3-(5-(4-acetyl-3-methylphenyl)-1H-pyrrolo[2,3-b]pyridin-3-yl)acrylamide | $^1$H NMR (400 MHz, DMSO-d$_6$) δ ppm, 12.26 (s, 1H), 8.63 (s, 1H), 8.52 (s, 1H), 7.96 (m, 2H), 7.73 (m, 2H), 7.61 (d, J = 16.04 Hz, 1H), 7.37 (s, 1H), 6.92 (s, 1H), 6.70 (d, J = 16 Hz, 1H), 3.57 (s, 3H), 2.64 (s, 3H). MS (ES) m/z 320 (M + H). |
| 340 | (E)-3-(2-(4-acetyl-3-methylphenyl)-5H-pyrrolo[2,3-b]pyrazin-7-yl)acrylamide | $^1$H NMR (400 MHz, DMSO-d$_6$) δ ppm, 12.01 (s, 1H), 8.95 (s, 1H), 8.24-8.17 (m, 2H), 7.96 (d, J = 8.61 Hz, 1H), 7.60 (d, J = 15.26 Hz, 1H), 7.54 (s, 1H), 7.46 (d, J = 7.82 Hz, 1H), 7.18 (d, J = 15.26 Hz, 1H), 6.83 (s, 1H), 2.56 (s, 3H), 1.69 (s, 3H). MS (ES) m/z 321 (M + H). |

TABLE 1-continued

Compound Examples — Spectral Data

| Example | Structure | Name | Spectral Data |
|---|---|---|---|
| 341 | 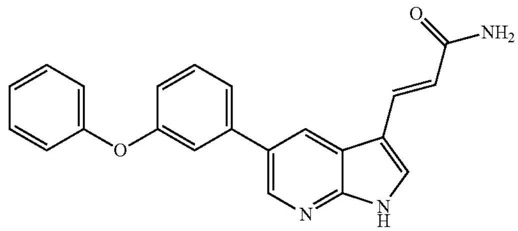 [SMILES: NC(=O)/C=C/c1c[nH]c2ncc(-c3cccc(Oc4ccccc4)c3)cc12] | (E)-3-(5-(3-phenoxyphenyl)-1H-pyrrolo[2,3-b]pyridin-3-yl)acrylamide | $^1$H NMR (400 MHz, DMSO-$d_6$) δ ppm, 12.20 (s, 1H), 8.57 (d, J = 1.95 Hz, 1H), 8.47 (d, J = 1.96 Hz, 1H), 7.95 (s, 1H), 7.60 (d, J = 15.65 Hz, 1H), 7.56-7.50 (m, 2H), 7.46-7.40 (m, 3H), 7.36 (br. s, 1H), 7.18-7.15 (m, 1H), 7.10 (d, J-8.61 Hz, 2H), 6.99 (d, J = 5.87 Hz, 1H), 6.91 (br. s, 1H), 6.70 (d, J = 16.04 Hz, 1H). MS (ES) m/z 356 (M + H). |
| 342 | 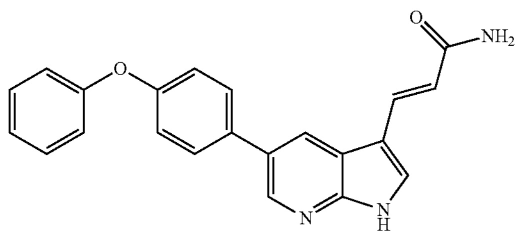 [SMILES: NC(=O)/C=C/c1c[nH]c2ncc(-c3ccc(Oc4ccccc4)cc3)cc12] | (E)-3-(5-(4-phenoxyphenyl)-1H-pyrrolo[2,3-b]pyridin-3-yl)acrylamide | $^1$H NMR (400 MHz, DMSO-$d_6$) δ ppm, 12.17 (s, 1H), 8.57 (d, J = 2.34 Hz, 1H), 8.44 (d, J = 1.95 Hz, 1H), 7.94 (d, J = 1.96 Hz, 1H), 7.78 (d,J=8.60 Hz, 2H), 7.60 (d, J = 16.05 Hz, 1H), 7.45-7.41 (m, 2H), 7.36 (br. s, 1H), 7.18-7.14 (m, 3H), 7.08 (d, J = 8.61 Hz, 2H), 6.90 (br. s, 1H), 6.70 (d, J = 16.04 Hz, 1H). MS (ES) m/z 356 (M + H). |
| 343 | 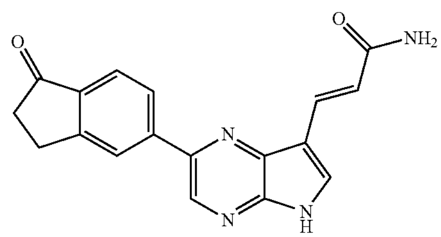 [SMILES: NC(=O)/C=C/c1c[nH]c2ncc(-c3ccc4c(c3)CCC4=O)nc12] | (E)-3-(2-(1-oxo-2,3-dihydro-1H-inden-5-yl)-5H-pyrrolo[2,3-b]pyrazin-7-yl)acrylamide | $^1$H NMR (400 MHz, DMSO-$d_6$) δ ppm, 12.54 (s, 1H), 9.07 (s, 1H), 8.46 (s, 1H), 8.36 (d, J = 6.4 Hz, 1 H), 8.27 (s, 1H), 7.77 (d, J = 6 Hz, 1H), 7.69 (s, 1H), 7.61 (d, J = 8.0 Hz, 1H)7.28 (d, J = 12.4 Hz, 1 H), 6.96 (s, 1H), 3.24(t, J = 4.4 Hz, 2 H) , 2.72(t, J = 4.8 Hz, 2 H). MS (ES) m/z 319 (M + H). |
| 344 | 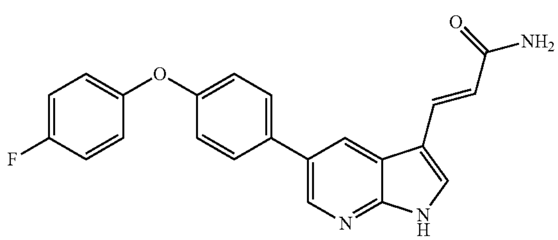 [SMILES: NC(=O)/C=C/c1c[nH]c2ncc(-c3ccc(Oc4ccc(F)cc4)cc3)cc12] | (E)-3-(5-(4-(4-fluorophenoxy)phenyl)-1H-pyrrolo[2,3-b]pyridin-3-yl)acrylamide | $^1$H NMR (400 MHz, DMSO-$d_6$) δ ppm, 12.17 (1, 1H), 8.57 (d, J = 1.95 Hz, 1H), 8.43 (d, J = 1.95 Hz, 1H), 7.94 (s, 1H), 7.78 (d, J = 8.60 Hz, 2H), 7.60 (d, J = 15.65 Hz, 1H), 7.36 (br. S, 1H), 7.30-7.25 (m, 2H), 7.16-7.12 (m, 3H), 6.90 (br. S, 1H), 6.70 (d, J = 16.04 Hz, 1H). MS (ES) m/z 374 (M + H). |
| 345 | 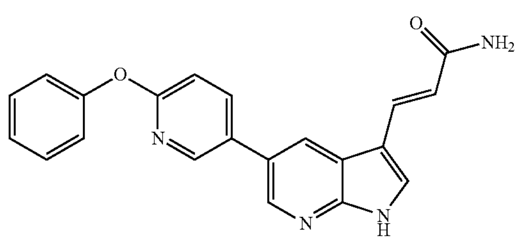 [SMILES: NC(=O)/C=C/c1c[nH]c2ncc(-c3ccc(Oc4ccccc4)nc3)cc12] | (E)-3-(5-(6-phenoxypyridin-3-yl)-1H-pyrrolo[2,3-b]pyridin-3-yl)acrylamide | $^1$H NMR(400 MHz, DMSO-$d_6$) δ ppm, 12.22 (s, 1H), 8.61 (s, 1H), 8.57 (s, 1H), 8.48 (s, 1H), 8.29-8.26 (m, 1H), 7.96 (s, 1H), 7.59 (d, J = 16.05 Hz, 1H), 7.48-7.44 (m, 2H), 7.31 (br. s, 1H), 7.26-7.23 (m, 1H), 7.20-7.17 (m, 3H), 6.92 (br. s, 1H), 6.70 (d, J = 15.65 Hz, 1H). MS (ES) m/z 357 (M + H). |
| 346 | 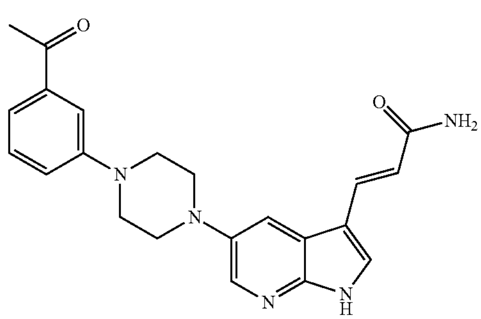 [SMILES: CC(=O)c1cccc(N2CCN(c3cnc4[nH]cc(/C=C/C(N)=O)c4c3)CC2)c1] | (E)-3-(5-(4-(3-acetylphenyl)piperazin-1-yl)-1H-pyrrolo[2,3-b]pyridin-3-yl)acrylamide | $^1$H NMR (400 MHz, DMSO-$d_6$) δ ppm, 11.89 (s, 1H), 8.23 (d, J = 2.35 Hz, 1H), 7.97 (d, J = 8.60 Hz, 1H), 7.81 (d, J = 2.73 Hz, 2H), 7.61 (d, J = 16 Hz, 1H), 7.54 (s, 1H), 7.35-7.11 (m, 3H), 6.86 (s, 1H), 6.55 (d, J = 16 Hz, 1H), 3.44-3.33 (m, 8H), 2.58 (s, 3H). MS (ES) m/z 390 (M + H). |

TABLE 1-continued

Compound Examples — Spectral Data

| Example | Name | Spectral Data |
|---|---|---|
| 347 | (E)-3-(5-(3-chloro-5-(trifluoromethyl)phenyl)-1H-pyrrolo[2,3-b]pyridin-3-yl)acrylamide | $^1$H NMR (400 MHz, DMSO-d$_6$) δ ppm, 12.31 (s, 1H), 8.69 (d, J = 1.96 Hz, 1H), 8.59 (d, J = 1.96 Hz, 1H), 8.21 (s, 1H), 8.11 (s, 1H), 8.00 (s, 1H), 7.88 (s, 1H), 7.63 (d, J = 16.05 Hz, 1H), 7.37 (br. s, 1H), 6.93 (br. s, 1H), 6.72 (d, J = 16.04 Hz, 1H). MS (ES) m/z 366 (M + H). |
| 348 | (E)-3-(5-(3-methyl-5-(trifluoromethyl)phenyl)-1H-pyrrolo[2,3-b]pyridin-3-yl)acrylamide | $^1$H NMR(400 MHz, DMSO-d$_6$) δ ppm, 12.29 (s, 1H), 8.63 (d, J = 1.96 Hz, 1H), 8.53 (d, J = 1.57 Hz, 1H), 7.96 (s, 1H), 7.94 (s, 1H), 7.87 (s, 1H), 7.62 (d, J = 15.65 Hz, 1H), 7.45 (br. s, 1H), 6.92 (br. s, 1H), 6.74 (d, J = 16.04 Hz, 1H), 2.50 (s, 3H). MS (ES) m/z 346 (M + H). |
| 349 | (E)-3-(5-(3-methoxy-5-(trifluoromethyl)phenyl)-1H-pyrrolo[2,3-b]pyridin-3-yl)acrylamide | $^1$H NMR(400 MHz, DMSO-d$_6$) δ ppm, 12.29 (s, 1H), 8.65 (d, J = 1.96 Hz, 1H), 8.53 (d, J = 1.96 Hz, 1H), 7.97 (s, 1H), 7.62 (d, J = 16.04 Hz, 1H), 7.40 (br. s, 1H), 7.27 (s, 1H), 6.92 (br. s, 1H), 6.72 (d, J = 16.04 Hz, 1H), 3.95 (s, 3H). MS (ES) m/z 362 (M + H). |
| 350 | (E)-3-(5-(2-chloro-6-(trifluoromethyl)pyridin-4-yl)-1H-pyrrolo[2,3-b]pyridin-3-yl)acrylamide | $^1$H NMR (400 MHz, DMSO-d$_6$) δ ppm, 12.04 (s, 1H), 8.89 (s, 1H), 8.79 (s, 1H), 8.43 (s, 1H), 8.38 (s, 1H), 8.03 (s, 1H), 7.65 (d, J = 15.65 Hz, 1H), 7.33 (br. s, 1H), 6.98 (br. s, 1H), 6.72 (d, J = 16.04 Hz, 1H). MS (ES) m/z 367 (M + H). |
| 351 | (E)-5-(3-(3-amino-3-oxoprop-1-en-1-yl)-1H-pyrrolo[2,3-b]pyridin-5-yl)-N,N,6-trimethylpicolinamide | $^1$H NMR (400 MHz, MeOD-d$_6$) δ ppm, 8.44 (s, 1H), 8.38 (s, 1H), 8.03-8.02 (d, J = 8 Hz, 1H), 7.91 (s, 1H), 7.80-7.77 (d, J = 15 Hz, 1H), 7.65-7.64 (d, J = 5 Hz, 1H), 6.74-6.71 (d, J = 15 Hz, 1H), 3.20 (s, 3H), 3.12 (s, 3H), 2.63 (s, 3H). MS (ES) m/z 350 (M + H). |
| 352 | (E)-3-(5-(3-oxo-2,3-dihydro-1H-inden-5-yl)-1H-pyrrolo[2,3-b]pyridin-3-yl)acrylamide | $^1$H NMR (400 MHz, DMSO-d$_6$) δ ppm, 12.21 (s, 1H), 8.61 (d, J = 1.95 Hz, 1H), 8.49 (d, J = 1.95 Hz, 1H), 8.08 (dd, J = 6.2 Hz, 1.95 Hz, 1H), 7.96-7.64 (m, 2H), 7.74 (d, J = 7.83 Hz, 1H), 7.61 (d, J = 16 Hz, 1H), 7.36 (s, 1H), 6.90 (s, 1H), 6.69 (d, J = 16 Hz, 1H), 2.74-2.72 (m, 2H), 2.67-2.66 (m, 2H). MS (ES) m/z 318 (M + H). |

TABLE 1-continued

Compound Examples — Spectral Data

| Example | Structure | Name | Spectral Data |
| --- | --- | --- | --- |
| 353 | 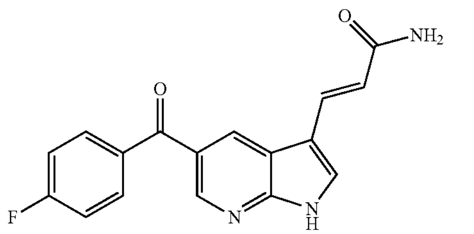 [SMILES: NC(=O)/C=C/c1c[nH]c2ncc(C(=O)c3ccc(F)cc3)cc12] | (E)-3-(5-(4-fluorobenzoyl)-1H-pyrrolo[2,3-b]pyridin-3-yl)acrylamide | $^1$H NMR (400 MHz, DMSO-$d_6$) δ ppm, 12.27 (s, 1H), 8.70 (d, J = 1.95 Hz, 1H), 8.58 (d, J = 1.95 Hz, 1H), 8.01-7.98 (m, 3H), 7.90-7.86 (m, 4H), 7.61 (d, J = 16 Hz, 1H), 7.46-7.41 (m, 2H), 7.38 (s, 1H), 6.92 (s, 1H), 6.73 (d, J = 16 Hz, 1H). MS (ES) m/z 386 (M + H). |
| 354 | 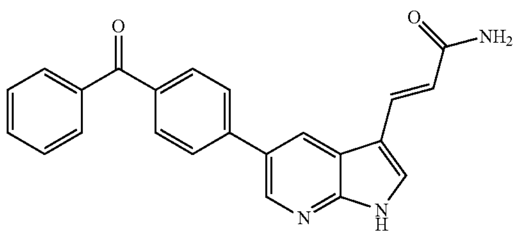 [SMILES: NC(=O)/C=C/c1c[nH]c2ncc(-c3ccc(C(=O)c4ccccc4)cc3)cc12] | (E)-3-(5-(4-benzoylphenyl)-1H-pyrrolo[2,3-b]pyridin-3-yl)acrylamide | $^1$H NMR (400 MHz, DMSO-$d_6$) δ ppm, 12.27 (s, 1H), 8.70 (d, J = 2.9 Hz, 1H), 8.58 (d, J = 1.9 Hz, 1H), 8.01-7.98 (m, 3H), 7.88 (d, J = 8.2 Hz, 2H), 7.80-7.78 (m, 2H), 7.73-7.69 (m, 1H), 7.64-7.58 (m, 3H), 7.37 (s, 1H), 6.93 (s, 1H), 6.73 (d, J = 16 Hz, 1H). MS (ES) m/z 368 (M + H). |
| 355 | 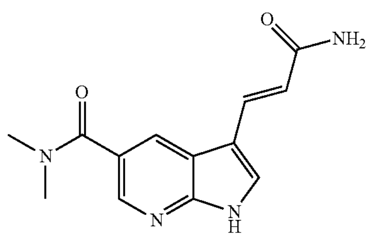 | (E)-3-(3-amino-3-oxoprop-1-en-1-yl)-N,N-dimethyl-1H-pyrrolo[2,3-b]pyridine-5-carboxamide | $^1$H NMR (400 MHz, DMSO-$d_6$) δ ppm, 12.21 (s, 1H), 8.63 (d, J = 1.95 Hz, 1H), 8.50 (d, J = 1.95 Hz, 1H), 7.95 (s, 1H), 7.84-7.82 (m, 2H), 7.60 (d, J = 16.04 Hz 1H), 7.55-7.53 (m, 2H), 7.37 (m, 2H), 7.37 (s, 1H), 6.91 (s, 1H), 3.16 (s, 6H). MS (ES) m/z 335 (M + H). |
| 356 | 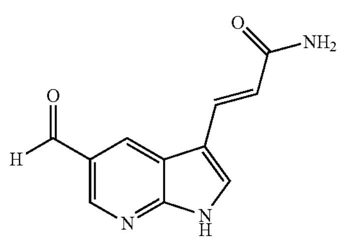 [SMILES: NC(=O)/C=C/c1c[nH]c2ncc(C=O)cc12] | (E)-3-(5-formyl-1H-pyrrolo[2,3-b]pyridin-3-yl)acrylamide | $^1$H NMR (400 MHz, DMSO-$d_6$) δ ppm, 12.27 (s, 1H), 10.08 (s, 1H), 8.70 (d, J = 1.95 Hz, 1H), 8.58 (d, J = 2.35 Hz, 1H), 8.04-8.00 (m, 3H), 7.98 (d, J = 2.74 Hz, 2H), 7.61 (d, J = 16.04 Hz, 1H), 7.37 (s, 1H), 6.93 (s, 1H), 6.73 (d, J = 16.04 Hz, 1H). MS (ES) m/z 292 (M + H). |
| 357 | 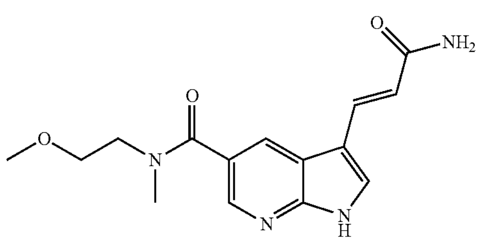 | (E)-3-(3-amino-3-oxoprop-1-en-1-yl)-N-(2-methoxyethyl)-N-methyl-1H-pyrrolo[2,3-b]pyridine-5-carboxamide | $^1$H NMR (400 MHz, DMSO-$d_6$) δ ppm, 12.21 (s, 1H), 8.63 (d, J = 1.95 Hz, 1H), 8.50 (d, J = 1.95 Hz, 1H), 7.95 (s, 1H), 7.60 (d, J = 15.65 Hz, 1H), 7.36 (s, 1H), 6.91 (s, 1H), 6.71 (d, J = 15.65 Hz, 1H), 3.68-3.52 (m, 2H), 3.46 (s, 1H), 3.29-3.22 (m, 2H), 3.00 (s, 1H). MS (ES) m/z 378 (M + H). |
| 358 | 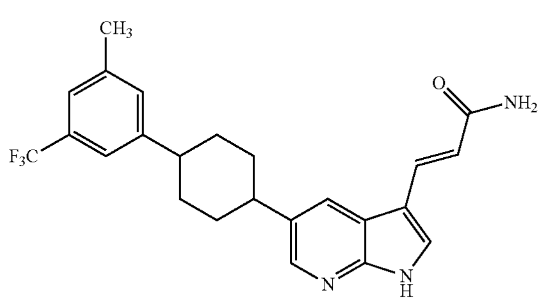 [SMILES: Cc1cc(C2CCC(c3cnc4[nH]cc(/C=C/C(N)=O)c4c3)CC2)cc(C(F)(F)F)c1] | (E)-3-(5-(4-(3-methyl-5-(trifluoromethyl)phenyl)cyclohexyl)-1H-pyrrolo[2,3-b]pyridin-3-yl)acrylamide | $^1$H NMR (400 MHz, DMSO-$d_6$) δ ppm, 11.89 (s, 1H), 8.21 (d, J = 2.35 Hz, 1H), 7.82-7.80 (m, 2H), 7.55 (d, J = 16.04 Hz, 1H), 7.35 (s, 1H), 7.14 (s, 1H), 7.06 (s, 1H), 6.94 (s, 1H), 6.87 (s, 1H), 6.54 (d, J = 16.04 Hz, 1H), 3.44-3.30 (m, 8H), 2.30-2.21 (m, 3H). MS (ES) m/z 430 (M + H). |

TABLE 1-continued

Compound Examples — Spectral Data

| Example | Structure | Name | Spectral Data |
|---|---|---|---|
| 359 | 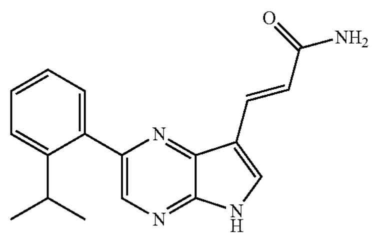 [SMILES: CC(C)c1ccccc1-c1cnc2[nH]cc(/C=C/C(N)=O)c2n1] | (E)-3-(2)-(2-isopropylphenyl)-5H-pyrrolo[2,3-b]pyrazin-7-yl)acrylamide | $^1$H NMR (400 MHz, DMSO-d$_6$) δ ppm, 12.50 (s, 1H), 8.37 (s, 1H), 8.26 (d, J = 1.96 Hz, 1H), 7.59 (d, J = 15.26 Hz, 1H), 7.53-7.44 (m, 3H), 7.39-7.38 (m, 1H), 7.33-7.29 (m, 1H), 7.07 (d, J = 15.65 Hz, 1H), 6.84 (br. s, 1H), 3.10-3.07 (m, 1H), 1.24-1.17 (m, 6H). MS (ES) m/z 307 (M + H). |
| 360 | 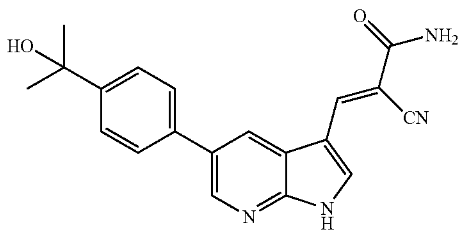 [SMILES: CC(C)(O)c1ccc(-c2cnc3[nH]cc(/C=C(\C#N)C(N)=O)c3c2)cc1] | (E)-2-cyano-3-(5-(4-(2-hydroxypropan-2-yl)phenyl)-1H-pyrrolo[2,3-b]pyridin-3-yl)acrylamide | $^1$H NMR (400 MHz, DMSO-d$_6$) δ ppm, 12.63 (s, 1H), 8.69(s, 1H), 8.52 (d, J = 5.42 Hz, 1H), 7.76-7.58 (m, 5H), 7.34 (s, 1H), 5.08 (s, 1H), 1.47 (s, 6H). MS (ES) m/z 347 (M + H). |
| 361 | 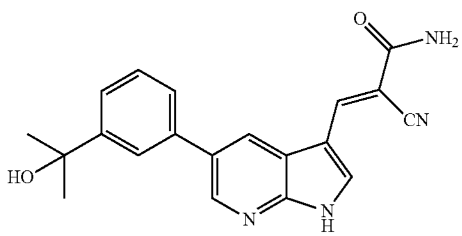 [SMILES: CC(C)(O)c1cccc(-c2cnc3[nH]cc(/C=C(\C#N)C(N)=O)c3c2)c1] | (E)-2-cyano-3-(5-(3-(2-hydroxypropan-2-yl)phenyl)-1H-pyrrolo[2,3-b]pyridin-3-yl)acrylamide | $^1$H NMR (400 MHz, DMSO-d$_6$) δ ppm, 12.92 (s, 1H), 8.68 (s, 2H), 8.54 (d, J = 7.40 Hz, 2H), 7.85 (d, J = 1.5 Hz, 1H), 7.81 (s, 1H), 7.61-7.57 (m, 2H), 7.51-7.49 (m, 1H), 7.46-7.42 (m, 1H), 5.11 (s, 1H), 1.50 (s, 6H). MS (ES) m/z 347 (M + H). |
| 362 | 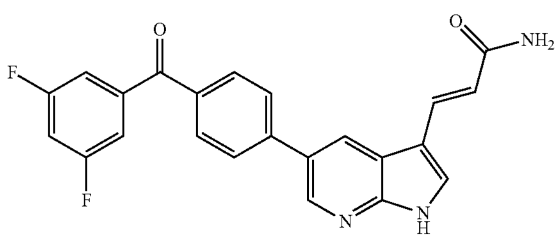 [SMILES: NC(=O)/C=C/c1c[nH]c2ncc(-c3ccc(C(=O)c4cc(F)cc(F)c4)cc3)cc12] | (E)-3-(5-(4-(3,5-difluorobenzoyl)phenyl)-1H-pyrrolo[2,3-b]pyridin-3-yl)acrylamide | $^1$H NMR (400 MHz, DMSO-d$_6$) δ ppm, 12.29 (s, 1H), 8.71 (d, J = 1.95 Jz, 1H), 8.59 (d, J = 1.95 Hz, 1H), 8.03-7.98 (m, 3H), 7.93-7.91 (m, 2H), 7.67-7.59 (m, 2H), 7.47-7.46 (m, 2H), 7.37 (s, 1H), 6.93-6.91 (m, 1H). MS (ES) m/z 404 (M + H). |
| 363 | 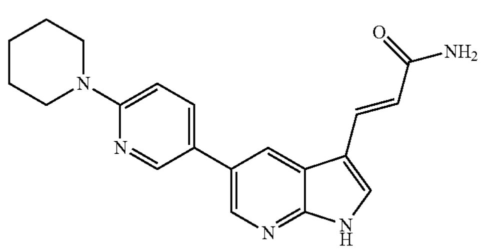 [SMILES: NC(=O)/C=C/c1c[nH]c2ncc(-c3ccc(N4CCCCC4)nc3)cc12] | (E)-3-(5-(6-(piperidin-1-yl)pyridin-3-yl)-1H-pyrrolo[2,3-b]pyridin-3-yl)acrylamide | $^1$H NMR (400 MHz, DMSO-d$_6$) δ ppm, 12.12 (s, 1H), 9.13 (s, 1H), 8.53 (dd, J = 1.95 Hz, 4.6Hz, 1H), 8.39 (d, J = 1.95 Hz, 1H), 7.90 (s, 1H), 7.58 (d, J = 15.60 Hz, 1H), 7.34 (s, 1H), 6.93 (m, 2H), 6.67 (m, 2H), 3.58 (m, 4H), 0.848 (m, 6H). MS (ES) m/z 348 (M + H). |
| 364 | 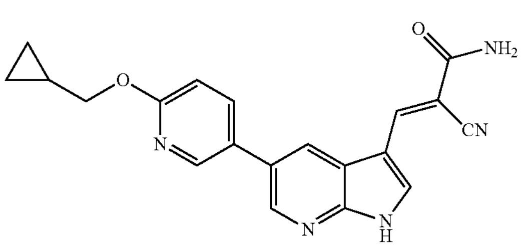 [SMILES: N#C/C(=C\c1c[nH]c2ncc(-c3ccc(OCC4CC4)nc3)cc12)C(N)=O] | (E)-2-cyano-3-(5-(6-(cyclopropyl-methoxy)pyridin-3-yl)-1H-pyrrolo[2,3-b]pyridin-3-yl)acrylamide | $^1$H NMR(400 MHz, DMSO-d$_6$) δ ppm, 12.67 (s, 1H), 8.68 (m, 2H), 8.54 (m, 3H), 8.13 (m, 1H), 7.75 (s, 1H), 7.57 (s, 1H), 6.96 (d, J = 9.02 Hz, 1H), 4.15 (d, J = 7.05 Hz, 2H), 1.28 (m, 1H), 0.57 (m, 2H), 0.35 (m, 2H). MS (ES) m/z 360 (M + H). |

TABLE 1-continued

Compound Examples — Spectral Data

| Example | Structure | Name | Spectral Data |
|---|---|---|---|
| 365 | 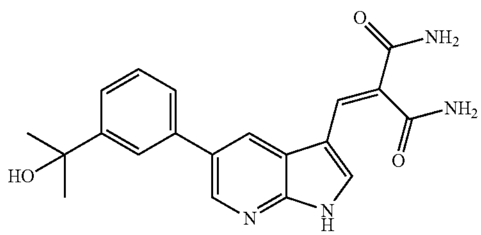 [SMILES: CC(C)(O)c1cccc(-c2cnc3[nH]cc(C=C(C(N)=O)C(N)=O)c3c2)c1] | 2-((5-(3-(2-hydroxypropan-2-yl)phenyl)-1H-pyrrolo[2,3-b]pyridin-3-yl)methylene)malonamide | MS (ES) m/z 365 (M + H). |

TABLE 2

Additional Examples

| Example | Structure | Name | Smiles |
|---|---|---|---|
| 366 | 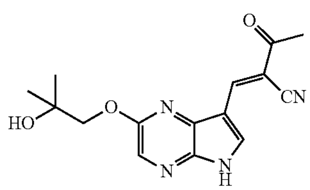 [SMILES: CC(=O)/C(C#N)=C/c1c[nH]c2ncc(OCC(C)(C)O)nc12] | (E)-2-((2-(2-hydroxy-2-methylpropoxy)-5H-pyrrolo[2,3-b]pyrazin-7-yl)methylene)-3-oxobutanenitrile | OC(C)(C)COC1=CN=C(NC=C2/C=C(C(#N)/C(C)=O)C2=N1 |
| 367 | 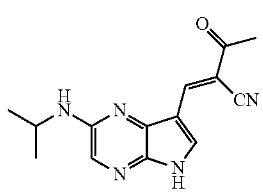 [SMILES: CC(=O)/C(C#N)=C/c1c[nH]c2ncc(NC(C)C)nc12] | (E)-2-((2-(isopropylamino)-5H-pyrrolo[2,3-b]pyrazin-7-yl)methylene)-3-oxobutanenitrile | CC(C)NC1=CN=C(NC=C2/C=C(C(#N)/C(C)=O)C2=N1 |
| 368 | 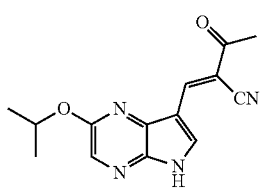 [SMILES: CC(=O)/C(C#N)=C/c1c[nH]c2ncc(OC(C)C)nc12] | (E)-2-((2-isopropoxy-5H-pyrrolo[2,3-b]pyrazin-7-yl)methylene)-3-oxobutanenitrile | CC(C)OC1=CN=C(NC=C2/C=C(C(#N)/C(C)=O)C2=N1 |
| 369 | 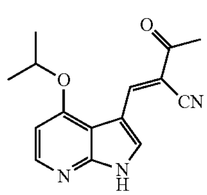 [SMILES: CC(=O)/C(C#N)=C/c1c[nH]c2nccc(OC(C)C)c12] | (E)-2-((4-isopropoxy-1H-pyrrolo[2,3-b]pyridin-3-yl)methylene)-3-oxobutanenitrile | O=C(C)/C(C#N)=C/C1=CNC2=NC=CC(OC(C)C)=C21 |
| 370 | 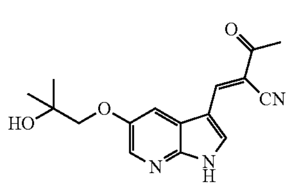 [SMILES: CC(=O)/C(C#N)=C/c1c[nH]c2ncc(OCC(C)(C)O)cc12] | (E)-2-((5-(2-hydroxy-2-methylpropoxy)-1H-pyrrolo[2,3-b]pyridin-3-yl)methylene)-3-oxobutanenitrile | OC(C)(C)COC1=CN=C(NC=C2/C=C(C(#N)/C(C)=O)C2=C1 |
| 371 | 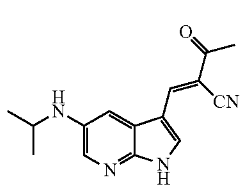 [SMILES: CC(=O)/C(C#N)=C/c1c[nH]c2ncc(NC(C)C)cc12] | (E)-2-((5-(isopropylamino)-1H-pyrrolo[2,3-b]pyridin-3-yl)methylene)-3-oxobutanenitrile | CC(C)NC1=CN=C(NC=C2/C=C(C(#N)/C(C)=O)C2=C1 |

TABLE 2-continued

Additional Examples

| Example | Name | Smiles |
|---|---|---|
| 372 | (E)-2-((5-isopropoxy-1H-pyrrolo[2,3-b]pyridin-3-yl)methylene)-oxobutanenitrile | CC(C)OC1=CN=C(NC=C2/C=C(C#N)/C(C)=O)C2=C1 |
| 373 | (E)-2,2,2-trifluoroethyl 4-(3-(3-amino-2-cyano-3-oxoprop-1-en-1-yl)-1H-pyrrolo[2,3-b]pyridin-5-yl)piperazine-1-carboxylate | NC(/C(C#N)=C/C1=CNC2=NC=C(N3CCN(C(OCC(F)(F)F)=O)CC3)C=C21)=O |
| 374 | (E)-2,2,2-trifluoroethyl 4-(3-(3-amino-3-oxoprop-1-en-1-yl)-1H-pyrrolo[2,3-b]pyridin-5-yl)piperazine-1-carboxylate | NC(/C=C/C1=CNC2=NC=C(N3CCN(C(OCC(F)(F)F)=O)CC3)C=C21)=O |
| 375 | (E)-2,2,2-trifluoroethyl 4-(7-(3-amino-2-cyano-3-oxoprop-1-en-1-yl)-5H-pyrrolo[2,3-b]pyrazin-2-yl)piperazine-1-carboxylate | NC(/C(C#N)=C/C1=CNC2=NC=C(N3CCN(C(OCC(F)(F)F)=O)CC3)N=C21)=O |
| 376 | (E)-2,2,2-trifluoroethyl 4-(7-(3-amino-3-oxoprop-1-en-1-yl)-5H-pyrrolo[2,3-b]pyrazin-2-yl)piperazine-1-carboxylate | NC(/C=C/C1=CNC2=NC=C(N3CCN(C(OCC(F)(F)F)=O)CC3)N=C21)=O |
| 377 | (E)-2-acetyl-4-(2-((1-hydroxypropan-2-yl)oxy)-5H-pyrrolo[2,3-b]pyrazin-7-yl)but-2-enenitrile | CC(CO)OC1=CN=C(NC=C2C/C=C(C#N)/C(C)=O)C2=N1 |
| 378 | (E)-2-acetyl-4-(2-(2-hydroxy-2-methylpropoxy)-5H-pyrrolo[2,3-b]pyrazin-7-yl)but-2-enenitrile | CC(/C(C#N)=C/CC1=CNC2=NC=C(OCC(C)(C)O)N=C21)=O |
| 379 | (E)-2-acetyl-4-(2-(cyclopentylamino)-5H-pyrrolo[2,3-b]pyrazin-7-yl)but-2-enenitrile | CC(/C(C#N)=C/CC1=CNC2=NC=C(NC3CCCC3)N=C21)=O |

TABLE 2-continued

Additional Examples

| Example | Structure | Name | Smiles |
|---|---|---|---|
| 380 | 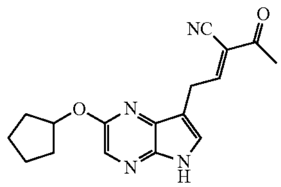 [SMILES: CC(=O)/C(C#N)=C/Cc1c[nH]c2ncc(OC3CCCC3)nc12] | (E)-2-acetyl-4-(2-(cyclopentyl-oxy)-5H-pyrrolo[2,3-b]pyrazin-7-yl)but-2-enenitrile | CC(/C(C#N)=C/CC1=CNC2=NC=C(OC3CCCC3)N=C21)=O |
| 381 | 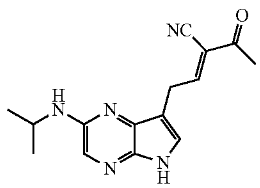 [SMILES: CC(=O)/C(C#N)=C/Cc1c[nH]c2ncc(NC(C)C)nc12] | (E)-2-acetyl-4-(2-(isopropyl-amino)-5H-pyrrolo[2,3-b]pyrazin-7-yl)but-2-enenitrile | CC(C)NC1=CN=C(NC=C2C/C=C(C#N)/C(C)=O)C2=N1 |
| 382 | 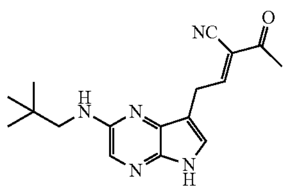 [SMILES: CC(=O)/C(C#N)=C/Cc1c[nH]c2ncc(NCC(C)(C)C)nc12] | (E)-2-acetyl-4-(2-(neopentyl-amino)-5H-pyrrolo[2,3-b]pyrazin-7-yl)but-2-enenitrile | CC(/C(C#N)=C/CC1=CNC2=NC=C(NCC(C)(C)C)N=C21)=O |
| 383 | 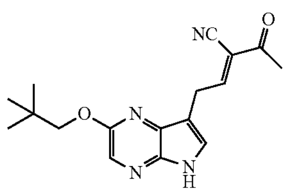 [SMILES: CC(=O)/C(C#N)=C/Cc1c[nH]c2ncc(OCC(C)(C)C)nc12] | (E)-2-acetyl-4-(2-(neopentyloxy)-pyrrolo[2,3-b]pyrazin-7-yl)but-2-enenitrile | CC(/C(C#N)=C/CC1=CNC2=NC=C(OCC(C)(C)C)N=C21)=O |
| 384 | 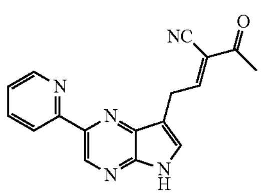 [SMILES: CC(=O)/C(C#N)=C/Cc1c[nH]c2ncc(-c3ccccn3)nc12] | (E)-2-acetyl-4-(2-(pyridin-2-yl)-5H-pyrrolo[2,3-b]pyrazin-7-yl)but-2-enenitrile | CC(/C(C#N)=C/CC1=CNC2=NC=C(C3=NC=CC=C3)N=C21)=O |
| 385 | 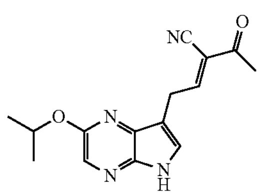 [SMILES: CC(=O)/C(C#N)=C/Cc1c[nH]c2ncc(OC(C)C)nc12] | (E)-2-acetyl-4-(2-isopropoxy-5H-pyrrolo[2,3-b]pyrazin-7-yl)but-2-enenitrile | CC(C)OC1=CN=C(NC=C2C/C=C(C#N)/C(C)=O)C2=N1 |
| 386 | 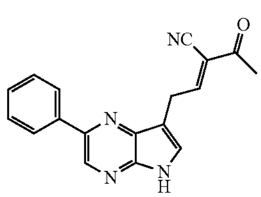 [SMILES: CC(=O)/C(C#N)=C/Cc1c[nH]c2ncc(-c3ccccc3)nc12] | (E)-2-acetyl-4-(2-phenyl-5H-pyrrolo[2,3-b]pyrazin-7-yl)but-2-enenitrile | CC(/C(C#N)=C/CC1=CNC2=NC=C(C3=CC=CC=C3)N=C21)=O |
| 387 | 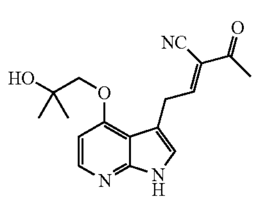 [SMILES: CC(=O)/C(C#N)=C/Cc1c[nH]c2nccc(OCC(C)(C)O)c12] | (E)-2-acetyl-4-(4-(2-hydroxy-2-methylpropoxy)-1H-pyrrolo[2,3-b]pyridin-3-yl)but-2-enenitrile | OC(C)(C)COC1=C2C(NC=C2C/C=C(C#N)/C(C)=O)=NC=C1 |

TABLE 2-continued

| Example | Structure | Name | Smiles |
|---|---|---|---|
| 388 | 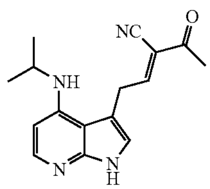 [SMILES: CC(=O)/C(C#N)=C/Cc1c[nH]c2nccc(NC(C)C)c12] | (E)-2-acetyl-4-(4-(isopropylamino)-1H-pyrrolo[2,3-b]pyridin-3-yl)but-2-enenitrile | CC(C)NC1═C2C(NC═C2C/C═C(C#N)/C(C)═O)═NC═C1 |
| 389 | 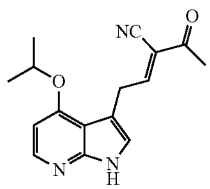 [SMILES: CC(=O)/C(C#N)=C/Cc1c[nH]c2nccc(OC(C)C)c12] | (E)-2-acetyl-4-(4-isopropoxy-1H-pyrrolo[2,3-b]pyridin-3-yl)but-2-enenitrile | CC(C)OC1═C2C(NC═C2C/C═C(C#N)/C(C)═O)═NC═C1 |
| 390 | 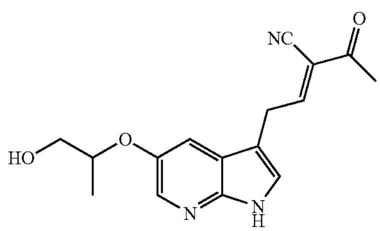 [SMILES: CC(=O)/C(C#N)=C/Cc1c[nH]c2ncc(OC(C)CO)cc12] | (E)-2-acetyl-4-(5-((1-hydroxy-propan-2-yl)oxy)-1H-pyrrolo[2,3-b]pyridin-3-yl)but-2-enenitrile | CC(CO)OC1═CN═C(NC═C2C/C═C(C#N)/C(C)═O)C2═C1 |
| 391 | 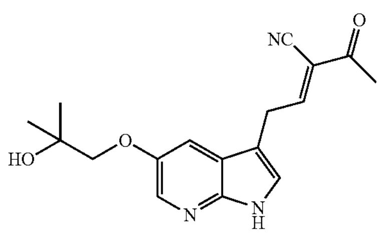 [SMILES: CC(=O)/C(C#N)=C/Cc1c[nH]c2ncc(OCC(C)(C)O)cc12] | (E)-2-acetyl-4-(5-(2-hydroxy-2-methylpropoxy)-1H-pyrrolo[2,3-b]pyridin-3-yl)but-2-enenitrile | CC(/C(C#N)═C/CC1═CNC2═NC═C(OCC(C)(C)O)C═C21)═ |
| 392 | 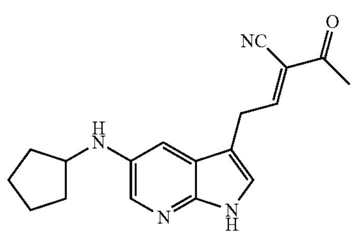 [SMILES: CC(=O)/C(C#N)=C/Cc1c[nH]c2ncc(NC3CCCC3)cc12] | (E)-2-acetyl-4-(5-(cyclopentyl-amino)-1H-pyrrolo[2,3-b]pyridin-3-yl)but-2-enenitrile | CC(/C(C#N)═C/CC1═CNC2═NC═C(NC3CCCC3)C═C21)═O |
| 393 | 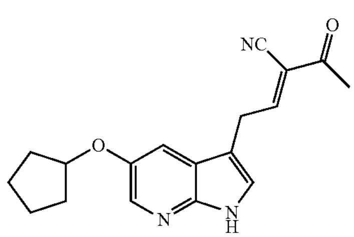 [SMILES: CC(=O)/C(C#N)=C/Cc1c[nH]c2ncc(OC3CCCC3)cc12] | (E)-2-acetyl-4-(5-(cyclopentyl-oxy)-1H-pyrrolo[2,3-b]pyridin-3-yl)but-2-enenitrile | CC(/C(C#N)═C/CC1═CNC2═NC═C(OC3CCCC3)C═C21)═O |

TABLE 2-continued

Additional Examples

| Example | Structure | Name | Smiles |
|---|---|---|---|
| 394 | 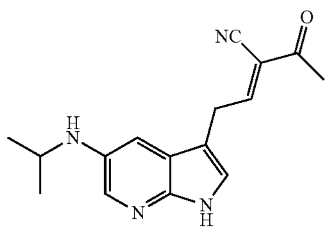 [SMILES: CC(=O)/C(C#N)=C/Cc1c[nH]c2ncc(NC(C)C)cc12] | (E)-2-acetyl-4-(5-(isopropyl-amino)-1H-pyrrolo[2,3-b]pyridin-3-yl)but-2-enenitrile | CC(C)NC1=CN=C(NC=C2C/C=C(C#N)/C(C)=O)C2=C1 |
| 395 | 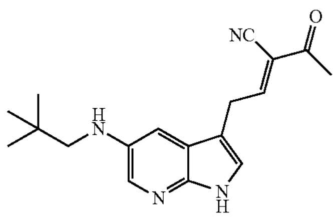 [SMILES: CC(=O)/C(C#N)=C/Cc1c[nH]c2ncc(NCC(C)(C)C)cc12] | (E)-2-acetyl-4-(5-(neopentyl-amino)-1H-pyrrolo[2,3-b]pyridin-3-yl)but-2-enenitrile | CC(/C(C#N)=C/CC1=CNC2=NC=C(NCC(C)(C)C)C=C21)=O |
| 396 | 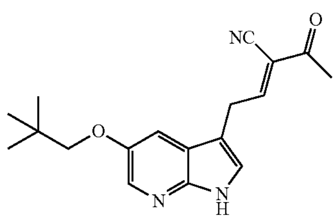 [SMILES: CC(=O)/C(C#N)=C/Cc1c[nH]c2ncc(OCC(C)(C)C)cc12] | (E)-2-acetyl-4-(5-(neopentyloxy)-1H-pyrrolo[2,3-b]pyridin-3-yl)but-2-enenitrile | CC(/C(C#N)=C/CC1=CNC2=NC=C(OCC(C)(C)C)C=C21)=O |
| 397 | 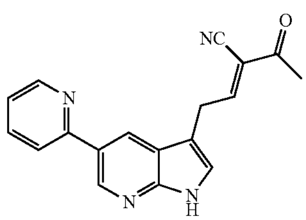 [SMILES: CC(=O)/C(C#N)=C/Cc1c[nH]c2ncc(-c3ccccn3)cc12] | (E)-2-acetyl-4-(5-(pyridin-2-yl)-1H-pyrrolo[2,3-b]pyridin-3-yl)but-2-enenitrile | CC(/C(C#N)=C/CC1=CNC2=NC=C(C3=NC=CC=C3)C=C21)=O |
| 398 | 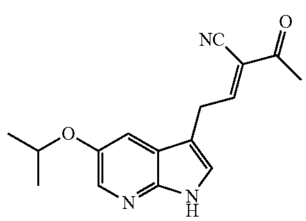 [SMILES: CC(=O)/C(C#N)=C/Cc1c[nH]c2ncc(OC(C)C)cc12] | (E)-2-acetyl-4-(5-isopropoxy-1H-pyrrolo[2,3-b]pyridin-3-yl)but-2-enenitrile | CC(C)OC1=CN=C(NC=C2C/C=C(C#N)/C(C)=O)C2=C1 |
| 399 | 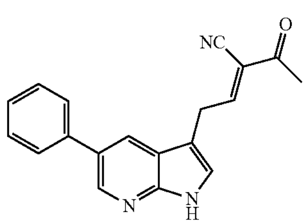 [SMILES: CC(=O)/C(C#N)=C/Cc1c[nH]c2ncc(-c3ccccc3)cc12] | (E)-2-acetyl-4-(5-phenyl-1H-pyrrolo[2,3-b]pyridin-3-yl)but-2-enenitrile | CC(/C(C#N)=C/CC1=CNC2=NC=C(C3=CC=CC=C3)C=C21)=O |
| 400 | 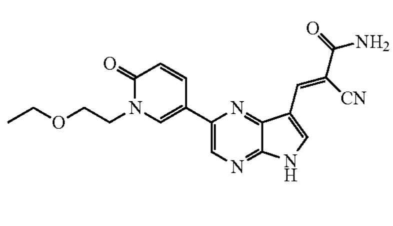 [SMILES: CCOCCn1cc(-c2cnc3[nH]cc(/C=C(\C#N)C(N)=O)c3n2)ccc1=O] | (E)-2-cyano-3-(2-(1-(2-ethoxy-ethyl)-6-oxo-1,6-dihydropyridin-3-yl)-5H-pyrrolo[2,3-b]pyrazin-7-yl)acrylamide | NC(/C(C#N)=C/C1=CNC2=NC=C(C(C=C3)=CN(CCOCC)C3=O)N=C21)=O |

TABLE 2-continued

Additional Examples

| Example | Name | Smiles |
|---|---|---|
| 401 | (E)-2-cyano-3-(2-(1-(2-isopropoxyethyl)-6-oxo-1,6-dihydropyridin-3-yl)-5H-pyrrolo[2,3-b]pyrazin-7-yl)acrylamide | NC(/C(C#N)=C/C1=CNC2=NC=C(C(C=C3)=CN(CCOC(C)C)C3=O)N=C21)=O |
| 402 | (E)-2-cyano-3-(2-(1-(cyclopropylmethyl)-6-oxo-1,6-dihydropyridin-3-yl)-5H-pyrrolo[2,3-b]pyrazin-7-yl)acrylamide | NC(/C(C#N)=C/C1=CNC2=NC=C(C(C=C3)=CN(CC4CC4)C3=O)N=C21)=O |
| 403 | (E)-2-cyano-3-(2-(2-hydroxy-2-methylpropoxy)-5H-pyrrolo[2,3-b]pyrazin-7-yl)acrylamide | OC(C)(C)COC1=CN=C(NC=C2/C=C(C#N)/C(N)=O)C2=N1 |
| 404 | (E)-2-cyano-3-(2-(3-(2-hydroxypropan-2-yl)phenyl)-5H-pyrrolo[2,3-b]pyrazin-7-yl)acrylamide | NC(/C(C#N)=C/C1=CNC2=NC=C(C3=CC=CC(C(C)(O)C)=C3)N=C21)=O |
| 405 | (E)-2-cyano-3-(2-(4-(2-hydroxypropan-2-yl)phenyl)-5H-pyrrolo[2,3-b]pyrazin-7-yl)acrylamide | NC(/C(C#N)=C/C1=CNC2=NC=C(C3=CC=C(C(C)(O)C)C=C3)N=C21)=O |
| 406 | (E)-2-cyano-3-(2-(4-(3,3-dimethylbutanoyl)piperazin-1-yl)-5H-pyrrolo[2,3-b]pyrazin-7-yl)acrylamide | NC(/C(C#N)=C/C1=CNC2=NC=C(N3CCN(C(CC(C)(C)C)=O)CC3)N=C21)=O |
| 407 | (E)-2-cyano-3-(2-(4-(3-methylbutanoyl)piperazin-1-yl)-5H-pyrrolo[2,3-b]pyrazin-7-yl)acrylamide | NC(/C(C#N)=C/C1=CNC2=NC=C(N3CCN(C(CC(C)C)=O)CC3N=C21)=O) |
| 408 | (E)-2-cyano-3-(2-(4-(4-methylpentanoyl)piperazin-1-yl)-5H-pyrrolo[2,3-b]pyrazin-7-yl)acrylamide | NC(/C(C#N)=C/C1=CNC2=NC=C(N3CCN(C(CCC(C)C)=O)CC3)N=C21)=O |

TABLE 2-continued

Additional Examples

| Example | Structure | Name | Smiles |
|---|---|---|---|
| 409 | 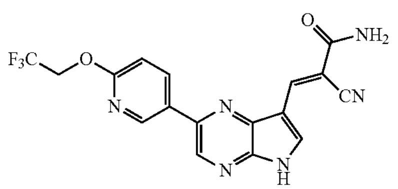 [SMILES: N#C/C(=C\c1c[nH]c2ncc(-c3ccc(OCC(F)(F)F)nc3)nc12)C(N)=O] | (E)-2-cyano-3-(2-(6-(2,2,2-trifluoroethoxy)pyridin-3-yl)-5H-pyrrolo[2,3-b]pyrazin-7-yl)acrylamide | NC(/C(C#N)=C/C1=CNC2=NC=C(C3=CC=C(OCC(F)(F)F)N=C3)N=C21)=O |
| 410 | 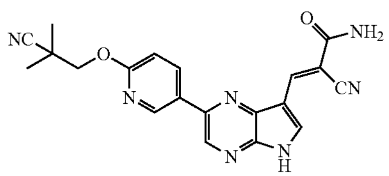 [SMILES: CC(C)(C#N)COc1ccc(-c2cnc3[nH]cc(/C=C(\C#N)C(N)=O)c3n2)cn1] | (E)-2-cyano-3-(2-(6-(2-cyano-2-methylpropoxy)pyridin-3-yl)-5H-pyrrolo[2,3-b]pyrazin-7-yl)acrylamide | NC(/C(C#N)=C/C1=CNC2=NC=C(C3=CC=C(OCC(C)(C#N)C)N=C3)N=C21)=O |
| 411 | 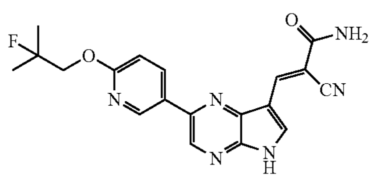 [SMILES: CC(C)(F)COc1ccc(-c2cnc3[nH]cc(/C=C(\C#N)C(N)=O)c3n2)cn1] | (E)-2-cyano-3-(2-(6-(2-fluoro-2-methylpropoxy)pyridin-3-yl)-5H-pyrrolo[2,3-b]pyrazin-7-yl)acrylamide | NC(/C(C#N)=C/C1=CNC2=NC=C(C3=CC=C(OCC(C)(F)C)N=C3)N=C21)=O |
| 412 | 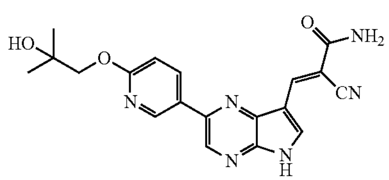 | (E)-2-cyano-3-(2-(6-(2-hydroxy-2-methylpropoxy)pyridin-3-yl)-5H-pyrrolo[2,3-b]pyrazin-7-yl)acrylamide | NC(/C(C#N)=C/C1=CNC2=NC=C(C3=CC=C(OCC(C)(O)C)N=C3)N=C21)=O |
| 413 | 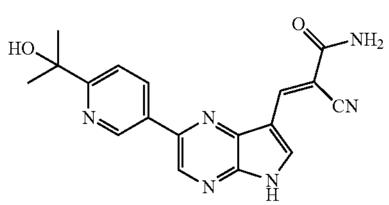 [SMILES: CC(C)(O)c1ccc(-c2cnc3[nH]cc(/C=C(\C#N)C(N)=O)c3n2)cn1] | (E)-2-cyano-3-(2-(6-(2-hydroxypropan-2-yl)pyridin-3-yl)-5H-pyrrolo[2,3-b]pyrazin-7-yl)acrylamide | NC(/C(C#N)=C/C1=CNC2=NC=C(C3=CC=C(C(C)(O)C)N=C3)N=C21)=O |
| 414 | 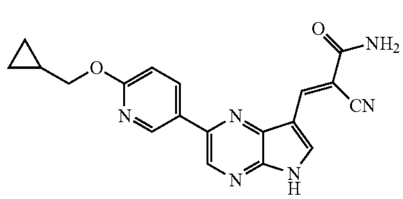 [SMILES: N#C/C(=C\c1c[nH]c2ncc(-c3ccc(OCC4CC4)nc3)nc12)C(N)=O] | (E)-2-cyano-3-(2-(6-(cyclopropylmethoxy)pyridin-3-yl)-5H-pyrrolo[2,3-b]pyrazin-7-yl)acrylamide | NC(/C(C#N)=C/C1=CNC2=NC=C(C3=CC=C(OCC4CC4)N=C3)N=C21)=O |
| 415 | 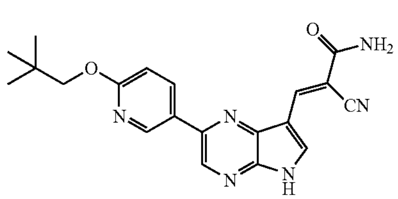 [SMILES: CC(C)(C)COc1ccc(-c2cnc3[nH]cc(/C=C(\C#N)C(N)=O)c3n2)cn1] | (E)-2-cyano-3-(2-(6-(neopentyloxy)pyridin-3-yl)-5H-pyrrolo[2,3-b]pyrazin-7-yl)acrylamide | NC(/C(C#N)=C/C1=CNC2=NC=C(C3=CC=C(OCC(C)(C)C)N=C3)N=C21)=O |
| 416 | 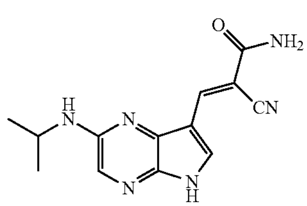 [SMILES: CC(C)Nc1cnc2[nH]cc(/C=C(\C#N)C(N)=O)c2n1] | (E)-2-cyano-3-(2-(isopropylamino)-5H-pyrrolo[2,3-b]pyrazin-7-yl)acrylamide | CC(C)NC1=CN=C(NC=C2/C=C(C#N)/C(N)=O)C2=N1 |

TABLE 2-continued

Additional Examples

| Example | Structure | Name | Smiles |
|---|---|---|---|
| 417 | 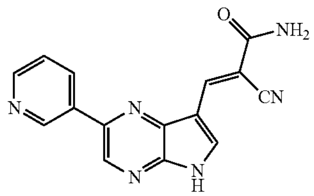 [SMILES: N#C/C(=C\c1c[nH]c2ncc(-c3cccnc3)nc12)C(N)=O] | (E)-2-cyano-3-(2-(pyridin-3-yl)-5H-pyrrolo[2,3-b]pyrazin-7-yl)acrylamide | NC(/C(C#N)=C/C1=CNC2=NC=C(C3=CC=CN=C3)N=C21)=O |
| 418 | 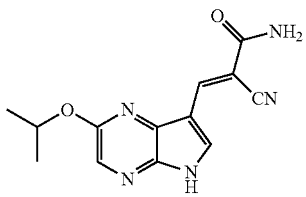 [SMILES: CC(C)Oc1cnc2[nH]cc(/C=C(\C#N)C(N)=O)c2n1] | (E)-2-cyano-3-(2-isopropoxy-5H-pyrrolo[2,3-b]pyrazin-7-yl)acrylamide | CC(C)OC1=CN=C(NC=C2/C=C(C#N)/C(N)=O)C2=N1 |
| 419 | 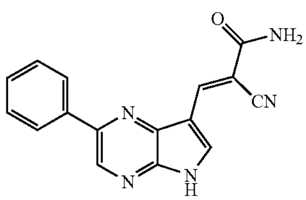 [SMILES: N#C/C(=C\c1c[nH]c2ncc(-c3ccccc3)nc12)C(N)=O] | (E)-2-cyano-3-(2-phenyl-5H-pyrrolo[2,3-b]pyrazin-7-yl)acrylamide | O=C(N)/C(C#N)=C/C1=CNC2=NC=C(C3=CC=CC=C3)N=C21 |
| 420 | 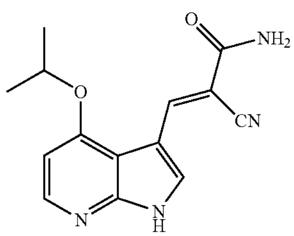 [SMILES: CC(C)Oc1ccnc2[nH]cc(/C=C(\C#N)C(N)=O)c12] | (E)-2-cyano-3-(4-isopropoxy-1H-pyrrolo[2,3-b]pyridin-3-yl)acrylamide | O=C(N)/C(C#N)=C/C1=CNC2=NC=CC(OC(C)C)=C21 |
| 421 | 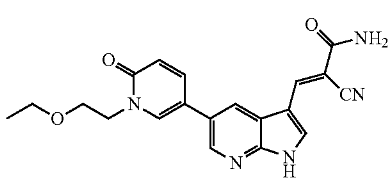 [SMILES: CCOCCn1cc(-c2cnc3[nH]cc(/C=C(\C#N)C(N)=O)c3c2)ccc1=O] | (E)-2-cyano-3-(5-(1-(2-ethoxyethyl)-6-oxo-1,6-dihydropyridin-3-yl)-1H-pyrrolo[2,3-b]pyridin-3-yl)acrylamide | NC(/C(C#N)=C/C1=CNC2=NC=C(C(C=C3)=CN(CCOCC)C3=O)C=C21)=O |
| 422 | 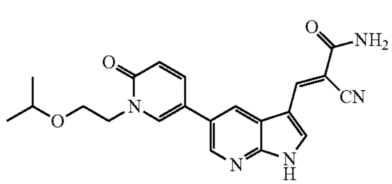 [SMILES: CC(C)OCCn1cc(-c2cnc3[nH]cc(/C=C(\C#N)C(N)=O)c3c2)ccc1=O] | (E)-2-cyano-3-(5-(1-(2-isopropoxyethyl)-6-oxo-1,6-dihydropyridin-3-yl)-1H-pyrrolo[2,3-b]pyridin-3-yl)acrylamide | NC(/C(C#N)=C/C1=CNC2=NC=C(C(C=C3)=CN(CCOC(C)C)C3=O)C=C21)=O |
| 423 | 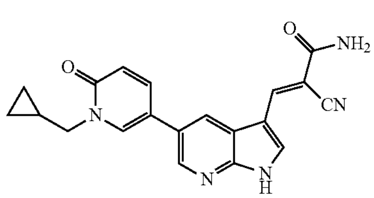 [SMILES: N#C/C(=C\c1c[nH]c2ncc(-c3ccc(=O)n(CC4CC4)c3)cc12)C(N)=O] | (E)-2-cyano-3-(5-(1-(cyclopropylmethyl)-6-oxo-1,6-dihydropyridin-3-yl)-1H-pyrrolo[2,3-b]pyridin-3-yl)acrylamide | NC(/C(C#N)=C/C1=CNC2=NC=C(C(C=C3)=CN(CC4CC4)C3=O)C=C21)=O |

TABLE 2-continued

Additional Examples

| Example | Name | Smiles |
|---|---|---|
| 424 | (E)-2-cyano-3-(5-(2-hydroxy-2-methylpropoxy)-1H-pyrrolo[2,3-b]pyridin-3-yl)acrylamide | OC(C)(C)COC1=CN=C(NC=C2/C=C(C#N)/C(N)=O)C2=C1 |
| 425 | (E)-2-cyano-3-(5-(4-(3,3-dimethylbutanoyl)piperazin-1-yl)-1H-pyrrolo[2,3-b]pyridin-3-yl)acrylamide | NC(/C(C#N)=C/C1=CNC2=NC=C(N3CCN(C(CC(C)(C)C)=O)CC3)C=C21)=O |
| 426 | (E)-2-cyano-3-(5-(4-(3-methylbutanoyl)piperazin-1-yl)-1H-pyrrolo[2,3-b]pyridin-3-yl)acrylamide | NC(/C(C#N)=C/C1=CNC2=NC=C(N3CCN(C(CC(C)C)=O)CC3)C=C21)=O |
| 427 | (E)-2-cyano-3-(5-(4-(4-methylpentanoyl)piperazin-1-yl)-1H-pyrrolo[2,3-b]pyridin-3-yl)acrylamide | NC(/C(C#N)=C/C1=CNC2=NC=C(N3CCN(C(CCC(C)C)=O)CC3)C=C21)=O |
| 428 | (E)-2-cyano-3-(5-(6-(2,2,2-trifluoroethoxy)pyridin-3-yl)-1H-pyrrolo[2,3-b]pyridin-3-yl)acrylamide | NC(/C(C#N)=C/C1=CNC2=NC=C(C3=CC=C(OCC(F)(F)F)N=C3)C=C21)=O |
| 429 | (E)-2-cyano-3-(5-(6-(2-cyano-2-methylpropoxy)pyridin-3-yl)-1H-pyrrolo[2,3-b]pyridin-3-yl)acrylamide | NC(/C(C#N)=C/C1=CNC2=NC=C(C3=CC=C(OCC(C)(C#N)C)N=C3)C=C21)=O |
| 430 | (E)-2-cyano-3-(5-(6-(2-fluoro-2-methylpropoxy)pyridin-3-yl)-1H-pyrrolo[2,3-b]pyridin-3-yl)acrylamide | NC(/C(C#N)=C/C1=CNC2=NC=C(C3=CC=C(OCC(C)(F)C)N=C3)C=C21)=O |
| 431 | (E)-2-cyano-3-(5-(6-(2-hydroxy-2-methylpropoxy)pyridin-3-yl)-1H-pyrrolo[2,3-b]pyridin-3-yl)acrylamide | NC(/C(C#N)=C/C1=CNC2=NC=C(C3=CC=C(OCC(C)(O)C)N=C3)C=C21)=O |

TABLE 2-continued

Additional Examples

| Example | Structure | Name | Smiles |
|---|---|---|---|
| 432 | 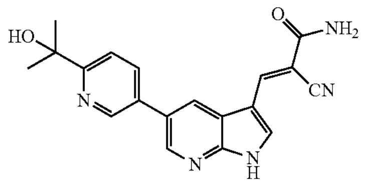 [SMILES: CC(C)(O)c1ccc(-c2cnc3[nH]cc(/C=C(\C#N)C(N)=O)c3c2)cn1] | (E)-2-cyano-3-(5-(6-(2-hydroxypropan-2-yl)pyridin-3-yl)-1H-pyrrolo[2,3-b]pyridin-3-yl)acrylamide | NC(/C(C#N)=C/C1=CNC2=NC=C(C3=CC=C(OCC(C)(O)C)N=C3)C=C21)=O |
| 433 | 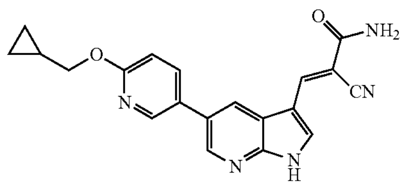 [SMILES: N#C/C(=C\c1c[nH]c2ncc(-c3ccc(OCC4CC4)nc3)cc12)C(N)=O] | (E)-2-cyano-3-(5-(6-(cyclopropylmethoxy)pyridin-3-yl)-1H-pyrrolo[2,3-b]pyridin-3-yl)acrylamide | NC(/C(C#N)=C/C1=CNC2=NC=C(C3=CC=C(OCC4CC4)N=C3)C=C21)=O |
| 434 | 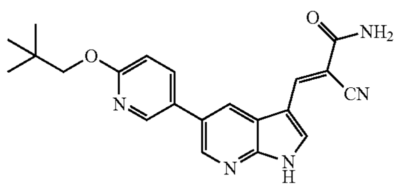 [SMILES: CC(C)(C)COc1ccc(-c2cnc3[nH]cc(/C=C(\C#N)C(N)=O)c3c2)cn1] | (E)-2-cyano-3-(5-(6-(neopentyloxy)pyridin-3-yl)-1H-pyrrolo[2,3-b]pyridin-3-yl)acrylamide | NC(/C(C#N)=C/C1=CNC2=NC=C(C3=CC=C(OCC(C)(C)C)N=C3)C=C21)=O |
| 435 | 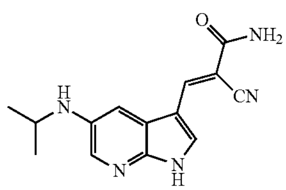 [SMILES: CC(C)Nc1cnc2[nH]cc(/C=C(\C#N)C(N)=O)c2c1] | (E)-2-cyano-3-(5-(isopropylamino)-1H-pyrrolo[2,3-b]pyridin-3-yl)acrylamide | CC(C)NC1=CN=C(NC=C2/C=C(C#N)/C(N)=O)C2=C1 |
| 436 | 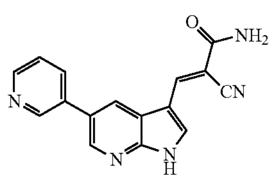 [SMILES: N#C/C(=C\c1c[nH]c2ncc(-c3cccnc3)cc12)C(N)=O] | (E)-2-cyano-3-(5-(pyridin-3-yl)-1H-pyrrolo[2,3-b]pyridin-3-yl)acrylamide | NC(/C(C#N)=C/C1=CNC2=NC=C(C3=CC=CN=C3)C=C21)=O |
| 437 | 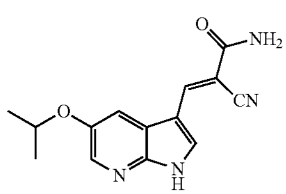 [SMILES: CC(C)Oc1cnc2[nH]cc(/C=C(\C#N)C(N)=O)c2c1] | (E)-2-cyano-3-(5-isopropoxy-1H-pyrrolo[2,3-b]pyridin-3-yl)acrylamide | CC(C)OC1=CN=C(NC=C2/C=C(C#N)/C(N)=O)C2=C1 |
| 438 | 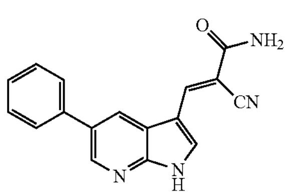 [SMILES: N#C/C(=C\c1c[nH]c2ncc(-c3ccccc3)cc12)C(N)=O] | (E)-2-cyano-3-(5-phenyl-1H-pyrrolo[2,3-b]pyridin-3-yl)acrylamide | O=C(N)/C(C#N)=C/C1=CNC2=NC=C(C3=CC=CC=C3)C=C21 |
| 439 | 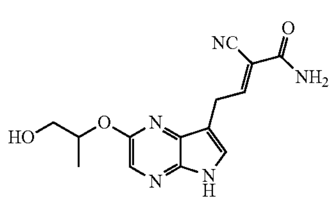 [SMILES: CC(CO)Oc1cnc2[nH]cc(C/C=C(\C#N)C(N)=O)c2n1] | (E)-2-cyano-4-(2-((1-hydroxypropan-2-yl)oxy)-5H-pyrrolo[2,3-b]pyrazin-7-yl)but-2-enamide | CC(CO)OC1=CN=C(NC=C2C/C=C(C#N)/C(N)=O)C2=N1 |

TABLE 2-continued

Additional Examples

| Example | Structure | Name | Smiles |
|---|---|---|---|
| 440 | 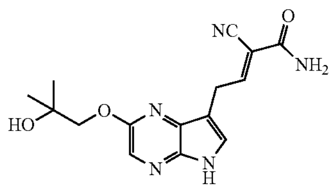 [SMILES: CC(C)(O)COc1cnc2[nH]cc(C/C=C(\C#N)C(N)=O)c2n1] | (E)-2-cyano-4-(2-(2-hydroxy-2-methylpropoxy)-5H-pyrrolo[2,3-b]pyrazin-7-yl)but-2-enamide | NC(/C(C#N)=C/CC1=CNC2=NC=C(OCC(C)(C)O)N=C21)=O |
| 441 | 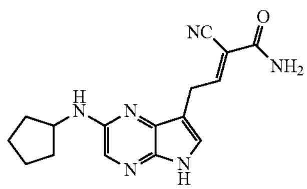 [SMILES: N#C/C(=C\Cc1c[nH]c2ncc(NC3CCCC3)nc12)C(N)=O] | (E)-2-cyano-4-(2-(cyclopentyl-amino)-5H-pyrrolo[2,3-b]pyrazin-7-yl)but-2-enamide | NC(/C(C#N)=C/CC1=CNC2=NC=C(NC3CCCC3)N=C21)=O |
| 442 | 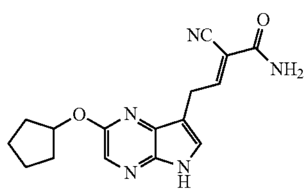 [SMILES: N#C/C(=C\Cc1c[nH]c2ncc(OC3CCCC3)nc12)C(N)=O] | (E)-2-cyano-4-(2-(cyclopentyloxy)-5H-pyrrolo[2,3-b]pyrazin-7-yl)but-2-enamide | NC(/C(C#N)=C/CC1=CNC2=NC=C(OC3CCCC3)N=C21)=O |
| 443 | 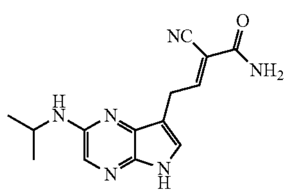 [SMILES: CC(C)Nc1cnc2[nH]cc(C/C=C(\C#N)C(N)=O)c2n1] | (E)-2-cyano-4-(2-(isopropylamino)-5H-pyrrolo[2,3-b]pyrazin-7-yl)but-2-enamide | CC(C)NC1=CN=C(NC=C2C/C=C(C#N)/C(N)=O)C2=N1 |
| 444 | 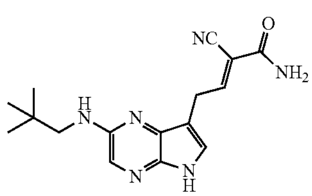 [SMILES: CC(C)(C)CNc1cnc2[nH]cc(C/C=C(\C#N)C(N)=O)c2n1] | (E)-2-cyano-4-(2-(neopentylamino)-5H-pyrrolo[2,3-b]pyrazin-7-yl)but-2-enamide | NC(/C(C#N)=C/CC1=CNC2=NC=C(NCC(C)(C)C)N=C21)=O |
| 445 | 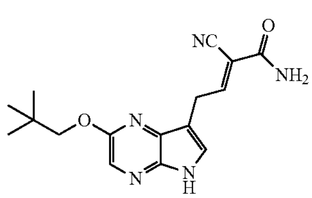 [SMILES: CC(C)(C)COc1cnc2[nH]cc(C/C=C(\C#N)C(N)=O)c2n1] | (E)-2-cyano-4-(2-(neopentyloxy)-5H-pyrrolo[2,3-b]pyrazin-7-yl)but-2-enamide | NC(/C(C#N)=C/CC1=CNC2=NC=C(OCC(C)(C)C)N=C21)=O |
| 446 | 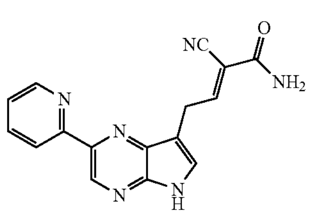 [SMILES: N#C/C(=C\Cc1c[nH]c2ncc(-c3ccccn3)nc12)C(N)=O] | (E)-2-cyano-4-(2-(pyridin-2-yl)-5H-pyrrolo[2,3-b]pyrazin-7-yl)but-2-enamide | NC(/C(C#N)=C/CC1=CNC2=NC=C(C3=NC=CC=C3)N=C21)=O |

TABLE 2-continued

Additional Examples

| Example | Structure | Name | Smiles |
|---|---|---|---|
| 447 | 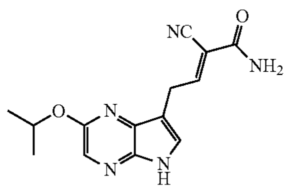 [SMILES: CC(C)Oc1cnc2[nH]cc(C/C=C(\C#N)C(N)=O)c2n1] | (E)-2-cyano-4-(2-isopropoxy-5H-pyrrolo[2,3-b]pyrazin-7-yl)but-2-enamide | CC(C)OC1=CN=C(NC=C2C/C=C(C#N)/C(N)=O)C2=N1 |
| 448 | 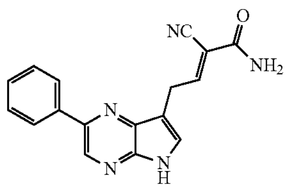 [SMILES: N#C/C(=C\Cc1c[nH]c2ncc(-c3ccccc3)nc12)C(N)=O] | (E)-2-cyano-4-(2-phenyl-5H-pyrrolo[2,3-b]pyrazin-7-yl)but-2-enamide | NC(/C(C#N)=C/CC1=CNC2=NC=C(C3=CC=CC=C3)N=C21)=O |
| 449 | 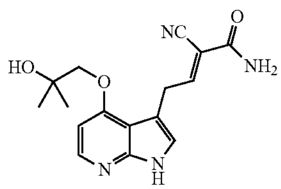 [SMILES: CC(C)(O)COc1ccnc2[nH]cc(C/C=C(\C#N)C(N)=O)c12] | (E)-2-cyano-4-(4-(2-hydroxy-2-methylpropoxy)-1H-pyrrolo[2,3-b]pyridin-3-yl)but-2-enamide | OC(C)(C)COC1=C2C(NC=C2C/C=C(C#N)/C(N)=O)=NC=C1 |
| 450 | 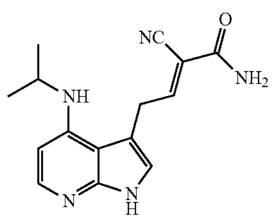 [SMILES: CC(C)Nc1ccnc2[nH]cc(C/C=C(\C#N)C(N)=O)c12] | (E)-2-cyano-4-(4-(isopropylamino)-1H-pyrrolo[2,3-b]pyridin-3-yl)but-2-enamide | CC(C)NC1=C2C(NC=C2C/C=C(C#N)/C(N)=O)=NC=C1 |
| 451 | 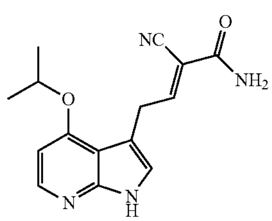 [SMILES: CC(C)Oc1ccnc2[nH]cc(C/C=C(\C#N)C(N)=O)c12] | (E)-2-cyano-4-(4-isopropoxy-1H-pyrrolo[2,3-b]pyridin-3-yl)but-2-enamide | CC(C)OC1=C2C(NC=C2C/C=C(C#N)/C(N)=O)=NC=C1 |
| 452 | 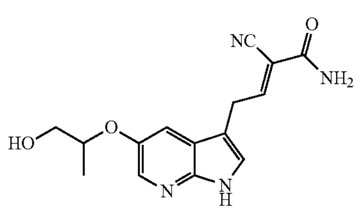 [SMILES: CC(CO)Oc1cnc2[nH]cc(C/C=C(\C#N)C(N)=O)c2c1] | (E)-2-cyano-4-(5-((1-hydroxypropan-2-yl)oxy)-1H-pyrrolo[2,3-b]pyridin-3-yl)but-2-enamide | CC(CO)OC1=CN=C(NC=C2C/C=C(C#N)/C(N)=O)C2=C1 |
| 453 | 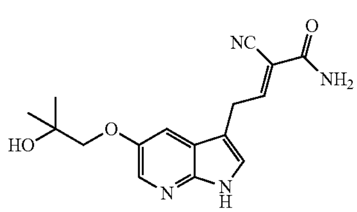 [SMILES: CC(C)(O)COc1cnc2[nH]cc(C/C=C(\C#N)C(N)=O)c2c1] | (E)-2-cyano-4-(5-(2-hydroxy-2-methylpropoxy)-1H-pyrrolo[2,3-b]pyridin-3-yl)but-2-enamide | NC(/C(C#N)=C/CC1=CNC2=NC=C(OCC(C)(C)O)C=C21)=O |

TABLE 2-continued

Additional Examples

| Example | Structure | Name | Smiles |
|---|---|---|---|
| 454 | 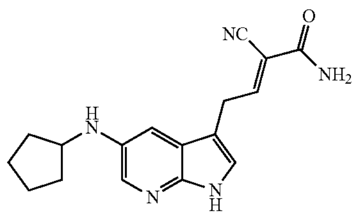 [SMILES: N#C/C(=C\Cc1c[nH]c2ncc(NC3CCCC3)cc12)C(N)=O] | (E)-2-cyano-4-(5-(cyclopentyl-amino)-1H-pyrrolo[2,3-b]pyridin-3-yl)but-2-enamide | NC(/C(C#N)=C/CC1=CNC2=NC=C(NC3CCCC3)C=C21)=O |
| 455 | 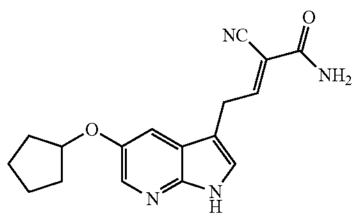 [SMILES: N#C/C(=C\Cc1c[nH]c2ncc(OC3CCCC3)cc12)C(N)=O] | (E)-2-cyano-4-(5-(cyclopentyloxy)-1H-pyrrolo[2,3-b]pyridin-3-yl)but-2-enamide | NC(/C(C#N)=C/CC1=CNC2=NC=C(OC3CCCC3)C=C21)=O |
| 456 | 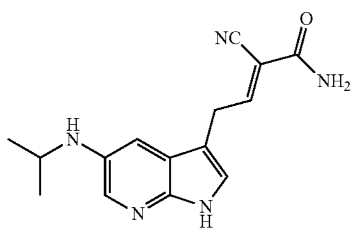 [SMILES: CC(C)Nc1cnc2[nH]cc(C/C=C(\C#N)C(N)=O)c2c1] | (E)-2-cyano-4-(5-(isopropylamino)-1H-pyrrolo[2,3-b]pyridin-3-yl)but-2-enamide | CC(C)NC1=CN=C(NC=C2C/C=C(C#N)/C(N)=O)C2=C1 |
| 457 | 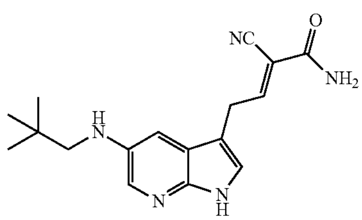 [SMILES: CC(C)(C)CNc1cnc2[nH]cc(C/C=C(\C#N)C(N)=O)c2c1] | (E)-2-cyano-4-(5-(neopentylamino)-1H-pyrrolo[2,3-b]pyridin-3-yl)but-2-enamide | NC(/C(C#N)=C/CC1=CNC2=NC=C(NCC(C)(C)C)C=C21)=O |
| 458 | 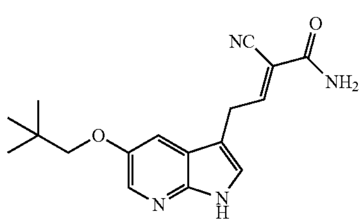 [SMILES: CC(C)(C)COc1cnc2[nH]cc(C/C=C(\C#N)C(N)=O)c2c1] | (E)-2-cyano-4-(5-(neopentyloxy)-1H-pyrrolo[2,3-b]pyridin-3-yl)but-2-enamide | NC(/C(C#N)=C/CC1=CNC2=NC=C(OCC(C)(C)C)C=C21)=O |
| 459 | 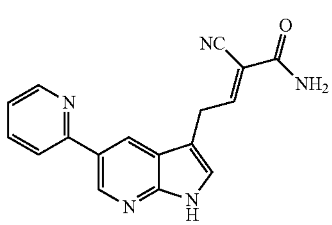 [SMILES: N#C/C(=C\Cc1c[nH]c2ncc(-c3ccccn3)cc12)C(N)=O] | (E)-2-cyano-4-(5-(pyridin-2-yl)-1H-pyrrolo[2,3-b]pyridin-3-yl)but-2-enamide | NC(/C(C#N)=C/CC1=CNC2=NC=C(C3=NC=CC=C3)C=C21)=O |

TABLE 2-continued

Additional Examples

| Example | Name | Smiles |
|---|---|---|
| 460 | (E)-2-cyano-4-(5-isopropoxy-1H-pyrrolo[2,3-b]pyridin-3-yl)but-2-enamide | CC(C)OC1=CN=C(NC=C2C/C=C(C#N)/C(N)=O)C2=C1 |
| 461 | (E)-2-cyano-4-(5-phenyl-1H-pyrrolo[2,3-b]pyridin-3-yl)but-2-enamide | NC(/C(C#N)=C/CC1=CNC2=NC=C(C3=CC=CC=C3)C=C21)=O |
| 462 | (E)-2-cyanoethyl 4-(3-(3-amino-3-oxoprop-1-en-1-yl)-1H-pyrrolo[2,3-b]pyridin-5-yl)piperazine-1-carboxylate | NC(/C=C/C1=CNC2=NC=C(N3CCN(C(OCCC#N)=O)CC3)C=C21)=O |
| 463 | (E)-2-cyanoethyl 4-(7-(3-amino-3-oxoprop-1-en-1-yl)-5H-pyrrolo[2,3-b]pyrazin-2-yl)piperazine-1-carboxylate | NC(/C=C/C1=CNC2=NC=C(N3CCN(C(OCCC#N)=O)CC3)N=C21)=O |
| 464 | (E)-2-fluoro-2-methylpropyl 4-(3-(3-amino-3-oxoprop-1-en-1-yl)-1H-pyrrolo[2,3-b]pyridin-5-yl)piperazine-1-carboxylate | NC(/C=C/C1=CNC2=NC=C(N3CCN(C(OCC(C)(F)C)=O)CC3)C=C21)=O |
| 465 | (E)-2-fluoro-2-methylpropyl 4-(7-(3-amino-3-oxoprop-1-en-1-yl)-5H-pyrrolo[2,3-b]pyrazin-2-yl)piperazine-1-carboxylate | NC(/C=C/C1=CNC2=NC=C(N3CCN(C(OCC(C)(F)C)=O)CC3)N=C21)=O |
| 466 | (E)-2-fluoroethyl 4-(3-(3-amino-2-cyano-3-oxoprop-1-en-1-yl)-1H-pyrrolo[2,3-b]pyridin-5-yl)piperazine-1-carboxylate | NC(/C(C#N)C/C1=CNC2=NC=C(N3CCN(C(OCCF)=O)CC3)C=C21)=O |
| 467 | (E)-2-fluoroethyl 4-(7-(3-amino-2-cyano-3-oxoprop-1-en-1-yl)-5H-pyrrolo[2,3-b]pyrazin-2-yl)piperazine-1-carboxylate | NC(/C(C#N)=C/C1=CNC2=NC=C(N3CCN(C(OCCF)=O)CC3)N=C21)=O |

TABLE 2-continued

Additional Examples

| Example | Structure | Name | Smiles |
|---|---|---|---|
| 468 | 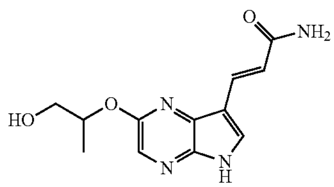 [SMILES: CC(CO)Oc1cnc2[nH]cc(/C=C/C(N)=O)c2n1] | (E)-3-(2-((1-hydroxypropan-2-yl)oxy)-5H-pyrrolo[2,3-b]pyrazin-7-yl)acrylamide | O=C(N)/C=C/C1=CNC2=NC=C(OC(C)CO)N=C21 |
| 469 | 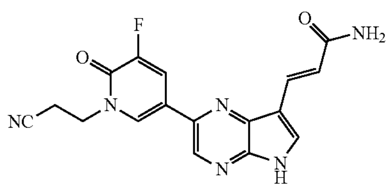 [SMILES: N#CCCn1cc(-c2cnc3[nH]cc(/C=C/C(N)=O)c3n2)ccc1=O] | (E)-3-(2-(1-(2-cyanoethyl)-5-fluoro-6-oxo-1,6-dihydropyridin-3-yl)-5H-pyrrolo[2,3-b]pyrazin-7-yl)acrylamide | NC(/C=C/C1=CNC2=NC=C(C(C=C3F)=CN(CCC#N)C3=O)N=C21)=O |
| 470 | 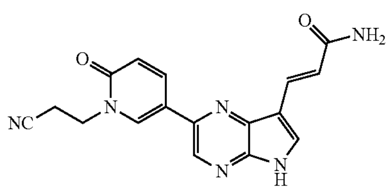 | (E)-3-(2-(1-(2-cyanoethyl)-6-oxo-1,6-dihydropyridin-3-yl)-5H-pyrrolo[2,3-b]pyrazin-7-yl)acrylamide | NC(/C=C/C1=CNC2=NC=C(C(C=C3)=CN(CCC#N)C3=O)N=C21)=O |
| 471 | 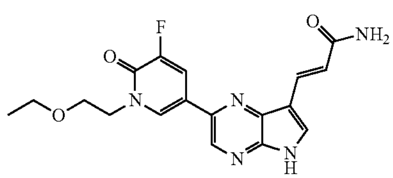 [SMILES: CCOCCn1cc(-c2cnc3[nH]cc(/C=C/C(N)=O)c3n2)cc(F)c1=O] | (E)-3-(2-(1-(2-ethoxyethyl)-5-fluoro-6-oxo-1,6-dihydropyridin-3-yl)-5H-pyrrolo[2,3-b]pyrazin-7-yl)acrylamide | NC(/C=C/C1=CNC2=NC=C(C(C=C3F)=CN(CCOCC)C3=O)N=C21)=O |
| 472 | 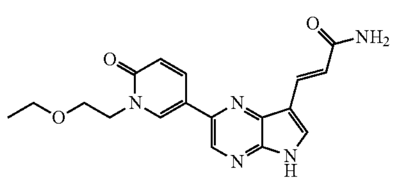 [SMILES: CCOCCn1cc(-c2cnc3[nH]cc(/C=C/C(N)=O)c3n2)ccc1=O] | (E)-3-(2-(1-(2-ethoxyethyl)-6-oxo-1,6-dihydropyridin-3-yl)-5H-pyrrolo[2,3-b]pyrazin-7-yl)acrylamide | NC(/C=C/C1=CNC2=NC=C(C(C=C3)=CN(CCOCC)C3=O)N=C21)=O |
| 473 | 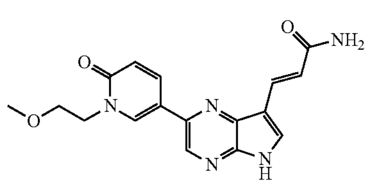 | (E)-3-(2-(1-(2-methoxyethyl)-6-oxo-1,6-dihydropyridin-3-yl)-5H-pyrrolo[2,3-b]pyrazin-7-yl)acrylamide | NC(/C=C/C1=CNC2=NC=C(C(C=C3)=CN(CCOC)C3=O)N=C21)=O |
| 474 | 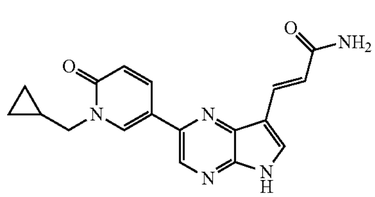 [SMILES: NC(=O)/C=C/c1c[nH]c2ncc(-c3ccc(=O)n(CC4CC4)c3)nc12] | (E)-3-(2-(1-(cyclopropylmethyl)-6-oxo-1,6-dihydropyridin-3-yl)-5H-pyrrolo[2,3-b]pyrazin-7-yl)acrylamide | NC(/C=C/C1=CNC2=NC=C(C(C=C3)=CN(CC4CC4)C3=O)N=C21)=O |

TABLE 2-continued

Additional Examples

| Example | Structure | Name | Smiles |
|---|---|---|---|
| 475 | 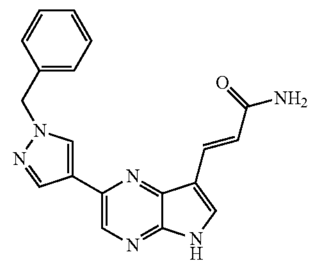 [SMILES: NC(=O)/C=C/c1c[nH]c2ncc(-c3cnn(Cc4ccccc4)c3)nc12] | (E)-3-(2-(1-benzyl-1H-pyrazol-4-yl)-5H-pyrrolo[2,3-b]pyrazin-7-yl)acrylamide | O=C(N)/C=C/C1=CNC2=NCC(C3=CN(CC4=CC=CC=C4)N=C3)N=C21 |
| 476 | 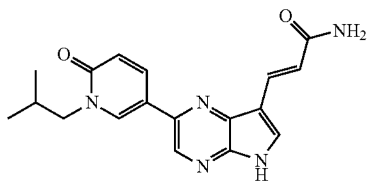 [SMILES: CC(C)Cn1cc(-c2cnc3[nH]cc(/C=C/C(N)=O)c3n2)ccc1=O] | (E)-3-(2-(1-isobutyl-6-oxo-1,6-dihydropyridin-3-yl)-5H-pyrrolo[2,3-b]pyrazin-7-yl)acrylamide | NC(/C=C/C1=CNC2=NC=C(C(C=C3)=CN(CC(C)C)C3=O)N=C21)=O |
| 477 | 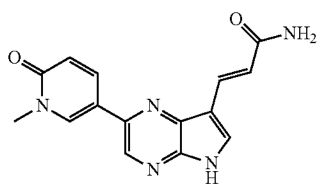 [SMILES: Cn1cc(-c2cnc3[nH]cc(/C=C/C(N)=O)c3n2)ccc1=O] | (E)-3-(2-(1-methyl-6-oxo-1,6-dihydropyridin-3-yl)-5H-pyrrolo[2,3-b]pyrazin-7-yl)acrylamide | NC(/C=C/C1=CNC2=NC=C(C(C=C3)=CN(C)C3=O)N=C21)=O |
| 478 | 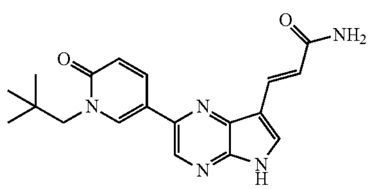 [SMILES: CC(C)(C)Cn1cc(-c2cnc3[nH]cc(/C=C/C(N)=O)c3n2)ccc1=O] | (E)-3-(2-(1-neopentyl-6-oxo-1,6-dihydropyridin-3-yl)-5H-pyrrolo[2,3-b]pyrazin-7-yl)acrylamide | NC(/C=C/C1=CNC2=NC=C(C(C=C3)=CN(CC(C)(C)C)C3=O)N=C21)=O |
| 479 | 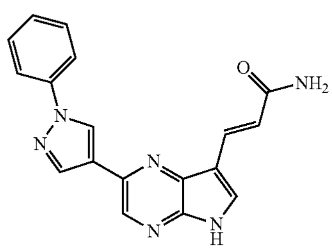 [SMILES: NC(=O)/C=C/c1c[nH]c2ncc(-c3cnn(-c4ccccc4)c3)nc12] | (E)-3-(2-(1-phenyl-1H-pyrazol-4-yl)-5H-pyrrolo[2,3-b]pyrazin-7-yl)acrylamide | O=C(N)/C=C/C1=CNC2=NC=C(C3=CN(C4=CC=CC=C4)N=C3)N=C21 |
| 480 | 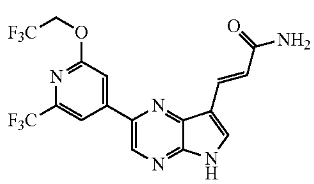 [SMILES: NC(=O)/C=C/c1c[nH]c2ncc(-c3cc(OCC(F)(F)F)nc(C(F)(F)F)c3)nc12] | (E)-3-(2-(2-(2,2,2-trifluoroethoxy)-6-(trifluoromethyl)pyridin-4-yl)-5H-pyrrolo[2,3-b]pyrazin-7-yl)acrylamide | NC(/C=C/C1=CNC2=NC=C(C3=CC(OCC(F)(F)F)=NC(C(F)(F)F)=C3)N=C21)=O |
| 481 | 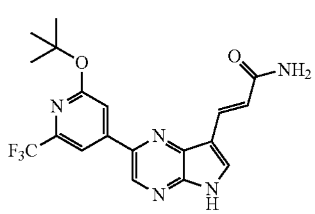 [SMILES: CC(C)(C)Oc1cc(-c2cnc3[nH]cc(/C=C/C(N)=O)c3n2)cc(C(F)(F)F)n1] | (E)-3-(2-(2-(tert-butoxy)-6-(trifluoromethyl)pyridin-4-yl)-5H-pyrrolo[2,3-b]pyrazin-7-yl)acrylamide | NC(/C=C/C1=CNC2=NC=C(C3=CC(OC(C)(C)C)=NC(C(F)(F)F)=C3)N=C21)=O |

TABLE 2-continued

Additional Examples

| Example | Name | Smiles |
|---|---|---|
| 482 | (E)-3-(2-(2-(trifluoromethoxy)-6-(trifluoromethyl)pyridin-4-yl)-5H-pyrrolo[2,3-b]pyrazin-7-yl)acrylamide | NC(/C=C/C1=CNC2=NC=C(C3=CC(OC(F)(F)F)=NC(C(F)(F)F)=C3)N=C21)=O |
| 483 | (E)-3-(2-(2,4-difluorophenyl)-5H-pyrrolo[2,3-b]pyrazin-7-yl)acrylamide | NC(/C=C/C1=CNC2=NC=C(C3=CC=C(F)C=C3F)N=C21)=O |
| 484 | (E)-3-(2-(2,6-bis(trifluoromethyl)pyridin-4-yl)-5H-pyrrolo[2,3-b]pyrazin-7-yl)acrylamide | NC(/C=C/C1=CNC2=NC=C(C3=CC(C(F)(F)F)=NC(C(F)(F)F)=C3)N=C21)=O |
| 485 | (E)-3-(2-(2-cyano-6-(trifluoromethyl)pyridin-4-yl)-5H-pyrrolo[2,3-b]pyrazin-7-yl)acrylamide | NC(/C=C/C1=CNC2=NC=C(C3=CC(C#N)=NC(C(F)(F)F)=C3)N=C21)=O |
| 486 | (E)-3-(2-(2-ethoxy-6-(trifluoromethyl)pyridin-4-yl)-5H-pyrrolo[2,3-b]pyrazin-7-yl)acrylamide | NC(/C=C/C1=CNC2=NC=C(C3=CC(OCC)=NC(C(F)(F)F)=C3)N=C21)=O |
| 487 | (E)-3-(2-(2-hydroxy-2-methylpropoxy)-5H-pyrrolo[2,3-b]pyrazin-7-yl)acrylamide | O=C(N)/C=C/C1=CNC2=NC=C(OCC(C)(O)C)N=C21 |
| 488 | (E)-3-(2-(2-isobutoxy-6-(trifluoromethyl)pyridin-4-yl)-5H-pyrrolo[2,3-b]pyrazin-7-yl)acrylamide | NC(/C=C/C1=CNC2=NC=C(C3=CC(OCC(C)C)=NC(C(F)(F)F)=C3)N=C21)=O |
| 489 | (E)-3-(2-(2-isobutyl-6-(trifluoromethyl)pyridin-4-yl)-5H-pyrrolo[2,3-b]pyrazin-7-yl)acrylamide | NC(/C=C/C1=CNC2=NC=C(C3=CC(CC(C)C)=NC(C(F)(F)F)=C3)N=C21)=O |

TABLE 2-continued

Additional Examples

| Example | Structure | Name | Smiles |
|---|---|---|---|
| 490 | 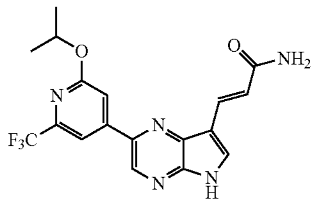 [SMILES: CC(C)Oc1cc(-c2cnc3[nH]cc(/C=C/C(N)=O)c3n2)cc(C(F)(F)F)n1] | (E)-3-(2-(2-isopropoxy-6-(trifluoromethyl)pyridin-4-yl)-5H-pyrrolo[2,3-b]pyrazin-7-yl)acrylamide | NC(/C=C/C1=CNC2=NC=C(C3=CC(OC(C)C)=NC(C(F)(F)F)=C3)N=C21)=O |
| 491 | 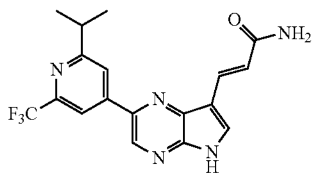 [SMILES: CC(C)c1cc(-c2cnc3[nH]cc(/C=C/C(N)=O)c3n2)cc(C(F)(F)F)n1] | (E)-3-(2-(2-isopropyl-6-(trifluoromethyl)pyridin-4-yl)-5H-pyrrolo[2,3-b]pyrazin-7-yl)acrylamide | NC(/C=C/C1=CNC2=NC=C(C3=CC(C(C)C)=NC(C(F)(F)F)=C3)N=C21)=O |
| 492 | 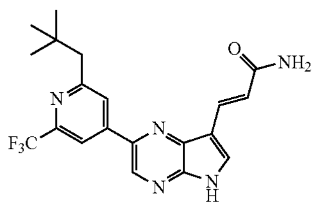 [SMILES: CC(C)(C)Cc1cc(-c2cnc3[nH]cc(/C=C/C(N)=O)c3n2)cc(C(F)(F)F)n1] | (E)-3-(2-(2-neopentyl-6-(trifluoromethyl)pyridin-4-yl)-5H-pyrrolo[2,3-b]pyrazin-7-yl)acrylamide | NC(/C=C/C1=CNC2=NC=C(C3=CC(CC(C)(C)C)=NC(C(F)(F)F)=C3)N=C21)=O |
| 493 | 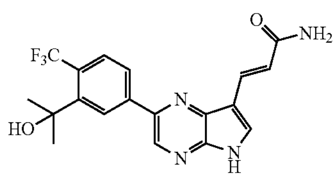 [SMILES: CC(C)(O)c1cc(-c2cnc3[nH]cc(/C=C/C(N)=O)c3n2)ccc1C(F)(F)F] | (E)-3-(2-(3-(2-hydroxypropan-2-yl)-4-(trifluoromethyl)phenyl)-5H-pyrrolo[2,3-b]pyrazin-7-yl)acrylamide | NC(/C=C/C1=CNC2=NC=C(C3=CC=C(C(F)(F)F)C(C(C)(O)C)=C3)N=C21)=O |
| 494 | 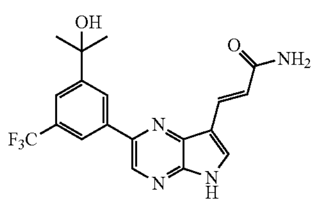 [SMILES: CC(C)(O)c1cc(-c2cnc3[nH]cc(/C=C/C(N)=O)c3n2)cc(C(F)(F)F)c1] | (E)-3-(2-(3-(2-hydroxypropan-2-yl)-5-(trifluoromethyl)phenyl)-5H-pyrrolo[2,3-b]pyrazin-7-yl)acrylamide | NC(/C=C/C1=CNC2=NC=C(C3=CC(C(C)(O)C)=CC(C(F)(F)F)=C3)N=C21)=O |
| 495 | 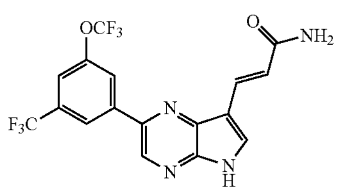 [SMILES: NC(=O)/C=C/c1c[nH]c2ncc(-c3cc(OC(F)(F)F)cc(C(F)(F)F)c3)nc12] | (E)-3-(2-(3-(trifluoromethoxy)-5-(trifluoromethyl)phenyl)-5H-pyrrolo[2,3-b]pyrazin-7-yl)acrylamide | NC(/C=C/C1=CNC2=NC=C(C3=CC(OC(F)(F)F)=CC(C(F)(F)F)=C3)N=C21)=O |
| 496 | 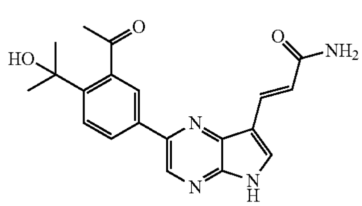 [SMILES: CC(=O)c1cc(-c2cnc3[nH]cc(/C=C/C(N)=O)c3n2)ccc1C(C)(C)O] | (E)-3-(2-(3-acetyl-4-(2-hydroxypropan-2-yl)phenyl)-5H-pyrrolo[2,3-b]pyrazin-7-yl)acrylamide | NC(/C=C/C1=CNC2=NC=C(C3=CC(C(C)=O)=C(C(C)(O)C)C=C3)N=C21)=O |

TABLE 2-continued

Additional Examples

| Example | Structure | Name | Smiles |
|---|---|---|---|
| 497 | 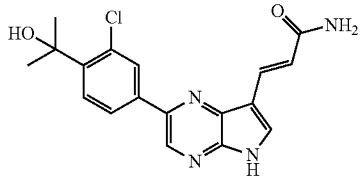 [SMILES: CC(C)(O)c1ccc(-c2cnc3[nH]cc(/C=C/C(N)=O)c3n2)cc1Cl] | (E)-3-(2-(3-chloro-4-(2-hydroxypropan-2-yl)phenyl)-5H-pyrrolo[2,3-b]pyrazin-7-yl)acrylamide | NC(/C=C/C1=CNC2=NC=C(C3=CC(C1)=C(C(C)(O)C)C=C3)N=C21)=O |
| 498 | 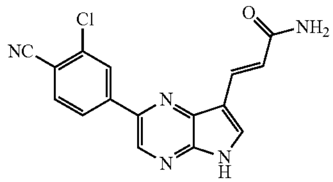 [SMILES: N#Cc1ccc(-c2cnc3[nH]cc(/C=C/C(N)=O)c3n2)cc1Cl] | (E)-3-(2-(3-chloro-4-cyanophenyl)-5H-pyrrolo[2,3-b]pyrazin-7-yl)acrylamide | NC(/C=C/C1=CNC2=NC=C(C3=CC(C1)=C(C#N)C=C3)N=C21)=O |
| 499 | 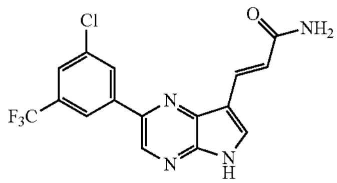 [SMILES: NC(=O)/C=C/c1c[nH]c2ncc(-c3cc(Cl)cc(C(F)(F)F)c3)nc12] | (E)-3-(2-(3-chloro-5-(trifluoromethyl)phenyl)-5H-pyrrolo[2,3-b]pyrazin-7-yl)acrylamide | NC(/C=C/C1=CNC2=NC=C(C3=CC(C1)=CC(C(F)(F)F)=C3)N=C21)=O |
| 500 | 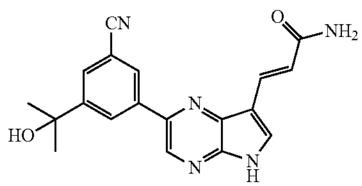 [SMILES: CC(C)(O)c1cc(C#N)cc(-c2cnc3[nH]cc(/C=C/C(N)=O)c3n2)c1] | (E)-3-(2-(3-cyano-5-(2-hydroxypropan-2-yl)phenyl)-5H-pyrrolo[2,3-b]pyrazin-7-yl)acrylamide | NC(/C=C/C1=CNC2=NC=C(C3=CC(C#N)=CC(C(C)(O)C)=C3)N=C21)=O |
| 501 | 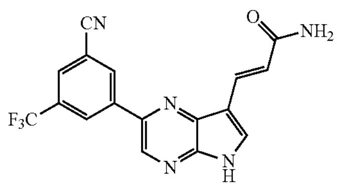 [SMILES: N#Cc1cc(-c2cnc3[nH]cc(/C=C/C(N)=O)c3n2)cc(C(F)(F)F)c1] | (E)-3-(2-(3-cyano-5-(trifluoromethyl)phenyl)-5H-pyrrolo[2,3-b]pyrazin-7-yl)acrylamide | NC(/C=C/C1=CNC2=NC=C(C3=CC(C#N)=CC(C(F)(F)F)=C3)N=C21)=O |
| 502 | 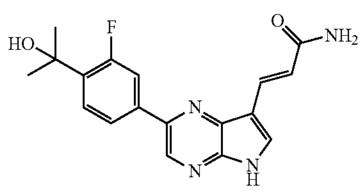 [SMILES: CC(C)(O)c1ccc(-c2cnc3[nH]cc(/C=C/C(N)=O)c3n2)cc1F] | (E)-3-(2-(3-fluoro-4-(2-hydroxypropan-2-yl)phenyl)-5H-pyrrolo[2,3-b]pyrazin-7-yl)acrylamide | NC(/C=C/C1=CNC2=NC=C(C3=CC(F)=C(C(C)(O)C)C=C3)N=C21)=O |
| 503 | 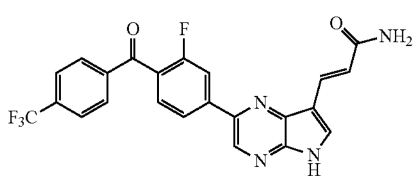 [SMILES: NC(=O)/C=C/c1c[nH]c2ncc(-c3ccc(C(=O)c4ccc(C(F)(F)F)cc4)c(F)c3)nc12] | (E)-3-(2-(3-fluoro-4-(4-(trifluoromethyl(benzoyl)phenyl)-5H-pyrrolo[2,3-b]pyrazin-7-yl)acrylamide | NC(/C=C/C1=CNC2=NC=C(C3=CC(F)=C(C(C4=CC=C(C(F)(F)F)C=C4)=O)C=C3)N=C21)=O |
| 504 | 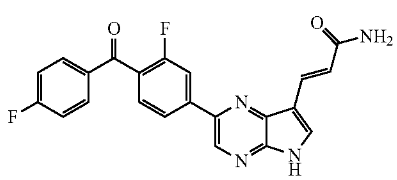 [SMILES: NC(=O)/C=C/c1c[nH]c2ncc(-c3ccc(C(=O)c4ccc(F)cc4)c(F)c3)nc12] | (E)-3-(2-(3-fluoro-4-(4-fluorobenzoyl)phenyl)-5H-pyrrolo[2,3-b]pyrazin-7-yl)acrylamide | NC(/C=C/C1=CNC2=NC=C(C3=CC(F)=C(C(C4=CC=C(F)C=C4)=O)C=C3)N=C21)=O |

TABLE 2-continued

Additional Examples

| Example | Structure | Name | Smiles |
|---|---|---|---|
| 505 | 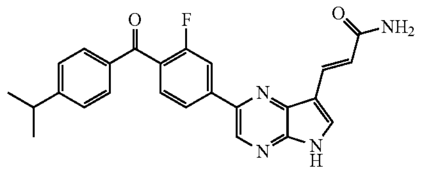 [SMILES: CC(C)c1ccc(C(=O)c2ccc(-c3cnc4[nH]cc(/C=C/C(N)=O)c4n3)cc2F)cc1] | (E)-3-(2-(3-fluoro-4-(4-isopropylbenzoyl)phenyl)-5H-pyrrolo[2,3-b]pyrazin-7-yl)acrylamide | NC(/C=C/C1=CNC2=NC=C(C3=CC(F)=C(C(C4=CC=C(C(C)C)C=C4)=O)C=C3)N=C21)=O |
| 506 | 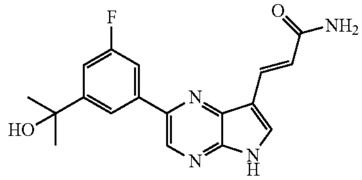 [SMILES: CC(C)(O)c1cc(F)cc(-c2cnc3[nH]cc(/C=C/C(N)=O)c3n2)c1] | (E)-3-(2-(3-fluoro-5-(2-hydroxypropan-2-yl)phenyl)-5H-pyrrolo[2,3-b]pyrazin-7-yl)acrylamide | NC(/C=C/C1=CNC2=NC=C(C3=CC(F)=CC(C(C)(O)C)=C3)N=C21)=O |
| 507 | 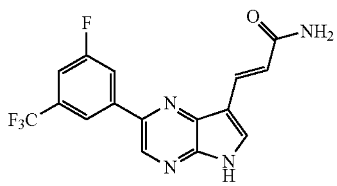 [SMILES: NC(=O)/C=C/c1c[nH]c2ncc(-c3cc(F)cc(C(F)(F)F)c3)nc12] | (E)-3-(2-(3-fluoro-5-(trifluoromethyl)phenyl)-5H-pyrrolo[2,3-b]pyrazin-7-yl)acrylamide | NC(/C=C/C1=CNC2=NC=C(C3=CC(F)=CC(C(F)(F)F)=C3)N=C21)=O |
| 508 | 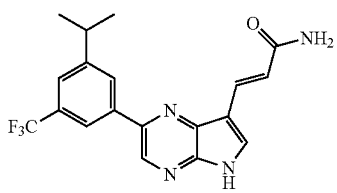 | (E)-3-(2-(3-isopropyl-5-(trifluoromethyl)phenyl)-5H-pyrrolo[2,3-b]pyrazin-7-yl)acrylamide | NC(/C=C/C1=CNC2=NC=C(C3=CC(C(C)C)=CC(C(F)(F)F)=C3)N=C21)=O |
| 509 | 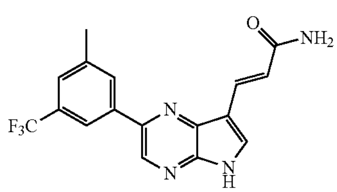 [SMILES: Cc1cc(-c2cnc3[nH]cc(/C=C/C(N)=O)c3n2)cc(C(F)(F)F)c1] | (E)-3-(2-(3-methyl-5-(trifluoromethyl)phenyl)-5H-pyrrolo[2,3-b]pyrazin-7-yl)acrylamide | NC(/C=C/C1=CNC2=NC=C(C3=CC(C)=CC(C(F)(F)F)=C3)N=C21)=O |
| 510 | 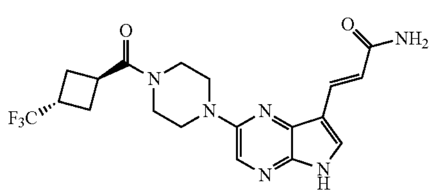 [SMILES: NC(=O)/C=C/c1c[nH]c2ncc(N3CCN(C(=O)[C@H]4C[C@H](C(F)(F)F)C4)CC3)nc12] | (E)-3-(2-(4-((1r,3r)-3-(trifluoromethyl)cyclobutanecarbonyl)piperazin-1-yl)-5H-pyrrolo[2,3-b]pyrazin-7-yl)acrylamide | NC(/C=C/C1=CNC2=NC=C(N3CCN(C([C@@H]4C[C@@H](C(F)(F)F)C4)=O)CC3)N=C21)=O |
| 511 | 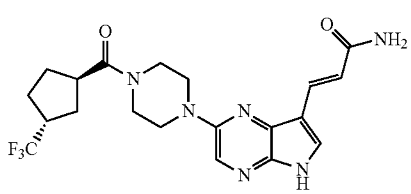 [SMILES: NC(=O)/C=C/c1c[nH]c2ncc(N3CCN(C(=O)[C@@H]4CC[C@@H](C(F)(F)F)C4)CC3)nc12] | (E)-3-(2-(4-((1R,3R)-3-(trifluoromethyl)cyclopentanecarbonyl)piperazin-1-yl)-5H-pyrrolo[2,3-b]pyrazin-7-yl)acrylamide | NC(/C=C/C1=CNC2=NC=C(N3CCN(C([C@@H]4CC[C@@H](C(F)(F)F)C4)=O)CC3)N=C21)=O |
| 512 | 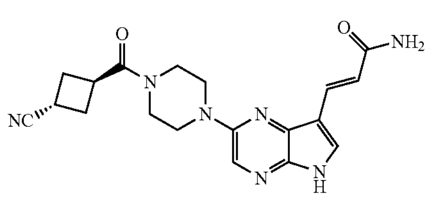 [SMILES: N#C[C@H]1C[C@H](C(=O)N2CCN(c3cnc4[nH]cc(/C=C/C(N)=O)c4n3)CC2)C1] | (E)-3-(2-(4-((1r,3r)-3-cyanocyclobutanecarbonyl)piperazin-1-yl)-5H-pyrrolo[2,3-b]pyrazin-7-yl)acrylamide | NC(/C=C/C1=CNC2=NC=C(N3CCN(C([C@@H]4C[C@@H](C#N)C4)=O)CC3)N=C21)=O |

TABLE 2-continued

Additional Examples

| Example | Structure | Name | Smiles |
|---|---|---|---|
| 513 | 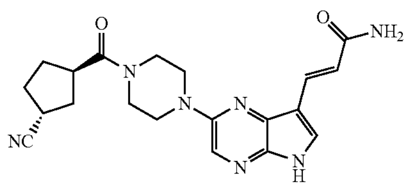 [SMILES: N#C[C@@H]1CC[C@@H](C(=O)N2CCN(c3cnc4[nH]cc(/C=C/C(N)=O)c4n3)CC2)C1] | (E)-3-(2-(4-((1R,3R)-3-cyanocyclopentanecarbonyl)piperazin-1-yl)-5H-pyrrolo[2,3-b]pyrazin-7-yl)acrylamide | NC(/C=C/C1=CNC2=NC=C(N3CCN(C([C@@H]4CC[C@@H](C#N)C4)=O)CC3)N=C21)=O |
| 514 | 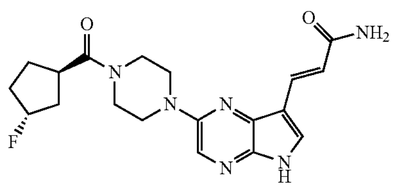 [SMILES: NC(=O)/C=C/c1c[nH]c2ncc(N3CCN(C(=O)[C@@H]4CC[C@@H](F)C4)CC3)nc12] | (E)-3-(2-(4-((1R,3R)-3-fluorocyclopentanecarbonyl)piperazin-1-yl)-5H-pyrrolo[2,3-b]pyrazin-7-yl)acrylamide | NC(/C=C/C1=CNC2=NC=C(N3CCN(C([C@@H]4CC[C@@H](F)C4)=O)CC3)N=C21)=O |
| 515 | 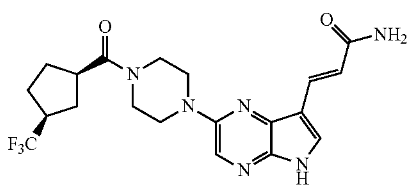 [SMILES: NC(=O)/C=C/c1c[nH]c2ncc(N3CCN(C(=O)[C@@H]4CC[C@H](C(F)(F)F)C4)CC3)nc12] | (E)-3-(2-(4-((1R,3S)-3-(trifluoromethyl)cyclopentanecarbonyl)piperazin-1-yl)-5H-pyrrolo[2,3-b]pyrazin-7-yl)acrylamide | NC(/C=C/C1=CNC2=NC=C(N3CCN(C([C@@H]4CC[C@H](C(F)(F)F)C4)=O)CC3)N=C21)=O |
| 516 | 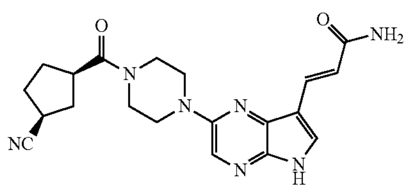 [SMILES: N#C[C@H]1CC[C@@H](C(=O)N2CCN(c3cnc4[nH]cc(/C=C/C(N)=O)c4n3)CC2)C1] | (E)-3-(2-(4-((1R,3S)-3-cyanocyclopentanecarbonyl)piperazin-1-yl)-5H-pyrrolo[2,3-H]pyrazin-7-yl)acrylamide | NC(/C=C/C1=CNC2=NC=C(N3CCN(C([C@@H]4CC[C@H](C#N)C4)=O)CC3)N=C21)=O |
| 517 | 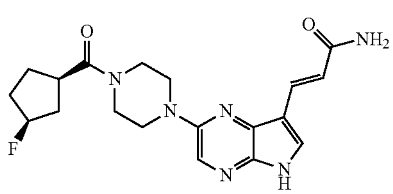 [SMILES: NC(=O)/C=C/c1c[nH]c2ncc(N3CCN(C(=O)[C@@H]4CC[C@H](F)C4)CC3)nc12] | (E)-3-(2-(4-((1R,3S)-3-fluorocyclopentanecarbonyl)piperazin-1-yl)-5H-pyrrolo[2,3-b]pyrazin-7-yl)acrylamide | NC(/C=C/C1=CNC2=NC=C(N3CCN(C([C@@H]4CC[C@H](F)C4)=O)CC3)N=C21)=O |
| 518 | 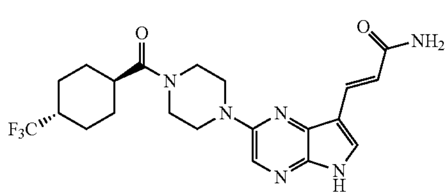 [SMILES: NC(=O)/C=C/c1c[nH]c2ncc(N3CCN(C(=O)[C@H]4CC[C@H](C(F)(F)F)CC4)CC3)nc12] | (E)-3-(2-(4-((1r,4r)-4-(trifluoromethyl)cyclohexanecarbonyl)piperazin-1-yl)-5H-pyrrolo[2,3-b]pyrazin-7-yl)acrylamide | NC(/OC/C1=CNC2=NC=C(N3CCN(C([C@@H]4CC[C@@H](C(F)(F)F)CC4)=O)CC3)N=C21)=O |
| 519 | 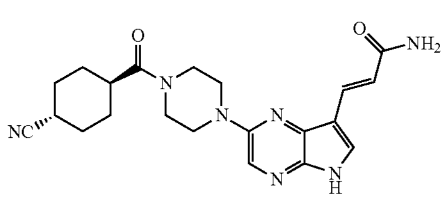 [SMILES: N#C[C@H]1CC[C@H](C(=O)N2CCN(c3cnc4[nH]cc(/C=C/C(N)=O)c4n3)CC2)CC1] | (E)-3-(2-(4-((1r,4r)-4-cyanocyclohexanecarbonyl)piperazin-1-yl)-5H-pyrrolo[2,3-b]pyrazin-7-yl)acrylamide | NC(/C=C/C1=CNC2=NC=C(N3CCN(C([C@@H]4CC[C@@H](C#N)CC4)=O)CC3)N=C21)=O |
| 520 | 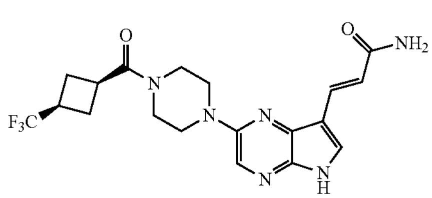 [SMILES: NC(=O)/C=C/c1c[nH]c2ncc(N3CCN(C(=O)[C@H]4C[C@@H](C(F)(F)F)C4)CC3)nc12] | (E)-3-(2-(4-((1s,3s)-3-(trifluoromethyl)cyclobutanecarbonyl)piperazin-1-yl)-5H-pyrrolo[2,3-b]pyrazin-7-yl)acrylamide | NC(/C=C/C1=CNC2=NC=C(N3CCN(C([C@@H]4C[C@H](C(F)(F)F)C4)=O)CC3)N=C21)=O |

TABLE 2-continued

Additional Examples

| Example | Name | Smiles |
|---|---|---|
| 521 | (E)-3-(2-(4-((1s,3s)-3-cyanocyclobutanecarbonyl)piperazin-1-yl)-5H-pyrrolo[2,3-b]pyrazin-7-yl)acrylamide | NC(/C═C/C1═CNC2═NC═C(N3CCN(C([C@@H]4C[C@H](C#N)C4)═O)CC3)═C21)═O |
| 522 | (E)-3-(2-(4-((1s,4s)-4-(trifluoromethyl)cyclohexanecarbonyl)piperazin-1-yl)-5H-pyrrolo[2,3-b]pyrazin-7-yl)acrylamide | NC(/OC/C1═CNC2═NC═C(N3CCN(C([C@ @H]4CC[C@H](C(F)(F)F)CC4)═O)CC3)N═C21)═O |
| 523 | (E)-3-(2-(4-((1s,4s)-4-cyanocyclohexanecarbonyl)piperazin-1-yl)-5H-pyrrolo[2,3-b]pyrazin-7-yl)acrylamide | NC(/C═C/C1═CNC2═NC═C(N3CCN(C([C@ @H]4CC[C@H](C#N)CC4)═O)CC3)N═C21)═O |
| 524 | (E)-3-(2-(4-(1,2-dimethyl-1H-imidazole-5-carbonyl)phenyl)-5H-pyrrolo[2,3-b]pyrazin-7-yl)acrylamide | NC(/C═C/C1═CNC2═NC═C(C3═CC═C(C(C4═CN═C(C)N4C)═O)C═C3)N═C21)═O |
| 525 | (E)-3-(2-(4-(1,4-dimethyl-1H-imidazole-2-carbonyl)phenyl)-5H-pyrrolo[2,3-b]pyrazin-7-yl)acrylamide | NC(/C═C/C1═CNC2═NC═C(C3═CC═C(C(C4═NC(C)═CN4C)═O)C═C3)N═C21)═O |
| 526 | (E)-3-(2-(4-(1-methyl-1H-imidazole-2-carbonyl)phenyl)-5H-pyrrolo[2,3-b]pyrazin-7-yl)acrylamide | NC(/C═C/C1═CNC2═NC═C(C3═CC═C(C(C4═NC═CN4C)═O)C═C3)N═C21)═O |
| 527 | (E)-3-(2-(4-(1-methyl-1H-imidazole-5-carbonyl)phenyl)-5H-pyrrolo[2,3-b]pyrazin-7-yl)acrylamide | NC(/C═C/C1═CNC2═NC═C(C3═CC═C(C(C4═CN═CN4C)═O)C═C3)N═C21)═O |
| 528 | (E)-3-(2-(4-(1-methyl-2-(trifluoromethyl)-1H-imidazole-5-carbonyl)phenyl)-5H-pyrrolo[2,3-b]pyrazin-7-yl)acrylamide | NC(/C═C/C1═CNC2═NC═C(C3═CC═C(C(C4═CN═C(C(F)(F)F)N4C)═O)C═C3)N═C21)═O |

TABLE 2-continued

Additional Examples

| Example | Name | Smiles |
|---|---|---|
| 529 | (E)-3-(2-(4-(1-methyl-4-(trifluoromethyl)-1H-imidazole-2-carbonyl)phenyl)-5H-pyrrolo[2,3-b]pyrazin-7-yl)acrylamide | NC(/C=C/C1=CNC2=NC=C(C3=CC=C(C(C4=NC(C(F)(F)F)=CN4C)=O)C=C3)N=C21)=O |
| 530 | (E)-3-(2-(4-(1-methyl-5-(trifluoromethyl)-1H-imidazole-2-carbonyl)phenyl)-5H-pyrrolo[2,3-b]pyrazin-7-yl)acrylamide | NC(/C=C/C1=CNC2=NC=C(C3=CC=C(C(C4=NC=C(C(F)(F)F)N4C)=O)C=C3)N=C21)=O |
| 531 | (E)-3-(2-(4-(2-(trifluoromethyl)thiazole-5-carbonyl)phenyl)-5H-pyrrolo[2,3-b]pyrazin-7-yl)acrylamide | NC(/C=C/C1=CNC2=NC=C(C3=CC=C(C(C4=CN=C(C(F)(F)F)S4)=O)C=C3)N=C21)=O |
| 532 | (E)-3-(2-(4-(2-cyanoacetyl)piperazin-1-yl)-5H-pyrrolo[2,3-b]pyrazin-7-yl)acrylamide | NC(/C=C/C1=CNC2=NC=C(N3CCN(C(CC#N)=O)CC3)N=C21)=O |
| 533 | (E)-3-(2-(4-(2-fluoro-1-methyl-1H-imidazole-5-carbonyl)phenyl)-5H-pyrrolo[2,3-b]pyrazin-7-yl)acrylamide | NC(/C=C/C1=CNC2=NC=C(C3=CC=C(C(C4=CN=C(F)N4C)=O)C=C3)N=C21)=O |
| 534 | (E)-3-(2-(4-(2-fluorothiazole-5-carbonyl)phenyl)-5H-pyrrolo[2,3-b]pyrazin-7-yl)acrylamide | NC(/C=C/C1=CNC2=NC=C(C3=CC=C(C(C4=CN=C(F)S4)=O)C=C3)N=C21)=O |
| 535 | (E)-3-(2-(4-(2-hydroxybutan-2-yl)phenyl)-5H-pyrrolo[2,3-b]pyrazin-7-yl)acrylamide | NC(/C=C/C1=CNC2=NC=C(C3=CC=C(C(CC)(O)C)C=C3)N=C21)=O |
| 536 | (E)-3-(2-(4-(2-hydroxypropan-2-yl)-3-(trifluoromethyl)phenyl)-5H-pyrrolo[2,3-b]pyrazin-7-yl)acrylamide | NC(/C=C/C1=CNC2=NC=C(C3=CC(C(F)(F)F)=C(C(C)(O)C)C=C3)N=C21)=O |

TABLE 2-continued

Additional Examples

| Example | Structure | Name | Smiles |
|---|---|---|---|
| 537 | 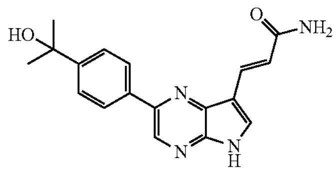 [SMILES: CC(C)(O)c1ccc(-c2cnc3[nH]cc(/C=C/C(N)=O)c3n2)cc1] | (E)-3-(2-(4-(2-hydroxypropan-2-yl)phenyl)-5H-pyrrolo[2,3-b]pyrazin-7-yl)acrylamide | NC(/C=C/C1=CNC2=NC=C(C3=CC=C(C(C)(O)C)C=C3)N=C2 |
| 538 | 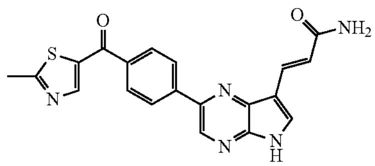 [SMILES: Cc1ncc(C(=O)c2ccc(-c3cnc4[nH]cc(/C=C/C(N)=O)c4n3)cc2)s1] | (E)-3-(2-(4-(2-methylthiazole-5-carbonyl)phenyl)-5H-pyrrolo[2,3-b]pyrazin-7-yl)acrylamide | NC(/C=C/C1=CNC2=NC=C(C3=CC=C(C(C4=CN=C(C)S4)=O)C=C3)N=C21)=O |
| 539 | 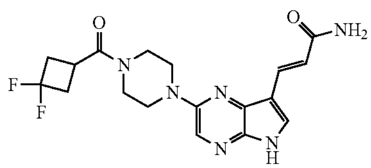 [SMILES: NC(=O)/C=C/c1c[nH]c2ncc(N3CCN(C(=O)C4CC(F)(F)C4)CC3)nc12] | (E)-3-(2-(4-(3,3-difluorocyclobutanecarbonyl)piperazin-1-yl)-5H-pyrrolo[2,3-b]pyrazin-7-yl)acrylamide | NC(/C=C/C1=CNC2=NC=C(N3CCN(C(C4CC(F)(F)C4)=O)CC3)N=C21)=O |
| 540 | 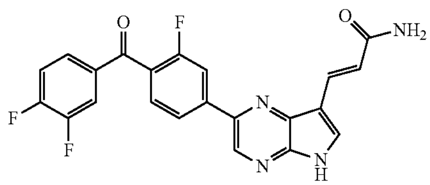 [SMILES: NC(=O)/C=C/c1c[nH]c2ncc(-c3ccc(C(=O)c4ccc(F)c(F)c4)c(F)c3)nc12] | (E)-3-(2-(4-(3,4-difluorobenzoyl)-3-fluorophenyl)-5H-pyrrolo[2,3-b]pyrazin-7-yl)acrylamide | NC(/C=C/C1=CNC2=NC=C(C3=CC(F)=C(C(C=CC=C(F)C(F)=C4)=O)C=C3)N=C21)=O |
| 541 | 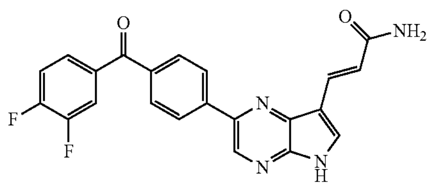 [SMILES: NC(=O)/C=C/c1c[nH]c2ncc(-c3ccc(C(=O)c4ccc(F)c(F)c4)cc3)nc12] | (E)-3-(2-(4-(3,4-difluorobenzoyl)phenyl)-5H-pyrrolo[2,3-b]pyrazin-7-yl)acrylamide | NC(/C=C/C1=CNC2=NC=C(C3=C=(C(C4=CC=C(F)C(F)=C4)=O)C=C3)N=C21)=O |
| 542 | 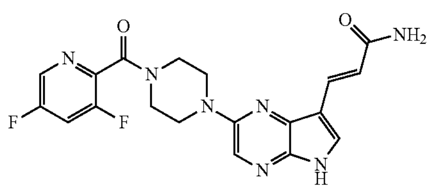 [SMILES: NC(=O)/C=C/c1c[nH]c2ncc(N3CCN(C(=O)c4ncc(F)cc4F)CC3)nc12] | (E)-3-(2-(4-(3,5-difluoropicolinoyl)piperazin-1-yl)-5H-pyrrolo[2,3-b]pyrazin-7-yl)acrylamide | NC(/C=C/C1=CNC2=NC=C(N3CCN(C(C4=NC=C(F)C=C4F)=O)CC3)N=C21)=O |
| 543 | 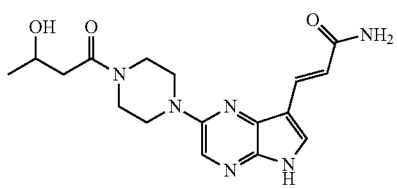 [SMILES: CC(O)CC(=O)N1CCN(c2cnc3[nH]cc(/C=C/C(N)=O)c3n2)CC1] | (E)-3-(2-(4-(3-hydroxybutanoyl)piperazin-1-yl)-5H-pyrrolo[2,3-b]pyrazin-7-yl)acrylamide | NC(/C=C/C1=CNC2=NC=C(N3CCN(C(CC(C)O)=O)CC3)N=C21)=O |
| 544 | 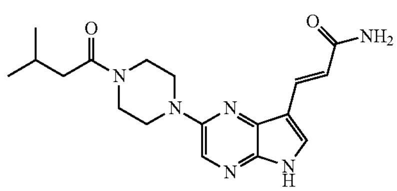 [SMILES: CC(C)CC(=O)N1CCN(c2cnc3[nH]cc(/C=C/C(N)=O)c3n2)CC1] | (E)-3-(2-(4-(3-methylbutanoyl)piperazin-1-yl)-5H-pyrrolo[2,3-b]pyrazin-7-yl)acrylamide | NC(/C=C/C1=CNC2=NC=C(N3CCN(C(CC(C)C)=O)CC3)N=C21)=O |

TABLE 2-continued

Additional Examples

| Example | Structure | Name | Smiles |
|---|---|---|---|
| 545 | 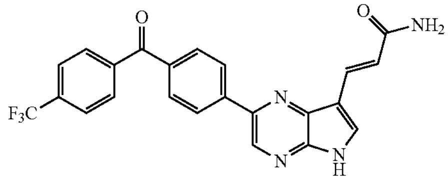 [SMILES: NC(=O)/C=C/c1c[nH]c2ncc(-c3ccc(C(=O)c4ccc(C(F)(F)F)cc4)cc3)nc12] | (E)-3-(2-(4-(4-(trifluoromethyl)benzoyl)phenyl)-5H-pyrrolo[2,3-H]pyrazin-7-yl)acrylamide | NC(/C=C/C1=CNC2=NC=C(C3=CC=C(C(C4=CC=C(C(F)(F)F)C=C4)=O)C=C3)N=C21)=O |
| 546 | 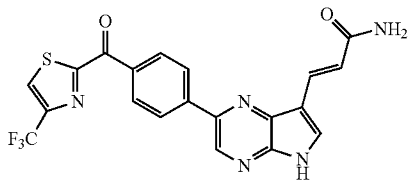 [SMILES: NC(=O)/C=C/c1c[nH]c2ncc(-c3ccc(C(=O)c4nc(C(F)(F)F)cs4)cc3)nc12] | (E)-3-(2-(4-(4-(trifluoromethyl)thiazole-2-carbonyl)phenyl)-5H-pyrrolo[2,3-b]pyrazin-7-yl)acrylamide | NC(/C=C/C1=CNC2=NC=C(C3=CC=C(C(C4=NC(C(F)(F)F)=CS4)=O)C=C3)N=C21)=O |
| 547 | 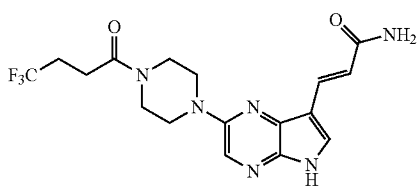 [SMILES: NC(=O)/C=C/c1c[nH]c2ncc(N3CCN(C(=O)CCC(F)(F)F)CC3)nc12] | (E)-3-(2-(4-(4,4,4-trifluorobutanoyl)piperazin-1-yl)-5H-pyrrolo[2,3-b]pyrazin-7-yl)acrylamide | NC(/C=C/C1=CNC2=NC=C(N3CCN(C(CCC(F)(F)F)=O)CC3)N=C21)=O |
| 548 | 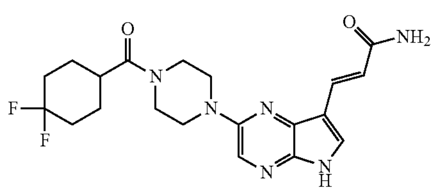 [SMILES: NC(=O)/C=C/c1c[nH]c2ncc(N3CCN(C(=O)C4CCC(F)(F)CC4)CC3)nc12] | (E)-3-(2-(4-(4,4-difluorocyclohexanecarbonyl)piperazin-l-yl)-5H-pyrrolo[2,3-b]pyrazin-7-yl)acrylamide | NC(/C=C/C1=CNC2=NC=C(N3CCN(C(C4CCC(F)(F)CC4)=O)CC3)N=C21)=O |
| 549 | 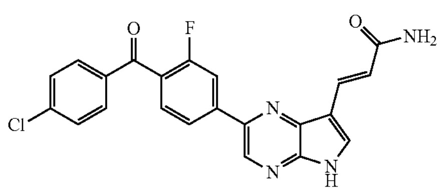 [SMILES: NC(=O)/C=C/c1c[nH]c2ncc(-c3ccc(C(=O)c4ccc(Cl)cc4)c(F)c3)nc12] | (E)-3-(2-(4-(4-chlorobenzoyl)-3-fluorophenyl)-5H-pyrrolo[2,3-b]pyrazin-7-yl)acrylamide | NC(/C=C/C1=CNC2=NC=C(C3=CC(F)=C(C(C4=CC=C(C1)C=C4)=O)C=C3)N=C21)=O |
| 550 | 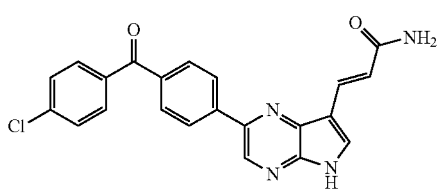 [SMILES: NC(=O)/C=C/c1c[nH]c2ncc(-c3ccc(C(=O)c4ccc(Cl)cc4)cc3)nc12] | (E)-3-(2-(4-(4-chlorobenzoyl)phenyl)-5H-pyrrolo[2,3-b]pyrazin-7-yl)acrylamide | NC(/C=C/C1=CNC2=NC=C(C3=CC=C(C(C4=CC=C(C1)C=C4)=O)C=C3)N=C21)=O |
| 551 | 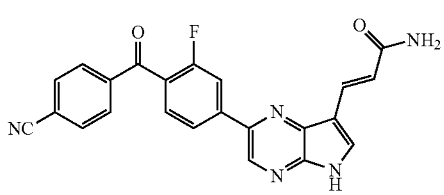 [SMILES: N#Cc1ccc(C(=O)c2ccc(-c3cnc4[nH]cc(/C=C/C(N)=O)c4n3)cc2F)cc1] | (E)-3-(2-(4-(4-cyanobenzoyl)-3-fluorophenyl)-5H-pyrrolo[2,3-b]pyrazin-7-yl)acrylamide | NC(/C=C/C1=CNC2=NC=C(C3=CC(F)=C(C(C4=CC=C(C#N)C=C4)=O)C=C3)N=C21)=O |
| 552 | 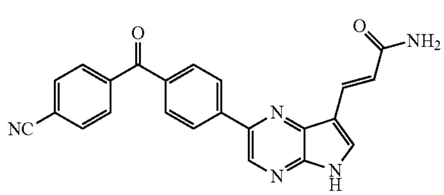 [SMILES: N#Cc1ccc(C(=O)c2ccc(-c3cnc4[nH]cc(/C=C/C(N)=O)c4n3)cc2)cc1] | (E)-3-(2-(4-(4-cyanobenzoyl)phenyl)-5H-pyrrolo[2,3-b]pyrazin-7-yl)acrylamide | NC(/C=C/C1=CNC2=NC=C(C3=CC=C(C(C4=CC=C(C#N)C=C4)=O)C=C3)N=C21)=O |

TABLE 2-continued

Additional Examples

| Example | Structure | Name | Smiles |
|---|---|---|---|
| 553 | 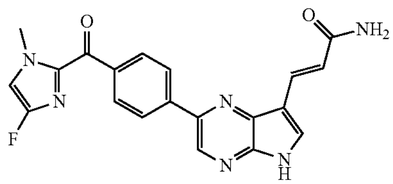 | (E)-3-(2-(4-(4-fluoro-1-methyl-1H-imidazole-2-carbonyl)phenyl)-5H-pyrrolo[2,3-b]pyrazin-7-yl)acrylamide | NC(/C=C/C1=CNC2=NC=C(C3=CC=C(C(C4=NC(F)=CN4C)=O)C=C3)N=C21)=O |
| 554 | 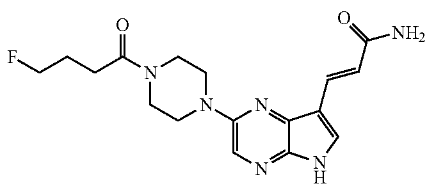 | (E)-3-(2-(4-(4-fluorobutanoyl)piperazin-1-yl)-5H-pyrrolo[2,3-b]pyrazin-7-yl)acrylamide | NC(/C=C/C1=CNC2=NC=C(N3CCN(C(CCCF)=O)CC3)N=C21)=O |
| 555 | 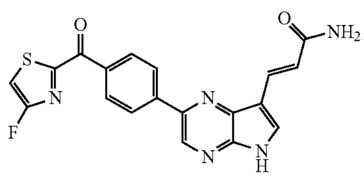 | (E)-3-(2-(4-(4-fluorothiazole-2-carbonyl)phenyl)-5H-pyrrolo[2,3-b]pyrazin-7-yl)acrylamide | NC(/C=C/C1=CNC2=NC=C(C3=CC=C(C(C4=NC(F)=CS4)=O)C=C3)N=C21)=O |
| 556 | 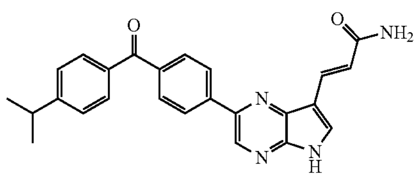 [SMILES: CC(C)c1ccc(C(=O)c2ccc(-c3cnc4[nH]cc(/C=C/C(N)=O)c4n3)cc2)cc1] | (E)-3-(2-(4-(4-isopropylbenzoyl)phenyl)-5H-pyrrolo[2,3-b]pyrazin-7-yl)acrylamide | NC(/C=C/C1=CNC2=NC=C(C3=CC=C(C(C4=CC=C(C(C)C)C=C4)=O)C=C3)N=C21)=O |
| 557 | 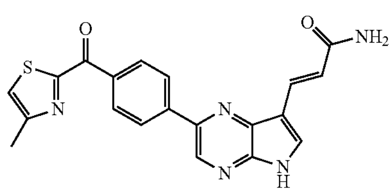 [SMILES: Cc1csc(C(=O)c2ccc(-c3cnc4[nH]cc(/C=C/C(N)=O)c4n3)cc2)n1] | (E)-3-(2-(4-(4-methylthiazole-2-carbonyl)phenyl)-5H-pyrrolo[2,3-b]pyrazin-7-yl)acrylamide | NC(/C=C/C1=CNC2=NC=C(C3=CC=C(C(C4=NC(C)=CS4)=O)C=C3)N=C21)=O |
| 558 | 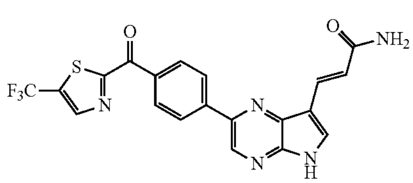 [SMILES: NC(=O)/C=C/c1c[nH]c2ncc(-c3ccc(C(=O)c4ncc(C(F)(F)F)s4)cc3)nc12] | (E)-3-(2-(4-(5-(trifluoromethyl)thiazole-2-carbonyl)phenyl)-5H-pyrrolo[2,3-b]pyrazin-7-yl)acrylamide | NC(/C=C/C1=CNC2=NC=C(C3=CC=C(C(C4=NC=C(C(F)(F)F)S4)=O)C=C3)N=C21)=O |
| 559 | 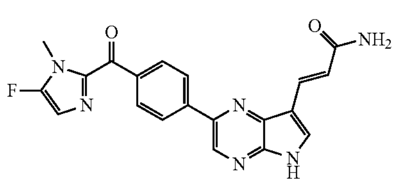 | (E)-3-(2-(4-(5-fluoro-1-methyl-1H-imidazole-2-carbonyl)phenyl)-5H-pyrrolo[2,3-b]pyrazin-7-yl)acrylamide | NC(/C=C/C1=CNC2=NC=C(C3=CC=C(C(C4=NC=C(F)N4C)=O)C=C3)N=C21)=O |
| 560 | 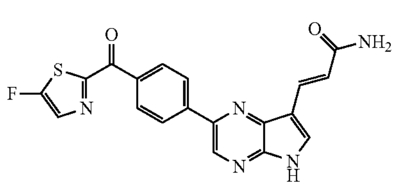 [SMILES: NC(=O)/C=C/c1c[nH]c2ncc(-c3ccc(C(=O)c4ncc(F)s4)cc3)nc12] | (E)-3-(2-(4-(5-fluorothiazole-2-carbonyl)phenyl)-5H-pyrrolo[2,3-b]pyrazin-7-yl)acrylamide | NC(/C=C/C1=CNC2=NC=C(C3=CC=C(C(C4=NC=C(F)S4)=O)C=C3)N=C21)=O |

TABLE 2-continued

Additional Examples

| Example | Structure | Name | Smiles |
|---|---|---|---|
| 561 | 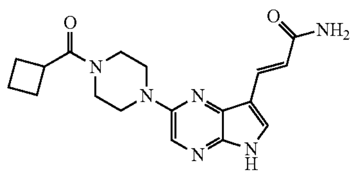 [SMILES: NC(=O)/C=C/c1c[nH]c2ncc(N3CCN(C(=O)C4CCC4)CC3)nc12] | (E)-3-(2-(4-(cyclobutanecarbonyl)piperazin-1-yl)-5H-pyrrolo[2,3-b]pyrazin-7-yl)acrylamide | NC(/C=C/C1=CNC2=NC=C(N3CCN(C(C4CCC4)=O)CC3)N=C21)=O |
| 562 | 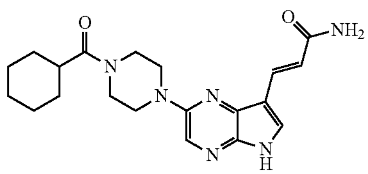 [SMILES: NC(=O)/C=C/c1c[nH]c2ncc(N3CCN(C(=O)C4CCCCC4)CC3)nc12] | (E)-3-(2-(4-(cyclohexanecarbonyl)piperazin-1-yl)-5H-pyrrolo[2,3-b]pyrazin-7-yl)acrylamide | NC(/C=C/C1=CNC2=NC=C(N3CCN(C(C4CCCCC4)=O)CC3)N=C21)=O |
| 563 | 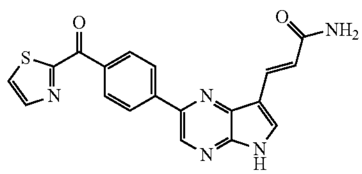 | (E)-3-(2-(4-(thiazole-2-carbonyl)phenyl)-5H-pyrrolo[2,3-b]pyrazin-7-yl)acrylamide | NC(/C=C/C1=CNC2=NC=C(C3=CC=C(C(C4=NC=CS4)=O)C=C3)N=C21)=O |
| 564 | 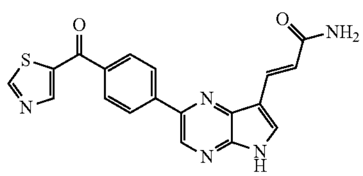 [SMILES: NC(=O)/C=C/c1c[nH]c2ncc(-c3ccc(C(=O)c4cncs4)cc3)nc12] | (E)-3-(2-(4-(thiazole-5-carbonyl)phenyl)-5H-pyrrolo[2,3-b]pyrazin-7-yl)acrylamide | NC(/C=C/C1=CNC2=NC=C(C3=CC=C(C(C4=CN=CS4)=O)C=C3)N=C21)=O |
| 565 | 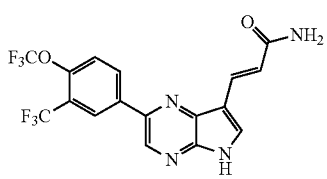 [SMILES: NC(=O)/C=C/c1c[nH]c2ncc(-c3ccc(OC(F)(F)F)c(C(F)(F)F)c3)nc12] | (E)-3-(2-(4-(trifluoromethoxy)-3-(trifluoromethyl)phenyl)-5H-pyrrolo[2,3-b]pyrazin-7-yl)acrylamide | NC(/C=C/C1=CNC2=NC=C(C3=CC=C(OC(F)(F)F)C(C(F)(F)F)=C3)N=C21)=O |
| 566 | 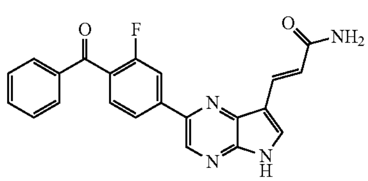 [SMILES: NC(=O)/C=C/c1c[nH]c2ncc(-c3ccc(C(=O)c4ccccc4)c(F)c3)nc12] | (E)-3-(2-(4-benzoyl-3-fluorophenyl)-5H-pyrrolo[2,3-b]pyrazin-7-yl)acrylamide | NC(/C=C/C1=CNC2=NC=C(C3=CC(F)=C(C(C4=CC=CC=C4)=O)C=C3)N=C21)=O |
| 567 | 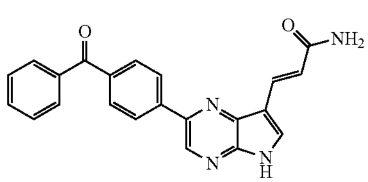 [SMILES: NC(=O)/C=C/c1c[nH]c2ncc(-c3ccc(C(=O)c4ccccc4)cc3)nc12] | (E)-3-(2-(4-benzoylphenyl)-5H-pyrrolo[2,3-b]pyrazin-7-yl)acrylamide | NC(/C=C/C1=CNC2=NC=C(C3=CC=C(C(C4=CC=CC=C4)=O)C=C3)N=C21)=O |
| 568 | 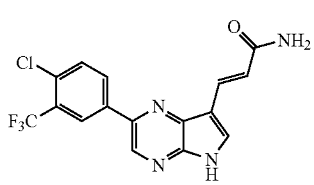 [SMILES: NC(=O)/C=C/c1c[nH]c2ncc(-c3ccc(Cl)c(C(F)(F)F)c3)nc12] | (E)-3-(2-(4-chloro-3-(trifluoromethyl)phenyl)-5H-pyrrolo[2,3-b]pyrazin-7-yl)acrylamide | NC(/C=C/C1=CNC2=NC=C(C3=CC=C(Cl)C(C(F)(F)F)=C3)N=C21)=O |

TABLE 2-continued

Additional Examples

| Example | Structure | Name | Smiles |
|---|---|---|---|
| 569 | 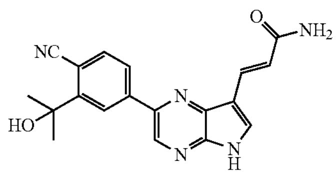 [SMILES: CC(C)(O)c1cc(-c2cnc3[nH]cc(/C=C/C(N)=O)c3n2)ccc1C#N] | (E)3-(2-(4-cyano-3-(2-hydroxypropan-2-yl)phenyl)-5H-pyrrolo[2,3-b]pyrazin-7-yl)acrylamide | NC(/C=C/C1=CNC2=NC=C(C3=CC=C(C#N)C(C(C)(O)C)=C3)N=C21)=O |
| 570 | 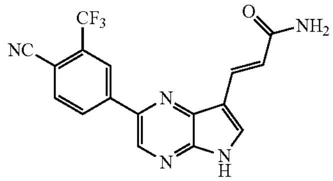 [SMILES: N#Cc1ccc(-c2cnc3[nH]cc(/C=C/C(N)=O)c3n2)cc1C(F)(F)F] | (E)-3-(2-(4-cyano-3-(trifluoromethyl)phenyl)-5H-pyrrolo[2,3-b]pyrazin-7-yl)acrylamide | NC(/C=C/C1=CNC2=NC=C(C3=CC(C(F)(F)F)=C(C#N)C=C3)N=C21)=O |
| 571 | 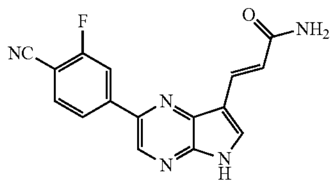 [SMILES: N#Cc1ccc(-c2cnc3[nH]cc(/C=C/C(N)=O)c3n2)cc1F] | (E)-3-(2-(4-cyano-3-fluorophenyl)-5H-pyrrolo[2,3-b]pyrazin-7-yl)acrylamide | NC(/C=C/C1=CNC2=NC=C(C3=CC(F)=C(C#N)C=C3)N=C21)=O |
| 572 | 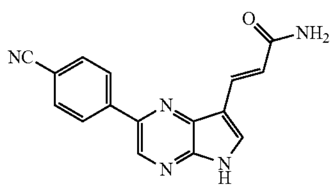 [SMILES: N#Cc1ccc(-c2cnc3[nH]cc(/C=C/C(N)=O)c3n2)cc1] | (E)-3-(2-(4-cyanophenyl)-5H-pyrrolo[2,3-b]pyrazin-7-yl)acrylamide | NC(/C=C/C1=CNC2=NC=C(C3=CC=C(C#N)C=C3)N=C21)=O |
| 573 | 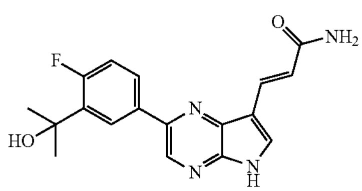 [SMILES: CC(C)(O)c1cc(-c2cnc3[nH]cc(/C=C/C(N)=O)c3n2)ccc1F] | (E)-3-(2-(4-fluoro-3-(2-hydroxypropan-2-yl)phenyl)-5H-pyrrolo[2,3-b]pyrazin-7-yl)acrylamide | NC(/C=C/C1=CNC2=NC=C(C3=CC=C(F)C(C(C)(O)C)=C3)N=C21)=O |
| 574 | 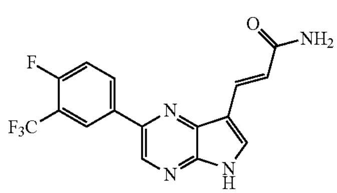 [SMILES: NC(=O)/C=C/c1c[nH]c2ncc(-c3ccc(F)c(C(F)(F)F)c3)nc12] | (E)-3-(2-(4-fluoro-3-(trifluoromethyl)phenyl)-5H-pyrrolo[2,3-b]pyrazin-7-yl)acrylamide | NC(/C=C/C1=CNC2=NC=C(C3=CC=C(F)C(C(F)(F)F)=C3)N=C21)=O |
| 575 | 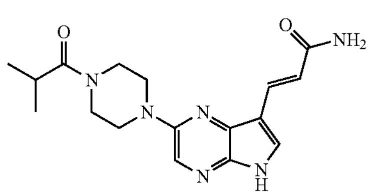 [SMILES: CC(C)C(=O)N1CCN(c2cnc3[nH]cc(/C=C/C(N)=O)c3n2)CC1] | (E)-3-(2-(4-isobutyrylpiperazin-1-yl)-5H-pyirolo[2,3-b]pyrazin-7-yl)acrylamide | NC(/C=C/C1=CNC2=NC=C(N3CCN(C(C(C)C)=O)CC3)N=C21)=O |
| 576 | 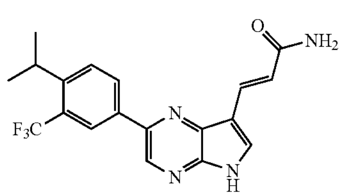 [SMILES: CC(C)c1ccc(-c2cnc3[nH]cc(/C=C/C(N)=O)c3n2)cc1C(F)(F)F] | (E)-3-(2-(4-isopropyl-3-(trifluoromethyl)phenyl)-5H-pyrrolo[2,3-b]pyrazin-7-yl)acrylamide | NC(/C=C/C1=CNC2=NC=C(C3=CC=C(C(C)C)C(C(F)(F)F)=C3)N=C21)=O |

TABLE 2-continued

Additional Examples

| Example | Name | Smiles |
|---|---|---|
| 577 | (E)-3-(2-(4-methylquinolin-3-yl)-5H-pyrrolo[2,3-b]pyrazin-7-y])acrylamide | NC(/C=C/C1=CNC2=NC=C(C3=C(C)C(C=CC=C4)=C4N=C3)N=C21)=O |
| 578 | (E)-3-(2-(4-pivaloylpiperazin-1-yl)-5H-pyrrolo[2,3-b]pyrazin-7-yl)acrylamide | NC(/C=C/C1=CNC2=NC=C(N3CCN(C(C(C)(C)C)=O)CC3)N=C21)=O |
| 579 | (E)-3-(2-(5-chloro-6-cyanopyridin-3-yl)-5H-pyrrolo[2,3-b]pyrazin-7-yl)acrylamide | NC(/C=C/C1=CNC2=NC=C(C3=CC(Cl)=C(C#N)N=C3)N=C21)=O |
| 580 | (E)-3-(2-(5-fluoro-1-(2-methoxyethyl)-6-oxo-1,6-dihydropyridin-3-yl)-5H-pyrrolo[2,3-b]pyrazin-7-yl)acrylamide | NC(/C=C/C1=CNC2=NC=C(C(C=C3F)=CN(CCOC)C3=O)N=C21)=O |
| 581 | (E)-3-(2-(5-fluoro-1-isobutyl-6-oxo-1,6-dihydropyridin-3-yl)-5H-pyrrolo[2,3-b]pyrazin-7-yl)acrylamide | NC(/C=C/C1=CNC2=NC=C(C(C=C3F)=CN(CC(C)C)C3=O)N=C21)=O |
| 582 | (E)-3-(2-(5-fluoro-1-methyl-6-oxo-1,6-dihydropyridin-3-yl)-5H-pyrrolo[2,3-b]pyrazin-7-yl)acrylamide | NC(/C=C/C1=CNC2=NC=C(C(C=C3F)=CN(C)C3=O)N=C21)=O |
| 583 | (E)-3-(2-(5-fluoro-1-neopentyl-6-oxo-1,6-dihydropyridin-3-yl)-5H-pyrrolo[2,3-b]pyrazin-7-yl)acrylamide | NC(/C=C/C1=CNC2=NC=C(C(C=C3F)=CN(CC(C)(C)C)C3=O)N=C21)=O |
| 584 | (E)-3-(2-(5-fluoro-6-(2-(2,2,2-trifluoroethoxy)ethoxy)pyridin-3-yl)-5H-pyrrolo[2,3-b]pyrazin-7-yl)acrylamide | NC(/C=C/C1=CNC2=NC=C(C3=CC(F)=C(OCCOCC(F)(F)F)N=C3)N=C21)=O |

TABLE 2-continued

Additional Examples

| Example | Structure | Name | Smiles |
|---|---|---|---|
| 585 | 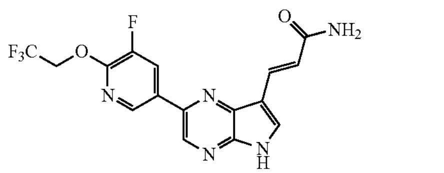 [SMILES: NC(=O)/C=C/c1c[nH]c2ncc(-c3cnc(OCC(F)(F)F)c(F)c3)nc12] | (E)-3-(2-(5-fluoro-6-(2,2,2-trifluoroethoxy)pyridin-3-yl)-5H-pyrrolo[2,3-b]pyrazin-7-yl)acrylamide | NC(/C=C/C1=CNC2=NC=C(C3=CC(F)=C(OCC(F)(F)F)N=C3)N=C21)=O |
| 586 | 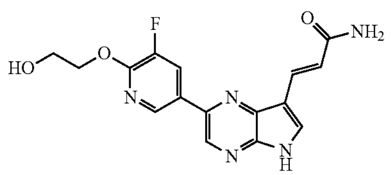 | (E)-3-(2-(5-fluoro-6-(2-hydroxyethoxy)pyridin-3-yl)-5H-pyrrolo[2,3-b]pyrazin-7-yl)acrylamide | NC(/C=C/C1=CNC2=NC=C(C3=CC(F)=C(OCCO)N=C3)N=C21)=O |
| 587 | 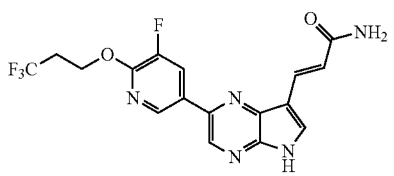 [SMILES: NC(=O)/C=C/c1c[nH]c2ncc(-c3cnc(OCCO)c(F)c3)nc12] | (E)-3-(2-(5-fluoro-6-(3,3,3-trifluoropropoxy)pyridin-3-yl)-5H-pyrrolo[2,3-b]pyrazin-7-yl)acrylamide | NC(/C=C/C1=CNC2=NC=C(C3=CC(F)=C(OCCC(F)(F)F)N=C3)N=C21)=O |
| 588 | 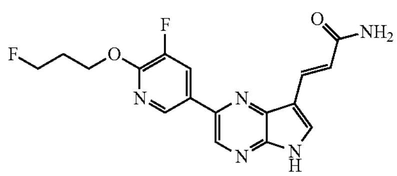 [SMILES: NC(=O)/C=C/c1c[nH]c2ncc(-c3cnc(OCCCF)c(F)c3)nc12] | (E)-3-(2-(5-fluoro-6-(3-fluoropropoxy)pyridin-3-yl)-5H-pyrrolo[2,3-b]pyrazin-7-yl)acrylamide | NC(/C=C/C1=CNC2=NC=C(C3=CC(F)=C(OCCCF)N=C3)N=C21)=O |
| 589 | 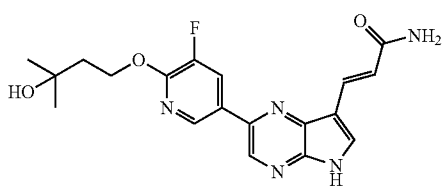 [SMILES: CC(C)(O)CCOc1ncc(-c2cnc3[nH]cc(/C=C/C(N)=O)c3n2)cc1F] | (E)-3-(2-(5-fluoro-6-(3-hydroxy-3-methylbutoxy)pyridin-3-yl)-5H-pyrrolo[2,3-b]pyrazin-7-yl)acrylamide | NC(/C=C/C1=CNC2=NC=C(C3=CC(F)=C(OCCC(C)(O)C)N=C3)N=C21)=O |
| 590 | 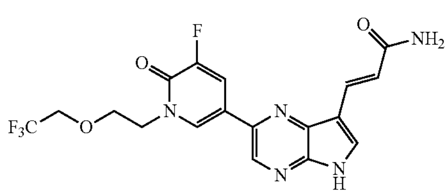 [SMILES: NC(=O)/C=C/c1c[nH]c2ncc(-c3cc(F)c(=O)n(CCOCC(F)(F)F)c3)nc12] | (E)-3-(2-(5-fluoro-6-oxo-1-(2-(2,2,2-trifluoroethoxy)ethyl)-1,6-dihydropyridin-3-yl)-5H-pyrrolo[2,3-b]pyrazin-7-yl)acrylamide | NC(/C=C/C1=CNC2=NC=C(C(C=C3F)=CN(CCOCC(F)(F)F)C3=O)N=C21)=O |
| 591 | 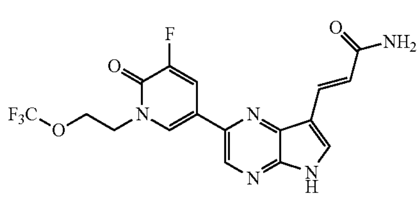 [SMILES: NC(=O)/C=C/c1c[nH]c2ncc(-c3cc(F)c(=O)n(CCOC(F)(F)F)c3)nc12] | (E)-3-(2-(5-fluoro-6-oxo-1-(2-(trifluoromethoxy)ethyl)-1,6-dihydropyridin-3-yl)-5H-pyrrolo[2,3-b]pyrazin-7-yl)acrylamide | NC(/C=C/C1=CNC2=NC=C(C(C=C3F)=CN(CCOC(F)(F)F)C3=O)N=C21)=O |
| 592 | 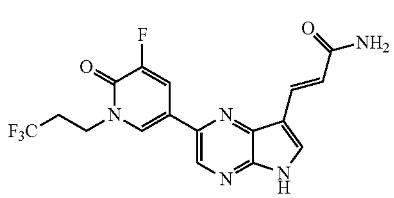 [SMILES: NC(=O)/C=C/c1c[nH]c2ncc(-c3cc(F)c(=O)n(CCC(F)(F)F)c3)nc12] | E)-3-(2-(5-fluoro-6-oxo-1-(3,3,3-trifluoropropyl)-1,6-dihydropyridin-3-yl)-5H-pyrrolo[2,3-b]pyrazin-7-yl)acrylamide | NC(/C=C/C1=CNC2=NC=C(C(C=C3F)=CN(CCC(F)(F)F)C3=O)N=C21)=O |

TABLE 2-continued

Additional Examples

| Example | Structure | Name | Smiles |
|---|---|---|---|
| 593 | 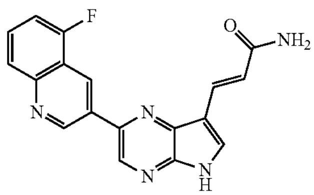 [SMILES: NC(=O)/C=C/c1c[nH]c2ncc(-c3cnc4cccc(F)c4c3)nc12] | (E)-3-(2-(5-fluoroquinolin-3-yl)-5H-pyrrolo[2,3-b]pyrazin-7-yl)acrylamide | NC(/C=C/C1=CNC2=NC=C(C3=CC(C(F)=CC=C4)=C4N=C3)N=C21)=O |
| 594 | 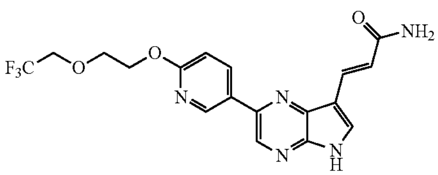 [SMILES: NC(=O)/C=C/c1c[nH]c2ncc(-c3ccc(OCCOCC(F)(F)F)nc3)nc12] | (E)-3-(2-(6-(2-(2,2,2-trifluoroethoxy)ethoxy)pyridin-3-yl)-5H-pyrrolo[2,3-b]pyrazin-7-yl)acrylamide | NC(/C=C/C1=CNC2=NC=C(C3=CC=C(OCCOCC(F)(F)F)N=C3)N=C21)=O |
| 595 | 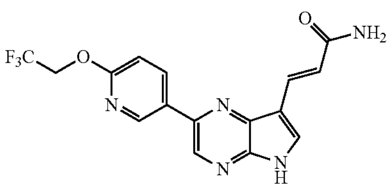 [SMILES: NC(=O)/C=C/c1c[nH]c2ncc(-c3ccc(OCC(F)(F)F)nc3)nc12] | (E)-3-(2-(6-(2,2,2-trifluoroethoxy)pyridin-3-yl)-5H-pyrrolo[2,3-b]pyrazin-7-yl)acrylamide | NC(/C=C/C1=CNC2=NC=C(C3=CC=C(OCC(F)(F)F)N=C3)N=C21)=O |
| 596 | 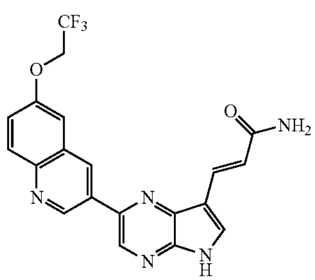 [SMILES: NC(=O)/C=C/c1c[nH]c2ncc(-c3cnc4ccc(OCC(F)(F)F)cc4c3)nc12] | (E)-3-(2-(6-(2,2,2-trifluoroethoxy)quinolin-3-yl)-5H-pyrrolo[2,3-b]pyrazin-7-yl)acrylamide | NC(/C=C/C1=CNC2=NC=C(C3=CC(C=C(OCC(F)(F)F)C=C4)=C4N=C3)N=C21)=O |
| 597 | 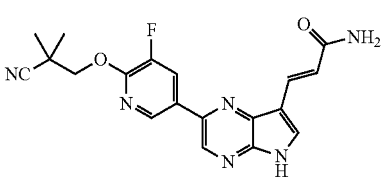 [SMILES: CC(C)(C#N)COc1ncc(-c2cnc3[nH]cc(/C=C/C(N)=O)c3n2)cc1F] | (E)-3-(2-(6-(2-cyano-2-methylpropoxy)-5-fluoropyridin-3-yl)-5H-pyrrolo[2,3-b]pyrazin-7-yl)acrylamide | NC(/C=C/C1=CNC2=NC=C(C3=CC(F)=C(OCC(C)(C)C#N)N=C3)N=C21)=O |
| 598 | 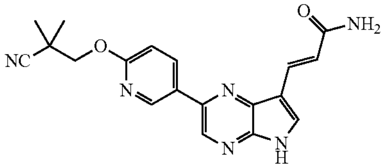 [SMILES: CC(C)(C#N)COc1ccc(-c2cnc3[nH]cc(/C=C/C(N)=O)c3n2)cn1] | (E)-3-(2-(6-(2-cyano-2-methylpropoxy)pyridin-3-yl)-5H-pyrrolo[2,3-b]pyrazin-7-yl)acrylamide | NC(/C=C/C1=CNC2=NC=C(C3=CC=C(OCC(C)(C)C#N)N=C3)N=C21)=O |
| 599 | 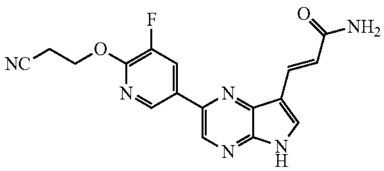 [SMILES: N#CCCOc1ncc(-c2cnc3[nH]cc(/C=C/C(N)=O)c3n2)cc1F] | (E)-3-(2-(6-(2-cyanoethoxy)-5-fluoropyridin-3-yl)-5H-pyrrolo[2,3-b]pyrazin-7-yl)acrylamide | NC(/C=C/C1=CNC2=NC=C(C3=CC(F)=C(OCCC#N)N=C3)N=C21)=O |

TABLE 2-continued

Additional Examples

| Example | Structure | Name | Smiles |
|---|---|---|---|
| 600 | 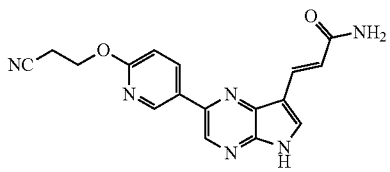 [SMILES: N#CCCOc1ccc(-c2cnc3[nH]cc(/C=C/C(N)=O)c3n2)cn1] | (E)-3-(2-(6-(2-cyanoethoxy)pyridin-3-yl)-5H-pyrrolo[2,3-b]pyrazin-7-yl)acrylamide | NC(/C=C/C1=CNC2=NC=C(C3=CC=C(OCCC#N)N=C3)N=C21)=O |
| 601 | 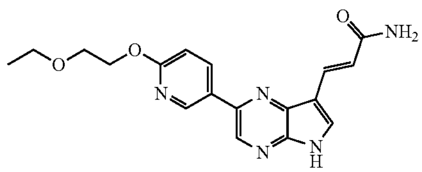 [SMILES: CCOCCOc1ccc(-c2cnc3[nH]cc(/C=C/C(N)=O)c3n2)cn1] | (E)-3-(2-(6-(2-ethoxyethoxy)pyridin-3-yl)-5H-pyrrolo[2,3-b]pyrazin-7-yl)acrylamide | NC(/C=C/C1=CNC2=NC=C(C3=CC=C(OCCOCC)N=C3)N=C21)=O |
| 602 | 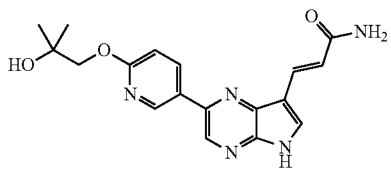 | (E)-3-(2-(6-(2-hydroxy-2-methylpropoxy)pyridin-3-yl)-5H-pyrrolo[2,3-b]pyrazin-7-yl)acrylamide | NC(/C=C/C1=CNC2=NC=C(C3=CC=C(OCC(C)(C)O)N=C3)N=C21)=O |
| 603 | 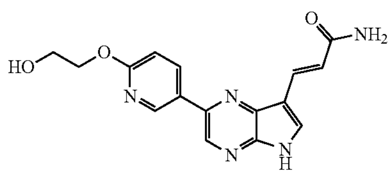 | (E)-3-(2-(6-(2-hydroxyethoxy)pyridin-3-yl)-5H-pyrrolo[2,3-b]pyrazin-7-yl)acrylamide | NC(/C=C/C1=CNC2=NC=C(C3=CC=C(OCCO)N=C3)N=C21)=O |
| 604 | 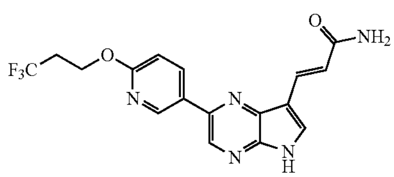 [SMILES: NC(=O)/C=C/c1c[nH]c2ncc(-c3ccc(OCCC(F)(F)F)nc3)nc12] | (E)-3-(2-(6-(3,3,3-trifluoropropoxy)pyridin-3-yl)-5H-pyrrolo[2,3-b]pyrazin-7-yl)acrylamide | NC(/C=C/C1=CNC2=NC=C(C3=CC=C(OCCC(F)(F)F)N=C3)N=C21)=O |
| 605 | 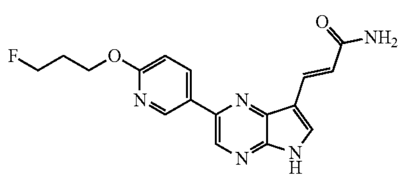 [SMILES: NC(=O)/C=C/c1c[nH]c2ncc(-c3ccc(OCCCF)nc3)nc12] | (E)-3-(2-(6-(3-fluoropropoxy)pyridin-3-yl)-5H-pyrrolo[2,3-b]pyrazin-7-yl)acrylamide | NC(/C=C/C1=CNC2=NC=C(C3=CC=C(OCCCF)N=C3)N=C21)=O |
| 606 | 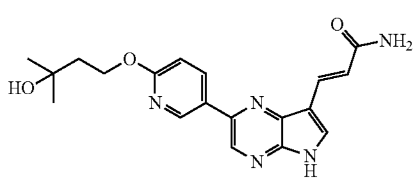 [SMILES: CC(C)(O)CCOc1ccc(-c2cnc3[nH]cc(/C=C/C(N)=O)c3n2)cn1] | (E)-3-(2-(6-(3-hydroxy-3-methylbutoxy)pyridin-3-yl)-5H-pyrrolo[2,3-b]pyrazin-7-yl)acrylamide | NC(/C=C/C1=CNC2=NC=C(C3=CC=C(OCCC(C)(=)C)N=C3)N=C21)=O |
| 607 | 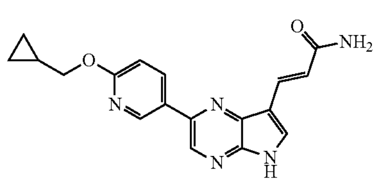 [SMILES: NC(=O)/C=C/c1c[nH]c2ncc(-c3ccc(OCC4CC4)nc3)nc12] | (E)-3-(2-(6-(cyclopropylmethoxy)pyridin-3-yl)-5H-pyrrolo[2,3-b]pyrazin-7-yl)acrylamide | NC(/C=C/C1=CNC2=NC=C(C3=CC=C(OCC4CC4)N=C3)N=C21)=O |

TABLE 2-continued

Additional Examples

| Example | Name | Smiles |
|---------|------|--------|
| 608 | (E)-3-(2-(6-(pyrrolidin-1-yl)pyridin-3-yl)-5H-pyrrolo[2,3-b]pyrazin-7-yl)acrylamide | NC(/C=C/C1=CNC2=NC=C(C3=CC=C(N4CCCC4)N=C3)N=C21)=O |
| 609 | (E)-3-(2-(6-(trifluoromethoxy)quinolin-3-yl)-5H-pyrrolo[2,3-b]pyrazin-7-yl)acrylamide | NC(/C=C/C1=CNC2=NC=C(C3=CC=C(OC(F)(F)F)C=C4)=C4N=C3)N=C21)=O |
| 610 | (E)-3-(2-(6-(trifluoromethyl)quinolin-3-yl)-5H-pyrrolo[2,3-b]pyrazin-7-yl)acrylamide | NC(/C=C/C1=CNC2=NC=C(C3=CC=C(C(F)(F)F)C=C4)=C4N=C3)N=C21)=O |
| 611 | (E)-3-(2-(6,7-difluoroquinolin-3-yl)-5H-pyrrolo[2,3-b]pyrazin-7-yl)acrylamide | NC(/C=C/C1=CNC2=NC=C(C3=CC(C=C(F)C(F)=C4)=C4N=C3)N=C21)=O |
| 612 | (E)-3-(2-(6-chloroquinolin-3-yl)-5H-pyrrolo[2,3-b]pyrazin-7-yl)acrylamide | NC(/C=C/C1=CNC2=NC=C(C3=CC=C(C(Cl)C=C4)=C4N=C3)N=C21)=O |
| 613 | (E)-3-(2-(6-cyano-5-(trifluoromethyl)pyridin-3-yl)-5H-pyrrolo[2,3-b]pyrazin-7-yl)acrylamide | NC(/C=C/C1=CNC2=NC=C(C3=CC(C(F)(F)F)=C(C#N)N=C3)N=C21)=O |
| 614 | (E)-3-(2-(6-cyano-5-fluoropyridin-3-yl)-5H-pyrrolo[2,3-b]pyrazin-7-yl)acrylamide | NC(/C=C/C1=CNC2=NC=C(C3=CC(F)=C(C#N)N=C3)N=C21)=O |

TABLE 2-continued

Additional Examples

| Example | Structure | Name | Smiles |
|---|---|---|---|
| 615 | 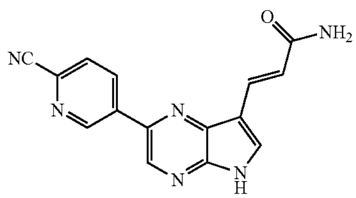 [SMILES: N#Cc1ccc(-c2cnc3[nH]cc(/C=C/C(N)=O)c3n2)cn1] | (E)-3-(2-(6-cyanopyridin-3-yl)-5H-pyrrolo[2,3-b]pyrazin-7-yl)acrylamide | NC(/C=C/C1=CNC2=NC=C(C3=CC=C(C#N)N=C3)N=C21)=O |
| 616 | 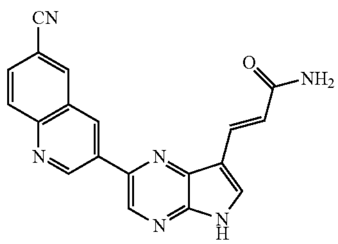 [SMILES: N#Cc1ccc2ncc(-c3cnc4[nH]cc(/C=C/C(N)=O)c4n3)cc2c1] | (E)-3-(2-(6-cyanoquinolin-3-yl)-5H-pyrrolo[2,3-b]pyrazin-7-yl)acrylamide | NC(/C=C/C1=CNC2=NC=C(C3=CC(C=C(C#N)C=C4)=C4N=C3)N=C21)=O |
| 617 | 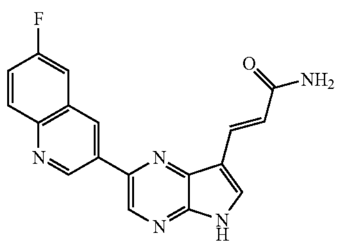 [SMILES: NC(=O)/C=C/c1c[nH]c2ncc(-c3cnc4ccc(F)cc4c3)nc12] | (E)-3-(2-(6-fluoroquinolin-3-yl)-5H-pyrrolo[2,3-b]pyrazin-7-yl)acrylamide | NC(/C=C/C1=CNC2=NC=C(C3=CC(C=C(F)C=C4)=C4N=C3)N=C21)=O |
| 618 | 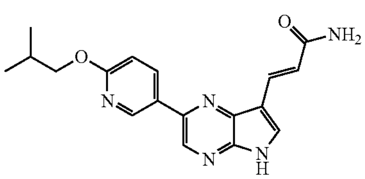 [SMILES: CC(C)COc1ccc(-c2cnc3[nH]cc(/C=C/C(N)=O)c3n2)cn1] | (E)-3-(2-(6-isobutoxypyridin-3-yl)-5H-pyrrolo[2,3-b]pyrazin-7-yl)acrylamide | NC(/C=C/C1=CNC2=NC=C(C3=CC=C(OCC(C)C)N=C3)N=C21)=O |
| 619 | 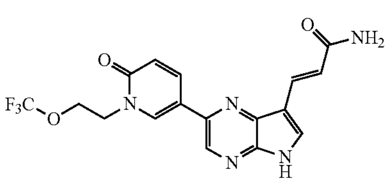 [SMILES: NC(=O)/C=C/c1c[nH]c2ncc(-c3ccc(=O)n(CCOC(F)(F)F)c3)nc12] | (E)-3-(2-(6-oxo-1-(2-(trifluoromethoxy)ethyl)-1,6-dihydropyridin-3-yl)-5H-pyrrolo[2,3-b]pyrazin-7-yl)acrylamide | NC(/C=C/C1=CNC2=NC=C(C(C=C3)=CN(CCOC(F)(F)F)C3=O)N=C21)=O |
| 620 | 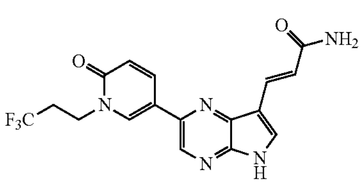 [SMILES: NC(=O)/C=C/c1c[nH]c2ncc(-c3ccc(=O)n(CCC(F)(F)F)c3)nc12] | (E)-3-(2-(6-oxo-1-(3,3,3-trifluoropropyl)-1,6-dihydropyridin-3-yl)-5H-pyrrolo[2,3-H]pyrazin-7-yl)acrylamide | NC(/C=C/C1=CNC2=NC=C(C(C=C3)=CN(CCC(F)(F)F)C3=O)N=C21)=O |
| 621 | 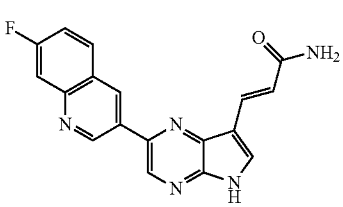 [SMILES: NC(=O)/C=C/c1c[nH]c2ncc(-c3cnc4cc(F)ccc4c3)nc12] | (E)-3-(2-(7-fluoroquinolin-3-yl)-5H-pyrrolo[2,3-b]pyrazin-7-yl)acrylamide | NC(/C=C/C1=CNC2=NC=C(C3=CC(C=CC(F)=C4)=C4N=C3)N=C21)=O |

TABLE 2-continued

Additional Examples

| Example | Structure | Name | Smiles |
|---|---|---|---|
| 622 | 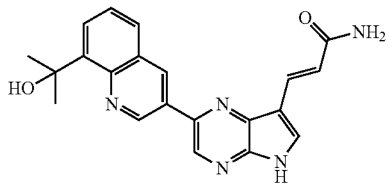 [SMILES: CC(C)(O)c1cccc2cc(-c3cnc4[nH]cc(/C=C/C(N)=O)c4n3)cnc12] | (E)-3-(2-(8-(2-hydroxypropan-2-yl)quinolin-3-yl)-5H-pyrrolo[2,3-b]pyrazin-7-yl)acrylamide | NC(/C=C/C1=CNC2=NC=C(C3=CC(C=CC=C4C(C)(O)C)=C4N=C3)N=C21)=O |
| 623 | 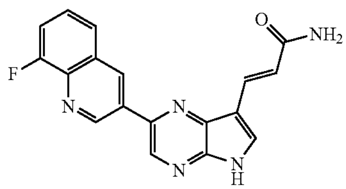 [SMILES: NC(=O)/C=C/c1c[nH]c2ncc(-c3cnc4c(F)cccc4c3)nc12] | (E)-3-(2-(8-fluoroquinolin-3-yl)-5H-pyrrolo[2,3-b]pyrazin-7-yl)acrylamide | NC(/C=C/C1=CNC2=NC=C(C3=CC(C=CC=C4F)=C4N=C3)N=C21)=O |
| 624 | 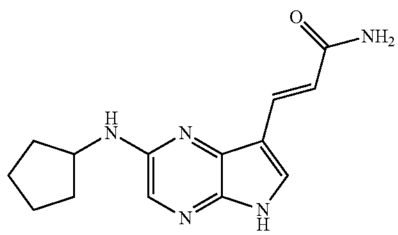 [SMILES: NC(=O)/C=C/c1c[nH]c2ncc(NC3CCCC3)nc12] | (E)-3-(2-(cyclopentylamino)-5H-pyrrolo[2,3-b]pyrazin-7-yl)acrylamide | O=C(N)/C=C/C1=CNC2=NC=C(NC3CCCC3)N=C21 |
| 625 | 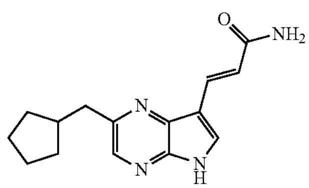 [SMILES: NC(=O)/C=C/c1c[nH]c2ncc(CC3CCCC3)nc12] | (E)-3-(2-(cyclopentylmethyl)-5H-pyrrolo[2,3-b]pyrazin-7-yl)acrylamide | O=C(N)/C=C/C1=CNC2=NC=C(CC3CCCC3)N=C21 |
| 626 | 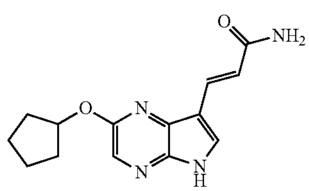 [SMILES: NC(=O)/C=C/c1c[nH]c2ncc(OC3CCCC3)nc12] | (E)-3-(2-(cyclopentyloxy)-5H-pyrrolo[2,3-b]pyrazin-7-yl)acrylamide | O=C(N)/C=C/C1=CNC2=NC=C(OC3CCCC3)N=C21 |
| 627 | 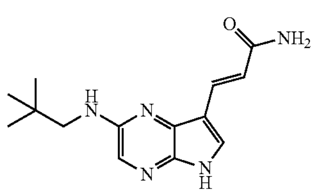 [SMILES: CC(C)(C)CNc1cnc2[nH]cc(/C=C/C(N)=O)c2n1] | (E)-3-(2-(neopentylamino)-5H-pyrrolo[2,3-b]pyrazin-7-yl)acrylamide | O=C(N)/C=C/C1=CNC2=NC=C(NCC(C)(C)C)N=C21 |
| 628 | 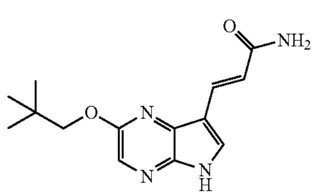 [SMILES: CC(C)(C)COc1cnc2[nH]cc(/C=C/C(N)=O)c2n1] | (E)-3-(2-(neopentyloxy)-5H-pyrrolo[2,3-b]pyrazin-7-yl)acrylamide | O=C(N)/C=C/C1=CNC2=NC=C(OCC(C)(C)C)N=C21 |

TABLE 2-continued

Additional Examples

| Example | Name | Smiles |
|---|---|---|
| 629 | (E)-3-(2-(pyridin-2-yl)-5H-pyrrolo[2,3-b]pyrazin-7-yl)acrylamide | O=C(N)/C=C/C1=CNC2=NC=C(C3=NC=CC=C3)N=C21 |
| 630 | (E)-3-(2-(pyridin-3-yl)-5H-pyrrolo[2,3-b]pyrazin-7-yl)acrylamide | NC(/C=C/C1=CNC2=NC=C(C3=CC=CN=C3)N=C21)=O |
| 631 | (E)-3-(2-(quinolin-3-yl)-5H-pyrrolo[2,3-b]pyrazin-7-yl)acrylamide | NC(/C=C/C1=CNC2=NC=C(C3=CC(C=CC=C4)=C4N=C3)N=C21)=O |
| 632 | (E)-3-(2-benzyl-5H-pyirolo[2,3-b]pyrazin-7-yl)acrylamide | O=C(N)/C=C/C1=CNC2=NC=C(CC3=CC=CC=C3)N=C21 |
| 633 | (E)-3-(2-isopropoxy-5H-pyrrolo[2,3-b]pyrazin-7-yl)acrylamide | O=C(N)/C=C/C1=CNC2=NC=C(OC(C)C)N=C21 |
| 634 | (E)-3-(2-phenoxy-5H-pyrrolo[2,3-b]pyrazin-7-yl)acrylamide | O=C(N)/C=C/C1=CNC2=NC=C(OC3=CC=CC=C3)N=C21 |
| 635 | (E)-3-(3-(3-amino-3-oxoprop-1-en-1-yl)-1H-pyrrolo[2,3-b]pyridin-5-yl)-N,N-dimethylbenzamide | NC(/C=C/C1=CNC2=NC=C(C3=CC=CC(C(N(C)C)=O)=C3)C=C21)=O |
| 636 | (E)-3-(4-((1-hydroxypropan-2-yl)oxy)-1H-pyrrolo[2,3-b]pyridin-3-yl)acrylamide | O=C(N)/C=C/C1=CNC2=NC=CC(OC(CO)C)=C21 |

TABLE 2-continued

Additional Examples

| Example | Structure | Name | Smiles |
|---|---|---|---|
| 637 | 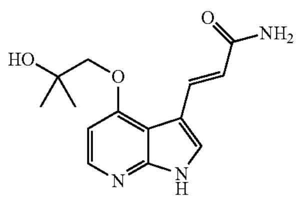 [SMILES: CC(C)(O)COc1ccnc2[nH]cc(/C=C/C(N)=O)c12] | (E)-3-(4-(2-hydroxy-2-methylpropoxy)-1H-pyrrolo[2,3-b]pyridin-3-yl)acrylamide | O=C(N)/C=C/C1=CNC2=NC=CC(OCC(C)(C)O)=C21 |
| 638 | 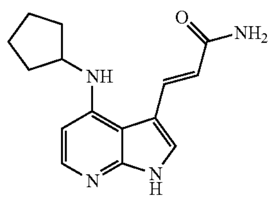 [SMILES: NC(=O)/C=C/c1c[nH]c2nccc(NC3CCCC3)c12] | (E)-3-(4-(cyclopentylamino)-1H-pyrrolo[2,3-b]pyridin-3-yl)acrylamide | O=C(N)/C=C/C1=CNC2=NC=CC(NC3CCCC3)=C21 |
| 639 | 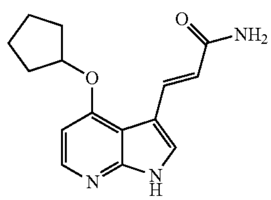 [SMILES: NC(=O)/C=C/c1c[nH]c2nccc(OC3CCCC3)c12] | (E)-3-(4-(cyclopentyloxy)-1H-pyrrolo[2,3-b]pyridin-3-yl)acrylamide | O=C(N)/C=C/C1=CNC2=NC=CC(OC3CCCC3)=C21 |
| 640 | 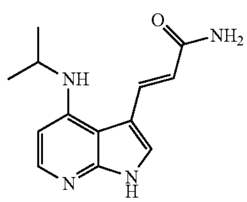 [SMILES: CC(C)Nc1ccnc2[nH]cc(/C=C/C(N)=O)c12] | (E)-3-(4-(isopropylamino)-1H-pyrrolo[2,3-b]pyridin-3-yl)acrylamide | O=C(N)/C=C/C1=CNC2=NC=CC(NC(C)C)=C21 |
| 641 | 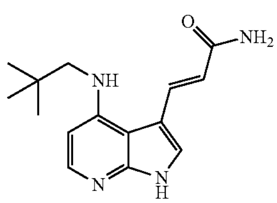 [SMILES: CC(C)(C)CNc1ccnc2[nH]cc(/C=C/C(N)=O)c12] | (E)-3-(4-(neopentylamino)-1H-pyrrolo[2,3-b]pyridin-3-yl)acrylamide | O=C(N)/C=C/C1=CNC2=NC=CC(NCC(C)(C)C)=C21 |
| 642 | 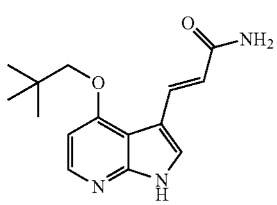 [SMILES: CC(C)(C)COc1ccnc2[nH]cc(/C=C/C(N)=O)c12] | (E)-3-(4-(neopentyloxy)-1H-pyrrolo[2,3-b]pyridin-3-yl)acrylamide | O=C(N)/C=C/C1=CNC2=NC=CC(OCC(C)(C)C)=C21 |
| 643 | 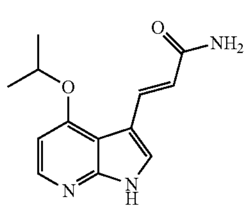 [SMILES: CC(C)Oc1ccnc2[nH]cc(/C=C/C(N)=O)c12] | (E)-3-(4-isopropoxy-1H-pyrrolo[2,3-b]pyridin-3-yl)acrylamide | O=C(N)/C=C/C1=CNC2=NC=CC(OC(C)C)=C21 |

TABLE 2-continued

Additional Examples

| Example | Structure | Name | Smiles |
|---|---|---|---|
| 644 | 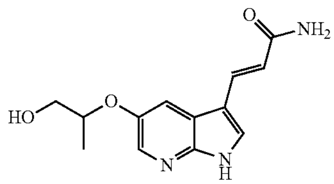 [SMILES: CC(CO)Oc1cnc2[nH]cc(/C=C/C(N)=O)c2c1] | (E)-3-(5-((1-hydroxypropan-2-yl)oxy)-1H-pyrrolo[2,3-b]pyridin-3-yl)acrylamide | O=C(N)/C=C/C1=CNC2=NC=C(OC(C)CO)C=C21 |
| 645 | 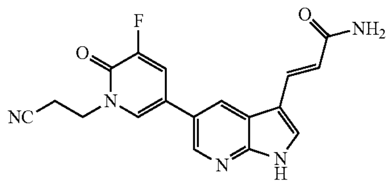 [SMILES: N#CCCn1cc(-c2cnc3[nH]cc(/C=C/C(N)=O)c3c2)cc(F)c1=O] | (E)-3-(5-(1-(2-cyanoethyl)-5-fluoro-6-oxo-1,6-dihydropyridin-3-yl)-1H-pyrrolo[2,3-b]pyridin-3-yl)acrylamide | NC(/C=C/C1=CNC2=NC=C(C(C=C3F)=CN(CCC#N)C3=O)C=C21)=O |
| 646 | 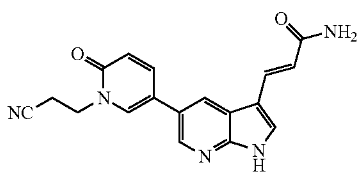 [SMILES: N#CCCn1cc(-c2cnc3[nH]cc(/C=C/C(N)=O)c3c2)ccc1=O] | (E)-3-(5-(1-(2-cyanoethyl)-6-oxo-1,6-dihydropyridin-3-yl)-1H-pyrrolo[2,3-b]pyridin-3-yl)acrylamide | NC(/C=C/C1=CNC2=NC=C(C(C=C3)=CN(CCC#N)C3=O)C=C21)=O |
| 647 | 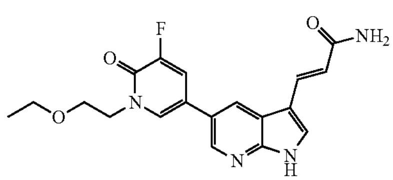 [SMILES: CCOCCn1cc(-c2cnc3[nH]cc(/C=C/C(N)=O)c3c2)cc(F)c1=O] | (E)-3-(5-(1-(2-ethoxyethyl)-5-fluoro-6-oxo-1,6-dihydropyridin-3-yl)-1H-pyrrolo[2,3-b]pyridin-3-yl)acrylamide | NC(/C=C/C1=CNC2=NC=C(C(C=C3F)=CN(CCOCC)C3=O)C=C21)=O |
| 648 | 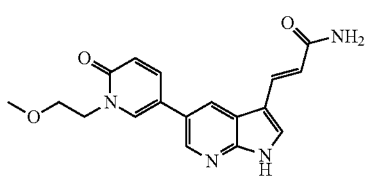 | (E)-3-(5-(1-(2-methoxyethyl)-6-oxo-1,6-dihydropyridin-3-yl)-1H-pyrrolo[2,3-b]pyridin-3-yl)acrylamide | NC(/C=C/C1=CNC2=NC=C(C(C=C3)=CN(CCOC)C3=O)C=C21)=O |
| 649 | 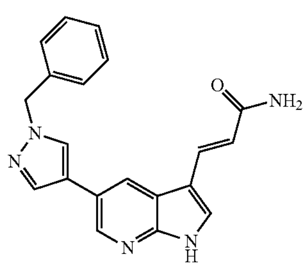 [SMILES: NC(=O)/C=C/c1c[nH]c2ncc(-c3cnn(Cc4ccccc4)c3)cc12] | (E)-3-(5-(1-benzyl-1H-pyrazol-4-yl)-1H-pyrrolo[2,3-b]pyridin-3-yl)acrylamide | O=C(N)/C=C/C1=CNC2=NC=C(C3=CN(CC4=CC=CC=C4)N=C3)C=C21 |
| 650 | 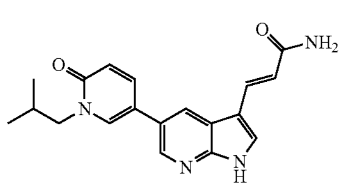 [SMILES: CC(C)Cn1cc(-c2cnc3[nH]cc(/C=C/C(N)=O)c3c2)ccc1=O] | (E)-3-(5-(1-isobutyl-6-oxo-1,6-dihydropyridin-3-yl)-1H-pyrrolo[2,3-b]pyridin-3-yl)acrylamide | NC(/C=C/C1=CNC2=NC=C(C(C=C3)=CN(CC(C)C)C3=O)C=C21)=O |

TABLE 2-continued

Additional Examples

| Example | Structure | Name | Smiles |
|---|---|---|---|
| 651 | 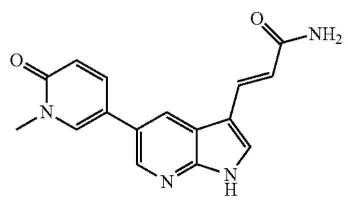 [SMILES: Cn1cc(-c2cnc3[nH]cc(/C=C/C(N)=O)c3c2)ccc1=O] | (E)-3-(5-(1-methyl-6-oxo-1,6-dihydropyridin-3-yl)-1H-pyrrolo[2,3-b]pyridin-3-yl)acrylamide | NC(/C=C/C1=CNC2=NC=C(C(C=C3)=CN(C)C3=O)C=C21)=O |
| 652 | 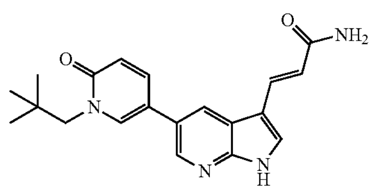 [SMILES: CC(C)(C)Cn1cc(-c2cnc3[nH]cc(/C=C/C(N)=O)c3c2)ccc1=O] | (E)-3-(5-(1-neopentyl-6-oxo-1,6-dihydropyridin-3-yl)-1H-pyrrolo[2,3-b]pyridin-3-yl)acrylamide | NC(/C=C/C1=CNC2=NC=C(C(C=C3)=CN(CC(C)(C)C)C3=O)C=C21)=O |
| 653 | 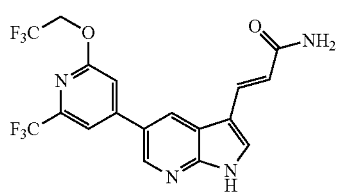 [SMILES: NC(=O)/C=C/c1c[nH]c2ncc(-c3cc(OCC(F)(F)F)nc(C(F)(F)F)c3)cc12] | (E)-3-(5-(2-(2,2,2-trifluoroethoxy)-6-(trifluoromethyl)pyridin-4-yl)-1H-pyrrolo[2,3-b]pyridin-3-yl)acrylamide | NC(/C=C/C1=CNC2=NC=C(C3=CC(OCC(F)(F)F)=NC(C(F)(F)F)=C3)C=C21)=O |
| 654 | 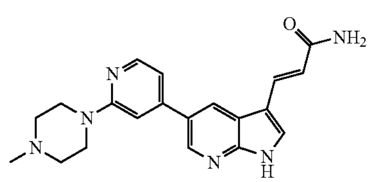 [SMILES: CN1CCN(c2cc(-c3cnc4[nH]cc(/C=C/C(N)=O)c4c3)ccn2)CC1] | (E)-3-(5-(2-(4-methylpiperazin-1-yl)pyridin-4-yl)-1H-pyrrolo[2,3-b]pyridin-3-yl)acrylamide | NC(/C=C/C1=CNC2=NC=C(C3=CC=NC(N4CCN(C)CC4)=C3)C=C21)=O |
| 655 | 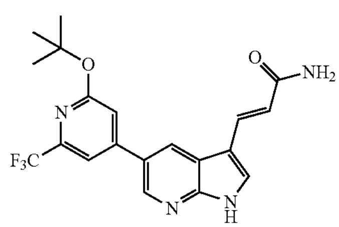 [SMILES: CC(C)(C)Oc1cc(-c2cnc3[nH]cc(/C=C/C(N)=O)c3c2)cc(C(F)(F)F)n1] | (E)-3-(5-(2-(tert-butoxy)-6-(trifluoromethyl)pyridin-4-yl)-1H-pyrrolo[2,3-b]pyridin-3-yl)acrylamide | NC(/C=C/C1=CNC2=NC=C(C3=CC(OC(C)(C)C)=NC(C(F)(F)F)=C3)C=C21)=O |
| 656 | 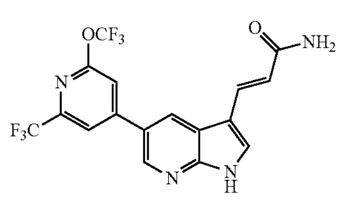 [SMILES: NC(=O)/C=C/c1c[nH]c2ncc(-c3cc(OC(F)(F)F)nc(C(F)(F)F)c3)cc12] | (E)3-(5-(2-(trifluoromethoxy)-6-(trifluoromethyl)pyridin-4-yl)-1H-pyrrolo[2,3-b]pyridin-3-yl)acrylamide | NC(/C=C/C1=CNC2=NC=C(C3=CC(OC(F)(F)F)=NC(C(F)(F)F)=C3)C=C21)=O |
| 657 | 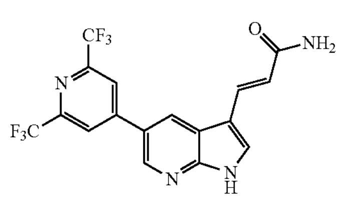 [SMILES: NC(=O)/C=C/c1c[nH]c2ncc(-c3cc(C(F)(F)F)nc(C(F)(F)F)c3)cc12] | (E)-3-(5-(2,6-bis(trifluoromethyl)pyridin-4-yl)-1H-pyrrolo[2,3-b]pyridin-3-yl)acrylamide | NC(/C=C/C1=CNC2=NC=C(C3=CC(C(F)(F)F)=NC(C(F)(F)F)=C3)C=C21)=O |

TABLE 2-continued

Additional Examples

| Example | Structure | Name | Smiles |
|---|---|---|---|
| 658 | 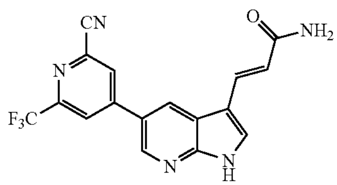 [SMILES: N#Cc1cc(-c2cnc3[nH]cc(/C=C/C(N)=O)c3c2)cc(C(F)(F)F)n1] | (E)-3-(5-(2-cyano-6-(trifluoromethyl)pyridin-4-yl)-1H-pyrrolo[2,3-b]pyridin-3-yl)acrylamide | NC(/C=C/C1=CNC2=NC=C(C3=CC(C#N)=NC(C(F)(F)F)=C3)C=C21)=O |
| 659 | 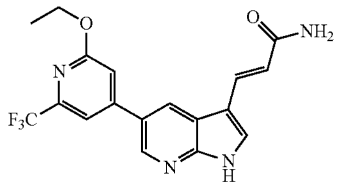 [SMILES: CCOc1cc(-c2cnc3[nH]cc(/C=C/C(N)=O)c3c2)cc(C(F)(F)F)n1] | (E)-3-(5-(2-ethoxy-6-(trifluoromethyl)pyridin-4-yl)-1H-pyrrolo[2,3-b]pyridin-3-yl)acrylamide | NC(/C=C/C1=CNC2=NC=C(C3=CC(OCC)=NC(C(F)(F)F)=C3)C=C21)=O |
| 660 | 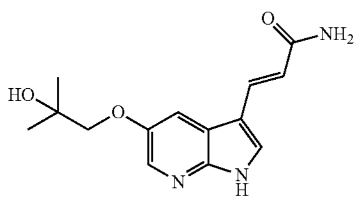 [SMILES: CC(C)(O)COc1cnc2[nH]cc(/C=C/C(N)=O)c2c1] | (E)-3-(5-(2-hydroxy-2-methylpropoxy)-1H-pyrrolo[2,3-b]pyridin-3-yl)acrylamide | O=C(N)/C=C/C1=CNC2=NC=C(OCC(C)(O)C)C=C21 |
| 661 | 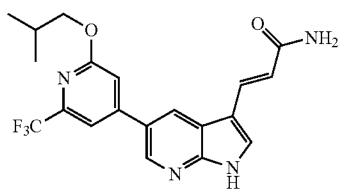 [SMILES: CC(C)COc1cc(-c2cnc3[nH]cc(/C=C/C(N)=O)c3c2)cc(C(F)(F)F)n1] | (E)-3-(5-(2-isobutoxy-6-(trifluoromethyl)pyridin-4-yl)-1H-pyrrolo[2,3-b]pyridin-3-yl)acrylamide | NC(/C=C/C1=CNC2=NC=C(C3=CC(OCC(C)C)=NC(C(F)(F)F)=C3)C=C21)=O |
| 662 | 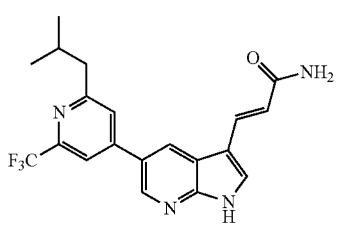 [SMILES: CC(C)Cc1cc(-c2cnc3[nH]cc(/C=C/C(N)=O)c3c2)cc(C(F)(F)F)n1] | (E)-3-(5-(2-isobutyl-6-(trifluoromethyl)pyridin-4-yl)-1H-pyrrolo[2,3-b]pyridin-3-yl)acrylamide | NC(/C=C/C1=CNC2=NC=C(C3=CC(CC(C)C)=NC(C(F)(F)F)=C3)C=C21)=O |
| 663 | 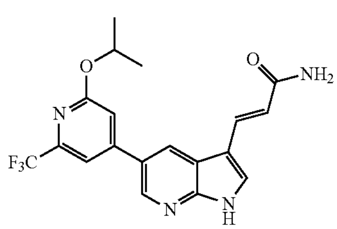 [SMILES: CC(C)Oc1cc(-c2cnc3[nH]cc(/C=C/C(N)=O)c3c2)cc(C(F)(F)F)n1] | (E)-3-(5-(2-isopropoxy-6-(trifluoromethyl)pyridin-4-yl)-1H-pyrrolo[2,3-b]pyridin-3-yl)acrylamide | NC(/C=C/C1=CNC2=NC=C(C3=CC(OC(C)C)=NC(C(F)(F)F)=C3)C#C21)=O |
| 664 | 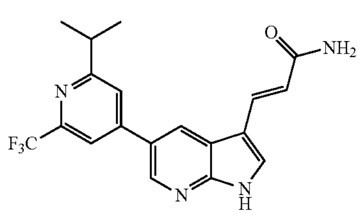 [SMILES: CC(C)c1cc(-c2cnc3[nH]cc(/C=C/C(N)=O)c3c2)cc(C(F)(F)F)n1] | (E)-3-(5-(2-isopropyl-6-(trifluoromethyl)pyridin-4-yl)-1H-pyrrolo[2,3-b]pyridin-3-yl)acrylamide | NC(/C=C/C1=CNC2=NC=C(C3=CC(C(C)C)=NC(C(F)(F)F)=C3)C=C21)=O |

TABLE 2-continued

Additional Examples

| Example | Structure | Name | Smiles |
|---|---|---|---|
| 665 | 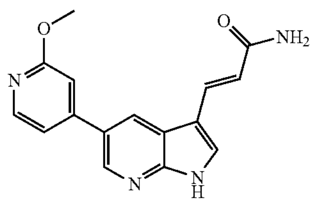 [SMILES: COc1cc(-c2cnc3[nH]cc(/C=C/C(N)=O)c3c2)ccn1] | (E)-3-(5-(2-methoxypyridin-4-yl)-1H-pyrrolo[2,3-b]pyridin-3-yl)acrylamide | NC(/C=C/C1=CNC2=NC=C(C3=CC(OC)=NC=C3)C=C21)=O |
| 666 | 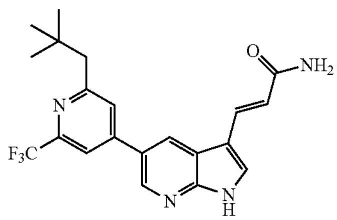 [SMILES: CC(C)(C)Cc1cc(-c2cnc3[nH]cc(/C=C/C(N)=O)c3c2)cc(C(F)(F)F)n1] | (E)-3-(5-(2-neopentyl-6-(trifluoromethyl)pyridin-4-yl)-1H-pyrrolo[2,3-b]pyridin-3-yl)acrylamide | NC(/C=C/C1=CNC2=NC=C(C3=CC(CC(C)(C)C)=NC(C(F)(F)F)=C3)C=C21)=O |
| 667 | 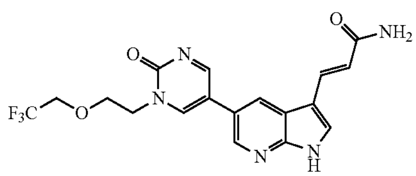 [SMILES: NC(=O)/C=C/c1c[nH]c2ncc(-c3cnc(=O)n(CCOCC(F)(F)F)c3)cc12] | (E)-3-(5-(2-oxo-1-(2-(2,2,2-trifluoroethoxy)ethyl)-1,2-dihydropyrimidin-5-yl)-1H-pyrrolo[2,3-b]pyridin-3-yl)acrylamide | NC(/C=C/C1=CNC2=NC=C(C(C=N3)=CN(CCOCC(F)(F)F)C3=O)C=C21)=O |
| 668 | 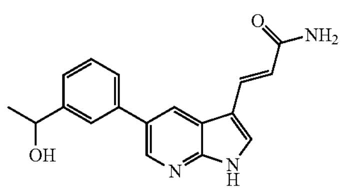 [SMILES: CC(O)c1cccc(-c2cnc3[nH]cc(/C=C/C(N)=O)c3c2)c1] | (E)-3-(5-(3-(1-hydroxyethyl)phenyl)-1H-pyrrolo[2,3-b]pyridin-3-yl)acrylamide | NC(/C=C/C1=CNC2=NC=C(C3=CC=CC(C(O)C)=C3)C=C21)=O |
| 669 | 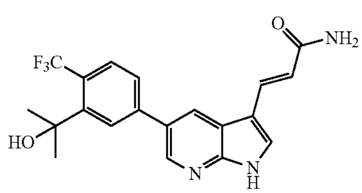 [SMILES: CC(C)(O)c1cc(-c2cnc3[nH]cc(/C=C/C(N)=O)c3c2)ccc1C(F)(F)F] | (E)-3-(5-(3-(2-hydroxypropan-2-yl)-4-(trifluoromethyl)phenyl)-1H-pyrrolo[2,3-b]pyridin-3-yl)acrylamide | NC(/C=C/C1=CNC2=NC=C(C3=CC=C(C(F)(F)F)C(C(C)(O)C)=C3)C=C21)=O |
| 670 | 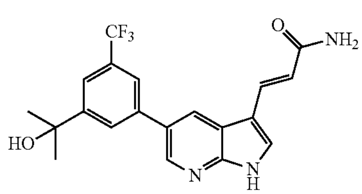 | (E)-3-(5-(3-(2-hydroxypropan-2-yl)-5-(trifluoromethyl)phenyl)-1H-pyrrolo[2,3-b]pyridin-3-yl)acrylamide | NC(/C=C/C1=CNC2=NC=C(C3=CC(C(F)(F)F)=CC(C(C)(O)C)=C3)C=C21)=O |
| 671 | 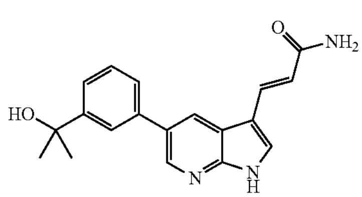 [SMILES: CC(C)(O)c1cccc(-c2cnc3[nH]cc(/C=C/C(N)=O)c3c2)c1] | (E)-3-(5-(3-(2-hydroxypropan-2-yl)phenyl)-1H-pyrrolo[2,3-b]pyridin-3-yl)acrylamide | NC(/C=C/C1=CNC2=NC=C(C3=CC=CC(C(C)(C)O)=C3)C=C21)=O |

TABLE 2-continued

Additional Examples

| Example | Structure | Name | Smiles |
|---|---|---|---|
| 672 | 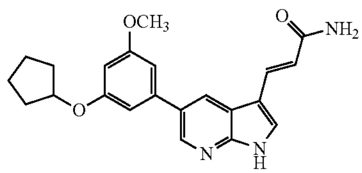 [SMILES: COc1cc(OC2CCCC2)cc(-c2cnc3[nH]cc(/C=C/C(N)=O)c3c2)c1] | (E)-3-(5-(3-(cyclopentyloxy)-5-methoxyphenyl)-1H-pyrrolo[2,3-b]pyridin-3-yl)acrylamide | NC(//C=C/C1=CNC2=NC=C(C3=CC(OC)=CC(OC4CCCC4)=C3)C=C21)=O |
| 673 | 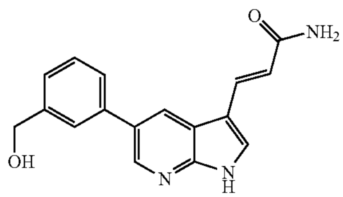 [SMILES: NC(=O)/C=C/c1c[nH]c2ncc(-c3cccc(CO)c3)cc12] | (E)-3-(5-(3-(hydroxymethyl)phenyl)-1H-pyrrolo[2,3-b]pyridin-3-yl)acrylamide | NC(//C=C/C1=CNC2=NC=C(C3=CC=CC(CO)=C3)C=C21)=O |
| 674 | 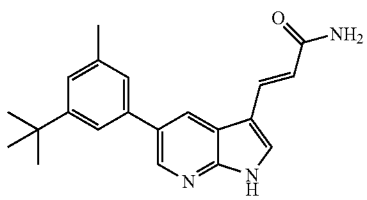 [SMILES: Cc1cc(-c2cnc3[nH]cc(/C=C/C(N)=O)c3c2)cc(C(C)(C)C)c1] | (E)-3-(5-(3-(tert-butyl)-5-methylphenyl)-1H-pyrrolo[2,3-b]pyridin-3-yl)acrylamide | NC(//C=C/C1=CNC2=NC=C(C3=CC(C)=CC(C(C)(C)C)=C3)C=C21)=O |
| 675 | 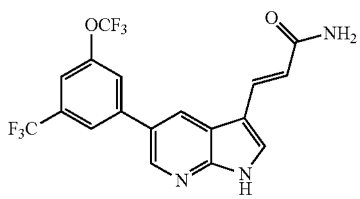 [SMILES: NC(=O)/C=C/c1c[nH]c2ncc(-c3cc(OC(F)(F)F)cc(C(F)(F)F)c3)cc12] | (E)-3-(5-(3-(trifluoromethoxy)-5-(trifluoromethyl)phenyl)-1H-pyrrolo[2,3-b]pyridin-3-yl)acrylamide | NC(//C=C/C1=CNC2=NC=C(C3=CC(OC(F)(F)F)=CC(C(F)(F)F)=C3)C=C21)=O |
| 676 | 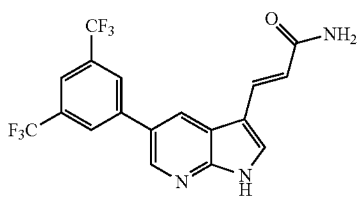 [SMILES: NC(=O)/C=C/c1c[nH]c2ncc(-c3cc(C(F)(F)F)cc(C(F)(F)F)c3)cc12] | (E)-3-(5-(3,5-bis(trifluoromethyl)phenyl)-1H-pyrrolo[2,3-b]pyridin-3-yl)acrylamide | NC(//C=C/C1=CNC2=NC=C(C3=CC(C(F)(F)F)=CC(C(F)(F)F)=C3)C=C21)=O |
| 677 | 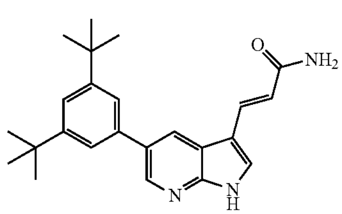 [SMILES: CC(C)(C)c1cc(-c2cnc3[nH]cc(/C=C/C(N)=O)c3c2)cc(C(C)(C)C)c1] | (E)-3-(5-(3,5-di-tert-butylphenyl)-1H-pyrrolo[2,3-b]pyridin-3-yl)acrylamide | NC(//C=C/C1=CNC2=NC=C(C3=CC(C(C)(C)C)=CC(C(C)(C)C)=C3)C=C21)=O |
| 678 | 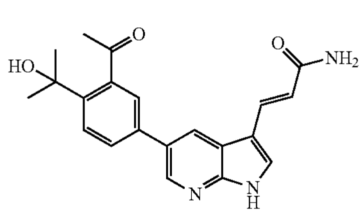 [SMILES: CC(=O)c1cc(-c2cnc3[nH]cc(/C=C/C(N)=O)c3c2)ccc1C(C)(C)O] | (E)-3-(5-(3-acetyl-4-(2-hydroxypropan-2-yl)phenyl)-1H-pyrrolo[2,3-b]pyridin-3-yl)acrylamide | NC(//C=C/C1=CNC2=NC=C(C3=CC(C(C)=O)=C(C(C)(C)O)C)=C3)C=C21)=O |

TABLE 2-continued

Additional Examples

| Example | Structure | Name | Smiles |
|---|---|---|---|
| 679 | 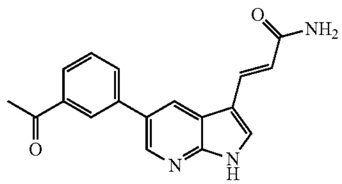 [SMILES: CC(=O)c1cccc(-c2cnc3[nH]cc(/C=C/C(N)=O)c3c2)c1] | (E)-3-(5-(3-acetylphenyl)-1H-pyrrolo[2,3-b]pyridin-3-yl)acrylamide | NC(/C=C/C1=CNC2=NC=C(C3=CC=CC(C(C)=O)=C3)C=C21)=O |
| 680 | 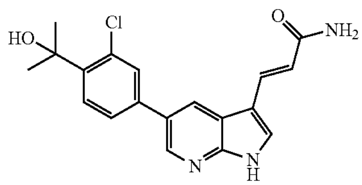 [SMILES: CC(C)(O)c1ccc(-c2cnc3[nH]cc(/C=C/C(N)=O)c3c2)cc1Cl] | (E)-3-(5-(3-chloro-4-(2-hydroxypropan-2-yl)phenyl)-1H-pyrrolo[2,3-b]pyridin-3-yl)acrylamide | NC(/C=C/C1=CNC2=NC=C(C3=CC(Cl)=C(C(C)(O)C)C=C3)C=C21)=O |
| 681 | 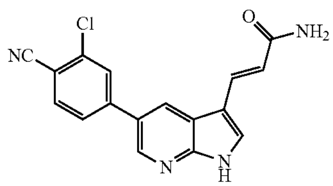 | (E)-3-(5-(3-chloro-4-cyanophenyl)-1H-pyrrolo[2,3-b]pyridin-3-yl)acrylamide | NC(/C=C/C1=CNC2=NC=C(C3=CC(Cl)=C(C#N)C=C3)C=C21)=O |
| 682 | 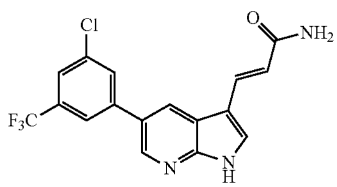 | (E)-3-(5-(3-chloro-5-(trifluoromethyl)phenyl)-1H-pyrrolo[2,3-b]pyridin-3-yl)acrylamide | NC(/C=C/C1=CNC2=NC=C(C3=CC(Cl)=CC(C(F)(F)F)=C3)C=C21)=O |
| 683 | 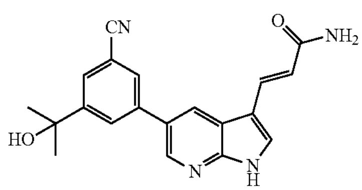 [SMILES: CC(C)(O)c1cc(C#N)cc(-c2cnc3[nH]cc(/C=C/C(N)=O)c3c2)c1] | (E)-3-(5-(3-cyano-5-(2-hydroxypropan-2-yl)phenyl)-1H-pyrrolo[2,3-b]pyridin-3-yl)acrylamide | NC(/C=C/C1=CNC2=NC=C(C3=CC(C#N)=CC(C(C)(O)C)=C3)C=C21)=O |
| 684 | 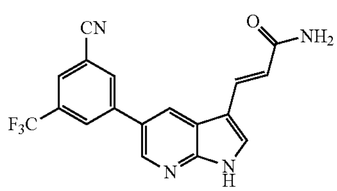 [SMILES: N#Cc1cc(-c2cnc3[nH]cc(/C=C/C(N)=O)c3c2)cc(C(F)(F)F)c1] | (E)-3-(5-(3-cyano-5-(trifluoromethyl)phenyl)-1H-pyrrolo[2,3-b]pyridin-3-yl)acrylamide | NC(/CC/C1=CNC2=NC=C(C3=CC(C#N)=CC(C(F)(F)F)=C3)C=C21)=O |
| 685 | 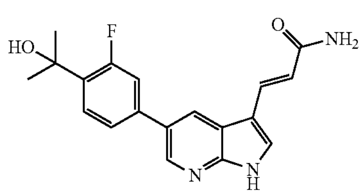 [SMILES: CC(C)(O)c1ccc(-c2cnc3[nH]cc(/C=C/C(N)=O)c3c2)cc1F] | (E)-3-(5-(3-fluoro-4-(2-hydroxypropan-2-yl)phenyl)-1H-pyrrolo[2,3-b]pyridin-3-yl)acrylamide | NC(/C=C/C1=CNC2=NC=C(C3=CC(F)=C(C(C)(O)C)C=C3)C=C21)=O |
| 686 | 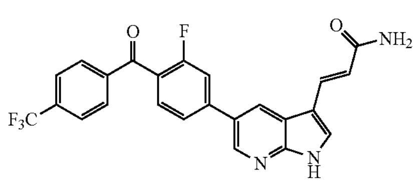 [SMILES: NC(=O)/C=C/c1c[nH]c2ncc(-c3ccc(C(=O)c4ccc(C(F)(F)F)cc4)c(F)c3)cc12] | (E)-3-(5-(3-fluoro-4-(4-(trifluoromethyl)benzoyl)phenyl)-1H-pyrrolo[2,3-b]pyridin-3-yl)acrylamide | NC(/C=C/C1=CNC2=NC=C(C3=CC(F)=C(C(C4=CC=C(C(F)(F)F)C=C4)=O)C=C3)C=C21)=O |

TABLE 2-continued

Additional Examples

| Example | Structure | Name | Smiles |
|---|---|---|---|
| 687 | 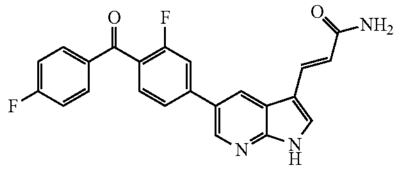 [SMILES: NC(=O)/C=C/c1c[nH]c2ncc(-c3ccc(C(=O)c4ccc(F)cc4)c(F)c3)cc12] | (E)-3-(5-(3-fluoro-4-(4-fluorobenzoyl)phenyl)-1H-pyrrolo[2,3-b]pyridin-3-yl)acrylamide | NC(/C=C/C1=CNC2=NC=C(C3=CC(F)=C(C(C4=CC=C(F)C=C4)=O)C=C3)C=C21)=O |
| 688 | 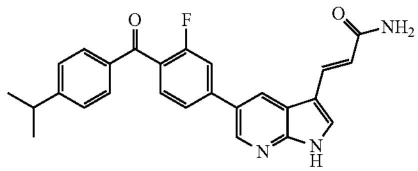 [SMILES: CC(C)c1ccc(C(=O)c2ccc(-c3cnc4[nH]cc(/C=C/C(N)=O)c4c3)cc2F)cc1] | (E)-3-(5-(3-fluoro-4-(4-isopropylbenzoyl)phenyl)-1H-pyrrolo[2,3-b]pyridin-3-yl)acrylamide | NC(/C=C/C1=CNC2=NC=C(C3=CC(F)=C(C(C4=CC=C(C(C)C)C=C4)=O)C=C3)C=C21)=O |
| 689 | 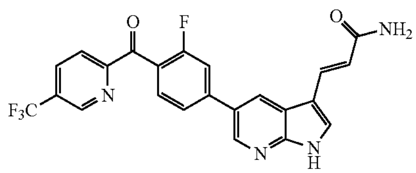 [SMILES: NC(=O)/C=C/c1c[nH]c2ncc(-c3ccc(C(=O)c4ccc(C(F)(F)F)cn4)c(F)c3)cc12] | (E)-3-(5-(3-fluoro-4-(5-(trifluoromethyl)picolinoyl)phenyl)-1H-pyrrolo[2,3-b]pyridin-3-yl)acrylamide | NC(/C=C/C1=CNC2=NC=C(C3=CC(F)=C(C(C4=CC=C(C(F)(F)F)C=N4)=O)C=C3)C=C21)=O |
| 690 | 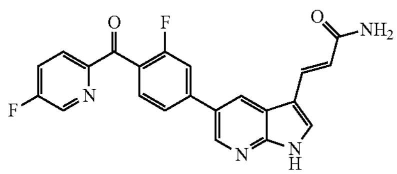 [SMILES: NC(=O)/C=C/c1c[nH]c2ncc(-c3ccc(C(=O)c4ccc(F)cn4)c(F)c3)cc12] | (E)-3-(5-(3-fluoro-4-(5-fluoropicolinoyl)phenyl)-1H-pyrrolo[2,3-b]pyridin-3-yl)acrylamide | NC(/C=C/C1=CNC2=NC=C(C3=CC(F)=C(C(C4=CC=C(F)C=N4)=O)C=C3)C=C21)=O |
| 691 | 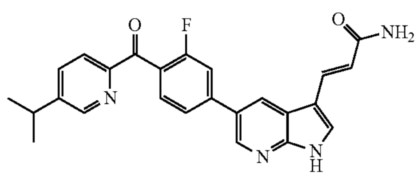 [SMILES: CC(C)c1ccc(C(=O)c2ccc(-c3cnc4[nH]cc(/C=C/C(N)=O)c4c3)cc2F)nc1] | (E)-3-(5-(3-fluoro-4-(5-isopropylpicolinoyl)phenyl)-1H-pyrrolo[2,3-b]pyridin-3-yl)acrylamide | NC(/C=C/C1=CNC2=NC=C(C3=CC(F)=C(C(C4=CC=C(C(C)C)C=N4)=O)C=C3)C=C21)=O |
| 692 | 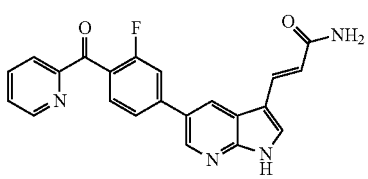 [SMILES: NC(=O)/C=C/c1c[nH]c2ncc(-c3ccc(C(=O)c4ccccn4)c(F)c3)cc12] | (E)-3-(5-(3-fluoro-4-picolinoylphenyl)-1H-pyrrolo[2,3-b]pyridin-3-yl)acrylamide | NC(/C=C/C1=CNC2=NC=C(C3=CC(F)=C(C(C4=CC=CC=N4)=O)C=C3)C=C21)=O |
| 693 | 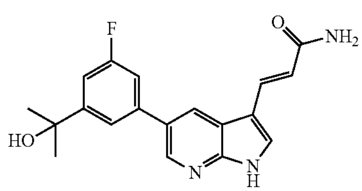 [SMILES: CC(C)(O)c1cc(F)cc(-c2cnc3[nH]cc(/C=C/C(N)=O)c3c2)c1] | (E)-3-(5-(3-fluoro-5-(2-hydroxypropan-2-yl)phenyl)-1H-pyrrolo[2,3-b]pyridin-3-yl)acrylamide | NC(/C=C/C1=CNC2=NC=C(C3=CC(F)=CC(C(C)(O)C)=C3)C=C21)=O |
| 694 | 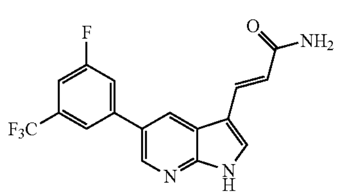 [SMILES: NC(=O)/C=C/c1c[nH]c2ncc(-c3cc(F)cc(C(F)(F)F)c3)cc12] | (E)-3-(5-(3-fluoro-5-(trifluoromethyl)phenyl)-1H-pyrrolo[2,3-b]pyridin-3-yl)acrylamide | NC(/C=C/C1=CNC2=NC=C(C3=CC(F)=CC(C(F)(F)F)=C3)C=C21)=O |

TABLE 2-continued

Additional Examples

| Example | Name | Smiles |
|---|---|---|
| 695 | (E)-3-(5-(3-isopropyl-5-(trifluoromethyl)phenyl)-1H-pyrrolo[2,3-b]pyridin-3-yl)acrylamide | NC(/C=C/C1=CNC2=NC=C(C3=CC(C(C)C)CC(C(F)(F)F)=C3)C=C21)=O |
| 696 | (E)-3-(5-(4-((1r,3r)-3-(trifluoromethyl)cyclobutanecarbonyl)piperazin-1-yl)-1H-pyrrolo[2,3-b]pyridin-3-yl)acrylamide | NC(/C=C/C1=CNC2=NC=C(N3CCN(C([C@@H]4C[C@@H](C(F)(F)F)C4)=O)CC3)C=C21)=O |
| 697 | (E)-3-(5-(4-((1R,3R)-3-(trifluoromethyl)cyclopentanecarbonyl)piperazin-1-yl)-1H-pyrrolo[2,3-b]pyridin-3-yl)acrylamide | NC(/C=C/C1=CNC2=NC=C(N3CCN(C([C@@H]4CC[C@@H](C(F)(F)F)C4)=O)CC3)C=C21)=O |
| 698 | (E)-3-(5-(4-((1r,3r)-3-cyanocyclobutanecarbonyl)piperazin-1-yl)-1H-pyrrolo[2,3-b]pyridin-3-yl)acrylamide | NC(/C=C/C1=CNC2=NC=C(N3CCN(C([C@@H]4C[C@@H](C#N)C4)=O)CC3)C=C21)=O |
| 699 | (E)-3-(5-(4-((1R,3R)-3-cyanocyclopentanecarbonyl)piperazin-1-yl)-1H-pyrrolo[2,3-b]pyridin-3-yl)acrylamide | NC(/C=C/C1=CNC2=NC=C(N3CCN(C([C@@H]4CC[C@@H](C#N)C4)=O)CC3)C=C21)=O |
| 700 | (E)-3-(5-(4-((1R,3R)-3-fluorocyclopentanecarbonyl)piperazin-1-yl)-1H-pyrrolo[2,3-b]pyridin-3-yl)acrylamide | NC(/C=C/C1=CNC2=NC=C(N3CCN(C([C@@H]4CC[C@@H](F)C4)=O)CC3)C=C21)=O |
| 701 | (E)-3-(5-(4-((1R,3S)-3-(trifluoromethyl)cyclopentanecarbonyl)piperazin-1-yl)-1H-pyrrolo[2,3-b]pyridin-3-yl)acrylamide | NC(/C=C/C1=CNC2=NC=C(N3CCN(C([C@@H]4CC[C@H](C(F)(F)F)C4)=O)CC3)C=C21)=O |
| 702 | (E)-3-(5-(4-((1R,3S)-3-cyanocyclopentanecarbonyl)piperazin-1-yl)-1H-pyrrolo[2,3-b]pyridin-3-yl)acrylamide | NC(/C=C/C1=CNC2=NC=C(N3CCN(C([C@@H]4CC[C@H](C#N)C4)=O)CC3)C=C21)=O |

TABLE 2-continued

Additional Examples

| Example | Structure | Name | Smiles |
|---|---|---|---|
| 703 | 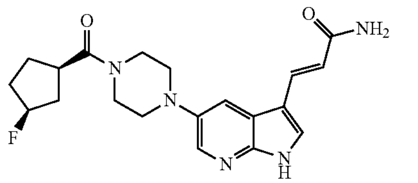 [SMILES: NC(=O)/C=C/c1c[nH]c2ncc(N3CCN(C(=O)[C@@H]4CC[C@H](F)C4)CC3)cc12] | (E)-3-(5-(4-(1R,3S)-3-fluorocyclopentanecarbonyl)piperazin-1-yl)-1H-pyrrolo[2,3-b]pyridin-3-yl)acrylamide | NC(/C=C/C1=CNC2=NC=C(N3CCN(C([C@@H]4CC[C@H](F)C4)=O)CC3)C=C21)=O |
| 704 | 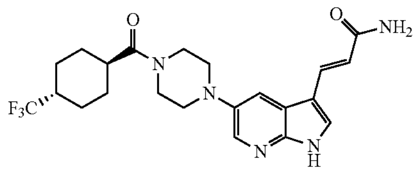 [SMILES: NC(=O)/C=C/c1c[nH]c2ncc(N3CCN(C(=O)[C@H]4CC[C@H](C(F)(F)F)CC4)CC3)cc12] | (E)-3-(5-(4-((1r,4r)-4-(trifluoromethyl)cyclohexane-carbonyl)piperazin-1-yl)-1H-pyrrolo[2,3-b]pyridin-3-yl)acrylamide | NC(/C=C/C1=CNC2=NC=C(N3CCN(C([C@@H]4CC[C@@H](C(F)(F)F)CC4)=O)CC3)C=C21)=O |
| 705 | 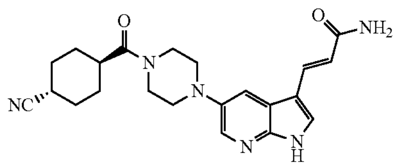 [SMILES: N#C[C@H]1CC[C@H](C(=O)N2CCN(c3cnc4[nH]cc(/C=C/C(N)=O)c4c3)CC2)CC1] | (E)-3-(5-(4-((1r,4r)-4-cyanocyclohexanecarbonyl)piperazin-1-yl)-1H-pyrrolo[2,3-b]pyridin-3-yl)acrylamide | NC(/C=C/C1=CNC2=NC=C(N3CCN(C([C@@H]4CC[C@@H](C#N)CC4)=O)CC3)C=C21)=O |
| 706 | 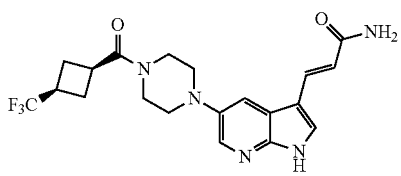 [SMILES: NC(=O)/C=C/c1c[nH]c2ncc(N3CCN(C(=O)[C@H]4C[C@@H](C(F)(F)F)C4)CC3)cc12] | (E)-3-(5-(4-((1s,3s)-3-(trifluoromethyl)cyclobutanecarbonyl)piperazin-1-yl)-1H-pyrrolo[2,3-b]pyridin-3-yl)acrylamide | NC(/C=C/C1=CNC2=NC=C(N3CCN(C([C@@H]4C[C@@H](C(F)(F)F)C4)=O)CC3)C=C21)=O |
| 707 | 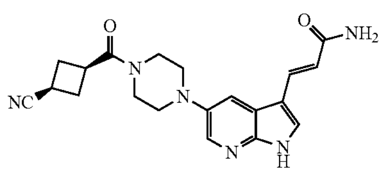 [SMILES: N#C[C@H]1C[C@@H](C(=O)N2CCN(c3cnc4[nH]cc(/C=C/C(N)=O)c4c3)CC2)C1] | (E)-3-(5-(4-((1s,3s)-3-cyanocyclobutanecarbonyl)piperazin-1-yl)-1H-pyrrolo[2,3-b]pyridin-3-yl)acrylamide | NC(/C=C/C1=CNC2=NC=C(N3CCN(C([C@@H]4C[C@@H](CN)#C4)=O)CC3)C=C21)=O |
| 708 | 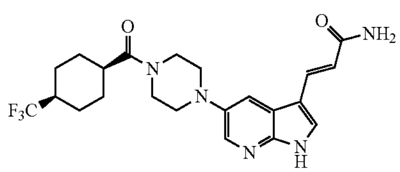 [SMILES: NC(=O)/C=C/c1c[nH]c2ncc(N3CCN(C(=O)[C@H]4CC[C@@H](C(F)(F)F)CC4)CC3)cc12] | (E)-3-(5-(4-((1s,4s)-4-(trifluoromethyl)cyclohexane-carbonyl)piperazin-1-yl)-1H-pyrrolo[2,3-b]pyridin-3-yl)acrylamide | NC(/C=C/C1=CNC2=NC=C(N3CCN(C([C@@H]4CC[C@H](C(F)(F)F)CC4)=O)CC3)C=C21)=O |
| 709 | 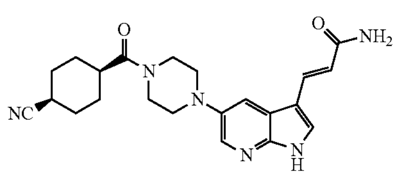 [SMILES: N#C[C@H]1CC[C@@H](C(=O)N2CCN(c3cnc4[nH]cc(/C=C/C(N)=O)c4c3)CC2)CC1] | (E)-3-(5-(4-((1s,4s)-4-cyanocyclohexanecarbonyl)piperazin-1-yl)-1H-pyrrolo[2,3-b]pyridin-3-yl)acrylamide | NC(/C=C/C1=CNC2=NC=C(N3CCN(C([C@@H]4CC[C@H](C#N)CC4)=O)CC3)C=C21)=O |
| 710 | 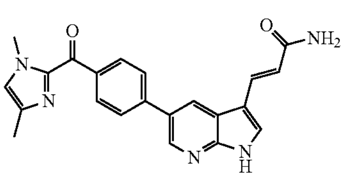 [SMILES: Cc1cn(C)c(C(=O)c2ccc(-c3cnc4[nH]cc(/C=C/C(N)=O)c4c3)cc2)n1] | (E)-3-(5-(4-(1,4-dimethyl-1H-imidazole-2-carbonyl)phenyl)-1H-pyrrolo[2,3-b]pyridin-3-yl)acrylamide | NC(/C=C/C1=CNC2=NC=C(C3=CC=C(C(C4=NC(C)=CN4C)=O)C=C3)C=C21)=O |

TABLE 2-continued

Additional Examples

| Example | Structure | Name | Smiles |
|---------|-----------|------|--------|
| 711 | 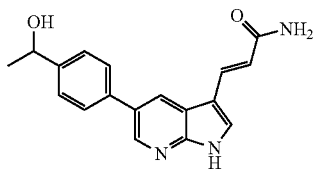 [SMILES: CC(O)c1ccc(-c2cnc3[nH]cc(/C=C/C(N)=O)c3c2)cc1] | (E)-3-(5-(4-(1-hydroxyethyl)phenyl)-1H-pyrrolo[2,3-b]pyridin-3-yl)acrylamide | NC(/C=C/C1=CNC2=NC=C(C3=CC=C(C(O)C)C=C3)C=C21)=O |
| 712 | 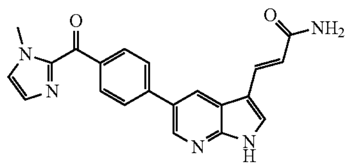 [SMILES: Cn1ccnc1C(=O)c1ccc(-c2cnc3[nH]cc(/C=C/C(N)=O)c3c2)cc1] | (E)-3-(5-(4-(1-methyl-1H-imidazole-2-carbonyl)phenyl)-1H-pyrrolo[2,3-b]pyridin-3-yl)acrylamide | NC(/C=C/C1=CNC2=NC=C(C3=CC=C(C(C4=NC=CN4C)=O)C=C3)C=C21)=O |
| 713 | 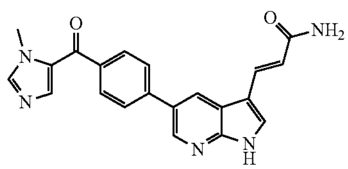 [SMILES: Cn1cncc1C(=O)c1ccc(-c2cnc3[nH]cc(/C=C/C(N)=O)c3c2)cc1] | (E)-3-(5-(4-(1-methyl-1H-imidazole-5-carbonyl)phenyl)-1H-pyrrolo[2,3-b]pyridin-3-yl)acrylamide | NC(/C=C/C1=CNC2=NC=C(C3=CC=C(C(C4=CN=CN4C)=O)C=C3)C=C21)=O |
| 714 | 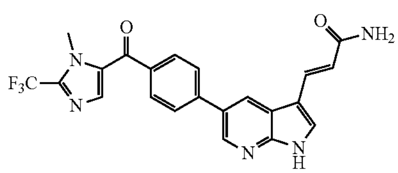 [SMILES: Cn1c(C(=O)c2ccc(-c3cnc4[nH]cc(/C=C/C(N)=O)c4c3)cc2)cnc1C(F)(F)F] | (E)-3-(5-(4-(1-methyl-2-(trifluoromethyl)-1H-imidazole-5-carbonyl)phenyl)-1H-pyrrolo[2,3-b]pyridin-3-yl)acrylamide | NC(/C=C/C1=CNC2=NC=C(C3=CC=C(C(C4=CN=C(C(F)(F)F)N4C)=O)C=C3)C=C21)=O |
| 715 | 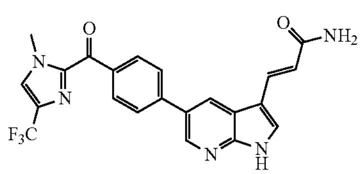 [SMILES: Cn1cc(C(F)(F)F)nc1C(=O)c1ccc(-c2cnc3[nH]cc(/C=C/C(N)=O)c3c2)cc1] | (E)-3-(5-(4-(1-methyl-4-(trifluoromethyl)-1H-imidazole-2-carbonyl)phenyl)-1H-pyrrolo[2,3-b]pyridin-3-yl)acrylamide | NC(/C=C/C1=CNC2=NC=C(C3=CC=C(C(C4=NC(C(F)(F)F)=CN4C)=O)C=C3)C=C21)=O |
| 716 | 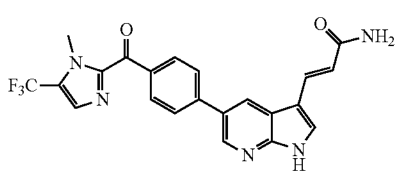 [SMILES: Cn1c(C(F)(F)F)cnc1C(=O)c1ccc(-c2cnc3[nH]cc(/C=C/C(N)=O)c3c2)cc1] | (E)-3-(5-(4-(1-methyl-5-(trifluoromethyl)-1H-imidazole-2-carbonyl)phenyl)-1H-pyrrolo[2,3-b]pyridin-3-yl)acrylamide | NC(/C=C/C1=CNC2=NC=C(C3=CC=C(C(C4=NC=C(C(F)(F)F)N4C)=O)C=C3)C=C21)=O |
| 717 | 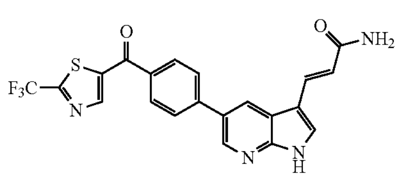 [SMILES: NC(=O)/C=C/c1c[nH]c2ncc(-c3ccc(C(=O)c4cnc(C(F)(F)F)s4)cc3)cc12] | (E)-3-(5-(4-(2-(trifluoromethyl)thiazole-5-carbonyl)phenyl)-1H-pyrrolo[2,3-b]pyridin-3-yl)acrylamide | NC(/C=C/C1=CNC2=NC=C(C3=CC=C(C(C4=CN=C(C(F)(F)F)S4)=O)C=C3)C=C21)=O |
| 718 | 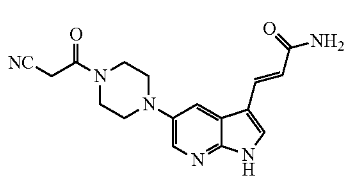 [SMILES: N#CCC(=O)N1CCN(c2cnc3[nH]cc(/C=C/C(N)=O)c3c2)CC1] | (E)-3-(5-(4-(2-cyanoacetyl)piperazin-1-yl)-1H-pyrrolo[2,3-b]pyridin-3-yl)acrylamide | NC(/C=C/C1=CNC2=NC=C(N3CCN(C(CC#N)=O)CC3)C=C21)=O |

TABLE 2-continued

Additional Examples

| Example | Name | Smiles |
|---|---|---|
| 719 | (E)-3-(5-(4-(2-ethoxyethyl)piperazin-1-yl)-1H-pyrrolo[2,3-b]pyridin-3-yl)acrylamide | NC(/C=C/C1=CNC2=NC=C(N3CCN(CCOCC)CC3)C=C21)=O |
| 720 | (E)-3-(5-(4-(2-fluoro-1-methyl-1H-imidazole-5-carbonyl)phenyl)-1H-pyrrolo[2,3-b]pyridin-3-yl)acrylamide | NC(/C=C/C1=CNC2=NC=C(C3=CC=C(C(C4=CN=C(F)N4C)=O)C=C3)C=C21)=O |
| 721 | (E)-3-(5-(4-(2-fluorothiazole-5-carbonyl)phenyl)-1H-pyrrolo[2,3-b]pyridin-3-yl)acrylamide | NC(/C=C/C1=CNC2=NC=C(C3=CC=C(C(C4=CN=C(F)S4)=O)C=C3)C=C21)=O |
| 722 | (E)-3-(5-(4-(2-hydroxypropan-2-yl)-3-(trifluoromethyl)phenyl)-1H-pyrrolo[2,3-b]pyridin-3-yl)acrylamide | NC(/C=C/C1=CNC2=NC=C(C3=CC=C(C(C)(O)C)C(C(F)(F)F)=C3)C=C21)=O |
| 723 | (E)-3-(5-(4-(2-hydroxypropan-2-yl)phenyl)-1H-pyrrolo[2,3-b]pyridin-3-yl)acrylamide | NC(/C=C/C1=CNC2=NC=C(C3=CC=C(C(C)(C)O)C=C3)C=C21)=O |
| 724 | (E)-3-(5-(4-(2-methylthiazole-5-carbonyl)phenyl)-1H-pyrrolo[2,3-b]pyridin-3-yl)acrylamide | NC(/C=C/C1=CNC2=NC=C(C3=CC=C(C(C4=CN=C(C)S4)=O)C=C3)C=C21)=O |
| 725 | (E)-3-(5-(4-(3,3-difluorocyclobutanecarbonyl)piperazin-1-yl)-1H-pyrrolo[2,3-b]pyridin-3-yl)acrylamide | NC(/C=C/C1=CNC2=NC=C(N3CCN(C(C4CC(F)(F)C4)=O)CC3)C=C21)=O |
| 726 | (E)-3-(5-(4-(3,4-difluorobenzoyl)-3-fluorophenyl)-1H-pyrrolo[2,3-b]pyridin-3-yl)acrylamide | NC(/C=C/C1=CNC2=NC=C(C3=CC(F)=C(C(C4=CC=C(F)C(F)=C4)=O)C=C3)C=C21)=O |

TABLE 2-continued

Additional Examples

| Example | Name | Smiles |
|---|---|---|
| 727 | (E)-3-(5-(4-(3,4-difluorobenzoyl)phenyl)-1H-pyrrolo[2,3-b]pyridin-3-yl)acrylamide | NC(/C=C/C1=CNC2=NC=C(C3=CC=C(C(C4=CC=C(F)C(F)C4)=O)C=C3)C=C21)=O |
| 728 | (E)-3-(5-(4-(3-hydroxybutanoyl)piperazin-1-yl)-1H-pyrrolo[2,3-b]pyridin-3-yl)acrylamide | NC(/C=C/C1=CNC2=NC=C(N3CCN(C(CC(C)O)=O)CC3)C=C21)=O |
| 729 | (E)-3-(5-(4-(3-methylbutanoyl)piperazin-1-yl)-1H-pyrrolo[2,3-b]pyridin-3-yl)acrylamide | NC(/C=C/C1=CNC2=NC=C(N3CCN(C(CC(C)C)=O)CC3)C=C21)=O |
| 730 | (E)-3-(5-(4-(4-(trifluoromethyl)benzoyl)phenyl)-1H-pyrrolo[2,3-b]pyridin-3-yl)acrylamide | NC(/C=C/C1=CNC2=NC=C(C3=CC=C(C(C4=CC=C(C(F)(F)F)C=C4)=O)C=C3)C=C21)=O |
| 731 | (E)-3-(5-(4-(4-(trifluoromethyl)thiazole-2-carbonyl)phenyl)-1H-pyrrolo[2,3-b]pyridin-3-yl)acrylamide | NC(/C=C/C1=CNC2=NC=C(C3=CC=C(C(C4=NC(C(F)(F)F)=CS4)=O)C=C3)C=C21)=O |
| 732 | (E)-3-(5-(4-(4,4,4-trifluorobutanoyl)piperazin-1-yl)-1H-pyrrolo[2,3-b]pyridin-3-yl)acrylamide | NC(/C=C/C1=CNC2=NC=C(N3CCN(C(CCC(F)(F)F)=O)CC3)C=C21)=O |
| 733 | (E)-3-(5-(4-(4,4-difluorocyclohexanecarbonyl)piperazin-1-yl)-1H-pyrrolo[2,3-b]pyridin-3-yl)acrylamide | NC(/C=C/C1=CNC2=NC=C(N3CCN(C(C4CCC(F)(F)CC4)=O)CC3)C=C21)=O |
| 734 | (E)-3-(5-(4-(4,5-difluoropicolinoyl)-3-fluorophenyl)-1H-pyrrolo[2,3-b]pyridin-3-yl)acrylamide | NC(/C=C/C1=CNC2=NC=C(C3=CC(F)=C(C(C4=NC=C(F)C(F)=C4)=O)C=C3)C=C21)=O |

TABLE 2-continued

Additional Examples

| Example | Name | Smiles |
|---|---|---|
| 735 | (E)-3-(5-(4-(4,5-difluoropicolinoyl)phenyl)-1H-pyrrolo[2,3-b]pyridin-3-yl)acrylamide | NC(/C=C/C1=CNC2=NC=C(C3=CC=C(C(C4=NC=C(F)C(F)=C4)=O)C=C3)C=C21)=O |
| 736 | (E)-3-(5-(4-(4-chlorobenzoyl)-3-fluorophenyl)-1H-pyrrolo[2,3-b]pyridin-3-yl)acrylamide | NC(/C=C/C1=CNC2=NC=C(C3=CC(F)=C(C(C4=CC=C(C1)C=C4)=O)C=C3)C=C21)=O |
| 737 | (E)-3-(5-(4-(4-chlorobenzoyl)phenyl)-1H-pyrrolo[2,3-b]pyridin-3-yl)acrylamide | NC(/C=C/C1=CNC2=NC=C(C3=CC=C(C(C4=CC=C(C1)C=C4)=O)C=C3)C=C21)=O |
| 738 | (E)-3-(5-(4-(4-cyanobenzoyl)-3-fluorophenyl)-1H-pyrrolo[2,3-b]pyridin-3-yl)acrylamide | NC(/C=C/C1=CNC2=NC=C(C3=CC(F)=C(C(C4=CC=C(C#N)C=C4)=O)C=C3)C=C21)=O |
| 739 | (E)-3-(5-(4-(4-cyanobenzoyl)phenyl)-1H-pyrrolo[2,3-b]pyridin-3-yl)acrylamide | NC(/C=C/C1=CNC2=NC=C(C3=CC=C(C(C4=CC=C(C#N)C=C4)=O)C=C3)C=C21)=O |
| 740 | (E)-3-(5-(4-(4-fluoro-1-methyl-1H-imidazole-2-carbonyl)phenyl)-1H-pyrrolo[2,3-b]pyridin-3-yl)acrylamide | NC(/C=C/C1=CNC2=NC=C(C3=CC=C(C(C4=NC(F)=CN4C)=O)C=C3)C=C21)=O |
| 741 | (E)-3-(5-(4-(4-fluorobutanoyl)piperazin-1-yl)-1H-pyrrolo[2,3-b]pyridin-3-yl)acrylamide | NC(/C=C/C1=CNC2=NC=C(N3CCN(C(CCCF)=O)CC3)C=C21)=O |
| 742 | (E)-3-(5-(4-(4-fluorothiazole-2-carbonyl)phenyl)-1H-pyrrolo[2,3-b]pyridin-3-yl)acrylamide | NC(/C=C/C1=CNC2=NC=C(C3=CC=C(C(C4=NC(F)=CS4)=O)C=C3)C=C21)=O |

TABLE 2-continued

Additional Examples

| Example | Name | Smiles |
|---|---|---|
| 743 | (E)-3-(5-(4-(4-isopropylbenzoyl)phenyl)-1H-pyrrolo[2,3-b]pyridin-3-yl)acrylamide | NC(/C=C/C1=CNC2=NC=C(C3=CC=C(C(C4=CC=C(C(C)C)C=C4)=O)C=C3)C=C21)=O |
| 744 | (E)-3-(5-(4-(4-isopropylpiperazine-1-carbonyl)phenyl)-1H-pyrrolo[2,3-b]pyridin-3-yl)acrylamide | NC(/C=C/C1=CNC2=NC=C(C3=CC=C(C(N4CCN(C(C)C)CC4)=O)C=C3)C=C21)=O |
| 745 | (E)-3-(5-(4-(4-methylthiazole-2-carbonyl)phenyl)-1H-pyrrolo[2,3-b]pyridin-3-yl)acrylamide | NC(/C=C/C1=CNC2=NC=C(C3=CC=C(C(C4=NC(C)=CS4)=O)C=C3)C=C21)=O |
| 746 | (E)-3-(5-(4-(5-(trifluoromethyl)picolinoyl)phenyl)-1H-pyrrolo[2,3-b]pyridin-3-yl)acrylamide | NC(/C=C/C1=CNC2=NC=C(C3=CC=C(C(C4=CC=C(C(F)(F)F)C=N4)=O)C=C3)C=C21)=O |
| 747 | (E)-3-(5-(4-(5-(trifluoromethyl)thiazole-2-carbonyl)phenyl)-1H-pyrrolo[2,3-b]pyridin-3-yl)acrylamide | NC(/C=C/C1=CNC2=NC=C(C3=CC=C(C(C4=NC=C(C(F)(F)F)S4)=O)C=C3)C=C21)=O |
| 748 | (E)-3-(5-(4-(5-chloropicolinoyl)-3-fluorophenyl)-1H-pyrrolo[2,3-b]pyridin-3-yl)acrylamide | NC(/C=C/C1=CNC2=NC=C(C3=CC(F)=C(C(C4=CC=C(Cl)C=N4)=O)C=C3)C=C21)=O |
| 749 | (E)-3-(5-(4-(5-chloropicolinoyl)phenyl)-1H-pyrrolo[2,3-b]pyridin-3-yl)acrylamide | NC(/C=C/C1=CNC2=NC=C(C3=CC=C(C(C4=CC=C(Cl)C=N4)=O)C=C3)C=C21)=O |
| 750 | (E)-3-(5-(4-(5-cyanopicolinoyl)-3-fluorophenyl)-1H-pyrrolo[2,3-b]pyridin-3-yl)acrylamide | NC(/C=C/C1=CNC2=NC=C(C3=CC(F)=C(C(C4=CC=C(C#N)C=N4)=O)C=C3)C=C21)=O |

TABLE 2-continued

Additional Examples

| Example | Structure | Name | Smiles |
|---|---|---|---|
| 751 | 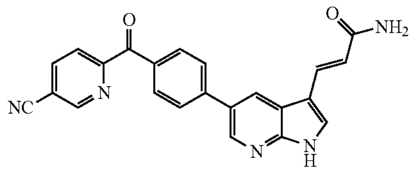 [SMILES: N#Cc1ccc(C(=O)c2ccc(-c3cnc4[nH]cc(/C=C/C(N)=O)c4c3)cc2)nc1] | (E)-3-(5-(4-(5-cyanopicolinoyl)phenyl)-1H-pyrrolo[2,3-b]pyridin-3-yl)acrylamide | NC(/C=C/C1=CNC2=NC=C(C3=CC=C(C(C4=CC=C(C#N)C=N4)=O)C=C3)C=C21)=O |
| 752 | 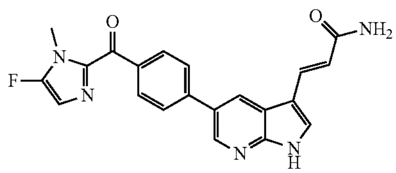 [SMILES: Cn1c(F)cnc1C(=O)c1ccc(-c2cnc3[nH]cc(/C=C/C(N)=O)c3c2)cc1] | (E)-3-(5-(4-(5-fluoro-1-methyl-1H-imidazole-2-carbonyl)phenyl)-1H-pyrrolo[2,3-b]pyridin-3-yl)acrylamide | NC(/C=C/C1=CNC2=NC=C(C3=CC=C(C(C4=NC=C(F)N4C)=O)C=C3)C=C21)=O |
| 753 | 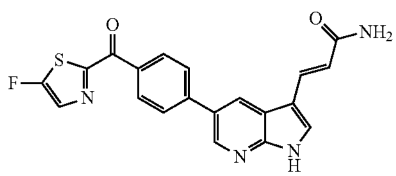 [SMILES: NC(=O)/C=C/c1c[nH]c2ncc(-c3ccc(C(=O)c4ncc(F)s4)cc3)cc12] | (E)-3-(5-(4-(5-fluorothiazole-2-carbonyl)phenyl)-1H-pyrrolo[2,3-b]pyridin-3-yl)acrylamide | NC(/C=C/C1=CNC2=NC=C(C3=CC=C(C(C4=NC=C(F)S4)=O)C=C3)C=C21)=O |
| 754 | 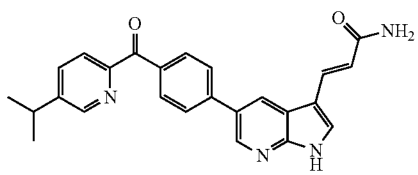 [SMILES: CC(C)c1ccc(C(=O)c2ccc(-c3cnc4[nH]cc(/C=C/C(N)=O)c4c3)cc2)nc1] | (E)-3-(5-(4-(5-isopropylpicolinoyl)phenyl)-1H-pyrrolo[2,3-b]pyridin-3-yl)acrylamide | NC(/C=C/C1=CNC2=NC=C(C3=CC=C(C(C4=CC=C(C(C)C)C=N4)=O)C=C3)C=C21)=O |
| 755 | 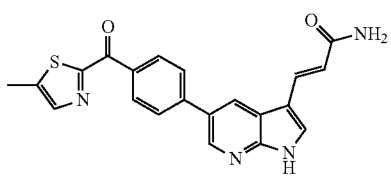 [SMILES: Cc1cnc(C(=O)c2ccc(-c3cnc4[nH]cc(/C=C/C(N)=O)c4c3)cc2)s1] | (E)-3-(5-(4-(5-methylthiazole-2-carbonyl)phenyl)-1H-pyrrolo[2,3-b]pyridin-3-yl)acrylamide | NC(/C=C/C1=CNC2=NC=C(C3=CC=C(C(C4=NC=C(C)S4)=O)C3)C=C21)=O |
| 756 | 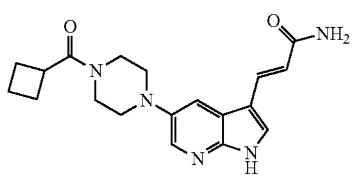 [SMILES: NC(=O)/C=C/c1c[nH]c2ncc(N3CCN(C(=O)C4CCC4)CC3)cc12] | (E)-3-(5-(4-(cyclobutanecarbonyl)piperazin-1-yl)-1H-pyrrolo[2,3-b]pyridin-3-yl)acrylamide | NC(/C=C/C1=CNC2=NC=C(N3CCN(C(C4CCC4)=O)CC3)C=C21)=O |
| 757 | 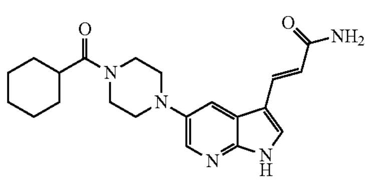 [SMILES: NC(=O)/C=C/c1c[nH]c2ncc(N3CCN(C(=O)C4CCCCC4)CC3)cc12] | (E)-3-(5-(4-(cyclohexane-carbonyl)piperazin-1-yl)-1H-pyrrolo[2,3-b]pyridin-3-yl)acrylamide | NC(/C=C/C1=CNC2=NC=C(N3CCN(C(C4CCCCC4)=O)CC3)C=C21)=O |
| 758 | 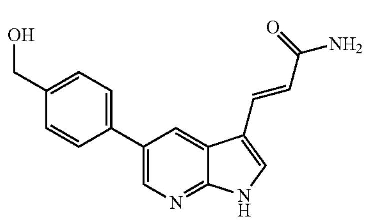 [SMILES: NC(=O)/C=C/c1c[nH]c2ncc(-c3ccc(CO)cc3)cc12] | (E)-3-(5-(4-(hydroxymethyl)phenyl)-1H-pyrrolo[2,3-b]pyridin-3-yl)acrylamide | NC(/C=C/C1=CNC2=NC=C(C3=CC=C(CO)C=C3)C=C21)=O |

TABLE 2-continued

Additional Examples

| Example | Structure | Name | Smiles |
|---|---|---|---|
| 759 | 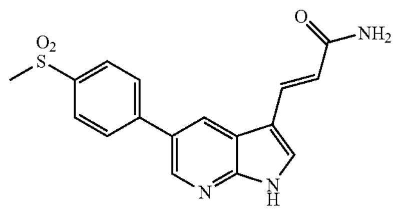 [SMILES: CS(=O)(=O)c1ccc(-c2cnc3[nH]cc(/C=C/C(N)=O)c3c2)cc1] | (E)-3-(5-(4-(methylsulfonyl)phenyl)-1H-pyrrolo[2,3-b]pyridin-3-yl)acrylamide | NC(/C=C/C1=CNC2=NC=C(C3=CC=C(S(C)(=O)=O)C=C3)C=C21)=O |
| 760 | 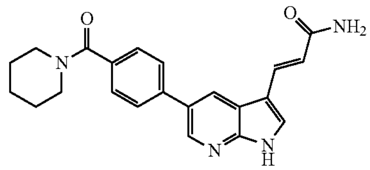 [SMILES: NC(=O)/C=C/c1c[nH]c2ncc(-c3ccc(C(=O)N4CCCCC4)cc3)cc12] | (E)-3-(5-(4-(piperidine-1-carbonyl)phenyl)-1H-pyrrolo[2,3-b]pyridin-3-y])acrylamide | NC(/C=C/C1=CNC2=NC=C(C3=CC=C(C(N4CCCCC4)=O)C=C3)C=C21)=O |
| 761 | 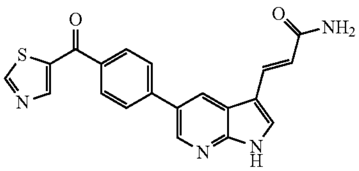 [SMILES: NC(=O)/C=C/c1c[nH]c2ncc(-c3ccc(C(=O)c4cncs4)cc3)cc12] | (E)-3-(5-(4-(thiazole-5-carbonyl)phenyl)-1H-pyrrolo[2,3-b]pyridin-3-yl)acrylamide | NC(/C=C/C1=CNC2=NC=C(C3=CC=C(C(C4=CN=CS4)=O)C=C3)C=C21)=O |
| 762 | 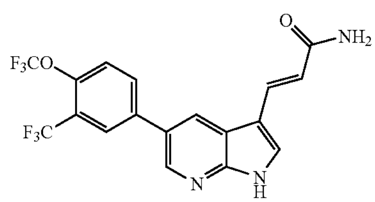 [SMILES: NC(=O)/C=C/c1c[nH]c2ncc(-c3ccc(OC(F)(F)F)c(C(F)(F)F)c3)cc12] | (E)-3-(5-(4-(trifluoromethoxy)-3-(trifluoromethyl)phenyl)-1H-pyrrolo[2,3-b]pyridin-3-yl)acrylamide | NC(/C=C/C1=CNC2=NC=C(C3=CC=C(OC(F)(F)F)C(C(F)(F)F)=C3)C=C21)=O |
| 763 | 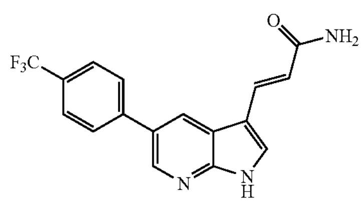 [SMILES: NC(=O)/C=C/c1c[nH]c2ncc(-c3ccc(C(F)(F)F)cc3)cc12] | (E)-3-(5-(4-(trifluoromethyl)phenyl)-1H-pyrrolo[2,3-b]pyridin-3-yl)acrylamide | NC(/C=C/C1=CNC2=NC=C(C3=CC=C(C(F)(F)F)C=C3)C=C21)=O |
| 764 | 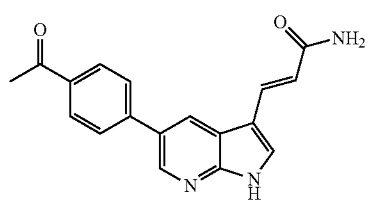 [SMILES: CC(=O)c1ccc(-c2cnc3[nH]cc(/C=C/C(N)=O)c3c2)cc1] | (E)-3-(5-(4-acetylphenyl)-1H-pyrrolo[2,3-b]pyridin-3-yl)acrylamide | NC(/C=C/C1=CNC2=NC=C(C3=CC=C(C(C)=O)C=C3)C=C21)=O |
| 765 | 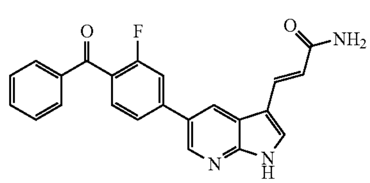 [SMILES: NC(=O)/C=C/c1c[nH]c2ncc(-c3ccc(C(=O)c4ccccc4)c(F)c3)cc12] | (E)-3-(5-(4-benzoyl-3-fluorophenyl)-1H-pyrrolo[2,3-b]pyridin-3-yl)acrylamide | NC(/C=C/C1=CNC2=NC=C(C3=CC(F)=C(C(C4=CC=CC=C4)=O)C=C3)C=C21)=O |
| 766 | 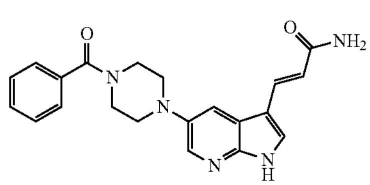 [SMILES: NC(=O)/C=C/c1c[nH]c2ncc(N3CCN(C(=O)c4ccccc4)CC3)cc12] | (E)-3-(5-(4-benzoylpiperazin-1-yl)-1H-pyrrolo[2,3-b]pyridin-3-yl)acrylamide | NC(/C=C/C1=CNC2=NC=C(N3CCN(C(C4=CC=CC=C4)=O)CC3)C=C21)=O |

TABLE 2-continued

Additional Examples

| Example | Structure | Name | Smiles |
|---|---|---|---|
| 767 | 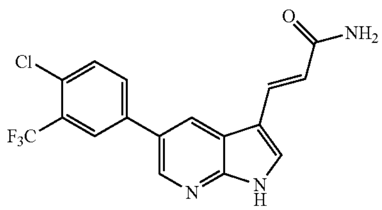 [SMILES: NC(=O)/C=C/c1c[nH]c2ncc(-c3ccc(Cl)c(C(F)(F)F)c3)cc12] | (E)-3-(5-(4-chloro-3-(trifluoromethyl)phenyl)-1H-pyrrolo[2,3-b]pyridin-3-yl)acrylamide | NC(/C=C/C1=CNC2=NC=C(C3=CC=C(C1)C(C(F)(F)F)=C3)C=C21)=O |
| 768 | 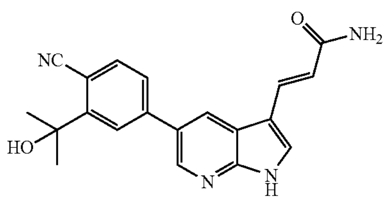 [SMILES: CC(C)(O)c1cc(-c2cnc3[nH]cc(/C=C/C(N)=O)c3c2)ccc1C#N] | (E)-3-(5-(4-cyano-3-(2-hydroxypropan-2-yl)phenyl)-1H-pyrrolo[2,3-b]pyridin-3-yl)acrylamide | NC(C=[S=I]CC[8]=CNC[3]()=NC=C(C[15]=CC=C(C#N)C(C(C)(O)C)=C @ 15)C=C@4@9)=O |
| 769 | 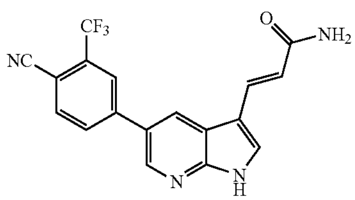 [SMILES: N#Cc1ccc(-c2cnc3[nH]cc(/C=C/C(N)=O)c3c2)cc1C(F)(F)F] | (E)-3-(5-(4-cyano-3-(trifluoromethyl)phenyl)-1H-pyrrolo[2,3-b]pyridin-3-yl)acrylamide | NC(/C=C7C1=CNC2=NC=C(C3=CC(C(F)(F)F)=C(C#N)C=C3)C=C21)=O |
| 770 | 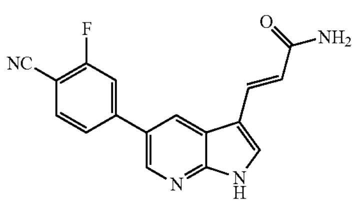 [SMILES: N#Cc1ccc(-c2cnc3[nH]cc(/C=C/C(N)=O)c3c2)cc1F] | (E)-3-(5-(4-cyano-3-fluorophenyl)-1H-pyrrolo[2,3-b]pyridin-3-yl)acrylamide | NC(/C=C/C1=CNC2=NC=C(C3=CC(F)=C(C#N)C=C3)C=C21)=O |
| 771 | 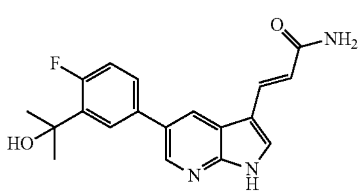 [SMILES: CC(C)(O)c1cc(-c2cnc3[nH]cc(/C=C/C(N)=O)c3c2)ccc1F] | (E)-3-(5-(4-fluoro-3-(2-hydroxypropan-2-yl)phenyl)-1H-pyrrolo[2,3-b]pyridin-3-yl)acrylamide | NC(/C=C/C1=CNC2=NC=C(C3=CC=C(F)C(C(C)(O)C)=C3)C=C21)=O |
| 772 | 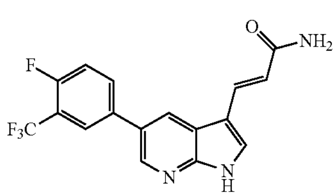 [SMILES: NC(=O)/C=C/c1c[nH]c2ncc(-c3ccc(F)c(C(F)(F)F)c3)cc12] | (E)-3-(5-(4-fluoro-3-(trifluoromethyl)phenyl)-1H-pyrrolo[2,3-b]pyridin-3-yl)acrylamide | NC(/C=C/C1=CNC2=NC=C(C3=CC=C(F)C(C(F)(F)F)=C3)C=C21)=O |
| 773 | 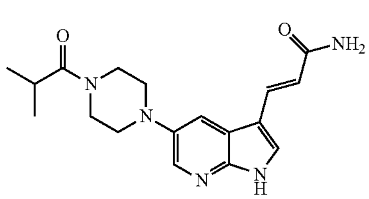 [SMILES: CC(C)C(=O)N1CCN(c2cnc3[nH]cc(/C=C/C(N)=O)c3c2)CC1] | (E)-3-(5-(4-isobutyrylpiperazin-1-yl)-1H-pyrrolo[2,3-b]pyridin-3-yl)acrylamide | NC(/C=C/C1=CNC2=NC=C(N3CCN(C(C(C)C)=O)CC3)C=C21)=O |

TABLE 2-continued

Additional Examples

| Example | Name | Smiles |
|---|---|---|
| 774 | (E)-3-(5-(4-isopropyl-3-(trifluoromethyl)phenyl)-1H-pyrrolo[2,3-b]pyridin-3-yl)acrylamide | NC(/C=C/C1=CNC2=NC=C(C3=CC=C(C(C)C)C(C(F)(F)F)=C3)C=C21)=O |
| 775 | (E)-3-(5-(4-methylquinolin-3-yl)-1H-pyrrolo[2,3-b]pyridin-3-yl)acrylamide | NC(/C=C/C1=CNC2=NC=C(C3=C(C)C(C=CC=C4)=C4N=C3)C=C21)=O |
| 776 | (E)-3-(5-(4-phenoxyphenyl)-1H-pyrrolo[2,3-b]pyridin-3-yl)acrylamide | NC(/C=C/C1=CNC2=NC=C(C3=CC=C(OC4=CC=CC=C4)C=C3)C=C21)=O |
| 777 | (E)-3-(5-(4-pivaloylpiperazin-1-yl)-1H-pyrrolo[2,3-b]pyridin-3-yl)acrylamide | NC(/C=C/C1=CNC2=NC=C(N3CCN(C(C(C)(C)C)=O)CC3)C=C21)=O |
| 778 | (E)-3-(5-(5-chloro-6-cyanopyridin-3-yl)-1H-pyrrolo[2,3-b]pyridin-3-yl)acrylamide | NC(/C=C/C1=CNC2=NC=C(C3=CC(C1)=C(C#N)N=C3)C=C21)=O |
| 779 | (E)-3-(5-(5-fluoro-1-(2-methoxyethyl)-6-oxo-1,6-dihydropyridin-3-yl)-1H-pyrrolo[2,3-b]pyridin-3-yl)acrylamide | NC(/C=C/C1=CNC2=NC=C(C(C=C3F)=CN(CCOC)C3=O)C=C21)=O |
| 780 | (E)-3-(5-(5-fluoro-1-isobutyl-6-oxo-1,6-dihydropyridin-3-yl)-1H-pyrrolo[2,3-b]pyridin-3-yl)acrylamide | NC(/C=C/C1=CNC2=NC=C(C(C=C3F)=CN(CC(C)C)C3=O)C=C21)=O |
| 781 | (E)-3-(5-(5-fluoro-1-methyl-6-oxo-1,6-dihydropyridin-3-yl)-1H-pyrrolo[2,3-b]pyridin-3-yl)acrylamide | NC(/C=C/C1=CNC2=NC=C(C(C=C3F)=CN(C)C3=O)C=C21)=O |

TABLE 2-continued

Additional Examples

| Example | Structure | Name | Smiles |
|---|---|---|---|
| 782 | 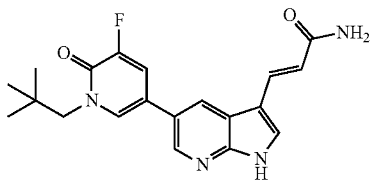 [SMILES: CC(C)(C)Cn1cc(-c2cnc3[nH]cc(/C=C/C(N)=O)c3c2)cc(F)c1=O] | (E)-3-(5-(5-fluoro-1-neopentyl-6-oxo-1,6-dihydropyridin-3-yl)-1H-pyrrolo[2,3-b]pyridin-3-yl)acrylamide | NC(/C=C/C1=CNC2=NC=C(C(C=C3F)=CN(CC(C)(C)C)C3=O)C=C21)=O |
| 783 | 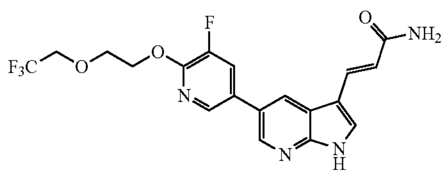 [SMILES: NC(=O)/C=C/c1c[nH]c2ncc(-c3cnc(OCCOCC(F)(F)F)c(F)c3)cc12] | (E)-3-(5-(5-fluoro-6-(2-(2,2,2-trifluoroethoxy)ethoxy)pyridin-3-yl)-1H-pyrrolo[2,3-b]pyridin-3-yl)acrylamide | NC(/C=C/C1=CNC2=NC=C(C3=CC(F)=C(OCCOCC(F)(F)F)N=C3)C=C21)=O |
| 784 | 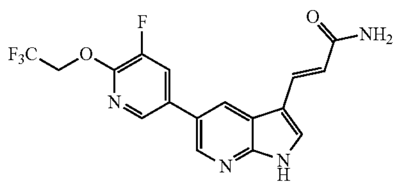 [SMILES: NC(=O)/C=C/c1c[nH]c2ncc(-c3cnc(OCC(F)(F)F)c(F)c3)cc12] | (E)-3-(5-(5-fluoro-6-(2,2,2-trifluoroethoxy)pyridin-3-yl)-1H-pyrrolo[2,3-b]pyridin-3-yl)acrylamide | NC(/C=C/C1=CNC2=NC=C(C3=CC(F)=C(OCC(F)(F)F)N=C3)C=C21)=O |
| 785 | 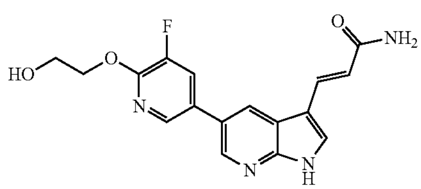 | (E)-3-(5-(5-fluoro-6-(2-hydroxyethoxy)pyridin-3-yl)-1H-pyrrolo[2,3-b]pyridin-3-yl)acrylamide | NC(/C=C/C1=CNC2=NC=C(C3=CC(F)=C(OCCO)N=C3)C=C21)=O |
| 786 | 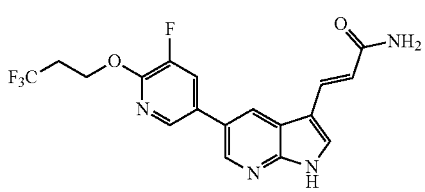 [SMILES: NC(=O)/C=C/c1c[nH]c2ncc(-c3cnc(OCCO)c(F)c3)cc12] | (E)-3-(5-(5-fluoro-6-(3,3,3-trifluoropropoxy)pyridin-3-yl)-1H-pyrrolo[2,3-b]pyridin-3-yl)acrylamide | NC(/C=C/C1=CNC2=NC=C(C3=CC(F)=C(OCCC(F)(F)F)N=C3)C=C21)=O |
| 787 | 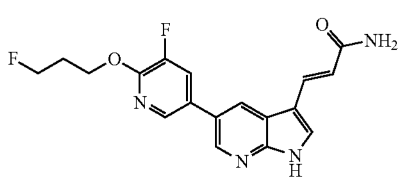 [SMILES: NC(=O)/C=C/c1c[nH]c2ncc(-c3cnc(OCCCF)c(F)c3)cc12] | (E)-3-(5-(5-fluoro-6-(3-fluoropropoxy)pyridin-3-yl)-1H-pyrrolo[2,3-b]pyridin-3-yl)acrylamide | NC(/C=C/C1=CNC2=NC=C(C3=CC(F)=C(OCCCF)N=C3)C=C21)=O |
| 788 | 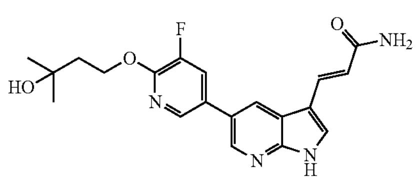 [SMILES: CC(C)(O)CCOc1ncc(-c2cnc3[nH]cc(/C=C/C(N)=O)c3c2)cc1F] | (E)-3-(5-(5-fluoro-6-(3-hydroxy-3-methylbutoxy)pyridin-3-yl)-1H-pyrrolo[2,3-b]pyridin-3-yl)acrylamide | NC(/C=C/C1=CNC2=NC=C(C3=CC(F)=C(OCCC(C)(O)C)N=C3)C=C21)=O |
| 789 | 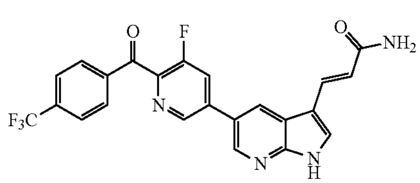 [SMILES: NC(=O)/C=C/c1c[nH]c2ncc(-c3cnc(C(=O)c4ccc(C(F)(F)F)cc4)c(F)c3)cc12] | (E)-3-(5-(5-fluoro-6-(4-(trifluoromethyl)benzoyl)pyridin-3-yl)-1H-pyrrolo[2,3-b]pyridin-3-yl)acrylamide | NC(/C=C/C1=CNC2=NC=C(C3=CC(F)=C(C(C4=CC=C(C(F)(F)F)C=C4)=O)N=C3)C=C21)=O |

TABLE 2-continued

Additional Examples

| Example | Structure | Name | Smiles |
|---|---|---|---|
| 790 | 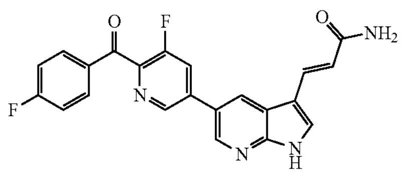 [SMILES: NC(=O)/C=C/c1c[nH]c2ncc(-c3cnc(C(=O)c4ccc(F)cc4)c(F)c3)cc12] | (E)-3-(5-(5-fluoro-6-(4-fluorobenzoyl)pyridin-3-yl)-1H-pyrrolo[2,3-b]pyridin-3-yl)acrylamide | NC(/C=C/C1=CNC2=NC=C(C3=CC(F)=C(C(C4=CC=C(F)C=C4)=O)N=C3)C=C21)=O |
| 791 | 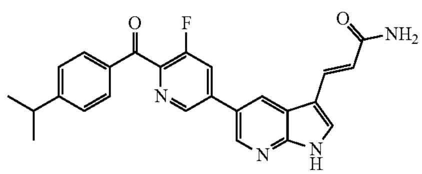 [SMILES: CC(C)c1ccc(C(=O)c2ncc(-c3cnc4[nH]cc(/C=C/C(N)=O)c4c3)cc2F)cc1] | (E)-3-(5-(5-fluoro-6-(4-isopropylbenzoyl)pyridin-3-yl)-1H-pyrrolo[2,3-b]pyridin-3-yl)acrylamide | NC(/C=C/C1=CNC2=NC=C(C3=CC(F)=C(C(C4=CC=C(C(C)C)C=C4)=O)N=C3)C=C21)=O |
| 792 | 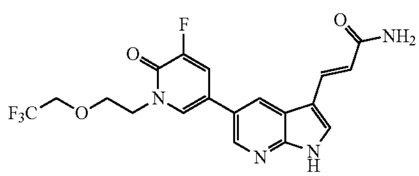 [SMILES: NC(=O)/C=C/c1c[nH]c2ncc(-c3cc(F)c(=O)n(CCOCC(F)(F)F)c3)cc12] | (E)-3-(5-(5-fluoro-6-oxo-1-(2-(2,2,2-trifluoroethoxy)ethyl)-1,6-dihydropyridin-3-yl)-1H-pyrrolo[2,3-b]pyridin-3-yl)acrylamide | NC(/C=C/C1=CNC2=NC=C(C(C=C3F)=CN(CCOCC(F)(F)F)C3=O)C=C21)=O |
| 793 | 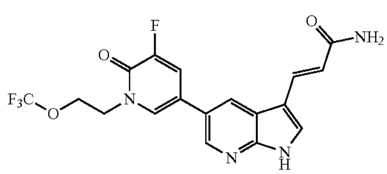 [SMILES: NC(=O)/C=C/c1c[nH]c2ncc(-c3cc(F)c(=O)n(CCOC(F)(F)F)c3)cc12] | (E)-3-(5-(5-fluoro-6-oxo-1-(2-(trifluoromethoxy)ethyl)-1,6-dihydropyridin-3-yl)-1H-pyrrolo[2,3-b]pyridin-3-yl)acrylamide | NC(/C=C/C1=CNC2=NC=C(C(C=C3F)=CN(CCOC(F)(F)F)C3=O)C=C21)=O |
| 794 | 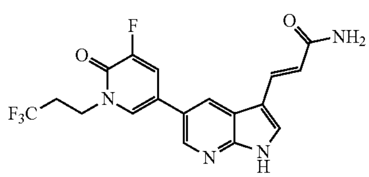 | (E)-3-(5-(5-fluoro-6-oxo-1-(3,3,3-trifluoropropyl)-1,6-dihydropyridin-3-yl)-1H-pyrrolo[2,3-b]pyridin-3-yl)acrylamide | NC(/C=C/C1=CNC2=NC=C(C(C=C3F)=CN(CCC(F)(F)F)C3=O)C=C21)=O |
| 795 | 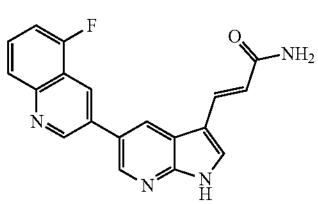 [SMILES: NC(=O)/C=C/c1c[nH]c2ncc(-c3cnc4cccc(F)c4c3)cc12] | (E)-3-(5-(5-fluoroquinolin-3-yl)-1H-pyrrolo[2,3-b]pyridin-3-yl)acrylamide | NC(/C=C/C1=CNC2=NC=C(C3=CC(C(F)=CC=C4)=C4N=C3)C=C21)=O |
| 796 | 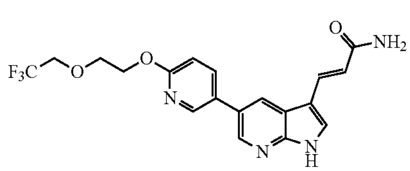 [SMILES: NC(=O)/C=C/c1c[nH]c2ncc(-c3ccc(OCCOCC(F)(F)F)nc3)cc12] | (E)-3-(5-(6-(2-(2,2,2-trifluoroethoxy)ethoxy)pyridin-3-yl)-1H-pyrrolo[2,3-b]pyridin-3-yl)acrylamide | NC(/C=C/C1=CNC2=NC=C(C3=CC=C(OCCOCC(F)(F)F)N=C3)C=C21)=O |
| 797 | 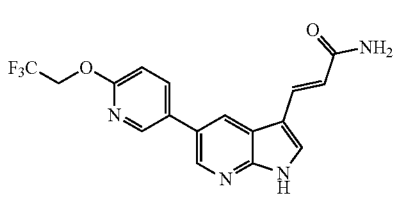 [SMILES: NC(=O)/C=C/c1c[nH]c2ncc(-c3ccc(OCC(F)(F)F)nc3)cc12] | (E)-3-(5-(6-(2,2,2-trifluoroethoxy)pyridin-3-yl)-1H-pyrrolo[2,3-b]pyridin-3-yl)acrylamide | NC(/C=C/C1=CNC2=NC=C(C3=CC=C(OCC(F)(F)F)N=C3)C=C21)=O |

TABLE 2-continued

Additional Examples

| Example | Structure | Name | Smiles |
|---|---|---|---|
| 798 | 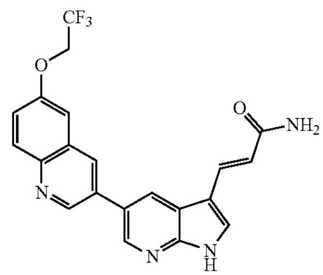 [SMILES: NC(=O)/C=C/c1c[nH]c2ncc(-c3cnc4ccc(OCC(F)(F)F)cc4c3)cc12] | (E)-3-(5-(6-(2,2,2-trifluoroethoxy)quinolin-3-yl)-1H-pyrrolo[2,3-b]pyridin-3-yl)acrylamide | NC(/C=C/C1=CNC2=NC=C(C3=CC(=C(OCC(F)(F)F)C=C4)=C4N=C3)C=C21)=O |
| 799 | 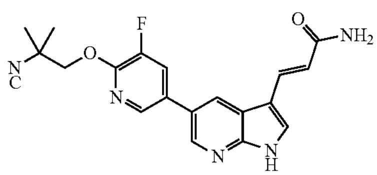 [SMILES: CC(C)(C#N)COc1ncc(-c2cnc3[nH]cc(/C=C/C(N)=O)c3c2)cc1F] | (E)-3-(5-(6-(2-cyano-2-methylpropoxy)-5-fluoropyridin-3-yl)-1H-pyrrolo[2,3-b]pyridin-3-yl)acrylamide | NC(/C=C/C1=CNC2=NC=C(C3=CC(F)=C(OCC(C)(C)C#N)N=C3)C=C21)=O |
| 800 | 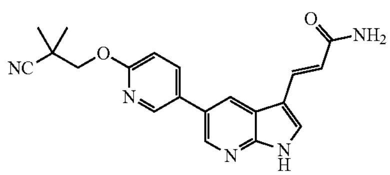 [SMILES: CC(C)(C#N)COc1ccc(-c2cnc3[nH]cc(/C=C/C(N)=O)c3c2)cn1] | (E)-3-(5-(6-(2-cyano-2-methylpropoxy)pyridin-3-yl)-1H-pyrrolo[2,3-b]pyridin-3-yl)acrylamide | NC(/C=C/C1=CNC2=NC=C(C3=CC=C(OCC(C)(C)C#N)N=C3)C=C21)=O |
| 801 | 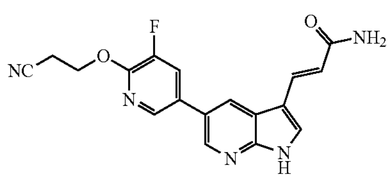 [SMILES: N#CCCOc1ncc(-c2cnc3[nH]cc(/C=C/C(N)=O)c3c2)cc1F] | (E)-3-(5-(6-(2-cyanoethoxy)-5-fluoropyridin-3-yl)-1H-pyrrolo[2,3-b]pyridin-3-yl)acrylamide | NC(/C=C/C1=CNC2=NC=C(C3=CC(F)=C(OCCC#N)N=C3)C=C21)=O |
| 802 | 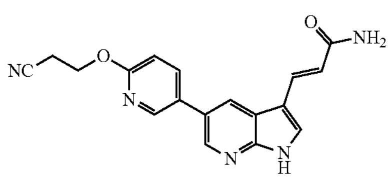 [SMILES: N#CCCOc1ccc(-c2cnc3[nH]cc(/C=C/C(N)=O)c3c2)cn1] | (E)-3-(5-(6-(2-cyanoethoxy)pyridin-3-yl)-1H-pyrrolo[2,3-b]pyridin-3-yl)acrylamide | NC(/C=C/C1=CNC2=NC=C(C3=CC=C(OCCC#N)N=C3)C=C21)=O |
| 803 | 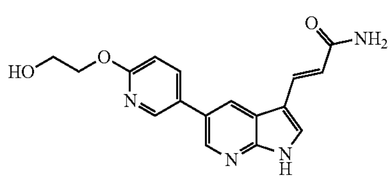 | (E)-3-(5-(6-(2-hydroxyethoxy)pyridin-3-yl)-1H-pyrrolo[2,3-b]pyridin-3-yl)acrylamide | NC(/C=C/C1=CNC2=NC=C(C3=CC=C(OCCO)N=C3)C=C21)=O |
| 804 | 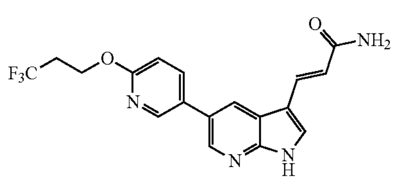 [SMILES: NC(=O)/C=C/c1c[nH]c2ncc(-c3ccc(OCCC(F)(F)F)nc3)cc12] | (E)-3-(5-(6-(3,3,3-trifluoropropoxy)pyridin-3-yl)-1H-pyrrolo[2,3-b]pyridin-3-yl)acrylamide | NC(/C=C/C1=CNC2=NC=C(C3=CC=C(OCCC(F)(F)F)N=C3)C=C21)=O |
| 805 | 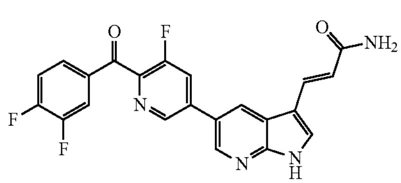 | (E)-3-(5-(6-(3,4-difluorobenzoyl)-5-fluoropyridin-3-yl)-1H-pyrrolo[2,3-b]pyridin-3-yl)acrylamide | NC(/C=C/C1=CNC2=NC=C(C3=CC(F)=C(C(C4=CC=C(F)C(F)=C4)=O)N=C3)C=C21)=O |

TABLE 2-continued

Additional Examples

| Example | Name | Smiles |
|---|---|---|
| 806 | (E)-3-(5-(6-(3,4-difluorobenzoyl)pyridin-3-yl)-1H-pyrrolo[2,3-b]pyridin-3-yl)acrylamide | NC(/C=C/C1=CNC2=NC=C(C3=CC=C(C(C4=CC=C(F)C(F)=C4)=O)N=C3)C=C21)=O |
| 807 | (E)-3-(5-(6-(3-fluoropropoxy)pyridin-3-yl)-1H-pyrrolo[2,3-b]pyridin-3-yl)acrylamide | NC(/C=C/C1=CNC2=NC=C(C3=CC=C(OCCCF)N=C3)C=C21)=O |
| 808 | (E)-3-(5-(6-(3-hydroxy-3-methylbutoxy)pyridin-3-yl)-1H-pyrrolo[2,3-b]pyridin-3-yl)acrylamide | NC(/C=C/C1=CNC2=NC=C(C3=CC=C(OCCC(C)(O)C)N=C3)C=C21)=O |
| 809 | (E)-3-(5-(6-(4-(trifluoromethyl)benzoyl)pyridin-3-yl)-1H-pyrrolo[2,3-b]pyridin-3-yl)acrylamide | NC(/C=C/C1=CNC2=NC=C(C3=CC=C(C(C4=CC=C(C(F)(F)F)C=C4)=O)N=C3)C=C21)=O |
| 810 | (E)-3-(5-(6-(4-chlorobenzoyl)-5-fluoropyridin-3-yl)-1H-pyrrolo[2,3-b]pyridin-3-yl)acrylamide | NC(/C=C/C1=CNC2=NC=C(C3=CC(F)=C(C(C4=CC=C(Cl)C=C4)=O)N=C3)C=C21)=O |
| 811 | (E)-3-(5-(6-(4-chlorobenzoyl)pyridin-3-yl)-1H-pyrrolo[2,3-b]pyridin-3-yl)acrylamide | NC(/C=C/C1=CNC2=NC=C(C3=CC=C(C(C4=CC=C(Cl)C=C4)=O)N=C3)C=C21)=O |
| 812 | (E)-3-(5-(6-(4-cyanobenzoyl)-5-fluoropyridin-3-yl)-1H-pyrrolo[2,3-b]pyridin-3-yl)acrylamide | NC(/C=C/C1=CNC2=NC=C(C3=CC(F)=C(C(C4=CC=C(C#N)C=C4)=O)N=C3)C=C21)=O |
| 813 | (E)-3-(5-(6-(4-cyanobenzoyl)pyridin-3-yl)-1H-pyrrolo[2,3-b]pyridin-3-yl)acrylamide | NC(/C=C/C1=CNC2=NC=C(C3=CC=C(C(C4=CC=C(C#N)C=C4)=O)N=C3)C=C21)=O |

TABLE 2-continued

Additional Examples

| Example | Name | Smiles |
|---|---|---|
| 814 | (E)-3-(5-(6-(4-isopropylbenzoyl)pyridin-3-yl)-1H-pyrrolo[2,3-b]pyridin-3-yl)acrylamide | NC(/C=C/C1=CNC2=NC=C(C3=CC=C(C(C4=CC=C(C(C)C)C=C4)=O)N=C3)C=C21)=O |
| 815 | (E)-3-(5-(6-(trifluoromethoxy)quinolin-3-yl)-1H-pyrrolo[2,3-b]pyridin-3-yl)acrylamide | NC(/C=C/C1=CNC2=NC=C(C3=CC(C=C(OC(F)(F)F)C=C4)=C4N=C3)C=C21)=O |
| 816 | (E)-3-(5-(6-(trifluoromethyl)quinolin-3-yl)-1H-pyrrolo[2,3-b]pyridin-3-yl)acrylamide | NC(/C=C/C1=CNC2=NC=C(C3=CC(C=C(C(F)(F)F)C=C4)=C4N=C3)C=C21)=O |
| 817 | (E)-3-(5-(6,7-difluoroquinolin-3-yl)-1H-pyrrolo[2,3-b]pyridin-3-yl)acrylamide | NC(/C=C/C1=CNC2=NC=C(C3=CC(C=C(F)C(F)=C4)=C4N=C3)C=C21)=O |
| 818 | (E)-3-(5-(6-benzoyl-5-fluoropyridin-3-yl)-1H-pyrrolo[2,3-b]pyridin-3-yl)acrylamide | NC(/C=C/C1=CNC2=NC=C(C3=CC(F)=C(C(C4=CC=CC=C4)=O)N=C3)C=C21)=O |
| 819 | (E)-3-(5-(6-chloroquinolin-3-yl)-1H-pyrrolo[2,3-b]pyridin-3-yl)acrylamide | NC(/C=C/C1=CNC2=NC=C(C3=CC(C=C(Cl)C=C4)=C4N=C3)C=C21)=O |
| 820 | (E)-3-(5-(6-cyano-5-(trifluoromethyl)pyridin-3-yl)-1H-pyrrolo[2,3-b]pyridin-3-yl)acrylamide | NC(/C=C/C1=CNC2=NC=C(C3=CC(C(F)(F)F)=C(C#N)N=C3)C=C21)=O |

TABLE 2-continued

Additional Examples

| Example | Structure | Name | Smiles |
|---|---|---|---|
| 821 | 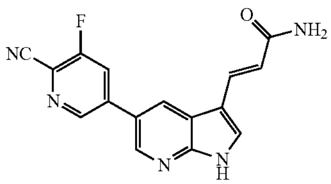 | (E)-3-(5-(6-cyano-5-fluoropyridin-3-yl)-1H-pyrrolo[2,3-b]pyridin-3-yl)acrylamide | NC(/C=C/C1=CNC2=NC=C(C3=CC(F)=C(C#N)N=C3)C=C21)=O |
| | | (E)-3-(5-(6-cyanopyridin-3-yl)-1H-pyrrolo[2,3-b]pyridin-3-yl)acrylamide | NC(/C=C/C1=CNC2=NC=C(C3=CC=C(C#N)N=C3)C=C21)=O |
| 822 | 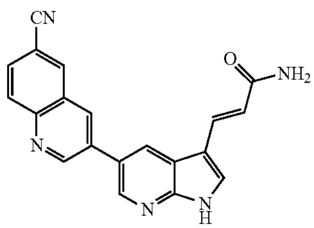 [SMILES: N#Cc1ccc2ncc(-c3cnc4[nH]cc(/C=C/C(N)=O)c4c3)cc2c1] | (E)-3-(5-(6-cyanoquinolin-3-yl)-1H-pyrrolo[2,3-b]pyridin-3-yl)acrylamide | NC(/C=C/C1=CNC2=NC=C(C3=CC(=C(C#N)C=C4)=C4N=C3)C=C21)=O |
| 823 | 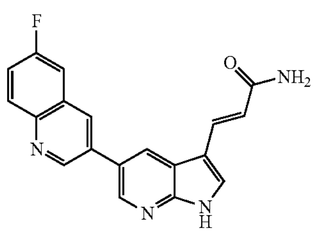 [SMILES: NC(=O)/C=C/c1c[nH]c2ncc(-c3cnc4ccc(F)cc4c3)cc12] | (E)-3-(5-(6-fluoroquinolin-3-yl)-1H-pyrrolo[2,3-b]pyridin-3-yl)acrylamide | NC(/C=C/C1=CNC2=NC=C(C3=CC(=C(F)C=C4)=C4N=C3)C=C21)=O |
| 824 | 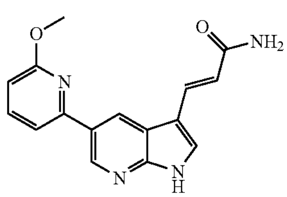 [SMILES: COc1cccc(-c2cnc3[nH]cc(/C=C/C(N)=O)c3c2)n1] | (E)-3-(5-(6-methoxypyridin-2-yl)-1H-pyrrolo[2,3-b]pyridin-3-yl)acrylamide | NC(/C=C/C1=CNC2=NC=C(C3=NC(OC)=CC=C3)C=C21)=O |
| 825 | 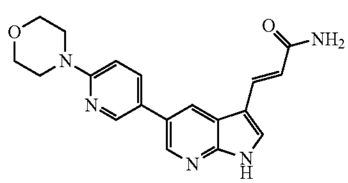 [SMILES: NC(=O)/C=C/c1c[nH]c2ncc(-c3ccc(N4CCOCC4)nc3)cc12] | (E)-3-(5-(6-morpholinopyridin-3-yl)-1H-pyrrolo[2,3-b]pyridin-3-yl)acrylamide | NC(/C=C/C1=CNC2=NC=C(C3=CC=C(N4CCOCC4)N=C3)C=C21)=O |
| 826 | 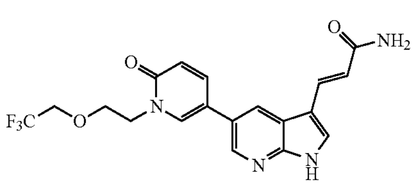 [SMILES: NC(=O)/C=C/c1c[nH]c2ncc(-c3ccc(=O)n(CCOCC(F)(F)F)c3)cc12] | (E)-3-(5-(6-oxo-1-(2-(2,2,2-trifluoroethoxy)ethyl)-1,6-dihydropyridin-3-yl)-1H-pyrrolo[2,3-b]pyridin-3-yl)acrylamide | NC(/C=C/C1=CNC2=NC=C(C(C=C3)=CN(CCOCC(F)(F)F)C3=O)C=C21)=O |

TABLE 2-continued

Additional Examples

| Example | Name | Smiles |
|---|---|---|
| 827 | (E)-3-(5-(6-oxo-1-(2-(trifluoromethoxy)ethyl)-1,6-dihydropyridin-3-yl)-1H-pyrrolo[2,3-b]pyridin-3-yl)acrylamide | NC(/C=C/C1=CNC2=NC=C(C(C=C3)=CN(CCOC(F)(F)F)C3=O)C=C21)=O |
| 828 | (E)-3-(5-(6-oxo-1-(3,3,3-trifluoropropyl)-1,6-dihydropyridin-3-yl)-1H-pyrrolo[2,3-b]pyridin-3-yl)acrylamide | NC(/C=C/C1=CNC2=NC=C(C(C=C3)=CN(CCC(F)(F)F)C3=O)C=C21)=O |
| 829 | (E)-3-(5-(7-fluoroquinolin-3-yl)-1H-pyrrolo[2,3-b]pyridin-3-yl)acrylamide | NC(/C=C/C1=CNC2=NC=C(C3=CC(=CC(F)=C4)=C4N=C3)C=C21)=O |
| 830 | (E)-3-(5-(8-(2-hydroxypropan-2-yl)quinolin-3-yl)-1H-pyrrolo[2,3-b]pyridin-3-yl)acrylamide | NC(/C=C/C1=CNC2=NC=C(C3=CC(=CC=C4C(C)(O)C)=C4N=C3)C=C21)=O |
| 831 | (E)-3-(5-(8-fluoroquinolin-3-yl)-1H-pyrrolo[2,3-b]pyridin-3-yl)acrylamide | NC(/C=C/C1=CNC2=NC=C(C3=CC(=CC=C4F)=C4N=C3)C=C21)=O |
| 832 | (E)-3-(5-(cyclopentylamino)-1H-pyrrolo[2,3-b]pyridin-3-yl)acrylamide | O=C(N)/C=C/C1=CNC2=NC=C(NC3CCCC3)C=C21 |
| 833 | (E)-3-(5-(cyclopentylmethyl)-1H-pyrrolo[2,3-b]pyridin-3-yl)acrylamide | O=C(N)/C=C/C1=CNC2=NC=C(CC3CCCC3)C=C21 |
| 834 | (E)-3-(5-(cyclopentyloxy)-1H-pyrrolo[2,3-b]pyridin-3-yl)acrylamide | O=C(N)/C=C/C1=CNC2=NC=C(OC3CCCC3)C=C21 |

TABLE 2-continued

Additional Examples

| Example | Name | Smiles |
|---|---|---|
| 835 | (E)-3-(5-(neopentylamino)-1H-pyrrolo[2,3-b]pyridin-3-yl)acrylamide | O=C(N)/C=C/C1=CNC2=NC=C(NCC(C)(C)C)C=C21 |
| 836 | (E)-3-(5-(neopentyloxy)-1H-pyrrolo[2,3-b]pyridin-3-yl)acrylamide | O=C(N)/C=C/C1=CNC2=NC=C(OCC(C)(C)C)C=C21 |
| 837 | (E)-3-(5-(pyridin-2-yl)-1H-pyrrolo[2,3-b]pyridin-3-yl)acrylamide | NC(/C=C/C1=CNC2=NC=C(C3=CC=CC=N3)C=C21)=O |
| 838 | (E)-3-(5-(pyrimidin-4-yl)-1H-pyrrolo[2,3-b]pyridin-3-yl)acrylamide | O=C(N)/C=C/C1=CNC2=NC=C(C3=NC=NC=C3)C=C21 |
| 839 | (E)-3-(5-benzyl-1H-pyrrolo[2,3-b]pyridin-3-yl)acrylamide | O=C(N)/C=C/C1=CNC2=NC=C(CC3=CC=CC=C3)C=C21 |
| 840 | (E)-3-(5-phenoxy-1H-pyrrolo[2,3-b]pyridin-3-yl)acrylamide | O=C(N)/C=C/C1=CNC2=NC=C(OC3=CC=CC=C3)C=C21 |
| 841 | (E)-3,3,3-trifluoropropyl 4-(3-(3-amino-3-oxoprop-1-en-1-yl)-1H-pyrrolo[2,3-b]pyridin-5-yl)piperazine-1-carboxylate | NC(/C=C/C1=CNC2=NC=C(N3CCN(C(OCCC(F)(F)F)=O)CC3)C=C21)=O |
| 842 | (E)-3,3,3-trifluoropropyl 4-(7-(3-amino-3-oxoprop-1-en-1-yl)-5H-pyrrolo[2,3-b]pyrazin-2-yl)piperazine-1-carboxylate | NC(/C=C/C1=CNC2=NC=C(N3CCN(C(OCCC(F)(F)F)=O)CC3)N=C21)=O |

TABLE 2-continued

Additional Examples

| Example | Structure | Name | Smiles |
|---|---|---|---|
| 843 | 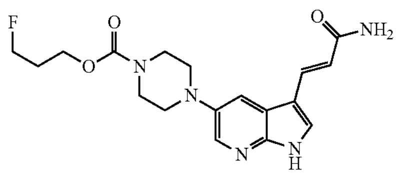 [SMILES: NC(=O)/C=C/c1c[nH]c2ncc(N3CCN(C(=O)OCCCF)CC3)cc12] | (E)-3-fluoropropyl 4-(3-(3-amino-3-oxoprop-1-en-1-yl)-1H-pyrrolo[2,3-b]pyridin-5-yl)piperazine-1-carboxylate | NC(/C═C/C1═CNC2═NC═C(N3CCN(C(OCCCF)═O)CC3)C═C21)═O |
| 844 | 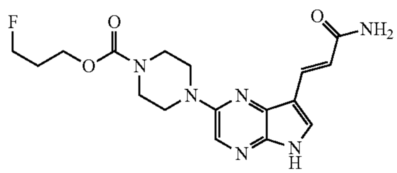 [SMILES: NC(=O)/C=C/c1c[nH]c2ncc(N3CCN(C(=O)OCCCF)CC3)nc12] | (E)-3-fluoropropyl 4-(7-(3-amino-3-oxoprop-1-en-1-yl)-5H-pyrrolo[2,3-b]pyrazin-2-yl)piperazine-1-carboxylate | NC(/C═C/C1═CNC2═NC═C(N3CCN(C(OCCCF)═O)CC3)N═C21)═O |
| 845 | 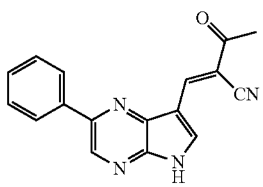 [SMILES: CC(=O)/C(C#N)=C/c1c[nH]c2ncc(-c3ccccc3)nc12] | (E)-3-oxo-2-((2-phenyl-5H-pyrrolo[2,3-b]pyrazin-7-yl)methylene)butanenitrile | O═C(C)/C(C#N)═C/C1═CNC2═NC═C(C3═CC═CC═C3)N═C21 |
| 846 | 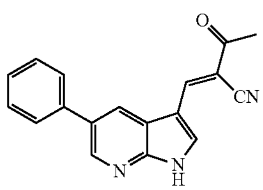 [SMILES: CC(=O)/C(C#N)=C/c1c[nH]c2ncc(-c3ccccc3)cc12] | (E)-3-oxo-2-((5-phenyl-1H-pyrrolo[2,3-b]pyridin-3-yl)methylene)butanenitrile | O═C(C)/C(C#N)═C/C1═CNC2═NC═C(C3═CC═CC═C3)C═C21 |
| 847 | 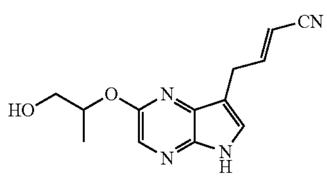 [SMILES: CC(CO)Oc1cnc2[nH]cc(C/C=C/C#N)c2n1] | (E)-4-(2-((1-hydroxypropan-2-yl)oxy)-5H-pyrrolo[2,3-b]pyrazin-7-yl)but-2-enenitrile | CC(CO)OC1═CN═C(NC═C2C/C═C/C#N)C2═N1 |
| 848 | 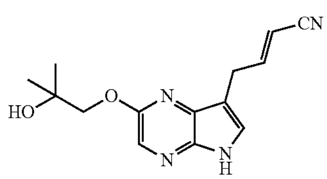 [SMILES: CC(C)(O)COc1cnc2[nH]cc(C/C=C/C#N)c2n1] | (E)-4-(2-(2-hydroxy-2-methylpropoxy)-5h-pyrrolo[2,3-b]pyrazin-7-yl)but-2-enenitrile | OC(C)(C)COC1═CN═C(NC═C2C/C═C/C#N)C2═N1 |
| 849 | 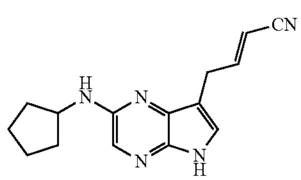 [SMILES: N#C/C=C/Cc1c[nH]c2ncc(NC3CCCC3)nc12] | (E)-4-(2-(cyclopentylamino)-5H-pyrrolo[2,3-b]pyrazin-7-yl)but-2-enenitrile | N#C/C═C/CC1═CNC2═NC═C(NC3CCCC3)N═C21 |
| 850 | 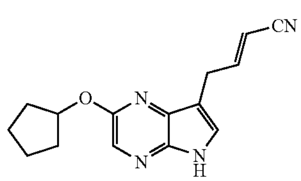 [SMILES: N#C/C=C/Cc1c[nH]c2ncc(OC3CCCC3)nc12] | (E)-4-(2-(cyclopentyloxy)-5H-pyrrolo[2,3-b]pyrazin-7-yl)but-2-enenitrile | N#C/C═C/CC1═CNC2═NC═C(OC3CCCC3)N═C21 |

TABLE 2-continued

Additional Examples

| Example | Structure | Name | Smiles |
|---|---|---|---|
| 851 | 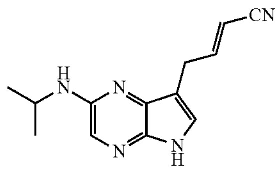 [SMILES: CC(C)Nc1cnc2[nH]cc(C/C=C/C#N)c2n1] | (E)-4-(2-(isopropylamino)-5H-pyrrolo[2,3-b]pyrazin-7-yl)but-2-enenitrile | CC(C)NC1=CN=C(NC=C2C/C=C/C#N)C2=N1 |
| 852 | 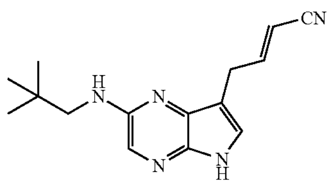 [SMILES: CC(C)(C)CNc1cnc2[nH]cc(C/C=C/C#N)c2n1] | (E)-4-(2-(neopentylamino)-5H-pyrrolo[2,3-b]pyrazin-7-yl)but-2-enenitrile | CC(C)(C)CNC1=CN=C(NC=C2C/C=C/C#N)C2=N1 |
| 853 | 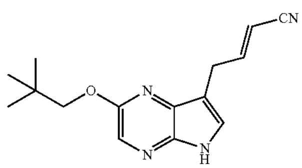 | (E)-4-(2-(neopentyloxy)-5H-pyrrolo[2,3-b]pyrazin-7-yl)but-2-enenitrile | CC(C)(C)COC1=CN=C(NC=C2C/C=C/C#N)C2=N1 |
| 854 | 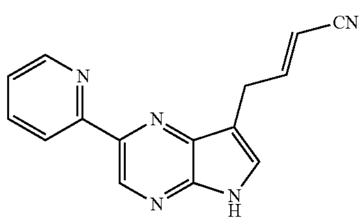 [SMILES: N#C/C=C/Cc1c[nH]c2ncc(-c3ccccn3)nc12] | (E)-4-(2-(pyridin-2-yl)-5H-pyrrolo[2,3-b]pyrazin-7-yl)but-2-enenitrile | N#C/C=C/CC1=CNC2=C3=NC=CC=C3)N=C21 |
| 855 | 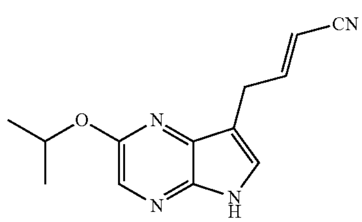 [SMILES: CC(C)Oc1cnc2[nH]cc(C/C=C/C#N)c2n1] | (E)-4-(2-isopropoxy-5H-pyrrolo[2,3-b]pyrazin-7-yl)but-2-enenitrile | CC(C)OC1=CN=C(NC=C2C/C=C/C#N)C2=N1 |
| 856 | 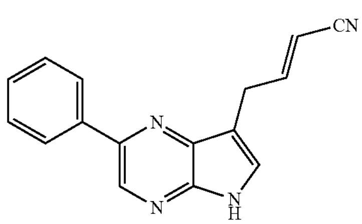 [SMILES: N#C/C=C/Cc1c[nH]c2ncc(-c3ccccc3)nc12] | (E)-4-(2-phenyl-5E-pyrrolo[2,3-b]pyrazin-7-yl)but-2-enenitrile | N#C/C=C/CC1=CNC2=NC=C(C3=CC=CC=C3)N=C21 |
| 857 | 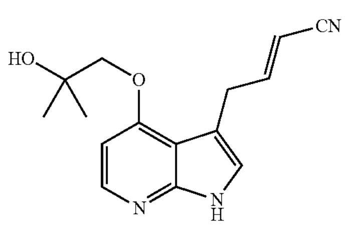 [SMILES: CC(C)(O)COc1ccnc2[nH]cc(C/C=C/C#N)c12] | (E)-4-(4-(2-hydroxy-2-methylpropoxy)-1H-pyrrolo[2,3-b]pyridin-3-yl)but-2-enenitrile | OC(C)(C)COC1=C2C(NC=C2C/C=C/C#N)=NC=C1 |

TABLE 2-continued

Additional Examples

| Example | Structure | Name | Smiles |
|---|---|---|---|
| 858 | 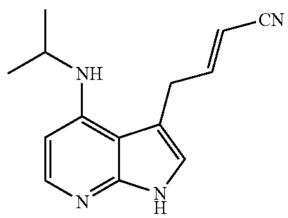 [SMILES: CC(C)Nc1ccnc2[nH]cc(C/C=C/C#N)c12] | (E)-4-(4-(isopropylamino)-1H-pyrrolo[2,3-b]pyridin-3-yl)but-2-enenitrile | CC(C)NC1=C2C(NC=C2C/C=C/C#N)=NC=C1 |
| 859 | 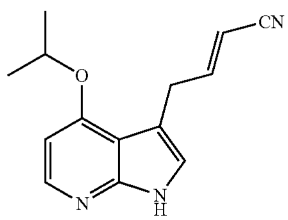 [SMILES: CC(C)Oc1ccnc2[nH]cc(C/C=C/C#N)c12] | (E)-4-(4-isopropoxy-1H-pyrrolo[2,3-b]pyridin-3-yl)but-2-enenitrile | CC(C)OC1=C2C(NC=C2C/C=C/C#N)=NC=C1 |
| 860 | 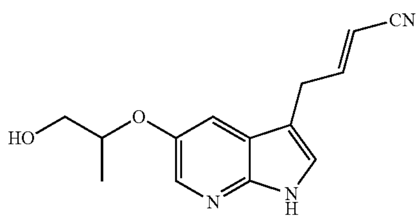 [SMILES: CC(CO)Oc1cnc2[nH]cc(C/C=C/C#N)c2c1] | (E)-4-(5-((1-hydroxypropan-2-yl)oxy)-1H-pyrrolo[2,3-b]pyridin-3-yl)but-2-enenitrile | CC(CO)OC1=CN=C(NC=C2C/C=C/C#N)C2=C1 |
| 861 | 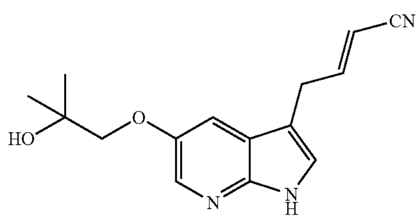 [SMILES: CC(C)(O)COc1cnc2[nH]cc(C/C=C/C#N)c2c1] | (E)-4-(5-(2-hydroxy-2-methylpropoxy)-1H-pyrrolo[2,3-b]pyridin-3-yl)but-2-enenitrile | OC(C)(C)COC1=CN=C(NC=C2C/C=C/C#N)C2=C1 |
| 862 | 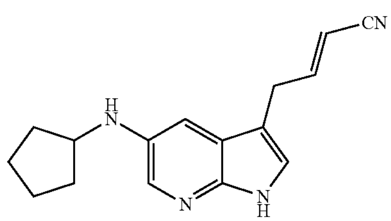 [SMILES: N#C/C=C/Cc1c[nH]c2ncc(NC3CCCC3)cc12] | (E)-4-(5-(cyclopentylamino)-1H-pyrrolo[2,3-b]pyridin-3-yl)but-2-enenitrile | N#C/C=C/CC1=CNC2=NC=C(NC3CCCC3)C=C21 |
| 863 | 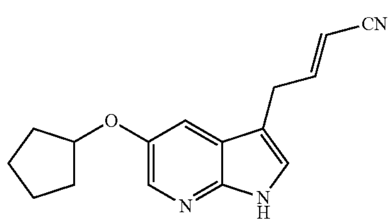 [SMILES: N#C/C=C/Cc1c[nH]c2ncc(OC3CCCC3)cc12] | (E)-4-(5-(cyclopentyloxy)-1H-pyrrolo[2,3-b]pyridin-3-yl)but-2-enenitrile | N#C/C=C/CC1=CNC2=NC=C(OC3CCCC3)C=C21 |
| 864 | 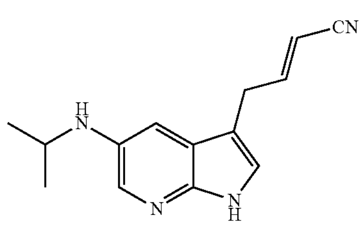 [SMILES: CC(C)Nc1cnc2[nH]cc(C/C=C/C#N)c2c1] | (E)-4-(5-(isopropylamino)-1H-pyrrolo[2,3-b]pyridin-3-yl)but-2-enenitrile | CC(C)NC1=CN=C(NC=C2C/C=C/C#N)C2=C1 |

TABLE 2-continued

Additional Examples

| Example | Structure | Name | Smiles |
|---|---|---|---|
| 865 | 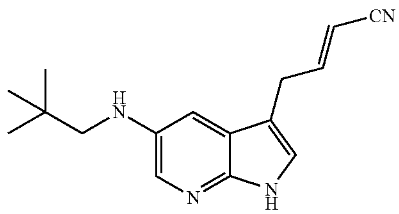 [SMILES: CC(C)(C)CNc1cnc2[nH]cc(C/C=C/C#N)c2c1] | (E)-4-(5-(neopentylamino)-1H-pyrrolo[2,3-b]pyridin-3-yl)but-2-enenitrile | CC(C)(C)CNC1=CN=C(NC=C2C/C=C/C#N)C2=C1 |
| 866 | 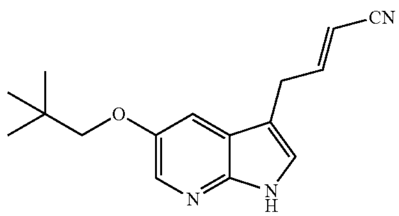 [SMILES: CC(C)(C)COc1cnc2[nH]cc(C/C=C/C#N)c2c1] | (E)-4-(5-(neopentyloxy)-1H-pyrrolo[2,3-b]pyridin-3-yl)but-2-enenitrile | CC(C)(C)COC1=CN=C(NC=C2C/C=C/C#N)C2=C1 |
| 867 | 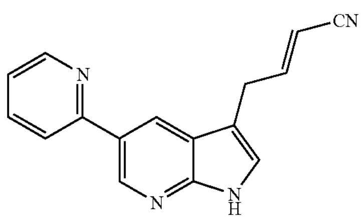 [SMILES: N#C/C=C/Cc1c[nH]c2ncc(-c3ccccn3)cc12] | (E)-4-(5-(pyridin-2-yl)-1H-pyrrolo[2,3-b]pyridin-3-yl)but-2-enenitrile | N#C/C=C/CC1=CNC2=NC=C(C3=NC=CC=C3)C=C21 |
| 868 | 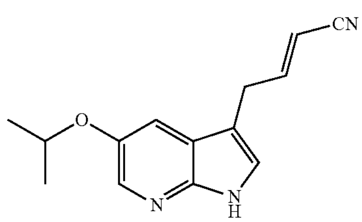 [SMILES: CC(C)Oc1cnc2[nH]cc(C/C=C/C#N)c2c1] | (E)-4-(5-isopropoxy-1H-pyrrolo[2,3-b]pyridin-3-yl)but-2-enenitrile | CC(C)OC1=CN=C(NC=C2C/C=C/C#N)C2=C1 |
| 869 | 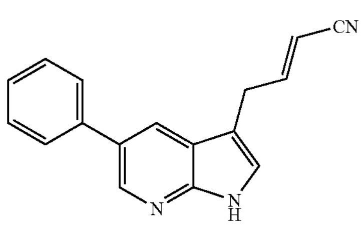 [SMILES: N#C/C=C/Cc1c[nH]c2ncc(-c3ccccc3)cc12] | (E)-4-(5-phenyl-1H-pyrrolo[2,3-b]pyridin-3-yl)but-2-enenitrile | N#C/C=C/CC1=CNC2=NC=C(C3=CC=CC=C3)C=C21 |
| 870 | 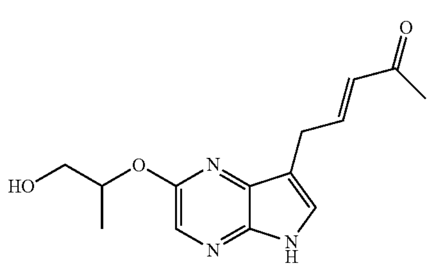 [SMILES: CC(=O)/C=C/Cc1c[nH]c2ncc(OC(C)CO)nc12] | (E)-5-(2-((1-hydroxypropan-2-yl)oxy)-5H-pyrrolo[2,3-b]pyrazin-7-yl)pent-3-en-2-one | CC(CO)OC1=CN=C(NC=C2C/C=C/C(C)=O)C2=N1 |

TABLE 2-continued

Additional Examples

| Example | Name | Smiles |
|---|---|---|
| 871 | (E)-5-(2-(1-phenyl-1H-pyrazol-4-yl)-5H-pyrrolo[2,3-b]pyrazin-7-yl)pent-3-en-2-one | CC(/C=C/CC1=CNC2=NC=C(C3=CN(C4=CC=CC=C4)N=C3)N=C21)=O |
| 872 | (E)-5-(2-(2-hydroxy-2-methylpropoxy)-5H-pyrrolo[2,3-b]pyrazin-7-yl)pent-3-en-2-one | CC(/C=C/CC1=CNC2=NC=C(OCC(C)(C)O)N=C21)=O |
| 873 | (E)-5-(2-(cyclopentylamino)-5H-pyrrolo[2,3-b]pyrazin-7-yl)pent-3-en-2-one | CC(/C=C/CC1=CNC2=NC=C(NC3CCCC3)N=C21)=O |
| 874 | (E)-5-(2-(cyclopentyloxy)-5H-pyrrolo[2,3-b]pyrazin-7-yl)pent-3-en-2-one | CC(/C=C/CC1=CNC2=NC=C(OC3CCCC3)N=C21)=O |
| 875 | (E)-5-(2-(isopropylamino)-5H-pyrrolo[2,3-b]pyrazin-7-yl)pent-3-en-2-one | CC(C)NC1=CN=C(NC=C2C/C=C/C(C)=O)C2=N1 |

TABLE 2-continued

Additional Examples

| Example | Structure | Name | Smiles |
|---|---|---|---|
| 876 | 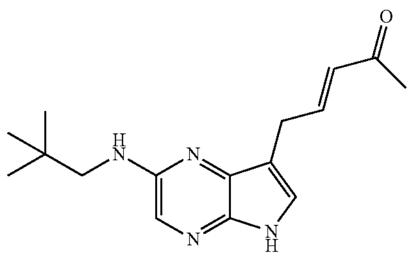 [SMILES: CC(=O)/C=C/Cc1c[nH]c2ncc(NCC(C)(C)C)nc12] | (E)-5-(2-(neopentylamino)-5H-pyrrolo[2,3-b]pyrazin-7-yl)pent-3-en-2-one | CC(/C=C/CC1=CNC2=NC=C(NCC(C)(C)C)N=C21)=O |
| 877 | 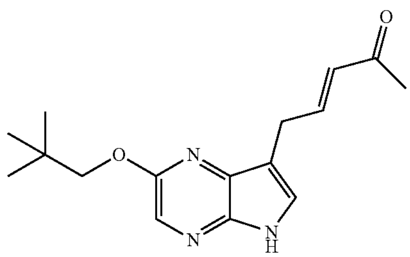 [SMILES: CC(=O)/C=C/Cc1c[nH]c2ncc(OCC(C)(C)C)nc12] | (E)-5-(2-(neopentyloxy)-5H-pyrrolo[2,3-b]pyrazin-7-yl)pent-3-en-2-one | CC(/C=C/CC1=CNC2=NC=C(OCC(C)(C)C)N=C21)=O |
| 878 | 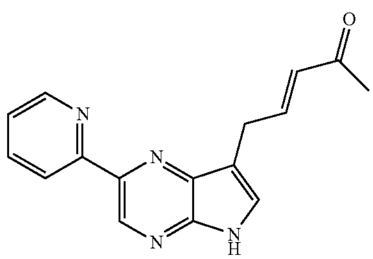 [SMILES: CC(=O)/C=C/Cc1c[nH]c2ncc(-c3ccccn3)nc12] | (E)-5-(2-(pyridin-2-yl)-5H-pyrrolo[2,3-b]pyrazin-7-yl)pent-3-en-2-one | CC(/C=C/CC1=CNC2=NC=C(C3=NC=CC=C3)N=C21)=O |
| 879 | 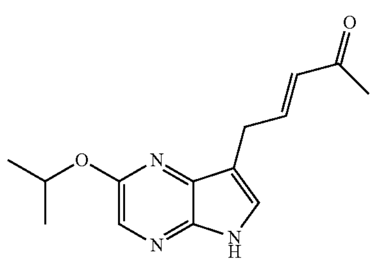 [SMILES: CC(=O)/C=C/Cc1c[nH]c2ncc(OC(C)C)nc12] | (E)-5-(2-isopropoxy-5H-pyrrolo[2,3-b]pyrazin-7-yl)pent-3-en-2-one | CC(C)OC1=CN=C(NC=C2C/C=C/C(C)=O)C2=N1 |
| 880 | 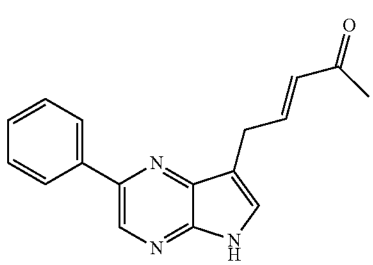 [SMILES: CC(=O)/C=C/Cc1c[nH]c2ncc(-c3ccccc3)nc12] | (E)-5-(2-phenyl-5H-pyrrolo[2,3-b]pyrazin-7-yl)pent-3-en-2-one | CC(/C=C/CC1=CNC2=NC=C(C3=CC=CC=C3)N=C21)=O |
| 881 | 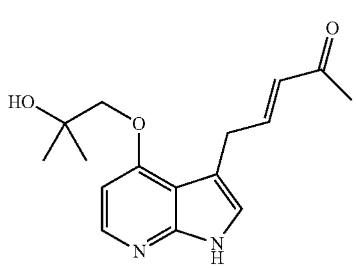 [SMILES: CC(=O)/C=C/Cc1c[nH]c2nccc(OCC(C)(C)O)c12] | (E)-5-(4-(2-hydroxy-2-methylpropoxy)-1H-pyrrolo[2,3-b]pyridin-3-yl)pent-3-en-2-one | OC(C)(C)COC1=C2C(NC=C2/C=C/C(C)=O)=NC=C1 |

TABLE 2-continued

Additional Examples

| Example | Structure | Name | Smiles |
|---|---|---|---|
| 882 | 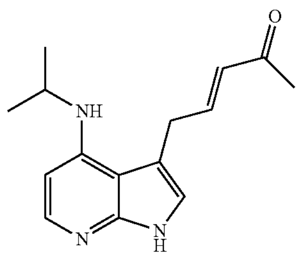 [SMILES: CC(=O)/C=C/Cc1c[nH]c2nccc(NC(C)C)c12] | (E)-5-(4-(isopropylamino)-1H-pyrrolo[2,3-b]pyridin-3-yl)pent-3-en-2-one | CC(C)NC1=C2C(NC=C2C/C=C/C(C)=O)=NC=C1 |
| 883 | 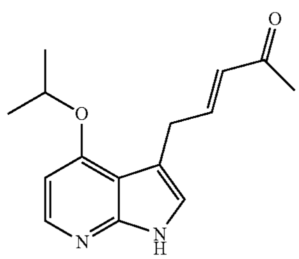 [SMILES: CC(=O)/C=C/Cc1c[nH]c2nccc(OC(C)C)c12] | (E)-5-(4-isopropoxy-1H-pyrrolo[2,3-b]pyridin-3-yl)pent-3-en-2-one | CC(C)OC1=C2C(NC=C2C/C=C/C(C)=O)=NC=C1 |
| 884 | 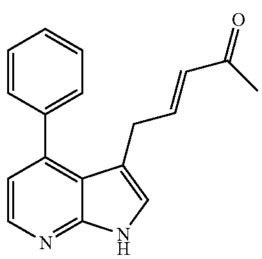 [SMILES: CC(=O)/C=C/Cc1c[nH]c2nccc(-c3ccccc3)c12] | (E)-5-(4-phenyl-1H-pyrrolo[2,3-b]pyridin-3-yl)pent-3-en-2-one | CC(/C=C/CC1=CNC2=NC=CC(C3=CC=CC=C3)=C21)=O |
| 885 | 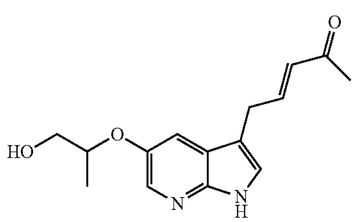 [SMILES: CC(=O)/C=C/Cc1c[nH]c2ncc(OC(C)CO)cc12] | (E)-5-(5-((1-hydroxypropan-2-yl)oxy)-1H-pyrrolo[2,3-b]pyridin-3-yl)pent-3-en-2-one | CC(CO)OC1=CN=C(NC=C2C/C=C/C(C)=O)C2=C1 |
| 886 | 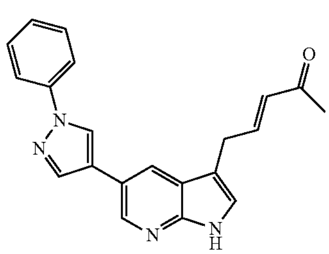 [SMILES: CC(=O)/C=C/Cc1c[nH]c2ncc(-c3cnn(-c4ccccc4)c3)cc12] | (E)-5-(5-(1-phenyl-1H-pyrazol-4-yl)-1H-pyrrolo[2,3-b]pyridin-3-yl)pent-3-en-2-one | CC(/C=C/CC1=CNC2=NC=C(C3=CN(C4=CC=CC=C4)N=C3)C=C21)=O |
| 887 | 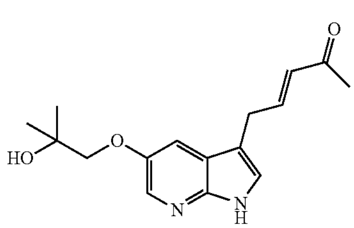 [SMILES: CC(=O)/C=C/Cc1c[nH]c2ncc(OCC(C)(C)O)cc12] | (E)-5-(5-(2-hydroxy-2-methylpropoxy)-1H-pyrrolo[2,3-b]pyridin-3-yl)pent-3-en-2-one | CC(/C=C/CC1=CNC2=NC=C(OCC(C)(C)O)C=C21)=O |

TABLE 2-continued

Additional Examples

| Example | Structure | Name | Smiles |
|---|---|---|---|
| 888 | 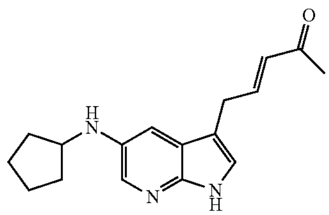 [SMILES: CC(=O)/C=C/Cc1c[nH]c2ncc(NC3CCCC3)cc12] | (E)-5-(5-(cyclopentylamino)-1H-pyrrolo[2,3-b]pyridin-3-yl)pent-3-en-2-one | CC(/C=C/CC1=CNC2=NC=C(NC3CCCC3)C=C21)=O |
| 889 | 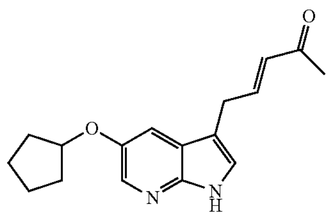 [SMILES: CC(=O)/C=C/Cc1c[nH]c2ncc(OC3CCCC3)cc12] | (E)-5-(5-(cyclopentyloxy)-1H-pyrrolo[2,3-b]pyridin-3-yl)pent-3-en-2-one | CC(/C=C/CC1=CNC2=NC=C(OC3CCCC3)C=C21)=O |
| 890 | 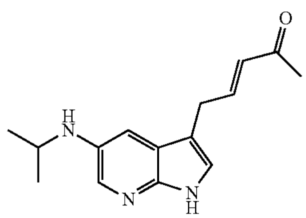 [SMILES: CC(=O)/C=C/Cc1c[nH]c2ncc(NC(C)C)cc12] | (E)-5-(5-(isopropylamino)-1H-pyrrolo[2,3-b]pyridin-3-yl)pent-3-en-2-one | CC(C)NC1=CN=C(NC=C2C/C=C/C(C)=O)C2=C1 |
| 891 | 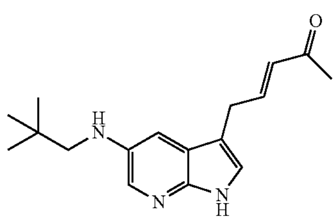 [SMILES: CC(=O)/C=C/Cc1c[nH]c2ncc(NCC(C)(C)C)cc12] | (E)-5-(5-(neopentylamino)-1H-pyrrolo[2,3-b]pyridin-3-yl)pent-3-en-2-one | CC(/C=C/CC1=CNC2=NC=C(NCC(C)(C)C)C=C21)=O |
| 892 | 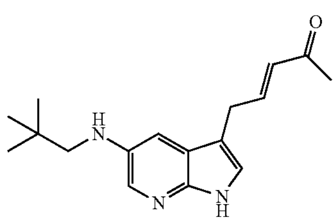 [SMILES: CC(=O)/C=C/Cc1c[nH]c2ncc(NCC(C)(C)C)cc12] | (E)-5-(5-(neopentyloxy)-1H-pyrrolo[2,3-b]pyridin-3-yl)pent-3-en-2-one | CC(/C=C/CC1=CNC2=NC=C(OCC(C)(C)C)C=C21)=O |
| 893 | 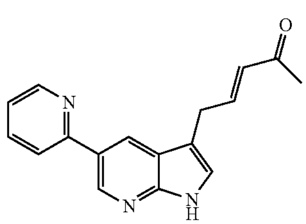 [SMILES: CC(=O)/C=C/Cc1c[nH]c2ncc(-c3ccccn3)cc12] | (E)-5-(5-(pyridin-2-yl)-1H-pyrrolo[2,3-b]pyridin-3-yl)pent-3-en-2-one | CC(/C=C/CC1=CNC2=NC=C(C3=NC=CC=C3)C=C21)=O |
| 894 | 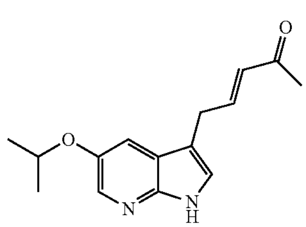 [SMILES: CC(=O)/C=C/Cc1c[nH]c2ncc(OC(C)C)cc12] | (E)-5-(5-isopropoxy-1H-pyrrolo[2,3-b]pyridin-3-yl)pent-3-en-2-one | CC(C)OC1=CN=C(NC=C2C/C=C/C(C)=O)C2=C1 |

TABLE 2-continued

Additional Examples

| Example | Name | Smiles |
|---|---|---|
| 895 | (E)-5-(5-phenyl-1H-pyrrolo[2,3-b]pyridin-3-yl)pent-3-en-2-one | CC(/C=C/CC1=CNC2=NC=C(C3=CC=CC=C3)C=C21)=O |
| 896 | (E)-ethyl 4-(3-(3-amino-2-cyano-3-oxoprop-1-en-1-yl)-1H-pyrrolo[2,3-b]pyridin-5-yl)piperazine-1-carboxylate | NC(/C(C#N)=C/C1=CNC2=NC=C(N3CCN(C(OCC)=O)CC3)C=C21)=O |
| 897 | (E)-ethyl 4-(7-(3-amino-2-cyano-3-oxoprop-1-en-1-yl)-5H-pyrrolo[2,3-b]pyrazin-2-yl)piperazine-1-carboxylate | NC(/C(C#N)=C/C1=CNC2=NC=C(N3CCN(C(OCC)=O)CC3)N=C21)=O |
| 898 | (E)-isobutyl 4-(3-(3-amino-2-cyano-3-oxoprop-1-en-1-yl)-1H-pyrrolo[2,3-b]pyridin-5-yl)piperazine-1-carboxylate | NC(/C(C#N)=C/C1=CNC2=NC=C(N3CCN(C(OCC(C)C)=O)CC3)C=C21)=O |
| 899 | (E)-isobutyl 4-(3-(3-amino-3-oxoprop-1-en-1-yl)-1H-pyrrolo[2,3-b]pyridin-5-yl)piperazine-1-carboxylate | NC(/C=C/C1=CNC2=NC=C(N3CCN(C(OCC(C)C)=O)CC3)C=C21)=O |
| 900 | (E)-isobutyl 4-(7-(3-amino-2-cyano-3-oxoprop-1-en-1-yl)-5H-pyrrolo[2,3-b]pyrazin-2-yl)piperazine-1-carboxylate | NC(/C(C#N)=C/C1=CNC2=NC=C(N3CCN(C(OCC(C)C)=O)CC3)N=C21)=O |
| 901 | (E)-isobutyl 4-(7-(3-amino-3-oxoprop-1-en-1-yl)-5H-pyrrolo[2,3-b]pyrazin-2-yl)piperazine-1-carboxylate | NC(/C=C/C1=CNC2=NC=C(N3CCN(C(OCC(C)C)=O)CC3)N=C21)=O |
| 902 | (E)-isopropyl 4-(3-(3-amino-2-cyano-3-oxoprop-1-en-1-yl)-1H-pyrrolo[2,3-b]pyridin-5-yl)piperazine-1-carboxylate | NC(/C(C#N)=C/C1=CNC2=NC=C(N3CCN(C(OC(C)C)=O)CC3)C=C21)=O |

TABLE 2-continued

Additional Examples

| Example | Structure | Name | Smiles |
|---|---|---|---|
| 903 | 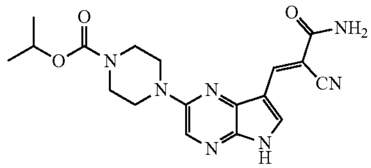 [SMILES: CC(C)OC(=O)N1CCN(c2cnc3[nH]cc(/C=C(\C#N)C(N)=O)c3n2)CC1] | (E)-isopropyl 4-(7-(3-amino-2-cyano-3-oxoprop-1-en-1-yl)-5H-pyrrolo[2,3-b]pyrazin-2-yl)piperazine-1-carboxylate | NC(/C(C#N)=C/C1=CNC2=NC=C(N3CCN(C(OC(C)C)=O)CC3)N=C21)=O |
| 904 | 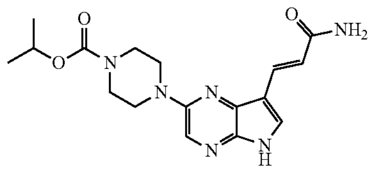 [SMILES: CC(C)OC(=O)N1CCN(c2cnc3[nH]cc(/C=C/C(N)=O)c3n2)CC1] | (E)-isopropyl 4-(7-(3-amino-3-oxoprop-1-en-1-yl)-5H-pyrrolo[2,3-b]pyrazin-2-yl)piperazine-1-carboxylate | NC(/C=C/C1=CNC2=NC=C(N3CCN(C(OC(C)C)=O)CC3)N=C21)=O |
| 905 | 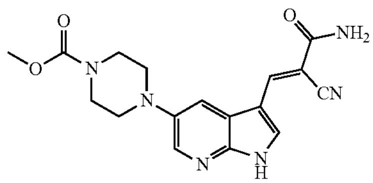 [SMILES: COC(=O)N1CCN(c2cnc3[nH]cc(/C=C(\C#N)C(N)=O)c3c2)CC1] | (E)-methyl 4-(3-(3-amino-2-cyano-3-oxoprop-1-en-1-yl)-1H-pyrrolo[2,3-b]pyridin-5-yl)piperazine-1-carboxylate | NC(/C(C#N)=C/C1=CNC2=NC=C(N3CCN(C(OC)=O)CC3)C=C21)=O |
| 906 | 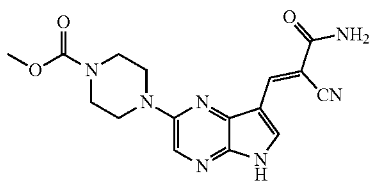 [SMILES: COC(=O)N1CCN(c2cnc3[nH]cc(/C=C(\C#N)C(N)=O)c3n2)CC1] | (E)-methyl 4-(7-(3-amino-2-cyano-3-oxoprop-1-en-1-yl)-5H-pyrrolo[2,3-b]pyrazin-2-yl)piperazine-1-carboxylate | NC(/C(C#N)=C/C1=CNC2=NC=C(N3CCN(C(OC)=O)CC3)N=C21)=O |
| 907 | 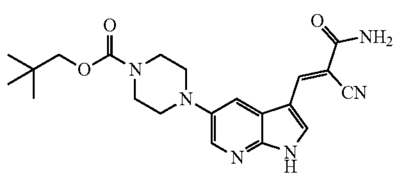 [SMILES: CC(C)(C)COC(=O)N1CCN(c2cnc3[nH]cc(/C=C(\C#N)C(N)=O)c3c2)CC1] | (E)-neopentyl 4-(3-(3-amino-2-cyano-3-oxoprop-1-en-1-yl)-1H-pyrrolo[2,3-b]pyridin-5-yl)piperazine-1-carboxylate | NC(/C(C#N)=C/C1=CNC2=NC=C(N3CCN(C(OCC(C)(C)C)=O)CC3)C=C21)=O |
| 908 | 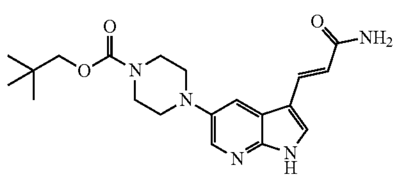 [SMILES: CC(C)(C)COC(=O)N1CCN(c2cnc3[nH]cc(/C=C/C(N)=O)c3c2)CC1] | (E)-neopentyl 4-(3-(3-amino-3-oxoprop-1-en-1-yl)-1H-pyrrolo[2,3-b]pyridin-5-yl)piperazine-1-carboxylate | NC(/C=C/C1=CNC2=NC=C(N3CCN(C(OCC(C)(C)C)=O)CC3)C=C21)=O |
| 909 | 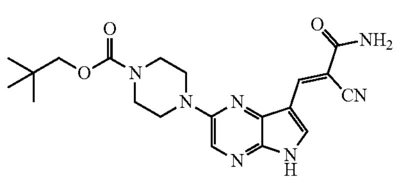 [SMILES: CC(C)(C)COC(=O)N1CCN(c2cnc3[nH]cc(/C=C(\C#N)C(N)=O)c3n2)CC1] | (E)-neopentyl 4-(7-(3-amino-2-cyano-3-oxoprop-1-en-1-yl)-5H-pyrrolo[2,3-b]pyrazin-2-yl)piperazine-1-carboxylate | NC(/C(C#N)=C/C1=CNC2=NC=C(N3CCN(C(OCC(C)(C)C)=O)CC3)N=C21)=O |
| 910 | 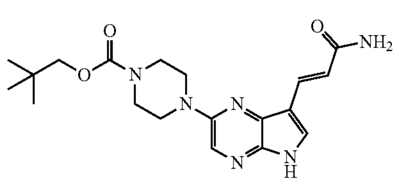 [SMILES: CC(C)(C)COC(=O)N1CCN(c2cnc3[nH]cc(/C=C/C(N)=O)c3n2)CC1] | (E)-neopentyl 4-(7-(3-amino-3-oxoprop-1-en-1-yl)-5H-pyrrolo[2,3-b]pyrazin-2-yl)piperazine-1-carboxylate | NC(/C=C/C1=CNC2=NC=C(N3CCN(C(OCC(C)(C)C)=O)CC3)N=C21)=O |

TABLE 2-continued

Additional Examples

| Example | Structure | Name | Smiles |
|---|---|---|---|
| 911 | 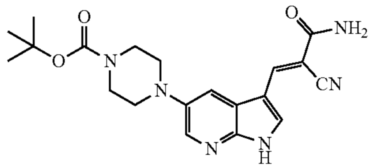 [SMILES: CC(C)(C)OC(=O)N1CCN(c2cnc3[nH]cc(/C=C(\C#N)C(N)=O)c3c2)CC1] | (E)-tert-butyl 4-(3-(3-amino-2-cyano-3-oxoprop-1-en-1-yl)-1H-pyrrolo[2,3-b]pyridin-5-yl)piperazine-1-carboxylate | NC(/C(C#N)=C/C1=CNC2=NC=C(N3CCN(C(OC(C)(C)C)=O)CC3)C=C21)=O |
| 912 | 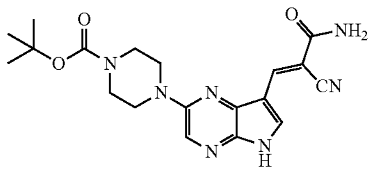 [SMILES: CC(C)(C)OC(=O)N1CCN(c2cnc3[nH]cc(/C=C(\C#N)C(N)=O)c3n2)CC1] | (E)-tert-butyl 4-(7-(3-amino-2-cyano-3-oxoprop-1-en-1-yl)-5H-pyrrolo[2,3-b]pyrazin-2-yl)piperazine-1-carboxylate | NC(/C(C#N)=C/C1=CNC2=NC=C(N3CCN(C(OC(C)(C)C)=O)CC3)N=C21)=O |
| 913 | 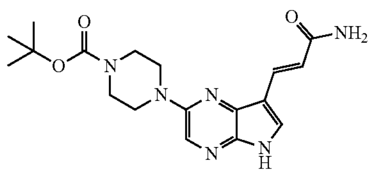 [SMILES: CC(C)(C)OC(=O)N1CCN(c2cnc3[nH]cc(/C=C/C(N)=O)c3n2)CC1] | (E)-tert-butyl 4-(7-(3-amino-3-oxoprop-1-en-1-yl)-5H-pyrrolo[2,3-b]pyrazin-2-yl)piperazine-1-carboxylate | NC(/C=C/C1=CNC2=NC=C(N3CCN(C(OC(C)(C)C)=O)CC3)N=C21)=O |
| 914 | 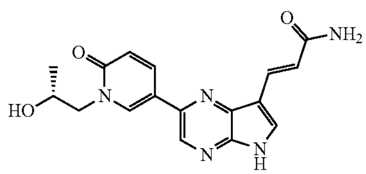 [SMILES: C[C@@H](O)Cn1cc(-c2cnc3[nH]cc(/C=C/C(N)=O)c3n2)ccc1=O] | (R,E)-3-(2-(1-(2-hydroxypropyl)-6-oxo-1,6-dihydropyridin-3-yl)-5H-pyrrolo[2,3-b]pyrazin-7-yl)acrylamide | NC(/C=C/C1=CNC2=NC=C(C(C=C3)=CN(C[C@H](O)C)C3=O)N=C21)=O |
| 915 | 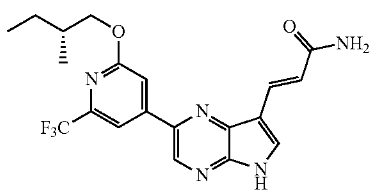 [SMILES: CC[C@@H](C)COc1cc(-c2cnc3[nH]cc(/C=C/C(N)=O)c3n2)cc(C(F)(F)F)n1] | (R,E)-3-(2-(2-(2-methylbutoxy)-6-(trifluoromethyl)pyridin-4-yl)-5H-pyrrolo[2,3-b]pyrazin-7-yl)acrylamide | NC(/C=C/C1=CNC2=NC=C(C3=CC(OC[C@@H](CC)C)=NC(C(F)(F)F)=C3)N=C21)=O |
| 916 | 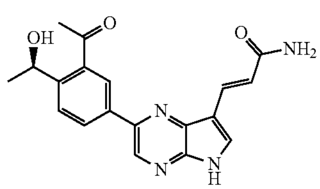 [SMILES: CC(=O)c1cc(-c2cnc3[nH]cc(/C=C/C(N)=O)c3n2)ccc1[C@@H](C)O] | (R,E)-3-(2-(3-acetyl-4-(1-hydroxyethyl)phenyl)-5H-pyrrolo[2,3-b]pyrazin-7-yl)acrylamide | NC(/C=C/C1=CNC2=NC=C(C3=CC(C(C)=O)=C([C@H](O)C)C=C3)N=C21)=O |
| 917 | 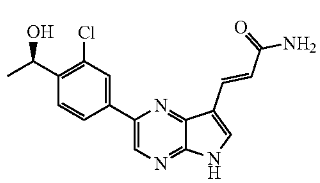 [SMILES: C[C@@H](O)c1ccc(-c2cnc3[nH]cc(/C=C/C(N)=O)c3n2)cc1Cl] | (R,E)-3-(2-(3-chloro-4-(1-hydroxyethyl)phenyl)-5E-pyrrolo[2,3-b]pyrazin-7-yl)acrylamide | NC(/C=C/C1=CNC2=NC=C(C3=CC(Cl)=C([C@H](O)C)C=C3)N=C21)=O |
| 918 | 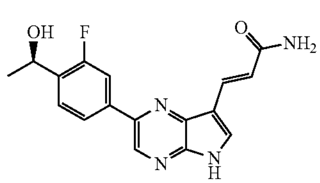 [SMILES: C[C@@H](O)c1ccc(-c2cnc3[nH]cc(/C=C/C(N)=O)c3n2)cc1F] | (R,E)-3-(2-(3-fluoro-4-(1-hydroxyethyl)phenyl)-5H-pyrrolo[2,3-b]pyrazin-7-yl)acrylamide | NC(/C=C/C1=CNC2=NC=C(C3=CC(F)=C([C@H](O)C)C=C3)N=C21)=O |

TABLE 2-continued

Additional Examples

| Example | Name | Smiles |
|---|---|---|
| 919 | (R,E)-3-(2-(4-(1-hydroxyethyl)-3-(trifluoromethyl)phenyl)-5H-pyrrolo[2,3-b]pyrazin-7-yl)acrylamide | NC(/C=C/C1=CNC2=NC=C(C3=CC(C(F)(F)F)=C([C@H](O)C)C=C3)N=C21)=O |
| 920 | (R,E)-3-(2-(4-(1-hydroxyethyl)phenyl)-5H-pyrrolo[2,3-b]pyrazin-7-yl)acrylamide | NC(/C=C/C1=CNC2=NC=C(C3=CC=C([C@H](O)C)C=C3)N=C21)=O |
| 921 | (R,E)-3-(2-(5-fluoro-1-(2-hydroxypropyl)-6-oxo-1,6-dihydropyridin-3-yl)-5H-pyrrolo[2,3-b]pyrazin-7-yl)acrylamide | NC(/C=C/C1=CNC2=NC=C(C(C=C3F)=CN(C[C@H](O)C)C3=O)N=C21)=O |
| 922 | (R,E)-3-(2-(5-fluoro-6-(2-hydroxypropoxy)pyridin-3-yl)-5H-pyrrolo[2,3-b]pyrazin-7-yl)acrylamide | NC(/C=C/C1=CNC2=NC=C(C3=CC(F)=C(OC[C@@H](C)O)N=C3)N=C21)=O |
| 923 | (R,E)-3-(2-(6-(2-cyanopropoxy)-5-fluoropyridin-3-yl)-5H-pyrrolo[2,3-b]pyrazin-7-yl)acrylamide | NC(/C=C/C1=CNC2=NC=C(C3=CC(F)=C(OC[C@H](C)C#N)N=C3)N=C21)=O |
| 924 | (R,E)-3-(2-(6-(2-cyanopropoxy)pyridin-3-yl)-5H-pyrrolo[2,3-b]pyrazin-7-yl)acrylamide | NC(/C=C/C1=CNC2=NC=C(C3=CC=C(OC[C@H](C)C#N)N=C3)N=C21)=O |
| 925 | (R,E)-3-(2-(6-(2-hydroxypropoxy)pyridin-3-yl)-5H-pyrrolo[2,3-b]pyrazin-7-yl)acrylamide | NC(/C=C/C1=CNC2=NC=C(C3=CC=C(OC[C@@H](C)O)N=C3)N=C21)=O |
| 926 | (R,E)-3-(5-(1-(2-hydroxypropyl)-6-oxo-1,6-dihydropyridin-3-yl)-1H-pyrrolo[2,3-b]pyridin-3-yl)acrylamide | NC(/C=C/C1=CNC2=NC=C(C(C=C3)=CN(C[C@H](O)C)C3=O)C=C21)=O |

TABLE 2-continued

Additional Examples

| Example | Structure | Name | Smiles |
|---|---|---|---|
| 927 | 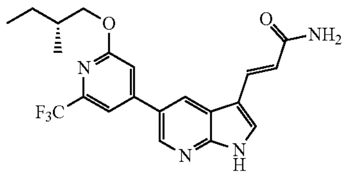 [SMILES: CC[C@@H](C)COc1cc(-c2cnc3[nH]cc(/C=C/C(N)=O)c3c2)cc(C(F)(F)F)n1] | (R,E)-3-(5-(2-(2-methylbutoxy)-6-(trifluoromethyl)pyridin-4-yl)-1H-pyrrolo[2,3-b]pyridin-3-yl)acrylamide | NC(/C=C/C1=CNC2=NC=C(C3=CC(OC[C@@H](CC)C)=NC(C(F)(F)F)=C3)C=C21)=O |
| 928 | 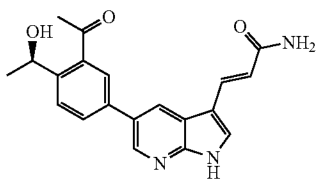 [SMILES: CC(=O)c1cc(-c2cnc3[nH]cc(/C=C/C(N)=O)c3c2)ccc1[C@@H](C)O] | (R,E)-3-(5-(3-acetyl-4-(1-hydroxyethyl)phenyl)-1H-pyrrolo[2,3-b]pyridin-3-yl)acrylamide | NC(/C=C/C1=CNC2=NC=C(C3=CC(C(C)=O)=C([C@H](O)C)C=C3)C=C21)=O |
| 929 | 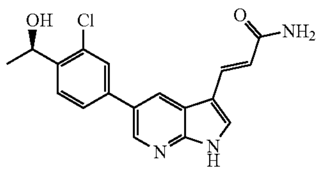 [SMILES: C[C@@H](O)c1ccc(-c2cnc3[nH]cc(/C=C/C(N)=O)c3c2)cc1Cl] | (R,E)-3-(5-(3-chloro-4-(1-hydroxyethyl)phenyl)-1H-pyrrolo[2,3-b]pyridin-3-yl)acrylamide | NC(/C=C/C1=CNC2=NC=C(C3=CC(Cl)=C([C@H](O)C)C=C3)C=C21)=O |
| 930 | 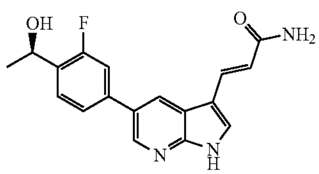 [SMILES: C[C@@H](O)c1ccc(-c2cnc3[nH]cc(/C=C/C(N)=O)c3c2)cc1F] | (R,E)-3-(5-(3-fluoro-4-(1-hydroxyethyl)phenyl)-1H-pyrrolo[2,3-b]pyridin-3-yl)acrylamide | NC(/C=C/C1=CNC2=NC=C(C3=CC(F)=C([C@H](O)C)C=C3)C=C21)=O |
| 931 | 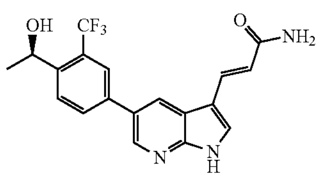 | (R,E)-3-(5-(4-(1-hydroxyethyl)-3-(trifluoromethyl)phenyl)-1H-pyrrolo[2,3-b]pyridin-3-yl)acrylamide | NC(/C=C/C1=CNC2=NC=C(C3=CC(C(F)(F)F)=C([C@H](O)C)C=C3)C=C21)=O |
| 932 | 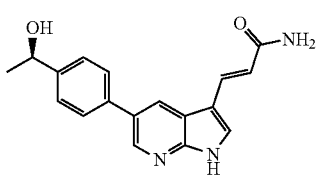 [SMILES: C[C@@H](O)c1ccc(-c2cnc3[nH]cc(/C=C/C(N)=O)c3c2)cc1] | (R,E)-3-(5-(4-(1-hydroxyethyl)phenyl)-1H-pyrrolo[2,3-b]pyridin-3-yl)acrylamide | NC(/C=C/C1=CNC2=NC=C(C3=CC=C([C@H](O)C)C=C3)C=C21)=O |
| 933 | 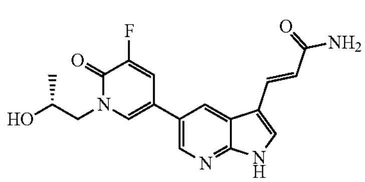 [SMILES: C[C@@H](O)Cn1cc(-c2cnc3[nH]cc(/C=C/C(N)=O)c3c2)cc(F)c1=O] | (R,E)-3-(5-(5-fluoro-1-(2-hydroxypropyl)-6-oxo-1,6-dihydropyridin-3-yl)-1H-pyrrolo[2,3-b]pyridin-3-yl)acrylamide | NC(/C=C/C1=CNC2=NC=C(C(C=C3F)=CN(C[C@H](O)C)C3=O)C=C21)=O |
| 934 | 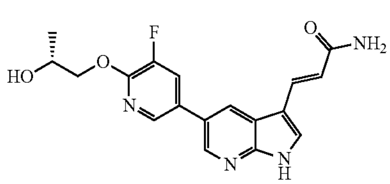 | (R,E)-3-(5-(5-fluoro-6-(2-hydroxypropoxy)pyridin-3-yl)-1H-pyrrolo[2,3-b]pyridin-3-yl)acrylamide | NC(/C=C/C1=CNC2=NC=C(C3=CC(F)=C(OC[C@@H](C)O)N=C3)C=C21)=O |

TABLE 2-continued

Additional Examples

| Example | Structure | Name | Smiles |
|---|---|---|---|
| 935 | 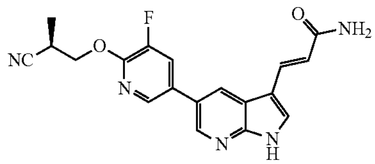 | (R,E)-3-(5-(6-(2-cyanopropoxy)-5-fluoropyridin-3-yl)-1H-pyrrolo[2,3-b]pyridin-3-yl)acrylamide | NC(/C=C/C1=CNC2=NC=C(C3=CC(F)=C(OC[C@H](C)C#N)N=C3)C=C21)=O |
| 936 | 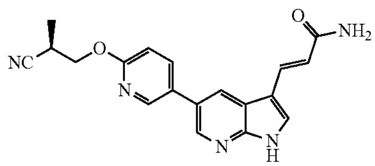 [SMILES: C[C@H](C#N)COc1ccc(-c2cnc3[nH]cc(/C=C/C(N)=O)c3c2)cn1] | (R,E)-3-(5-(6-(2-cyanopropoxy)pyridin-3-yl)-1H-pyrrolo[2,3-b]pyridin-3-yl)acrylamide | NC(/C=C/C1=CNC2=NC=C(C3=CC=C(OC[C@H](C)C#N)N=C3)C=C21)=O |
| 937 | 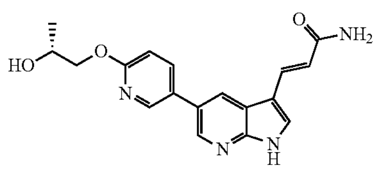 [SMILES: C[C@@H](O)COc1ccc(-c2cnc3[nH]cc(/C=C/C(N)=O)c3c2)cn1] | (R,E)-3-(5-(6-(2-hydroxypropoxy)pyridin-3-yl)-1H-pyrrolo[2,3-b]pyridin-3-yl)acrylamide | NC(/C=C/C1=CNC2=NC=C(C3=CC=C(OC[C@@H](C)O)N=C3)C=C21)=O |
| 938 | 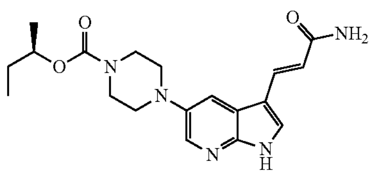 [SMILES: CC[C@@H](C)OC(=O)N1CCN(c2cnc3[nH]cc(/C=C/C(N)=O)c3c2)CC1] | R,E)-sec-butyl 4-(3-(3-amino-3-oxoprop-1-en-1-yl)-1H-pyrrolo[2,3-b]pyridin-5-yl)piperazine-1-carboxylate | NC(/C=C/C1=CNC2=NC=C(N3CCN(C(O[C@ @H](CC)C)=O)CC3)C=C21)=O |
| 939 | 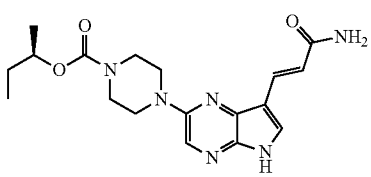 [SMILES: CC[C@@H](C)OC(=O)N1CCN(c2cnc3[nH]cc(/C=C/C(N)=O)c3n2)CC1] | (R,E)-sec-buty 4-(7-(3-amino-3-oxoprop-1-en-1-yl)-5H-pyrrolo[2,3-b]pyrazin-2-yl)piperazine-1-carboxylate | NC(/C=C/C1=CNC2=NC=C(N3CCN(C(O[C@ @H](CC)C)=O)CC3)N=C21)=O |
| 940 | 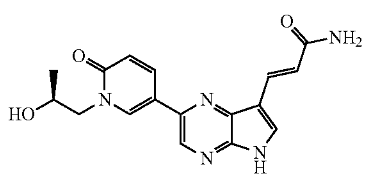 [SMILES: C[C@H](O)Cn1cc(-c2cnc3[nH]cc(/C=C/C(N)=O)c3n2)ccc1=O] | (S,E)-3-(2-(1-(2-hydroxypropyl)-6-oxo-1,6-dihydropyridin-3-yl)-5H-pyrrolo[2,3-b]pyrazin-7-yl)acrylamide | NC(/C=C/C1=CNC2=NC=C(C(C=C3)=CN(C[C@ @H](O)C)C3=O)N=C21)=O |
| 941 | 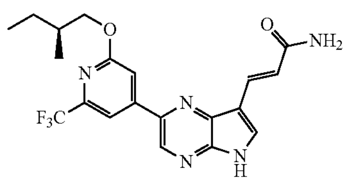 [SMILES: CC[C@H](C)COc1cc(-c2cnc3[nH]cc(/C=C/C(N)=O)c3n2)cc(C(F)(F)F)n1] | (S,E)-3-(2-(2-(2-methylbutoxy)-6-(trifluoromethyl)pyridin-4-yl)-5H-pyrrolo[2,3-b]pyrazin-7-yl)acrylamide | NC(/C=C/C1=CNC2=NC=C(C3=CC(OC[C@H](CC)C)=NC(C(F)(F)F)=C3)N=C21)=O |
| 942 | 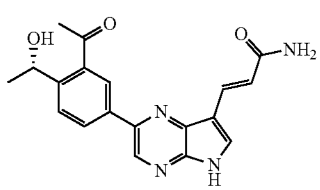 [SMILES: CC(=O)c1cc(-c2cnc3[nH]cc(/C=C/C(N)=O)c3n2)ccc1[C@H](C)O] | (S,E)-3-(2-(3-acetyl-4-(1-hydroxyethyl)phenyl)-5H-pyrrolo[2,3-b]pyrazin-7-yl)acrylamide | NC(/C=C/C1=CNC2=NC=C(C3=CC(C(C)=O)=C([C@ @H](O)C)C=C3)N=C21)=O |

TABLE 2-continued

Additional Examples

| Example | Name | Smiles |
|---|---|---|
| 943 | (S,E)-3-(2-(3-chloro-4-(1-hydroxyethyl)phenyl)-5H-pyrrolo[2,3-b]pyrazin-7-yl)acrylamide | NC(/C=C/C1=CNC2=NC=C(C3=CC(C1)=C([C@@H](O)C)C=C3)N=C21)=O |
| 944 | (S,E)-3-(2-(3-fluoro-4-(1-hydroxyethyl)phenyl)-5H-pyrrolo[2,3-b]pyrazin-7-yl)acrylamide | NC(/C=C/C1=CNC2=NC=C(C3=CC(F)=C([C@@H](O)C)C=C3)N=C21)=O |
| 945 | (S,E)-3-(2-(4-(1-hydroxyethyl)-3-(trifluoromethyl)phenyl)-5H-pyrrolo[2,3-b]pyrazin-7-yl)acrylamide | NC(/C=C/C1=CNC2=NC=C(C3=CC(C(F)(F)F)=C([C@@H](O)C)C=C3)N=C21)=O |
| 946 | (S,E)-3-(2-(4-(1-hydroxyethyl)phenyl)-5H-pyrrolo[2,3-b]pyrazin-7-yl)acrylamide | NC(/C=C/C1=CNC2=NC=C(C3=CC=C([C@@H](O)C)C=C3)N=C21)=O |
| 947 | (S,E)-3-(2-(5-fluoro-1-(2-hydroxypropyl)-6-oxo-1,6-dihydropyridin-3-yl)-5H-pyrrolo[2,3-b]pyrazin-7-yl)acrylamide | NC(/C=C/C1=CNC2=NC=C(C(C=C3F)=CN(C[C@@H](O)C)C3=O)N=C21)=O |
| 948 | (S,E)-3-(2-(5-fluoro-6-(2-hydroxypropoxy)pyridin-3-yl)-5H-pyrrolo[2,3-b]pyrazin-7-yl)acrylamide | NC(/C=C/C1=CNC2=NC=C(C3=CC(F)=C(OC[C@H](C)O)N=C3)N=C21)=O |
| 949 | (S,E)-3-(2-(6-(2-hydroxypropoxy)pyridin-3-yl)-5H-pyrrolo[2,3-b]pyrazin-7-yl)acrylamide | NC(/C=C/C1=CNC2=NC=C(C3=CC=C(OC[C@H](C)O)N=C3)N=C21)=O |
| 950 | (S,E)-3-(5-(1-(2-hydroxypropyl)-6-oxo-1,6-dihydropyridin-3-yl)-1H-pyrrolo[2,3-b]pyridin-3-yl)acrylamide | NC(/C=C/C1=CNC2=NC=C(C(C=C3)=CN(C[C@@H](O)C)C3=O)C=C21)=O |

TABLE 2-continued

Additional Examples

| Example | Structure | Name | Smiles |
|---|---|---|---|
| 951 | 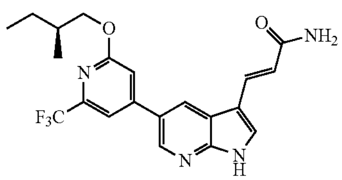 [SMILES: CC[C@H](C)COc1cc(-c2cnc3[nH]cc(/C=C/C(N)=O)c3c2)cc(C(F)(F)F)n1] | (S,E)-3-(5-(2-(2-methylbutoxy)-6-(trifluoromethyl)pyridin-4-yl)-1H-pyrrolo[2,3-b]pyridin-3-yl)acrylamide | NC(/C=C/C1=CNC2=NC=C(C3=CC(OC[C@H](CC)C)=NC(C(F)(F)F)=C3)C=C21)=O |
| 952 | 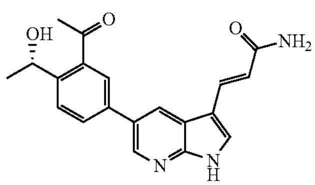 [SMILES: CC(=O)c1cc(-c2cnc3[nH]cc(/C=C/C(N)=O)c3c2)ccc1[C@H](C)O] | (S,E)-3-(5-(3-acetyl-4-(1-hydroxyethyl)phenyl)-1H-pyrrolo[2,3-b]pyridin-3-yl)acrylamide | NC(/C=C/C1=CNC2=NC=C(C3=CC(C(C)O)=C([C@@H](O)C)C=C3)C=C21)=O |
| 953 | 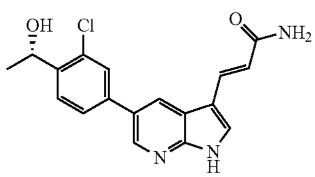 [SMILES: C[C@H](O)c1ccc(-c2cnc3[nH]cc(/C=C/C(N)=O)c3c2)cc1Cl] | (S,E)-3-(5-(3-chloro-4-(1-hydroxyethyl)phenyl)-1H-pyrrolo[2,3-b]pyridin-3-yl)acrylamide | NC(/C=C/C1=CNC2=NC=C(C3=CC(Cl)=C([C@@H](O)C)C=C3)C=C21)=O |
| 954 | 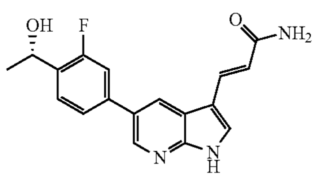 [SMILES: C[C@H](O)c1ccc(-c2cnc3[nH]cc(/C=C/C(N)=O)c3c2)cc1F] | (S,E)-3-(5-(3-fluoro-4-(1-hydroxyethyl)phenyl)-1H-pyrrolo[2,3-b]pyridin-3-yl)acrylamide | NC(/C=C/C1=CNC2=NC=C(C3=CC(F)=C([C@@H](O)C)C=C3)C=C21)=O |
| 955 | 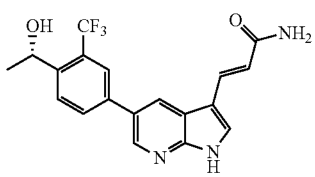 [SMILES: C[C@H](O)c1ccc(-c2cnc3[nH]cc(/C=C/C(N)=O)c3c2)cc1C(F)(F)F] | (S,E)-3-(5-(4-(1-hydroxyethyl)-3-(trifluoromethyl)phenyl)-1H-pyrrolo[2,3-b]pyridin-3-yl)acrylamide | NC(/C=C/C1=CNC2=NC=C(C3=CC(C(F)(F)F)=C([C@@H](O)C)C=C3)C=C21)=O |
| 956 | 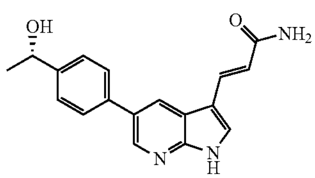 | (S,E)-3-(5-(4-(1-hydroxyethyl)phenyl)-1H-pyrrolo[2,3-b]pyridin-3-yl)acrylamide | NC(/C=C/C1=CNC2=NC=C(C3=CC=C([C@@H](O)C)C=C3)C=C21)=O |
| 957 | 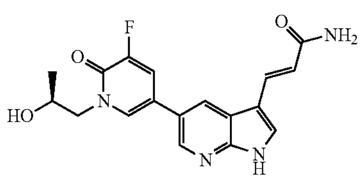 | (S,E)-3-(5-(5-fluoro-1-(2-hydroxypropyl)-6-oxo-1,6-dihydropyridin-3-yl)-1H-pyrrolo[2,3-b]pyridin-3-yl)acrylamide | NC(/C=C/C1=CNC2=NC=C(C(C=C3F)=CN(C[C@@H](O)C)C3=O)C=C21)=O |
| 958 | 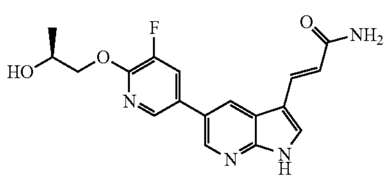 [SMILES: C[C@H](O)COc1ncc(-c2cnc3[nH]cc(/C=C/C(N)=O)c3c2)cc1F] | (S,E)-3-(5-(5-fluoro-6-(2-hydroxypropoxy)pyridin-3-yl)-1H-pyrrolo[2,3-b]pyridin-3-yl)acrylamide | NC(/C=C/C1=CNC2=NC=C(C3=CC(F)=C(OC[C@H](C)O)N=C3)C=C21)=O |

TABLE 2-continued

Additional Examples

| Example | Name | Smiles |
|---|---|---|
| 959 | (S,E)-3-(5-(6-(2-cyanopropoxy)-5-fluoropyridin-3-yl)-1H-pyrrolo[2,3-b]pyridin-3-yl)acrylamide | NC(/C=C/C1=CNC2=NC=C(C3=CC(F)=C(OC[C@ @H](C)C#N)N=C3)C=C21)=O |
| 960 | (S,E)-3-(5-(6-(2-cyanopropoxy)pyridin-3-yl)-1H-pyrrolo[2,3-b]pyridin-3-yl)acrylamide | NC(/C=C/C1=CNC2=NC=C(C3=CC=C(OC[C@ @H](C)C#N)N=C3)C=C21)=O |
| 961 | (S,E)-3-(5-(6-(2-hydroxypropoxy)pyridin-3-yl)-1H-pyrrolo[2,3-b]pyridin-3-yl)acrylamide | NC(/C=C/C1=CNC2=NC=C(C3=CC=C(OC[C@H](C)O)N=C3)C=C21)=O |
| 963 | (S,E)-sec-butyl 4-(7-(3-amino-3-oxoprop-1-en-1-yl)-5H-pyrrolo[2,3-b]pyrazin-2-yl)piperazine-1-carboxylate | NC(/C=C/C1=CNC2=NC=C(N3CCN(C(O[C@H](CC)C)=O)CC3)N=C21)=O |
| 964 | (Z)-4-(2-((1-hydroxypropan-2-yl)oxy)-5H-pyrrolo[2,3-b]pyrazin-7-yl)but-2-enenitrile | CC(CO)OC1=CN=C(NC=C2C/C=C\C#N)C2=N1 |
| 695 | (Z)-4-(2-(2-hydroxy-2-methylpropoxy)-5H-pyrrolo[2,3-b]pyrazin-7-yl)but-2-enenitrile | OC(C)(C)COC1=CN=C(NC=C2C/C=C\C#N)C2=N1 |
| 966 | (Z)-4-(2-(cyclopentylamino)-5H-pyrrolo[2,3-b]pyrazin-7-yl)but-2-enenitrile | N#C/C=C\CC1=CNC2=NC=C(NC3CCCC3)N=C21 |
| 967 | (Z)-4-(2-(cyclopentyloxy)-5H-pyrrolo[2,3-b]pyrazin-7-yl)but-2-enenitrile | N#C/C=C\CC1=CNC2=NC=C(OC3CCCC3)N=C21 |

TABLE 2-continued

Additional Examples

| Example | Structure | Name | Smiles |
|---|---|---|---|
| 968 | 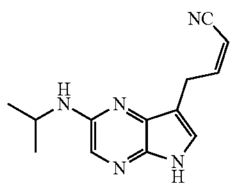 [SMILES: CC(C)Nc1cnc2[nH]cc(C/C=C\C#N)c2n1] | (Z)-4-(2-(isopropylamino)-5H-pyrrolo[2,3-b]pyrazin-7-yl)but-2-enenitrile | CC(C)NC1=CN=C(NC=C2C/C=C\C#N)C2=N1 |
| 969 | 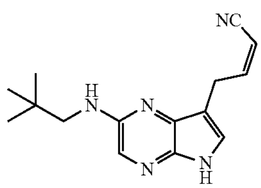 [SMILES: CC(C)(C)CNc1cnc2[nH]cc(C/C=C\C#N)c2n1] | (Z)-4-(2-(neopentylamino)-5H-pyrrolo[2,3-b]pyrazin-7-yl)but-2-enenitrile | CC(C)(C)CNC1=CN=C(NC=C2C/C=C\C#N)C2=N1 |
| 970 | 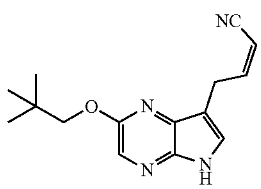 [SMILES: CC(C)(C)COc1cnc2[nH]cc(C/C=C\C#N)c2n1] | (Z)-4-(2-(neopentyloxy)-5H-pyrrolo[2,3-b]pyrazin-7-yl)but-2-enenitrile | CC(C)(C)COC1=CN=C(NC=C2C/C=C\C#N)C2=N1 |
| 971 | 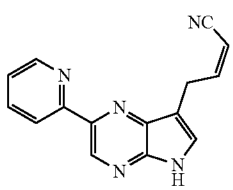 [SMILES: N#C/C=C\Cc1c[nH]c2ncc(-c3ccccn3)nc12] | (Z)-4-(2-(pyridin-2-yl)-5H-pyrrolo[2,3-b]pyrazin-7-yl)but-2-enenitrile | N#C/C=C\CC1=CNC2=NC=C(C3=NC=C=C3)N=C21 |
| 972 | 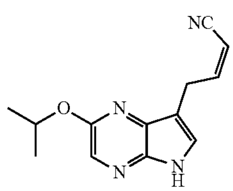 [SMILES: CC(C)Oc1cnc2[nH]cc(C/C=C\C#N)c2n1] | (Z)-4-(2-isopropoxy-5H-pyrrolo[2,3-b]pyrazin-7-yl)but-2-enenitrile | CC(C)OC1=CN=C(NC=C2C/C=C\C#N)C2=N1 |
| 973 | 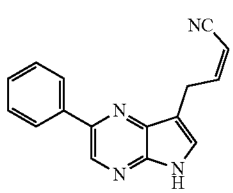 [SMILES: N#C/C=C\Cc1c[nH]c2ncc(-c3ccccc3)nc12] | (Z)-4-(2-phenyl-5H-pyrrolo[2,3-b]pyrazin-7-yl)but-2-enenitrile | N#C/C=C\CC1=CNC2=NC=C(C3=CC=CC=C3)N=C21 |
| 974 | 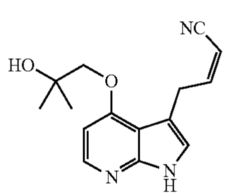 [SMILES: CC(C)(O)COc1ccnc2[nH]cc(C/C=C\C#N)c12] | (Z)-4-(4-(2-hydroxy-2-methylpropoxy)-1H-pyrrolo[2,3-b]pyridin-3-yl)but-2-enenitrile | OC(C)(C)COC1=C2C(NC=C2C/C=C\C#N)=NC=C1 |

TABLE 2-continued

Additional Examples

| Example | Structure | Name | Smiles |
|---|---|---|---|
| 975 | 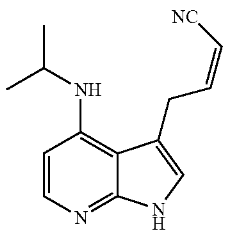 [SMILES: CC(C)Nc1ccnc2[nH]cc(C/C=C\C#N)c12] | (Z)-4-(4-(isopropylamino)-1H-pyrrolo[2,3-b]pyridin-3-yl)but-2-enenitrile | CC(C)NC1=C2C(NC=C2C/C=C\C#N)=NC=C1 |
| 976 | 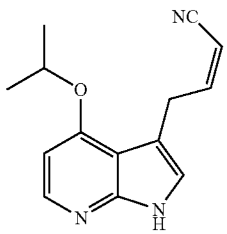 [SMILES: CC(C)Oc1ccnc2[nH]cc(C/C=C\C#N)c12] | (Z)-4-(4-isopropoxy-1H-pyrrolo[2,3-b]pyridin-3-yl)but-2-enenitrile | CC(C)OC1=C2C(NC=C2C/C=C\C#N)=NC=C1 |
| 977 | 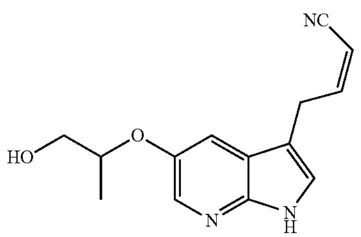 [SMILES: CC(CO)Oc1cnc2[nH]cc(C/C=C\C#N)c2c1] | (Z)-4-(5-((1-hydroxypropan-2-yl)oxy)-1H-pyrrolo[2,3-H]pyridin-3-yl)but-2-enenitrile | CC(CO)OC1=CN=C(NC=C2C/C=C\C#N)C2=C1 |
| 978 | 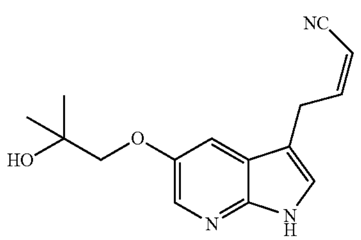 [SMILES: CC(C)(O)COc1cnc2[nH]cc(C/C=C\C#N)c2c1] | (Z)-4-(5-(2-hydroxy-2-methylpropoxy)-1H-pyrrolo[2,3-b]pyridin-3-yl)but-2-enenitrile | OC(C)(C)COC1=CN=C(NC=C2C/C=C\C#N)C2=C1 |
| 979 | 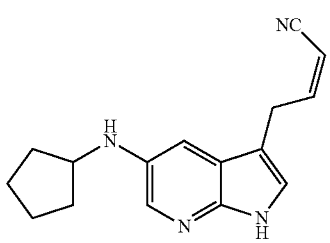 [SMILES: N#C/C=C\Cc1c[nH]c2ncc(NC3CCCC3)cc12] | (Z)-4-(5-(cyclopentylamino)-1H-pyrrolo[2,3-b]pyridin-3-yl)but-2-enenitrile | N#C/C=C\CC1=CNC2=NC=C(NC3CCCC3)C=C21 |
| 980 | 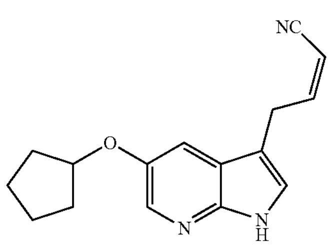 [SMILES: N#C/C=C\Cc1c[nH]c2ncc(OC3CCCC3)cc12] | (Z)-4-(5-(cyclopentyloxy)-1H-pyrrolo[2,3-b]pyridin-3-yl)but-2-enenitrile | N#C/C=C\CC1=CNC2=NC=C(OC3CCCC3)C=C21 |

TABLE 2-continued

Additional Examples

| Example | Structure | Name | Smiles |
|---|---|---|---|
| 981 | 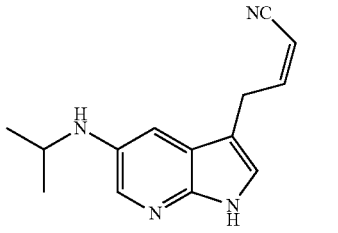 [SMILES: CC(C)Nc1cnc2[nH]cc(C/C=C\C#N)c2c1] | (Z)-4-(5-(isopropylamino)-1H-pyrrolo[2,3-b]pyridin-3-yl)but-2-enenitrile | CC(C)NC1=CN=C(NC=C2C/C=C\C#N)C2=C1 |
| 982 | 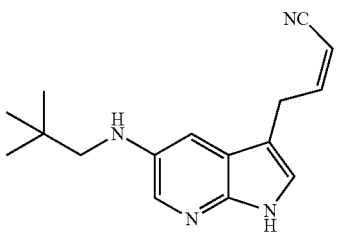 [SMILES: CC(C)(C)CNc1cnc2[nH]cc(C/C=C\C#N)c2c1] | (Z)-4-(5-(neopentylamino)-1H-pyrrolo[2,3-b]pyridin-3-yl)but-2-enenitrile | CC(C)(C)CNC1=CN=C(NC=C2C/C=C\C#N)C2=C1 |
| 983 | 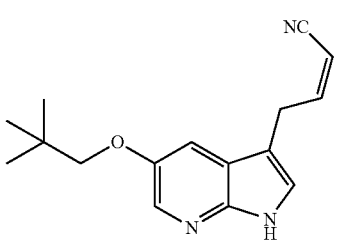 [SMILES: CC(C)(C)COc1cnc2[nH]cc(C/C=C\C#N)c2c1] | (Z)-4-(5-(neopentyloxy)-1H-pyrrolo[2,3-b]pyridin-3-yl)but-2-enenitrile | CC(C)(C)COC1=CN=C(NC=C2C/C=C\C#N)C2=C1 |
| 984 | 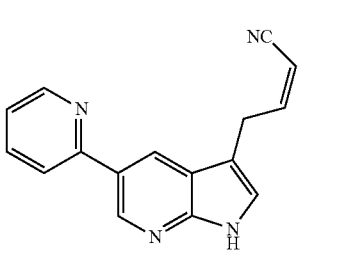 [SMILES: N#C/C=C\Cc1c[nH]c2ncc(-c3ccccn3)cc12] | (Z)-4-(5-(pyridin-2-yl)-1H-pyrrolo[2,3-b]pyridin-3-yl)but-2-enenitrile | N#C/C=C\CC1=CNC2=NC=C(C3=NC=CC=C3)C=C21 |
| 985 | 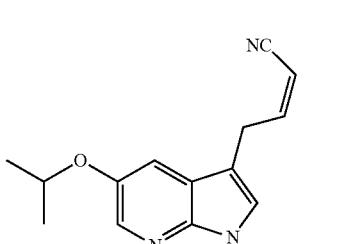 | (Z)-4-(5-isopropoxy-1H-pyrrolo[2,3-b]pyridin-3-yl)but-2-enenitrile | CC(C)OC1=CN=C(NC=C2C/C=C\C#N)C2=C1 |
| 986 | 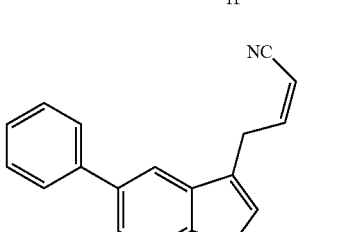 | (Z)-4-(5-phenyl-1H-pyrrolo[2,3-b]pyridin-3-yl)but-2-enenitrile | N#C/C=C\CC1=CNC2=NC=C(C3=CC=CC=C3)C=C21 |

TABLE 2-continued

Additional Examples

| Example | Structure | Name | Smiles |
|---|---|---|---|
| 987 | 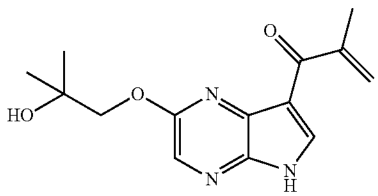 [SMILES: C=C(C)C(=O)c1c[nH]c2ncc(OCC(C)(C)O)nc12] | 1-(2-(2-hydroxy-2-methylpropoxy)-5H-pyrrolo[2,3-b]pyrazin-7-yl)-2-methylprop-2-en-1-one | OC(C)(C)COC1=CN=C(NC=C2C(C(C)=C)=O)C2=N1 |
| 988 | 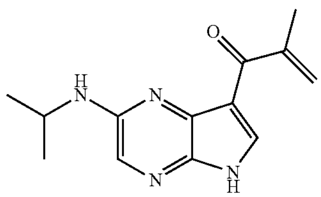 [SMILES: C=C(C)C(=O)c1c[nH]c2ncc(NC(C)C)nc12] | 1-(2-(isopropylamino)-5H-pyrrolo[2,3-b]pyrazin-7-yl)-2-methylprop-2-en-1-one | CC(C)NC1=CN=C(NC=C2C(C(C)=C)=O)C2=N1 |
| 989 | 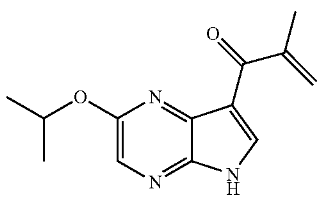 [SMILES: C=C(C)C(=O)c1c[nH]c2ncc(OC(C)C)nc12] | 1-(2-isopropoxy-5H-pyrrolo[2,3-b]pyrazin-7-yl)-2-methylprop-2-en-1-one | CC(C)OC1=CN=C(NC=C2C(C(C)=C)=O)C2=N1 |
| 990 | 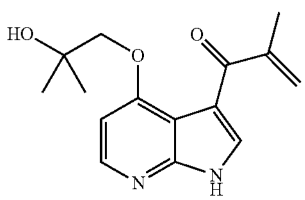 [SMILES: C=C(C)C(=O)c1c[nH]c2nccc(OCC(C)(C)O)c12] | 1-(4-(2-hydroxy-2-methylpropoxy)-1H-pyrrolo[2,3-b]pyridin-3-yl)-2-methylprop-2-en-1-one | OC(C)(C)COC1=C2C(NC=C2C(C(C)=C)=O)=NC=C1 |
| 991 | 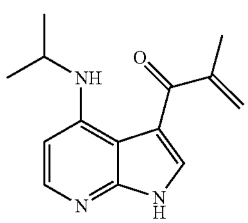 [SMILES: C=C(C)C(=O)c1c[nH]c2nccc(NC(C)C)c12] | 1-(4-(isopropylamino)-1H-pyrrolo[2,3-b]pyridin-3-yl)-2-methylprop-2-en-1-one | CC(C)NC1=C2C(NC=C2C(C(C)=C)=O)=NC=C1 |
| 992 | 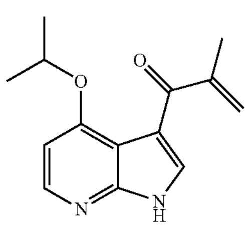 [SMILES: C=C(C)C(=O)c1c[nH]c2nccc(OC(C)C)c12] | 1-(4-isopropoxy-1H-pyrrolo[2,3-b]pyridin-3-yl)-2-methylprop-2-en-1-one | CC(C)OC1=C2C(NC=C2C(C(C)=C)=O)=NC=C1 |
| 993 | 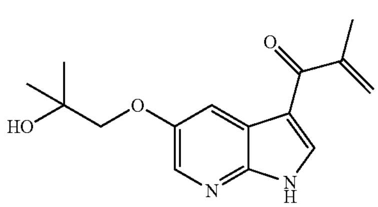 [SMILES: C=C(C)C(=O)c1c[nH]c2ncc(OCC(C)(C)O)cc12] | 1-(5-(2-hydroxy-2-methylpropoxy)-1H-pyrrolo[2,3-b]pyridin-3-yl)-2-methylprop-2-en-1-one | OC(C)(C)COC1=CN=C(NC=C2C(C(C)=C)=O)C2=C1 |

TABLE 2-continued

Additional Examples

| Example | Structure | Name | Smiles |
|---|---|---|---|
| 994 | 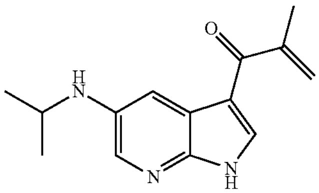 [SMILES: C=C(C)C(=O)c1c[nH]c2ncc(NC(C)C)cc12] | 1-(5-(isopropylamino)-1H-pyrrolo[2,3-b]pyridin-3-yl)-2-methylprop-2-en-1-one | CC(C)NC1=CN=C(NC=C2C(C(C)=C)=O)C2=C1 |
| 995 | 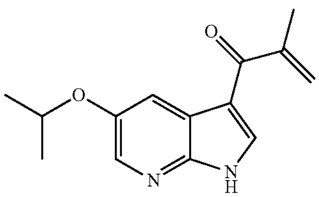 [SMILES: C=C(C)C(=O)c1c[nH]c2ncc(OC(C)C)cc12] | 1-(5-isopropoxy-1H-pyrrolo[2,3-b]pyridin-3-yl)-2-methylprop-2-en-1-one | CC(C)OC1=CN=C(NC=C2C(C(C)=C)=O)C2=C1 |
| 996 | 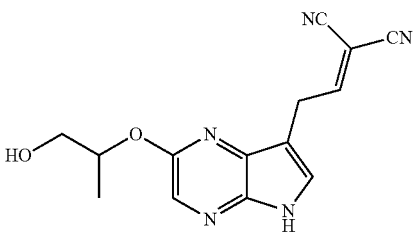 [SMILES: CC(CO)Oc1cnc2[nH]cc(CC=C(C#N)C#N)c2n1] | 2-(2-(2-((1-hydroxypropan-2-yl)oxy)-5H-pyrrolo[2,3-b]pyrazin-7-yl)ethylidene)malononitrile | CC(CO)OC1=CN=C(NC=C2C/C=C(C#N)/C#N)C2=N1 |
| 997 | 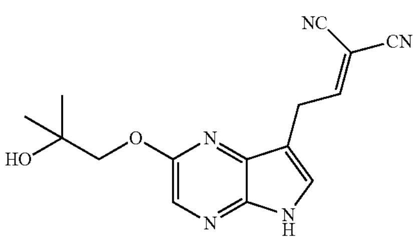 [SMILES: CC(C)(O)COc1cnc2[nH]cc(CC=C(C#N)C#N)c2n1] | 2-(2-(2-(2-hydroxy-2-methylpropoxy)-5H-pyrrolo[2,3-b]pyrazin-7-yl)ethylidene)malononitrile | OC(C)(C)COC1=CN=C(NC=C2C/C=C(C#N)/C#N)C2=N1 |
| 998 | 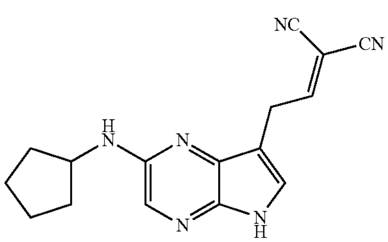 [SMILES: N#CC(C#N)=CCc1c[nH]c2ncc(NC3CCCC3)nc12] | 2-(2-(2-(cyclopentylamino)-5H-pyrrolo[2,3-b]pyrazin-7-yl)ethylidene)malononitrile | N#C/C(C#N)=C/CC1=CNC2=NC=C(NC3CCCC3)N=C21 |
| 999 | 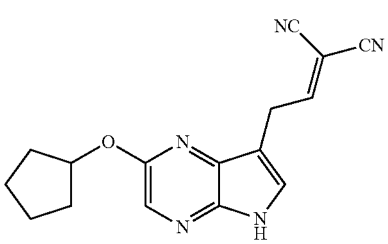 [SMILES: N#CC(C#N)=CCc1c[nH]c2ncc(OC3CCCC3)nc12] | 2-(2-(2-(cyclopentyloxy)-5H-pyrrolo[2,3-b]pyrazin-7-yl)ethylidene)malononitrile | N#C/C(C#N)=C/CC1=CNC2=NC=C(OC3CCCC3)N=C21 |

TABLE 2-continued

Additional Examples

| Example | Structure | Name | Smiles |
|---|---|---|---|
| 1000 | 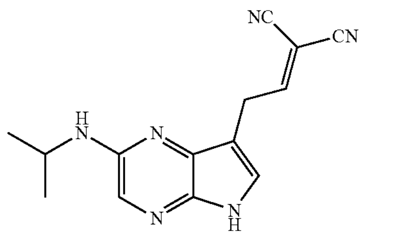 [SMILES: CC(C)Nc1cnc2[nH]cc(CC=C(C#N)C#N)c2n1] | 2-(2-(2-(isopropylamino)-5H-pyrrolo[2,3-b]pyrazin-7-yl)ethylidene)malononitrile | CC(C)NC1=CN=C(NC=C2C/C=C(C#N)/C#N)C2=N1 |
| 1001 | 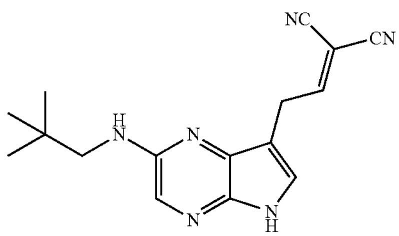 [SMILES: CC(C)(C)CNc1cnc2[nH]cc(CC=C(C#N)C#N)c2n1] | 2-(2-(2-(neopentylamino)-5H-pyrrolo[2,3-b]pyrazin-7-yl)ethylidene)malononitrile | CC(C)(C)CNC1=CN=C(NC=C2C/C=C(C#N)/C#N)C2=N1 |
| 1002 | 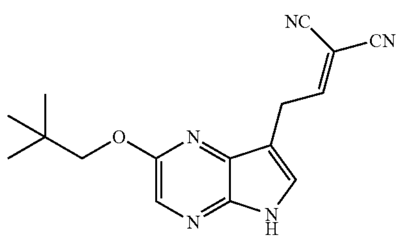 [SMILES: CC(C)(C)COc1cnc2[nH]cc(CC=C(C#N)C#N)c2n1] | 2-(2-(2-(neopentyloxy)-5H-pyrrolo[2,3-b]pyrazin-7-yl)ethylidene)malononitrile | CC(C)(C)COC1=CN=C(NC=C2C/C=C(C#N)/C#N)C2=N1 |
| 1003 | 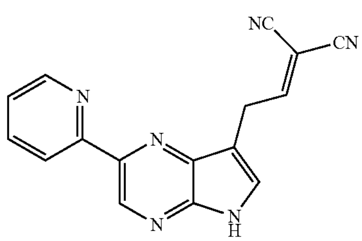 [SMILES: N#CC(C#N)=CCc1c[nH]c2ncc(-c3ccccn3)nc12] | 2-(2-(2-(pyridin-2-yl)-5H-pyrrolo[2,3-b]pyrazin-7-yl)ethylidene)malononitrile | N#C/C(C#N)=C/CC1=CNC2=NC=C(C3=NC=CC=C3)N=C21 |
| 1004 | 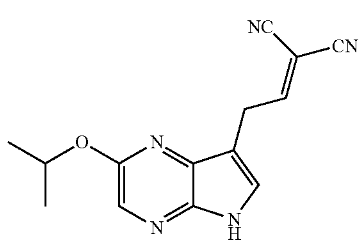 | 2-(2-(2-isopropoxy-5H-pyrrolo[2,3-b]pyrazin-7-yl)ethylidene)malononitrile | CC(C)OC1=CN=C(NC=C2C/C=C(C#N)/C#N)C2=N1 |
| 1005 | 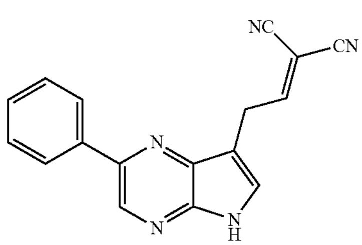 [SMILES: N#CC(C#N)=CCc1c[nH]c2ncc(-c3ccccc3)nc12] | 2-(2-(2-phenyl-5H-pyrrolo[2,3-b]pyrazin-7-yl)ethylidene)malnonitrile | N#C/C(C#N)=C/CC1=CNC2=NC=C(C3=CC=CC=C3)N=C21 |

TABLE 2-continued

Additional Examples

| Example | Structure | Name | Smiles |
|---|---|---|---|
| 1006 | 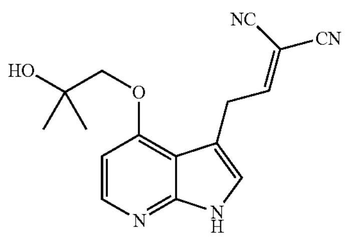 [SMILES: CC(C)(O)COc1ccnc2[nH]cc(CC=C(C#N)C#N)c12] | 2-(2-(4-(2-hydroxy-2-methylpropoxy)-1H-pyrrolo[2,3-b]pyridin-3-yl)ethylidene)malononitrile | OC(C)(C)COC1=C2C(NC=C2C/C=C(C#N)/C#N)=NC=C1 |
| 1007 | 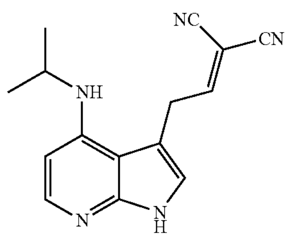 [SMILES: CC(C)Nc1ccnc2[nH]cc(CC=C(C#N)C#N)c12] | 2-(2-(4-(isopropylamino)-1H-pyrrolo[2,3-b]pyridin-3-yl)ethylidene)malononitrile | CC(C)NC1=C2C(NC=C2C/C=C(C#N)/C#N)=NC=C1 |
| 1008 | 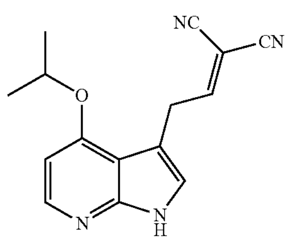 [SMILES: CC(C)Oc1ccnc2[nH]cc(CC=C(C#N)C#N)c12] | 2-(2-(4-isopropoxy-1H-pyrrolo[2,3-b]pyridin-3-yl)ethylidene)malononitrile | CC(C)OC1=C2C(NC=C2C/C=C(C#N)/C#N)=NC=C1 |
| 1009 | 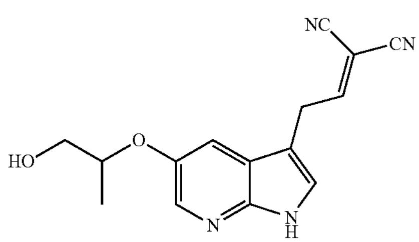 [SMILES: CC(CO)Oc1cnc2[nH]cc(CC=C(C#N)C#N)c2c1] | 2-(2-(5-((1-hydroxypropan-2-yl)oxy)-1H-pyrrolo[2,3-b]pyridin-3-yl)ethylidene)malononitrile | CC(CO)OC1=CN=C(NC=C2C/C=C(C#N)/C#N)C2=C1 |
| 1010 | 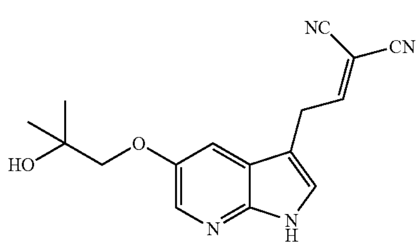 [SMILES: CC(C)(O)COc1cnc2[nH]cc(CC=C(C#N)C#N)c2c1] | 2-(2-(5-(2-hydroxy-2-methylpropoxy)-1H-pyrrolo[2,3-b]pyridin-3-yl)ethylidene)malononitrile | OC(C)(C)COC1=CN=C(NC=C2C/C=C(C#N)/C#N)C2=C1 |

TABLE 2-continued

Additional Examples

| Example | Structure | Name | Smiles |
|---|---|---|---|
| 1011 | 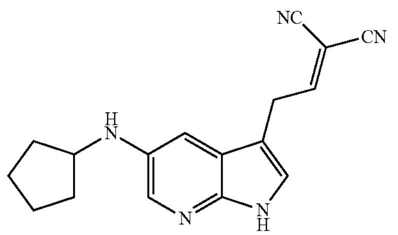 [SMILES: N#CC(C#N)=CCc1c[nH]c2ncc(NC3CCCC3)cc12] | 2-(2-(5-(cyclopentylamino)-1H-pyrrolo[2,3-b]pyridin-3-yl)ethylidene)malononitrile | N#C/C(C#N)=C/CC1=CNC2=NC=C(NC3CCCC3)C=C21 |
| 1012 | 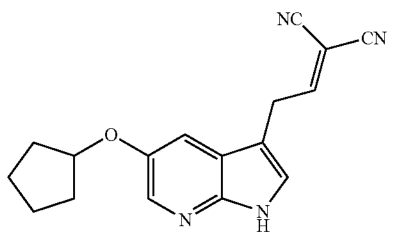 [SMILES: N#CC(C#N)=CCc1c[nH]c2ncc(OC3CCCC3)cc12] | 2-(2-(5-(cyclopentyloxy)-1H-pyrrolo[2,3-b]pyridin-3-yl)ethylidene)malononitrile | N#C/C(C#N)=C/CC1=CNC2=NC=C(OC3CCCC3)C=C21 |
| 1013 | 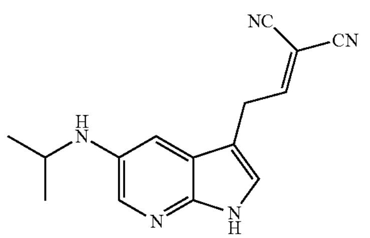 [SMILES: CC(C)Nc1cnc2[nH]cc(CC=C(C#N)C#N)c2c1] | 2-(2-(5-(isopropylamino)-1H-pyrrolo[2,3-b]pyridin-3-yl)ethylidene)malononitrile | CC(C)NC1=CN=C(NC=C2C/C=C(C#N)/C#N)C2=C1 |
| 1014 | 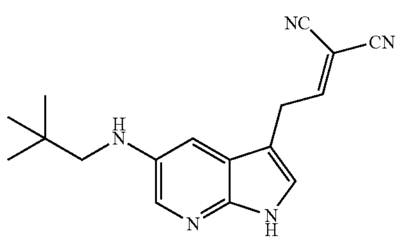 [SMILES: CC(C)(C)CNc1cnc2[nH]cc(CC=C(C#N)C#N)c2c1] | 2-(2-(5-(neopentylamino)-1H-pyrrolo[2,3-b]pyridin-3-yl)ethylidene)malononitrile | CC(C)(C)CNC1=CN=C(NC=C2C/C=C(C#N)/C#N)C2=C1 |
| 1015 | 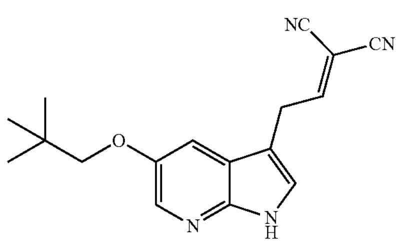 [SMILES: CC(C)(C)COc1cnc2[nH]cc(CC=C(C#N)C#N)c2c1] | 2-(2-(5-(neopentyloxy)-1H-pyrrolo[2,3-b]pyridin-3-yl)ethylidene)malononitrile | CC(C)(C)COC1=CN=C(NC=C2C/C=C(C#N)/C#N)C2=C1 |
| 1016 | 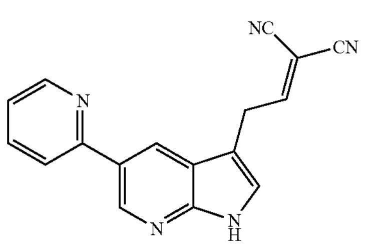 [SMILES: N#CC(C#N)=CCc1c[nH]c2ncc(-c3ccccn3)cc12] | 2-(2-(5-(pyridin-2-yl)-1H-pyrrolo[2,3-b]pyridin-3-yl)ethylidene)malononitrile | N#C/C(C#N)=C/CC1=CNC2=NC=C(C3=NC=CC=C3)C=C21 |

TABLE 2-continued

Additional Examples

| Example | Structure | Name | Smiles |
|---|---|---|---|
| 1017 | 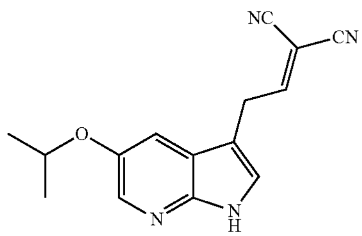 [SMILES: CC(C)Oc1cnc2[nH]cc(CC=C(C#N)C#N)c2c1] | 2-(2-(5-isopropoxy-1H-pyrrolo[2,3-b]pyridin-3-yl)ethylidene)malononitrile | CC(C)OC1=CN=C(NC=C2C/C=C(C#N)/C#N)C2=C1 |
| 1018 | 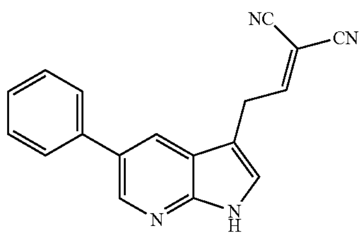 [SMILES: N#CC(C#N)=CCc1c[nH]c2ncc(-c3ccccc3)cc12] | 2-(2-(5-phenyl-1H-pyrrolo[2,3-b]pyridin-3-yl)ethylidene)malononitrile | N#C/C(C#N)=C/CC1=CNC2=NC=C(C3=CC=CC=C3)C=C21 |
| 1019 | 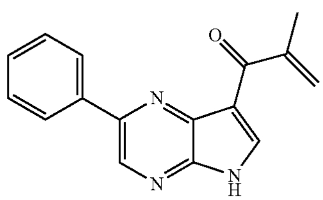 [SMILES: C=C(C)C(=O)c1c[nH]c2ncc(-c3ccccc3)nc12] | 2-methyl-1-(2-phenyl-5H-pyrrolo[2,3-b]pyrazin-7-yl)prop-2-en-1-one | O=C(C(C)=C)C1=CNC2=NC=C(C3=CC=CC=C3)N=C21 |

Biological Activity Assays

Compounds disclosed herein which are tested in the following assays are expected to be efficacious in the assays.

TAK1, a key downstream effector of TGF-β, has been implicated in transformation and metastasis of cancer cells as well as in the development of resistance to chemotherapeutic drugs and ionizing radiation. Mitogen-activated protein kinase kinase 7-interacting protein 1 (TAB1) is a TAK1 signaling molecule.

TAK1-TAB1 Binding Inhibitory Potency:

The ability of candidate compounds to interact with TAK1-TAB1 is quantitated by a competitive binding assay using the LanthaScreen technology developed by Life Technologies. This assay is based on the binding of a proprietary, Alexa Fluor® 647-labeled, ATP-competitive kinase inhibitor (kinase tracer-236) to the TAK1-TAB1 construct in presence of a europium-conjugated antibody, resulting in a FRET (fluorescence resonance energy transfer) signal. Displacement of the kinase tracer by compound results in a lower emission ratio upon excitation of the europium chelate. Candidate compounds are designed as potential irreversible inhibitors of TAK1-TAB1, capable of ligating to an active site cysteine residue. The time dependent nature of irreversible inhibition is investigated by performing the binding assay with and without a pre-incubation of compound and TAK1-TAB1. An increase in potency in the pre-incubated assay suggests the candidate compound could be irreversibly modifying TAK-TAB or having a slowly reversible mechanism.

The inhibitory potency of candidate compounds is measured in 20 mM HEPES pH 7.5, 10 mM $MgCl_2$, 0.01% BSA, 0.0005% Tween-20, and 2% DMSO in the presence of 10 nM TAK1-TAB1, 2 nM Eu-anti-his antibody, and 100 nM kinase tracer-236 using a 384-well plate format. Background signal is defined in the absence of TAK1-TAB1 and uninhibited signal is defined in the presence of vehicle (2% DMSO) alone. Compounds were evaluated in an 11 point dose-response ranging from 20 μM to 0.34 nM. The binding assays are performed under two conditions to evaluate time dependence of inhibition. For the pre-incubation assay, TAK1-TAB1 and Eu-anti-his antibody are preincubated with compound or vehicle for two hours prior to the addition of kinase tracer. The non-preincubated assay is run in which TAK1-TAB1 and Eu-anti-his antibody are added to a mixture of compound and kinase tracer. $IC_{50}$ values of compounds are determined using a 4 parameter logistical fit of emission ratio as a function of the concentration of compound.

Compounds were tested in accordance with the above described assay, without pre-incubation, yielding the values described below:

TABLE 3

TAK1-TAB1 Binding Assay

| Example | Structure | TAK1-Tab (2 h PI) Inhibition IC$_{50}$ uM<br>+ indicates ≤ 1 μM<br>− indicates > 1 μM | IL-6 Production Inhibition IC$_{50}$ uM<br>+ indicates ≤ 1 μM<br>− indicates > 1 μM |
|---|---|---|---|
| 1 | 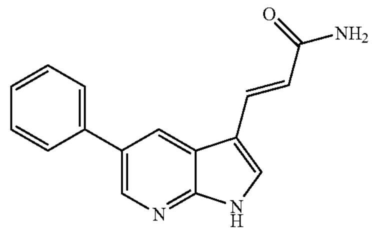 [SMILES: NC(=O)/C=C/c1c[nH]c2ncc(-c3ccccc3)cc12] | + | + |
| 2 | 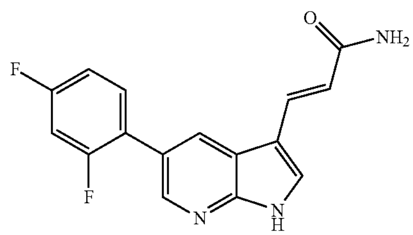 [SMILES: NC(=O)/C=C/c1c[nH]c2ncc(-c3ccc(F)cc3F)cc12] | + | + |
| 3 | 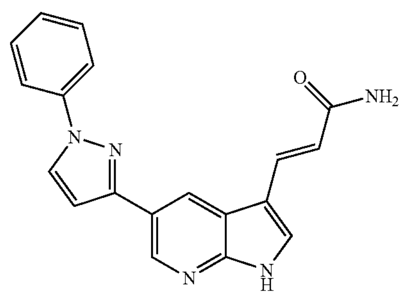 [SMILES: NC(=O)/C=C/c1c[nH]c2ncc(-c3ccn(-c4ccccc4)n3)cc12] | + | + |
| 4 | 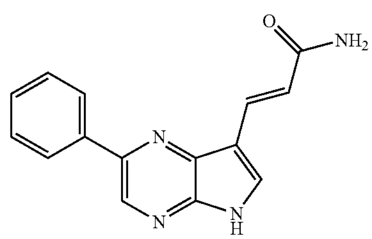 [SMILES: NC(=O)/C=C/c1c[nH]c2ncc(-c3ccccc3)nc12] | + | + |
| 5 | 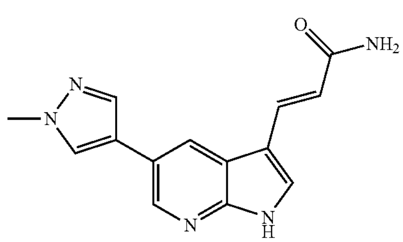 [SMILES: Cn1cc(-c2cnc3[nH]cc(/C=C/C(N)=O)c3c2)cn1] | + | + |
| 6 | 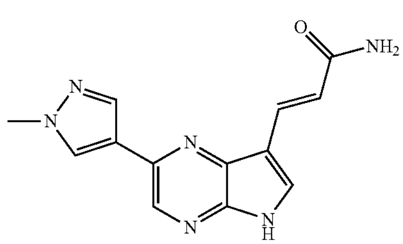 [SMILES: Cn1cc(-c2cnc3[nH]cc(/C=C/C(N)=O)c3n2)cn1] | + | + |

TABLE 3-continued

TAK1-TAB1 Binding Assay

| Example | Structure | TAK1-Tab (2 h PI) Inhibition IC$_{50}$ uM + indicates ≤ 1 μM − indicates > 1 μM | IL-6 Production Inhibition IC$_{50}$ uM + indicates ≤ 1 μM − indicates > 1 μM |
|---|---|---|---|
| 7 | 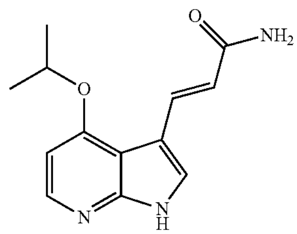 [SMILES: CC(C)Oc1ccnc2[nH]cc(/C=C/C(N)=O)c12] | + | + |
| 8 | 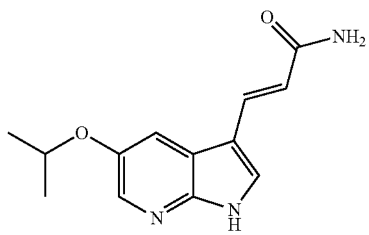 [SMILES: CC(C)Oc1cnc2[nH]cc(/C=C/C(N)=O)c2c1] | + | + |
| 9 | 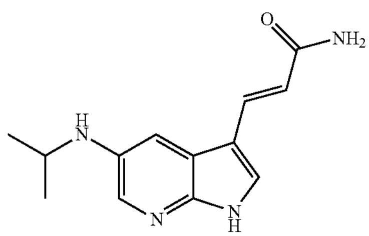 | + | + |
| 10 | 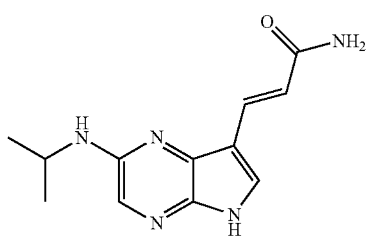 [SMILES: CC(C)Nc1cnc2[nH]cc(/C=C/C(N)=O)c2n1] | + | + |
| 11 | 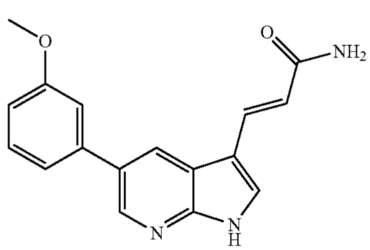 [SMILES: COc1cccc(-c2cnc3[nH]cc(/C=C/C(N)=O)c3c2)c1] | + | + |
| 12 | 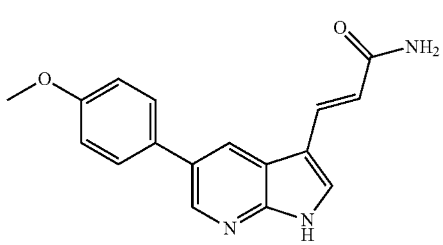 [SMILES: COc1ccc(-c2cnc3[nH]cc(/C=C/C(N)=O)c3c2)cc1] | + | + |

TABLE 3-continued

TAK1-TAB1 Binding Assay

| Example | Structure | TAK1-Tab (2 h PI) Inhibition IC$_{50}$ uM + indicates ≤ 1 μM − indicates > 1 μM | IL-6 Production Inhibition IC$_{50}$ uM + indicates ≤ 1 μM − indicates > 1 μM |
|---|---|---|---|
| 13 | 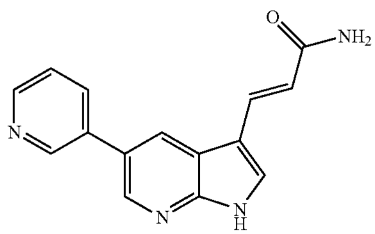 [SMILES: NC(=O)/C=C/c1c[nH]c2ncc(-c3cccnc3)cc12] | + | + |
| 14 | 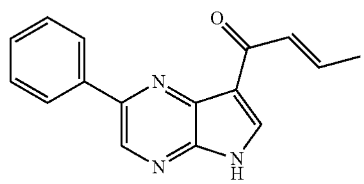 [SMILES: C/C=C/C(=O)c1c[nH]c2ncc(-c3ccccc3)nc12] | − | |
| 15 | 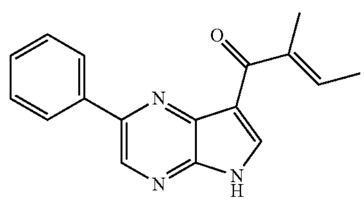 [SMILES: C/C=C(\C)C(=O)c1c[nH]c2ncc(-c3ccccc3)nc12] | − | |
| 16 | 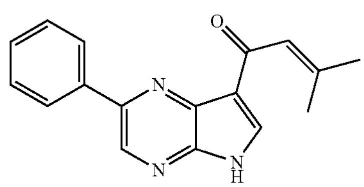 [SMILES: CC(C)=CC(=O)c1c[nH]c2ncc(-c3ccccc3)nc12] | − | |
| 17 | 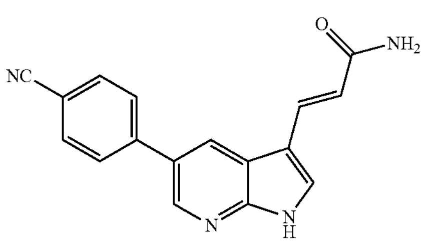 [SMILES: N#Cc1ccc(-c2cnc3[nH]cc(/C=C/C(N)=O)c3c2)cc1] | + | + |
| 18 | 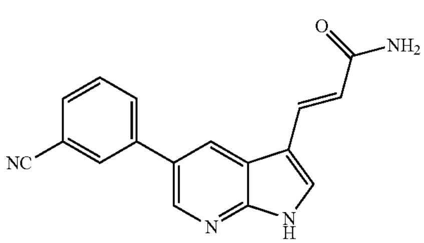 [SMILES: N#Cc1cccc(-c2cnc3[nH]cc(/C=C/C(N)=O)c3c2)c1] | + | + |

TABLE 3-continued

TAK1-TAB1 Binding Assay

| Example | Structure | TAK1-Tab (2 h PI) Inhibition IC$_{50}$ uM + indicates ≤ 1 μM − indicates > 1 μM | IL-6 Production Inhibition IC$_{50}$ uM + indicates ≤ 1 μM − indicates > 1 μM |
|---|---|---|---|
| 20 | (structure) | + | + |
| 23 | (structure) | + | − |
| 32 | (structure) | + | + |
| 39 | (structure) | + | + |
| 226 | (structure) | + | + |
| 232 | (structure) | − | |

TABLE 3-continued

TAK1-TAB1 Binding Assay

| Example | Structure | TAK1-Tab (2 h PI) Inhibition IC$_{50}$ uM<br>+ indicates ≤ 1 μM<br>− indicates > 1 μM | IL-6 Production Inhibition IC$_{50}$ uM<br>+ indicates ≤ 1 μM<br>− indicates > 1 μM |
|---|---|---|---|
| 233 | 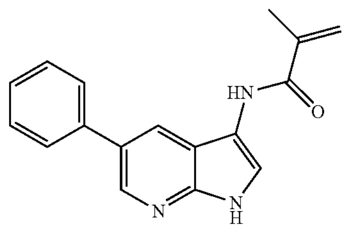 [SMILES: C=C(C)C(=O)Nc1c[nH]c2ncc(-c3ccccc3)cc12] | − | |
| 234 | 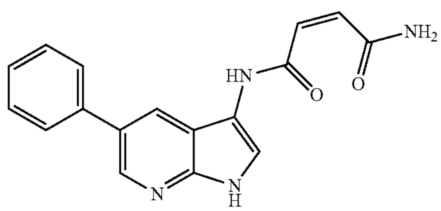 [SMILES: NC(=O)/C=C\C(=O)Nc1c[nH]c2ncc(-c3ccccc3)cc12] | − | + |
| 235 | 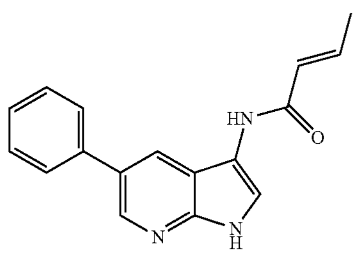 [SMILES: C/C=C/C(=O)Nc1c[nH]c2ncc(-c3ccccc3)cc12] | − | |
| 236 | 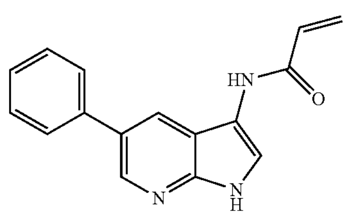 [SMILES: C=CC(=O)Nc1c[nH]c2ncc(-c3ccccc3)cc12] | − | |
| 237 | 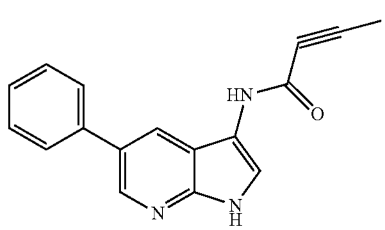 [SMILES: CC#CC(=O)Nc1c[nH]c2ncc(-c3ccccc3)cc12] | | + |
| 238 | 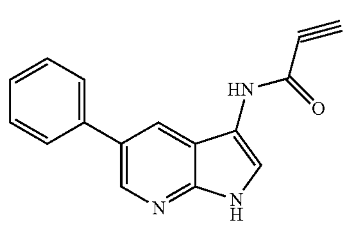 [SMILES: C#CC(=O)Nc1c[nH]c2ncc(-c3ccccc3)cc12] | − | |

TABLE 3-continued

TAK1-TAB1 Binding Assay

| Example | Structure | TAK1-Tab (2 h PI) Inhibition IC$_{50}$ uM + indicates ≤ 1 μM − indicates > 1 μM | IL-6 Production Inhibition IC$_{50}$ uM + indicates ≤ 1 μM − indicates > 1 μM |
|---|---|---|---|
| 239 | 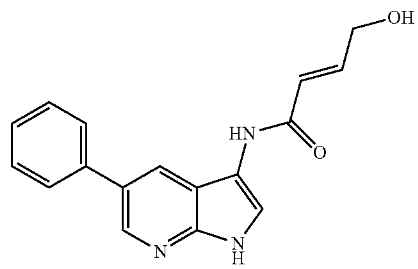 [SMILES: O=C(/C=C/CO)Nc1c[nH]c2ncc(-c3ccccc3)cc12] | + | |
| 240 | 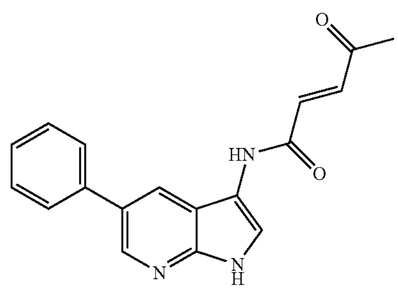 [SMILES: CC(=O)/C=C/C(=O)Nc1c[nH]c2ncc(-c3ccccc3)cc12] | + | + |
| 241 | 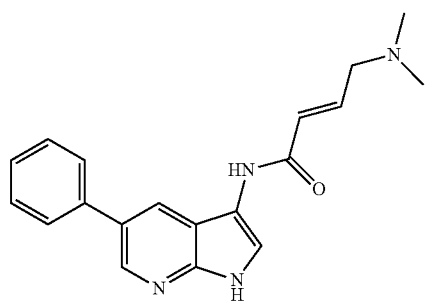 [SMILES: CN(C)C/C=C/C(=O)Nc1c[nH]c2ncc(-c3ccccc3)cc12] | − | |
| 242 | 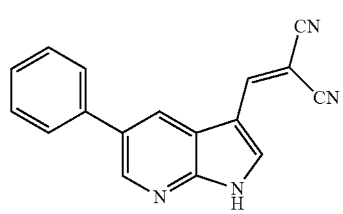 [SMILES: N#CC(C#N)=Cc1c[nH]c2ncc(-c3ccccc3)cc12] | − | |
| 244 | 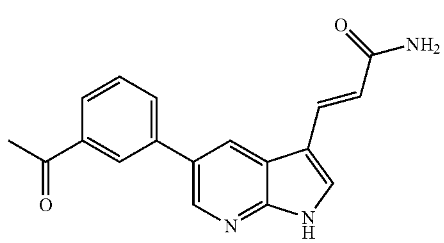 [SMILES: CC(=O)c1cccc(-c2cnc3[nH]cc(/C=C/C(N)=O)c3c2)c1] | + | + |

TABLE 3-continued

TAK1-TAB1 Binding Assay

| Example | Structure | TAK1-Tab (2 h PI) Inhibition IC$_{50}$ uM + indicates ≤ 1 μM − indicates > 1 μM | IL-6 Production Inhibition IC$_{50}$ uM + indicates ≤ 1 μM − indicates > 1 μM |
|---|---|---|---|
| 245 | 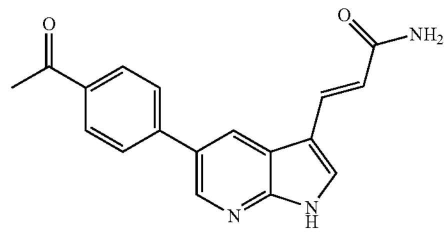 [SMILES: CC(=O)c1ccc(-c2cnc3[nH]cc(/C=C/C(N)=O)c3c2)cc1] | + | + |
| 246 | 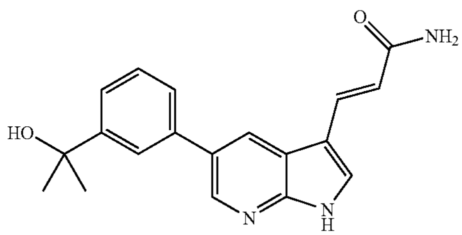 [SMILES: CC(C)(O)c1cccc(-c2cnc3[nH]cc(/C=C/C(N)=O)c3c2)c1] | + | + |
| 247 | 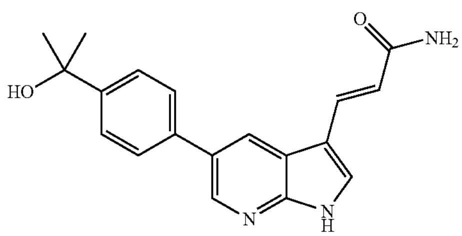 [SMILES: CC(C)(O)c1ccc(-c2cnc3[nH]cc(/C=C/C(N)=O)c3c2)cc1] | + | + |
| 248 | 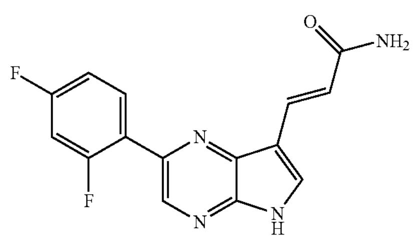 [SMILES: NC(=O)/C=C/c1c[nH]c2ncc(-c3ccc(F)cc3F)nc12] | + | + |
| 249 | 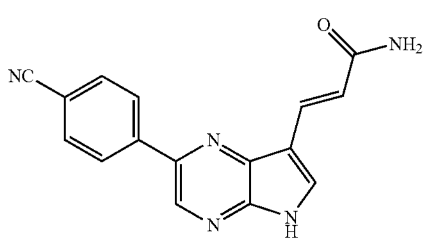 [SMILES: N#Cc1ccc(-c2cnc3[nH]cc(/C=C/C(N)=O)c3n2)cc1] | + | + |
| 250 | 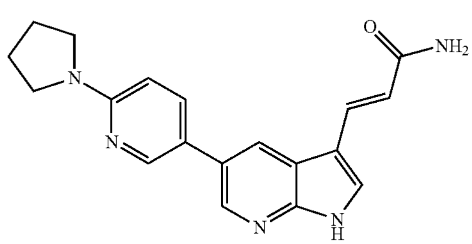 [SMILES: NC(=O)/C=C/c1c[nH]c2ncc(-c3ccc(N4CCCC4)nc3)cc12] | + | + |

TABLE 3-continued

TAK1-TAB1 Binding Assay

| Example | Structure | TAK1-Tab (2 h PI) Inhibition IC$_{50}$ uM + indicates ≤ 1 μM − indicates > 1 μM | IL-6 Production Inhibition IC$_{50}$ uM + indicates ≤ 1 μM − indicates > 1 μM |
|---|---|---|---|
| 251 | 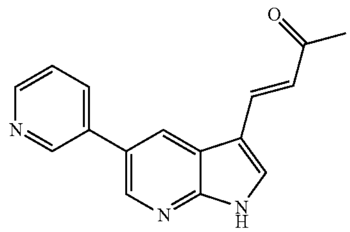 [SMILES: CC(=O)/C=C/c1c[nH]c2ncc(-c3cccnc3)cc12] | + | − |
| 252 | 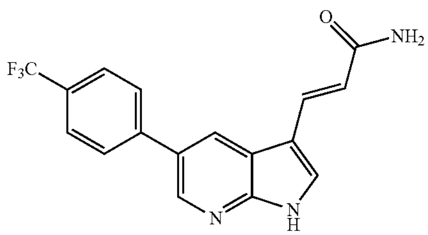 [SMILES: NC(=O)/C=C/c1c[nH]c2ncc(-c3ccc(C(F)(F)F)cc3)cc12] | + | + |
| 253 | 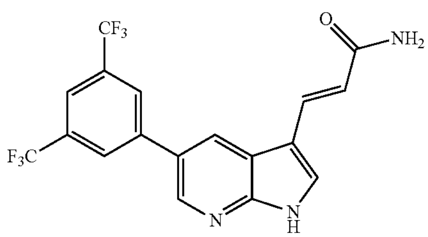 [SMILES: NC(=O)/C=C/c1c[nH]c2ncc(-c3cc(C(F)(F)F)cc(C(F)(F)F)c3)cc12] | + | + |
| 254 | 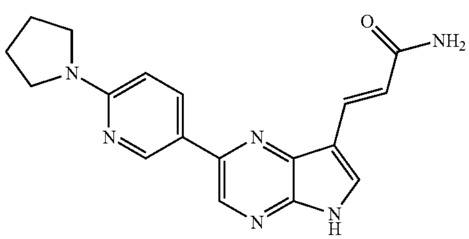 [SMILES: NC(=O)/C=C/c1c[nH]c2ncc(-c3ccc(N4CCCC4)nc3)nc12] | − | |
| 255 | 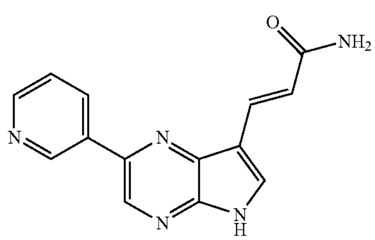 [SMILES: NC(=O)/C=C/c1c[nH]c2ncc(-c3cccnc3)nc12] | − | |
| 256 | 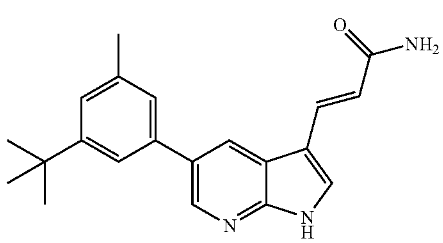 [SMILES: Cc1cc(-c2cnc3[nH]cc(/C=C/C(N)=O)c3c2)cc(C(C)(C)C)c1] | + | + |

TABLE 3-continued

TAK1-TAB1 Binding Assay

| Example | Structure | TAK1-Tab (2 h PI) Inhibition IC$_{50}$ uM + indicates ≤ 1 μM − indicates > 1 μM | IL-6 Production Inhibition IC$_{50}$ uM + indicates ≤ 1 μM − indicates > 1 μM |
|---|---|---|---|
| 257 | 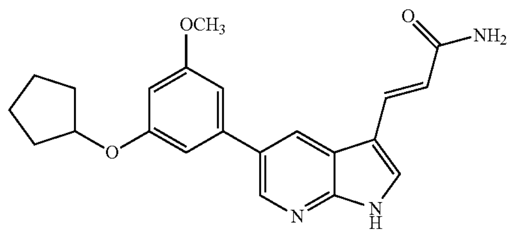 [SMILES: COc1cc(OC2CCCC2)cc(-c2cnc3[nH]cc(/C=C/C(N)=O)c3c2)c1] | + | + |
| 258 | 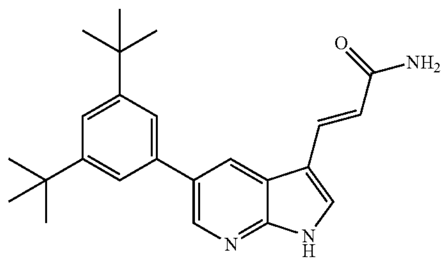 [SMILES: CC(C)(C)c1cc(-c2cnc3[nH]cc(/C=C/C(N)=O)c3c2)cc(C(C)(C)C)c1] | + | + |
| 259 | 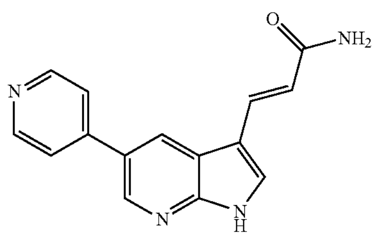 [SMILES: NC(=O)/C=C/c1c[nH]c2ncc(-c3ccncc3)cc12] | + | + |
| 260 | 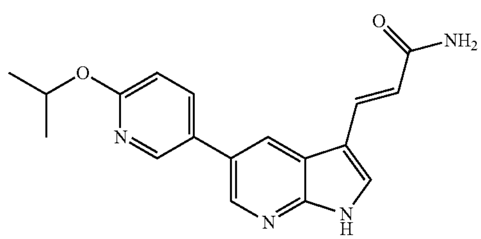 [SMILES: CC(C)Oc1ccc(-c2cnc3[nH]cc(/C=C/C(N)=O)c3c2)cn1] | + | + |
| 261 | 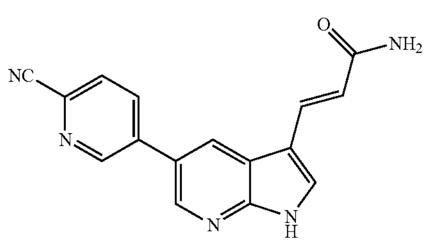 [SMILES: N#Cc1ccc(-c2cnc3[nH]cc(/C=C/C(N)=O)c3c2)cn1] | + | + |
| 262 | 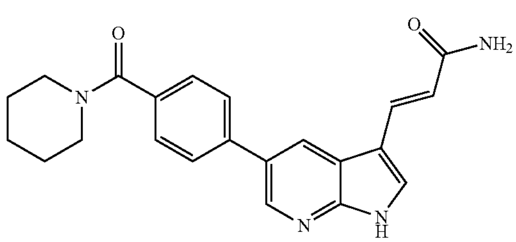 [SMILES: NC(=O)/C=C/c1c[nH]c2ncc(-c3ccc(C(=O)N4CCCCC4)cc3)cc12] | + | + |

TABLE 3-continued

TAK1-TAB1 Binding Assay

| Example | Structure | TAK1-Tab (2 h PI) Inhibition IC$_{50}$ uM<br>+ indicates ≤ 1 μM<br>− indicates > 1 μM | IL-6 Production Inhibition IC$_{50}$ uM<br>+ indicates ≤ 1 μM<br>− indicates > 1 μM |
|---|---|---|---|
| 263 | 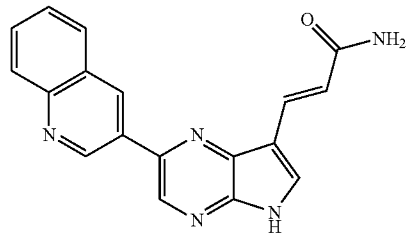 [SMILES: NC(=O)/C=C/c1c[nH]c2ncc(-c3cnc4ccccc4c3)nc12] | + | + |
| 264 | 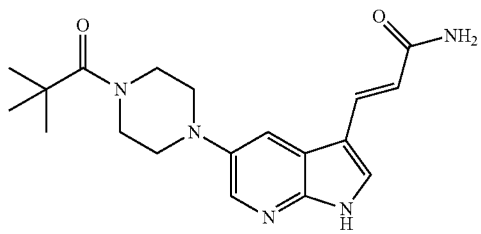 [SMILES: CC(C)(C)C(=O)N1CCN(c2cnc3[nH]cc(/C=C/C(N)=O)c3c2)CC1] | + | + |
| 265 | 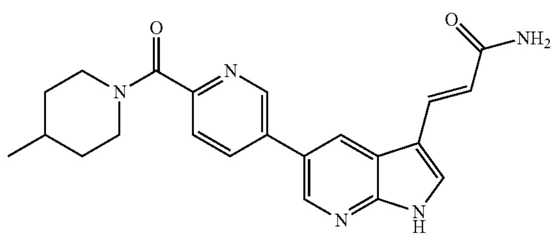 [SMILES: CC1CCN(C(=O)c2ccc(-c3cnc4[nH]cc(/C=C/C(N)=O)c4c3)cn2)CC1] | + | − |
| 266 | 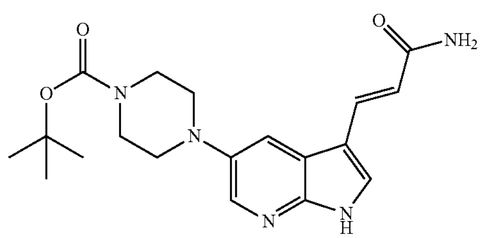 [SMILES: CC(C)(C)OC(=O)N1CCN(c2cnc3[nH]cc(/C=C/C(N)=O)c3c2)CC1] | + | + |
| 267 | 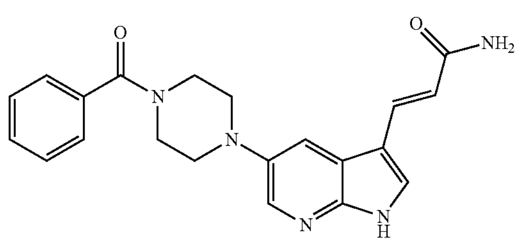 [SMILES: NC(=O)/C=C/c1c[nH]c2ncc(N3CCN(C(=O)c4ccccc4)CC3)cc12] | + | − |
| 268 | 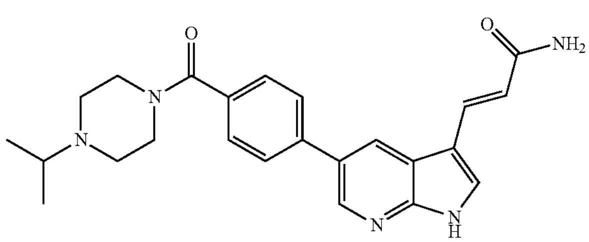 [SMILES: CC(C)N1CCN(C(=O)c2ccc(-c3cnc4[nH]cc(/C=C/C(N)=O)c4c3)cc2)CC1] | + | + |

TABLE 3-continued
TAK1-TAB1 Binding Assay
| Example | Structure | TAK1-Tab (2 h PI) Inhibition IC$_{50}$ uM + indicates ≤ 1 μM − indicates > 1 μM | IL-6 Production Inhibition IC$_{50}$ uM + indicates ≤ 1 μM − indicates > 1 μM |
|---|---|---|---|
| 269 | 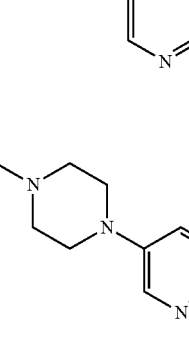 | + | + |
| 270 | 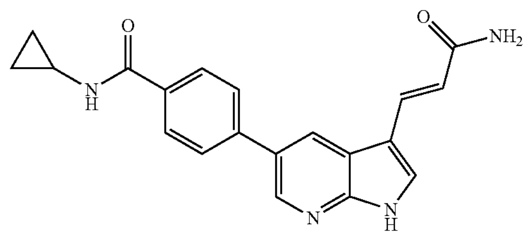 [SMILES: NC(=O)/C=C/c1c[nH]c2ncc(-c3ccc(C(=O)NC4CC4)cc3)cc12] | + | − |
| 271 | 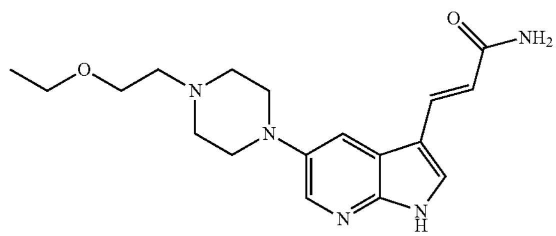 [SMILES: CCOCCN1CCN(c2cnc3[nH]cc(/C=C/C(N)=O)c3c2)CC1] | + | + |
| 272 | 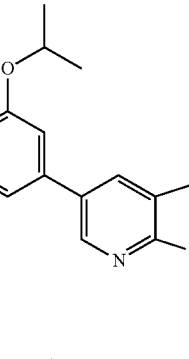 | + | + |
| 273 | 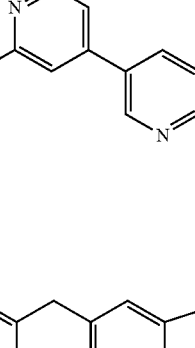 | + | + |
| 274 | 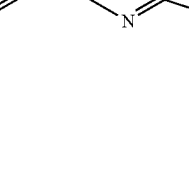 | + | + |

TABLE 3-continued
TAK1-TAB1 Binding Assay
| Example | Structure | TAK1-Tab (2 h PI) Inhibition IC$_{50}$ uM + indicates ≤ 1 μM − indicates > 1 μM | IL-6 Production Inhibition IC$_{50}$ uM + indicates ≤ 1 μM − indicates > 1 μM |
|---|---|---|---|
| 275 | 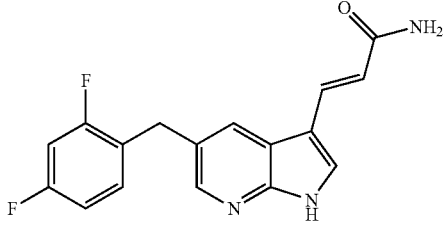 [SMILES: NC(=O)/C=C/c1c[nH]c2ncc(Cc3ccc(F)cc3F)cc12] | + | + |
| 276 | 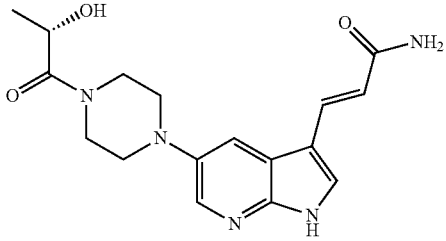 [SMILES: C[C@H](O)C(=O)N1CCN(c2cnc3[nH]cc(/C=C/C(N)=O)c3c2)CC1] | + | − |
| 277 | 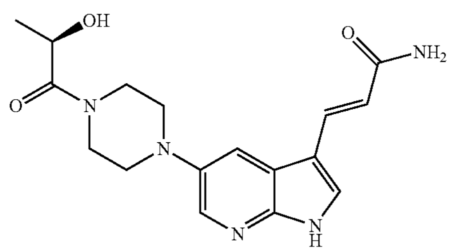 [SMILES: C[C@@H](O)C(=O)N1CCN(c2cnc3[nH]cc(/C=C/C(N)=O)c3c2)CC1] | + | − |
| 278 | 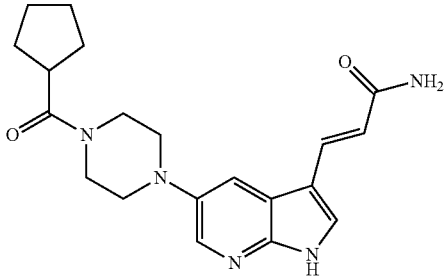 [SMILES: NC(=O)/C=C/c1c[nH]c2ncc(N3CCN(C(=O)C4CCCC4)CC3)cc12] | + | − |
| 279 | 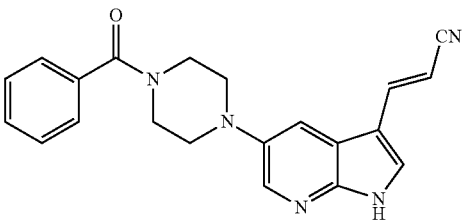 [SMILES: N#C/C=C/c1c[nH]c2ncc(N3CCN(C(=O)c4ccccc4)CC3)cc12] | + | − |

TABLE 3-continued

TAK1-TAB1 Binding Assay

| Example | Structure | TAK1-Tab (2 h PI) Inhibition IC$_{50}$ uM + indicates ≤ 1 μM − indicates > 1 μM | IL-6 Production Inhibition IC$_{50}$ uM + indicates ≤ 1 μM − indicates > 1 μM |
|---|---|---|---|
| 280 | 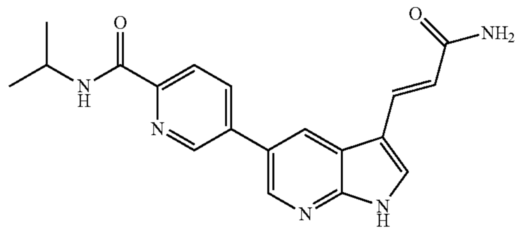 [SMILES: CC(C)NC(=O)c1ccc(-c2cnc3[nH]cc(/C=C/C(N)=O)c3c2)cn1] | + | + |
| 281 | 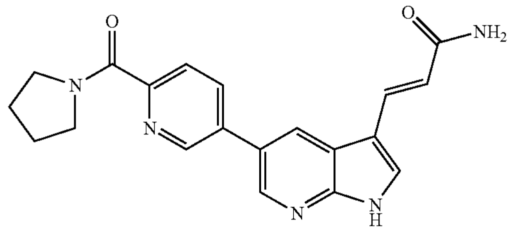 [SMILES: NC(=O)/C=C/c1c[nH]c2ncc(-c3ccc(C(=O)N4CCCC4)nc3)cc12] | + | − |
| 282 | 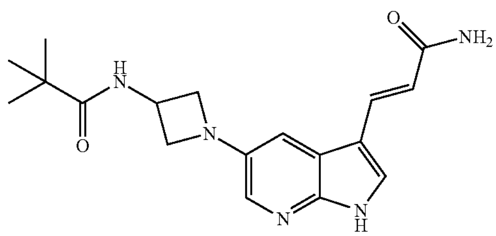 [SMILES: CC(C)(C)C(=O)NC1CN(c2cnc3[nH]cc(/C=C/C(N)=O)c3c2)C1] | − | − |
| 283 | 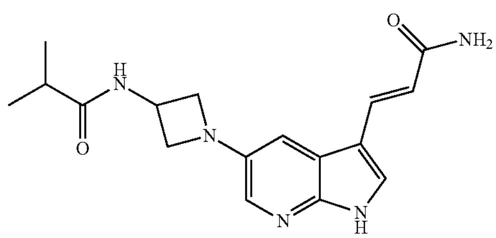 [SMILES: CC(C)C(=O)NC1CN(c2cnc3[nH]cc(/C=C/C(N)=O)c3c2)C1] | + | + |
| 284 | 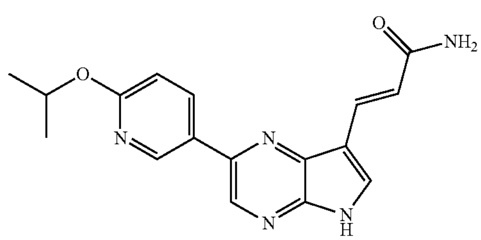 [SMILES: CC(C)Oc1ccc(-c2cnc3[nH]cc(/C=C/C(N)=O)c3n2)cn1] | + | + |
| 285 | 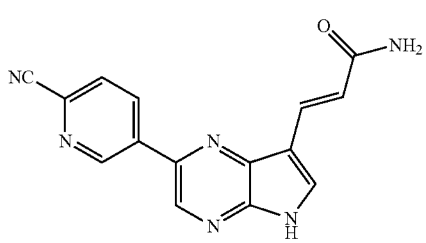 [SMILES: N#Cc1ccc(-c2cnc3[nH]cc(/C=C/C(N)=O)c3n2)cn1] | + | + |

US 9,499,551 B2
313 314
TABLE 3-continued
TAK1-TAB1 Binding Assay
| Example | Structure | TAK1-Tab (2 h PI) Inhibition IC$_{50}$ uM<br>+ indicates ≤ 1 μM<br>– indicates > 1 μM | IL-6 Production Inhibition IC$_{50}$ uM<br>+ indicates ≤ 1 μM<br>– indicates > 1 μM |
|---|---|---|---|
| 286 | 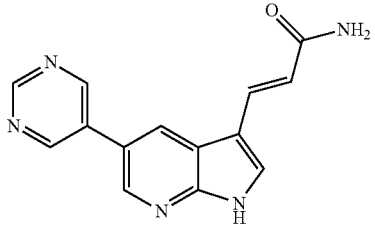 [SMILES: NC(=O)/C=C/c1c[nH]c2ncc(-c3cncnc3)cc12] | + | – |
| 287 | 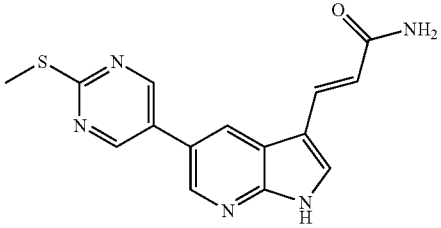 [SMILES: CSc1ncc(-c2cnc3[nH]cc(/C=C/C(N)=O)c3c2)cn1] | + | + |
| 288 | 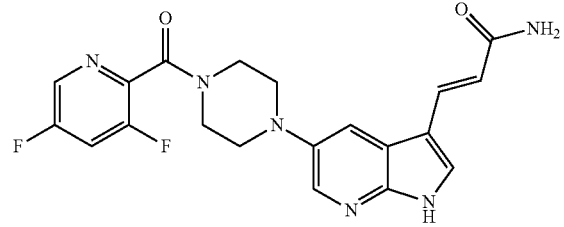 [SMILES: NC(=O)/C=C/c1c[nH]c2ncc(N3CCN(C(=O)c4ncc(F)cc4F)CC3)cc12] | + | – |
| 289 | 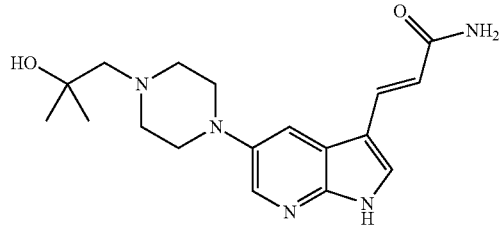 [SMILES: CC(C)(O)CN1CCN(c2cnc3[nH]cc(/C=C/C(N)=O)c3c2)CC1] | + | – |
| 290 | 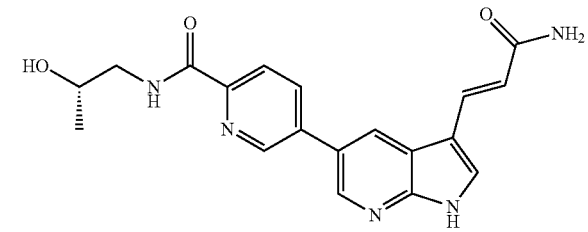 [SMILES: C[C@H](O)CNC(=O)c1ccc(-c2cnc3[nH]cc(/C=C/C(N)=O)c3c2)cn1] | + | – |
| 291 | 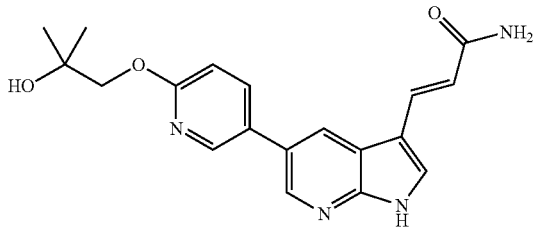 [SMILES: CC(C)(O)COc1ccc(-c2cnc3[nH]cc(/C=C/C(N)=O)c3c2)cn1] | + | + |

TABLE 3-continued

TAK1-TAB1 Binding Assay

| Example | Structure | TAK1-Tab (2 h PI) Inhibition IC$_{50}$ uM + indicates ≤ 1 μM − indicates > 1 μM | IL-6 Production Inhibition IC$_{50}$ uM + indicates ≤ 1 μM − indicates > 1 μM |
|---|---|---|---|
| 292 | 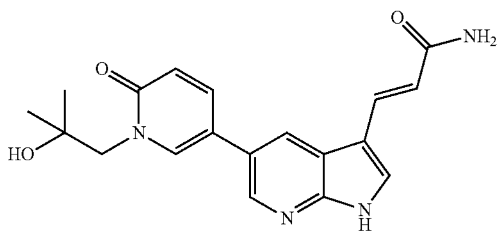 [SMILES: CC(C)(O)Cn1cc(-c2cnc3[nH]cc(/C=C/C(N)=O)c3c2)ccc1=O] | + | − |
| 293 | 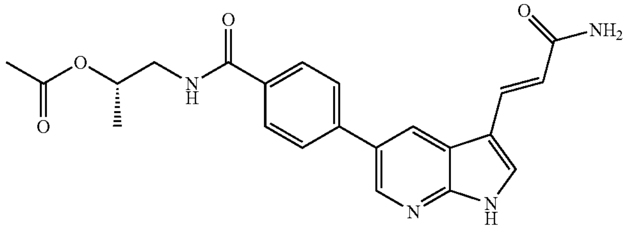 [SMILES: CC(=O)O[C@@H](C)CNC(=O)c1ccc(-c2cnc3[nH]cc(/C=C/C(N)=O)c3c2)cc1] | + | − |
| 294 | 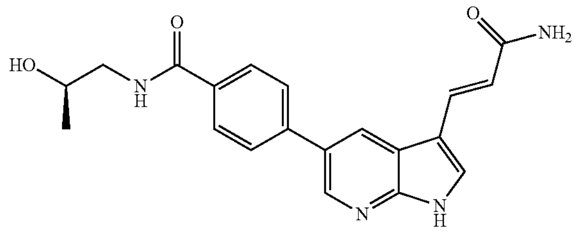 [SMILES: C[C@@H](O)CNC(=O)c1ccc(-c2cnc3[nH]cc(/C=C/C(N)=O)c3c2)cc1] | + | − |
| 295 | 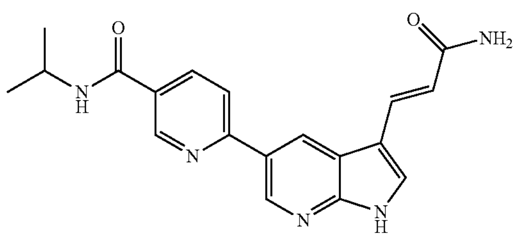 [SMILES: CC(C)NC(=O)c1ccc(-c2cnc3[nH]cc(/C=C/C(N)=O)c3c2)nc1] | + | − |
| 296 | 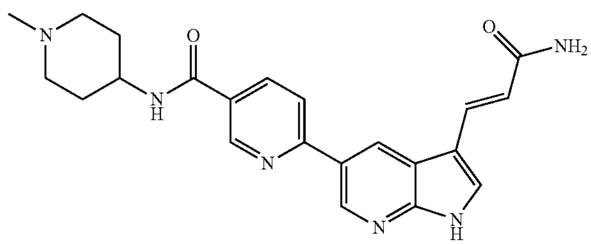 [SMILES: CN1CCC(NC(=O)c2ccc(-c3cnc4[nH]cc(/C=C/C(N)=O)c4c3)nc2)CC1] | + | − |
| 297 | 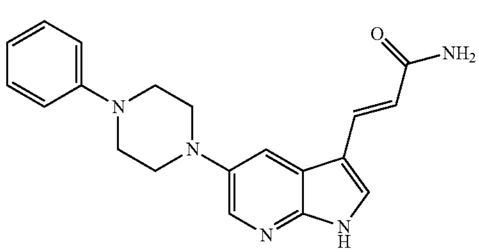 [SMILES: NC(=O)/C=C/c1c[nH]c2ncc(N3CCN(c4ccccc4)CC3)cc12] | + | + |

TABLE 3-continued

TAK1-TAB1 Binding Assay

| Example | Structure | TAK1-Tab (2 h PI) Inhibition IC$_{50}$ uM + indicates ≤ 1 μM − indicates > 1 μM | IL-6 Production Inhibition IC$_{50}$ uM + indicates ≤ 1 μM − indicates > 1 μM |
| --- | --- | --- | --- |
| 298 | 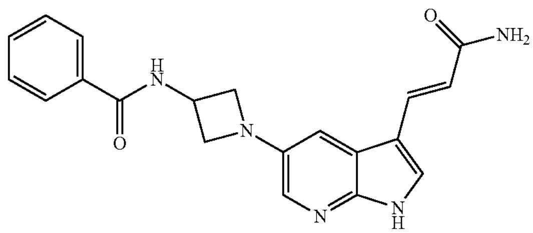 [SMILES: NC(=O)/C=C/c1c[nH]c2ncc(N3CC(NC(=O)c4ccccc4)C3)cc12] | + | + |
| 299 | 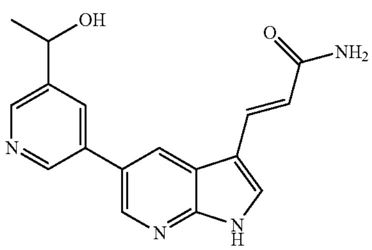 [SMILES: CC(O)c1cncc(-c2cnc3[nH]cc(/C=C/C(N)=O)c3c2)c1] | + | − |
| 300 | 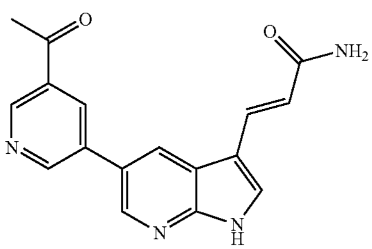 [SMILES: CC(=O)c1cncc(-c2cnc3[nH]cc(/C=C/C(N)=O)c3c2)c1] | + | + |
| 301 | 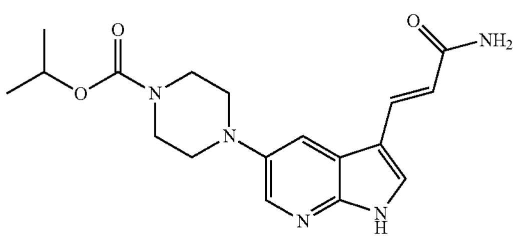 [SMILES: CC(C)OC(=O)N1CCN(c2cnc3[nH]cc(/C=C/C(N)=O)c3c2)CC1] | + | |
| 302 | 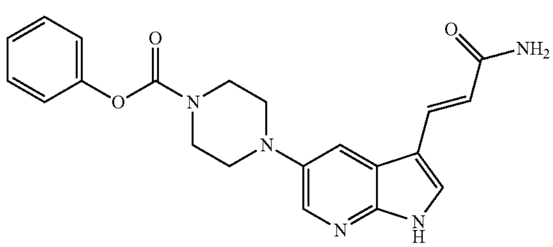 [SMILES: NC(=O)/C=C/c1c[nH]c2ncc(N3CCN(C(=O)Oc4ccccc4)CC3)cc12] | + | |
| 303 | 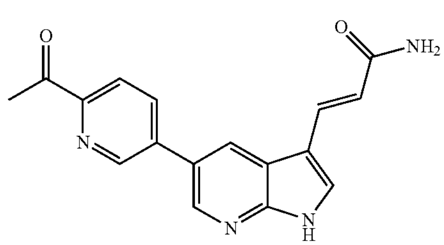 [SMILES: CC(=O)c1ccc(-c2cnc3[nH]cc(/C=C/C(N)=O)c3c2)cn1] | + | |

TABLE 3-continued

TAK1-TAB1 Binding Assay

| Example | Structure | TAK1-Tab (2 h PI) Inhibition IC$_{50}$ uM + indicates ≤ 1 μM − indicates > 1 μM | IL-6 Production Inhibition IC$_{50}$ uM + indicates ≤ 1 μM − indicates > 1 μM |
|---|---|---|---|
| 304 | 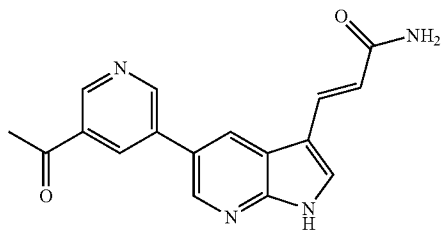 [SMILES: CC(=O)c1cncc(-c2cnc3[nH]cc(/C=C/C(N)=O)c3c2)c1] | + | |
| 305 | 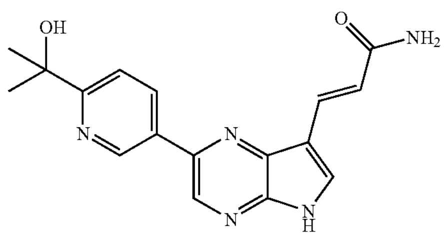 [SMILES: CC(C)(O)c1ccc(-c2cnc3[nH]cc(/C=C/C(N)=O)c3n2)cn1] | + | |
| 306 | 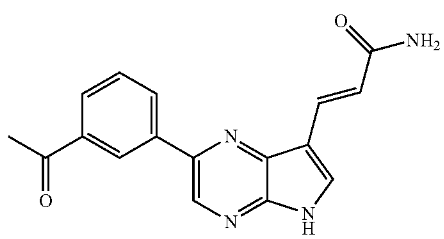 [SMILES: CC(=O)c1cccc(-c2cnc3[nH]cc(/C=C/C(N)=O)c3n2)c1] | + | |
| 307 | 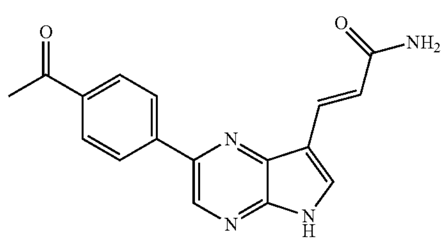 [SMILES: CC(=O)c1ccc(-c2cnc3[nH]cc(/C=C/C(N)=O)c3n2)cc1] | + | |
| 308 | 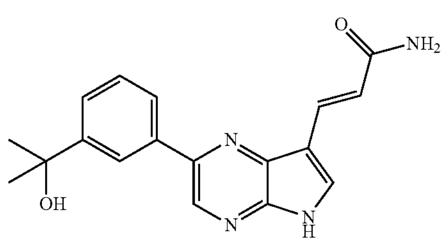 [SMILES: CC(C)(O)c1cccc(-c2cnc3[nH]cc(/C=C/C(N)=O)c3n2)c1] | + | |
| 309 | 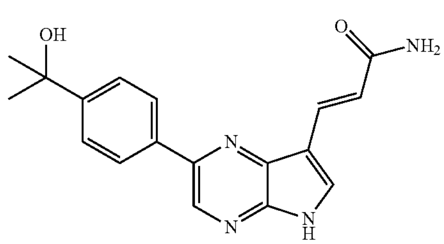 [SMILES: CC(C)(O)c1ccc(-c2cnc3[nH]cc(/C=C/C(N)=O)c3n2)cc1] | + | |

TABLE 3-continued

TAK1-TAB1 Binding Assay

| Example | Structure | TAK1-Tab (2 h PI) Inhibition IC$_{50}$ uM<br>+ indicates ≤ 1 μM<br>− indicates > 1 μM | IL-6 Production Inhibition IC$_{50}$ uM<br>+ indicates ≤ 1 μM<br>− indicates > 1 μM |
|---|---|---|---|
| 310 | 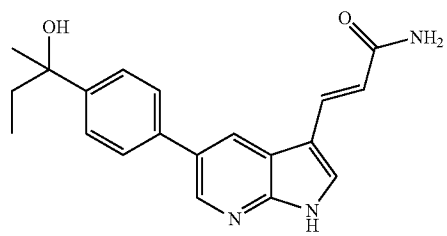 [SMILES: CCC(C)(O)c1ccc(-c2cnc3[nH]cc(/C=C/C(N)=O)c3c2)cc1] | + | |
| 311 | 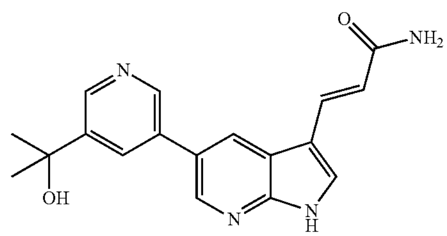 [SMILES: CC(C)(O)c1cncc(-c2cnc3[nH]cc(/C=C/C(N)=O)c3c2)c1] | + | |
| 312 | 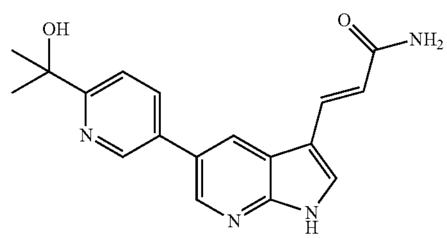 [SMILES: CC(C)(O)c1ccc(-c2cnc3[nH]cc(/C=C/C(N)=O)c3c2)cn1] | + | |
| 313 | 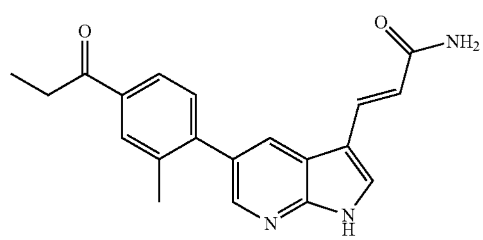 | + | |
| 314 | 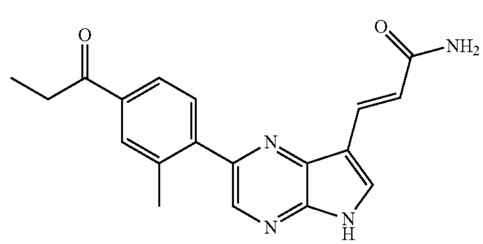 [SMILES: CCC(=O)c1ccc(-c2cnc3[nH]cc(/C=C/C(N)=O)c3c2)c(C)c1] | + | |
| 315 | 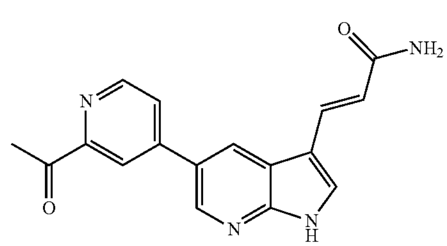 [SMILES: CC(=O)c1cc(-c2cnc3[nH]cc(/C=C/C(N)=O)c3c2)ccn1] | + | |

TABLE 3-continued

TAK1-TAB1 Binding Assay

| Example | Structure | TAK1-Tab (2 h PI) Inhibition IC$_{50}$ uM<br>+ indicates ≤ 1 μM<br>− indicates > 1 μM | IL-6 Production Inhibition IC$_{50}$ uM<br>+ indicates ≤ 1 μM<br>− indicates > 1 μM |
|---|---|---|---|
| 316 | 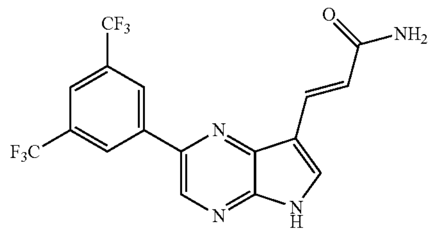 [SMILES: NC(=O)/C=C/c1c[nH]c2ncc(-c3cc(C(F)(F)F)cc(C(F)(F)F)c3)nc12] | + | |
| 317 | 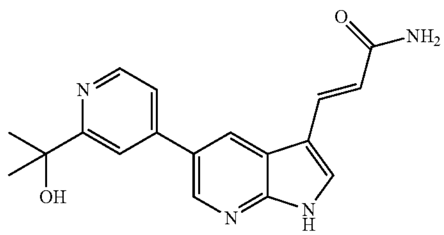 [SMILES: CC(C)(O)c1cc(-c2cnc3[nH]cc(/C=C/C(N)=O)c3c2)ccn1] | + | |
| 318 | 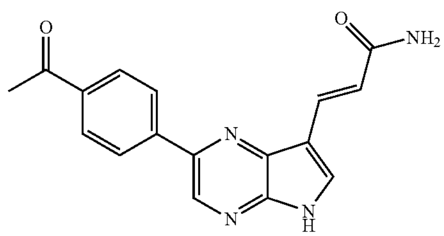 [SMILES: CC(=O)c1ccc(-c2cnc3[nH]cc(/C=C/C(N)=O)c3n2)cc1] | + | |
| 319 | 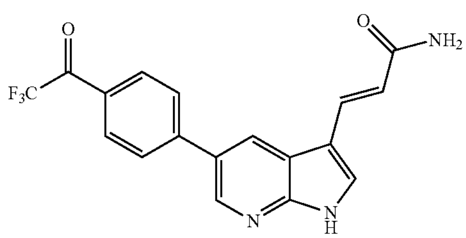 [SMILES: NC(=O)/C=C/c1c[nH]c2ncc(-c3ccc(C(=O)C(F)(F)F)cc3)cc12] | + | |
| 320 | 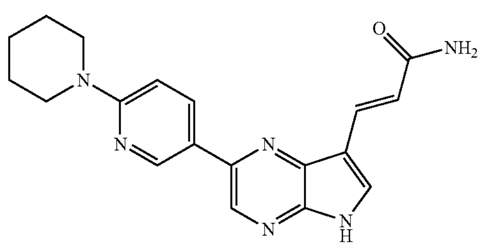 [SMILES: NC(=O)/C=C/c1c[nH]c2ncc(-c3ccc(N4CCCCC4)nc3)nc12] | + | |
| 321 | 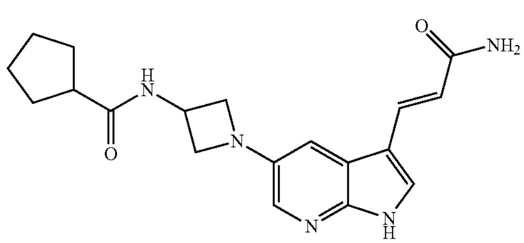 [SMILES: NC(=O)/C=C/c1c[nH]c2ncc(N3CC(NC(=O)C4CCCC4)C3)cc12] | + | |

TABLE 3-continued

TAK1-TAB1 Binding Assay

| Example | Structure | TAK1-Tab (2 h PI) Inhibition IC$_{50}$ uM + indicates ≤ 1 μM − indicates > 1 μM | IL-6 Production Inhibition IC$_{50}$ uM + indicates ≤ 1 μM − indicates > 1 μM |
|---------|-----------|---------|---------|
| 322 | 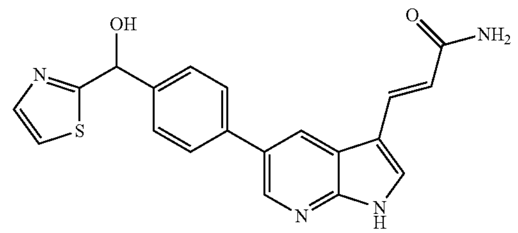 [SMILES: NC(=O)/C=C/c1c[nH]c2ncc(-c3ccc(C(O)c4nccs4)cc3)cc12] | + | |
| 323 | 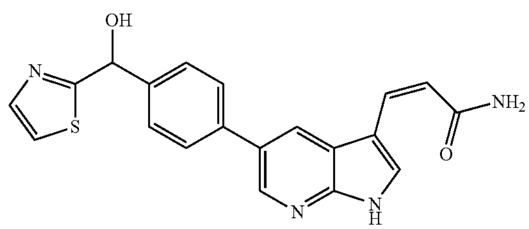 [SMILES: NC(=O)/C=C\c1c[nH]c2ncc(-c3ccc(C(O)c4nccs4)cc3)cc12] | + | |
| 324 | 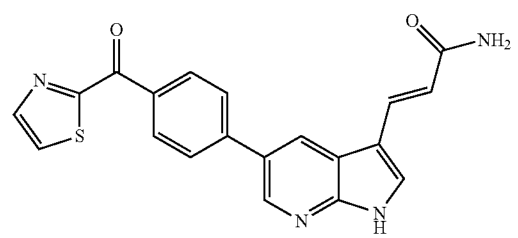 [SMILES: NC(=O)/C=C/c1c[nH]c2ncc(-c3ccc(C(=O)c4nccs4)cc3)cc12] | + | |
| 325 | 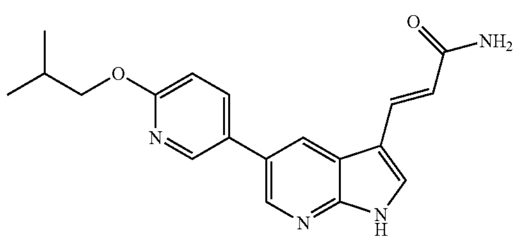 [SMILES: CC(C)COc1ccc(-c2cnc3[nH]cc(/C=C/C(N)=O)c3c2)cn1] | + | |
| 326 | 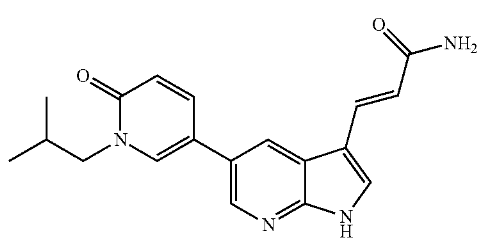 [SMILES: CC(C)Cn1cc(-c2cnc3[nH]cc(/C=C/C(N)=O)c3c2)ccc1=O] | + | |
| 327 | 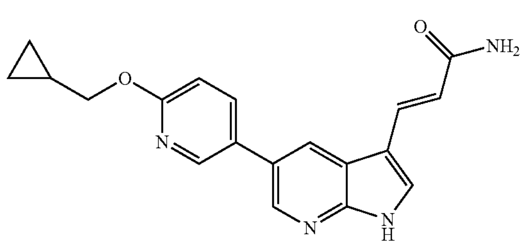 [SMILES: NC(=O)/C=C/c1c[nH]c2ncc(-c3ccc(OCC4CC4)nc3)cc12] | + | |

TABLE 3-continued
TAK1-TAB1 Binding Assay
| Example | Structure | TAK1-Tab (2 h PI) Inhibition IC$_{50}$ uM<br>+ indicates ≤ 1 μM<br>− indicates > 1 μM | IL-6 Production Inhibition IC$_{50}$ uM<br>+ indicates ≤ 1 μM<br>− indicates > 1 μM |
|---|---|---|---|
| 328 | 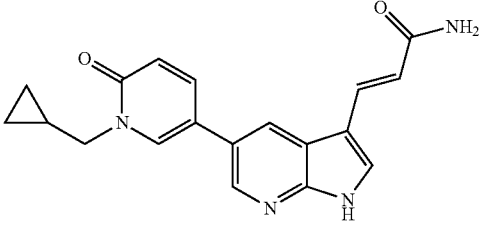 [SMILES: NC(=O)/C=C/c1c[nH]c2ncc(-c3ccc(=O)n(CC4CC4)c3)cc12] | | + |
| 329 | 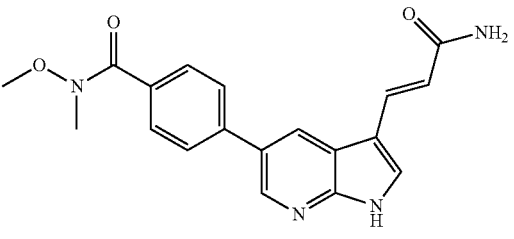 [SMILES: CON(C)C(=O)c1ccc(-c2cnc3[nH]cc(/C=C/C(N)=O)c3c2)cc1] | | + |
| 330 | 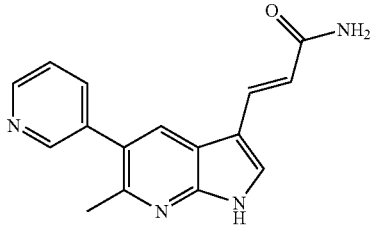 [SMILES: Cc1nc2[nH]cc(/C=C/C(N)=O)c2cc1-c1cccnc1] | | + |
| 331 | 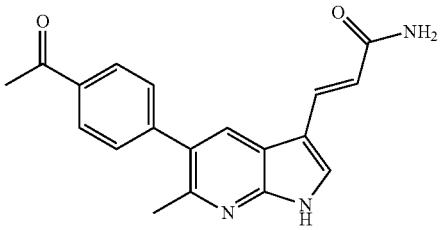 [SMILES: CC(=O)c1ccc(-c2cc3c(/C=C/C(N)=O)c[nH]c3nc2C)cc1] | | + |
| 332 | 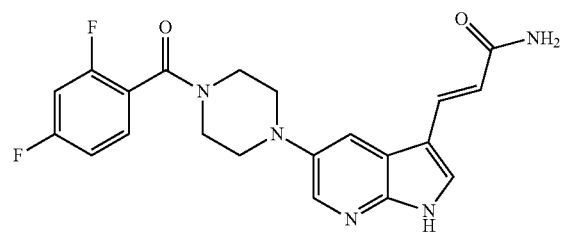 [SMILES: NC(=O)/C=C/c1c[nH]c2ncc(N3CCN(C(=O)c4ccc(F)cc4F)CC3)cc12] | | + |
| 333 | 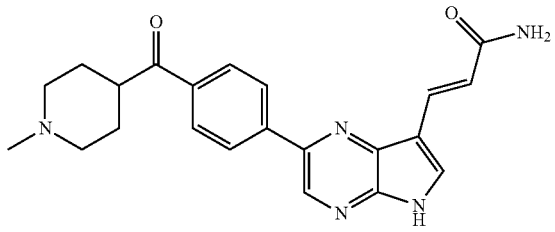 | | + |

TABLE 3-continued
TAK1-TAB1 Binding Assay
| Example | Structure | TAK1-Tab (2 h PI) Inhibition IC$_{50}$ uM + indicates ≤ 1 μM − indicates > 1 μM | IL-6 Production Inhibition IC$_{50}$ uM + indicates ≤ 1 μM − indicates > 1 μM |
|---|---|---|---|
| 334 | 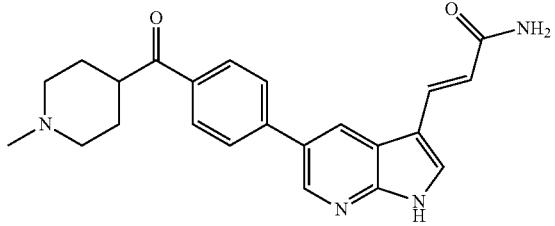 [SMILES: CN1CCC(C(=O)c2ccc(-c3cnc4[nH]cc(/C=C/C(N)=O)c4c3)cc2)CC1] | + | |
| 335 | 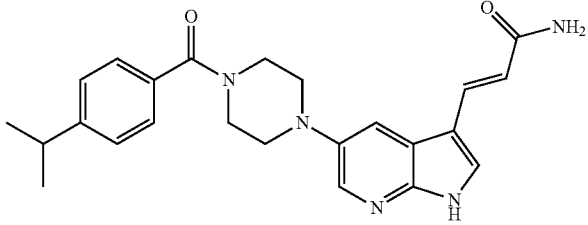 [SMILES: CC(C)c1ccc(C(=O)N2CCN(c3cnc4[nH]cc(/C=C/C(N)=O)c4c3)CC2)cc1] | + | |
| 336 | 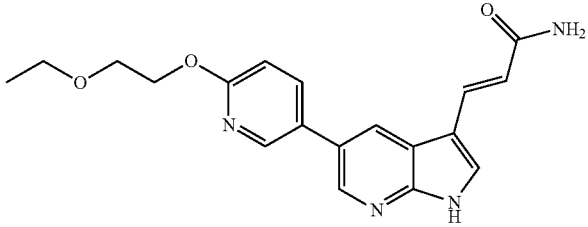 [SMILES: CCOCCOc1ccc(-c2cnc3[nH]cc(/C=C/C(N)=O)c3c2)cn1] | + | |
| 337 | 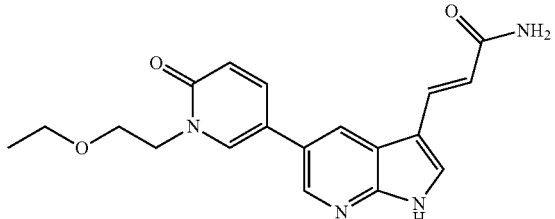 | + | |
| 338 | 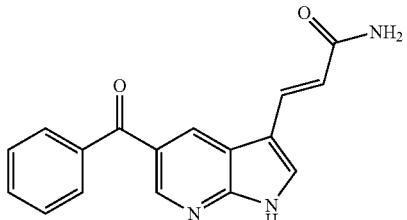 | + | |
| 339 | 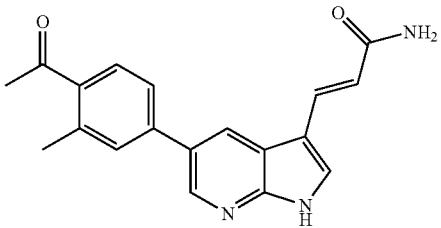 [SMILES: CC(=O)c1ccc(-c2cnc3[nH]cc(/C=C/C(N)=O)c3c2)cc1C] | + | |

TABLE 3-continued

TAK1-TAB1 Binding Assay

| Example | Structure | TAK1-Tab (2 h PI) Inhibition IC$_{50}$ uM + indicates ≤ 1 μM − indicates > 1 μM | IL-6 Production Inhibition IC$_{50}$ uM + indicates ≤ 1 μM − indicates > 1 μM |
|---|---|---|---|
| 340 | 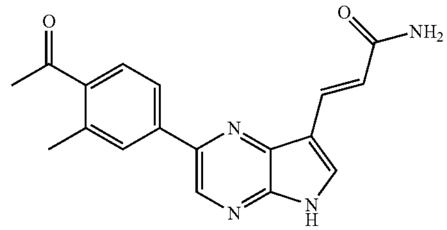 [SMILES: CC(=O)c1ccc(-c2cnc3[nH]cc(/C=C/C(N)=O)c3n2)cc1C] | + | |
| 341 | 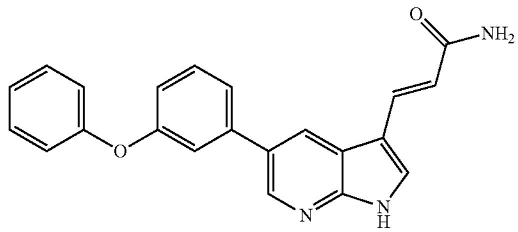 [SMILES: NC(=O)/C=C/c1c[nH]c2ncc(-c3cccc(Oc4ccccc4)c3)cc12] | + | |
| 342 | 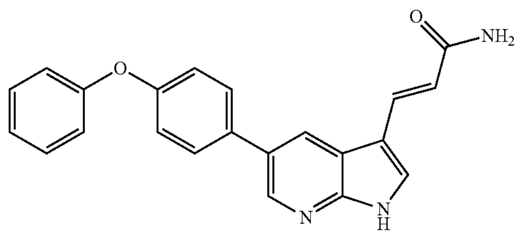 [SMILES: NC(=O)/C=C/c1c[nH]c2ncc(-c3ccc(Oc4ccccc4)cc3)cc12] | + | |
| 343 | 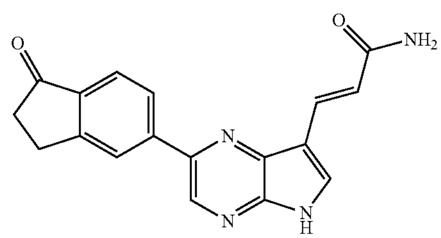 [SMILES: NC(=O)/C=C/c1c[nH]c2ncc(-c3ccc4c(c3)CCC4=O)nc12] | + | |
| 344 | 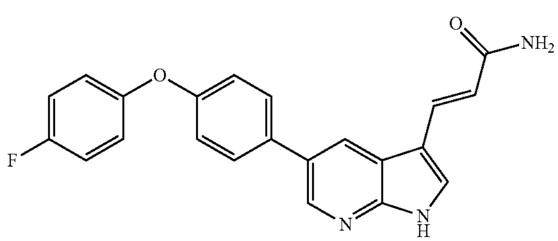 [SMILES: NC(=O)/C=C/c1c[nH]c2ncc(-c3ccc(Oc4ccc(F)cc4)cc3)cc12] | + | |
| 345 | 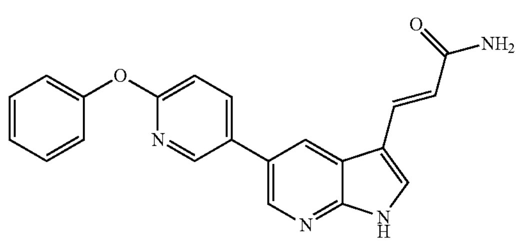 [SMILES: NC(=O)/C=C/c1c[nH]c2ncc(-c3ccc(Oc4ccccc4)nc3)cc12] | + | |

TABLE 3-continued

TAK1-TAB1 Binding Assay

| Example | Structure | TAK1-Tab (2 h PI) Inhibition IC$_{50}$ uM + indicates ≤ 1 μM − indicates > 1 μM | IL-6 Production Inhibition IC$_{50}$ uM + indicates ≤ 1 μM − indicates > 1 μM |
|---|---|---|---|
| 346 | 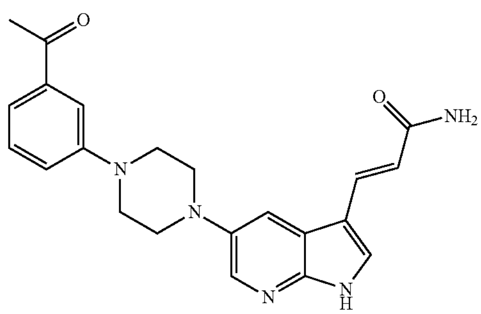 [SMILES: CC(=O)c1cccc(N2CCN(c3cnc4[nH]cc(/C=C/C(N)=O)c4c3)CC2)c1] | | + |
| 347 | 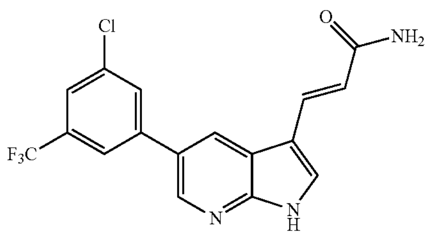 [SMILES: NC(=O)/C=C/c1c[nH]c2ncc(-c3cc(Cl)cc(C(F)(F)F)c3)cc12] | | + |
| 348 | 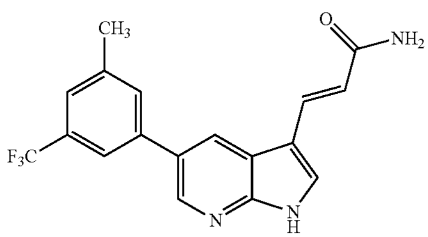 | | + |
| 349 | 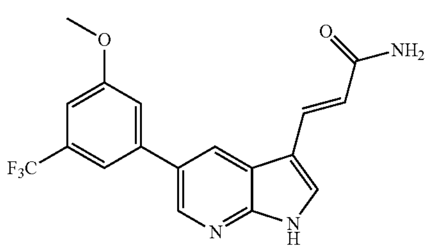 [SMILES: COc1cc(-c2cnc3[nH]cc(/C=C/C(N)=O)c3c2)cc(C(F)(F)F)c1] | | + |
| 350 | 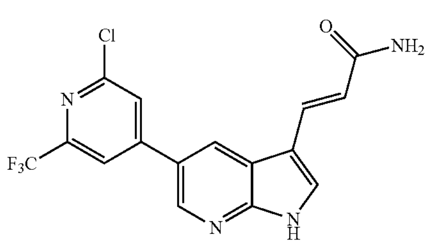 [SMILES: NC(=O)/C=C/c1c[nH]c2ncc(-c3cc(Cl)nc(C(F)(F)F)c3)cc12] | | + |

TABLE 3-continued

TAK1-TAB1 Binding Assay

| Example | Structure | TAK1-Tab (2 h PI) Inhibition IC$_{50}$ uM + indicates ≤ 1 μM − indicates > 1 μM | IL-6 Production Inhibition IC$_{50}$ uM + indicates ≤ 1 μM − indicates > 1 μM |
|---|---|---|---|
| 351 | 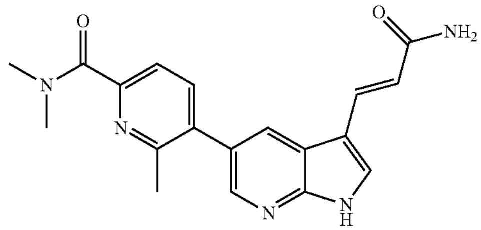 [SMILES: Cc1nc(C(=O)N(C)C)ccc1-c1cnc2[nH]cc(/C=C/C(N)=O)c2c1] | + | |
| 352 | 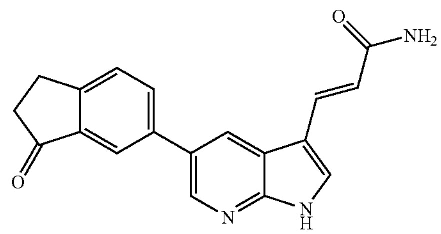 [SMILES: NC(=O)/C=C/c1c[nH]c2ncc(-c3ccc4c(c3)C(=O)CC4)cc12] | + | |
| 353 | 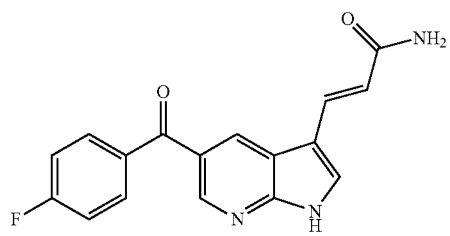 [SMILES: NC(=O)/C=C/c1c[nH]c2ncc(C(=O)c3ccc(F)cc3)cc12] | + | |
| 354 | 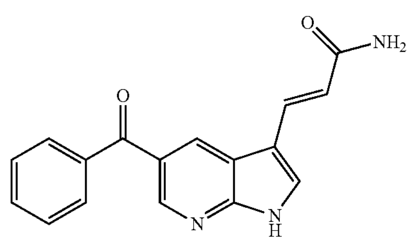 [SMILES: NC(=O)/C=C/c1c[nH]c2ncc(C(=O)c3ccccc3)cc12] | + | |
| 355 | 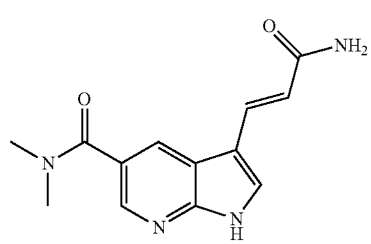 [SMILES: CN(C)C(=O)c1cnc2[nH]cc(/C=C/C(N)=O)c2c1] | + | |
| 356 | 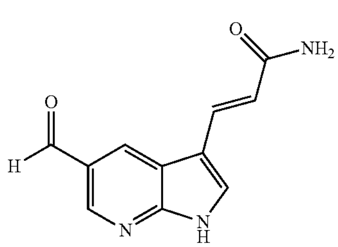 [SMILES: NC(=O)/C=C/c1c[nH]c2ncc(C=O)cc12] | + | |

TABLE 3-continued

TAK1-TAB1 Binding Assay

| Example | Structure | TAK1-Tab (2 h PI) Inhibition IC$_{50}$ uM + indicates ≤ 1 μM − indicates > 1 μM | IL-6 Production Inhibition IC$_{50}$ uM + indicates ≤ 1 μM − indicates > 1 μM |
|---|---|---|---|
| 357 | 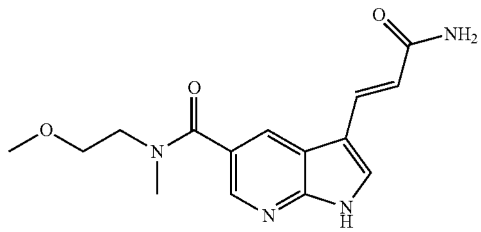 [SMILES: COCCN(C)C(=O)c1cnc2[nH]cc(/C=C/C(N)=O)c2c1] | | + |
| 358 | 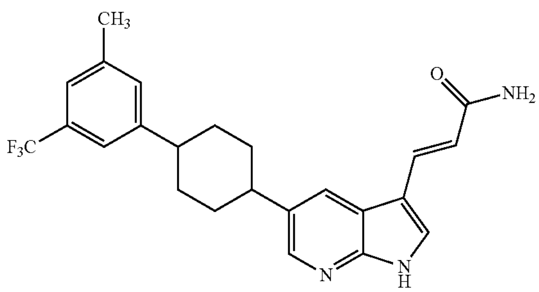 [SMILES: Cc1cc(C2CCC(c3cnc4[nH]cc(/C=C/C(N)=O)c4c3)CC2)cc(C(F)(F)F)c1] | | + |
| 359 | 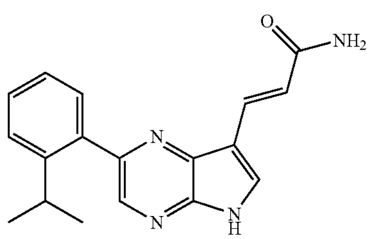 [SMILES: CC(C)c1ccccc1-c1cnc2[nH]cc(/C=C/C(N)=O)c2n1] | | + |
| 360 | 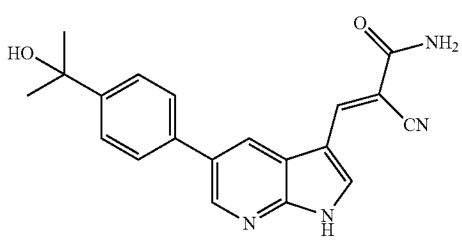 [SMILES: CC(C)(O)c1ccc(-c2cnc3[nH]cc(/C=C(\C#N)C(N)=O)c3c2)cc1] | | + |
| 361 | 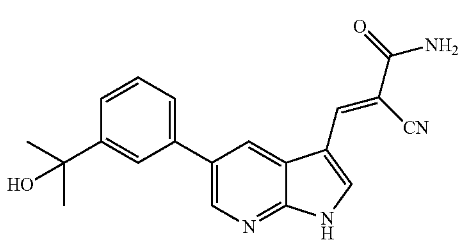 [SMILES: CC(C)(O)c1cccc(-c2cnc3[nH]cc(/C=C(\C#N)C(N)=O)c3c2)c1] | | + |
| 362 | 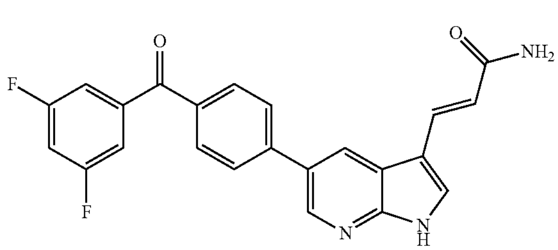 [SMILES: NC(=O)/C=C/c1c[nH]c2ncc(-c3ccc(C(=O)c4cc(F)cc(F)c4)cc3)cc12] | | + |

TABLE 3-continued

TAK1-TAB1 Binding Assay

| Example | Structure | TAK1-Tab (2 h PI) Inhibition IC$_{50}$ uM<br>+ indicates ≤ 1 µM<br>− indicates > 1 µM | IL-6 Production Inhibition IC$_{50}$ uM<br>+ indicates ≤ 1 µM<br>− indicates > 1 µM |
|---|---|---|---|
| 363 | 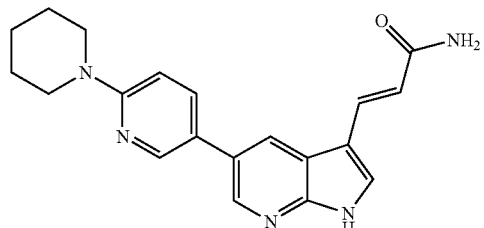 | + | |
| 364 | 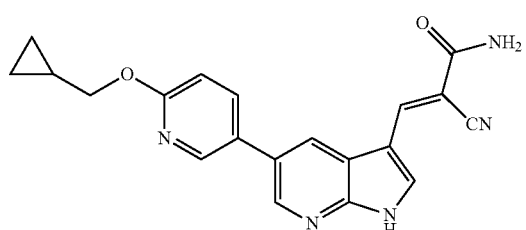 | + | |
| 365 | 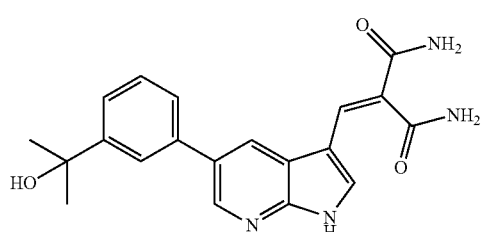 | + | |

TAK1 is also a key mediator of pro-inflammatory and stress signals. Cellular activation of TAK1 activity is promoted by pro-inflammatory cytokines such as tumor necrosis factor-α (TNF-α) and interleukin-1β (IL-1β) as well as by the engagement of T cell, B cell and toll-like receptors.

LPS Stimulated IL-6 Production in PBMC Cells:

Lipopolysaccharide (LPS) stimulated IL-6 Production in Human Peripheral Blood Mononuclear Cells (PBMC): The cellular efficacy of compound candidates is determined using peripheral blood mononuclear cells purified from human whole blood, based upon the methods of Burnette et al. (2009) Pharmacology, 84:42-60. PBMC produce a number of cytokines (IL6, IL8, IL1β and TNFα) in response to stimulation with LPS. To induce the production of inflammatory mediators, PBMC are plated at a final concentration of 2×105 cells/well in a 96 well flat bottom plate in DMEM medium supplemented with 10% fetal bovine serum, 100 units/ml penicillin and 100 µg/ml streptomycin (Gibco BRL Life Technologies). Cells are treated with or without inhibitors for 1-3 hrs then stimulated with 100 ng/ml LPS (serotype 011:B4, Sigma) for an additional 3 hrs at 37° C. with 5% $CO_2$. The supernatants are removed and stored at −20° C. until they are to be assayed. The levels of inflammatory mediators are determined using commercial MSD cytokine kits (Meso Scale Discovery) as per the manufacturer's instructions. Standard curves are based on 7 steps of 4× serial dilutions, with a wide dynamic range of 10000 pg/ml to 2.4 pg/ml, and a blank. Lower limit of detection (LLOD) is calculated at the commonly used 3× the standard deviation of the blank.

LPS Stimulated IL6 Production in Human Whole Blood:

Whole blood contains cytokine producing cells such as macrophages and monocytes. Cytokines produced in human whole blood in response to LPS include IL6, IL8 and TNFα. To induce the production of inflammatory mediators, 200 µl of fresh human whole blood are plated per well of a 96 well round bottom plate. The blood is treated with or without inhibitors (final DMSO concentration in all cases 0.1%) for 1-3 hrs then stimulated with 100 ng/ml LPS (serotype 011:B4, Sigma) for an additional 18 hrs at 37° C. with 5% $CO_2$. Plasma samples are generated by pelleting the red blood cells at 1200×g and removing the plasma. Plasma samples are stored at −20° C. until they are to be assayed. The levels of inflammatory mediators are determined using commercial MSD cytokine kits (Meso Scale Discovery) as described above.

TNFα Stimulated JNK Phosphorylation in HCT-116 Cells.

JNK is phosphorylated in response to TNFα in HCT-116 cells and is TAK dependent. To determine compound efficacy for inhibition of JNK phosphorylation, HCT-116 cells are plated at 3×104 cells/well in 96 well flat bottom plates in McCoy's 5a (ATCC) supplemented with 10% fetal bovine serum, 100 units/ml penicillin and 100 µg/ml streptomycin (Gibco BRL Life Technologies). Cells are rested for 18 hrs at 37° C. with 5% $CO_2$, then media is changed to McCoy's 5a supplemented with 1% fetal bovine serum, 100 units/ml penicillin and 100 g/ml streptomycin. After cells rest for an additional 2 hrs, they are treated with and without inhibitors (0.1% final DMSO concentration) for 1 hr, followed by 20 min stimulation with 10 ng/ml TNFα (R & D Systems) at 37° C. with 5% $CO_2$. Media is removed and cells are washed once with cold PBS. Cells are lysed in MSD lysis buffer and levels of both phosphorylated and total JNK are determined using the commercial MSD kit (Meso Scale Discovery) as per the manufacturer's instructions. Data are presented as the ratio of phosphorylated JNK to total JNK.

Reduction of Chemo-Resistance:

The potential ability of candidate compounds to decrease pancreatic cancer resistance to cytotoxicity induced by standard chemotherapeutics is evaluated with an in vitro cell-based assay. Cell proliferation $IC_{50}$ values for each candidate compound are determined in the gemcitabine resistant human pancreatic cell line PANC-1. Two dose response curves will then be generated, one for gemcitabine alone, and the other for gemcitabine in the constant presence of the candidate compound at its $IC_{50}$. For a candidate to be considered successful at decreasing gemcitabine resistance, the decrease in cell survival must be more than simply an additive effect of the two compounds. Successful candidates are further evaluated against other chemotherapeutics such as cisplatin, and also to determine if the increase in sensitivity is due to general toxicity or increased induction of apoptosis.

Nude Mouse Xenograft Model:

Evidence of in vivo efficacy of TAK1 inhibitors is evaluated using a mouse xenograft model of human pancreatic tumor growth. Female athymic nude mice (6- to 8-weeks old) are maintained in specific pathogen-free conditions. To produce pancreatic tumors, pancreatic cancer cells are harvested from sub-confluent cultures by brief exposure to 0.05% trypsin and 0.02% EDTA. Trypsin activity is stopped with medium containing 10% fetal bovine serum, and the cells washed once in serum-free medium and resuspended in serum-free Hanks balanced salt solution. To administer cells, mice are anesthetized and the tumor cell suspension injected in the left abdominal flank. Compound is orally administered at various dose levels (6 mice/dose group) daily over a 4 week period. Mice are weighed weekly and tumor growth observed. When the tumor reaches a volume greater than 2000 $mm^3$ mice are euthanized and tumor volume quantitated via imaging analysis.

Assessment of Anti-Cancer Activity of Test Compounds by MTT Based Cell Proliferation Assay:

Anti-tumor growth potential of test compounds are evaluated in vitro using various human tumor cells, available from the American Type Culture Collection ATCC), such as A549 lung tumor cells, DU145 prostate tumor cells, HT29 colon cancer cells, MIA PaCa-2 pancreatic cancer cells, MCF-7 ($ER^+$) breast tumor cells and BEAS-2B cells (immortalized normal lung epithelial cells) as control [Hida, et al., Clin. Cancer Res. 6, 2006-2011 (2000)]. Test compound effect on cell proliferation is determined using the MTT based cell proliferation assay. MTT based cell proliferation assays are described in U.S. Pat. No. 8,143,237.

MTT [3-(4,5-dimethylthiazol-2-yl)-2,5-diphenyltetrazolium bromide] incorporation based cell proliferation assay is performed using the MTT cell proliferation assay kit (Roche Applied Sciences, Germany). The assay is carried out according to the instruction provided by the vendor. Briefly, equal numbers of cells are plated in 96-well flat-bottomed plates and are incubated with test compounds at various concentrations for a period of three days. Vehicle control culture wells receive an equal volume of vehicle solution. Thereafter, 0.5 mg/ml of MTT reagent is added to each well and the microplate is incubated further for 4 hours at 37° C. in presence of 5% $CO_2$. Cells are then solubilized by adding solubilizing solution and allowed to incubate at 37° C. overnight. After complete solubilization of the formazan crystals, the absorbance is read at 540 nm in a microplate reader (BioRad, USA). The results (mean optical density (OD)±standard deviation (SD)) obtained from quadruplicate wells are used to calculate the inhibition of cell proliferation (50% of inhibitory concentration, $IC_{50}$) of the test compounds.

Suppression of Lung Cancer Cell Migration:

Efficacy testing is done to evaluate test compound suppression of lung cancer cell migration, a model of metastasis. Methods to evaluate lung cancer cell migration are described in Park, et al. Mol. Med. Reports 3, 1007-1013 (2010).

Cell Culture:

Human lung cancer cells A549 are obtained from American Type Culture Collection (ATCC, Manassas, Va.). Cells are incubated in RPMI-1640 medium supplemented with 10% fetal bovine serum (FBS) and penicillin/streptomycin (GibcoBRL, Grand Island, N.Y., USA).

Monolayer Wound Healing Assay:

Cell proliferation in confluent A549 monolayers is blocked by a 30 minute pre-incubation in the presence of mitomycin C (3 µg/ml). Test compounds, in cell culture buffer, are added to confluent monolayers 30 minutes before wound induction. A549 monolayers are subsequently scratched with a pipette tip. Wound areas are evaluated with phase contrast microscopy on an inverted microscope. Images of the same areas are obtained at intervals from zero to 96 hours. Cell migration rate via wound healing is evaluated from the images using Paint.Net v.3.10 software. Cell migration is expressed as the fold change in the migration area, relative to untreated control cells at the same time period.

Compound Formulations for Intravenous (IV), Oral Gavage (PO) or Intraperitoneal (IP) Administration:

Compounds are formulated for administration using 25% hydroxypropyl-beta-cyclodextrin-PBS buffer (HBCD-PBS) at 1 mg/ml. HBCD-PBS is the preferred formulation media for compound administration. Additional formulation vehicles may also be used, including 2% Tween 80 in saline, and 20% polyethylene glycol (PEG-300) in 0.9% sodium chloride in water.

Determination of Maximum Tolerated Dose (MTD) of Test Compounds in Rats:

In order to estimate the doses of test compounds for use in efficacy testing in animal models of cancer, it is determined at what doses adverse events occur. Methods to determine MTD in rats are described in Rao, et al., Mol. Cancer Ther. 5, 1530-1538 (2006).

In order to determine doses for efficacy studies, the maximum tolerated dose (MTD) is determined. Male F344 rats are fed various concentrations of test compounds for six weeks. MTD is determined based on the highest dose that causes a 10% loss in body weight without mortality or signs of toxicity. Body weights are recorded twice weekly. Animals are examined daily for signs of toxicity. At termination, animals are euthanized and organs dissected and examined.

Anti-Inflammatory Efficacy—Rat Carrageenan Foot Pad Edema:

The compounds of the present invention are evaluated for efficacy in vivo in a model of inflammation. Methods to determine efficacy in rat carrageenan foot pad edema are described in U.S. Pat. No. 5,760,068.

Male Sprague Dawley rats are selected for equal average body weight per group. After fasting, with free access to water sixteen hours prior to test, animals are dosed orally (1 mL) with test compounds in a vehicle containing 0.5% methylcellulose and 0.025% surfactant. The control group is dosed with vehicle alone.

One hour after dosing, a subplantar injection of 0.1 mL of 1% solution of carrageenan/sterile 0.9% saline is administered in one foot, to all animals. The volume of the injected foot is measured using a displacement plethysmometer. Foot volume is measured again three hours after carrageenan injection. The three hour foot volume measurement is compared between treated and control groups; the percent inhibition of edema is calculated.

Anti-Inflammatory Efficacy—Rat Carrageenan-Induced Analgesia Test:

The compounds of the present invention are evaluated for efficacy in vivo in a model of inflammatory analgesia. Methods to determine efficacy in rat carrageenan-induced analgesia test are described in U.S. Pat. No. 5,760,068.

Male Sprague Dawley rats are selected for equal average body weight per group. After fasting, with free access to water sixteen hours prior to test, animals are dosed orally (1 mL) with test compounds in vehicle containing 0.5% methylcellulose and 0.025% surfactant. Control groups are dosed with vehicle alone.

One hour after dosing, a subplantar injection of 0.1 mL of 1% solution of carrageenan/sterile 0.9% saline is administered in one foot, to all animals. Three hours after carrageenan injection, rats are placed in a plexiglass container with a high intensity lamp under the floor. After twenty minutes, thermal stimulation is begun on either the injected or the uninjected foot. Foot withdrawal is determined by a photoelectric cell. The time until foot withdrawal is measured and compared between treated and control groups. The percent inhibition of the hyperalgesic foot withdrawal is calculated.

Efficacy in Collagen-Induced Arthritis:

The compounds of the present invention are evaluated in a mouse autoimmune model of rheumatoid arthritis. Methods to determine efficacy in collagen-induced arthritis in the mouse are described by Grimstein, et al. (2011) J. Tranlational Med. 9, 1-13.

Six week-old male DBA/1J mice are obtained from The Jackson Laboratory. At eight weeks of age, mice are orally administered test compounds daily. Mice are immunized by intradermal injection, at twelve weeks of age, with 0.1 ml of emulsion containing 100 μg of bovine type II collagen (bCII). At 21 days following immunization, mice are boosted with 0.1 ml of bCII (100 μg) emulsified in equal volume of incomplete Freund's Adjuvant (IFA) (Difco, Detroit, Mich.). All mice are monitored three times for the incidence of arthritis and evaluation of a clinical score, ranging from 0-4 was used (0: no swelling or redness; 1: detectable arthritis with erythema; 2: significant swelling and redness; 3: severe swelling and redness from joint to digit; 4: joint stiffness or deformity with ankylosis). The score is calculated from the average cumulative value of all four paws. Severe arthritis is defined as a score >3.

For terminal evaluation of arthritis, mice are euthanized 28 days after initial immunization. The two hind limbs are removed, fixed in formalin, decalcified in RDO solution (Apex Engineering, Aurora, Ill.) for 10-20 min depending on tissue size and examined for pliability. Sections are cut (4 μm thick) and stained with hematoxylin and eosin. Histological evaluation is performed by examining for infiltration of immune cells, hyperplasia, pannus formation and bone deformation for each paw, using a scale ranging from 0-3, according to severity of pathological changes (0: normal, 1: mild, 2: moderate, 3: severe).

Tumor Growth Inhibition in Xenograft Mouse Model of Non-Small Cell Lung Cancer (NSCLC):

Efficacy testing is done in animal models of cancer tumors. Methods to determine tumor growth inhibition in xenograft mouse models of NSCLC are described in Williams, et al., Clin. Cancer Res. 7, 724-733 (2001)

Female HRLN nu/nu mice are injected subcutaneously with $1 \times 10^7$ MV-522 cells in 0.1 ml of phosphate-buffered saline. Treatment is initiated when tumors measure 5×5 mm. Mice are weighed and tumors measured by calipers twice weekly. Animals are euthanized and tumors harvested and measured after 67 days or when animal dies. Drug efficacy is measured based on animal survival and tumor growth.

Tumor Growth Inhibition in Xenograft Mouse Model of Colon Cancer:

Efficacy testing is done in animal models of cancer tumors. Methods to determine tumor growth inhibition in xenograft mouse models of colon cancer are described in Carie, et al., J. Drug Delivery 2011, 1-9 (Article ID 869027).

Female HRLN nu/nu mice are injected subcutaneously with $5 \times 10^7$ HT-29 cells in 0.1 ml of phosphate-buffered saline. Treatment is initiated when tumors measure 5×5 mm. Mice are weighed and tumors measured by calipers twice weekly. Animals are euthanized and tumors harvested and measured after 67 days or when animal dies. Drug efficacy is measured based on animal survival and tumor growth.

Growth Inhibition of Gallbladder Adenocarcinoma in Transgenic Mice:

Efficacy testing is done in animal models of cancer tumors. Gallbladder adenocarcinoma in transgenic mice is described in Kiguchi, et al., Mol. Cancer Ther. 6, 1709-1717 (2007).

Homozygous BK5.ErbB-2 transgenic mice, that overexpress rat ErbB-2, and nontransgenic littermates receive a control AIN76A diet or an experimental diet containing the test compound for one month. The transgenic mice develop adenocarcinoma of the gallbladder with a 90% incidence. Ultrasound image analysis and histologic evaluation are used to determine compound effects on gall bladder tumor reversion to a milder phenotype and inhibition of tumor progression.

Inhibition of Colon Cancer in Azomethane-Treated Rats:

Efficacy testing is done in animal models of cancer tumors. Colon cancer in azomethane-treated rats is described in Rao, et al., Mol. Cancer Ther. 5, 1530-1538 (2006).

Male F344 rats (Charles River Breeding Laboratories) are given test compounds blended into the diet. Efficacy of test compounds are determined following initiation of azoxymethane-induced colon cancer. Rats are randomly distributed by weight into various groups and housed in cages. Azomethane treated animals are injected subcutaneous (s.c.), twice weekly, at 15 mg/kg body weight. Vehicle-treated groups are injected with normal saline. Rats are placed on control diet or diets containing test compounds, two weeks after the second injection of azomethane or saline. Body weights are measured every two weeks until termination, 52 weeks after the last azoxymethane treatment. Organs are dissected and examined using a dissecting microscope.

Colon tumors with a diameter of >0.4 cm are fixed in 10% neutral buffered formalin for histopathologic evaluation.

Test compounds are evaluated for effect on colonocyte proliferation. Proliferating cell nuclear antigen (PCNA) expression is determined by immunohistochemistry. Paraffin-embedded colons are sectioned and mounted on slides. PCNA antibody (PharMingen, San Diego, Calif.), at a 1:200 dilution, is added for 1 hour. Sections are washed, then incubated with secondary anti-rabbit IgG (30 minutes). Following washing, avidin biotin-complex reagent (Vector Laboratories, Burlingame, Calif.) is added. Sections are washed and 3,3"-diaminobenzidine is added and sections are counterstained with hematoxylin. Proliferation index is calculated based on the number of positive cells (brown nucleus) per crypt.

OTHER EMBODIMENTS

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

All references cited in this specification are hereby incorporated by reference. The discussion of the references herein is intended merely to summarize the assertions made by their authors and no admission is made that any reference constitutes prior art relevant to patentability. Applicant reserves the right to challenge the accuracy and pertinence of the cited references.

What is claimed is:
1. A compound of Formula (I):

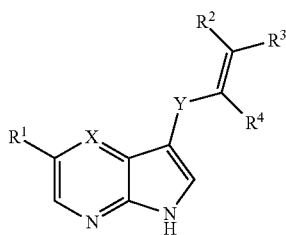

(I)

or a pharmaceutically acceptable salt thereof, wherein:
$R^1$ is chosen from $C_{2-6}$ alkyl, $OC_{3-7}$ cycloalkyl, $C_{1-4}$ alkylamino, $N(R^4)_2$, $NH(CH_2)_nC_{3-7}$cycloalkyl, CN, $C(O)N(R^4)_2$, $C(O)C_{1-4}$ alkyl, C(O)aryl, C(O)heteroaryl, $CH_2$aryl, CHFaryl, $CH_2$heteroaryl, CHFheteroaryl, heterocyclyl, aryl and heteroaryl; wherein each alkyl, cycloalkyl, heterocyclyl, aryl or heteroaryl group of $R^1$ may be optionally substituted with one or more $R^5$ substituents;
$R^2$ is chosen from hydrogen, fluoro, $C_{1-6}$ alkyl, $C(O)R^4$, CN, $C(O)NH_2$, and $C(O)NHCH_3$;
$R^3$ is chosen from $C(O)R^4$, CN, $C(O)NH_2$, $C(O)NHCH_3$, C(O)alkyl, $C(O)C_{1-6}$ alkylN$(R^4)_2$, and $C(O)C_{1-6}$ alkylOR$^4$; or when $R^2$ is $C(O)R^4$, $C(O)NH_2$, $C(O)NHCH_3$, or CN, then $R^3$ is chosen from hydrogen, fluoro, and $CH_3$;

each $R^4$ is independently chosen from hydrogen, $C_{1-6}$ alkyl, and $C_{3-6}$ cycloalkyl;
wherein each $R^4$ together with the atoms to which they are attached optionally form a heterocycloalkyl or heteroaryl ring, which may be optionally substituted with one or more $R^5$ substituents;
each $R^5$ is independently chosen from $C_{1-6}$ alkyl, $(CH_2)_nC_{3-7}$ cycloalkyl, OH, $OC_{1-6}$ alkyl, $OCF_3$, O-aryl, O-heteroaryl, $CH_2$aryl, $CH_2$heteroaryl, CH(OH)aryl, CH(OH)heteroaryl, $O(CH_2)_nC_{3-6}$ cycloalkyl, $C_{1-4}$ alkylamino, $NHC_{3-7}$ cycloalkyl, $N(R^4)_2$, NHC(O)alkyl, NHC(O)aryl, NHC(O)heteroaryl, CN, $C(O)N(R^4)_2$, $C(O)OC_{1-6}$ alkyl, C(O)O-aryl, C(O)O-heteroaryl, $C(O)C_{1-6}$ alkyl, $C(O)CF_3$, $C(O)C_{3-7}$ cycloalkyl, C(O)aryl, C(O)heteroaryl, C(O)heterocyclyl, trifluoromethyl, halo, $S(O)_2CH_3$, $S(O)CH_3$, $SCH_3$, aryl, and heteroaryl; wherein each alkyl, cycloalkyl, aryl, heteroaryl or heterocyclyl of $R^5$ may be optionally substituted with one or more $R^6$;
each $R^6$ is independently chosen from halo, $C_{1-6}$ alkyl, $C_{3-6}$ cycloalkyl, $CF_3$, OH, $OCH_3$, $OCH_2CH_3$, $OCH_2CH_2CH_2F$, $O(CH_2)_nCF_3$, and CN;
$R^7$ is chosen from hydrogen, $C_{1-6}$ alkyl, $OC_{1-6}$ alkyl, $OC_{3-7}$ cycloalkyl, $C_{1-4}$ alkylamino, $NHC_{1-6}$ alkyl, $NHC_{3-7}$ alkyl, CN, trifluoromethyl, halo, aryl and heteroaryl; wherein alkyl, aryl or heteroaryl groups of $R^7$ may be optionally substituted with one or more $R^5$ substituents;
X is $CR^7$;
Y is chosen from a bond, $CH_2$, CHF, C(O), and NHC(O); and
n is chosen from 0, 1, and 2.

2. The compound of claim 1, wherein the compound has formula (II)

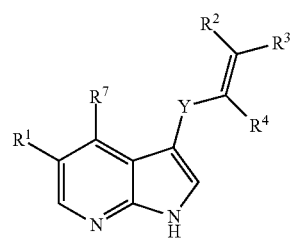

(II)

wherein:
$R^1$ is chosen from $C_{2-6}$ alkyl, $OC_{3-7}$ cycloalkyl, $C_{1-4}$ alkylamino, $N(R^4)_2$, CN, $C(O)N(R^4)_2$, $C(O)C_{1-4}$ alkyl, C(O)aryl, C(O)heteroaryl, $CH_2$aryl, CHFaryl, $CH_2$heteroaryl, CHFheteroaryl, aryl and heteroaryl;
wherein each alkyl, aryl or heteroaryl group of $R^1$ may be optionally substituted with one or more $R^5$ substituents;
$R^2$ is chosen from hydrogen, fluoro, $C_{1-6}$ alkyl, $C(O)R^4$, CN, $C(O)NH_2$, and $C(O)NHCH_3$;
$R^3$ is chosen from $C(O)R^4$, CN, $C(O)NH_2$, $C(O)NHCH_3$, C(O)alkyl, $C(O)C_{1-6}$ alkylN$(R^4)_2$, and $C(O)C_{1-6}$ alkylOR$^4$; or when $R^2$ is $C(O)R^4$, $C(O)NH_2$, $C(O)NHCH_3$, or CN, then $R^3$ is chosen from hydrogen, fluoro and $CH_3$;
each $R^4$ is independently chosen from hydrogen, $C_{1-6}$ alkyl, and $C_{3-6}$ cycloalkyl;
wherein each $R^4$ together with the atoms to which they are attached optionally form a heterocycloalkyl or heteroaryl ring, which may be optionally substituted with one or more $R^5$ substituents;

each $R^5$ is independently chosen from $C_{1-4}$ alkyl, OH, $OC_{1-6}$ alkyl, $CH_2$aryl, $CH_2$heteroaryl, $O(CH_2)_nC_{3-6}$ cycloalkyl, $C_{1-4}$ alkylamino, $NHC_{3-7}$ cycloalkyl, $N(R^4)_2$, NHC(O)alkyl, NHC(O)aryl, NHC(O)heteroaryl, CN, $C(O)N(R^4)_2$, $C(O)OC_{1-6}$ alkyl, $C(O)C_{1-6}$ alkyl, $C(O)C_{3-7}$ cycloalkyl, C(O)aryl, C(O)heteroaryl, C(O)heterocyclyl, trifluoromethyl, halo, $S(O)_2CH_3$, $S(O)CH_3$, $SCH_3$, aryl, and heteroaryl; wherein each alkyl, aryl, heteroaryl or heterocyclyl of $R^5$ may be optionally substituted with one or more $R^6$;

each $R^6$ is independently chosen from halo, $C_{1-4}$ alkyl, $C_{3-6}$ cycloalkyl, $CF_3$, OH, $OCH_3$ and CN;

$R^7$ is chosen from hydrogen, $C_{1-6}$ alkyl, $OC_{1-6}$ alkyl, $OC_{3-7}$ cycloalkyl, $C_{1-4}$ alkylamino, $NHC_{1-6}$ alkyl, $NHC_{3-7}$ alkyl, CN, trifluoromethyl, halo, aryl and heteroaryl; wherein alkyl, aryl or heteroaryl groups of $R^7$ may be optionally substituted with one or more $R^5$ substituents;

Y is chosen from a bond, $CH_2$, CHF, C(O), and NHC(O); and n is chosen from 0, 1, and 2.

3. The compound of claim 2, wherein the compound has formula (III):

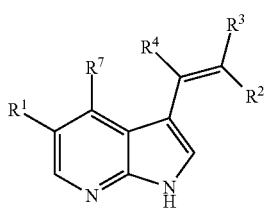

(III)

wherein:

$R^1$ is chosen from $C_{2-6}$ alkyl, $OC_{3-7}$ cycloalkyl, $C_{1-4}$ alkylamino, $N(R^4)_2$, CN, $C(O)N(R^4)_2$, $C(O)C_{1-4}$ alkyl, C(O)aryl, C(O)heteroaryl, $CH_2$aryl, CHFaryl, $CH_2$heteroaryl, CHFheteroaryl, aryl and heteroaryl; wherein each alkyl, aryl or heteroaryl group of $R^1$ may be optionally substituted with one or more $R^5$ substituents;

$R^2$ is chosen from hydrogen, fluoro, $C_{1-6}$ alkyl, $C(O)R^4$, CN, $C(O)NH_2$, and $C(O)NHCH_3$;

$R^3$ is chosen from $C(O)R^4$, CN, $C(O)NH_2$, $C(O)NHCH_3$, C(O)alkyl, $C(O)_{C1-6}$ alkyl$N(R^4)_2$, and $C(O)C_{1-6}$ alkyl$OR^4$; or when $R^2$ is $C(O)R^4$, $C(O)NH_2$, $C(O)NHCH_3$, or CN, then $R^3$ is chosen from hydrogen, fluoro and $CH_3$;

each $R^4$ is independently chosen from hydrogen, $C_{1-6}$ alkyl, and $C_{3-6}$ cycloalkyl;

wherein each $R^4$ together with the atoms to which they are attached optionally form a heterocycloalkyl or heteroaryl ring, which may be optionally substituted with one or more $R^5$ substituents;

each $R^5$ is independently chosen from $C_{1-4}$ alkyl, OH, $OC_{1-6}$ alkyl, $CH_2$aryl, $CH_2$heteroaryl, $O(CH_2)_nC_{3-6}$ cycloalkyl, $C_{1-4}$ alkylamino, $NHC_{3-7}$ cycloalkyl, $N(R^4)_2$, NHC(O)alkyl, NHC(O)aryl, NHC(O)heteroaryl, CN, $C(O)N(R^4)_2$, $C(O)OC_{1-6}$ alkyl, $C(O)C_{1-6}$ alkyl, $C(O)C_{3-7}$ cycloalkyl, C(O)aryl, C(O)heteroaryl, C(O)heterocyclyl, trifluoromethyl, halo, $S(O)_2CH_3$, $S(O)CH_3$, $SCH_3$, aryl, and heteroaryl; wherein each alkyl, aryl, heteroaryl or heterocyclyl of $R^5$ may be optionally substituted with one or more $R^6$;

each $R^6$ is independently chosen from halo, $C_{1-4}$ alkyl, $C_{3-6}$ cycloalkyl, $CF_3$, OH, $OCH_3$, and CN;

$R^7$ is chosen from hydrogen, $C_{1-6}$ alkyl, $OC_{1-6}$ alkyl, $OC_{3-7}$ cycloalkyl, $C_{1-4}$ alkylamino, $NHC_{1-6}$ alkyl, $NHC_{3-7}$ alkyl, CN, trifluoromethyl, halo, aryl and heteroaryl, wherein alkyl, aryl or heteroaryl groups of $R^7$ may be optionally substituted with one or more $R^5$ substituents;

wherein alkyl, aryl or heteroaryl groups of $R^7$ may be optionally substituted with one or more $R^5$ substituents; and n is chosen from 0, 1, and 2.

4. The compound of claim 3, wherein:

$R^1$ is chosen from $C_{2-6}$ alkyl, $OC_{3-7}$ cycloalkyl, $C_{1-4}$ alkylamino, $NH_2$, $NHC_{1-6}$ alkyl, $N(C_{1-4}$ alkyl$)_2$, CN, aryl and heteroaryl; wherein each alkyl, aryl or heteroaryl group of $R^1$ may be optionally substituted with one or more $R^5$ substituents;

$R^2$ is chosen from hydrogen, fluoro, alkyl, $C(O)R^4$, CN, $C(O)NH_2$, and $C(O)NHCH_3$;

$R^3$ is chosen from $C(O)R^4$, CN, $C(O)NH_2$, $C(O)NHCH_3$, C(O)alkyl, $C(O)C_{1-6}$alkyl$N(R^4)_2$, $C(O)C_{1-6}$ alkyl$OR^4$; or when $R^2$ is $C(O)R^4$, $C(O)NH_2$, $C(O)NHCH_3$, or CN, $R^3$ is chosen from hydrogen, fluoro and $CH_3$;

each $R^4$ is independently chosen from hydrogen, $C_{1-6}$ alkyl, and $C_{3-6}$ cycloalkyl;

wherein each $R^4$ together with the atoms to which they are attached optionally form a heterocycloalkyl or heteroaryl ring, which may be optionally substituted with one or more $R^5$ substituents;

each $R^5$ is independently chosen from $C_{1-4}$ alkyl, OH, $OC_{1-6}$ alkyl, $CH_2$aryl, $CH_2$heteroaryl, $O(CH_2)_nC_{3-6}$ cycloalkyl, $C_{1-4}$ alkylamino, $NHC_{3-7}$ cycloalkyl, $N(R^4)_2$, NHC(O)alkyl, NHC(O)aryl, NHC(O)heteroaryl, CN, $C(O)N(R^4)_2$, $C(O)OC_{1-6}$ alkyl, $C(O)C_{1-6}$ alkyl, $C(O)C_{3-7}$ cycloalkyl, C(O)aryl, C(O)heteroaryl, C(O)heterocyclyl, trifluoromethyl, halo, CN, $S(O)_2CH_3$, $S(O)CH_3$, $SCH_3$, aryl, and heteroaryl; wherein each alkyl, aryl, heteroaryl or heterocyclyl of $R^5$ may be optionally substituted with one or more $R^6$;

each $R^6$ is independently chosen from halo, $C_{1-4}$ alkyl, $C_{3-6}$ cycloalkyl, $CF_3$, OH, $OCH_3$ and CN;

$R^7$ is chosen from hydrogen, $C_{1-6}$ alkyl, $OC_{1-6}$ alkyl, $OC_{3-7}$ cycloalkyl, $C_{1-4}$ alkylamino, $NHC_{1-6}$ alkyl, $NHC_{3-7}$ alkyl, CN, trifluoromethyl, halo, aryl and heteroaryl, wherein alkyl, aryl or heteroaryl groups of $R^7$ may be optionally substituted with one or more $R^5$ substituents; and n is chosen from 0, 1, and 2.

5. The compound of claim 4, wherein:

$R^1$ is chosen from $OC_{3-7}$ cycloalkyl, $NHC_{1-6}$ alkyl, CN, aryl and heteroaryl; wherein each alkyl, aryl or heteroaryl group of $R^1$ may be optionally substituted with one or more $R^5$ substituents;

$R^2$ is chosen from hydrogen, fluoro, alkyl, $C(O)R^4$, CN, $C(O)NH_2$, and $C(O)NHCH_3$;

$R^3$ is chosen from $C(O)R^4$, CN, $C(O)NH_2$, C(O)alkyl, $C(O)C_{1-6}$ alkyl$OR^4$; or when $R^2$ is $C(O)R^4$, $C(O)NH_2$, $C(O)NHCH_3$, or CN, $R^3$ is chosen from hydrogen, fluoro and $CH_3$;

each $R^4$ is independently chosen from hydrogen, $C_{1-6}$ alkyl, and $C_{3-6}$ cycloalkyl;

wherein each $R^4$ together with the atoms to which they are attached optionally form a heterocycloalkyl or heteroaryl ring, which may be optionally substituted with one or more $R^5$ substituents;

each $R^5$ is independently chosen from $C_{1-4}$ alkyl, OH, $OC_{1-6}$ alkyl, $O(CH_2)_nC_{3-6}$ cycloalkyl, $C_{1-4}$ alkylamino, $NHC_{1-6}$ alkyl, $NHC_{3-7}$ cycloalkyl $N(C_{1-4}$ alkyl$)_2$, NHC (O)alkyl, CN, trifluoromethyl, halo, aryl, and heteroaryl, wherein alkyl, aryl or heteroaryl groups of $R^5$ may be optionally substituted with $R^6$;

each $R^6$ is independently chosen from halo, $CF_3$, $OCH_3$, and CN;

$R^7$ is chosen from hydrogen, $OC_{1-6}$ alkyl, $OC_{3-7}$ cycloalkyl, $NHC_{1-6}$ alkyl, $NHC_{3-7}$ alkyl CN, trifluoromethyl, halo, aryl and heteroaryl wherein alkyl, aryl or heteroaryl groups of $R^7$ may be optionally substituted with one or more $R^5$ substituents; and n is chosen from 0 and 1.

6. The compound of claim 1, wherein:

$R^1$ is chosen from $OC_{3-7}$ cycloalkyl, $C_{1-4}$ alkylamino, $N(R^4)_2$, $NH(CH_2)_nC_{3-7}$ cycloalkyl, $C(O)N(R^4)_2$, $C(O)$aryl, $C(O)$heteroaryl, $CH_2$aryl, $CH_2$heteroaryl, heterocyclyl, aryl and heteroaryl; wherein each alkyl, cycloalkyl, heterocyclyl, aryl or heteroaryl group of $R^1$ may be optionally substituted with one or more $R^5$ substituents;

$R^2$ is chosen from hydrogen, fluoro, $C(O)R^4$, CN, $C(O)NH_2$, and $C(O)NHCH_3$;

$R^3$ is chosen from $C(O)R^4$, CN, $C(O)NH_2$, $C(O)NHCH_3$, and $C(O)$alkyl; or when $R^2$ is $C(O)R^4$, $C(O)NH_2$, $C(O)NHCH_3$, or CN, then $R^3$ is chosen from hydrogen and $CH_3$;

each $R^4$ is independently chosen from hydrogen, $C_{1-6}$ alkyl, and $C_{3-6}$ cycloalkyl;

wherein each $R^4$ together with the atoms to which they are attached optionally form a heterocycloalkyl or heteroaryl ring, which may be optionally substituted with one or more $R^5$ substituents;

each $R^5$ is independently chosen from $C_{1-6}$ alkyl, $(CH_2)_nC_{3-7}$ cycloalkyl, OH, $OC_{1-6}$ alkyl, O-aryl, $O(CH_2)_nC_{3-6}$ cycloalkyl, $C_{1-4}$ alkylamino, $NHC_{3-7}$ cycloalkyl, $N(R^4)_2$, NHC(O)alkyl, CN, $C(O)N(R^4)_2$, $C(O)C_{1-4}$ alkyl, $C(O)OC_{1-6}$ alkyl, $C(O)O$-aryl, $C(O)O$-heteroaryl, $C(O)CF_3$, $C(O)$aryl, $C(O)$heteroaryl, $C(O)$heterocyclyl, trifluoromethyl, halo, $S(O)_2CH_3$, aryl, and heteroaryl; wherein each alkyl, cycloalkyl, aryl, heteroaryl or heterocyclyl of $R^5$ may be optionally substituted with one or more $R^6$;

each $R^6$ is independently chosen from halo, $C_{1-6}$ alkyl, $C_{3-6}$ cycloalkyl, $CF_3$, $OCH_3$, $OCH_2CH_3$, $OCH_2CH_2CH_2F$, $O(CH_2)_nCF_3$, and CN;

$R^7$ is chosen from hydrogen, $C_{1-6}$ alkyl, and CN; wherein alkyl, aryl or heteroaryl groups of $R^7$ may be optionally substituted with one or more $R^5$ substituents;

X is $CR^7$;

Y is chosen from a bond, $CH_2$, C(O), and NHC(O); and n is chosen from 0, 1, and 2.

7. The compound of claim 6, wherein:

$R^1$ is chosen from $N(R^4)_2$, $C(O)N(R^4)_2$, $C(O)$aryl, $C(O)$heteroaryl, heterocycle heterocyclyl, aryl and heteroaryl; wherein each alkyl, cycloalkyl, heterocyclyl, aryl or heteroaryl group of $R^1$ may be optionally substituted with one or more $R^5$ substituents;

$R^2$ is chosen from hydrogen, $C(O)R^4$, CN, $C(O)NH_2$, and $C(O)NHCH_3$;

$R^3$ is chosen from $C(O)R^4$, CN, $C(O)NH_2$, $C(O)NHCH_3$, and $C(O)$alkyl; or when $R^2$ is $C(O)R^4$, $C(O)NH_2$, $C(O)NHCH_3$, or CN, then $R^3$ is chosen from hydrogen and $CH_3$;

each $R^4$ is independently chosen from hydrogen, and $C_{1-6}$ alkyl; wherein each $R^4$ together with the atoms to which they are attached optionally form a heterocloalkyl or heteroaryl ring, which may be optionally substituted with one or more $R^5$ substituents;

each $R^5$ is independently chosen from $C_{1-6}$ alkyl, $(CH_2)_nC_{3-7}$ cycloalkyl, OH, $OC_{1-6}$ alkyl, $O(CH_2)_nC_{3-6}$ cycloalkyl, $C_{1-4}$ alkylamino, $NHC_{3-7}$ cycloalkyl, $N(R^4)_2$, NHC(O)alkyl, CN, $C(O)N(R^4)_2$, $C(O)C_{1-4}$ alkyl, $C(O)OC_{1-6}$ alkyl, $C(O)O$-aryl, $C(O)O$-heteroaryl, $C(O)CF_3$, $C(O)$aryl, $C(O)$heteroaryl, trifluoromethyl, halo, $S(O)_2CH_3$, aryl, and heteroaryl; wherein each alkyl, cycloalkyl, aryl, heteroaryl or heterocyclyl of $R^5$ may be optionally substituted with one or more $R^6$;

each $R^6$ is independently chosen from halo, $C_{1-6}$ alkyl, $C_{3-6}$ cycloalkyl, $CF_3$, $OCH_3$, $OCH_2CH_3$, $O(CH_2)_nCF_3$, and CN;

$R^7$ is hydrogen;

X is $CR^7$;

Y is chosen from a bond, $CH_2$, and C(O); and n is chosen from 0, 1, and 2.

8. A compound selected from the group consisting of:

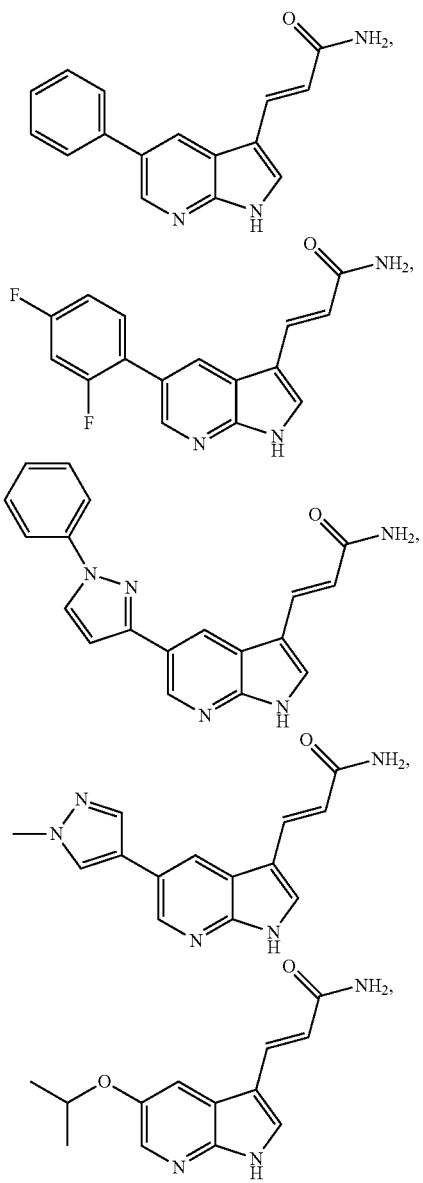

351
-continued
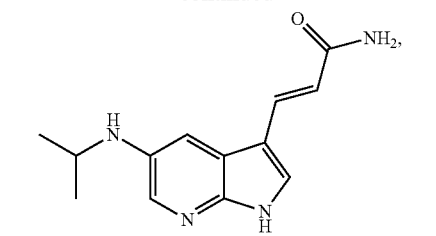
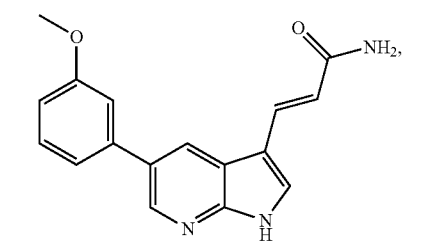
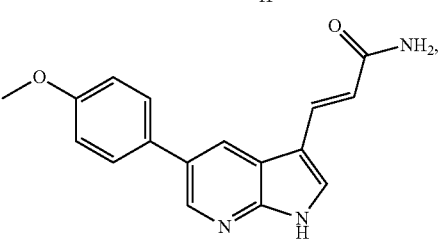
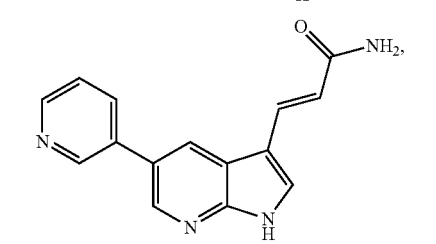
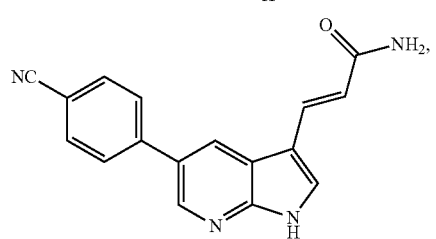
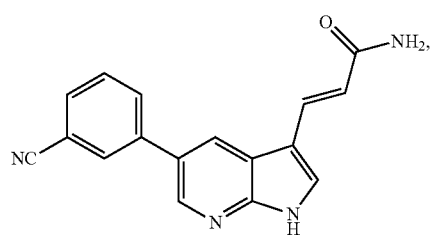
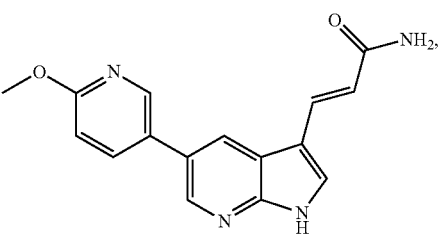
352
-continued
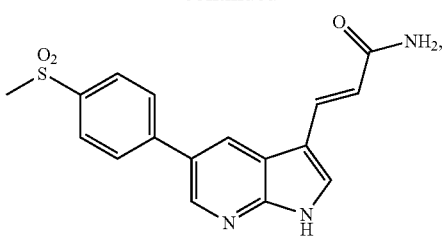
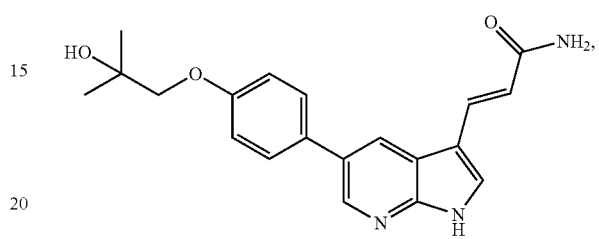
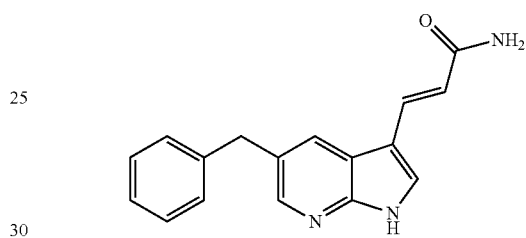
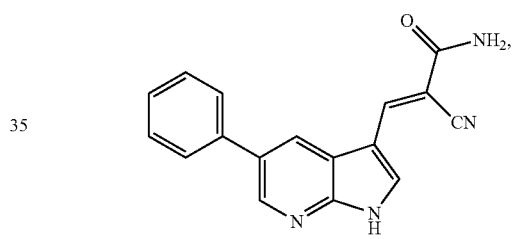
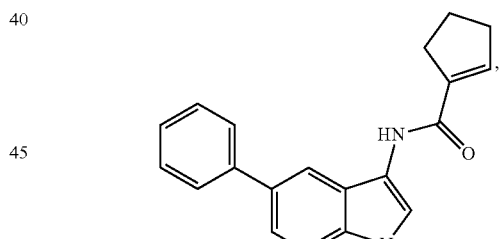
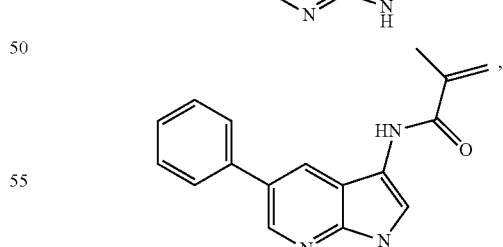
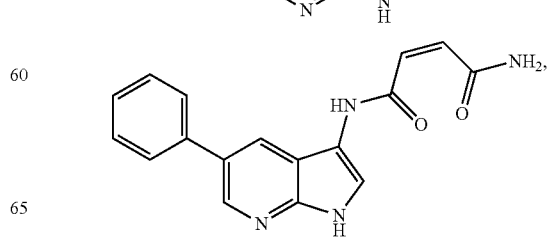

353
-continued
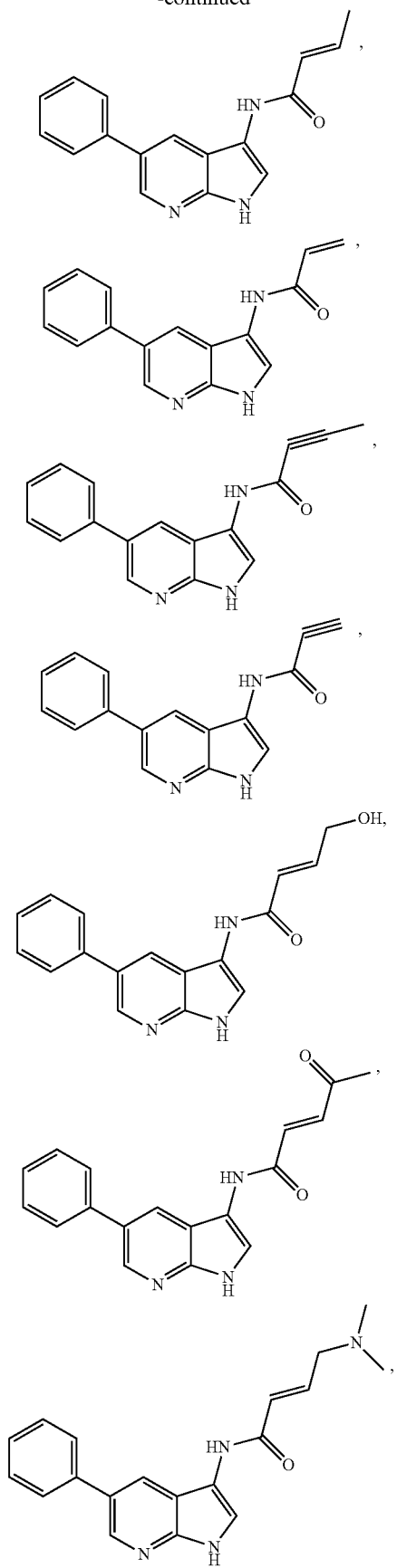
354
-continued
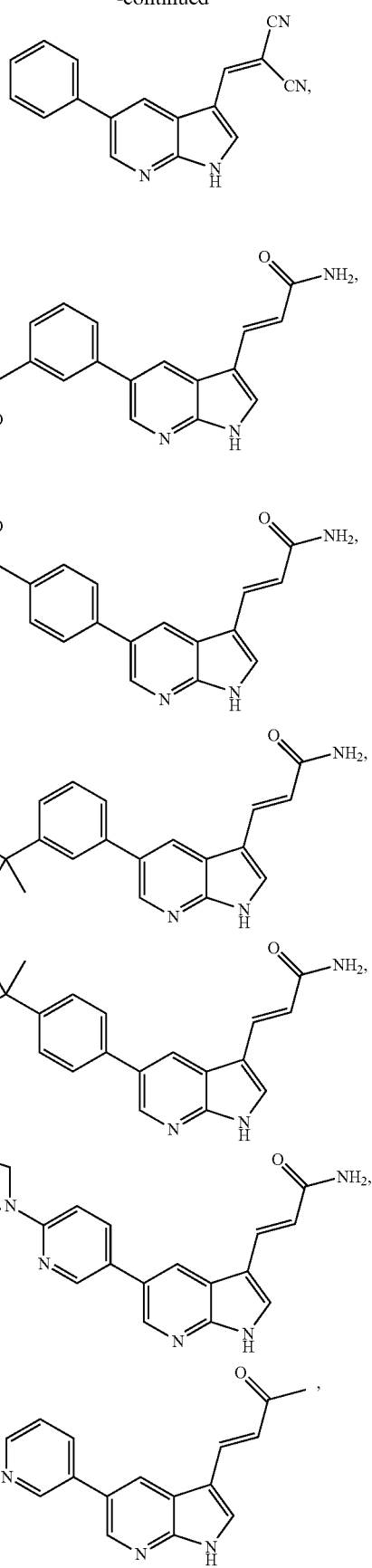

355
-continued
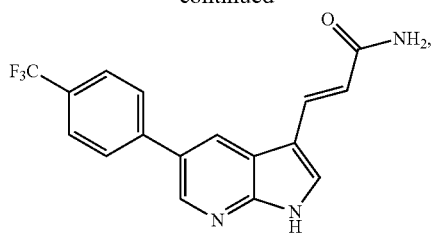
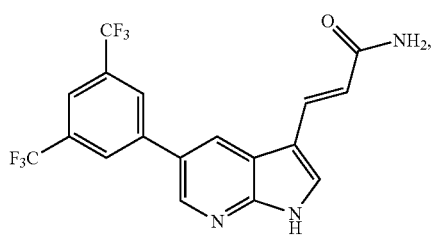
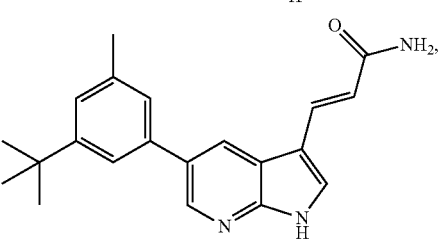
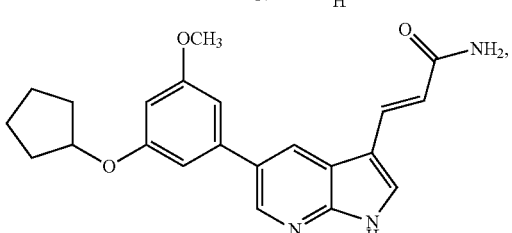
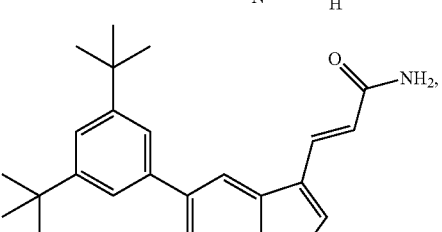
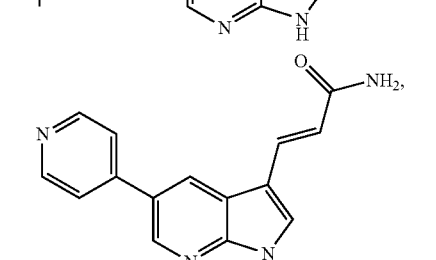
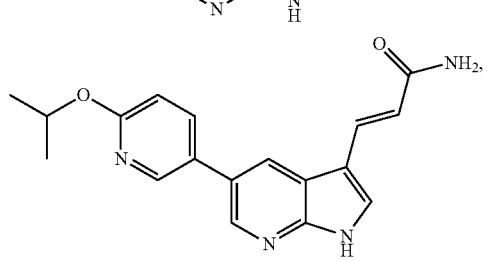
356
-continued
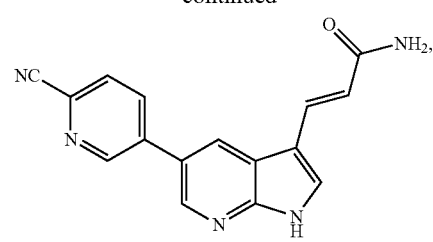
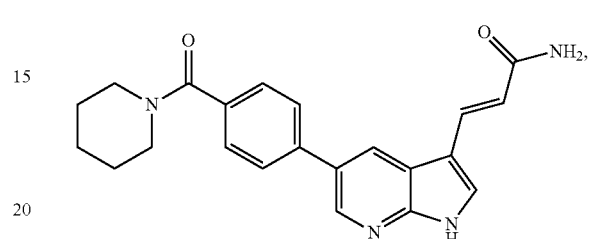
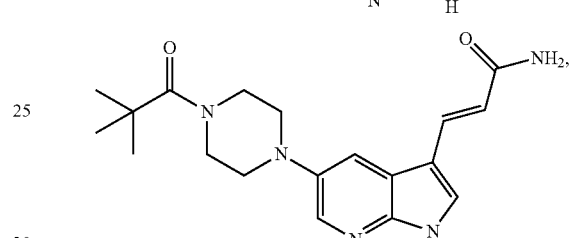
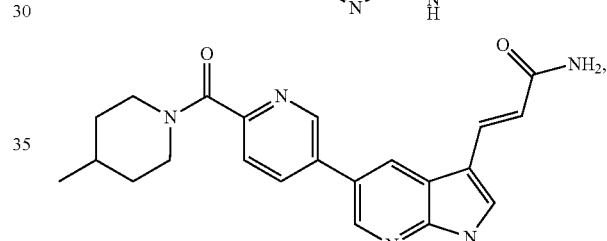
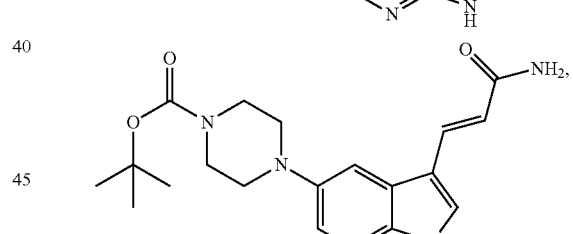
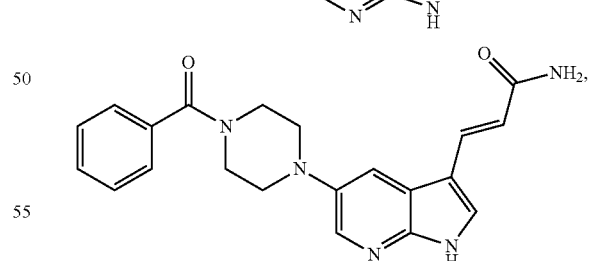
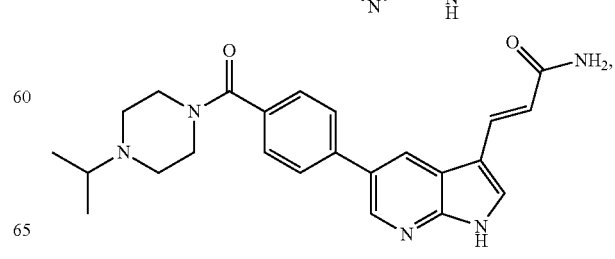

357
-continued
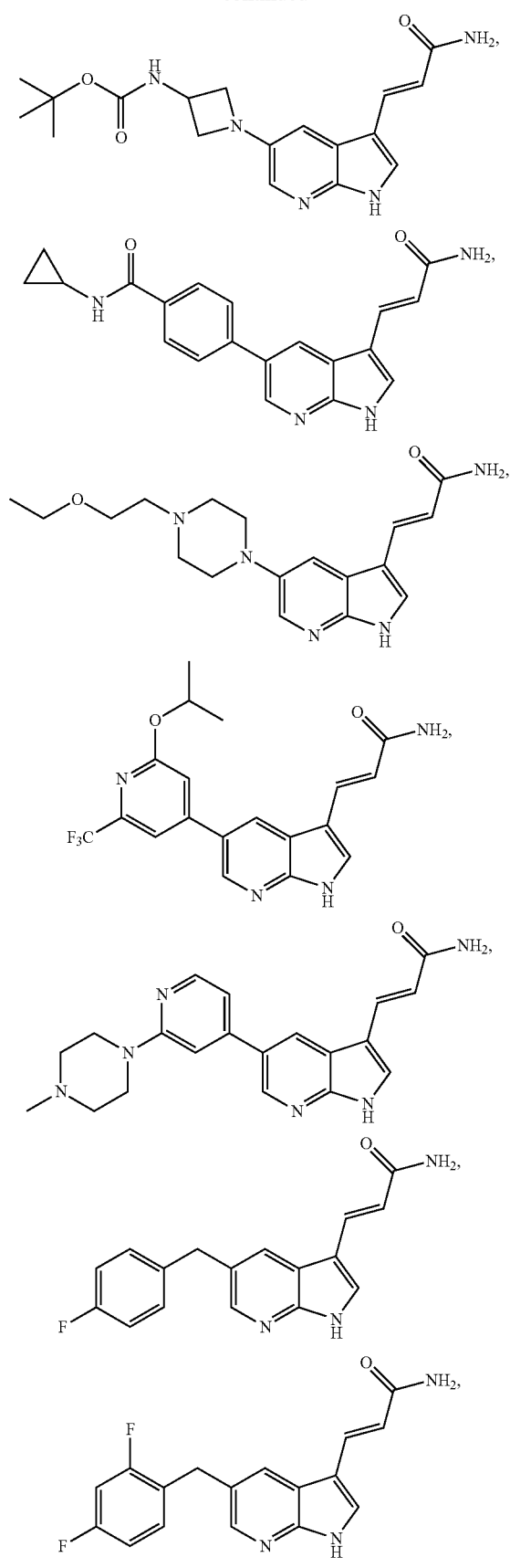
358
-continued
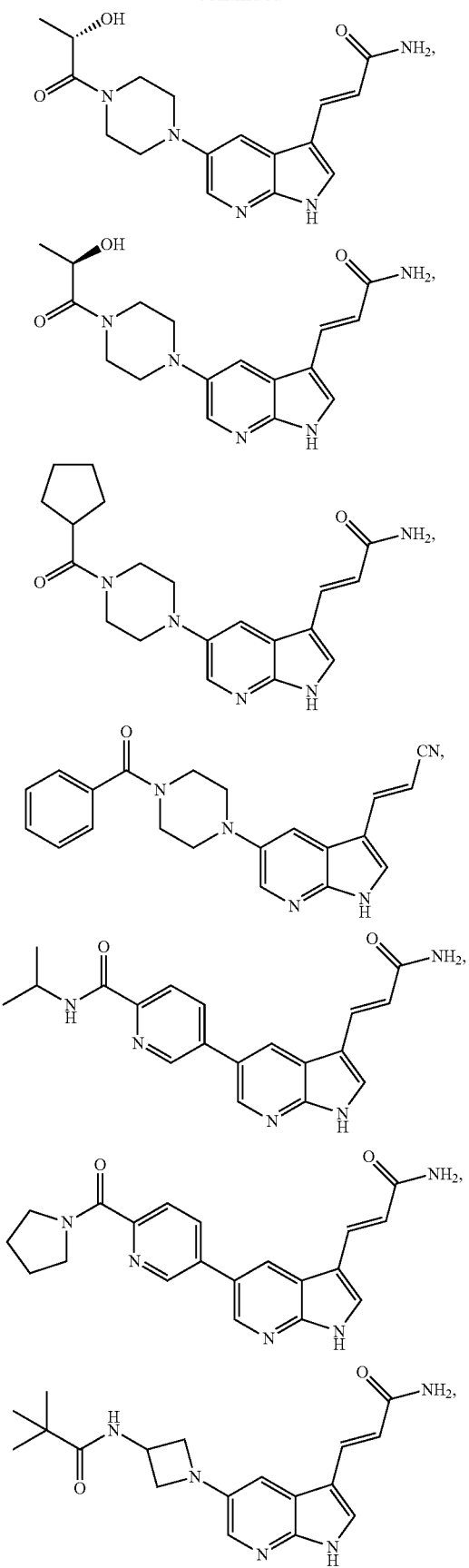

359
-continued
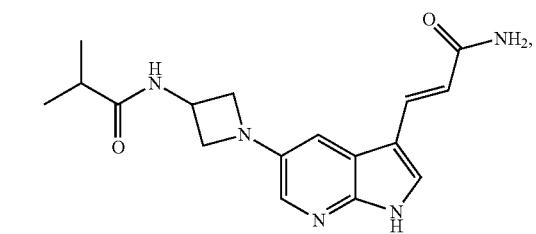
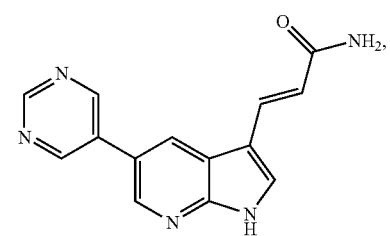
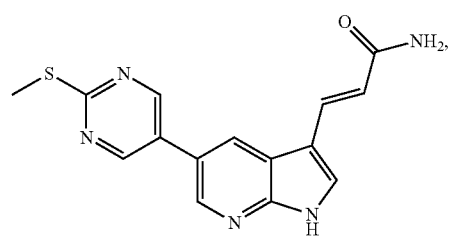
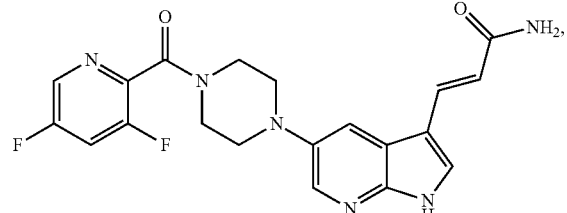
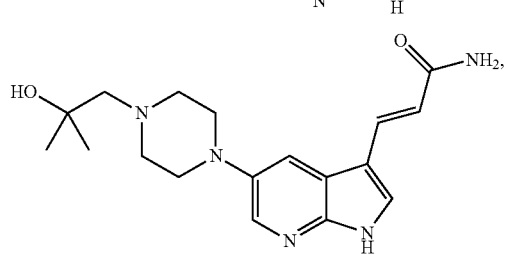
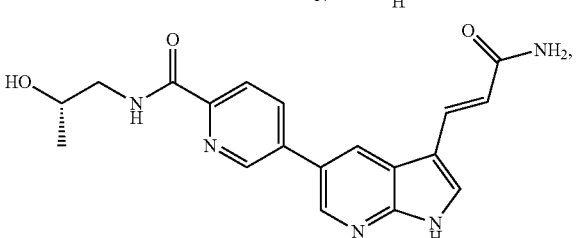
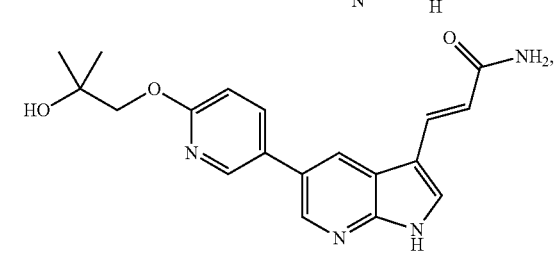
360
-continued
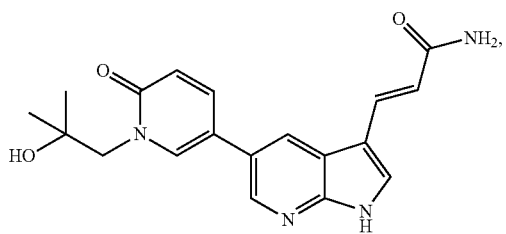
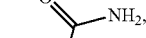

361
-continued
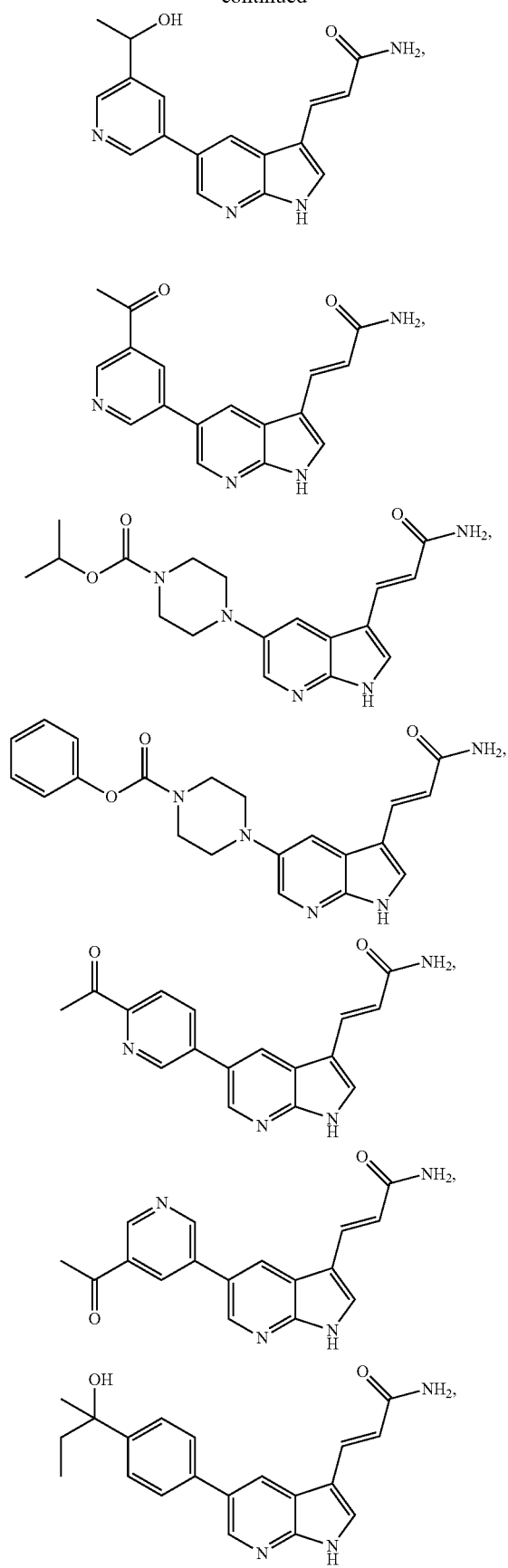
362
-continued
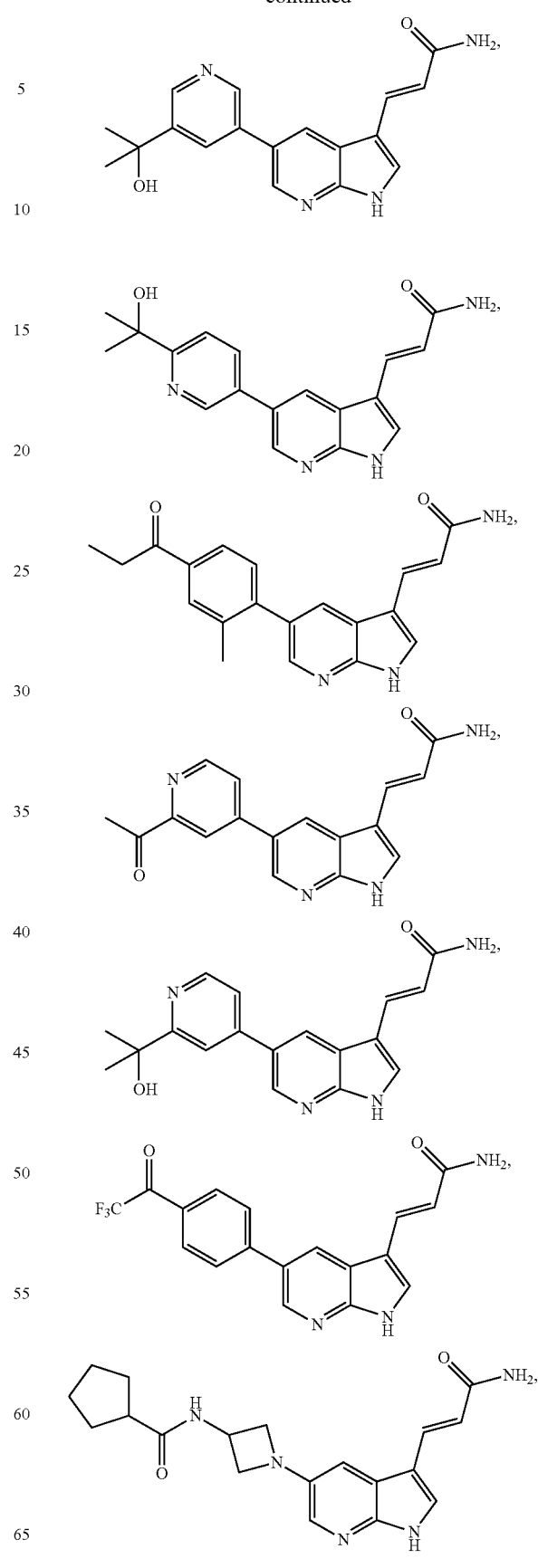

363
-continued
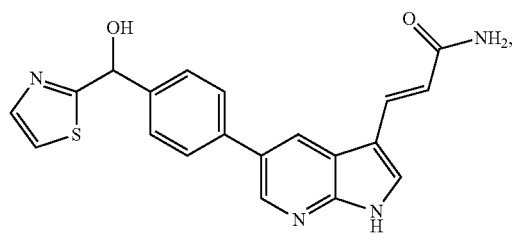
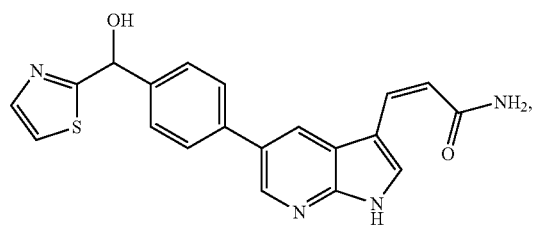
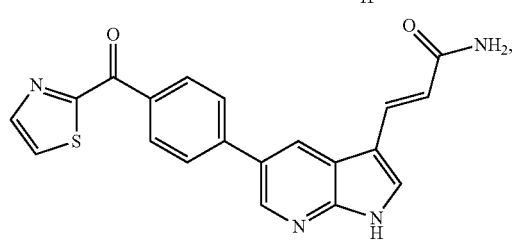
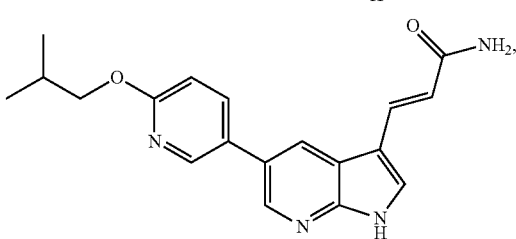
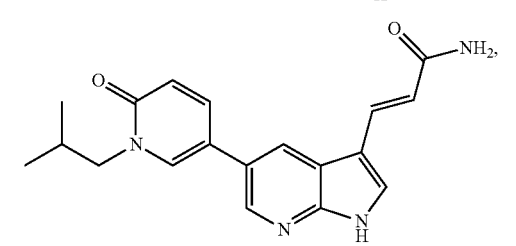
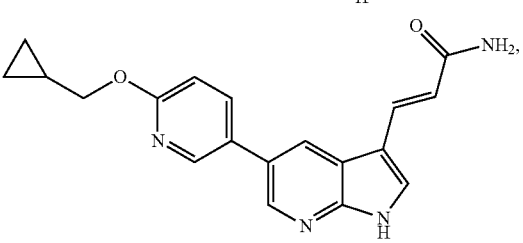
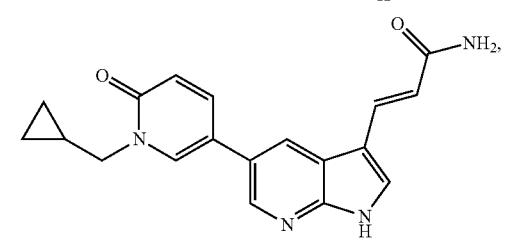
364
-continued
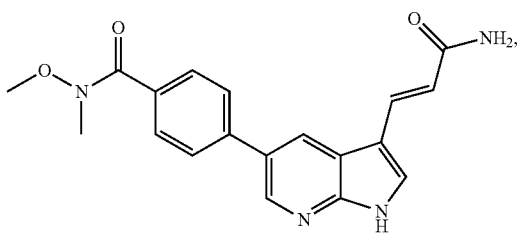
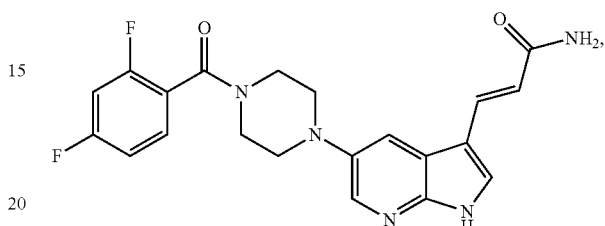
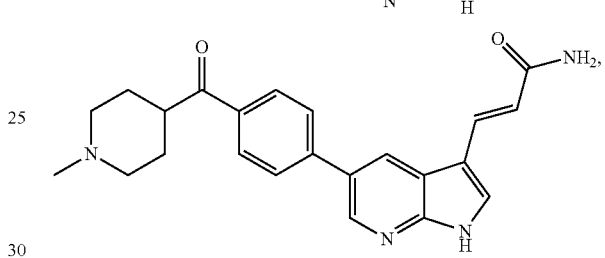
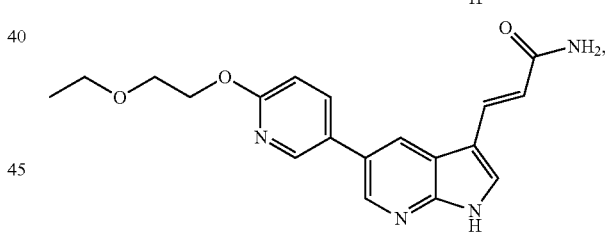
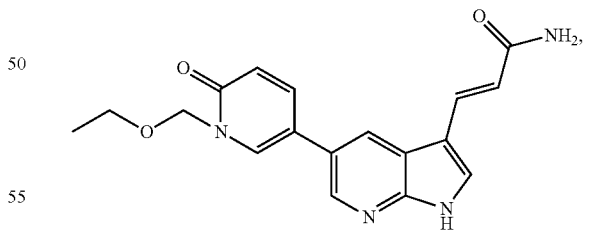
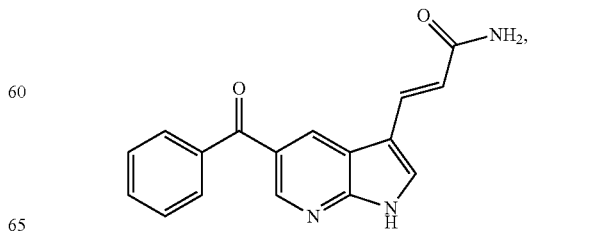

365
-continued
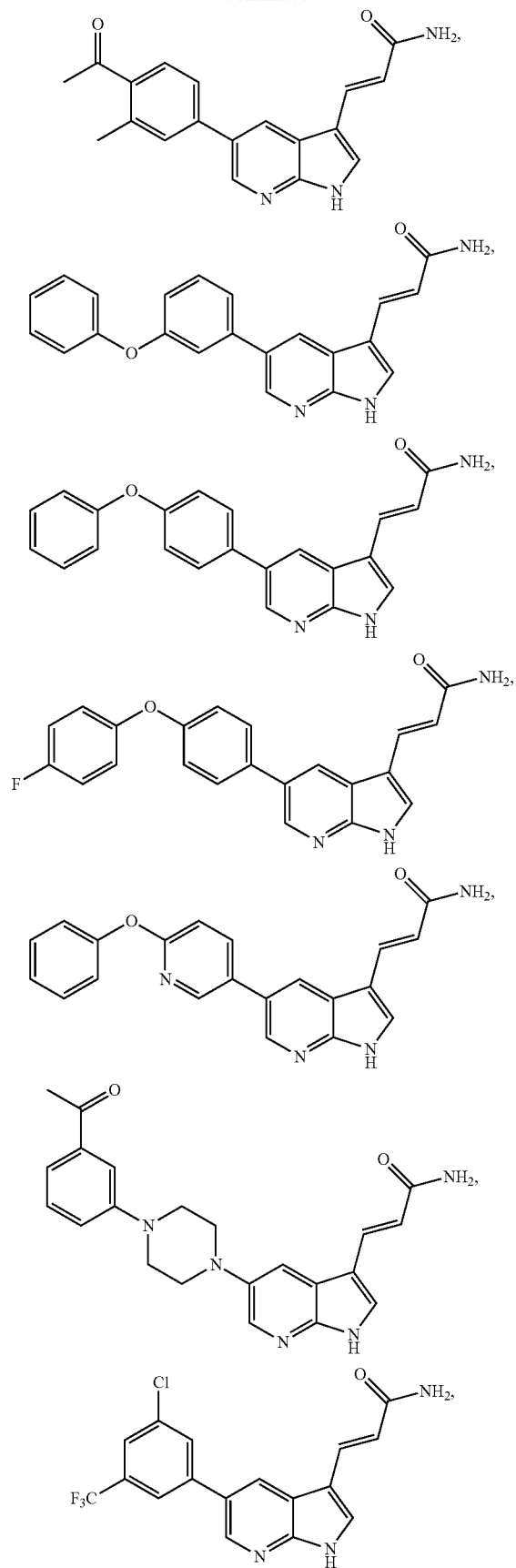
366
-continued
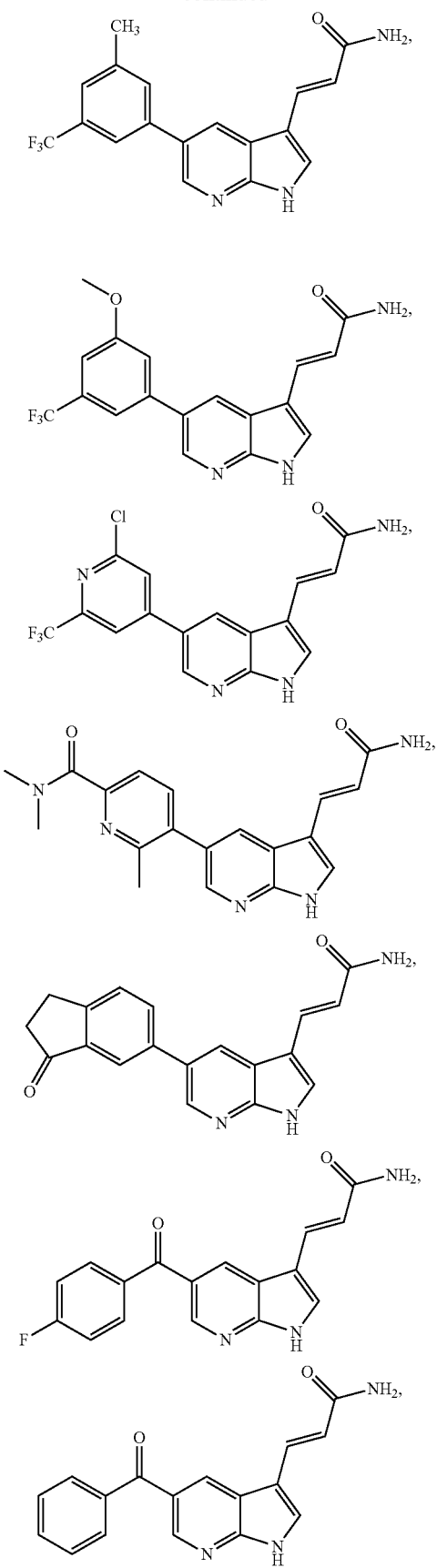

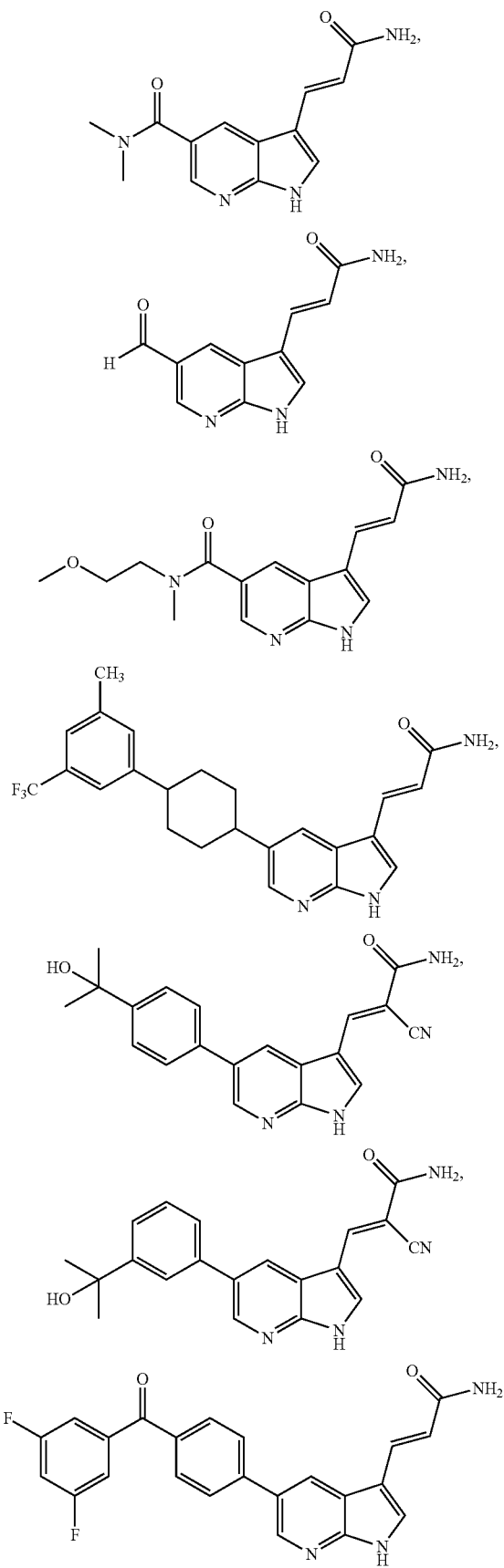
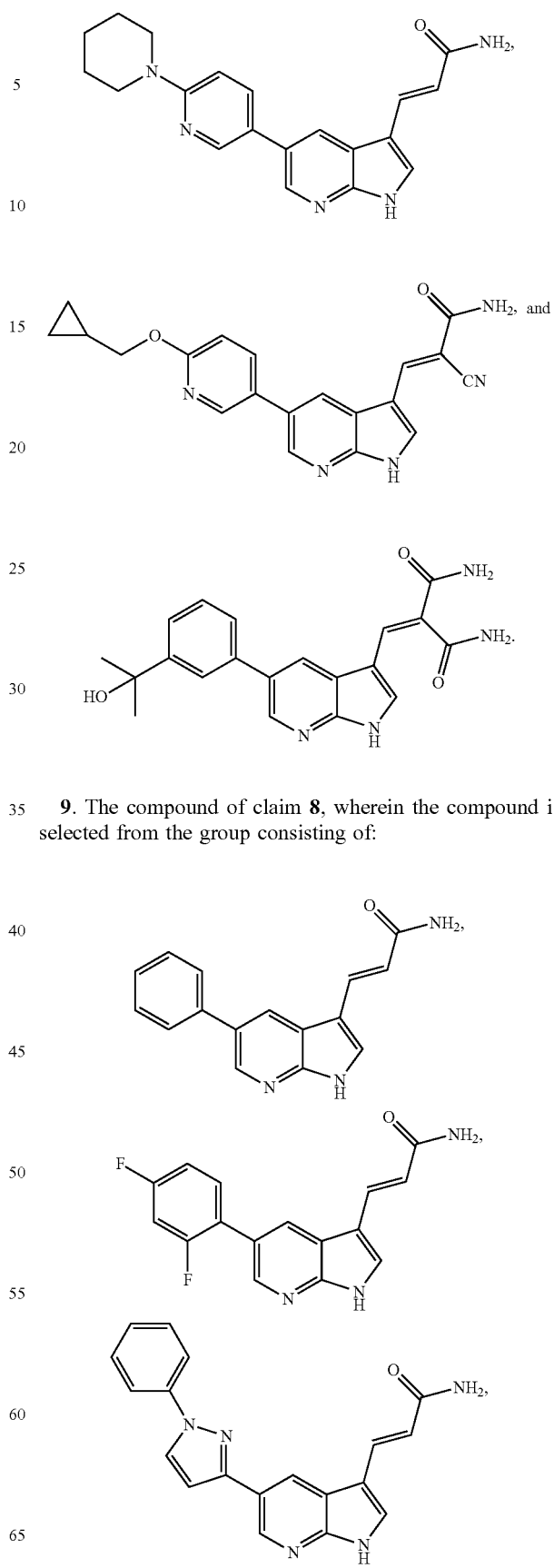
9. The compound of claim 8, wherein the compound is selected from the group consisting of:

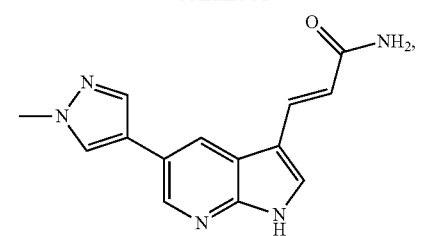
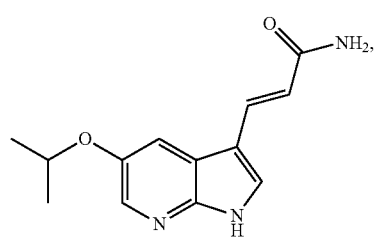
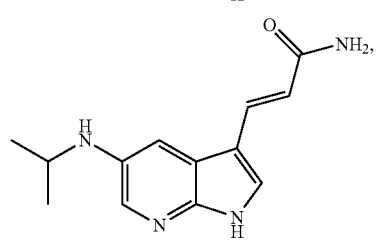
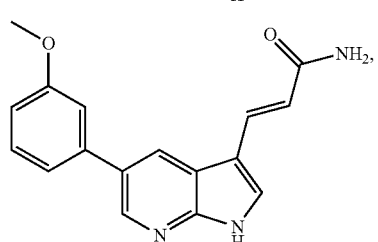
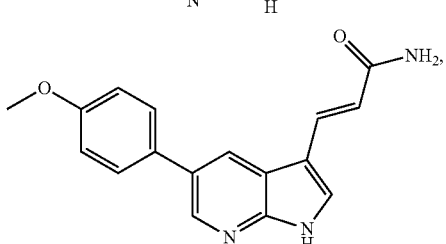
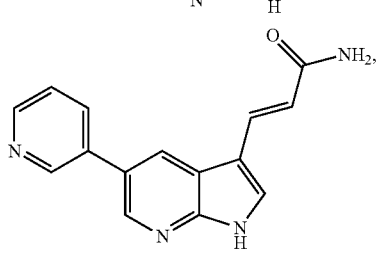
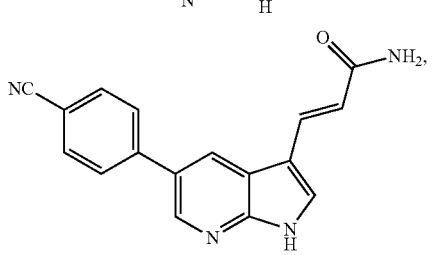
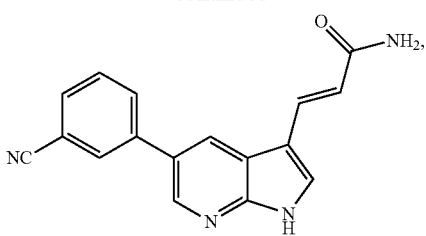
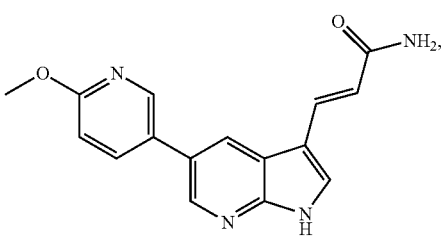
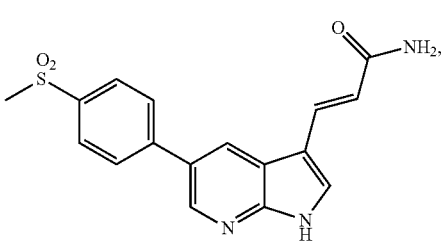
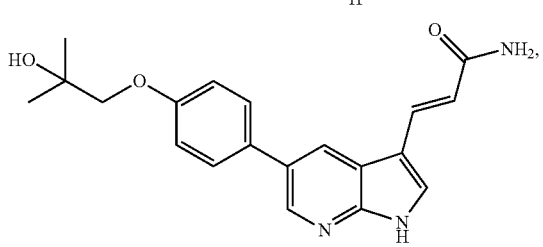
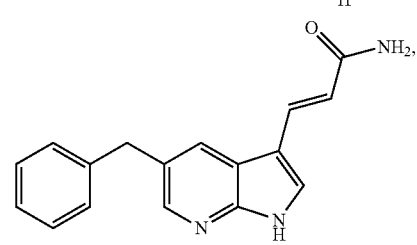
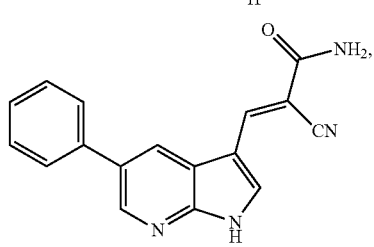
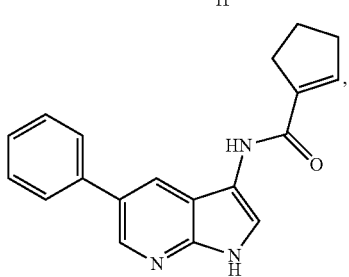

371
-continued
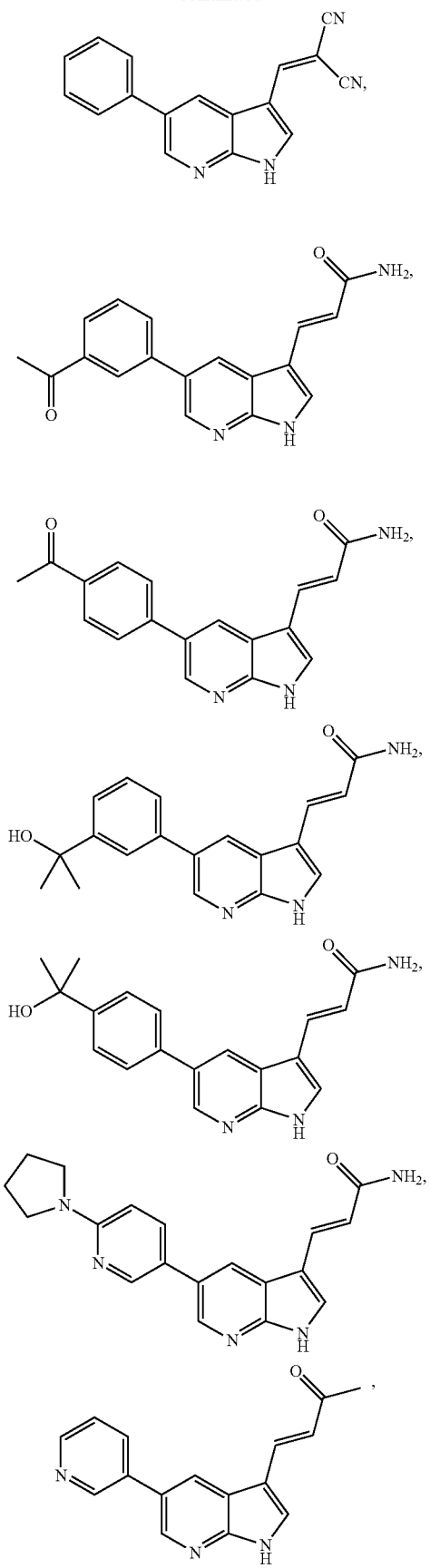
372
-continued
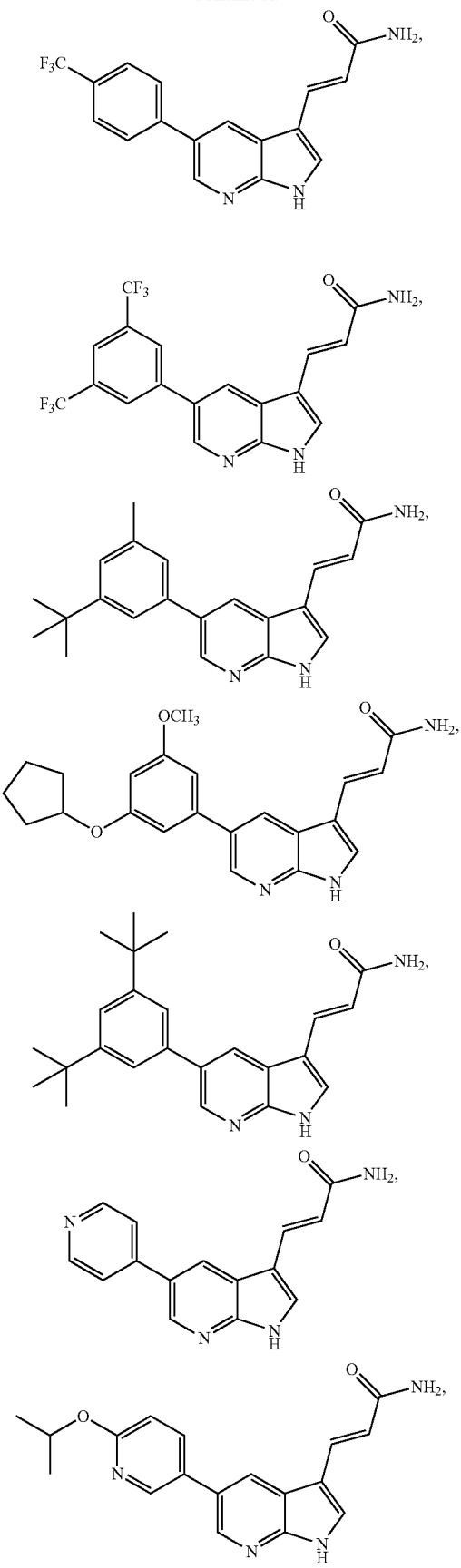

373
-continued
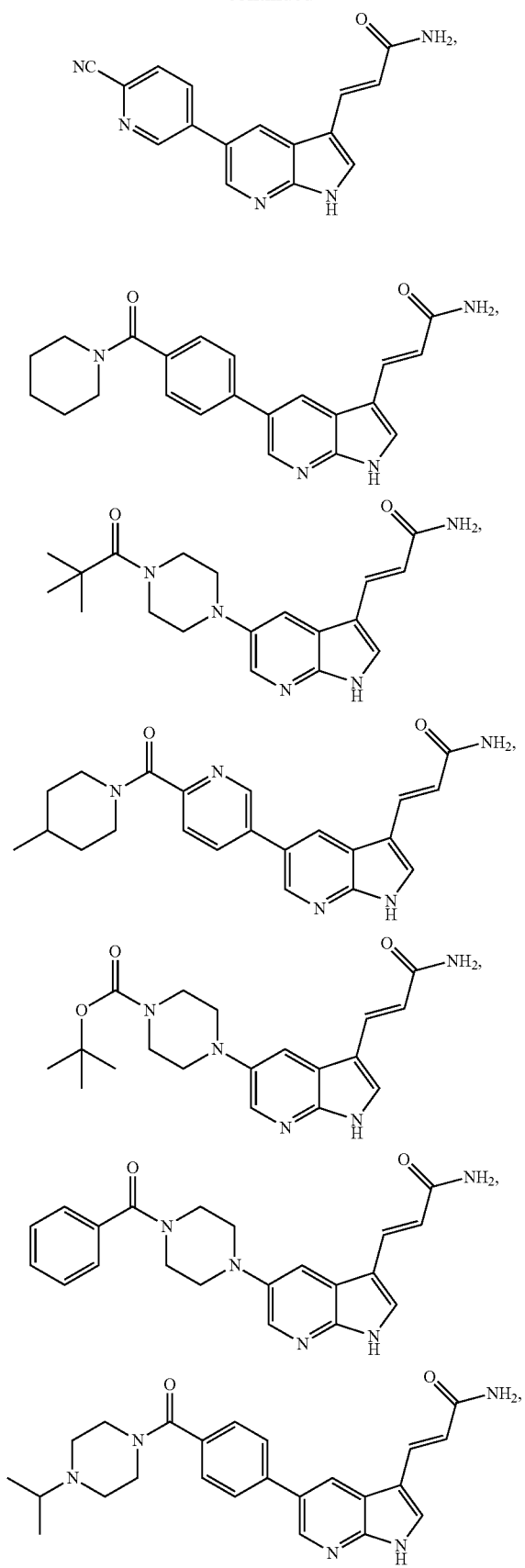
374
-continued
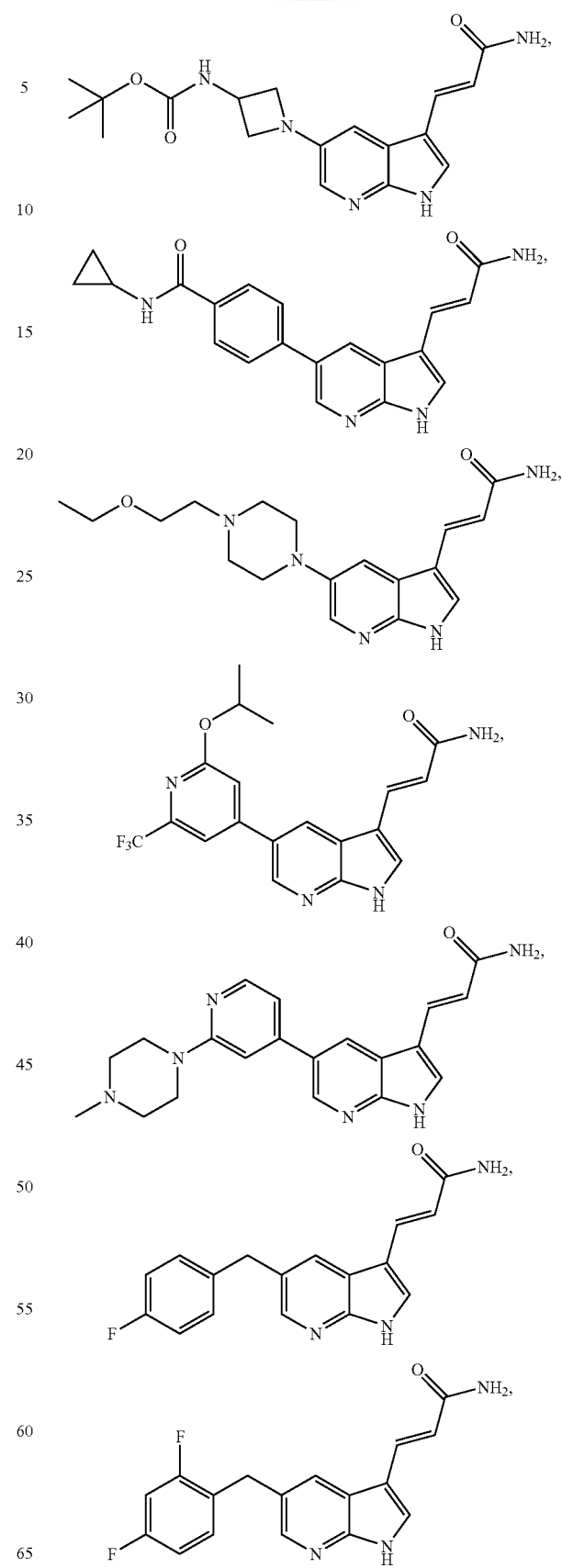

375
-continued
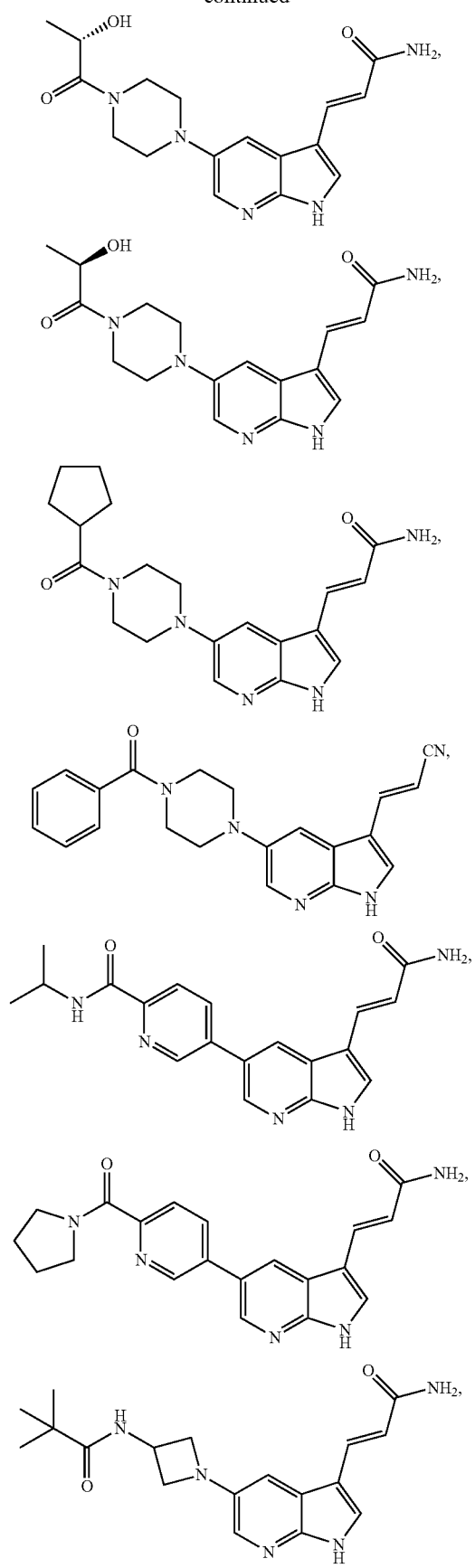
376
-continued
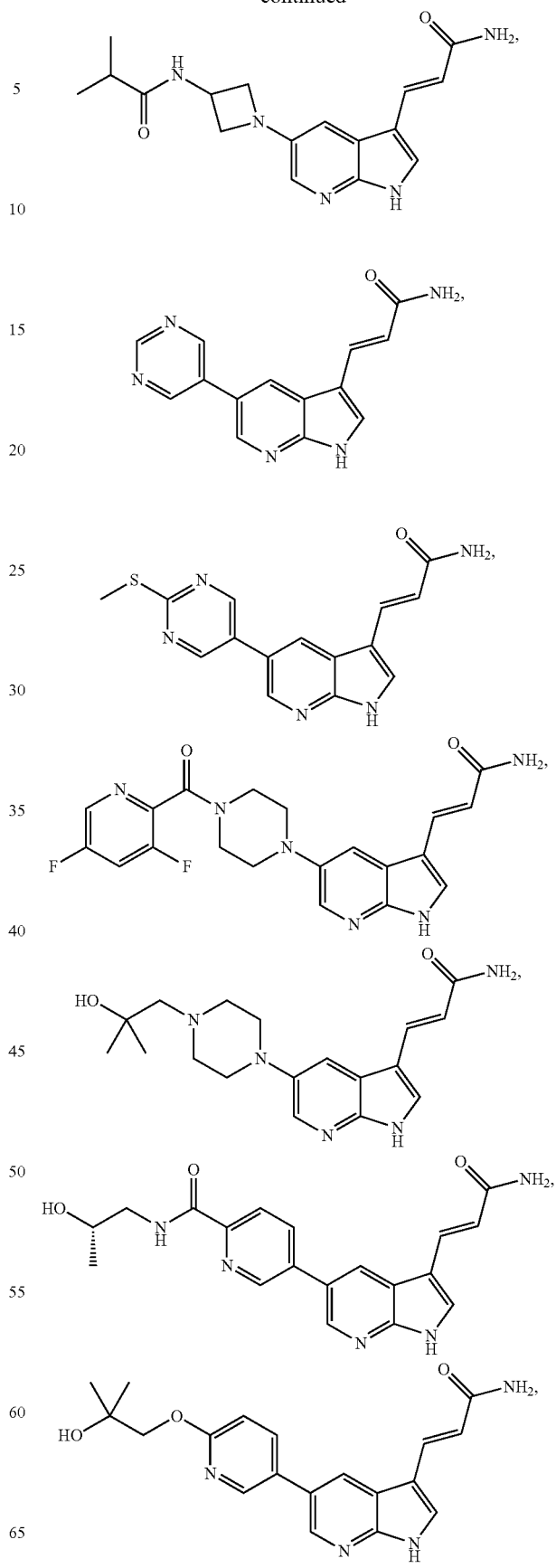

377
-continued
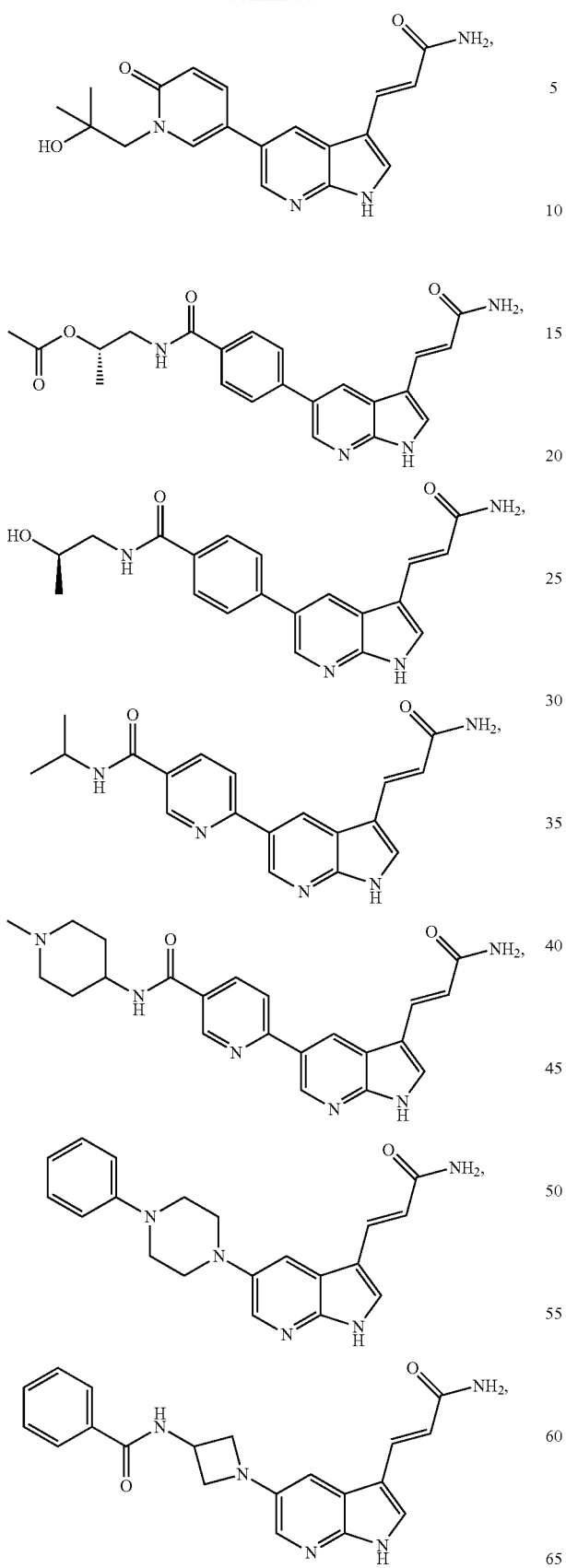
378
-continued
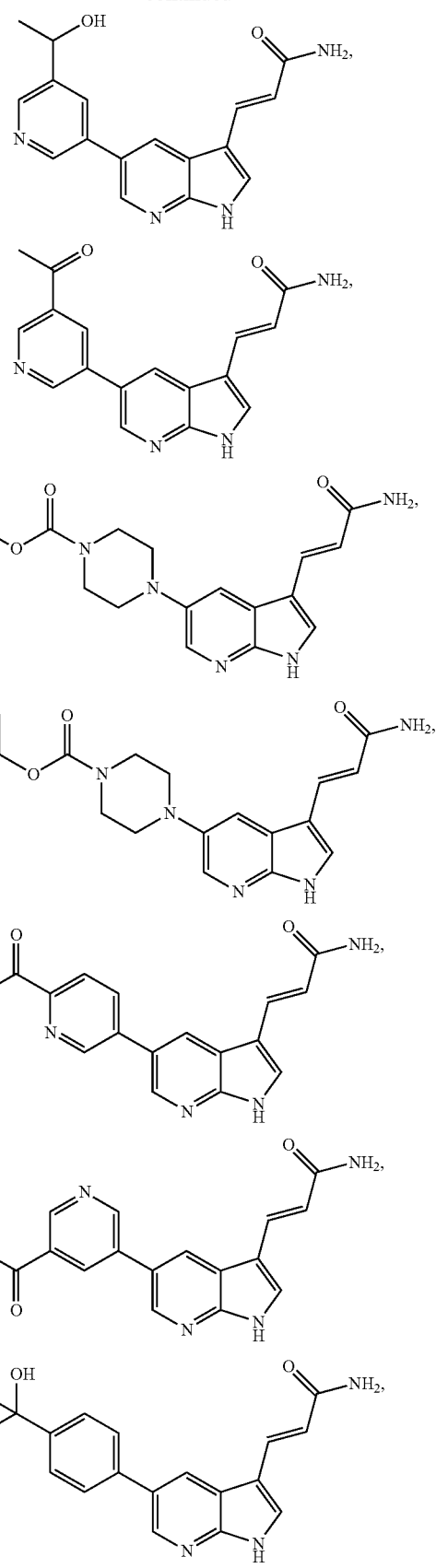

379
-continued
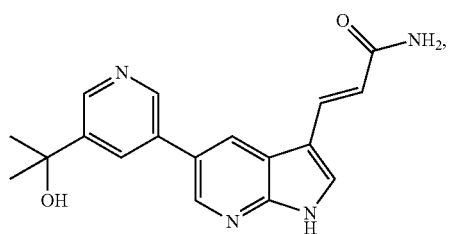
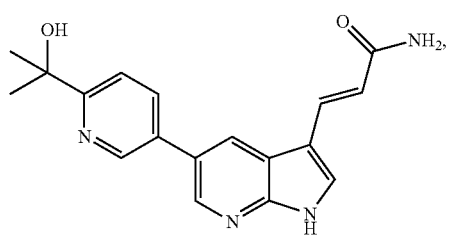
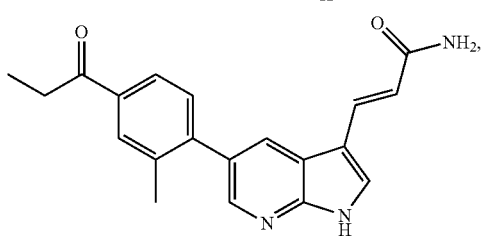
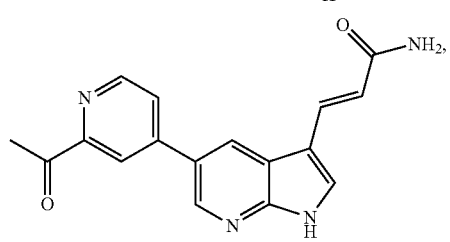
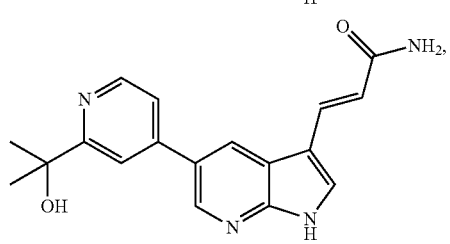
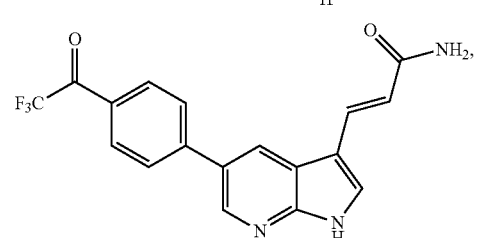
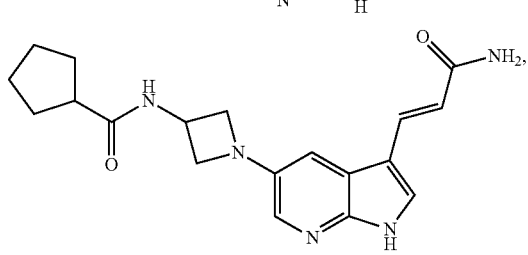
380
-continued
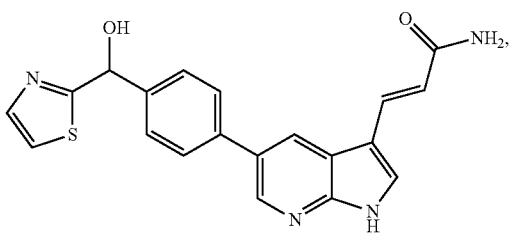
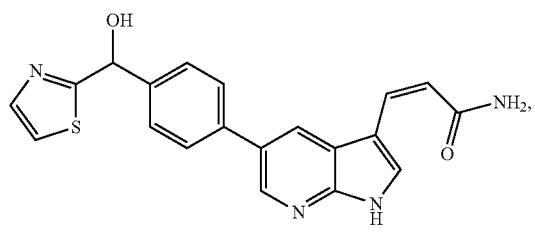
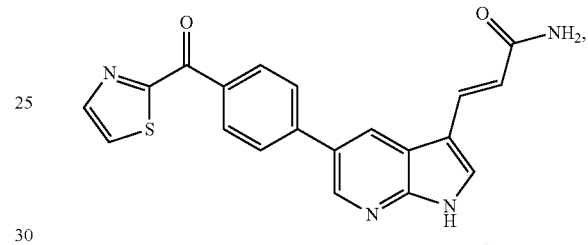
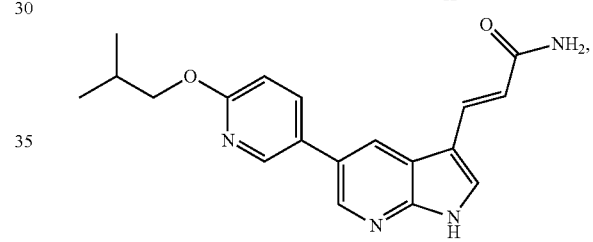
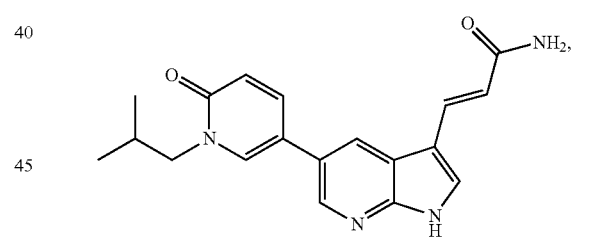
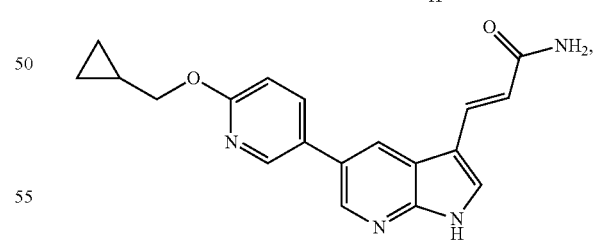
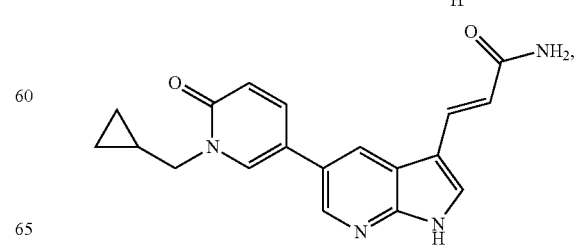

381
-continued
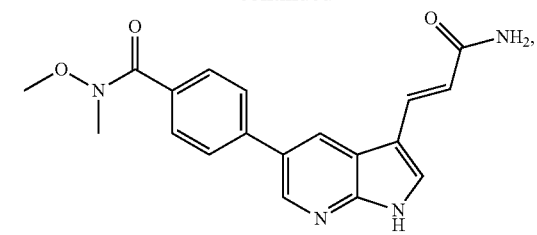
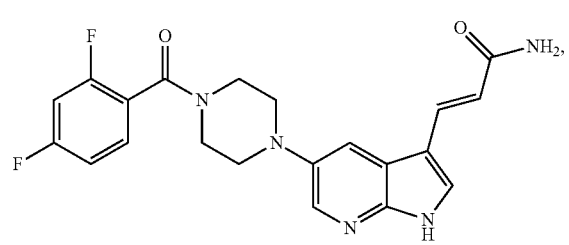
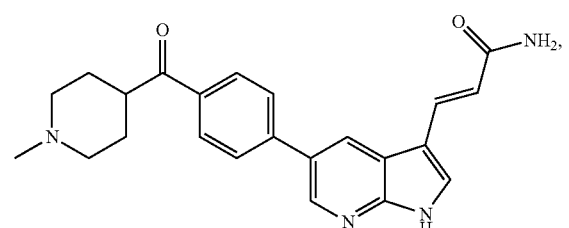
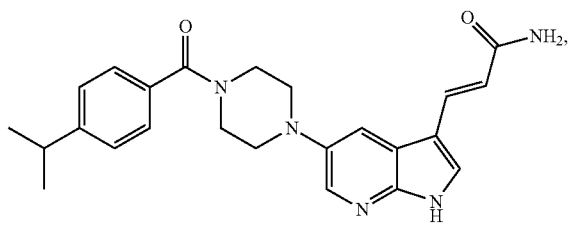
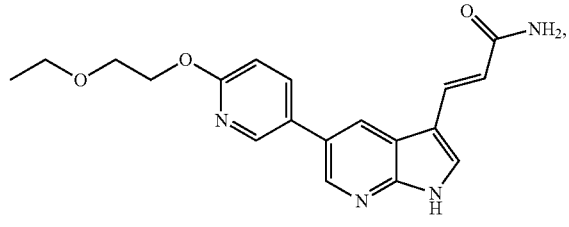
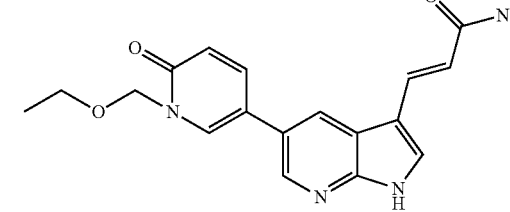
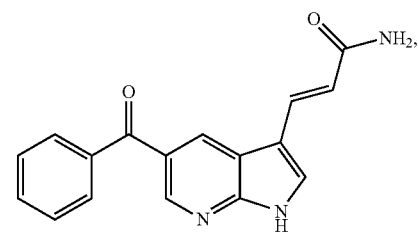
382
-continued
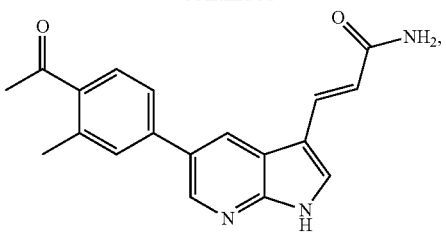
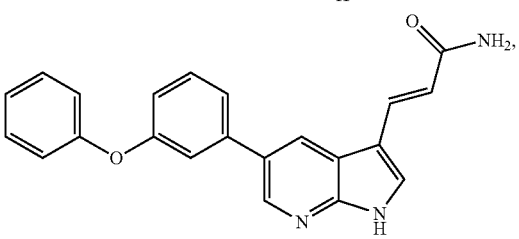
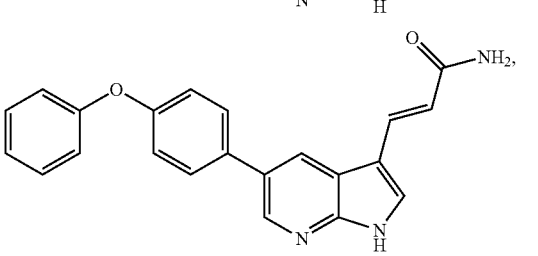
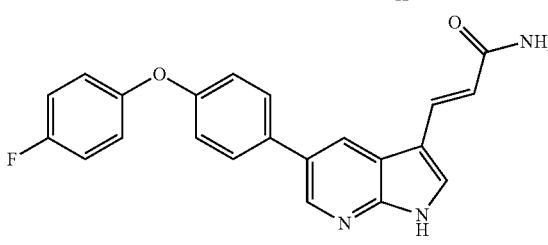
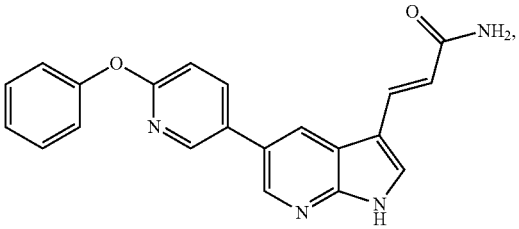
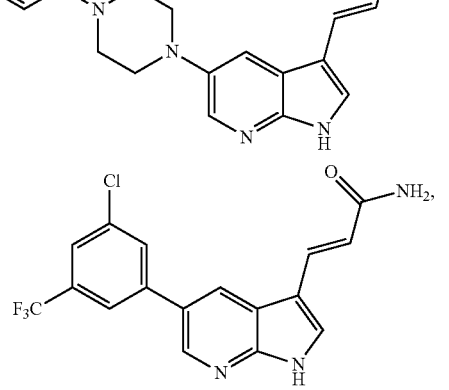

383
-continued
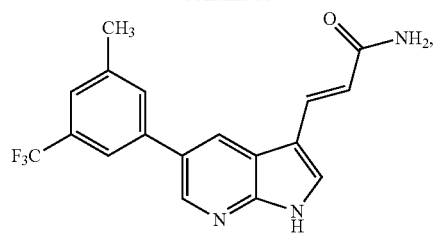
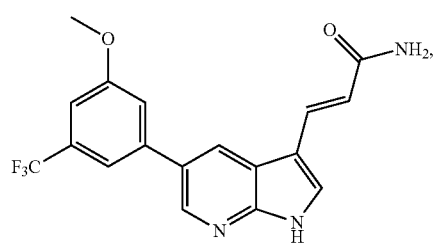
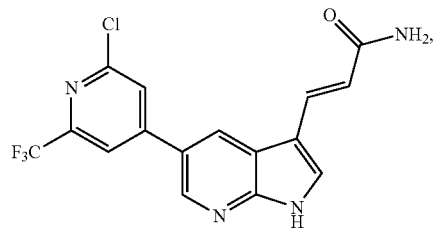
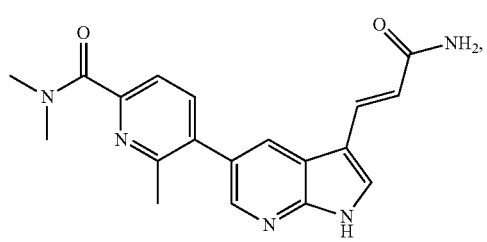
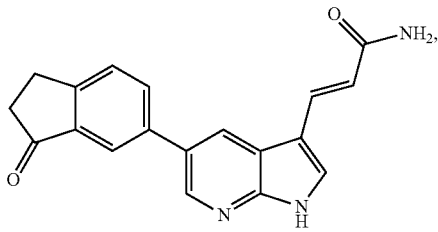
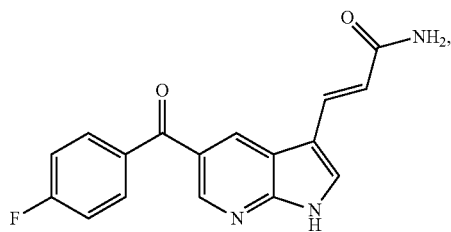
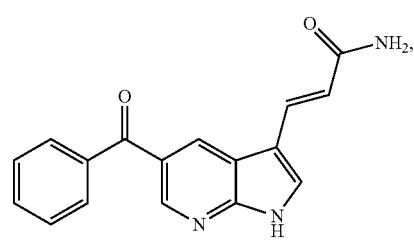
384
-continued
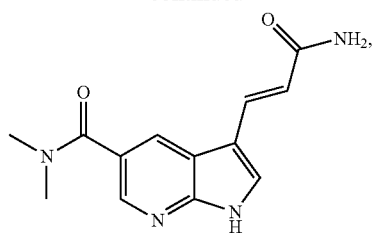
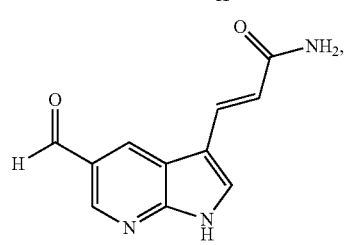
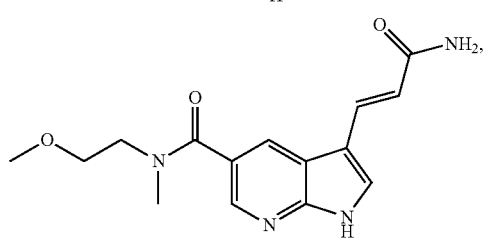
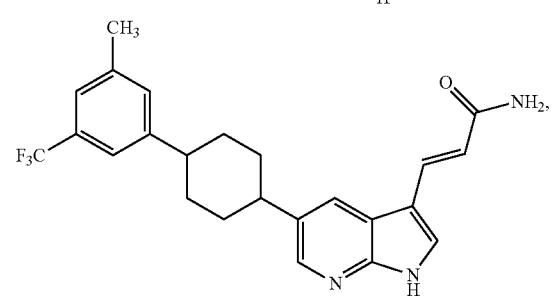
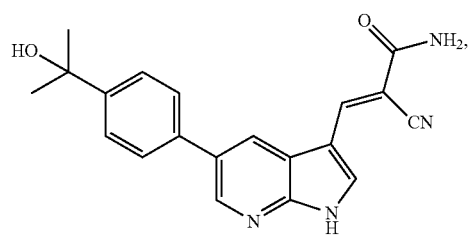
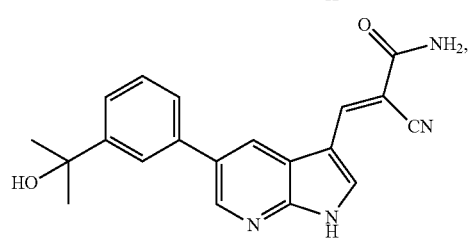
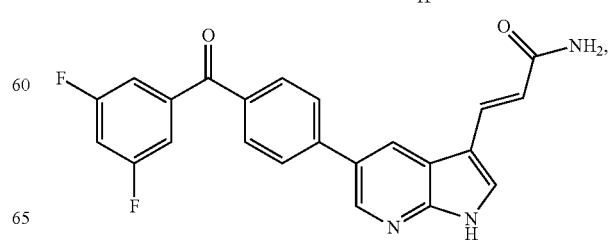

385
-continued
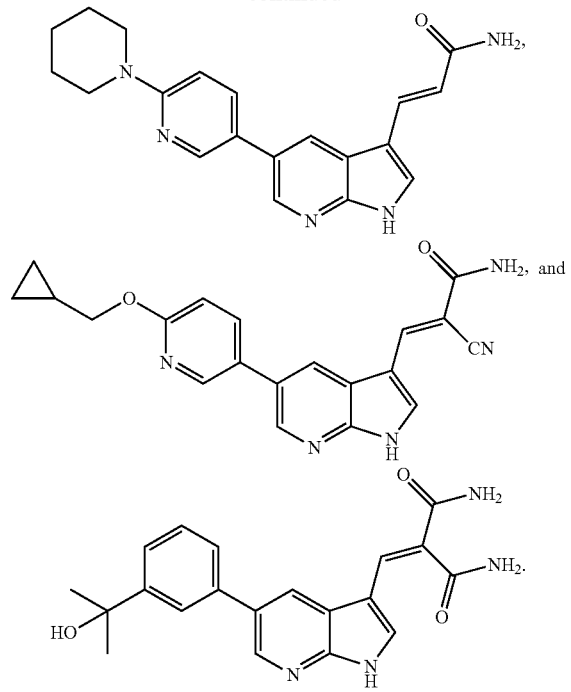
10. The compound of claim 9, wherein the compound is selected from the group consisting of:
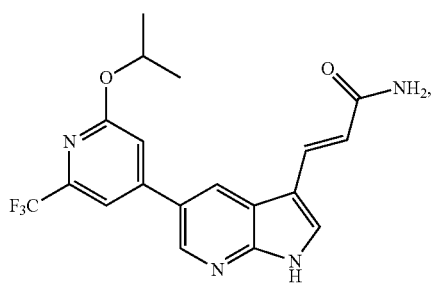
386
-continued
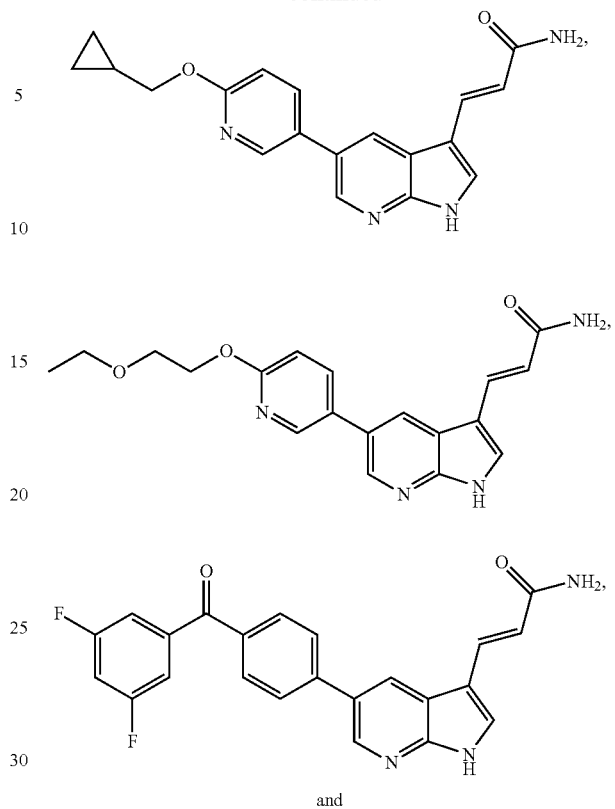
and
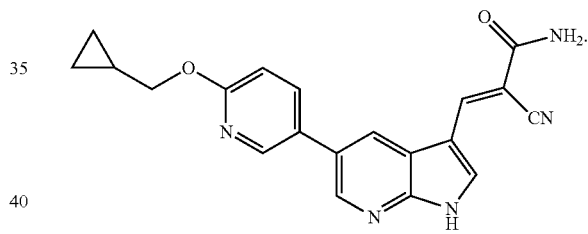
* * * * *